US008778871B2

(12) United States Patent
Kitada et al.

(10) Patent No.: US 8,778,871 B2
(45) Date of Patent: Jul. 15, 2014

(54) METASTIN DERIVATIVES AND USE THEREOF

(75) Inventors: Chieko Kitada, Osaka (JP); Taiji Asami, Ibaraki (JP); Naoki Nishizawa, Ibaraki (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 1131 days.

(21) Appl. No.: 12/286,671

(22) Filed: Oct. 1, 2008

(65) Prior Publication Data

US 2009/0298765 A1 Dec. 3, 2009

Related U.S. Application Data

(63) Continuation of application No. 11/630,698, filed on Dec. 20, 2006, now Pat. No. 7,625,869, which is a continuation of application No. PCT/JP2005/012021, filed on Jun. 23, 2005.

(30) Foreign Application Priority Data

Jun. 25, 2004 (JP) ................................ 2004-187671
Dec. 15, 2004 (JP) ................................ 2004-363311

(51) Int. Cl.
*A61K 38/17* (2006.01)
*C07K 14/47* (2006.01)

(52) U.S. Cl.
USPC ........................................... 514/1.3; 530/350

(58) Field of Classification Search
None
See application file for complete search history.

(56) References Cited

U.S. PATENT DOCUMENTS

| | | | |
|---|---|---|---|
| 6,699,965 B1 | 3/2004 | Watanabe et al. |
| 6,800,611 B2 | 10/2004 | Fujii et al. |
| 7,625,869 B2 | 12/2009 | Kitada et al. |
| 7,754,220 B2 | 7/2010 | Ohtaki et al. |
| 2003/0096956 A1 | 5/2003 | Suenaga et al. |
| 2004/0142875 A1 | 7/2004 | Fujii et al. |
| 2004/0185525 A1 | 9/2004 | Nishimura et al. |
| 2004/0236077 A1 | 11/2004 | Matsumoto et al. |
| 2005/0176091 A1 | 8/2005 | Yamada et al. |
| 2005/0240008 A1 | 10/2005 | Ohtaki et al. |
| 2006/0035875 A1 | 2/2006 | Shiotsu et al. |
| 2006/0241051 A1 | 10/2006 | Kitada et al. |
| 2006/0287227 A1 | 12/2006 | Ohtaki et al. |
| 2009/0093615 A1 | 4/2009 | Asami et al. |
| 2009/0099334 A1 | 4/2009 | Asami et al. |
| 2009/0105152 A1 | 4/2009 | Asami et al. |
| 2009/0215700 A1 | 8/2009 | Asami et al. |
| 2009/0318365 A1 | 12/2009 | Kitada et al. |
| 2010/0215637 A1 | 8/2010 | Klinken et al. |
| 2010/0286035 A1 | 11/2010 | Ohtaki et al. |
| 2010/0331520 A1 | 12/2010 | Asami et al. |
| 2011/0059888 A1 | 3/2011 | Asami et al. |
| 2011/0118172 A1 | 5/2011 | Asami et al. |
| 2012/0015868 A1 | 1/2012 | Asami et al. |

FOREIGN PATENT DOCUMENTS

| | | |
|---|---|---|
| EP | 0162575 A | 11/1985 |
| EP | 0472220 A1 | 2/1992 |
| EP | 1126028 A1 | 8/2001 |
| EP | 2002320496 | 11/2002 |
| EP | 1 577 323 A1 | 9/2005 |
| EP | 1 604 682 A1 | 12/2005 |
| JP | 9-169735 | 6/1997 |
| JP | 2002 320496 A | 11/2002 |
| JP | 2003-026601 | 1/2003 |
| JP | 2003 300906 A | 10/2003 |
| JP | 2004 217651 A | 8/2004 |
| RU | 2002102081 | 9/2003 |
| RU | 2006/145886 A | 1/2006 |
| RU | 2005135739 A | 3/2006 |
| RU | 2306147 C2 | 9/2007 |
| RU | 2311920 C2 | 12/2007 |
| RU | 2333221 C2 | 9/2008 |
| RU | 2344831 C2 | 1/2009 |
| RU | 2008125063 A | 12/2009 |
| WO | 9611953 | 4/1996 |
| WO | 9611953 A1 | 4/1996 |
| WO | WO-97/14682 | 4/1997 |
| WO | WO-97/40071 | 10/1997 |
| WO | WO-98/39448 | 9/1998 |
| WO | WO-00/24890 A | 5/2000 |
| WO | 0100228 | 1/2001 |
| WO | 0141812 A2 | 6/2001 |
| WO | WO-01/44469 A1 | 6/2001 |

(Continued)

OTHER PUBLICATIONS

Harms et al., Clinical and Experimental Metastasis, 2003, 20, pp. 11-18.*
Masui et al.,Biochem. Biophys. Res. Com., 2004, 315, pp. 85-92.*
Bruehlmeier et al., "Stabilization of neurotensin analogues: effect on peptide catabolism, biodistribution and tumor binding," Nuclear Medicine and Biology (2002), 29:321-327.
Cudic et al., "Development of novel antibacterial peptides that kill resistant isolates," Peptides (2002), 23:2071-2083.

(Continued)

*Primary Examiner* — Karlheinz R Skowronek
*Assistant Examiner* — Roy Teller
(74) *Attorney, Agent, or Firm* — Edwards Wildman Palmer LLP; David G. Conlin; Lisa Swiszcz

(57) ABSTRACT

The invention provides stable metastin derivatives having excellent biological activities (a cancer metastasis suppressing activity, a cancer growth suppressing activity, etc.). By modifying the constituent amino acids of metastin with specific modifying groups, metastin derivatives having more improved blood stability, etc. than native metastin and showing excellent cancer metastasis suppressing activity or cancer growth suppressing activity have been found. Furthermore, it has been found that these metastin derivatives exhibit effects of suppressing gonadotropic hormone secretion, suppressing sex hormone secretion, etc., which are wholly different from the effects heretofore known.

4 Claims, 12 Drawing Sheets

(56) References Cited

FOREIGN PATENT DOCUMENTS

| WO | 0172295 | 10/2001 |
|---|---|---|
| WO | 0179286 A2 | 10/2001 |
| WO | WO-01/74377 A1 | 10/2001 |
| WO | WO-01/75104 A1 | 10/2001 |
| WO | WO-02/085399 A1 | 10/2002 |
| WO | WO-02/092829 A1 | 11/2002 |
| WO | WO-03/027149 A1 | 4/2003 |
| WO | WO-03/060125 A1 | 7/2003 |
| WO | WO-2004/038021 A1 | 5/2004 |
| WO | WO-2004/060264 | 7/2004 |
| WO | WO-2004/060264 A | 7/2004 |
| WO | WO-2004/063221 A | 7/2004 |
| WO | 2004073730 A1 | 9/2004 |
| WO | WO-2004/080479 A1 | 9/2004 |
| WO | WO-2004/087622 A2 | 10/2004 |
| WO | 2004093894 A2 | 11/2004 |
| WO | WO-2004/096855 A2 | 11/2004 |
| WO | WO-2004/101747 A2 | 11/2004 |
| WO | WO-2004/106289 A1 | 12/2004 |
| WO | 2005042744 A1 | 5/2005 |
| WO | WO-2005/095973 A2 | 10/2005 |
| WO | 2005117939 A2 | 12/2005 |
| WO | WO-2006/001499 A2 | 1/2006 |
| WO | WO-2007/072997 A1 | 6/2007 |
| WO | 2007084211 A2 | 7/2007 |
| WO | WO-2007/084211 A2 | 7/2007 |
| WO | 2007109135 A2 | 9/2007 |
| WO | 2008050897 | 5/2008 |
| WO | 2009131191 A1 | 10/2009 |
| WO | 2010/033224 A1 | 3/2010 |

OTHER PUBLICATIONS

European Search Report for related application EP09075257, dated Oct. 6, 2010.
Y. Terao et al., "Expression of KiSS-a, a Metastasis Suppressor Gene, in Trophoblast Giant Cells of the Rat Placenta." Biochimica et Biophysica Acta 1678 (2004) 102-110.
T. Masui et al., "Metastin and its variant forms suppress migration of pancreatic cancer cells." Biochemical and Biophysical Research Communications 315 (2004) 85-92.
M. L. Gottsch et al., "A Role for Kisspeptins in the Regulation of Gonadotropin Secretion in the Mouse." Endocrinology 2004 145(9):4073-4077.
T. Ohtaki et al., "Metastasis suppressor gene KiSS-1 encodes peptide ligand of a G-protein-coupled receptor." Nature vol. 411, May 31, 2001 pp. 613-617.
A. Niita et al., "Genome Information Convergent Type of Drug Development Research: Depolymerization of the Cancer Metastasis Suppressor Gene, KiSS-1 (Metastin). 2003 Yuki 2B-13-2."
A. Dutta et al., "Polypeptides. Part 15 Synthesis and Biological Activity of ∝-Aza-analogues of Luliberin modified in Positions 6 and 10." Journal of the Chemical Society, Perkin Transactions 1, No. 2, 1979, pp. 379-388.
M. Kotani et al., "The Metastasis Suppressor Gene KiSS-1 Encodes Kisspeptins, the Natural Ligands of the Orphan G Protein-coupled Receptor GPR54", *The Journal of Biological Chemistry*, vol. 276, pp. 34631-34636 (2001).
M. Ringel et al., "Metastin Receptor is Overexpressed in Papillary Thyroid Cancer and Activates MAP Kinase in Thyroid Cancer Cells", *The Journal of Clinical Endocrinology & Metabolism*, 87(5), pp. 2399-2402 (2002).
S. Han et al., "Orphan G Protein-coupled receptors MrgA1 and MrgC11 are Distinctively Activated by RF-amide-related Peptides Through the Gα11 Pathway", *PNAS*, vol. 99, No. 23, pp. 14740-14745 (Nov. 12, 2002).
Y. Horikoshi et al., "Dramatic Elevation of Plasma Metastin Concentrations in Human Pregnancy: Metastin as a Novel Plascenta-Derived Hormone in Humans", *The Journal of Clinical endocrinology & Metabolism*, 88(2), pp. 914-919 (2003).
Georgian Srch Rpt, GE, Nov. 16, 2010, Srch Rpt for Georgian patent appln AP2007011265.
Official Action of Japanese Patent Application No. JP2008-245073, issued Mar. 31, 2009.
Muir et al., "AXOR12, a Novel Human G Protein-coupled Receptor, Activated by the Peptide KiSS-1", *The Journal of Biological Chemistry*, 276(31), pp. 28969-28975 (2001).
Search Report for Corresponding Georgian Application No. AP 2006 010770 dated Nov. 30, 2009 together with it's English translation.
European Search Report for EP04719659.
Nature 1998 vol. 393 pp. 272-276.
Nature 1998 vol. 393 pp. 211-212.
Biochem J 2001 vol. 354 pp. 379-385.
European Search Report for EP03768337.2—Mar. 4, 2008.
Supplementary European Search Report for Corresponding European Patent Application Serial No. EP 09803004, completed Dec. 6, 2012 (5 pages).
Roberts M.J. et al., Advanced Drug Delivery Reviews, vol. 54, No. 4, Jun. 17, 2002, pp.459-476.
S. Hinuma et al., "A prolactin-releasing peptide in the brain", Nature, vol. 393, pp. 272-276 (1998).
J.C. Meunier et al., "Molecular Neuroendocrinology: Working backwards to find answers", Nature, vol. 393, pp. 211-212 (1998).
H. Satake et al., "Characterization of a cDNA encoding a novel avian hypothalamic neuropeptide exerting an inhibitory effect on gonadotropin release", Biochem. J., vol.354, pp. 379-385 (2001).
Roberts et al., "Trends in the risks and benefits to patients with cancer participating in phase 1 clinical trials", JAMA, vol. 292, pp. 2130-2140 (2004).
Kola et al., "Can the pharmaceutical industry reduce attrition rates?", Nature Review Drug Discovery, vol. 3, pp. 711-715 (2004).
Gura et al., "Cancer models: systems for identifying new drugs are often faulty", Science, vol. 278, pp. 1041-1042 (1997).
Leaf et al., "Why we are losing the war on cancer (and how to win it)", Health Administrator, XVII, pp. 172-183 (2005).
"Expert Scientific Group on Phase One Clinical Trials Final Report", pp. C1, C35-C38 (Nov. 30, 2006).
Kamb et al., "What's wrong with our cancer models?", Nature Review Drug Discovery, vol. 4, pp. 161-165 (2005).
Navenot et al., "Kisspeptin-10-induced signaling of GPR54 negatively regulates chemotactic responses mediated by CXCR4: a potential mechanism for the metastases suppressor activity of Kisspeptins", Cancer Research, vol. 54, pp. 10450-10456 (2005).
Steeg et al., "Metastasis Suppressor Genes: Basic Biology and Potential Clinical Use", Clinical Breast Cancer, vol. 4, pp. 51-62 (2003).
Harms et al., "KISS1 metastasis suppression and emergent pathways", Clinical & Experimental Metastasis, vol. 20, pp. 11-18 (2003).
Cancer Drug Design & Discovery, Neidle, Stephen ed. (Elsevier/Academic Press, 2008), pp. 427-431.
Masai et al., "Metastin and its variant forms suppress migration of pancreatic cancer cells", Biochem. Biophys. Res. Com., vol. 315, pp. 85-92 (2004).
Jiang et al., "KISS1 suppresses metastasis in human ovarian cancer via inhibition of protein kinase C alpha", Clinical and Experimental Metastasis, vol. 22, pp. 369-376 (2005).
Nash et el., "The KISS1 metastasis suppressor: mechanistic insights and clinical utility", Front. Biosci., vol. 11, pp. 647-659 (2006).
M.K. Clements et al., "FMRF amide-related neuropeptides are agonists of the orphan G-protein-coupled receptor GPR54", Biochemical and Biophysical Research Communications, 284(5), pp. 1189-1193 (2001).
C. Frochot et al., "A solid-phase synthesis of three AZA-, iminoaza- and reduced AZA- peptides from the same precursor", Letters in Peptide Science, 4(4-6), pp. 219-225 (1997).
L.J. Stafford et al., "Identification and characterization of mouse metastatis-suppressor KISS1 and its G-protein-coupled receptor", Cancer Research, American Association for Cancer Research, 62(19), pp. 5399-5404 (2002).

(56) References Cited

OTHER PUBLICATIONS

N. Venkatesan et al., "Synthesis and Enzyme Inhibitory Activities of Novel Peptide Isosteres", *Current Medicinal Chemistry*, vol. 9, pp. 2243-2270 (2002).

K. Tomita et al., "Structure—Activity Relationship Study on Small Peptidic GPR54 Agonists", *Bioorganic & Medicinal Chemistry*, vol. 14, pp. 7595-7603 (2006).

A. Niida et al., "Design and Synthesis of Downsized Metaslin (45-54) Analogs with Maintenance of High GPR54 Agonistic Activity", *Bioorganic & Medicinal Chemistry*, vol. 16, pp. 134-137 (2006).

Makri et al., 2008, Cancer Treatment Reviews, 34: 682-692.

Dhillo, 2008, Journal of Neuroendocrinology, 20: 963-970.

Mead et al., 2007, British Journal of Pharmacology, 151: 1143-1153.

\* cited by examiner

METASTIN DERIVATIVES AND USE THEREOF

TECHNICAL FIELD

The present invention relates to metastin derivatives and use thereof.

BACKGROUND ART

Human-derived metastin (also termed KiSS-1 peptide) (WO 00/24890) and rat or mouse-derived metastin (WO 01/75104) are known. Also, sustained released preparations containing metastin are known (WO 02/85399).

Reportedly, metastin has an effect of suppressing cancer metastasis and is therefore effective for preventing or treating cancers (for example, lung cancer, gastric cancer, liver cancer, pancreatic cancer, colorectal cancer, rectal cancer, colonic cancer, prostate cancer, ovarian cancer, cervical cancer, breast cancer, renal cancer, bladder cancer, brain tumor, etc.); metastin also has an effect of controlling pancreatic function and is effective for preventing or treating pancreatic diseases (e.g., acute or chronic pancreatitis, pancreatic cancer, etc.); and metastin further has an effect of controlling placental function and is effective for preventing or treating choriocarcinoma, hydatid mole, invasive mole, miscarriage, fetal hypoplasia, abnormal glucose metabolism, abnormal lipid metabolism or abnormal delivery (WO 00/24890; WO 01/75104; WO 02/85399).

DISCLOSURE OF THE INVENTION

The present invention aims at providing stable metastin derivatives having excellent biological activities (a cancer metastasis suppressing activity, a cancer growth suppressing activity, etc.).

The present inventors have made extensive studies to solve the foregoing problems and as a result, have found that by modifying the amino acids, which constitute metastin, with a specific modifying group, unexpectedly metastin derivative show improved blood stability, etc. as compared to native metastin and further exhibit an excellent cancer metastasis suppressing activity or a cancer growth suppressing activity. The present inventors have further found that unexpectedly these metastin derivatives have an effect of suppressing gonadotropic hormone secretion, an effect of suppressing sex hormone secretion, etc., which are totally different from the effects known so far. Based on these findings, the present inventors have continued further investigations and come to accomplish the present invention.

That is, the present invention provides the following features and so on.

(1) A metastin derivative (II) represented by formula:

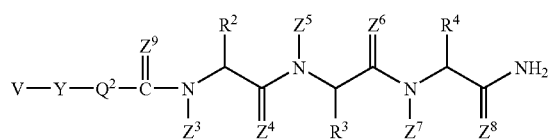

[wherein;
V represents a group represented by formula:

$$P-W^1-W^2-\underset{(Z^1)_n}{\overset{Q^1}{|}}$$

or a group represented by formula:

$$P\diagdown_{W^1}-\underset{(P')_n}{|}$$

n represents 0 or 1;
$W^1$ represents N, CH or O (provided that when $W^1$ is N or CH, n represents 1 and when $W^1$ is O, n represents 0);
$W^2$ represents N or CH;
$Z^1$, $Z^3$, $Z^5$ and $Z^7$ each represents hydrogen atom or a $C_{1-3}$ alkyl group;
$Z^4$, $Z^6$ and $Z^8$ each represents hydrogen atom, O or S;
$R^2$ represents (1) hydrogen atom or (2) a cyclic or linear $C_{1-10}$ alkyl group, (3) a $C_{1-10}$ alkyl group consisting of a cyclic alkyl group and a linear alkyl group, or (4) a $C_{1-8}$ alkyl group optionally substituted with a substituent selected from the group consisting of an optionally substituted carbamoyl group, an optionally substituted hydroxyl group and an optionally substituted aromatic cyclic group;
$R^3$ represents (1) a $C_{1-8}$ alkyl group having an optionally substituted basic group and optionally having an additional substituent, (2) an aralkyl group having an optionally substituted basic group and optionally having an additional substituent, (3) a $C_{1-4}$ alkyl group having a non-aromatic cyclic hydrocarbon group of carbon atoms not greater than 7 having an optionally substituted basic group, and optionally having an additional substituent, or (4) a $C_{1-4}$ alkyl group having a non-aromatic heterocyclic group of carbon atoms not greater than 7 having an optionally substituted basic group, and optionally having an additional substituent;
$R^4$ represents a $C_{1-4}$ alkyl group, which may optionally be substituted with a substituent selected from the group consisting of (1) an optionally substituted $C_{6-12}$ aromatic hydrocarbon group, (2) an optionally substituted 5- to 14-membered aromatic heterocyclic group consisting of 1 to 7 carbon atoms and hetero atoms selected from the group consisting of nitrogen, oxygen and sulfur atoms, (3) an optionally substituted $C_{8-14}$ aromatic fused cyclic group, (4) an optionally substituted 5- to 14-membered aromatic fused heterocyclic group consisting of 3 to 11 carbon atoms and hetero atoms selected from the group consisting of nitrogen, oxygen and sulfur atoms, (5) an optionally substituted non-aromatic cyclic hydrocarbon group having carbon atoms not greater than 7, and (6) an optionally substituted non-aromatic heterocyclic group having carbon atoms not greater than 7;
$Q^1$ represents a $C_{1-4}$ alkyl group, which may optionally be substituted with a substituent selected from the group consisting of (1) an optionally substituted $C_{6-12}$ aromatic hydrocarbon group, (2) an optionally substituted 5- to 14-membered aromatic heterocyclic group consisting of 1 to 7 carbon atoms and hetero atoms selected from the group consisting of nitrogen, oxygen and sulfur atoms, (3) an optionally substituted $C_{8-14}$ aromatic fused cyclic group, (4) an optionally substituted 5- to 14-membered aromatic fused heterocyclic group consisting of 3 to 11 carbon atoms and hetero atoms selected from the group consisting of nitrogen, oxygen and sulfur atoms, (5) an optionally substituted non-aromatic cyclic hydrocarbon group having carbon atoms not greater than 7, and (6) an optionally substituted non-aromatic heterocyclic group having carbon atoms not greater than 7;

$Q^2$ represents (1) $CH_2$, which may optionally be substituted with an optionally substituted $C_{1-4}$ alkyl group with a substituent selected from the group consisting of carbamoyl group and hydroxyl group, (2) NH, which may optionally be substituted with an optionally substituted $C_{1-4}$ alkyl group with a substituent selected from the group consisting of carbamoyl group and hydroxyl group, or (3) O;

Y represents a group represented by formula: —CONH—, —CSNH—, —CH$_2$NH—, —NHCO—, —CH$_2$O—, —CH$_2$S—, —COO—, —CSO—, —CH$_2$CH$_2$—, or —CH=CH—, which may optionally be substituted with a $C_{1-6}$ alkyl group; and, $Z^9$ represents hydrogen atom, O or S; and, P and P', which may be the same or different, each may form a ring by combining P and P' or P and Q$^1$ together and represents:

(1) hydrogen atom;

(2) an optional amino acid residue continuously or discontinuously bound from the C terminus of the 1-48 amino acid sequence in the amino acid sequence represented by SEQ ID NO: 1;

(3) a group represented by formula:

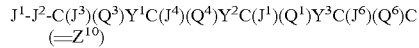

(wherein:
$J^1$ represents (a) hydrogen atom or (b) (i) a $C_{1-15}$ acyl group, (ii) a $C_{1-15}$ alkyl group, (iii) a $C_{6-14}$ aryl group, (iv) carbamoyl group, (v) carboxyl group, (vi) sulfino group, (vii) amidino group, (viii) glyoxyloyl group or (ix) amino group, which groups may optionally be substituted with a substituent containing an optionally substituted cyclic group;

$J^2$ represents (1) NH optionally substituted with a $C_{1-6}$ alkyl group, (2) $CH_2$ optionally substituted with a $C_{1-6}$ alkyl group, (3) O or (4) S;

$J^3$ through $J^6$ each represents hydrogen atom or a $C_{1-3}$ alkyl group;

$Q^3$ through $Q^6$ each represents a $C_{1-4}$ alkyl group, which may optionally have a substituent selected from the group consisting of:

(1) an optionally substituted $C_{6-12}$ aromatic hydrocarbon group, (2) an optionally substituted 5- to 14-membered aromatic heterocyclic group consisting of 1 to 7 carbon atoms and hetero atoms selected from the group consisting of nitrogen, oxygen and sulfur atoms, (3) an optionally substituted $C_{8-14}$ aromatic fused cyclic group, (4) an optionally substituted 5- to 14-membered aromatic fused heterocyclic group consisting of 3 to 11 carbon atoms and hetero atoms selected from the group consisting of nitrogen, oxygen and sulfur atoms, (5) an optionally substituted non-aromatic cyclic hydrocarbon group having carbon atoms not greater than 7, (6) an optionally substituted non-aromatic heterocyclic group having carbon atoms not greater than 7, (7) an optionally substituted amino group, (8) an optionally substituted guanidino group, (9) an optionally substituted hydroxyl group,

(10) an optionally substituted carboxyl group,

(11) an optionally substituted carbamoyl group, and

(12) an optionally substituted sulfhydryl group, or hydrogen atom;

$J^3$ and $Q^3$, $J^4$ and $Q^4$, $J^5$ and $Q^5$ or $J^6$ and $Q^6$ may be combined together, or, $J^2$ and $Q^3$, $Y^1$ and $Q^4$, $Y^2$ and $Q^5$, or $Y^3$ and, $Q^6$ may be combined together, to form a ring;

$Y^1$ through $Y^3$ each represents a group represented by formula:

—CON(J$^{13}$)-, —CSN(J$^{13}$)-, —C(J$^{14}$)N(J$^{13}$)- or —N(J$^{13}$)CO— (wherein J$^{13}$ and J$^{14}$ each represents hydrogen atom or a $C_{1-3}$ alkyl group); and, $Z^{10}$ represents hydrogen atom, O or S);

(4) a group represented by formula:

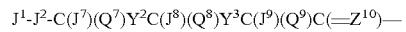

(wherein:
$J^1$ and $J^2$, each has the same significance as described above;

$J^7$ through $J^9$ have the same significance as for $J^3$;

$Q^7$ through $Q^9$ have the same significance as for $Q^3$;

$Y^2$ and $Y^3$ each has the same significance as described above;

$Z^{10}$ has the same significance as described above;

$J^7$ and $Q^7$, $J^8$ and $Q^8$ or $J^9$ and $Q^9$ may be combined together, or, $J^2$ and $Q^7$, $Y^2$ and $Q^8$ or $Y^3$ and $Q^9$ may be combined together, to form a ring);

(5) a group represented by formula:

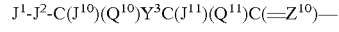

(wherein:
$J^1$ and $J^2$ have the same significance as described above represents;

$J^{10}$ and $J^{11}$ have the same significance as for $J^3$;

$Q^{10}$ and $Q^{11}$ have the same significance as for $Q^3$;

$Y^3$ has the same significance as described above;

$Z^{10}$ has the same significance as described above; and, $J^{10}$ and $Q^{10}$ or $J^{11}$ and $Q^{11}$ may be combined together, or $J^2$ and $Q^{10}$ or $Y^3$ and $Q^{11}$ may be combined together, to form a ring);

(6) a group represented by formula:

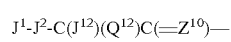

(wherein;
$J^1$ and $J^2$ have the same significance as described above;

$J^{12}$ has the same significance as for $J^3$;

$Q^{12}$ has the same significance as for $Q^3$;

$Z^{10}$ has the same significance as described above; and, $J^{12}$ and $Q^{12}$ may be combined together, or $J^2$ and $Q^{12}$ may be combined together, to form a ring); or, (7) a group represented by formula:

(wherein:
$J^1$ has the same significance as described above)] (provided that a peptide consisting of the amino acid sequence of 1-54, 2-54, 3-54, 4-54, 5-54, 6-54, 7-54, 8-54, 9-54, 10-54, 11-54, 12-54, 13-54, 14-54, 15-54, 16-54, 17-54, 18-54, 19-54, 20-54, 21-54, 22-54, 23-54, 24-54, 25-54, 26-54, 27-54, 28-54, 29-54, 30-54, 31-54, 32-54, 33-54, 34-54, 35-54, 36-54, 37-54, 38-54, 39-54, 40-54, 41-54, 42-54, 43-54, 44-54, 45-54, 46-54, 47-54, 48-54 or 49-54 in the amino acid sequence represented by SEQ ID NO: 1 is excluded), or a salt thereof.

(2) The metastin derivative (II) according to (1), wherein V is a group represented by formula:

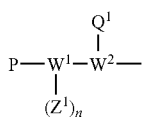

(wherein each symbol has the same significance as defined in (1)), or a salt thereof.
(3) The metastin derivative (II) according to (1), wherein V is a group represented by formula:

(wherein each symbol has the same significance as defined in (1)), or a salt thereof.
The present invention further provides the following features, and so on.
(4) A prodrug of the metastin derivative (II) according to (1) or a salt thereof.
(5) A pharmaceutical comprising the metastin derivative (II) according to (1) or a salt thereof, or a prodrug thereof.
(6) The pharmaceutical according to (5), which is an agent for suppressing cancer metastasis or an agent for suppressing cancer growth.
(7) The pharmaceutical according to (5), which is an agent for preventing or treating cancer.
(8) The pharmaceutical according to (5), which is an agent for controlling pancreatic function.
(9) The pharmaceutical according to (5), which is an agent for preventing or treating acute or chronic pancreatitis or pancreatic cancer.
(10) The pharmaceutical according to (5), which is an agent for controlling placental function.
(11) The pharmaceutical according to (5), which is an agent for preventing or treating choriocarcinoma, hydatid mole, invasive mole, miscarriage, fetal hypoplasia, abnormal glucose metabolism, abnormal lipid metabolism or induction of delivery.
(12) The pharmaceutical according to (5), which is an agent for improving gonadal function.
(13) The pharmaceutical according to (5), which is an agent for preventing or treating hormone-dependent cancer, infertility, endometriosis, early puberty or myoma of the uterus.
(14) The pharmaceutical according to (5), which is an agent for inducing or stimulating ovulation.
(15) The pharmaceutical according to (5), which is a gonadotropic hormone secretagogue agent or a sex hormone secretagogue agent.
(16) The pharmaceutical according to (5), which is an agent for preventing or treating Alzheimer's disease or moderate cognitive impairment.
(17) A method for suppressing cancer metastasis or cancer growth, which comprises administering to a mammal an effective dose of the metastin derivative (II) according to (1) or a salt thereof, or a prodrug thereof.
(18) A method for preventing or treating cancer, which comprises administering to a mammal an effective dose of the metastin derivative (II) according to (1) or a salt thereof, or a prodrug thereof.
(19) A method for controlling pancreatic function, which comprises administering to a mammal an effective dose of the metastin derivative (II) according to (1) or a salt thereof, or a prodrug thereof.
(20) A method for preventing or treating acute or chronic pancreatitis or pancreatic cancer, which comprises administering to a mammal an effective dose of the metastin derivative (II) according to (1) or a salt thereof, or a prodrug thereof.
(21) A method for controlling placental function, which comprises administering to a mammal an effective dose of the metastin derivative (II) according to (1) or a salt thereof, or a prodrug thereof.
(22) A method for preventing or treating choriocarcinoma, hydatid mole, invasive mole, miscarriage, fetal hypoplasia, abnormal glucose metabolism, abnormal lipid metabolism or induction of delivery, which comprises administering to a mammal an effective dose of the metastin derivative (II) according to (1) or a salt thereof, or a prodrug thereof.
(23) A method for improving gonadal function, which comprises administering to a mammal an effective dose of the metastin derivative (II) according to (1) or a salt thereof, or a prodrug thereof.
(24) A method for preventing or treating hormone-dependent cancer, infertility, endometriosis, early puberty or myoma of the uterus, which comprises administering to a mammal an effective dose of the metastin derivative (II) according to (1) or a salt thereof, or a prodrug thereof.
(25) A method for inducing or stimulating ovulation, which comprises administering to a mammal an effective dose of the metastin derivative (II) according to (1) or a salt thereof, or a prodrug thereof.
(26) A method for promoting gonadotropic hormone secretion or promoting sex hormone secretion, which comprises administering to a mammal an effective dose of the metastin derivative (II) according to (1) or a salt thereof, or a prodrug thereof.
(27) A method for preventing or treating Alzheimer's disease or moderate cognitive impairment, which comprises administering to a mammal an effective dose of the metastin derivative (II) according to (1) or a salt thereof, or a prodrug thereof.
(28) Use of the metastin derivative (II) according to (1) or a salt thereof, or a prodrug thereof to manufacture an agent for suppressing cancer metastasis or an agent for suppressing cancer growth.
(29) Use of the metastin derivative (II) according to (1) or a salt thereof, or a prodrug thereof to manufacture an agent for preventing or treating cancer.
(30) Use of the metastin derivative (II) according to (1) or a salt thereof, or a prodrug thereof to manufacture an agent for controlling pancreatic function.
(31) Use of the metastin derivative (II) according to (1) or a salt thereof, or a prodrug thereof to manufacture an agent for preventing or treating acute or chronic pancreatitis or pancreatic cancer.
(32) Use of the metastin derivative (II) according to (1) or a salt thereof, or a prodrug thereof to manufacture an agent for controlling placental function.
(33) Use of the metastin derivative (II) according to (1) or a salt thereof, or a prodrug thereof to manufacture an agent for preventing or treating choriocarcinoma, hydatid mole, invasive mole, miscarriage, fetal hypoplasia, abnormal glucose metabolism, abnormal lipid metabolism or induction of delivery.
(34) Use of the metastin derivative (II) according to (1) or a salt thereof, or a prodrug thereof to manufacture an agent for improving gonadal function.
(35) Use of the metastin derivative (II) according to (1) or a salt thereof, or a prodrug thereof to manufacture an agent for preventing or treating hormone-dependent cancer, infertility, endometriosis, early puberty or myoma of the uterus.

(36) Use of the metastin derivative (II) according to (1) or a salt thereof, or a prodrug thereof to manufacture an agent for inducing or stimulating ovulation.

(37) Use of the metastin derivative (II) according to (1) or a salt thereof, or a prodrug thereof to manufacture a gonadotropic hormone secretagogue agent or a sex hormone secretagogue agent.

(38) Use of the metastin derivative (II) according to (1) or a salt thereof, or a prodrug thereof to manufacture an agent for preventing or treating Alzheimer's disease or moderate cognitive impairment.

(39) A pancreatic glucagon secretagogue agent comprising the metastin derivative (II) according to (1) or a salt thereof, or a prodrug thereof.

(40) An agent for promoting urine formation comprising the metastin derivative (II) according to (1) or a salt thereof, or a prodrug thereof.

(41) An agent for preventing or treating obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders or lipotoxicity, comprising the metastin derivative (II) according to (1) or a salt thereof, or a prodrug thereof.

(42) A method for promoting pancreatic glucagon secretion, which comprises administering to a mammal an effective dose of the metastin derivative (II) according to (1) or a salt thereof, or a prodrug thereof.

(43) A method for promoting urine formation, which comprises administering to a mammal an effective dose of the metastin derivative (II) according to (1) or a salt thereof, or a prodrug thereof.

(44) A method for preventing or treating obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders or lipotoxicity, which comprises administering to a mammal an effective dose of the metastin derivative (II) according to (1) or a salt thereof, or a prodrug thereof.

(45) Use of the metastin derivative (II) according to (1) or a salt thereof, or a prodrug thereof to manufacture a pancreatic glucagon secretagogue agent.

(46) Use of the metastin derivative (II) according to (1) or a salt thereof, or a prodrug thereof to manufacture an agent for promoting urine formation.

(47) Use of the metastin derivative (II) according to (1) or a salt thereof, or a prodrug thereof to manufacture an agent for preventing or treating obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders or lipotoxicity.

(48) An agent for suppressing gonadotropic hormone secretion or an agent for suppressing sex hormone secretion comprising the metastin derivative (III) represented by formula:

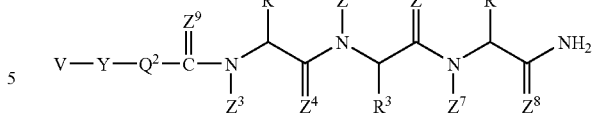

[wherein:
V' represents a group represented by formula:

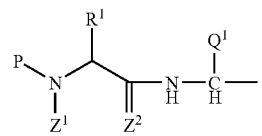

a group represented by formula:

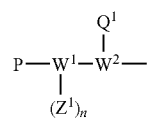

or a group represented by formula:

n represents 0 or 1;
$W^1$ represents N, CH or O (provided that $W^1$ is N or CH, n represents 1, and when $W^1$ is O, n represents 0);
$W^2$ represents N or CH;
$Z^1$, $Z^3$, $Z^5$ and $Z^7$ each represents hydrogen atom or a $C_{1-3}$ alkyl group;
$Z^2$, $Z^4$, $Z^6$ and $Z^8$ each represents hydrogen atom, O or S;
$R^1$ represents (1) hydrogen atom, (2) a $C_{1-8}$ alkyl group optionally substituted with a substituent selected from the group consisting of an optionally substituted carbamoyl group, an optionally substituted hydroxyl group and an optionally substituted aromatic cyclic group, (3) a cyclic or linear $C_{1-10}$ alkyl group or (4) a $C_{1-10}$ alkyl group consisting of a cyclic alkyl group and a linear alkyl group, or (5) an optionally substituted aromatic cyclic group;
$R^1$ represents (1) hydrogen atom or (2) a cyclic or linear $C_{1-10}$ alkyl group, (3) a $C_{1-10}$ alkyl group consisting of a cyclic alkyl group and a linear alkyl group, or (4) a $C_{1-8}$ alkyl group optionally substituted with a substituent selected from the group consisting of an optionally substituted carbamoyl group, an optionally substituted hydroxyl group and an optionally substituted aromatic cyclic group;
$R^3$ represents (1) a $C_{1-8}$ alkyl group having an optionally substituted basic group and optionally having an additional substituent, (2) an aralkyl group having an optionally substituted basic group and optionally having an additional substituent, (3) a $C_{1-4}$ alkyl group having a non-aromatic cyclic hydrocarbon group of carbon atoms not greater than 7 having an optionally substituted basic group, and optionally having an additional substituent, or (4) a $C_{1-4}$ alkyl group having a non-aromatic heterocyclic group of carbon atoms not greater than 7 having an optionally substituted basic group, and optionally having an additional substituent;

$R^4$ represents a $C_{1-4}$ alkyl group, which may optionally be substituted with a substituent selected from the group consisting of (1) an optionally substituted $C_{6-12}$ aromatic hydrocarbon group, (2) an optionally substituted 5- to 14-membered aromatic heterocyclic group consisting of 1 to 7 carbon atoms and hetero atoms selected from the group consisting of nitrogen, oxygen and sulfur atoms, (3) an optionally substituted $C_{8-14}$ aromatic fused cyclic group, (4) an optionally substituted 5- to 14-membered aromatic fused heterocyclic group consisting of 3 to 11 carbon atoms and hetero atoms selected from the group consisting of nitrogen, oxygen and sulfur atoms, (5) an optionally substituted non-aromatic cyclic hydrocarbon group having carbon atoms not greater than 7, and (6) an optionally substituted non-aromatic heterocyclic group having carbon atoms not greater than 7;

$Q^1$ represents a $C_{1-4}$ alkyl group, which may optionally be substituted with a substituent selected from the group consisting of (1) an optionally substituted $C_{6-12}$ aromatic hydrocarbon group, (2) an optionally substituted 5- to 14-membered aromatic heterocyclic group consisting of 1 to 7 carbon atoms and hetero atoms selected from the group consisting of nitrogen, oxygen and sulfur atoms, (3) an optionally substituted $C_{8-14}$ aromatic fused cyclic group, (4) an optionally substituted 5- to 14-membered aromatic fused heterocyclic group consisting of 3 to 11 carbon atoms and hetero atoms selected from the group consisting of nitrogen, oxygen and sulfur atoms, (5) an optionally substituted non-aromatic cyclic hydrocarbon group having carbon atoms not greater than 7, and (6) an optionally substituted non-aromatic heterocyclic group having carbon atoms not greater than 7;

$Q^2$ represents (1) $CH_2$, which may optionally be substituted with an optionally substituted $C_{1-4}$ alkyl group with a substituent selected from the group consisting of carbamoyl group and hydroxyl group, (2) NH, which may optionally be substituted with an optionally substituted $C_{1-4}$ alkyl group with a substituent selected from the group consisting of carbamoyl group and hydroxyl group, or (3) O; Y represents a group represented by formula: —CONH—, —CSNH—, —CH$_2$NH—, —NHCO—, —CH$_2$O—, —CH$_2$S—, —COO—, —CSO—, —CH$_2$CH$_2$—, or —CH=CH—, which may optionally be substituted with a $C_{1-6}$ alkyl group; and, $Z^9$ represents hydrogen atom, O or S; and, P and P', which may be the same or different, each may form a ring by combining P and P' or P and $Q^1$ together and represents:

(1) hydrogen atom;
(2) an optional amino acid residue continuously or discontinuously bound from the C terminus of the 1-48 amino acid sequence in the amino acid sequence represented by SEQ ID NO: 1;
(3) a group represented by formula:

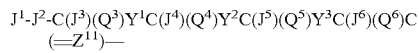

(wherein:
$J^1$ represents (a) hydrogen atom or (b) (i) a $C_{1-15}$ acyl group, (ii) a $C_{1-15}$ alkyl group, (iii) a $C_{6-14}$ aryl group, (iv) carbamoyl group, (v) carboxyl group, (vi) sulfino group, (vii) amidino group, (viii) glyoxyloyl group or (ix) amino group, which groups may optionally be substituted with a substituent containing an optionally substituted cyclic group;

$J^2$ represents (1) NH optionally substituted with a $C_{1-6}$ alkyl group, (2) $CH_2$ optionally substituted with a $C_{1-6}$ alkyl group, (3) O or (4) S;

$J^3$ through $J^6$ each represents hydrogen atom or a $C_{1-3}$ alkyl group;

$Q^3$ through $Q^6$ each represents a $C_{1-4}$ alkyl group, which may optionally have a substituent selected from the group consisting of:

(1) an optionally substituted $C_{6-12}$ aromatic hydrocarbon group,
(2) an optionally substituted 5- to 14-membered aromatic heterocyclic group consisting of 1 to 7 carbon atoms and hetero atoms selected from the group consisting of nitrogen, oxygen and sulfur atoms,
(3) an optionally substituted $C_{8-14}$ aromatic fused cyclic group,
(4) an optionally substituted 5- to 14-membered aromatic fused heterocyclic group consisting of 3 to 11 carbon atoms and hetero atoms selected from the group consisting of nitrogen, oxygen and sulfur atoms,
(5) an optionally substituted non-aromatic cyclic hydrocarbon group having carbon atoms not greater than 7,
(6) an optionally substituted non-aromatic heterocyclic group having carbon atoms not greater than 7,
(7) an optionally substituted amino group,
(8) an optionally substituted guanidino group,
(9) an optionally substituted hydroxyl group,
(10) an optionally substituted carboxyl group,
(11) an optionally substituted carbamoyl group, and
(12) an optionally substituted sulfhydryl group, or hydrogen atom;

$J^3$ and $Q^3$, $J^4$ and $Q^4$, $J^5$ and $Q^5$ or $J^6$ and $Q^6$ may be combined together, or, $Z^1$ and $R^1$, $J^2$ and $Q^3$, $Y^1$ and $Q^4$, $Y^2$ and $Q^5$, or $Y^3$ and $Q^6$ may be combined together, to form a ring;

$Y^1$ through $Y^3$ each represents a group represented by formula:
—CON($J^{13}$)—, —CSN($J^{13}$)—, —C($J^{14}$)N($J^{13}$)— or —N($J^{13}$)CO— (wherein $J^{13}$ and $J^{14}$ each represents hydrogen atom or a $C_{1-3}$ alkyl group); and, $Z^{10}$ represents hydrogen atom, O or S);
(4) a group represented by formula:

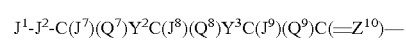

(wherein:
$J^1$ and $J^2$, each has the same significance as described above;
$J^7$ through $J^9$ have the same significance as for $J^3$;
$Q^7$ through $Q^9$ have the same significance as for $Q^3$;
$Y^2$ and $Y^3$ each has the same significance as described above;
$Z^{10}$ has the same significance as described above;
$J^7$ and $Q^7$, $J^8$ and $Q^8$ or $J^9$ and $Q^9$ may be combined together, or, $J^2$ and $Q^7$, $Y^2$ and $Q^8$ or $Y^3$ and $Q^9$ may be combined together, to form a ring);
(5) a group represented by formula:

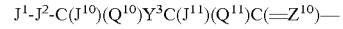

(wherein:
$J^1$ and $J^2$ have the same significance as described above represents;
$J^{10}$ and $J^{11}$ have the same significance as for $J^3$;
$Q^{10}$ and $Q^{11}$ have the same significance as for $Q^3$;
$Y^3$ has the same significance as described above;
$Z^{10}$ has the same significance as described above; and, $J^{10}$ and $Q^{10}$ or $J^{11}$ and $Q^{11}$ may be combined together, or $J^2$ and $Q^{10}$ or $Y^3$ and $Q^{11}$ may be combined together, to form a ring);

(6) a group represented by formula:

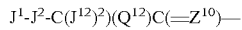

$J^1$-$J^2$-C($J^{12})^2$)($Q^{12}$)C(=$Z^{10}$)—

(wherein;
$J^1$ and $J^2$ have the same significance as described above;
$J^{12}$ has the same significance as for $J^3$;
$Q^{12}$ has the same significance as for $Q^3$;
$Z^{10}$ has the same significance as described above; and
$J^{12}$ and $Q^{12}$ may be combined together, or $J^2$ and $Q^{12}$ may be combined together, to form a ring); or, (7) a group represented by formula:
$J^1$- (wherein $J^1$ has the same significance as described above)]
or a salt thereof, or a prodrug thereof.

(49) The agent according to (48), wherein the metastin derivative (III) is the metastin derivative (II) according to (1).

(50) The agent according to (48), wherein V' is a group represented by formula:

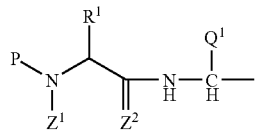

(wherein each symbol has the same significance as described in (48)).

(51) The agent according to (48), wherein V' is a group represented by formula:

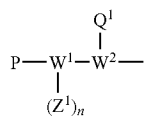

(wherein each symbol has the same significance as described in (48)).

(52) The agent according to (48), wherein V' is a group represented by formula:

(wherein each symbol has the same significance as described in (48)).

(53) The agent according to (48), wherein the metastin derivative (III) is:

(1) D-Tyr-Asn-Trp-Asn-Ser-Phe-Gly-Leu-Arg(Me)-Phe-NH₂ (Compound No. 141), (2) D-Tyr-Asn-Trp-Asn-Ser-Phe-Gly-Leu-Arg(Me)-Trp-NH₂ (Compound No. 174), (3) 3-(3-Indolyl)propionyl-Asn-Ser-Phe-AzaGly-Leu-Arg(Me)-Phe-NH₂ (Compound No. 260), (4) 3-Phenylpropionyl-Asn-Ser-Phe-AzaGly-Leu-Arg(Me)-Phe-NH₂ (Compound No. 269), (5) 2-(indol-3-yl)ethylcarbamoyl-Asn-Ser-Phe-AzaGly-Leu-Arg(Me)-Phe-NH₂ (Compound No. 279), (6) D-Tyr-Asn-Pya(4)-Asn-Ser-Phe-AzaGly-Leu-Arg(Me)-Phe-NH₂ (Compound No. 286), (7) D-Tyr-Asn-Trp-Asn-Ser-PheΨ(CSNH)Gly-Leu-Arg(Me)-Phe-NH₂ (Compound No. 296), (8) TyrΨ(CH₂NH)Asn-D-Trp-Asn-Ser-Phe-AzaGly-Leu-Arg(Me)-Phe-NH₂ (Compound No. 300), (9) D-Tyr-D-Asn-Pya(4)-Asn-Ser-Phe-AzaGly-Leu-Arg(Me)-Phe-NH₂ (Compound No. 303),

(10) D-Tyr-D-Pya(4)-Asn-Ser-Phe-AzaGly-Leu-Arg(Me)-Phe-NH₂ (Compound No. 305),

(11) D-Tyr-Asn-Trp-Asn-Ser-Phe-AzaGly-Leu-Arg(Me)-Phe(4F)-NH₂ (Compound No. 318),

(12) D-Tyr-Asn-Trp-Asn-Ser-PheΨ(NHCO)Gly-Leu-Arg(Me)-Phe-NH₂ (Compound No. 319),

(13) 3-(3-Pyridyl)propionyl-Asn-Ser-Phe-AzaGly-Leu-Arg(Me)-Phe-NH₂ (Compound No. 322),

(14) 4-Imidazoleacetyl-Asn-Ser-Phe-AzaGly-Leu-Arg(Me)-Phe-NH₂ (Compound No. 323),

(15) GuAmb-Phe-AzaGly-Leu-Arg(Me)-Phe-NH₂ (Compound No. 332),

(16) GuAmb-Phe-Gly-Leu-Arg(Me)-Phe-NH₂ (Compound No. 333),

(17) GuAmb-Phe-AzaGly-Leu-Arg(Me)-Trp-NH₂ (Compound No. 334),

(18) 3-(3-Indolyl)propionyl-Phe-AzaGly-Leu-Arg(Me)-Phe-NH₂ (Compound No. 339),

(19) Benzoyl-Phe-AzaGly-Leu-Arg(Me)-Phe-NH₂ (Compound No. 341),

(20) Indole-3-acetyl-Phe-AzaGly-Leu-Arg(Me)-Phe-NH₂ (Compound No. 345),

(21) Ac-Phe-AzaGly-Leu-Arg(Me)-Phe-NH₂ (Compound No. 346),

(22) Benzoyl-Phe-AzaGly-Leu-Arg(Me)-Trp-NH₂ (Compound No. 353),

(23) 3-(3-Indolyl)propionyl-Phe-AzaGly-Leu-Arg(Me)-Trp-NH₂ (Compound No. 354),

(24) Ac-Phe-AzaGly-Leu-Arg(Me)-Trp-NH₂ (Compound No. 358),

(25) 2-(Indol-3-yl)ethylcarbamoyl-Phe-AzaGly-Leu-Arg(Me)-Phe-NH₂ (Compound No. 364),

(26) 2-(Indol-3-yl)ethylcarbamoyl-Phe-AzaGly-Leu-Arg(Me)-Trp-NH₂ (Compound No. 369),

(27) (2S)-2-acethoxy-3-phenylpropionyl-Phe-AzaGly-Leu-Arg(Me)-Trp-NH₂ (Compound No. 373),

(28) (2S)-2-(3-Indolylprpionyloxy)-3-phenylpropionyl-AzaGly-Leu-Arg(Me)-Trp-NH₂ (Compound No. 379),

(29) (2S)-2-Benzoyloxy-3-phenylpropionyl-AzaGly-Leu-Arg(Me)-Trp-NH₂ (Compound No. 380),

(30) D-Tyr-D-Pya(4)-Asn-Ser-Phe-AzaGly-Leu-Arg(Me)-Trp-NH₂ (Compound No. 385),

-continued

(31) 3-(3-Pyridyl)propionyl-Asn-Ser-Phe-AzaGly-Leu-Arg(Me)-Trp-NH$_2$ (Compound No. 386),

(32) Dibenzylcarbamoyl-AzaGly-Leu-Arg(Me)-Trp-NH$_2$ (Compound No. 393),

(33) Benzylphenethylcarbamoyl-AzaGly-Leu-Arg(Me)-Trp-NH$_2$ (Compound No. 417),

(34) Benzoyl-PheΨ(NHCO)Gly-Leu-Arg(Me)-Trp-NH$_2$ (Compound No. 423),

(35) Benzoyl-AzaPhe-AzaGly-Leu-Arg(Me)-Trp-NH$_2$ (Compound No. 431),

(36) 3-Pyridinecarbonyl-Phe-AzaGly-Leu-Arg(Me)-Trp-NH$_2$ (Compound No. 432),

(37) 2-Pyridinecarbonyl-Phe-AzaGly-Leu-Arg(Me)-Trp-NH$_2$ (Compound No. 435),

(38) 4-Pyridinecarbonyl-Phe-AzaGly-Leu-Arg(Me)-Trp-NH$_2$ (Compound No. 436),

(39) Propionyl-Phe-AzaGly-Leu-Arg(Me)-Trp-NH$_2$ (Compound No. 437),

(40) Isobutyryl-Phe-AzaGly-Leu-Arg(Me)-Trp-NH$_2$ (Compound No. 438),

(41) Cyclohexanecarbonyl-Phe-AzaGly-Leu-Arg(Me)-Trp-NH$_2$ (Compound No. 439),

(42) Phenylacetyl-Phe-AzaGly-Leu-Arg(Me)-Trp-NH$_2$ (Compound No. 440),

(43) Benzoyl-Pya(2)-AzaGly-Leu-Arg(Me)-Trp-NH$_2$ (Compound No. 441),

(44) 6-Methylnicotinoyl-Phe-AzaGly-Leu-Arg(Me)-Trp-NH$_2$ (Compound No. 445),

(45) Pyrazinecarbonyl-Phe-AzaGly-Leu-Arg(Me)-Trp-NH$_2$ (Compound No. 446),

(46) Cyclopropanecarbonyl-Phe-AzaGly-Leu-Arg(Me)-Trp-NH$_2$ (Compound No. 447),

(47) Trifluoroacetyl-Phe-AzaGly-Leu-Arg(Me)-Trp-NH$_2$ (Compound No. 448),

(48) Benzoyl-Cha-AzaGly-Leu-Arg(Me)-Trp-NH$_2$ (Compound No. 449),

(49) Cyclopropanecarbonyl-Cha-AzaGly-Leu-Arg(Me)-Trp-NH$_2$ (Compound No. 451),

(50) (R)-3-hydroxy-2-methylpropionyl-Phe-AzaGly-Leu-Arg(Me)-Trp-NH$_2$ (Compound No. 452),

(51) 2-Hydroxyisobutyryl-Phe-AzaGly-Leu-Arg(Me)-Trp-NH$_2$ (Compound No. 453),

(52) 3-Furancarbonyl-Phe-AzaGly-Leu-Arg(Me)-Trp-NH$_2$ (Compound No. 454),

(53) Pyrrole-2-carbonyl-Phe-AzaGly-Leu-Arg(Me)-Trp-NH$_2$ (Compound No. 455),

(54) 4-Imidazolecarbonyl-Phe-AzaGly-Leu-Arg(Me)-Trp-NH$_2$ (Compound No. 459),

(55) 6-Hydroxynicotinoyl-Phe-AzaGly-Leu-Arg(Me)-Trp-NH$_2$ (Compound No. 462),

(56) 6-Chloronicotinoyl-Phe-AzaGly-Leu-Arg(Me)-Trp-NH$_2$ (Compound No. 463),

(57) 6-(Trifluoromethyl)nicotinoyl-Phe-AzaGly-Leu-Arg(Me)-Trp-NH$_2$ (Compound No. 464),

(58) Dimethylcarbamoyl-Phe-AzaGly-Leu-Arg(Me)-Trp-NH$_2$ (Compound No. 467),

(59) 1-Azetidinecarbonyl-Phe-AzaGly-Leu-Arg(Me)-Trp-NH$_2$ (Compound No. 468),

(60) 4-Pyridinecarbonyl-Phe-AzaGly-Leu-Arg(Me)-Phe-NH$_2$ (Compound No. 471),

(61) 4-Aminobenzoyl-Phe-AzaGly-Leu-Arg(Me)-Trp-NH$_2$ (Compound No. 472),

(62) 4-Aminomethylbenzoyl-Phe-AzaGly-Leu-Arg(Me)-Trp-NH$_2$ (Compound No. 473),

(63) Pyrrole-3-carbonyl-Phe-AzaGly-Leu-Arg(Me)-Trp-NH$_2$ (Compound No. 474),

(64) Pyrimidine-4-carbonyl-Phe-AzaGly-Leu-Arg(Me)-Trp-NH$_2$ (Compound No. 475),

(65) Pyrimidine-2-carbonyl-Phe-AzaGly-Leu-Arg(Me)-Trp-NH$_2$ (Compound No. 479),

(66) Pyridazine-4-carbonyl-Phe-AzaGly-Leu-Arg(Me)-Trp-NH$_2$ (Compound No. 480),

(67) D-Tyr-D-Pya(4)-Asn-Ser-Phe-AzaGly-Leu-Har-Trp-NH$_2$ (Compound No. 481),

(68) D-Tyr-D-Pya(4)-Asn-Ser-Phe-AzaGly-Leu-Lys-Phe-NH$_2$ (Compound No. 487),

(69) D-Tyr-D-Pya(4)-Asn-Ser-Phe-AzaGly-Leu-Har-Phe-NH$_2$ (Compound No. 488),

(70) D-Tyr-Pya(4)-Asn-Ser-Phe-AzaGly-Leu-Arg(Me)-Phe-NH$_2$ (Compound No. 490),

(71) D-Tyr-D-Pya(4)-Asn-Trp-Phe-AzaGly-Leu-Arg(Me)-Trp-NH$_2$ (Compound No. 491),

(72) D-Tyr-D-Pya(4)-Ala-Ser-Phe-AzaGly-Leu-Arg(Me)-Trp-NH$_2$ (Compound No. 492),

(73) D-Tyr-D-Pya(4)-Thr-Ser-Phe-AzaGly-Leu-Arg(Me)-Trp-NH$_2$ (Compound No. 493),

(74) D-Tyr-D-Pya(4)-Asn-Ser-Cha-Gly-Leu-Arg(Me)-Trp-NH$_2$ (Compound No. 496),

(75) D-Tyr-D-Pya(4)-Asn-Ser-Cha-Ala-Leu-Arg(Me)-Trp-NH$_2$ (Compound No. 497),

(76) D-Tyr-D-Pya(4)-Asn-Ile-Phe-AzaGly-Leu-Arg(Me)-Trp-NH$_2$ (Compound No. 498),

(77) 3-Phenylpropionyl-Asn-Ser-Phe-AzaGly-Leu-Arg(Me)-Trp-NH$_2$ (Compound No. 499),

(78) 3-Phenylpropionyl-Ala-Ser-Phe-AzaGly-Leu-Arg(Me)-Trp-NH$_2$ (Compound No. 500),

(79) D-Tyr-D-Pya(4)-Asn-Thr-Phe-AzaGly-Leu-Arg(Me)-Trp-NH$_2$ (Compound No. 501),

(80) D-Tyr-Pya(4)-Ala-Ser-Phe-AzaGly-Leu-Arg(Me)-Trp-NH$_2$ (Compound No. 502),

(81) D-Tyr-D-Trp-Ala-Ser-Phe-AzaGly-Leu-Arg(Me)-Trp-NH$_2$ (Compound No. 503),

(82) 6-Aminocaproyl-D-Tyr-D-Pya(4)-Asn-Ser-Phe-AzaGly-Leu-Arg(Me)-Phe-NH$_2$ (Compound No. 504),

(83) 3-Phenylpropionyl-Asn-Thr-Phe-AzaGly-Leu-Arg(Me)-Trp-NH$_2$ (Compound No. 505),

(84) 3-Phenylpropionyl-Asn-Ile-Phe-AzaGly-Leu-Arg(Me)-Trp-NH$_2$ (Compound No. 506),

(85) 3-Phenylpropionyl-Asn-Ser-Trp-AzaGly-Leu-Arg(Me)-Trp-NH$_2$ (Compound No. 507),

(86) 3-Phenylpropionyl-Asn-Ser-Phe(4F)-AzaGly-Leu-Arg(Me)-Trp-NH$_2$ (Compound No. 508),

(87) Benzoyl-Asn-Ser-Phe-AzaGly-Leu-Arg(Me)-Trp-NH$_2$ (Compound No. 509),

(88) Ac-Asn-Ser-Phe-AzaGly-Leu-Arg(Me)-Trp-NH$_2$ (Compound No. 510),

(89) D-Tyr-D-Trp-Ala-Thr-Phe-AzaGly-Leu-Arg(Me)-Trp-NH$_2$ (Compound No. 511),

(90) D-Tyr-D-Trp-Asn-Thr-Phe-AzaGly-Leu-Arg(Me)-Trp-NH$_2$ (Compound No. 512),

(91) D-Tyr-D-Trp-Abu-Ser-Phe-AzaGly-Leu-Arg(Me)-Trp-NH$_2$ (Compound No. 513),

(92) D-Tyr-D-Phe-Ala-Ser-Phe-AzaGly-Leu-Arg(Me)-Trp-NH$_2$ (Compound No. 514),

(93) D-Tyr-D-Pya(4)-Asn-Val-Phe-AzaGly-Leu-Arg(Me)-Trp-NH$_2$ (Compound No. 515),

(94) des(1)-Ac-[D-Tyr2,D-Pya(4)3,AzaGly7,Arg(Me)9]MS10 (Compound No. 516),

(95) des(1-3)-3-Phenylpropionyl-[Hyp5,AzaGly7,Arg(Me)9,Trp10]MS10 (Compound No. 517),

(96) des(1-3)-3-Phenylpropionyl-[Cha6,Arg(Me)9,Trp10]MS10 (Compound No. 518),

(97) des(1-3)-Phenylacetyl-[AzaGly7,Arg(Me)9,Trp10]MS10 (Compound No. 519),

(98) des(1)-[D-Tyr2,D-Pya(4)3,AzaGly7]MS10 (Compound No. 521),

(99) des(1-3)-Benzoyl-[Thr5,AzaGly7,Arg(Me)9,Trp10]MS10 (Compound No. 522), (100) des(1-3)-Benzoyl-[Thr5,Phe(4F)6,AzaGly7,Arg(Me)9,Trp10]MS10 (Compound No. 523), (101) des(1-3)-3-Phenylpropionyl-[Pro5,AzaGly7,Arg(Me)9,Trp10]MS10 (Compound No. 524), (102) des(1)-[D-Tyr2,D-Pya(4)3,Hyp5,AzaGly7,Arg(Me)9,Trp10]MS10 (Compound No. 527), (103) des(1)-[D-Tyr2,D-Pya(4)3,Pro5,AzaGly7,Arg(Me)9,Trp10]MS10 (Compound No. 528), (104) des(1)-[D-Tyr2,D-Pya(4)3,Tle5,AzaGly7,Arg(Me)9,Trp10]MS10 (Compound No. 529), (105) des(1)-[D-Tyr2,D-Pya(4)3,Phg5,AzaGly7,Arg(Me)9,Trp10]MS10 (Compound No. 530), (106) des(1-3)-3-Phenylpropionyl-[Pic(2)5,AzaGly7,Arg(Me)9,Trp10]MS10 (Compound No. 531), (107) des(1-3)-3-Phenylpropionyl-[Aze(2)5,AzaGly7,Arg(Me)9,Trp10]MS10 (Compound No. 532), (108) des(1-3)-3-Phenylpropionyl-[D-Pro5,AzaGly7,Arg(Me)9,Trp10]MS10 (Compound No. 533), (109) des(1-3)-Cyclopropanecarbonyl-[AzaGly7,Arg(Me)9,Trp10]MS10 (Compound No. 534), (110) des(1-3)-2-Naphthoyl-[AzaGly7,Arg(Me)9,Trp10]MS10 (Compound No. 535), (111) [Arg1,D-Tyr2,D-Pya(4)3,AzaGly7,Arg(Me)9,Trp10]MS10 (Compound No. 536), (112) Arg-[Arg1,D-Tyr2,D-Pya(4)3,AzaGly7,Arg(Me)9,Trp10]MS10 (Compound No. 537), (113) Arg-[Acp1,D-Tyr2,D-Pya(4)3,AzaGly7,Arg(Me)9,Trp10]MS10 (Compound No. 538), (114) des(1)-[D-Tyr2,D-Trp3,Val5,AzaGly7,Arg(Me)9,Trp10]MS10 (Compound No. 539), (115) des(1)-[D-Tyr2,D-Trp3,AzaGly7,Arg(Me)9,Trp10]MS10 (Compound No. 540), (116) D-Arg-[Acp1,D-Tyr2,D-Trp3,Thr5,AzaGly7,Arg(Me)9,Trp10]MS10 (Compound No. 541), (117) D-Arg-D-Arg-[Acp1,D-Tyr2,D-Trp3,Thr5,AzaGly7,Arg(Me)9,Trp10]MS10 (Compound No. 542), (118) des(1-3)-Benzoyl-[Phe(4F)6,AzaGly7,Arg(Me)9,Trp10]MS10 (Compound No. 545), (119) des(1-3)-3-Phenylpropionyl-[Ser(Ac)5,AzaGly7,Arg(Me)9,Trp10]MS10 (Compound No. 546), (120) des(1)-[D-Tyr2,D-Pya(4)3,Ser(Ac)5,AzaGly7,Arg(Me)9,Trp10]MS10 (Compound No. 547), (121) des(1)-[D-Tyr2,D-Pya(4)3,AzaGly7,Arg(Me)9,10Ψ,CSNH]MS10 (Compound No. 548), (122) des(1)-Ac-[D-Tyr2,D-Trp3,Thr5,AzaGly7,Arg(Me)9,Trp10]MS10 (Compound No. 550), (123) Ac-D-Arg-[Acp1,D-Tyr2,D-Trp3,Thr5,AzaGly7,Arg(Me)9,Trp10]MS10 (Compound No. 551), (124) D-Dap-[Acp1,D-Tyr2,D-Trp3,Thr5,AzaGly7,Arg(Me)9,Trp10]MS10 (Compound No. 552), (125) D-Nle-[Acp1,D-Tyr2,D-Trp3,Thr5,AzaGly7,Arg(Me)9,Trp10]MS10 (Compound No. 553), (126) D-Arg-[β-Ala1,D-Tyr2,D-Trp3,Thr5,AzaGly7,Arg(Me)9,Trp10]MS10 (Compound No. 554), (127) D-Arg-[γ-Abu1,D-Tyr2,D-Trp3,Thr5,AzaGly7,Arg(Me)9,Trp10]MS10 (Compound No. 555), (128) D-Arg-D-Arg-[γ-Abu1,D-Tyr2,D-Trp3,Thr5,AzaGly7,Arg(Me)9,Trp10]MS10 (Compound No. 556), (129) D-Arg-D-Arg-D-Arg-[γ-Abu1,D-Tyr2,D-Trp3,Thr5,AzaGly7,Arg(Me)9,Trp10]MS10 (Compound No. 557), (130) des(1)-Ac-[D-Tyr2,D-Trp3,AzaGly7,Arg(Me)9,Trp10]MS10 (Compound No. 558), (131) des(1-2)-3-(4-Hydroxyphenyl)propionyl-[D-Trp3,Thr5,AzaGly7,Arg(Me)9,Trp10]MS10 (Compound No. 559), (132) D-Arg-[Acp1,D-Tyr2,D-Trp3,Abu4,AzaGly7,Arg(Me)9,Trp10]MS10 (Compound No. 561), (133) des(1)-Ac-[D-Tyr2,D-Pya(4)3,Thr5,AzaGly7,Arg(Me)9,Trp10]MS10 (Compound No. 562), (134) des(1)-Ac-[D-Tyr2,D-Trp3,Aze(2)5,AzaGly7,Arg(Me)9,Trp10]MS10 (Compound No. 563), (135) des(1)-Ac-[D-Tyr2,D-Trp3,Val5,AzaGly7,Arg(Me)9,Trp10]MS10 (Compound No. 564), (136) des(1)-Benzoyl-[D-Tyr2,D-Trp3,Thr5,AzaGly7,Arg(Me)9,Trp10]MS10 (Compound No. 565), (137) des(1)-Cyclopropanecarbonyl-[D-Tyr2,D-Trp3,Thr5,AzaGly7,Arg(Me)9,Trp10]MS10 (Compound No. 566), (138) des(1)-Butyryl-[D-Tyr2,D-Trp3,Thr5,AzaGly7,Arg(Me)9,Trp10]MS10 (Compound No. 567), (139) Ac-[D-Arg1,D-Tyr2,D-Trp3,Thr5,AzaGly7,Arg(Me)9,Trp10]MS10 (Compound No. 568), (140) des(1)-Ac-[D-Tyr2,D-Trp3,Thr5,6Ψ7,CH2NH,Arg(Me)9,Trp10]MS10 (Compound No. 569), (141) des(1)-Me-[D-Tyr2,D-Trp3,Thr5,AzaGly7,Arg(Me)9,Trp10]MS10 (Compound No. 570), (142) des(1)-Ac-[D-Tyr2,D-Trp3,Thr5,AzaGly7,Arg(Me)9]MS10 (Compound No. 571), (143) des(1)-[D-Trp2,D-Pya(4)3,AzaGly7,Arg(Me)9,Trp10]MS10 (Compound No. 572), (144) des(1)-Ac-[D-Tyr2,D-Trp3,Abu4,AzaGly7,Arg(Me)9,Trp10]MS10 (Compound No. 573), (145) des(1)-Ac-[D-Tyr2,D-Trp3,Gln4,AzaGly7,Arg(Me)9,Trp10]MS10 (Compound No. 576), (146) des(1)-Ac-[D-Tyr2,D-Trp3,Ser4,AzaGly7,Arg(Me)9,Trp10]MS10 (Compound No. 577), (147) des(1)-Ac-[D-Tyr2,D-Trp3,Thr4,AzaGly7,Arg(Me)9,Trp10]MS10 (Compound No. 578), (148) des(1)-Ac-[D-Tyr2,D-Trp3,Alb4,AzaGly7,Arg(Me)9,Trp10]MS10 (Compound No. 579), (149) des(1)-Ac-[D-Tyr2,D-Trp3,Ser(Me)5,AzaGly7,Arg(Me)9,Trp10]MS10 (Compound No. 580), (150) des(1)-Ac-[D-Tyr2,D-Trp3,Dap(Ac)4,AzaGly7,Arg(Me)9,Trp10]MS10 (Compound No. 584), (151) des(1)-Ac-[D-Tyr2,D-Trp3,Dap(For)4,AzaGly7,Arg(Me)9,Trp10]MS10 (Compound No. 585), (152) des(1)-Ac-[D-Tyr2,Thr5,D-Phe6,AzaGly7,Arg(Me)9,Trp10]MS10 (Compound No. 586), (153) des(1)-Ac-[D-Tyr2,D-Trp3,Thr5,AzaGly7,Arg(Me)9,Nal(2)10]MS10 (Compound No. 589), (154) des(1)-Ac-[D-Tyr2,D-Trp3,Thr5,AzaGly7,Arg(Me)9,Thi10]MS10 (Compound No. 590), (155) des(1)-Ac-[D-Tyr2,D-Trp3,Thr5,AzaGly7,Arg(Me)9,Tyr10]MS10 (Compound No. 591), (156) des(1)-Ac-[D-Tyr2,D-Trp3,Thr5,AzaGly7,Arg(Me)9,Phe(4F)10]MS10 (Compound No. 592), (157) des(1)-Ac-[D-Tyr2,D-Trp3,Thr5,AzaGly7,Arg(Me)9,Hph10]MS10 (Compound No. 594), (158) des(1)-Ac-[D-Tyr2,D-Trp3,Thr5,AzaGly7,Arg(Me)9,Cha10]MS10 (Compound No. 595), (159) des(1)-Ac-[D-Tyr2,D-Trp3,Thr5,AzaGly7,Arg(Me)9,Leu10]MS10 (Compound No. 596), (160) des(1)-Ac-[D-Tyr2,D-Trp3,Thr5,D-Phe6,AzaGly7,Arg(Me)9,Trp10]MS10 (Compound No. 597), (161) des(1)-Ac-[D-Tyr2,D-Trp3,Thr5,Arg(Me)9,Trp10]MS10 (Compound No. 598), (162) des(1)-Ac-[D-Tyr2,D-Trp3,Thr5,AzaGly7,Orn9,Trp10]MS10 (Compound No. 599), (163) des(1)-Ac-[D-Tyr2,D-Trp3,Thr5,AzaGly7,Trp10]MS10 (Compound No. 600), (164) des(1)-Ac-[D-Tyr2,D-Trp3,Thr5,D-Phe6,Arg(Me)9,Trp10]MS10 (Compound No. 601), (165) des(1)-Ac-[D-NMeTyr2,D-Trp3,Thr5,AzaGly7,Arg(Me)9,Trp10]MS10 Compound No. 602), (166) des(1)-Ac-[D-Tyr2,D-Pya(4)3,Thr5,D-Phe6,AzaGly7,Arg(Me)9,Trp10]MS10 (Compound No. 603), (167) des(1)-Ac-[D-Tyr2,D-Trp3,Thr5,AzaGly7,Arg(Tos)9,Trp10]MS10 (Compound No. 604), (168) des(1)-Ac-[D-Tyr2,D-Trp3,Thr5,AzaGly7,Arg(NO2)9,Trp10]MS10 (Compound No. 605), (169) des(1)-Ac-[D-Tyr2,D-Trp3,Thr5,AzaGly7,Arg(Me2)asym9,Trp10]MS10 (Compound No. 607), (170) des(1)-Ac-[D-Tyr2,D-Trp3,Thr5,AzaGly7,Arg(Me2)sym9,Trp10]MS10 (Compound No. 608), (171) des(1)-Ac-[D-Tyr2,D-Trp3,Thr5,AzaGly7,Arg(Et)9,Trp10]MS10 (Compound No. 609), (172) des(1)-Ac-[D-Tyr2,D-Trp3,Thr5,AzaGly7,Lys(Me2)9,Trp10]MS10 (Compound No. 610), (173) des(1)-Ac-[Tyr2,D-Pya(4)3,Thr5,AzaGly7,Arg(Me)9,Trp10]MS10 (Compound No. 611), (174) des(1)-For-[D-Tyr2,D-Trp3,Thr5,AzaGly7,Arg(Me)9,Trp10]MS10 (Compound No. 612), (175) des(1)-Propionyl-[D-Tyr2,D-Trp3,Thr5,AzaGly7,Arg(Me)9,Trp10]MS10 (Compound No. 613), (176) des(1)-Amidino-[D-Tyr2,D-Trp3,Thr5,AzaGly7,Arg(Me)9,Trp10]MS10 (Compound No. 614), (177) des(1)-Ac-[Tyr2,D-Pya(4)3,Thr5,AzaGly7,Arg(Me)9,Trp10]MS10 (Compound No. 615), (178) des(1)-Ac-[D-Ala2,D-Trp3,Thr5,AzaGly7,Arg(Me)9,Trp10]MS10 (Compound No. 616), (179) des(1)-Ac-[D-Leu2,D-Trp3,Thr5,AzaGly7,Arg(Me)9,Trp10]MS10 (Compound No. 617), (180) des(1)-Ac-[D-Phe2,D-Trp3,Thr5,AzaGly7,Arg(Me)9,Trp10]MS10 (Compound No. 618), (181) des(1)-Ac-[D-Nal(1)2,D-Trp3,Thr5,AzaGly7,Arg(Me)9,Trp10]MS10 (Compound No. 619), (182) des(1)-Ac-[D-Nal(2)2,D-Trp3,Thr5,AzaGly7,Arg(Me)9,Trp10]MS10 (Compound No. 620), (183) des(1)-Ac-[D-Lys2,D-Trp3,Thr5,AzaGly7,Arg(Me)9,Trp10]MS10 (Compound No. 621)

(184) des(1)-Ac-[D-Glu2,D-Trp3,Thr5,AzaGly7,Arg(Me)9,Trp10]MS10 (Compound No. 622), (185) des(1)-Ac-[D-Tyr2,Thr5,AzaGly7,Arg(Me)9,Trp10]MS10 (Compound No. 623), (186) des(1)-Ac-[D-Tyr2,Pya(4)3,Thr5,AzaGly7,Arg(Me)9,Trp10]MS10 (Compound No. 624), (187) des(1)-Ac-[D-Tyr2,D-Ala3,Thr5,AzaGly7,Arg(Me)9,Trp10]MS10 (Compound No. 625), (188) des(1)-Ac-[D-Tyr2,D-Leu3,Thr5,AzaGly7,Arg(Me)9,Trp10]MS10 (Compound No. 626), (189) des(1)-Ac-[D-Tyr2,D-Phe3,Thr5,AzaGly7,Arg(Me)9,Trp10]MS10 (Compound No. 627), (190) des(1)-Ac-[D-Tyr2,D-Thr3,Thr5,AzaGly7,Arg(Me)9,Trp10]MS10 (Compound No. 628), (191) des(1)-Ac-[D-Tyr2,D-Lys3,Thr5,AzaGly7,Arg(Me)9,Trp10]MS10 (Compound No. 629), -continued (192) des(1)-Ac-[D-Tyr2,D-Glu3,Thr5,AzaGly7,
Arg(Me)9,Trp10]MS10 (Compound No. 630), (193) des(1)-Ac-[D-Tyr2,D-Trp3,Thr5,Ala6,
AzaGly7,Arg(Me)9,Trp10]MS10 (Compound No. 631), (194) des(1)-Ac-[D-Tyr2,D-Trp3,Thr5,Leu6,
AzaGly7,Arg(Me)9,Trp10]MS10 (Compound No. 632), (195) des(1)-Ac-[D-Tyr2,D-Trp3,Thr5,Lys6,
AzaGly7,Arg(Me)9,Trp10]MS10 (Compound No. 633), (196) des(1)-Ac-[D-Tyr2,D-Trp3,Thr5,Glu6,
AzaGly7,Arg(Me)9,Trp10]MS10 (Compound No. 634), (197) des(1)-Ac-[D-Tyr2,D-Trp3,Thr5,Pya(4)6,
AzaGly7,Arg(Me)9,Trp10]MS10 (Compound No. 635), (198) des(1)-Ac-[D-Tyr2,D-Trp3,Thr5,NMePhe6,
AzaGly7,Arg(Me)9,Trp10]MS10 (Compound No. 636), (199) des(1)-Ac-[D-Tyr2,D-Trp3,Thr5,Phe(4F)6,
AzaGly7,Arg(Me)9,Trp10]MS10 (Compound No. 637), (200) des(1)-Ac-[D-Tyr2,D-Pya(4)3,Thr5,Phe(4F)6,
AzaGly7,Arg(Me)9,Trp10]MS10 (Compound No. 638), (201) des(1)-Ac-[D-Tyr2,D-Trp3,Thr5,
AzaGly7,Lys9,Trp10]MS10 (Compound No. 639), (202) des(1)-Ac-[D-Tyr2,D-Trp3,Thr5,AzaGly7,
Ala8,Arg(Me)9,Trp10]MS10 (Compound No. 641), (203) des(1)-Ac[D-Tyr2,D-Trp3,Thr5,AzaGly7,
Val8,Arg(Me)9,Trp10]MS10 (Compound No. 642), (204) des(1)-Ac-[D-Tyr2,D-Trp3,Thr5,AzaGly7,
Phe8,Arg(Me)9,Trp10]MS10 (Compound No. 643), (205) des(1)-Ac-[D-Tyr2,D-Trp3,Thr5,AzaGly7,
Ser8,Arg(Me)9,Trp10]MS10 (Compound No. 644), (206) des(1)-Ac-[D-Tyr2,D-Trp3,Thr5,
AzaGly7,Har9,Trp10]MS10 (Compound No. 645), (207) des(1)-Ac-[D-Tyr2,D-Trp3,Thr5,AzaGly7,
Har(Me)9,Trp10]MS10 (Compound No. 646), (208) des(1)-Ac-[D-Tyr2,D-Trp3,Asp4,Thr5,AzaGly7,
Arg(Me)9,Trp10]MS10 (Compound No. 647), (209) [Gly1,D-Tyr2,D-Trp3,Thr5,AzaGly7,
Arg(Me)9,Trp10]MS10 (Compound No. 648), (210) Ac-[Gly1,D-Tyr2,D-Trp3,Thr5,AzaGly7,
Arg(Me)9,Trp10]MS10 (Compound No. 649), (211) [D-Tyr1,D-Tyr2,D-Trp3,Thr5,AzaGly7,
Arg(Me)9,Trp10]MS10 (Compound No. 650), (212) Ac-[D-Tyr1,D-Tyr2,D-Trp3,Thr5,AzaGly7,
Arg(Me)9,Trp10]MS10 (Compound No. 651), (213) pGlu-des(1)-[D-Tyr2,D-Trp3,Thr5,AzaGly7,
Arg(Me)9,Trp10]MS10 (Compound No. 652), (214) des(1)-Ac-[D-Tyr2,D-Trp3,D-Asn4,Thr5,AzaGly7,
Arg(Me)9,Trp10]MS10 (Compound No. 653), (215) des(1)-Ac-[D-Tyr2,D-Trp3,D-Thr5,AzaGly7,
Arg(Me)9,Trp10]MS10 (Compound No. 654), (216) des(1)-Ac-[D-Tyr2,D-Trp3,NMeAsn4,Thr5,
AzaGly7,Arg(Me)9,Trp10]MS10 (Compound No. 655), (217) des(1)-Ac-[D-Tyr2,D-Trp3,NMeSer5,
AzaGly7,Arg(Me)9,Trp10]MS10 (Compound No. 656), (218) des(1)-Ac-[D-Tyr2,Pro3,Thr5,AzaGly7,
Arg(Me)9,Trp10]MS10 (Compound No. 657), (219) des(1)-Ac-[D-Tyr2,D-Pya(2)3,Thr5,AzaGly7,
Arg(Me)9,Trp10]MS10 (Compound No. 658), (220) des(1)-Ac-[D-Tyr2,D-Trp3,allo-Thr5,AzaGly7,
Arg(Me)9,Trp10]MS10 (Compound No. 659), (221) des(1)-Ac-[D-Tyr2,D-Pya(3)3,Thr5,AzaGly7,
Arg(Me)9,Trp10]MS10 (Compound No. 660), (222) des(1)-Ac-[D-Tyr2,D-Pro3,Thr5,AzaGly7,
Arg(Me)9,Trp10]MS10 (Compound No. 661), (223) des(1)-Ac-[D-Tyr2,Tic3,Thr5,AzaGly7,
Arg(Me)9,Trp10]MS10 (Compound No. 662), (224) des(1)-Ac-[D-Trp2,D-Trp3,Thr5,AzaGly7,
Arg(Me)9,Trp10]MS10 (Compound No. 663), (225) des(1)-Ac-[Tyr2,Thr5,AzaGly7,Arg(Me)9,
Trp10]MS10 (Compound No. 664), (226) des(1-2)-[D-Trp3,Thr5,AzaGly7,Arg(Me)9,
Trp10]MS10 (Compound No. 665), (227) des(1-2)-Ac-[D-Trp3,Thr5,AzaGly7,Arg(Me)9,
Trp10]MS10 (Compound No. 666), (228) des(1-2)-Hexanoyl-[D-Trp3,Thr5,AzaGly7,Arg
(Me)9,
Trp10]MS10 (Compound No. 667), (229) des(1-2)-Cyclohexanecarbonyl-[D-Trp3,Thr5,
AzaGly7,Arg(Me)9,Trp10]MS10 (Compound No. 668), (230) des(1-2)-Benzoyl-[D-Trp3,Thr5,AzaGly7,
Arg(Me)9,Trp10]MS10 (Compound No. 669), (231) des(1-2)-3-Pyridinepropionyl-[D-Trp3,Thr5,
AzaGly7,Arg(Me)9,Trp10]MS10 (Compound No. 670), (232) des(1-2)-Adipoyl-[D-Trp3,Thr5,AzaGly7,
Arg(Me)9,Trp10]MS10 (Compound No. 671), (233) des(1)-Ac-[D-Tyr2,NMeTrp3,Thr5,AzaGly7,
Arg(Me)9,Trp10]MS10 (Compound No. 672), (234) des(1-2)-6-Aminocaproyl-[D-Trp3,Thr5,AzaGly7,
Arg(Me)9,Trp10]MS10 (Compound No. 674), (235) [D-Tyr2,D-Trp3,Thr5,AzaGly7,Arg(Me)9,
Trp10]MS10 (Compound No. 675)

(236) Ac-[D-Tyr2,D-Trp3,Thr5,AzaGly7,Arg(Me)9,
Trp10]MS10 (Compound No. 676)

(237) Ac-des(1)-[D-Tyr2,D-Trp3,Thr5,AzaGly7,
Nva8,Arg(Me)9,Trp10]MS10 (Compound No. 677)

(238) Ac-des(1)-[D-Tyr2,D-Trp3,Thr5,AzaGly7,
Ile8,Arg(Me)9,Trp10]MS10 (Compound No. 678)

(239) des(1-2)-Amidino-[D-Trp3,Thr5,AzaGly7,
Arg(Me)9,Trp10]MS10 (Compound No. 679)

(240) des(1-2)-Glycoloyl-[D-Trp3,Thr5,AzaGly7,
Arg(Me)9,Trp10]MS10 (Compound No. 680)

(241) des(1)-Glycoloyl-[D-Tyr2,D-Trp3,Thr5,AzaGly7,
Arg(Me)9,Trp10]MS10 (Compound No. 681)

(242) des(1)-Ac-[D-Tyr2,D-Trp3,Thr5,AzaGly7,
Gln8,Arg(Me)9,Trp10]MS10 (Compound No. 682)

(243) des(1)-Ac-[D-Tyr2,D-Pya(4)3,
Thr5,AzaGly7,Arg(Me)9]MS10 (Compound No. 685)

(244) des(1)-Ac-[D-Tyr2,D-Trp3,Gly4,
AzaGly7,Arg(Me)9,Trp10]MS10 (Compound No. 686)

-continued (245) des(1)-Ac-[D-Tyr2,D-Trp3,Thr5,AzaGly7, Pya(4)9,Trp10]MS10 (Compound No. 688)

(246) des(1)-Ac-[D-Tyr2,D-Trp3,Thr5,AzaGly7, Arg(Me)9,D-Trp10]MS10 (Compound No. 689)

(247) des(1)-Ac-[D-Tyr2,D-Trp3,Thr5,Tyr6, AzaGly7,Arg(Me)9,Trp10]MS10 (Compound No. 691)

(248) des(1)-Ac-[D-Tyr2,D-Trp3,Thr5,Trp6,AzaGly7, Arg(Me)9,Trp10]MS10 (Compound No. 692)

(249) des(1)-Ac-[D-Tyr2,D-Trp3,Thr5,Tyr(Me)6, AzaGly7,Arg(Me)9,Trp10]MS10 (Compound No. 693)

(250) des(1)-Ac-[D-Tyr2,D-Trp3,Thr5,Nal(2)6, AzaGly7,Arg(Me)9,Trp10]MS10 (Compound No. 694)

(251) des(1)-Ac-[D-Tyr2,D-Trp3,Thr5,Thi6, AzaGly7,Arg(Me)9,Trp10]MS10 (Compound No. 695)

(252) des(1)-Ac-[D-Tyr2,D-Trp3,Thr5,Cha6, AzaGly7,Arg(Me)9,Trp10]MS10 (Compound No. 696)

(253) des(1)-Ac-[D-Tyr2,D-Trp3,Thr5,AzaGly7, Abu8,Arg(Me)9,Trp10]MS10 (Compound No. 698)

(254) des(1)-Ac-[D-Tyr2,D-Trp3,Thr5,AzaGly7, γMeLeu8,Arg(Me)9,Trp10]MS10 (Compound No. 699)

(255) des(1)-Ac-[D-Tyr2,D-Trp3,Thr5, Aib8,,Arg(Me)9,Trp10]MS10 (Compound No. 700)

(256) des(1)-Ac-[D-Tyr2,D-Trp3,Dap4,AzaGly7, Arg(Me)9,Trp10]MS10 (Compound No. 701)

(257) des(1)-Ac-[D-Tyr2,D-Trp3,Asp(NHMe)4,Thr5, AzaGly7,Arg(Me)9,Trp10]MS10 (Compound No. 702)

(258) des(1)-Ac-[D-Tyr2,D-Trp3,Asp(NMe2)4,Thr5, AzaGly7,Arg(Me)9,Trp10]MS10 (Compound No. 703).

(54) The agent according to (48) to (53), which is a down-regulating agent for gonadotropic hormone or sex hormone.
(55) The agent according to (48) to (53), which is a down-regulating agent for human OT7T175 (metastin receptor) protein consisting of the amino acid sequence represented by SEQ ID NO: 9.
(56) The agent according to (48) to (55), which is an agent for preventing or treating hormone-dependent cancer.
(57) A method for suppressing gonadotropic hormone secretion or suppressing sex hormone secretion, which comprises administering to a mammal an effective dose of the metastin derivative (III) according to (48) or a salt thereof, or a prodrug thereof.
(58) A method for down regulating gonadotropic hormone or sex hormone, which comprises administering to a mammal an effective dose of the metastin derivative according to (48) or a salt thereof, or a prodrug thereof.
(59) A method for down regulating human OT7T175 (metastin receptor) protein consisting of the amino acid sequence represented by SEQ ID NO: 9, which comprises administering to a mammal an effective dose of the metastin derivative according to (48) or a salt thereof, or a prodrug thereof.
(60) A method for preventing or treating hormone-dependent cancer, which comprises administering to a mammal an effective dose of the metastin derivative according to (48) or a salt thereof, or a prodrug thereof.
(61) Use of the metastin derivative according to (48) or a salt thereof, or a prodrug thereof to manufacture an agent for suppressing gonadotropic hormone secretion or an agent for suppressing sex hormone secretion.
(62) Use of the metastin derivative according to (48) or a salt thereof, or a prodrug thereof to manufacture a down-regulating agent for gonadotropic hormone or sex hormone.
(63) Use of the metastin derivative according to (48) or a salt thereof, or a prodrug thereof to manufacture a down-regulating agent for human OT7T175 (metastin receptor) protein consisting of the amino acid sequence represented by SEQ ID NO: 9.
(64) Use of the metastin derivative according to (48) or a salt thereof, or a prodrug thereof to manufacture an agent for preventing or treating hormone-dependent cancer.
(65) A metastin derivative represented by formula:

XX0-XX2-XX3-XX4-XX5-XX6-AzaGly-XX8-XX9-XX10-NH$_2$ (wherein:
XX0 represents formyl, $C_{1-6}$ alkanoyl, cyclopropanecarbonyl, 6-(acetyl-D-arginylamino)caproyl, 6-((R)-2,3-diaminopropionylamino)caproyl, 6-(D-norleucylamino)caproyl, 4-(D-arginylamino)butyryl, 3-(4-Hydroxyphenyl)propionyl, glycyl, tyrosyl, acetylglycyl, acetyltyrosyl, D-tyrosyl, acetyl-D-tyrosyl, pyroglutamyl, 3-(pyridine-3-yl)propionyl, adipoyl or 6-aminocaproyl;
XX2 represents Tyr, D-Tyr, D-Ala, D-Leu, D-Phe, D-Lys, D-Trp or bond arm;
XX3 represents Trp, Pro, 4-pyridylalanine, Tic, D-Trp, D-Ala, D-Leu, D-Phe, D-Lys, D-Glu, D-2-pyridylalanine, D-3-pyridylalanine or D-4-pyridylalanine;
XX4 represents Asn, 2-amino-3-ureidopropion acid, $N^{G2}$-formyldiaminopropionic acid or N-acetyldiaminopropionic acid;
XX5 represents Ser, Thr or Val;
XX6 represents Phe, Tyr, Trp, Tyr(Me), Thi, Nal(2), Cha, 4-pyridylalanine or 4-fluorophenylalanine;
AzaGly represents azaglycine;
XX8 represents Leu, Nva or Val;
XX9 represents Arg, Orn, Arg(Me) or Arg(symMe2);
XX10 represents Phe, Trp, 2-naphthylalanine, 2-thienylalanine, tyrosine or 4-fluorophenylalanine), or a salt thereof.

(66) D-Tyr-D-Pya(4)-Asn-Ser-Phe-AzaGly-Leu-Arg(Me)-Phe-NH$_2$ (Compound No. 305), D-Tyr-D-Pya(4)-Asn-Ser-Phe-AzaGly-Leu-Arg(Me)-Trp-NH$_2$ (Compound No. 385), D-Tyr-D-Pya(4)-Asn-Thr-Phe-AzaGly-Leu-Arg(Me)-Trp-NH$_2$ (Compound No. 501), Benzoyl-Asn-Ser-Phe-AzaGly-Leu-Arg(Me)-Trp-NH$_2$ (Compound No. 509), D-Tyr-D-Trp-Asn-Thr-Phe-AzaGly-Leu-Arg(Me)-Trp-NH$_2$ (Compound No. 512), Ac-D-Tyr-D-Pya(4)-Asn-Ser-Phe-AzaGly-Leu-Arg(Me)-Phe-NH$_2$ (Compound No. 516), -continued D-Tyr-D-Trp-Asn-Ser-Phe-AzaGly-Leu-Arg(Me)-Trp-NH$_2$ (Compound No. 540), D-Arg-Acp-D-Tyr-D-Trp-Asn-Thr-Phe-AzaGly-Leu-Arg(Me)-Trp-NH$_2$ (Compound No. 541), Benzoyl-Asn-Ser-Phe(4F)-AzaGly-Leu-Arg(Me)-Trp-NH$_2$ (Compound No. 545), D-Tyr-D-Pya(4)-Asn-Ser-Phe-AzaGly-Leu-Arg(Me)-PheΨ(CSNH)NH$_2$ (Compound No. 548), Ac-D-Tyr-D-Trp-Asn-Thr-Phe-AzaGly-Leu-Arg(Me)-Trp-NH$_2$ (Compound No. 550), Ac-D-Arg-Acp-D-Tyr-D-Trp-Asn-Thr-Phe-AzaGly-Leu-Arg(Me)-Trp-NH$_2$ (Compound No. 551), D-Dap-Acp-D-Tyr-D-Trp-Asn-Thr-Phe-AzaGly-Leu-Arg(Me)-Trp-NH$_2$ (Compound No. 552), D-Nle-Acp-D-Tyr-D-Trp-Asn-Thr-Phe-AzaGly-Leu-Arg(Me)-Trp-NH$_2$ (Compound No. 553), D-Arg-γ-Abu-D-Tyr-D-Trp-Asn-Thr-Phe-AzaGly-Leu-Arg(Me)-Trp-NH$_2$ (Compound No. 555), Ac-D-Tyr-D-Trp-Asn-Ser-Phe-AzaGly-Leu-Arg(Me)-Trp-NH$_2$ (Compound No. 558), 3-(4-Hydroxyphenyl)propionyl-D-Trp-Asn-Thr-Phe-AzaGly-Leu-Arg(Me)-Trp-NH$_2$ (Compound No. 559), Ac-D-Tyr-D-Pya(4)-Asn-Thr-Phe-AzaGly-Leu-Arg(Me)-Trp-NH$_2$ (Compound No. 562), Ac-D-Tyr-D-Trp-Asn-Val-Phe-AzaGly-Leu-Arg(Me)-Trp-NH$_2$ (Compound No. 564), Cyclopropanecarbonyl-D-Tyr-D-Trp-Asn-Thr-Phe-AzaGly-Leu-Arg(Me)-Trp-NH$_2$ (Compound No. 566), Butyryl-D-Tyr-D-Trp-Asn-Thr-Phe-AzaGly-Leu-Arg(Me)-Trp-NH$_2$ (Compound No. 567), Ac-D-Tyr-D-Trp-Asn-Thr-Phe-AzaGly-Leu-Arg(Me)-Phe-NH$_2$ (Compound No. 571), Ac-D-Tyr-D-Trp-Alb-Ser-Phe-AzaGly-Leu-Arg(Me)-Trp-NH$_2$ (Compound No. 579), Ac-D-Tyr-D-Trp-Asn-Ser(Me)-Phe-AzaGly-Leu-Arg(Me)-Trp-NH$_2$ (Compound No. 580), Ac-D-Tyr-D-Trp-Dap(Ac)-Ser-Phe-AzaGly-Leu-Arg(Me)-Trp-NH$_2$ (Compound No. 584), Ac-D-Tyr-D-Trp-Dap(For)-Ser-Phe-AzaGly-Leu-Arg(Me)-Trp-NH$_2$ (Compound No. 585), Ac-D-Tyr-D-Trp-Asn-Thr-Phe-AzaGly-Leu-Arg(Me)-Nal(2)-NH$_2$ (Compound No. 589), Ac-D-Tyr-D-Trp-Asn-Thr-Phe-AzaGly-Leu-Arg(Me)-Thi-NH$_2$ (Compound No. 590), Ac-D-Tyr-D-Trp-Asn-Thr-Phe-AzaGly-Leu-Arg(Me)-Tyr-NH$_2$ (Compound No. 591), Ac-D-Tyr-D-Trp-Asn-Thr-Phe-AzaGly-Leu-Arg(Me)-Phe(4F)-NH$_2$ (Compound No. 592), Ac-D-Tyr-D-Trp-Asn-Thr-Phe-AzaGly-Leu-Orn-Trp-NH$_2$ (Compound No. 599), Ac-D-Tyr-D-Trp-Asn-Thr-Phe-AzaGly-Leu-Arg-Trp-NH$_2$ (Compound No. 600), Ac-D-NMeTyr-D-Trp-Asn-Thr-Phe-AzaGly-Leu-Arg(Me)-Trp-NH$_2$ (Compound No. 602), Ac-D-Tyr-D-Trp-Asn-Thr-Phe-AzaGly-Leu-Arg(symMe2)-Trp-NH$_2$ (Compound No. 608), For-D-Tyr-D-Trp-Asn-Thr-Phe-AzaGly-Leu-Arg(Me)-Trp-NH$_2$ (Compound No. 612), Propionyl-D-Tyr-D-Trp-Asn-Thr-Phe-AzaGly-Leu-Arg(Me)-Trp-NH$_2$ (Compound No. 613), Ac-Tyr-D-Trp-Asn-Thr-Phe-AzaGly-Leu-Arg(Me)-Trp-NH$_2$ (Compound No. 615), Ac-D-Ala-D-Trp-Asn-Thr-Phe-AzaGly-Leu-Arg(Me)-Trp-NH$_2$ (Compound No. 616), -continued Ac-D-Leu-D-Trp-Asn-Thr-Phe-AzaGly-Leu-Arg(Me)-Trp-NH$_2$ (Compound No. 617), Ac-D-Phe-D-Trp-Asn-Thr-Phe-AzaGly-Leu-Arg(Me)-Trp-NH$_2$ (Compound No. 618), Ac-D-Lys-D-Trp-Asn-Thr-Phe-AzaGly-Leu-Arg(Me)-Trp-NH$_2$ (Compound No. 621), Ac-D-Tyr-Trp-Asn-Thr-Phe-AzaGly-Leu-Arg(Me)-Trp-NH$_2$ (Compound No. 623), Ac-D-Tyr-D-Ala-Asn-Thr-Phe-AzaGly-Leu-Arg(Me)-Trp-NH$_2$ (Compound No. 625), Ac-D-Tyr-D-Leu-Asn-Thr-Phe-AzaGly-Leu-Arg(Me)-Trp-NH$_2$ (Compound No. 626), Ac-D-Tyr-D-Phe-Asn-Thr-Phe-AzaGly-Leu-Arg(Me)-Trp-NH$_2$ (Compound No. 627), Ac-D-Tyr-D-Lys-Asn-Thr-Phe-AzaGly-Leu-Arg(Me)-Trp-NH$_2$ (Compound No. 629), Ac-D-Tyr-D-Glu-Asn-Thr-Phe-AzaGly-Leu-Arg(Me)-Trp-NH$_2$ (Compound No. 630), Ac-D-Tyr-D-Trp-Asn-Thr-Pya(4)-AzaGly-Leu-Arg(Me)-Trp-NH$_2$ (Compound No. 635), Ac-D-Tyr-D-Trp-Asn-Thr-Phe(4F)-AzaGly-Leu-Arg(Me)-Trp-NH$_2$ (Compound No. 637), Ac-D-Tyr-D-Pya(4)-Asn-Thr-Phe(4F)-AzaGly-Leu-Arg(Me)-Trp-NH$_2$ (Compound No. 638), Ac-D-Tyr-D-Trp-Asn-Thr-Phe-AzaGly-Val-Arg(Me)-Trp-NH$_2$ (Compound No. 642), Gly-D-Tyr-D-Trp-Asn-Thr-Phe-AzaGly-Leu-Arg(Me)-Trp-NH$_2$ (Compound No. 648), Ac-Gly-D-Tyr-D-Trp-Asn-Thr-Phe-AzaGly-Leu-Arg(Me)-Trp-NH$_2$ (Compound No. 649), D-Tyr-D-Tyr-D-Trp-Asn-Thr-Phe-AzaGly-Leu-Arg(Me)-Trp-NH$_2$ (Compound No. 650), Ac-D-Tyr-D-Tyr-D-Trp-Asn-Thr-Phe-AzaGly-Leu-Arg(Me)-Trp-NH$_2$ (Compound No. 651), pGlu-D-Tyr-D-Trp-Asn-Thr-Phe-AzaGly-Leu-Arg(Me)-Trp-NH$_2$ (Compound No. 652), Ac-D-Tyr-Pro-Asn-Thr-Phe-AzaGly-Leu-Arg(Me)-Trp-NH$_2$ (Compound No. 657), Ac-D-Tyr-D-Pya(2)-Asn-Thr-Phe-AzaGly-Leu-Arg(Me)-Trp-NH$_2$ (Compound No. 658), Ac-D-Tyr-D-Pya(3)-Asn-Thr-Phe-AzaGly-Leu-Arg(Me)-Trp-NH$_2$ (Compound No. 660), Ac-D-Tyr-Tic-Asn-Thr-Phe-AzaGly-Leu-Arg(Me)-Trp-NH$_2$ (Compound No. 662), Ac-D-Trp-D-Trp-Asn-Thr-Phe-AzaGly-Leu-Arg(Me)-Trp-NH$_2$ (Compound No. 663), Ac-D-Trp-Asn-Thr-Phe-AzaGly-Leu-Arg(Me)-Trp-NH$_2$ (Compound No. 666), Hexanoyl-D-Trp-Asn-Thr-Phe-AzaGly-Leu-Arg(Me)-Trp-NH$_2$ (Compound No. 667), 3-Pyridinepropionyl-D-Trp-Asn-Thr-Phe-AzaGly-Leu-Arg(Me)-Trp-NH$_2$ (Compound No. 670), Adipoyl-D-Trp-Asn-Thr-Phe-AzaGly-Leu-Arg(Me)-Trp-NH$_2$ (Compound No. 671), Ac-D-Tyr-NMeTrp-Asn-Thr-Phe-AzaGly-Leu-Arg(Me)-Trp-NH$_2$ (Compound No. 672), 6-Aminocaproyl-D-Trp-Asn-Thr-Phe-AzaGly-Leu-Arg(Me)-Trp-NH$_2$ (Compound No. 674), or salts thereof.

(67) Ac-D-Tyr-D-Trp-Asn-Thr-Phe-AzaGly-Leu-Arg(Me)-Trp-NH$_2$ (Compound No. 550), Ac-D-Arg-Acp-D-Tyr-D-Trp-Asn-Thr-Phe-AzaGly-Leu-Arg(Me)-Trp-NH$_2$ (Compound No. 551), D-Dap-Acp-D-Tyr-D-Trp-Asn-Thr-Phe-AzaGly-Leu-Arg(Me)-Trp-NH$_2$ (Compound No. 552), Ac-D-Tyr-D-Trp-Asn-Ser-Phe-AzaGly-Leu-Arg(Me)-Trp-NH$_2$ (Compound No. 558), -continued 3-(4-Hydroxyphenyl)propionyl-D-Trp-Asn-Thr-Phe-AzaGly-Leu-Arg(Me)-Trp-NH$_2$ (Compound No. 559), Ac-D-Tyr-D-Pya(4)-Asn-Thr-Phe-AzaGly-Leu-Arg(Me)-Trp-NH$_2$ (Compound No. 562), Ac-D-Tyr-D-Trp-Asn-Thr-Phe-AzaGly-Leu-Arg(Me)-Phe-NH$_2$ (Compound No. 571), Ac-D-Tyr-D-Trp-Aib-Ser-Phe-AzaGly-Leu-Arg(Me)-Trp-NH$_2$ (Compound No. 579), Ac-D-Tyr-D-Trp-Dap(For)-Ser-Phe-AzaGly-Leu-Arg(Me)-Trp-NH$_2$ (Compound No. 585), Ac-D-Tyr-D-Trp-Asn-Thr-Phe-AzaGly-Leu-Arg(Me)-Nal(2)-NH$_2$ (Compound No. 589), Ac-D-Tyr-D-Trp-Asn-Thr-Phe-AzaGly-Leu-Arg(Me)-Phe(4F)-NH$_2$ (Compound No. 592), For-D-Tyr-D-Trp-Asn-Thr-Phe-AzaGly-Leu-Arg(Me)-Trp-NH$_2$ (Compound No. 612), Propionyl-D-Tyr-D-Trp-Asn-Thr-Phe-AzaGly-Leu-Arg(Me)-Trp-NH$_2$ (Compound No. 613), Ac-D-Phe-D-Trp-Asn-Thr-Phe-AzaGly-Leu-Arg(Me)-Trp-NH$_2$ (Compound No. 618), Ac-D-Tyr-D-Phe-Asn-Thr-Phe-AzaGly-Leu-Arg(Me)-Trp-NH$_2$ (Compound No. 627), Ac-D-Tyr-D-Trp-Asn-Thr-Phe(4F)-AzaGly-Leu-Arg(Me)-Trp-NH$_2$ (Compound No. 637), Ac-D-Tyr-D-Pya(4)-Asn-Thr-Phe(4F)-AzaGly-Leu-Arg(Me)-Trp-NH$_2$ (Compound No. 638), Ac-D-Tyr-D-Pya(2)-Asn-Thr-Phe-AzaGly-Leu-Arg(Me)-Trp-NH$_2$ (Compound No. 658), Ac-D-Tyr-D-Pya(3)-Asn-Thr-Phe-AzaGly-Leu-Arg(Me)-Trp-NH$_2$ (Compound No. 660), Ac-D-Trp-D-Trp-Asn-Thr-Phe-AzaGly-Leu-Arg(Me)-Trp-NH$_2$ (Compound No. 663), or salts thereof.

(68) The agent according to (48) above, which is an agent for potentiating immunity (prophylactic agent for infection after bone-marrow transplant, an agent for potentiating immunity intended for cancer).

(69) The agent according to (48) above, which is a prophylactic/therapeutic agent for bulbospinal muscular atrophy.

(70) The agent according to (48) above, which is a prophylactic/therapeutic agent for protecting ovary.

(71) The agent according to (48) above, which is a prophylactic/therapeutic agent for benign prostate hypertrophy (BPH).

(72) The agent according to (48) above, which is a prophylactic/therapeutic agent for gender identity disorder.

(73) The agent according to (48) above, which is a prophylactic/therapeutic agent for in vitro fertilization (IVF).

BEST MODE OF EMBODIMENTS OF THE INVENTION

Figure 1:
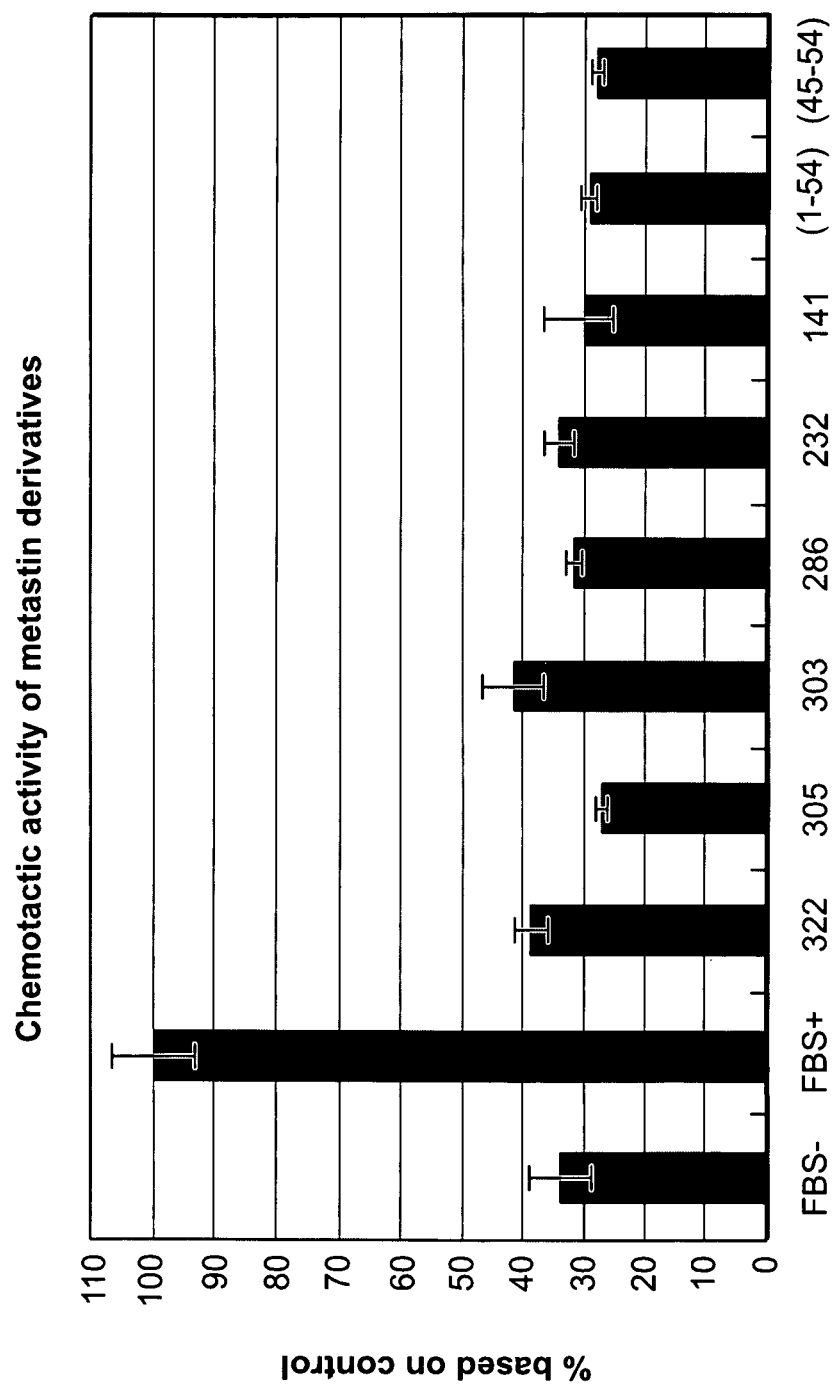
FIG. 1 shows evaluation of the chemotaxis inhibition activity of Compound Nos. 322, 305, 303, 286, 232 and 141 using hOT7T175-expressed CHO cells. On the abscissa, FBS− designates the absence of FBS, FBS+ designates the presence of FBS, 322 designates the addition of Compound No. 322, 305 designates the addition of Compound No. 305, 303 designates the addition of Compound No. 303, 286 designates the addition of Compound No. 286, 232 designates the addition of Compound No. 232, 141 designates the addition of Compound No. 141, (1-54) designates the addition of metastin (1-54), and (45-54) designates the addition of metastin 45-54. The ordinate denotes a relative activity when the chemotactic activity in the presence of FBS is made 100%.

In the formulae described above, n represents 0 or 1; $W^1$ represents N, CH or O (provided that $W^1$ is N or CH, n represents 1, and when $W^1$ is O, n represents 0); $W^2$ represents N or CH; $Z^1$, $Z^3$, $Z^5$ and $Z^7$ each represents hydrogen atom or a $C_{1-3}$ alkyl group; and $Z^2$, $Z^4$, $Z^6$ and $Z^8$ each represents hydrogen atom, O or S;

wherein, when $Z^2$, $Z^4$, $Z^6$ or $Z^8$ represents hydrogen atom, a structure of the moiety represented by $>C=Z^2$, $>C=Z^4$, $>C=Z^6$ or $>C=Z^8$ each indicates a structure of $>CH_2$.

The $C_{1-3}$ alkyl group used includes methyl group, ethyl group, propyl group and isopropyl group.

$W^1$ is preferably N and $W^2$ is preferably CH.

Preferred combinations of $Z^1$ through $Z^8$ further include the cases that $Z^1$ and $Z^3$ represent hydrogen atom, each of $Z^5$ and $Z^7$ represents hydrogen atom or a $C_{1-3}$ alkyl group and each of $Z^2$, $Z^4$, $Z^6$ and $Z^8$ represents O or S.

More preferably, the combinations of $Z^1$ through $Z^8$ include:

(a) the case where $Z^1$ is hydrogen atom, $Z^3$ is hydrogen atom, $Z^5$ is hydrogen atom and $Z^7$ is hydrogen atom, and $Z^2$ is O, $Z^4$ is O, $Z^6$ is O and $Z^8$ is O;

(b) the case where $Z^1$ is hydrogen atom, $Z^3$ is hydrogen atom, $Z^5$ is hydrogen atom and $Z^7$ is hydrogen atom, and $Z^2$ is O, $Z^4$ is O, $Z^6$ is O and $Z^8$ is S;

(c) the case where $Z^1$ and $Z^3$ are hydrogen atom and $Z^5$ is hydrogen atom, $Z^7$ is methyl group and $Z^2$ is O, and $Z^4$ is O, $Z^6$ is O and $Z^8$ is O; etc. Among these cases, (a) and (b) are preferred.

$R^1$ represents (1) hydrogen atom, (2) a $C_{1-8}$ alkyl group optionally substituted with a substituent selected from the group consisting of an optionally substituted carbamoyl group, an optionally substituted hydroxyl group and an optionally substituted aromatic cyclic group, (3) a cyclic or linear $C_{1-10}$ alkyl group or (4) a $C_{1-10}$ alkyl group consisting of a cyclic alkyl group and a linear alkyl group, or (5) an optionally substituted aromatic cyclic group. Inter alia, preferred $R^1$ includes (1) hydrogen atom or (2) a $C_{1-8}$ alkyl group optionally substituted with a substituent selected from the group consisting of an optionally substituted carbamoyl group, an optionally substituted hydroxyl group and an optionally substituted aromatic cyclic group, more preferably includes (1) hydrogen atom or (2) a $C_{1-8}$ alkyl group substituted with a substituent selected from the group consisting of an optionally substituted carbamoyl group, an optionally substituted hydroxyl group and an optionally substituted aromatic cyclic group.

The "$C_{1-8}$ alkyl group" used includes, for example, a linear $C_{1-8}$ alkyl group such as methyl, ethyl, propyl, isopropyl, butyl, isobutyl, sec-butyl, tert-butyl, pentyl, isopentyl, neopentyl, hexyl, heptyl, octyl, etc., and a cyclic $C_{3-8}$ alkyl group such as cyclopropyl, cyclobutyl, cyclopentyl, cyclohexyl, etc. $C_{1-3}$ alkyl groups such as methyl, ethyl, etc. are particularly preferred.

The "optionally substituted carbamoyl group" used includes, for example, carbamoyl, a mono-$C_{1-6}$ alkylcarbamoyl group (e.g., methylcarbamoyl, ethylcarbamoyl, etc.), a di-$C_{1-6}$ alkylcarbamoyl group (e.g., dimethylcarbamoyl, diethylcarbamoyl, ethylmethylcarbamoyl, etc.), a mono- or di-$C_{6-14}$ arylcarbamoyl group (e.g., phenylcarbamoyl, 1-naphthylcarbamoyl, 2-naphthylcarbamoyl, etc.), a mono- or di-5- or 7-membered heterocyclic carbamoyl group containing 1 to 4 hetero atoms of 1 or 2 species selected from nitrogen, sulfur and oxygen atoms in addition to carbon atoms (e.g., 2-pyridylcarbamoyl, 3-pyridylcarbamoyl, 4-pyridylcarbamoyl, 2-thienylcarbamoyl, 3-thienylcarbamoyl, etc.) and the like.

The "optionally substituted hydroxyl group" used includes, for example, hydroxy group, an optionally substituted $C_{1-6}$ alkoxy group, an optionally substituted $C_{6-14}$ aryloxy group, an optionally substituted $C_{7-16}$ aralkyloxy group, etc. The "optionally substituted $C_{1-6}$ alkoxy group," "optionally substituted $C_{6-14}$ aryloxy group" and "optionally substituted $C_{7-16}$ aralkyloxy group" used are those of the "optionally substituted $C_{1-6}$ alkoxy group," "optionally substituted $C_{6-14}$ aryloxy group" and "optionally substituted $C_{7-16}$ aralkyloxy group" in Substituent group A, which will be later described.

The "aromatic cyclic group" in "optionally substituted aromatic cyclic group" includes, for example, an aromatic hydrocarbon group, aromatic heterocyclic group, an aromatic fused cyclic group, an aromatic fused heterocyclic group, etc.

The "aromatic hydrocarbon group" used includes, for example, a $C_{6-14}$ aryl group such as phenyl, 2-biphenylyl, 3-biphenylyl, 4-biphenylyl, cyclooctatetraenyl, etc.

The "aromatic heterocyclic group" used includes, for example, a 5- to 14-membered, preferably 5- to 10-membered, more preferably 5- or 6-membered aromatic heterocyclic group containing 1 to 4 hetero atoms of 1 or 2 species selected from nitrogen, sulfur and oxygen atoms in addition to carbon atoms. Specific examples are thienyl (e.g., 2-thienyl, 3-thienyl), furyl (e.g., 2-furyl, 3-furyl), pyridyl (e.g., 2-pyridyl, 3-pyridyl, 4-pyridyl), thiazolyl (e.g., 2-thiazolyl, 4-thiazolyl, 5-thiazolyl), oxazolyl (e.g., 2-oxazolyl, 4-oxazolyl), pyrazinyl, pyrimidinyl (e.g., 2-pyrimidinyl, 4-pyrimidinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), pyridazinyl (e.g., 3-pyridazinyl, 4-pyridazinyl), isothiazolyl (e.g., 3-isothiazolyl), isooxazolyl (e.g., 3-isooxazolyl), etc.

The "aromatic fused cyclic group" used includes a $C_{8-14}$ aromatic fused cyclic group such as naphthyl (e.g., 1-naphthyl, 2-naphthyl), anthryl (e.g., 2-anthryl, 9-anthryl) and the like.

The "aromatic fused heterocyclic group" used includes, for example, a 5- to 14-membered (preferably 5- to 10-membered) bicyclic or tricyclic aromatic heterocyclic group containing 1 to 4 hetero atoms of 1 or 2 species selected from nitrogen, sulfur and oxygen atoms in addition to 3 to 11 carbon atoms, or a monovalent group formed by removing one optional hydrogen atom from a 7- to 10-membered aromatic bridged-hetero ring in 5- to 14-membered (preferably 5- to 10-membered) ring containing 1 to 4 hetero atoms of 1 or 2 species selected from nitrogen, sulfur and oxygen atoms in addition to carbon atoms. Specific examples of these groups used are quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl), indolyl (e.g., 1-indolyl, 2-indolyl, 3-indolyl), 2-benzothiazolyl, benzo[b]thienyl, (e.g., 2-benzo[b]thienyl, 3-benzo[b]thienyl), benzo[b]furanyl (e.g., 2-benzo[b]furanyl, 3-benzo[b]furanyl) and the like.

The "substituent" used for the "aromatic cyclic group" includes a substituent selected from the Substituent group A, which will be later described.

For $R^1$, there are used hydrogen atom, carbamoylmethyl, 2-carbamoylethyl, hydroxymethyl, 1-hydroxyethyl, benzyl, 4-hydroxybenzyl, 2-pyridylmethyl, 3-pyridylmethyl, 4-pyridylmethyl, 2-thienylmethyl, 3-thienylmethyl, 1-naphthylmethyl, 2-naphthylmethyl, 3-indolemethyl, methyl, ethyl, propyl, isopropyl, butyl, isobutyl, sec-butyl, tert-butyl, cyclohexylmethyl, phenyl, acetoxymethyl, methoxymethyl, etc., preferably, hydroxymethyl, 1-hydroxyethyl, benzyl, 4-hydroxybenzyl, 3-indolemethyl, methyl, isobutyl, etc., and more preferably, hydroxymethyl, 1-hydroxyethyl, etc.

$R^2$ represents (1) hydrogen atom, (2) a cyclic or linear $C_{1-10}$ alkyl group, (3) a $C_{1-10}$ alkyl group consisting of a cyclic alkyl group and a linear alkyl group, or (4) a $C_{1-8}$ alkyl group optionally substituted with a substituent selected from the group consisting of an optionally substituted carbamoyl group, an optionally substituted hydroxyl group and an optionally substituted aromatic cyclic group. Among them, preferred are (1) hydrogen atom, (2) a cyclic or linear $C_{1-10}$ alkyl group, or (3) a $C_{1-10}$ alkyl group consisting of a cyclic alkyl group and a linear alkyl group. In particular, (3) a $C_{1-10}$ alkyl group consisting of a cyclic alkyl group and a linear alkyl group is preferred.

The cyclic $C_{1-10}$ alkyl group used includes, for example, a $C_{3-8}$ cycloalkyl group such as cyclopropyl, cyclobutyl, cyclopentyl, cyclohexyl, etc.

Examples of the linear $C_{1-10}$ alkyl group include methyl, ethyl, propyl, isopropyl, butyl, isobutyl, sec-butyl, tert-butyl, pentyl, isopentyl, neopentyl, hexyl, heptyl, octyl, nonanyl, decanyl, etc.

The $C_{1-10}$ alkyl group consisting of a cyclic alkyl group and a linear alkyl group used includes, for example, a $C_{3-7}$ cycloalkyl-$C_{1-3}$ alkyl group such as cyclopentylmethyl, cyclohexylmethyl, etc.

Examples of $R^2$ include methyl, ethyl, propyl, isopropyl, butyl, isobutyl, sec-butyl, tert-butyl, cyclohexylmethyl, benzyl, hydroxymethyl, 2-carbamoylethyl, tert-pentyl, etc.; among them, preferred are methyl, ethyl, propyl, isopropyl, isobutyl, sec-butyl, tert-butyl, etc., more preferably, propyl, isopropyl, isobutyl, etc.

$R^3$ represents:
(1) a $C_{1-8}$ alkyl group having an optionally substituted basic group and optionally having an additional substituent,
(2) an aralkyl group having an optionally substituted basic group and optionally having an additional substituent,
(3) a $C_{1-4}$ alkyl group having a non-aromatic cyclic hydrocarbon group of carbon atoms not greater than 7 having an optionally substituted basic group, and optionally having an additional substituent, or,
(4) a $C_{1-4}$ alkyl group having a non-aromatic heterocyclic group of carbon atoms not greater than 7 having an optionally substituted basic group, and optionally having an additional substituent.

The "optionally substituted basic group" used includes, for example, (1) a guanidino group optionally having 1 or 2 substituents from a $C_{1-6}$ alkyl, a $C_{1-6}$ acyl (e.g., methyl, ethyl, propyl, isopropyl, butyl, acetyl, propionyl, etc.), etc., (2) an amino group optionally having 1 to 3 substituents from a $C_{1-6}$ alkyl, a $C_{1-6}$ acyl (e.g., methyl, ethyl, propyl, isopropyl, butyl, acetyl, propionyl, etc.), etc., (3) a $C_{1-6}$ alkylcarbonylamino group (e.g., acetamido) optionally substituted with a guanidino group optionally having 1 or 2 substituents from a $C_{1-6}$ alkyl, a $C_{1-6}$ acyl (e.g., methyl, ethyl, propyl, isopropyl, butyl, acetyl, propionyl, etc.), etc., (4) a $C_{1-6}$ alkylcarbonylamino group (e.g., acetamido) optionally substituted with an amino group optionally having 1 to 3 substituents from a $C_{1-6}$ alkyl, a $C_{1-6}$ acyl (e.g., methyl, ethyl, propyl, isopropyl, butyl, acetyl, propionyl, etc.), etc. Among them, preferred are guanidino, N-methylguanidino, N,N-dimethylguanidino, N,N'-dimethylguanidino, N-ethylguanidino, N-acetylguanidino, amino, N-methylamino, N,N-dimethylamino, aminoacetamido, guanidinoacetamido, amidino, etc.

The "additional substituent" other than the "optionally substituted basic group" used includes a substituent selected from the Substituent group A later described.

Examples of the "$C_{1-8}$ alkyl group" used are methyl, ethyl, propyl, isopropyl, butyl, isobutyl, sec-butyl, tert-butyl, pentyl, isopentyl, neopentyl, hexyl, heptyl, octyl, etc.

The "aralkyl group" used includes, for example, a $C_{7-16}$ aralkyl group such as benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, 4-biphenylylmethyl, etc.

The "non-aromatic cyclic hydrocarbon group of carbon atoms not greater than 7" used includes, for example, a $C_{3-7}$ cycloalkyl group such as cyclopropyl, cyclobutyl, cyclopentyl, cyclohexyl, etc.

The "non-aromatic heterocyclic group of carbon atoms not greater than 7" used includes, for example, a 5- to 10-membered non-aromatic heterocyclic group containing 1 to 4 hetero atoms of 1 or 2 species selected from nitrogen, sulfur and oxygen atoms in addition to 1 to 7 carbon atoms, etc. Specifically examples used are pyrrolidinyl (e.g., 1-pyrrolidinyl, 2-pyrrolidinyl, 3-pyrrolidinyl), oxazolidinyl (e.g., 2-oxazolidinyl), imidazolinyl (e.g., 1-imidazolinyl, 2-imidazolinyl, 4-imidazolinyl), piperidinyl (e.g., 1-piperidinyl, 2-piperidinyl, 3-piperidinyl, 4-piperidinyl), piperazinyl (e.g., 1-piperazinyl, 2-piperazinyl), morpholino, thiomorpholino, etc.

Examples of the "$C_{1-4}$ alkyl group" used include methyl, ethyl, propyl, isopropyl, butyl, isobutyl, sec-butyl, tert-butyl, etc.

For $R^3$, there are used, for example, (1) 3-guanidinopropyl, 3-(N-methylguanidino)propyl, 3-(N,N-dimethylguanidino)propyl, 3-(N,N'-dimethylguanidino)propyl, 3-(N-ethylguanidino)propyl, 3-(N-propylguanidino)propyl, 3-(N-acetylguanidino)propyl, 4-guanidinobutyl, 4-(N-methylguanidino)butyl, 2-guanidinoethyl, 2-(N-methylguanidino)ethyl, 4-aminobutyl, 4-(N-methylamino)butyl, 4-(N,N-dimethylamino)butyl, 3-aminopropyl, 2-aminoethyl, aminomethyl, aminoacetamidomethyl, guanidinoacetamidomethyl, 2-(guanidinocarbonyl)ethyl, (2) 4-guanidinobenzyl, 4-aminobenzyl, (3) 4-guanidinocyclohexylmethyl, 4-aminocyclohexylmethyl, (4) 1-amidinopiperidin-4-ylmethyl, 4-pyridylmethyl, etc., preferably, 3-guanidinopropyl, 3-(N-methylguanidino)propyl, 3-(N,N-dimethylguanidino)propyl, 3-(N,N'-dimethylguanidino)propyl, 3-(N-ethylguanidino)propyl, 3-(N-propylguanidino)propyl, 3-(N-acetylguanidino)propyl, 4-guanidinobutyl, 4-(N-methylguanidino)butyl, 2-guanidinoethyl, 2-(N-methylguanidino)ethyl, 4-aminobutyl, 4-(N-methylamino)butyl, 4-(N,N-dimethylamino)butyl, 3-aminopropyl, 2-aminoethyl, 4-aminobenzyl, aminoacetamidomethyl, guanidinoacetamidomethyl, etc., and more preferably, 3-guanidinopropyl, 3-(N-methylguanidino)propyl, 3-(N,N-dimethylguanidino)propyl, 3-(N,N'-dimethylguanidino)propyl, 3-(N-ethylguanidino)propyl, 3-(N-acetylguanidino)propyl, 4-guanidinobutyl, 4-(N-methylguanidino)butyl, 2-guanidinoethyl, 4-aminobutyl, etc.

$R^4$ represents a $C_{1-4}$ alkyl group, which may optionally be substituted with a substituent selected from the group consisting of:
(1) an optionally substituted $C_{6-12}$ aromatic hydrocarbon group;
(2) an optionally substituted 5- to 14-membered aromatic heterocyclic group consisting of 1 to 7 carbon atoms and hetero atoms selected from the group consisting of nitrogen, oxygen and sulfur atoms;
(3) an optionally substituted $C_{8-14}$ aromatic fused cyclic group;
(4) an optionally substituted 5- to 14-membered aromatic fused heterocyclic group consisting of 3 to 11 carbon atoms and hetero atoms selected from the group consisting of nitrogen, oxygen and sulfur atoms;
(5) an optionally substituted non-aromatic cyclic hydrocarbon group having carbon atoms not greater than 7, and
(6) an optionally substituted non-aromatic heterocyclic group having carbon atoms not greater than 7; and preferably, a $C_{1-4}$ alkyl group substituted with a substituent selected from the group consisting of:
(1) an optionally substituted $C_{6-12}$ aromatic hydrocarbon group;
(2) an optionally substituted 5- to 14-membered aromatic heterocyclic group consisting of 1 to 7 carbon atoms and hetero atoms selected from the group consisting of nitrogen, oxygen and sulfur atoms;
(3) an optionally substituted $C_{8-14}$ aromatic fused cyclic group;
(4) an optionally substituted 5- to 14-membered aromatic fused heterocyclic group consisting of 3 to 11 carbon atoms and hetero atoms selected from the group consisting of nitrogen, oxygen and sulfur atoms;
(5) an optionally substituted non-aromatic cyclic hydrocarbon group having carbon atoms not greater than 7; and,
(6) an optionally substituted non-aromatic heterocyclic group having carbon atoms not greater than 7.

Examples of the "$C_{1-4}$ alkyl group" used include methyl, ethyl, propyl, isopropyl, butyl, isobutyl, sec-butyl, tert-butyl, etc.

The "$C_{6-12}$ aromatic hydrocarbon group" used includes, for example, a monocyclic $C_{6-12}$ aromatic hydrocarbon group such as phenyl, cyclooctatetraenyl, etc.

The "5- to 14-membered aromatic heterocyclic group consisting of 1 to 7 carbon atoms and hetero atoms selected from the group consisting of nitrogen, oxygen and sulfur atoms" used includes, for example, a 5- to 14-membered, preferably 5- to 10-membered, more preferably 5- or 6-membered monocyclic aromatic heterocyclic group containing 1 to 4 hetero atoms of 1 or 2 species selected from nitrogen, sulfur and oxygen atoms in addition to 1 to 7 carbon atoms. Specific examples used are thienyl (e.g., 2-thienyl, 3-thienyl), furyl (e.g., 2-furyl, 3-furyl), pyridyl (e.g., 2-pyridyl, 3-pyridyl, 4-pyridyl), thiazolyl (e.g., 2-thiazolyl, 4-thiazolyl, 5-thiazolyl), oxazolyl (e.g., 2-oxazolyl, 4-oxazolyl), pyrazinyl, pyrimidinyl (e.g., 2-pyrimidinyl, 4-pyrimidinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), pyridazinyl (e.g., 3-pyridazinyl, 4-pyridazinyl), isothiazolyl (e.g., 3-isothiazolyl), isoxazolyl (e.g., 3-isoxazolyl), etc.

The "$C_{8-14}$ aromatic fused cyclic group" used includes, for example, naphthyl (e.g., 1-naphthyl, 2-naphthyl), anthryl (e.g., 2-anthryl, 9-anthryl), etc.

The "optionally substituted 5- to 14-membered aromatic fused heterocyclic group consisting of 3 to 11 carbon atoms and hetero atoms selected from the group consisting of nitrogen, oxygen and sulfur atoms" includes, for example, a 5- to 14-membered (preferably 5- to 10-membered) bicyclic or tricyclic aromatic heterocyclic group containing 1 to 4 hetero atoms of 1 or 2 species selected from nitrogen, sulfur and oxygen atoms in addition to 3 to 11 carbon atoms, or a monovalent group formed by removing one optional hydrogen atom from a 7- to 10-membered aromatic bridged-hetero ring in 5- to 14-membered (preferably 5- to 10-membered) ring containing 1 to 4 hetero atoms of 1 or 2 species selected from nitrogen, sulfur and oxygen atoms in addition to carbon atoms. Specific examples used are quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl), indolyl (e.g., 1-indolyl, 2-indolyl, 3-indolyl), 2-benzothiazolyl, benzo[b]thienyl, (e.g., 2-benzo[b]thienyl, 3-benzo[b]thienyl), benzo[b]furanyl (e.g., 2-benzo[b]furanyl, 3-benzo[b]furanyl), etc.

The "non-aromatic cyclic hydrocarbon group of carbon atoms not greater than 7" used includes, for example, a $C_{3-7}$ cycloalkyl group such as cyclopropyl, cyclobutyl, cyclopentyl, cyclohexyl, etc.

The "non-aromatic heterocyclic group of carbon atoms not greater than 7" used includes, for example, a 5- or 10-membered non-aromatic heterocyclic group containing 1 to 4 hetero atoms of 1 or 2 species selected from nitrogen, sulfur and oxygen atoms, in addition to 1 to 7 carbon atoms, such as pyrrolidinyl (e.g., 1-pyrrolidinyl, 2-pyrrolidinyl, 3-pyrrolidinyl), oxazolidinyl (e.g., 2-oxazolidinyl), imidazolinyl (e.g., 1-imidazolinyl, 2-imidazolinyl, 4-imidazolinyl), piperidinyl (e.g., 1-piperidinyl, 2-piperidinyl, 3-piperidinyl, 4-piperidinyl), piperazinyl (e.g., 1-piperazinyl, 2-piperazinyl), morpholino, thiomorpholino, etc.

The substituents used for these "$C_{6-12}$ aromatic hydrocarbon group," "5- to 14-membered aromatic heterocyclic group consisting of 1 to 7 carbon atoms and hetero atoms selected from the group consisting of nitrogen, oxygen and sulfur atoms," "$C_{8-14}$ aromatic fused cyclic group," "5- to 14-membered aromatic fused heterocyclic group consisting of 3 to 11 carbon atoms and hetero atoms selected from the group consisting of nitrogen, oxygen and sulfur atoms," "non-aromatic cyclic hydrocarbon group of carbon atoms not greater than 7" and "non-aromatic heterocyclic group of carbon atoms not greater than 7" include, for example, substituents selected from oxo, a halogen atom (e.g., fluorine, chlorine, bromine, iodine, etc.), $C_{1-3}$ alkylenedioxy (e.g., methylenedioxy, ethylenedioxy, etc.), nitro, cyano, an optionally substituted $C_{1-6}$ alkyl, an optionally substituted $C_{2-6}$ alkenyl, an optionally substituted $C_{2-6}$ alkynyl, an optionally substituted $C_{3-8}$ cycloalkyl, an optionally substituted $C_{6-14}$ aryl, an optionally substituted $C_{7-16}$ aralkyl, an optionally substituted $C_{1-6}$ alkoxy, hydroxy, an optionally substituted $C_{6-14}$ aryloxy, an optionally substituted $C_{7-16}$ aralkyloxy, mercapto, an optionally substituted $C_{1-6}$ alkylthio, an optionally substituted $C_{6-14}$ arylthio, an optionally substituted $C_{7-16}$ aralkylthio, an optionally substituted amino[amino, an optionally substituted mono- or di-$C_{1-6}$ alkyl-amino (e.g., methylamino, dimethylamino, ethylamino, diethylamino, propylamino, isopropylamino, etc.), an optionally substituted mono- or di-$C_{2-6}$ alkenyl-amino (e.g., vinylamino, propenylamino, isoprope- nylamino), an optionally substituted $C_{2-6}$ alkynylamino (e.g., 2-butyn-1-yl-amino, 4-pentyn-1-yl-amino, 5-hexyn-1-yl-amino), an optionally substituted mono- or di-$C_{3-8}$ cycloalkyl-amino (e.g., cyclopropylamino, cyclohexylamino), an optionally substituted $C_{6-14}$ arylamino (e.g., phenylamino, diphenylamino, naphthylamino), an optionally substituted $C_{1-6}$ alkoxyamino (e.g., methoxyamino, ethoxyamino, propoxyamino, isopropoxyamino), formylamino, an optionally substituted $C_{1-6}$ alkylcarbonylamino (e.g., acetylamino, propionylamino, pivaloylamino, etc.), an optionally substituted $C_{3-8}$ cycloalkylcarbonylamino (e.g., cyclopropylcarbonylamino, cyclopentylcarbonylamino, cyclohexylcarbonylamino, etc.), an optionally substituted $C_{6-14}$ aryl-carbonylamino (e.g., benzoylamino, naphthoylamino, etc.), an optionally substituted $C_{1-6}$ alkoxy-carbonylamino (e.g., methoxycarbonylamino, ethoxycarbonylamino, propoxycarbonylamino, butoxycarbonylamino, etc.), an optionally substituted $C_{1-6}$ alkylsulfonylamino (e.g., methylsulfonylamino, ethylsulfonylamino, etc.), an optionally substituted $C_{6-14}$ arylsulfonylamino (e.g., phenylsulfonylamino, 2-naphthylsulfonylamino, 1-naphthylsulfonylamino, etc.)], formyl, carboxy, an optionally substituted $C_{1-6}$ alkylcarbonyl (e.g., acetyl, propionyl, pivaloyl, etc.), an optionally substituted $C_{3-8}$ cycloalkylcarbonyl (e.g., cyclopropylcarbonyl, cyclopentylcarbonyl, cyclohexylcarbonyl, 1-methyl-cyclohexyl-carbonyl, etc.), an optionally substituted $C_{6-14}$ arylcarbonyl (e.g., benzoyl, 1-naphthoyl, 2-naphthoyl, etc.), an optionally substituted $C_{7-16}$ aralkylcarbonyl (e.g., phenylacetyl, 3-phenylpropionyl, etc.), an optionally substituted 5- to 7-membered heterocyclic carbonyl containing 1 to 4 hetero atoms of 1 or 2 species selected from nitrogen, sulfur and oxygen atoms in addition to carbon atoms (e.g., nicotinoyl, isonicotinoyl, thenoyl, furoyl, morpholinocarbonyl, thiomorpholinocarbonyl, piperazin-1-ylcarbonyl, pyrrolidin-1-ylcarbonyl, etc.), an optionally esterified carboxyl, an optionally substituted carbamoyl group, an optionally substituted $C_{1-6}$ alkylsulfonyl (e.g., methylsulfonyl, ethylsulfonyl, etc.), an optionally substituted $C_{1-6}$ alkylsulfinyl (e.g., methylsulfinyl, ethylsulfinyl, etc.), an optionally substituted $C_{6-14}$ arylsulfonyl (e.g., phenylsulfonyl, 1-naphthylsulfonyl, 2-naphthylsulfonyl, etc.), an optionally substituted $C_{6-14}$ arylsulfinyl (e.g., phenylsulfinyl, 1-naphthylsulfinyl, 2-naphthylsulfinyl, etc.), an optionally substituted $C_{1-6}$ alkylcarbonyloxy (e.g., acetoxy, propionyloxy, etc.), an optionally substituted $C_{6-14}$ aryl-carbonyloxy (e.g., benzoyloxy, naphthylcarbonyloxy, etc.), an optionally substituted $C_{1-6}$ alkoxy-carbonyloxy (e.g., methoxycarbonyloxy, ethoxycarbonyloxy, propoxycarbonyloxy, butoxycarbonyloxy, etc.), an optionally substituted a mono-$C_{1-6}$ alkylcarbamoyloxy (e.g., methylcarbamoyloxy, ethylcarbamoyloxy, etc.), an optionally substituted di-$C_{1-6}$ alkylcarbamoyloxy (e.g., dimethylcarbamoyloxy, diethylcarbamoyloxy, etc.), an optionally substituted a mono- or di-$C_{6-14}$ arylcarbamoyloxy (e.g., phenylcarbamoyloxy, naphthylcarbamoyloxy, etc.), an optionally substituted heterocyclic group, sulfo, sulfamoyl, sulfinamoyl, sulfenamoyl, or a group of 2 or more (e.g., 2 or 3) of these substituents combined, and the like (Substituent group A). The number of the substituents is not particularly limited but these rings may have 1 to 5, preferably 1 to 3 substituents in substitutable positions, and when there are two or more substituents, each substituent may be the same or different.

The "optionally esterified carboxyl used in the Substituent group A includes, for example, an optionally substituted $C_{1-6}$ alkoxy-carbonyl (e.g., methoxycarbonyl, ethoxycarbonyl, propoxycarbonyl, tert-butoxycarbonyl, etc.), an optionally substituted $C_{6-14}$ aryloxy-carbonyl (e.g., phenoxycarbonyl, etc.), an optionally substituted $C_{7-16}$ aralkyloxy-carbonyl (e.g., benzyloxycarbonyl, phenethyloxycarbonyl, etc.), and the like.

The "$C_{1-6}$ alkyl" in the "optionally substituted $C_{1-6}$ alkyl" used in the Substituent group A includes, for example, methyl, ethyl, propyl, isopropyl, butyl, isobutyl, sec-butyl, tert-butyl, pentyl, isopentyl, neopentyl, hexyl, etc.

The "$C_{2-6}$ alkenyl" in the "optionally substituted $C_{2-6}$ alkenyl" used in the Substituent group A includes, for example, vinyl, propenyl, isopropenyl, 2-buten-1-yl, 4-penten-1-yl, 5-hexen-1-yl, etc.

The "$C_{2-6}$ alkynyl" in the "optionally substituted $C_{2-6}$ alkynyl" used in the Substituent group A includes, for example, 2-butyn-1-yl, 4-pentyn-1-yl, 5-hexyn-1-yl, etc.

The "$C_{3-8}$ cycloalkyl" in the "optionally substituted $C_{3-8}$ cycloalkyl" used in the Substituent group A includes, for example, cyclopropyl, cyclobutyl, cyclopentyl, cyclohexyl, etc.

The $C_{6-14}$ aryl in the optionally substituted $C_{6-14}$ aryl used in the Substituent group A includes, for example, phenyl, 1-naphthyl, 2-naphthyl, 2-biphenylyl, 3-biphenylyl, 4-biphenylyl, 2-anthryl, etc.

The "$C_{7-16}$ aralkyl" in the "optionally substituted $C_{7-16}$ aralkyl" used in the Substituent group A includes, for example, benzyl, phenethyl, diphenyllmethyl, 1-naphthylmethyl, 2-naphthylmethyl, 2,2-diphenyllethyl, 3-phenylpropyl, 4-phenylbutyl, 5-phenylpentyl, 2-biphenylylmethyl, 3-biphenylylmethyl, 4-biphenylylmethyl), etc.

The "$C_{1-6}$ alkoxy" in the "optionally substituted $C_{1-6}$ alkoxy" used in the Substituent group A includes, for example, methoxy, ethoxy, propoxy, isopropoxy, butoxy, isobutoxy, sec-butoxy, pentyloxy, hexyloxy, etc.

The "$C_{6-14}$ aryloxy" in the "optionally substituted $C_{6-14}$ aryloxy" used in the Substituent group A includes, for example, phenyloxy, 1-naphthyloxy, 2-naphthyloxy, etc.

The "$C_{7-16}$ aralkyloxy" in the "optionally substituted $C_{7-16}$ aralkyloxy" used in the Substituent group A includes, for example, benzyloxy, phenethyloxy, etc.

The "$C_{1-6}$ alkylthio" in the "optionally substituted $C_{1-6}$ alkylthio" used in the Substituent group A includes, for example, methylthio, ethylthio, propylthio, isopropylthio, butylthio, sec-butylthio, tert-butylthio, etc.

The "$C_{6-14}$ arylthio" in the "optionally substituted $C_{6-14}$ arylthio" used in the Substituent group A includes, for example, phenylthio, 1-naphthylthio, 2-naphthylthio, etc.

The "$C_{7-16}$ aralkylthio" in the "optionally substituted $C_{7-16}$ aralkylthio" used in the Substituent group A includes, for example, benzylthio, phenethylthio, etc.

The substituents used in the Substituent group A for these "$C_{1-6}$ alkoxy-carbonyl," "$C_{1-6}$ alkyl group," "$C_{2-6}$ alkenyl," "$C_{2-6}$ alkynyl," "$C_{1-6}$ alkoxy," "$C_{1-6}$ alkylthio," $C_{1-6}$ alkylamino," $C_{2-6}$ alkenyl-amino," "$C_{2-6}$ alkynylamino," $C_{1-6}$ alkoxyamino," "$C_{1-6}$ alkylcarbonyl," "$C_{1-6}$ alkylsulfonyl," "$C_{1-6}$ alkylsulfinyl," "$C_{1-6}$ alkylcarbonylamino," "$C_{1-6}$ alkoxy-carbonylamino," "$C_{1-6}$ alkylsulfonylamino," "$C_{1-6}$ alkylcarbonyloxy," "$C_{1-6}$ alkoxy-carbonyloxy," "mono-$C_{1-6}$ alkylcarbamoyloxy" and "di-$C_{1-6}$ alkylcarbamoyloxy" include 1 to 5 substituents selected from, for example, a halogen atom (e.g., fluorine atom, chlorine atom, bromine atom, iodine atom), carboxy, hydroxy, amino, a mono- or di-$C_{1-6}$ alkylamino, a mono- or di-$C_{6-14}$ arylamino, a $C_{3-8}$ cycloalkyl, a $C_{1-6}$ alkoxy, a $C_{1-6}$ alkoxy-carbonyl, a $C_{1-6}$ alkylthio, a $C_{1-6}$ alkylsulfinyl, a $C_{1-6}$ alkylsulfonyl, the optionally esterified carboxyl described above, carbamoyl, thiocarbamoyl, a mono-$C_{1-6}$ alkylcarbamoyl (e.g., methylcarbamoyl, ethylcarbamoyl, etc.), a di-$C_{1-6}$ alkylcarbamoyl (e.g., dimethylcarbamoyl, diethylcarbamoyl, ethylmethylcarbamoyl, etc.), a mono- or di-$C_{6-14}$ arylcarbamoyl (e.g., phenylcarbamoyl, 1-naphthylcarbamoyl, 2-naphthylcarbamoyl, etc.), a mono- or di-5- to 7-membered heterocyclic carbamoyl containing 1 to 4 hetero atoms of 1 or 2 species selected from nitrogen, sulfur and oxygen atoms in addition to carbon atoms (e.g., 2-pyridylcarbamoyl, 3-pyridylcarbamoyl, 4-pyridylcarbamoyl, 2-thienylcarbamoyl, 3-thienylcarbamoyl, etc.) and the like.

The substituents used in the Substituent group A for the "$C_{6-14}$ aryloxy-carbonyl," "$C_{7-16}$ aralkyloxy-carbonyl," "$C_{3-8}$ cycloalkyl," "$C_{6-14}$ aryl," "$C_{7-16}$ aralkyl," "$C_{6-14}$ aryloxy," "$C_{7-16}$ aralkyloxy," "$C_{6-14}$ arylthio," "$C_{7-16}$ aralkylthio," $C_{3-8}$ cycloalkyl-amino, $C_{6-14}$ arylamino, "$C_{3-8}$ cycloalkylcarbonyl," "$C_{6-14}$ aryl-carbonyl," "$C_{7-16}$ aralkylcarbonyl," "5- to 7-membered heterocyclic carbonyl containing 1 to 4 hetero atoms of 1 or 2 species selected from nitrogen, sulfur and oxygen atoms in addition to carbon atoms," "$C_{6-14}$ arylsulfonyl," "$C_{6-14}$ arylsulfinyl," "$C_{3-8}$ cycloalkylcarbonylamino," "$C_{6-14}$ aryl-carbonylamino," "$C_{6-14}$ arylsulfonylamino," "$C_{6-14}$ aryl-carbonyloxy" and "mono- or di-$C_{6-14}$ arylcarbamoyloxy" include 1 to 5 substituents selected from, for example, a halogen atom, hydroxy, carboxy, nitro, cyano, the optionally substituted $C_{1-6}$ alkyl described above, the optionally substituted $C_{2-6}$ alkenyl described above, the optionally substituted $C_{2-6}$ alkynyl described above, the optionally substituted $C_{3-8}$ cycloalkyl described above, the optionally substituted $C_{1-6}$ alkoxy described above, the optionally substituted $C_{1-6}$ alkylthio described above, the optionally substituted $C_{1-6}$ alkylsulfinyl described above, the optionally substituted $C_{1-6}$ alkylsulfonyl described above, the optionally esterified carboxyl described above, carbamoyl, thiocarbamoyl, a mono-$C_{1-6}$ alkylcarbamoyl, a di-$C_{1-6}$ alkylcarbamoyl, a mono- or di-$C_{6-14}$ arylcarbamoyl, a mono- or di-5- to 7-membered heterocyclic carbamoyl containing 1 to 4 hetero atoms of 1 or 2 species selected from nitrogen, sulfur and oxygen atoms in addition to carbon atoms, and the like.

The "optionally substituted heterocyclic group" used in the Substituent group A includes, for example, a 5- to 14-membered (monocyclic, bicyclic or tricyclic) heterocyclic group containing 1 to 4 hetero atoms of 1 or 2 species selected from nitrogen, sulfur and oxygen atoms in addition to carbon atoms, which may optionally be substituted with a halogen atom, hydroxy, carboxy, nitro, cyano, the optionally substituted $C_{1-6}$ alkyl described above, the optionally substituted $C_{2-6}$ alkenyl described above, the optionally substituted $C_{2-6}$ alkynyl described above, the optionally substituted $C_{3-8}$ cycloalkyl described above, the optionally substituted $C_{6-14}$ aryl described above, the optionally substituted $C_{1-6}$ alkoxy described above, the optionally substituted $C_{1-6}$ alkylthio described above, the optionally substituted $C_{6-14}$ arylthio described above, the optionally substituted $C_{7-16}$ aralkylthio described above, the optionally substituted $C_{1-6}$ alkylsulfinyl described above, the optionally substituted $C_{6-14}$ arylsulfinyl described above, the optionally substituted $C_{1-6}$ alkylsulfonyl described above, the optionally substituted $C_{6-14}$ arylsulfonyl described above, the optionally esterified carboxyl described above, carbamoyl, thiocarbamoyl, a mono-$C_{1-6}$ alkylcarbamoyl, a di-lower alkylcarbamoyl, a mono- or di-$C_{6-14}$ arylcarbamoyl, a mono- or di-5- or 7-membered heterocyclic carbamoyl containing 1 to 4 hetero atoms of 1 or 2 species selected from nitrogen, sulfur and oxygen atoms in addition to carbon atoms, or the like; preferably (i) a 5- to 14-membered (preferably, 5- to 10-membered) aromatic heterocyclic group, (ii) a 5- to 10-membered non-aromatic heterocyclic group or (iii) a monovalent group formed by removing one optional hydrogen atom from 7- to 10-membered bridged-hetero ring, and more preferably, a 5-memberedaromatic heterocyclic group. Specifically used are an aromatic heterocyclic group such as thienyl (e.g., 2-thienyl, 3-thienyl), furyl (e.g., 2-furyl, 3-furyl), pyridyl (e.g., 2-pyridyl, 3-pyridyl, 4-pyridyl), thiazolyl (e.g., 2-thiazolyl, 4-thiazolyl, 5-thiazolyl), oxazolyl (e.g., 2-oxazolyl, 4-oxazolyl), quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl), pyrazinyl, pyrimidinyl (e.g., 2-pyrimidinyl, 4-pyrimidinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), pyridazinyl (e.g., 3-pyridazinyl, 4-pyridazinyl), isothiazolyl (e.g., 3-isothiazolyl), isoxazolyl (e.g., 3-isoxazolyl), indolyl (e.g., 1-indolyl, 2-indolyl, 3-indolyl), 2-benzothiazolyl, benzo[b]thienyl, (e.g., 2-benzo[b]thienyl, 3-benzo[b]thienyl), benzo[b]furanyl (e.g., 2-benzo[b]furanyl, 3-benzo[b]furanyl), etc., a non-aromatic heterocyclic group such as pyrrolidinyl (e.g., 1-pyrrolidinyl, 2-pyrrolidinyl, 3-pyrrolidinyl), oxazolidinyl (e.g., 2-oxazolidinyl), imidazolinyl (e.g., 1-imidazolinyl, 2-imidazolinyl, 4-imidazolinyl), piperidinyl (e.g., 1-piperidinyl, 2-piperidinyl, 3-piperidinyl, 4-piperidinyl), piperazinyl (e.g., 1-piperazinyl, 2-piperazinyl), morpholino, thiomorpholino, etc.

The "optionally substituted carbamoyl group" used in the Substituent group A includes a carbamoyl group, which may optionally be substituted with the optionally substituted $C_{1-6}$ alkyl described above, an optionally substituted $C_{2-6}$ alkenyl, an optionally substituted $C_{2-6}$ alkynyl, an optionally substituted $C_{3-8}$ cycloalkyl, an optionally substituted $C_{6-14}$ aryl, an optionally substituted heterocyclic group, etc., and specific examples are carbamoyl, thiocarbamoyl, a mono-$C_{1-6}$ alkylcarbamoyl (e.g., methylcarbamoyl, ethylcarbamoyl, etc.), di-$C_{1-6}$ alkylcarbamoyl (e.g., dimethylcarbamoyl, diethylcarbamoyl, ethylmethylcarbamoyl, etc.), $C_{1-6}$ alkyl($C_{1-6}$ alkoxy) carbamoyl (e.g., methyl(methoxy)carbamoyl, ethyl(methoxy)carbamoyl), a mono- or di-$C_{6-14}$ arylcarbamoyl (e.g., phenylcarbamoyl, 1-naphthylcarbamoyl, 2-naphthylcarbamoyl, etc.), a mono- or di-5- to 7-memberedheterocyclic carbamoyl containing 1 to 4 hetero atoms of 1 or 2 species selected from nitrogen, sulfur and oxygen atoms in addition to carbon atoms (e.g., 2-pyridylcarbamoyl, 3-pyridylcarbamoyl, 4-pyridylcarbamoyl, 2-thienylcarbamoyl, 3-thienylcarbamoyl, etc.), a 5- to 7-membered cyclic carbamoyl (e.g., 1-pyrrolidinylcarbonyl, 1-piperidinylcarbonyl, hexamethyleneiminocarbonyl), and the like.

The "optionally substituted amino" used in the Substituent group A includes an amino, which may optionally be substituted with 1 or 2 groups selected from the optionally substituted $C_{1-6}$ alkyl, the optionally substituted $C_{2-6}$ alkenyl described above, the optionally substituted $C_{2-6}$ alkynyl described above, the optionally substituted $C_{3-8}$ cycloalkyl described above, the optionally substituted $C_{6-14}$ aryl described above, the optionally substituted $C_{1-6}$ alkoxy described above described above, formyl, the optionally substituted $C_{1-6}$ alkylcarbonyl described above, the optionally substituted $C_{3-8}$ cycloalkylcarbonyl described above, the optionally substituted $C_{6-14}$ aryl-carbonyl described above, the optionally substituted $C_{1-6}$ alkoxy-carbonyl described above, the optionally substituted $C_{1-6}$ alkylsulfonyl described above, an optionally substituted $C_{6-14}$ arylsulfonyl) and the like.

More preferably, the substituents for the "$C_{6-12}$ aromatic hydrocarbon group," "5- to 14-membered aromatic heterocyclic group consisting of 1 to 7 carbon atoms and hetero atoms selected from the group consisting of nitrogen, oxygen and sulfur atoms," "$C_{8-14}$ aromatic fused cyclic group," "5- to 14-membered aromatic fused heterocyclic group consisting of 3 to 11 carbon atoms and hetero atoms selected from the group consisting of nitrogen, oxygen and sulfur atoms," "non-aromatic cyclic hydrocarbon group of carbon atoms not greater than 7" and "non-aromatic heterocyclic group of carbon atoms not greater than 7" are a halogen atom, hydroxy, a $C_{1-6}$ alkoxy, an optionally halogenated $C_{1-6}$ alkyl, an optionally halogenated $C_{1-6}$ alkoxy, amino, nitro, cyano, etc.

Examples of $R^4$ used include:
(1) "a $C_{1-4}$ alkyl group having an optionally substituted $C_{6-12}$ aromatic hydrocarbon group" such as benzyl, 2-fluorobenzyl, 3-fluorobenzyl, 4-fluorobenzyl, 4-chlorobenzyl, 3,4-difluorobenzyl, 3,4-dichlorobenzyl, pentafluorobenzyl, 4-hydroxybenzyl, 4-methoxybenzyl, 3-trifluoromethylbenzyl, 4-aminobenzyl, 4-nitrobenzyl, 4-cyanobenzyl, phenethyl, etc.;
(2) "a $C_{1-4}$ alkyl group having an optionally substituted 5- to 14-membered aromatic heterocyclic group consisting of 1 to 7 carbon atoms and hetero atoms selected from the group consisting of nitrogen, oxygen and sulfur atoms" such as 2-pyridylmethyl, 3-pyridylmethyl, 4-pyridylmethyl, 2-thienylmethyl, 3-thienylmethyl, 4-thiazolylmethyl, etc.;
(3) "a $C_{1-4}$ alkyl group having an optionally substituted $C_{8-14}$ aromatic fused cyclic group" such as 1-naphthylmethyl, 2-naphthylmethyl, inden-2-ylmethyl, etc.;
(4) "a $C_{1-4}$ alkyl group having an optionally substituted 5- to 14-membered aromatic fused heterocyclic group consisting of 3 to 11 carbon atoms and hetero atoms selected from the group consisting of nitrogen, oxygen and sulfur atoms" such as 3-indolemethyl, 1-formylindol-3-ylmethyl, 3-benzo[b]thienylmethyl, 2-quinolylmethyl, etc.;
(5) "a $C_{1-4}$ alkyl group having an optionally substituted non-aromatic cyclic hydrocarbon group having carbon atoms not greater than 7" such as cyclohexylmethyl, cyclopentylmethyl, indan-2-ylmethyl, etc.;
(6) "a $C_{1-4}$ alkyl group having an optionally substituted non-aromatic heterocyclic group having carbon atoms not greater than 7" such as 4-piperidinylmethyl, tetrahydrofurfuryl, tetrahydrofuran-2-yl, tetrahydropyran-3-yl, indolin-3-yl, etc., preferably, benzyl, 2-fluorobenzyl, 3-fluorobenzyl, 4-fluorobenzyl, 4-hydroxybenzyl, 4-aminobenzyl, 4-nitrobenzyl, 4-chlorobenzyl, 4-methoxybenzyl, 4-cyanobenzyl, 3-trifluoromethylbenzyl, 3,4-dichlorobenzyl, 3,4-difluorobenzyl, pentafluorobenzyl, 3-pyridylmethyl, 4-pyridylmethyl, 3-indolemethyl, 1-formylindol-3-ylmethyl, 3-benzo[b]thienylmethyl, 2-quinolylmethyl, 1-naphthylmethyl, 2-naphthylmethyl, cyclohexylmethyl, phenethyl, etc., and more preferably, benzyl, 2-fluorobenzyl, 3-fluorobenzyl, 4-fluorobenzyl, 4-hydroxybenzyl, 4-aminobenzyl, 4-nitrobenzyl, 4-chlorobenzyl, 4-methoxybenzyl, 4-cyanobenzyl, 3-trifluoromethylbenzyl, 3,4-dichlorobenzyl, 3,4-difluorobenzyl, pentafluorobenzyl, 3-pyridylmethyl, 4-pyridylmethyl, 3-indolemethyl, 3-benzo[b]thienylmethyl, 1-naphthylmethyl, 2-naphthylmethyl, cyclohexylmethyl, etc.

$Q^1$ represents a $C_{1-4}$ alkyl group optionally substituted with a substituent selected from the group consisting of:
(1) an optionally substituted $C_{6-12}$ aromatic hydrocarbon group;
(2) an optionally substituted 5- to 14-membered aromatic heterocyclic group consisting of 1 to 7 carbon atoms and hetero atoms selected from the group consisting of nitrogen, oxygen and sulfur atoms;
(3) an optionally substituted $C_{8-14}$ aromatic fused cyclic group;
(4) an optionally substituted 5- to 14-membered aromatic fused heterocyclic group consisting of 3 to 11 carbon atoms and hetero atoms selected from the group consisting of nitrogen, oxygen and sulfur atoms;

(5) an optionally substituted non-aromatic cyclic hydrocarbon group having carbon atoms not greater than 7; and
(6) an optionally substituted non-aromatic heterocyclic group having carbon atoms not greater than 7; and the same substituents as in $R^4$ are used.

Examples of $Q^1$ include:
(1) "a $C_{1-4}$ alkyl group having an optionally substituted $C_{6-12}$ aromatic hydrocarbon group" such as benzyl, 2-fluorobenzyl, 3-fluorobenzyl, 4-fluorobenzyl, 4-chlorobenzyl, 3,4-difluorobenzyl, 3,4-dichlorobenzyl, pentafluorobenzyl, 4-hydroxybenzyl, 4-methoxybenzyl, 4-trifluoromethylbenzyl, 4-aminobenzyl, 4-nitrobenzyl, 4-cyanobenzyl, phenethyl, etc.;
(2) "a $C_{1-4}$ alkyl group having an optionally substituted 5- to 14-membered aromatic heterocyclic group consisting of 1 to 7 carbon atoms and hetero atoms selected from the group consisting of nitrogen, oxygen and sulfur atoms" such as 2-pyridylmethyl, 3-pyridylmethyl, 4-pyridylmethyl, 2-thienylmethyl, 3-thienylmethyl, 4-thiazolylmethy, etc.;
(3) "a $C_{1-4}$ alkyl group having optionally substituted $C_{8-14}$ aromatic fused cyclic group," such as 1-naphthylmethyl, 2-naphthylmethyl, inden-2-ylmethyl;
(4) "a $C_{1-4}$ alkyl group having an optionally substituted 5- to 14-membered aromatic fused heterocyclic group consisting of 3 to 11 carbon atoms and hetero atoms selected from the group consisting of nitrogen, oxygen and sulfur atoms" such as 3-indolemethyl, 1-formylindol-3-ylmethyl, 3-benzo[b]thienylmethyl, 2-quinolylmethyl, etc.;
(5) "a $C_{1-4}$ alkyl group having an optionally substituted non-aromatic cyclic hydrocarbon group having carbon atoms not greater than 7" such as cyclohexylmethyl, cyclopentylmethyl, indan-2-ylmethyl, etc.;
(6) "a $C_{1-4}$ alkyl group having an optionally substituted non-aromatic heterocyclic group having carbon atoms not greater than 7" such as 4-piperidinylmethyl, tetrahydrofurfuryl, tetrahydrofuran-2-yl, tetrahydropyran-3-yl, indolin-3-yl, etc.; preferably, cyclohexylmethyl, benzyl, 4-fluorobenzyl, 4-hydroxybenzyl, 4-methoxybenzyl, pentafluorobenzyl, 2-pyridylmethyl, 4-pyridylmethyl, 1-naphthylmethyl, 2-naphthylmethyl, 3-indolemethyl, 2-thienylmethyl, etc. and more preferably, benzyl, 4-fluorobenzyl, cyclohexylmethyl, etc.

$Q^2$ represents (1) $CH_2$, which may optionally be substituted with an optionally substituted $C_{1-4}$ alkyl group with a substituent selected from the group consisting of carbamoyl group and hydroxyl group, (2) NH, which may optionally be substituted with an optionally substituted $C_{1-4}$ alkyl group with a substituent selected from the group consisting of carbamoyl group and hydroxyl group, or (3) O.

Examples of the "$C_{1-4}$ alkyl group" used are methyl, ethyl, propyl, isopropyl, butyl, isobutyl, sec-butyl, tert-butyl, etc.

Preferably, $Q^2$ is $CH_2$, $CH(CH_3)$, $CH(CH_2OH)$, NH, or the like.

Y represents a group represented by formula: —CONH—, —CSNH—, —CH$_2$NH—, —NHCO—, —CH$_2$O—, —CH$_2$S—, —COO—, —CSO—, —CH$_2$CH$_2$—, or —CH=CH—, which may optionally be substituted with a $C_{1-6}$ alkyl group.

Examples of the "$C_{1-6}$ alkyl group" used are methyl, ethyl, propyl, isopropyl, butyl, isobutyl, sec-butyl, tert-butyl, pentyl, isopentyl, neopentyl, hexyl, etc.

Preferably, Y is a group represented by formula: —CONH—, —CSNH—, —NHCO—, —CH$_2$NH—, —CH$_2$O—, —COO— or —CSO— (more preferably, the group represented by formula: —CONH—, —CSNH—, —NHCO— or —CH$_2$NH—).

$Z^9$ represents hydrogen atom, O or S, preferably O or S;
wherein, when $Z^9$ represents hydrogen atom, a structure of the moiety represented by >C=$Z^9$ indicates a structure of >CH$_2$.

P and P', which may be the same or different, each may form a ring by combining P and P' or P and $Q^1$ together and represents:
(1) hydrogen atom;
(2) an optional amino acid residue continuously or discontinuously bound from the C terminus of the 1-48 amino acid sequence in the amino acid sequence represented by SEQ ID NO: 1;
(3) a group represented by formula: $J^1$-$J^2$-C($J^3$)($Q^3$)$Y^1$C($J^4$)($Q^4$)$Y^2$C($J^5$)($Q^5$)$Y^3$C($J^6$)($Q^6$)C(=$Z^{10}$)— (wherein each symbol has the same significance as described above);
(4) a group represented by formula: -$J^1$-$J^2$-C($J^7$)($Q^7$)$Y^2$C($J^8$)($Q^8$)$Y^3$C($J^9$)($Q^9$)C(=$Z^{10}$)— (wherein each symbol has the same significance as described above);
(5) a group represented by formula: $J^1$-$J^2$-C($J^{10}$)($Q^{10}$)$Y^3$C($J^{11}$)($Q^{11}$)C(=$Z^{10}$)— (wherein each symbol has the same significance as described above);
(6) a group represented by formula: $J^1$-$J^2$-C($J^{12}$)($Q^{12}$)C(=$Z^{10}$)— (wherein each symbol has the same significance as described above); or,
(7) a group represented by formula: $J^1$ (wherein $J^1$ has the same significance as described above).

Specific examples of the "optional amino acid residue continuously or discontinuously bound from the C terminus of the 1-48 amino acid sequence represented by SEQ ID NO: 1" used include:

```
(1) Asn- (2) Trp Asn-, (3) Asn Trp Asn-, (4) Tyr Asn Trp Asn-, (5) Asn Tyr Asn Trp Asn-, (6) Pro Asn Tyr Asn Trp Asn-, (7) Leu Pro Asn Tyr Asn Trp Asn-, (8) Asp Leu Pro Asn Tyr Asn Trp Asn-, (9) Lys Asp Leu Pro Asn Tyr Asn Trp Asn-,

(10) Glu Lys Asp Leu Pro Asn Tyr Asn Trp Asn-,

(11) Arg Glu Lys Asp Leu Pro Asn Tyr Asn Trp Asn-,
```

-continued

(12) Gln Arg Glu Lys Asp Leu Pro Asn Tyr Asn Trp Asn-,

(13) Val Gln Arg Glu Lys Asp Leu Pro Asn Tyr Asn Trp Asn-,

(14) Leu Val Gln Arg Glu Lys Asp Leu Pro Asn Tyr Asn Trp Asn-,

(15) Val Leu Val Gln Arg Glu Lys Asp Leu Pro Asn Tyr Asn Trp Asn-,

(16) Ala Val Leu Val Gln Arg Glu Lys Asp Leu Pro Asn Tyr Asn Trp Asn-,

(17) Gly Ala Val Leu Val Gln Arg Glu Lys Asp Leu Pro Asn Tyr Asn Trp Asn-,

(18) Gln Gly Ala Val Leu Val Gln Arg Glu Lys Asp Leu Pro Asn Tyr Asn Trp Asn-,

(19) Pro Gln Gly Ala Val Leu Val Gln Arg Glu Lys Asp Leu Pro Asn Tyr Asn Trp Asn-,

(20) Ala Pro Gln Gly Ala Val Leu Val Gln Arg Glu Lys Asp Leu Pro Asn Tyr Asn Trp Asn-,

(21) Pro Ala Pro Gln Gly Ala Val Leu Val Gln Arg Glu Lys Asp Leu Pro Asn Tyr Asn Trp Asn-,

(22) Ile Pro Ala Pro Gln Gly Ala Val Leu Val Gln Arg Glu Lys Asp Leu Pro Asn Tyr Asn Trp Asn-,

(23) Gln Ile Pro Ala Pro Gln Gly Ala Val Leu Val Gln Arg Glu Lys Asp Leu Pro Asn Tyr Asn Trp Asn-,

(24) Arg Gln Ile Pro Ala Pro Gln Gly Ala Val Leu Val Gln Arg Glu Lys Asp Leu Pro Asn Tyr Asn Trp Asn-,

(25) Ser Arg Gln Ile Pro Ala Pro Gln Gly Ala Val Leu Val Gln Arg Glu Lys Asp Leu Pro Asn Tyr Asn Trp Asn-,

(26) His Ser Arg Gln Ile Pro Ala Pro Gln Gly Ala Val Leu Val Gln Arg Glu Lys Asp Leu Pro Asn Tyr Asn Trp Asn-,

(27) Pro His Ser Arg Gln Ile Pro Ala Pro Gln Gly Ala Val Leu Val Gln Arg Glu Lys Asp Leu Pro Asn Tyr Asn Trp Asn-,

(28) Ala Pro His Ser Arg Gln Ile Pro Ala Pro Gln Gly Ala Val Leu Val Gln Arg Glu Lys Asp Leu Pro Asn Tyr Asn Trp Asn-,

(29) Ser Ala Pro His Ser Arg Gln Ile Pro Ala Pro Gln Gly Ala Val Leu Val Gln Arg Glu Lys Asp Leu Pro Asn Tyr Asn Trp Asn-,

(30) Leu Ser Ala Pro His Ser Arg Gln Ile Pro Ala Pro Gln Gly Ala Val Leu Val Gln Arg Glu Lys Asp Leu Pro Asn Tyr Asn Trp Asn-,

(31) Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn-,

(32) Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn-,

(33) Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn-,

(34) Gln Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn-,

(35) Arg Gln Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn-,

(36) Ser Arg Gln Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn-,

(37) Gly Ser Arg Gln Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn-,

(38) Ser Gly Ser Arg Gln Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn-,

(39) Ser Ser Gly Ser Arg Gln Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn-,

(40) Glu Ser Ser Gly Ser Arg Gln Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn-,

-continued

(41) Pro Glu Ser Ser Gly Ser Arg Gln Gln Pro Gly Leu Ser Ala Pro His Ser Arg Gln Ile
Pro Ala Pro Gln Gly Ala Val Leu Val Gln Arg Glu Lys Asp Leu Pro Asn Tyr Asn Trp
Asn-,

(42) Pro Pro Glu Ser Ser Gly Ser Arg Gln Gln Pro Gly Leu Ser Ala Pro His Ser Arg Gln
Ile Pro Ala Pro Gln Gly Ala Val Leu Val Gln Arg Glu Lys Asp Leu Pro Asn Tyr Asn
Trp Asn-,

(43) Pro Pro Pro Glu Ser Ser Gly Ser Arg Gln Gln Pro Gly Leu Ser Ala Pro His Ser Arg
Gln Ile Pro Ala Pro Gln Gly Ala Val Leu Val Gln Arg Glu Lys Asp Leu Pro Asn Tyr
Asn Trp Asn-,

(44) Ser Pro Pro Pro Glu Ser Ser Gly Ser Arg Gln Gln Pro Gly Leu Ser Ala Pro His Ser
Arg Gln Ile Pro Ala Pro Gln Gly Ala Val Leu Val Gln Arg Glu Lys Asp Leu Pro Asn
Tyr Asn Trp Asn-,

(45) Leu Ser Pro Pro Pro Glu Ser Ser Gly Ser Arg Gln Gln Pro Gly Leu Ser Ala Pro His
Ser Arg Gln Ile Pro Ala Pro Gln Gly Ala Val Leu Val Gln Arg Glu Lys Asp Leu Pro
Asn Tyr Asn Trp Asn-,

(46) Ser Leu Ser Pro Pro Pro Glu Ser Ser Gly Ser Arg Gln Gln Pro Gly Leu Ser Ala Pro
His Ser Arg Gln Ile Pro Ala Pro Gln Gly Ala Val Leu Val Gln Arg Glu Lys Asp Leu
Pro Asn Tyr Asn Trp Asn-,

(47) Thr Ser Leu Ser Pro Pro Pro Glu Ser Ser Gly Ser Arg Gln Gln Pro Gly Leu Ser Ala
Pro His Ser Arg Gln Ile Pro Ala Pro Gln Gly Ala Val Leu Val Gln Arg Glu Lys Asp
Leu Pro Asn Tyr Asn Trp Asn-,

(48) Gly Thr Ser Leu Ser Pro Pro Pro Glu Ser Ser Gly Ser Arg Gln Gln Pro Gly Leu Ser
Ala Pro His Ser Arg Gln Ile Pro Ala Pro Gln Gly Ala Val Leu Val Gln Arg Glu Lys
Asp Leu Pro Asn Tyr Asn Trp Asn-, etc.

$J^1$ represents (a) hydrogen atom or (b) (i) a $C_{1-15}$ acyl group, (ii) a $C_{1-15}$ alkyl group, (iii) a $C_{6-14}$ aryl group, (iv) carbamoyl group, (v) carboxyl group, (vi) sulfino group, (vii) amidino group, (viii) glyoxyloyl group or (ix) amino group, which groups may optionally be substituted with a substituent containing an optionally substituted cyclic group.

The "cyclic group" used includes, for example, "an optionally substituted an aromatic hydrocarbon group," "an optionally substituted aromatic heterocyclic group," "an optionally substituted an aromatic fused cyclic group," "an optionally substituted an aromatic fused heterocyclic group," "an optionally substituted non-aromatic cyclic hydrocarbon group," "an optionally substituted non-aromatic heterocyclic group", etc., and as the "aromatic hydrocarbon group," "aromatic heterocyclic group," "aromatic fused cyclic group" and "aromatic fused heterocyclic group," the same groups given above are used.

The "non-aromatic cyclic hydrocarbon group" used includes, for example, a $C_{3-8}$ cycloalkyl group such as cyclopropyl, cyclobutyl, cyclopentyl, cyclohexyl, etc.

The "non-aromatic heterocyclic group" used includes, for example, a 5- or 10-membered non-aromatic heterocyclic group containing 1 to 4 hetero atoms of 1 or 2 species selected from nitrogen, sulfur and oxygen atoms in addition to 1 to 7 carbon atoms such as pyrrolidinyl (e.g., 1-pyrrolidinyl, 2-pyrrolidinyl, 3-pyrrolidinyl), oxazolidinyl (e.g., 2-oxazolidinyl), imidazolinyl (e.g., 1-imidazolinyl, 2-imidazolinyl, 4-imidazolinyl), piperidinyl (e.g., 1-piperidinyl, 2-piperidinyl, 3-piperidinyl, 4-piperidinyl), piperazinyl (e.g., 1-piperazinyl, 2-piperazinyl), morpholino, thiomorpholino, etc.

The substituent optionally present on the "cyclic group" includes the same substituents given for the Substituent group A described above.

The "$C_{1-15}$ acyl group" used includes, for example, formyl, a $C_{1-14}$ alkylcarbonyl (e.g., a $C_{1-6}$ alkylcarbonyl such as acetyl, propionyl, pivaloyl, etc.) and the like.

Examples of the "$C_{1-15}$ alkyl group" used include methyl, ethyl, propyl, isopropyl, butyl, isobutyl, sec-butyl, tert-butyl, pentyl, isopentyl, neopentyl, hexyl, heptyl, octyl, nonanyl, decanyl, etc.

Examples of the "$C_{6-14}$ aryl group" used include phenyl, 1-naphthyl, 2-naphthyl, biphenyl, etc.

(1) The $C_{1-15}$ acyl group, which may optionally be substituted with a substituent containing a cyclic group, includes (i) formyl, (ii) a $C_{1-14}$ alkylcarbonyl (e.g., a $C_{1-6}$ alkylcarbonyl such as acetyl, propionyl, pivaloyl, etc.), (iii) a $C_{3-8}$ cycloalkylcarbonyl (e.g., cyclopropylcarbonyl, cyclopentylcarbonyl, cyclohexylcarbonyl, 1-methylcyclohexylcarbonyl, etc.), (iv) a $C_{3-8}$ cycloalkyl-$C_{1-6}$ alkylcarbonyl (e.g., cyclopropylacetyl, cyclopentylacetyl, cyclohexylacetyl, etc.), (v) a $C_{6-14}$ aryl-carbonyl (e.g., benzoyl, 1-naphthoyl, 2-naphthoyl, etc.), a $C_{6-14}$ aralkylcarbonyl (e.g., phenylacetyl, 3-phenylpropionyl, etc.), (vi) a 5- to 7-membered monocyclic heterocyclic carbonyl containing 1 to 4 hetero atoms of 1 or 2 species selected from nitrogen, sulfur and oxygen atoms in addition to carbon atoms (e.g., nicotinoyl, isonicotinoyl, thenoyl, furoyl, morpholinocarbonyl, thiomorpholinocarbonyl, piperazin-1-ylcarbonyl, pyrrolidin-1-ylcarbonyl, etc.), (vii) a 5- to 7-membered monocyclic heterocyclic-$C_{1-6}$ alkylcarbonyl containing 1 to 4 hetero atoms of 1 or 2 species selected from nitrogen, sulfur and oxygen atoms in addition to carbon atoms (e.g., 3-pyridylacetyl, 4-pyridylacetyl, 2-thienylacetyl, 2-furylacetyl, morpholinoacetyl, thiomorpholinoacetyl, piperidin-2-acetyl, pyrrolidine-2-ylacetyl, etc.), (viii) a 5- to 14-membered (preferably, 5- to 10-membered) bicyclic or tricyclic aromatic heterocyclic carbonyl containing 1 to 4 hetero atoms of 1 or 2 species selected from nitrogen, sulfur and oxygen atoms in addition to 3 to 11 carbon atoms (e.g., 2-indolecarbonyl, 3-indolecarbonyl, 2-quinolylcarbonyl, 1-isoquinolylcarbonyl, 2-benzo[b]thienylcarbonyl, 2-benzo[b]furanylcarbonyl, etc.), (ix) a 5- to 14-membered (preferably 5- to 10-membered) bicyclic or tricyclic aromatic heterocyclic-$C_{1-6}$ alkylcarbonyl containing 1 to 4 hetero atoms of 1 or 2 species selected from nitrogen, sulfur and oxygen atoms in addition to 3 to 11 carbon atoms (e.g., 2-indoleacetyl, 3-indoleacetyl, 2-quinolylacetyl, 1-isoquinolylacetyl, 2-benzo[b]thienylacetyl, 2-benzo[b]furanylacetyl, etc.), etc., preferably, acetyl, 2-indolecarbonyl, 3-indolecarbonyl, 3-indoleacetyl, 3-indolepropionyl, 2-indolinecarbonyl, 3-phenylpropionyl, diphenylacetyl, 2-pyridinecarbonyl, 3-pyridinecarbonyl, 4-pyridinecarbonyl, 1-pyridinioacetyl, 2-pyridineacetyl, 3-pyridineacetyl, 4-pyridineacetyl, 3-(1-pyridinio)propionyl, 3-(pyridin-2-yl)propionyl, 3-(pyridin-3-yl)propionyl, 3-(pyridin-4-yl)propionyl, 4-imidazoleacetyl, cyclohexanecarbonyl, 1-piperidineacetyl, 1-methyl-1-piperidinioacetyl, 4-piperidinecarbonyl, 2-pyrimidinecarbonyl, 4-pyrimidinecarbonyl, 5-pyrimidinecarbonyl, 2-pyrimidineacetyl, 4-pyrimidineacetyl, 5-pyrimidineacetyl, 3-(pyrimidine-2-yl)propionyl, 3-(pyrimidine-4-yl)propionyl, 3-(pyrimidine-5-yl)propionyl, butanoyl, hexanoyl, octanoyl, D-glucuronyl, amino-(4-hydroxyphenyl)acetyl), etc.

(2) The $C_{1-15}$ alkyl group used, which may optionally be substituted with a substituent containing a cyclic group, includes, for example, (i) a mono- or di-$C_{1-15}$ alkyl (e.g., methyl, ethyl, propyl, isopropyl, butyl, isobutyl, sec-butyl, tert-butyl, pentyl, isopentyl, neopentyl, hexyl, heptyl, octyl, nonanyl, decanyl), (ii) a mono- or di-$C_{3-8}$ cycloalkyl (e.g., cyclopropyl, cyclopentyl, etc.), (iii) a mono- or di-$C_{3-8}$ cycloalkyl-$C_{1-7}$ alkyl (e.g., cyclopropylmethyl, cyclopentylmethyl, cyclohexylethyl, etc.), (iv) a mono- or di-$C_{7-15}$ aralkyl (e.g., benzyl, phenethyl, etc.), (v) a mono- or di-5- to 7-membered monocyclic heterocyclic-$C_{1-6}$ alkyl group containing 1 to 4 hetero atoms of 1 or 2 species selected from nitrogen, sulfur and oxygen atoms in addition to carbon atoms (e.g., 3-pyridylmethyl, 4-pyridylmethyl, 2-thienylmethyl, furfuryl, etc.), (vi) a mono- or di-5- to 14-membered (preferably, 5- to 10-membered) bicyclic or tricyclic aromatic heterocyclic-$C_{1-6}$ alkyl group containing 1 to 4 hetero atoms of 1 or 2 species selected from nitrogen, sulfur and oxygen atoms in addition to 3 to 11 carbon atoms (e.g., 2-indolemethyl, 3-indolemethyl, 3-(indol-3-yl)propyl, 2-quinolylmethyl, 1-isoquinolylmethyl, 2-benzo[b]thienylmethyl, 2-benzo[b]furanylmethyl, etc.), etc., preferably, methyl, ethyl, benzyl, 3-(indol-3-yl)propyl, etc.

(3) The $C_{6-14}$ aryl group used, which may optionally be substituted with a substituent containing a cyclic group, includes, for example, a $C_{6-14}$ aryl group (e.g., phenyl, naphthyl, biphenyl), which may optionally be substituted with (i) a $C_{6-14}$ carbocyclic group (e.g., cycloalkyl, phenyl, 1-naphthyl, 2-naphthyl, etc.), (ii) a 5- to 7-membered monocyclic heterocyclic group containing 1 to 4 hetero atoms of 1 or 2 species selected from nitrogen, sulfur and oxygen atoms in addition to carbon atoms (e.g., 3-pyridyl, 2-thienyl, etc.), (iii) a 5- to 14-membered containing 1 to 4 hetero atoms of 1 or 2 species selected from nitrogen, sulfur and oxygen atoms in addition to 3 to 11 carbon atoms (preferably, 5- to 10-membered) bicyclic or tricyclic aromatic heterocyclic group (e.g., 2-indolyl, 3-indolyl, 2-quinolyl, 1-isoquinolyl, 2-benzo[b]thienyl, 2-benzo[b]furanyl, etc.), etc.

(4) The optionally substituted carbamoyl group used, which may optionally be substituted with a substituent containing a cyclic group, includes, for example, (i) carbamoyl, (ii) a mono- or di-$C_{1-15}$ alkylcarbamoyl group (e.g., methylcarbamoyl, ethylcarbamoyl, (iii) a mono- or di-$C_{3-8}$ cycloalkyl-carbamoyl (e.g., cyclopropylcarbamoyl, cyclopentylcarbamoyl, cyclohexylcarbamoyl, etc.), (iv) a mono- or di-$C_{3-8}$ cycloalkyl-$C_{1-6}$ alkyl-carbamoyl (e.g., cyclopropylmethylcarbamoyl, cyclopentylmethylcarbamoyl, 2-cyclohexylethylcarbamoyl, etc.) (v) a mono- or di-$C_{6-14}$ aryl-carbamoyl (e.g., phenylcarbamoyl, etc.), a mono- or di-$C_{6-14}$ aralkyl-carbamoyl (e.g., benzylcarbamoyl, phenethylcarbamoyl, etc.), (vi) a mono- or di-5- to 7-membered monocyclic heterocyclic carbamoyl containing 1 to 4 hetero atoms of 1 or 2 species selected from nitrogen, sulfur and oxygen atoms in addition to carbon atoms (e.g., 3-pyridinecarbamoyl, 2-thiophenecarbamoyl, piperidin-3-ylcarbamoyl, etc.), (vii) a mono- or di-5- to 7-membered monocyclic heterocyclic-$C_{1-6}$ alkylcarbamoyl containing 1 to 4 hetero atoms of 1 or 2 species selected from nitrogen, sulfur and oxygen atoms in addition to carbon atoms (e.g., 3-pyridylmethylcarbamoyl, 2-(pyridin-2-yl)ethylcarbamoyl, 2-(piperidin-1-yl)ethylcarbamoyl, etc.), (viii) a mono- or di-5- to 14-membered containing 1 to 4 hetero atoms of 1 or 2 species selected from nitrogen, sulfur and oxygen atoms in addition to 3 to 11 carbon atoms (preferably, 5- to 10-membered) bicyclic or tricyclic aromatic heterocyclic carbamoyl (e.g., 4-indolecarbamoyl, 5-indolecarbamoyl, 3-quinolylcarbamoyl, 5-quinolylcarbamoyl, etc.), (ix) a mono- or di-5- to 14-membered (preferably, 5- to 10-membered) bicyclic or tricyclic aromatic heterocyclic-$C_{1-6}$ alkylcarbonyl containing 1 to 4 hetero atoms of 1 or 2 species selected from nitrogen, sulfur and oxygen atoms in addition to 3 to 11 carbon atoms (e.g., benzimidazole-2-ylmethylcarbamoyl, 2-(indol-3-yl)ethylcarbamoyl, etc.), (x) a 5- to 7-membered cyclic carbamoyl (e.g., 1-pyrrolidinylcarbonyl, 1-piperidinylcarbonyl, hexamethyleneiminocarbonyl, etc.), (xi) a $C_{1-15}$ acylcarbamoyl (the $C_{1-15}$ acyl herein has the same significance as for the "$C_{1-15}$ acyl group" in the "$C_{1-15}$ acyl group used, which may optionally be substituted with a substituent containing a cyclic group"), (xii) a $C_{1-15}$ alkylaminocarbamoyl (the $C_{1-15}$ alkyl herein has the same significance as for the "$C_{1-15}$ alkyl group" in the "$C_{1-15}$ alkyl group, which may optionally be substituted with a substituent containing a cyclic group"), (xiii) a $C_{6-14}$ arylaminocarbamoyl (the $C_{6-14}$ aryl group herein has the same significance as for the "$C_{6-14}$ aryl group, which may optionally be substituted with a substituent containing a cyclic group"), etc., preferably, 2-(indol-3-yl)ethylcarbamoyl, etc.

(5) The carboxyl group used, which may optionally be substituted with a substituent containing a cyclic group, includes, for example, (i) a $C_{1-15}$ alkyloxycarbonyl (the $C_{1-15}$ alkyl herein has the same significance as for the "$C_{1-15}$ alkyl group" in the "$C_{1-15}$ alkyl group, which may optionally be substituted with a substituent containing a cyclic group," e.g., tert-butyloxycarbonyl, benzyloxycarbonyl, 9-fluorenylmethoxycarbonyl), (ii) a $C_{6-14}$ aryloxycarbonyl (the $C_{6-14}$ aryl herein has the same significance as for the "$C_{6-14}$ aryl group" in the "$C_{6-14}$ aryl group, which may optionally be substituted with a substituent containing a cyclic group," e.g., phenoxycarbonyl), etc.

(6) The sulfino group used, which may optionally be substituted with a substituent containing a cyclic group, includes, for example, (i) a $C_{1-15}$ alkylsulfonyl (the $C_{1-15}$ alkyl herein has the same significance as for the "$C_{1-15}$ alkyl group" in the "$C_{1-15}$ alkyl group, which may optionally be substituted with a substituent containing a cyclic group," e.g., benzylsulfonyl), (ii) a $C_{6-14}$ arylsulfonyl (the $C_{6-14}$ aryl herein has the same significance as for the "$C_{6-14}$ aryl group" in the "$C_{6-14}$ aryl group, which may optionally be substituted with a substituent containing a cyclic group," e.g., tosyl), etc.

(7) The amidino group used, which may optionally be substituted with a substituent containing a cyclic group, includes, for example, (i) amidino, (ii) a $C_{1-15}$ alkylamidino (the $C_{1-15}$ alkyl herein has the same significance as for the "$C_{1-15}$ alkyl group" in the "$C_{1-15}$ alkyl group, which may optionally be substituted with a substituent containing a cyclic group," e.g., N-methylamidino), (iii) a $C_{1-15}$ acylamidino (the $C_{1-15}$ acyl herein has the same significance as for the "$C_{1-15}$ acyl group" in the "$C_{1-15}$ acyl group, which may optionally be substituted with a substituent containing a cyclic group," e.g., N-acetylamidino), etc.

(8) The glyoxyloyl group used, which may optionally be substituted with a substituent containing a cyclic group, includes, for example, (i) a $C_{1-15}$ alkyloxalyl (the $C_{1-15}$ alkyl herein has the same significance as for the "$C_{1-15}$ alkyl group" in the "$C_{1-15}$ alkyl group, which may optionally be substituted with a substituent containing a cyclic group," e.g., ethyloxalyl), (ii) a $C_{6-14}$ aryloxalyl (the $C_{6-14}$ aryl herein has the same significance as for the "$C_{6-14}$ aryl group" in the "$C_{6-14}$ aryl group, which may optionally be substituted with a substituent containing a cyclic group," e.g., phenyloxalyl), etc.

(9) The amino group used, which may optionally be substituted with a substituent containing a cyclic group, includes, for example, (i) a $C_{1-15}$ alkylamino (the $C_{1-15}$ alkyl herein has the same significance as for the "$C_{1-15}$ alkyl group" in the "$C_{1-15}$ alkyl group, which may optionally be substituted with a substituent containing a cyclic group."

Among those described above, $J^1$ is preferably hydrogen atom, formyl, acetyl, 3-indolecarbonyl, 3-(indol-3-yl)propionyl, 3-phenylpropionyl, diphenylacetyl, 3-(pyridin-3-yl)propionyl, 4-imidazoleacetyl, cyclohexanecarbonyl, 1-piperidineacetyl, 1-methyl-1-piperidinioacetyl, 4-piperidinecarbonyl, hexanoyl, amino-(4-hydroxyphenyl)acetyl, D-glucuronyl, 2-(indol-3-yl)ethylcarbamoyl, tert-butyloxycarbonyl, 9-fluorenylmethoxycarbonyl, amidino, 4-guanidomethylbenzoyl, benzoyl, 3-indoleacetyl, benzyloxycarbonyl, tosyl, phenyl, benzyl, phenethyl, 3-pyridinecarbonyl, 2-pyridinecarbonyl, 4-pyridinecarbonyl, propionyl, isobutyryl, phenylacetyl, 2-methylnicotinoyl, 5-methylnicotinoyl, 6-methylnicotinoyl, pyrazinecarbonyl, cyclopropanecarbonyl, trifluoroacetyl, (R)-3-hydroxy-2-methylpropionyl, 2-hydroxyisobutyryl, 3-furancarbonyl, pyrrole-2-carbonyl, 4-imidazolecarbonyl, 6-hydroxynicotinoyl, 6-chloronicotinoyl, 6-(trifluoromethyl)nicotinoyl, dimethylcarbamoyl, 1-azetidinecarbonyl, 2-azetidinecarbonyl, 4-aminobenzoyl, 4-aminomethylbenzoyl, pyrrole-3-carbonyl, pyrimidine-4-carbonyl, pyrimidine-2-carbonyl, pyridazine-4-carbonyl, 6-aminocaproyl, glycyl, glycylglycyl, glycylglycylglycyl, alanylalanylalanyl, alanylalanylalanylalanyl, acetylglycyl, acetylglycylglycyl, acetylglycylglycylglycyl, acetylalanylalanylalanyl, acetylalanylalanylalanylalanyl, D-arginylglycyl, D-arginylglycylglycyl, D-arginylglycylglycylglycyl, D-arginylalanylalanylalanyl, D-arginylalanylalanylalanylalanyl, acetyl-D-arginylglycyl, acetyl-D-arginylglycylglycyl, acetyl-D-arginylglycylglycylglycyl, acetyl-D-arginylalanylalanylalanyl, acetyl-D-arginylalanylalanylalanylalanyl, cyclopropanecarbonyl, cyclopentanecarbonyl, cyclobutanecarbonyl, cyclohexanecarbonyl, 1-naphthoyl, 2-naphthoyl, arginyl, arginylarginyl, 6-(arginylamino)caproyl, 6-(D-arginylamino)caproyl, 6-(D-arginyl-D-arginylamino)caproyl, 6-(acetyl-D-arginylamino)caproyl, 6-((R)-2,3-diaminopropionylamino)caproyl, 6-(D-norleucylamino)caproyl, 3-(D-arginylamino)propionyl, 4-(D-arginylamino)butyryl, 4-(D-arginyl-D-arginylamino)butyryl, 4-(D-arginyl-D-arginyl-D-arginylamino)butyryl, 3-(4-hydroxyphenyl)propionyl, butyryl, methyl, adipoyl, pyroglutamyl, glycoloyl, etc., and more preferably used are hydrogen atom, formyl, acetyl, propionyl, 3-indolecarbonyl, 3-(indol-3-yl)propionyl, 3-phenylpropionyl, 3-(pyridin-3-yl)propionyl, 4-imidazoleacetyl, cyclohexanecarbonyl, hexanoyl, amino-(4-hydroxyphenyl)acetyl, 2-(indol-3-yl)ethylcarbamoyl, 9-fluorenylmethoxycarbonyl, amidino, 4-guanidomethylbenzoyl, benzoyl, 3-indoleacetyl, benzyl, phenethyl, 3-pyridinecarbonyl, 2-pyridinecarbonyl, 4-pyridinecarbonyl, isobutyryl, phenylacetyl, 6-methylnicotinoyl, pyrazinecarbonyl, cyclopropanecarbonyl, trifluoroacetyl, (R)-3-hydroxy-2-methylpropionyl, 2-hydroxyisobutyryl, 3-furancarbonyl, pyrrole-2-carbonyl, 4-imidazolecarbonyl, 6-hydroxynicotinoyl, 6-chloronicotinoyl, 6-(trifluoromethyl)nicotinoyl, dimethylcarbamoyl, 1-azetidinecarbonyl, 4-aminobenzoyl, 4-aminomethylbenzoyl, pyrrole-3-carbonyl, pyrimidine-4-carbonyl, pyrimidine-2-carbonyl, pyridazine-4-carbonyl, 6-aminocaproyl, cyclopropanecarbonyl, 2-naphthoyl, arginyl, 6-(arginylamino)caproyl, 6-(D-arginylamino)caproyl, 6-(D-arginyl-D-arginylamino)caproyl, 6-(acetyl-D-arginylamino)caproyl, 6-((R)-2,3-diaminopropionylamino)caproyl, 6-(D-norleucylamino)caproyl, 3-(D-arginylamino)propionyl, 4-(D-arginylamino)butyryl, 4-(D-arginyl-D-arginylamino)butyryl, 4-(D-arginyl-D-arginyl-D-arginylamino)butyryl, 3-(4-hydroxyphenyl)propionyl, butyryl, adipoyl, pyroglutamyl, etc.

$J^2$ represents (1) NH optionally substituted with a $C_{1-6}$ alkyl group, (2) $CH_2$ optionally substituted with a $C_{1-6}$ alkyl group, (3) O or (4) S.

The "$C_{1-6}$ alkyl group" used includes methyl, ethyl, propyl, isopropyl, butyl, isobutyl, sec-butyl, tert-butyl, pentyl, isopentyl, neopentyl, hexyl, etc.

Preferably, $J^2$ is NH.

$J^3$ through $J^{12}$ each represents hydrogen atom or a $C_{1-3}$ alkyl group.

The "$C_{1-3}$ alkyl group" used includes methyl, ethyl, propyl, isopropyl, etc.

Preferably, $J^3$ is hydrogen atom.
Preferably, $J^4$ is hydrogen atom.
Preferably, $J^5$ is hydrogen atom.
Preferably, $J^6$ is hydrogen atom.
Preferably, $J^7$ is hydrogen atom.
Preferably, $J^8$ is hydrogen atom.
Preferably, $J^9$ is hydrogen atom.
Preferably, $J^{10}$ is hydrogen atom.
Preferably, $J^{11}$ is hydrogen atom.
Preferably, $J^{12}$ is hydrogen atom.

$Q^3$ through $Q^{12}$ each represents a $C_{1-4}$ alkyl group, which may optionally have a substituent selected from the group consisting of:

(1) an optionally substituted $C_{6-12}$ aromatic hydrocarbon group;

(2) an optionally substituted 5- to 14-membered aromatic heterocyclic group consisting of 1 to 7 carbon atoms and hetero atoms selected from the group consisting of nitrogen, oxygen and sulfur atoms;

(3) an optionally substituted $C_{8-14}$ aromatic fused cyclic group;

(4) an optionally substituted 5- to 14-membered aromatic fused heterocyclic group consisting of 3 to 11 carbon atoms and hetero atoms selected from the group consisting of nitrogen, oxygen and sulfur atoms;

(5) an optionally substituted non-aromatic cyclic hydrocarbon group having carbon atoms not greater than 7;

(6) an optionally substituted non-aromatic heterocyclic group having carbon atoms not greater than 7;

(7) an optionally substituted amino group;

(8) an optionally substituted guanidino group;

(9) an optionally substituted hydroxyl group;

(10) an optionally substituted carboxyl group;

(11) an optionally substituted carbamoyl group; and,

(12) an optionally substituted sulfhydryl group; or hydrogen atom.

Preferably, $Q^3$ through $Q^9$ include a $C_{1-4}$ alkyl group having a substituent selected from the group consisting of:

(1) an optionally substituted $C_{6-12}$ aromatic hydrocarbon group;

(2) an optionally substituted 5- to 14-membered aromatic heterocyclic group consisting of 1 to 7 carbon atoms and hetero atoms selected from the group consisting of nitrogen, oxygen and sulfur atoms;
(3) an optionally substituted $C_{8-14}$ aromatic fused cyclic group;
(4) an optionally substituted 5- to 14-membered aromatic fused heterocyclic group consisting of 3 to 11 carbon atoms and hetero atoms selected from the group consisting of nitrogen, oxygen and sulfur atoms;
(5) an optionally substituted non-aromatic cyclic hydrocarbon group having carbon atoms not greater than 7;
(6) an optionally substituted non-aromatic heterocyclic group having carbon atoms not greater than 7;
(7) an optionally substituted amino group;
(8) an optionally substituted guanidino group;
(9) an optionally substituted hydroxyl group;
(10) an optionally substituted carboxyl group;
(11) an optionally substituted carbamoyl group; and,
(12) an optionally substituted sulfhydryl group; or hydrogen atom.

The "optionally substituted $C_{6-12}$ aromatic hydrocarbon group," "optionally substituted 5- to 14-membered aromatic heterocyclic group consisting of 1 to 7 carbon atoms and hetero atoms selected from the group consisting of nitrogen, oxygen and sulfur atoms," "optionally substituted $C_{8-14}$ aromatic fused cyclic group," "optionally substituted 5- to 14-membered aromatic fused heterocyclic group consisting of 3 to 11 carbon atoms and hetero atoms selected from the group consisting of nitrogen, oxygen and sulfur atoms," "optionally substituted non-aromatic cyclic hydrocarbon group having carbon atoms not greater than 7" and "optionally substituted non-aromatic heterocyclic group having carbon atoms not greater than 7" used are the same as those given above.

(1) As the $C_{1-4}$ alkyl group having an optionally substituted $C_{6-12}$ aromatic hydrocarbon group, there are used, for example, benzyl, 4-hydroxybenzyl, 2-chlorobenzyl, 3-chlorobenzyl, 4-chlorobenzyl, 4-aminobenzyl, etc.

(2) As the $C_{1-4}$ alkyl group having an optionally substituted 5- to 14-membered aromatic heterocyclic group consisting of 1 to 7 carbon atoms and hetero atoms selected from the group consisting of nitrogen, oxygen and sulfur atoms, there are used, for example, 2-pyridylmethyl, 3-pyridylmethyl, 4-pyridylmethyl, 4-imidazolemethyl, etc.

(3) As the $C_{1-4}$ alkyl group having an optionally substituted $C_{8-14}$ aromatic fused cyclic group, there are used, for example, 1-naphthylmethyl, 2-naphthylmethyl, etc.

(4) As the $C_{1-4}$ alkyl group having an optionally substituted 5- to 14-membered aromatic fused heterocyclic group consisting of 3 to 11 carbon atoms and hetero atoms selected from the group consisting of nitrogen, oxygen and sulfur atoms, there are used, for example, 3-indolemethyl, 1-formylindol-3-ylmethyl, 2-quinolylmethyl, etc.

(5) As the $C_{1-4}$ alkyl group having an optionally substituted non-aromatic cyclic hydrocarbon group having carbon atoms not greater than 7, there are used, for example, cyclohexylmethyl, etc.

(6) As the $C_{1-4}$ alkyl group having an optionally substituted non-aromatic heterocyclic group having carbon atoms not greater than 7, there are used, for example, piperidin-1-ylmethyl, etc.

(7) As the $C_{1-4}$ alkyl group having an optionally substituted amino group, there are used, for example, 2-aminoethyl, 3-aminopropyl, 4-aminobutyl, 4-acetamidobutyl, etc.

(8) As the $C_{1-4}$ alkyl group having an optionally substituted guanidino group, there are used, for example, 3-guanidinopropyl, 3-(N-tosyl)guanidinopropyl, etc.

(9) As the $C_{1-4}$ alkyl group having an optionally substituted hydroxyl group, there are used, for example, hydroxymethyl, 1-hydroxyethyl, benzyloxymethyl, etc.

(10) As the $C_{1-4}$ alkyl group having an optionally substituted carboxyl group, there are used, for example, carboxylmethyl, 2-carboxylethyl, benzyloxycarbonylmethyl, etc.

(11) As the $C_{1-4}$ alkyl group having an optionally substituted carbamoyl group, there are used, for example, carbamoylmethyl, 2-carbamoylethyl, xanthylcarbamoyl, etc.

(12) As the $C_{1-4}$ alkyl group having an optionally substituted sulfhydryl group, there are used, for example, sulfhydrylmethyl, 2-(methylsulfhydryl)ethyl, etc.

(13) As the unsubstituted $C_{1-4}$ alkyl group, there are used, for example, methyl, ethyl, propyl, isopropyl, butyl, isobutyl, sec-butyl, tert-butyl, etc.

Preferably, $Q^3$ is hydrogen atom, 4-hydroxybenzyl, 3-pyridylmethyl, 4-pyridylmethyl, methyl, isobutyl, hydroxymethyl, carboxymethyl, 4-aminobutyl, etc., and more preferably, 4-hydroxybenzyl, 3-pyridylmethyl, 4-pyridylmethyl, etc.

Preferably, $Q^4$ includes carbamoylmethyl, 2-carbamoylethyl, 4-hydroxybenzyl, 4-imidazolemethyl, isobutyl, hydroxymethyl, 1-hydroxyethyl, carboxymethyl, 4-aminobutyl, etc., and more preferably, carbamoylmethyl, 2-carbamoylethyl, 4-hydroxybenzyl, etc.

Preferably, $Q^5$ includes benzyl, 2-chlorobenzyl, 3-chlorobenzyl, 4-chlorobenzyl, 4-aminobenzyl, 2-pyridylmethyl, 3-pyridylmethyl, 4-pyridylmethyl, 1-naphthylmethyl, 2-naphthylmethyl, 3-indolemethyl, 1-formylindol-3-ylmethyl, 2-quinolylmethyl, cyclohexylmethyl, hydroxymethyl, 1-hydroxyethyl, methyl, isopropyl, isobutyl, sec-butyl, carboxymethyl, 4-aminobutyl, etc., more preferably, benzyl, 2-chlorobenzyl, 3-chlorobenzyl, 4-chlorobenzyl, 4-aminobenzyl, 2-pyridylmethyl, 3-pyridylmethyl, 4-pyridylmethyl, 1-naphthylmethyl, 2-naphthylmethyl, 3-indolemethyl, 2-quinolylmethyl, cyclohexylmethyl, 1-hydroxyethyl, isopropyl, isobutyl, sec-butyl, etc.

Preferably, $Q^6$ is methyl, hydroxymethyl, 1-hydroxyethyl, carbamoylmethyl, 2-carbamoylethyl, etc., more preferably, carbamoylmethyl, etc.

Preferably, $Q^7$ is 4-hydroxybenzyl, carbamoylmethyl, 3-pyridylmethyl, methyl, isobutyl, benzyl, 4-aminobutyl, 3-indolemethyl, etc., more preferably, 4-hydroxybenzyl, etc.

Preferably, $Q^8$ is benzyl, 2-pyridylmethyl, 3-pyridylmethyl, 4-pyridylmethyl, 2-naphthylmethyl, 3-indolemethyl, hydroxymethyl, cyclohexylmethyl, sec-butyl, 1-hydroxyethyl, methyl, methyl, isobutyl, 4-aminobutyl, 3-carboxypropyl, etc., more preferably, 4-pyridylmethyl, 3-indolemethyl, sec-butyl, etc.

Preferably, $Q^9$ is hydrogen atom, methyl, ethyl, hydroxymethyl, 1-hydroxyethyl, carbamoylmethyl, 2-carbamoylethyl, ureidomethyl, acetamidomethyl, formamidemethyl, methylcarbamoylmethyl, dimethylcarbamoylmethyl, etc., more preferably, carbamoylmethyl, ureidomethyl, etc.

Preferably, $Q^{10}$ is 4-hydroxybenzyl, 3-indolemethyl, methyl, 1-hydroxyethyl, 3-guanidinopropyl, etc., more preferably, 3-indolemethyl, etc.

Preferably, $Q^{11}$ is carbamoylmethyl, etc.

Preferably, $Q^{12}$ is methyl, carbamoylmethyl, etc., more preferably, carbamoylmethyl, etc.

$Y^1$ through $Y^3$ each represents a group represented by formula: —CON($J^{13}$)-, —CSN($J^{13}$)-, —C($J^{14}$)N($J^{13}$)- or —N($J^{13}$)CO— ($J^{13}$ and $J^{14}$ each represents hydrogen atom or a $C_{1-3}$ alkyl group).

As the $C_{1-3}$ alkyl group represented by $J^{13}$ and $J^{14}$, there is used methyl, ethyl, propyl or isopropyl.

$J^{13}$ is hydrogen atom.

$J^{14}$ is hydrogen atom.

$Y^1$ is preferably a group represented by formula: —CONH— or —CH$_2$NH—, etc.

$Y^2$ is preferably a group represented by formula: —CONH— or —CH$_2$NH—, etc.

$Y^3$ is preferably a group represented by formula: —CONH—, etc.

$J^3$ and $Q^3$, $J^4$ and $Q^4$, $J^5$ and $Q^5$, $J^6$ and $Q^6$, $J^7$ and $Q^7$, $J^8$ and $Q^8$, $J^9$ and $Q^9$, $J^{10}$ and $Q^{10}$, $J^{11}$ and $Q^{11}$, and $J^{12}$ and $Q^{12}$ may be combined together to form a ring. In this case, for example, cyclopentane, cyclohexane, piperidine, etc. are formed by $C(J^3)(Q^3)$, $C(J^4)(Q^4)$, $C(J^5)(Q^5)$, $C(J^6)(Q^6)$, $C(J^7)(Q^7)$, $C(J^8)(Q^8)$, $C(J^9)(Q^9)$, $C(J^{10})(Q^{10})$, $C(J^{11})(Q^{11})$ or $C(J^{12})(Q^{12})$.

$Z^1$ and $R^1$, $J^2$ and $Q^3$, $Y^1$ and $Q^4$, $Y^2$ and $Q^5$, $Y^3$ and $Q^6$, $J^2$ and $Q^7$, $Y^2$ and $Q^8$, $Y^3$ and $Q^9$, $J^2$ and $Q^{10}$, $Y^3$ and $Q^{11}$, and $J^2$ and $Q^{12}$ (preferably, $J^2$ and $Q^3$, $Y^1$ and $Q^4$, $Y^2$ and $Q^5$, $Y^3$ and $Q^6$, $J^2$ and $Q^7$, $Y^2$ and $Q^8$, $Y^3$ and $Q^9$, $J^2$ and $Q^{10}$, $Y^3$ and $Q^{11}$, and $J^2$ and $Q^{12}$) may be combined together to form a ring. Alternatively, the ring formed may be optionally substituted, or annealed.

In the case where $Z^1$ and $R^1$, $J^2$ and $Q^3$, $J^2$ and $Q^7$, $J^2$ and $Q^{10}$, or $J^2$ and $Q^{12}$ May be combined together to form a ring, for example, azetidine, pyrrolidine, piperidine or thiazolidine is formed by $Z^1$—N—CH—$R^1$, $J^2$-$C(J^3)(Q^3)$, $J^2$-$C(J^7)(Q^7)$, $J^2$-$C(J^{11})(Q^{11})$ or $J^2$-$C(J^{12})(Q^{12})$. Alternatively, the ring formed may be optionally substituted, or annealed. $Z^1$—N—CH—$R^1$ is preferably azetidine, pyrrolidine, 4-hydroxypyrrolidine, piperidine, etc.

In the case where $Y^1$ and $Q^4$, $Y^2$ and $Q^5$, $Y^3$ and $Q^6$, $Y^2$ and $Q^8$, $Y^3$ and $Q^9$, or $Y^3$ and $Q^{11}$ may be combined together to form a ring, for example, pyrrolidine-2-carbonyl, piperidin-2-carbonyl or thiazolidine-4-carbonyl is formed by $Y^1C(J^4)(Q^4)$, $Y^2C(J^5)(Q^5)$, $Y^3C(J^6)(Q^6)$, $Y^2C(J^8)(Q^8)$, $Y^3C(J^9)(Q^9)$, or $Y^3C(J^{11})(Q^{11})$ Alternatively, the ring formed may be optionally substituted, or annealed.

Preferred examples of the group represented by formula: $J^1$-$J^2$-$C(J^3)(Q^3)Y^1C(J^4)(Q^4)Y^2C(J^5)(Q^5)Y^3C(J^6)(Q^6)C(=Z^{10})$— include:

Tyr Asn Trp Asn-,
Tyr Asn Trp D-Asn-,
Tyr Asn D-Trp Asn-,
Tyr D-Asn Trp Asn-,
D-Tyr Asn Trp Asn-,
Tyr Lys Trp Asn-,
Tyr Asp Trp Asn-,
Tyr Tyr Trp Asn-,
Tyr Leu Trp Asn-,
Tyr Asn Ala Asn-,
Tyr Asn Leu Asn-,
Tyr Asn Ser Asn-,
Tyr Asn Asp Asn-,
Tyr Asn Lys Asn-,
Ala Asn Trp Asn-,
Leu Asn Trp Asn-,
Ser Asn Trp Asn-,
Asp Asn Trp Asn-,
Lys Asn Trp Asn-,
Tyr Asn Trp(For)Asn-,
D-Tyr Asn D-Trp Asn-,
D-Tyr Asn Ala Asn-,
D-Tyr Asn Ser Asn-,
D-Tyr Asn Cha Asn-,
D-Tyr Asn Thr Asn-,
D-Tyr Asn Ile Asn-,
D-Tyr Gln Trp Asn-,
D-Tyr Thr Trp Asn-,
D-Tyr Asn Val Asn-,
D-Tyr D-Asn Trp Asn-,
D-Tyr D-Asn D-Trp Asn-,
D-Tyr Asn Phe Asn-,
D-Tyr Asn Nal(1) Asn-,
D-Tyr Asn Nal(2) Asn-,
D-Tyr Asn Phe(2Cl) Asn-,
D-Tyr Asn Phe(3Cl) Asn-,
D-Tyr Asn Phe(4Cl) Asn-,
D-Tyr Asn Phe(4NH$_2$) Asn-,
D-Tyr Asn Pya(3) Asn-,
D-Tyr D-Asn Phe Asn-,
D-Tyr D-Asn Cha Asn-,
D-Tyr D-Asn Thr Asn-,
D-Tyr Asn Pya(2) Asn-,
D-Tyr Asn Pya(4) Asn-,
D-Tyr D-Ser Trp Asn-,
D-Tyr D-His Trp Asn-,
D-Pya(3) D-Asn Cha Asn-,
D-Pya(3) D-Tyr Cha Asn-,
TyrΨ(CH$_2$NH)Asn Trp Asn-,
D-Tyr AsnΨ(CH$_2$NH)Trp Asn-,
TyrΨ(CH$_2$NH)Asn D-Trp Asn-,
D-Tyr Asn Ala(2-Qui) Asn-,
D-Tyr Asn D-Pya(4) Asn-,
D-Tyr D-Asn Pya(4) Asn-,
Tyr D-Asn Cha Asn-,
Dap D-Tyr Asn Trp Asn-
Arg D-Tyr D-Pya(4) Asn-
Arg Arg D-Tyr D-Pya(4) Asn-
Arg Acp D-Tyr D-Pya(4) Asn-
D-Arg Acp D-Tyr D-Trp Asn-
D-Arg D-Arg Acp D-Tyr D-Trp Asn-
Ac D-Arg Acp D-Tyr D-Trp Asn-
D-Dap Acp D-Tyr D-Trp Asn-
D-Nle Acp D-Tyr D-Trp Asn-
D-Arg β-Ala D-Tyr D-Trp Asn-
D-Arg γ-Abu D-Tyr D-Trp Asn-
D-Arg D-Arg γ-Abu D-Tyr D-Trp Asn-
D-Arg D-Arg D-Arg γ-Abu D-Tyr D-Trp Asn-
Gly D-Tyr D-Trp Asn-
Ac Gly D-Tyr D-Trp Asn-
D-Tyr D-Tyr D-Trp Asn-
Ac D-Tyr D-Tyr D-Trp Asn-
pGlu D-Tyr D-Trp Asn-
Tyr D-Tyr D-Trp Asn-
Ac Tyr D-Tyr D-Trp Asn-, and the like.

Preferred examples of the group represented by formula: $J^1$-$J^2$-$C(J^7)(Q^7)Y^2C(J^8)(Q^8)Y^3C(J^9)(Q^9)C(=Z^{10})$— include:

Fmoc Asn Trp Asn-,
D-Asn Trp Asn-,
D-Tyr Trp Asn-,
D-Tyr D-Trp Asn-,
D-Tyr Ser Asn-,
D-Tyr Thr Asn-,
D-Tyr Ile Asn-,
D-Tyr Phe Asn-,
D-Tyr Nal(2) Asn-,
D-Pya(3) Phe Asn-,
D-Pya(3) Trp Asn-,
D-Tyr D-Pya(4) Asn-,
D-Asn Cha Asn-
D-Tyr D-Pya(4) Ala- D-Tyr D-Pya(4) Thr-
D-Tyr Pya(4) Ala-
D-Tyr D-Trp Ala-
D-Tyr D-Trp Abu-
D-Tyr D-Phe Ala-6-Aminocaproyl-
D-Tyr D-Pya(4) Asn-
Ac D-Tyr D-Pya(4) Asn-
Benzoyl D-Tyr D-Trp Asn-
Cyclopropanecarbonyl D-Tyr D-Trp Asn-
Butyryl D-Tyr D-Trp Asn-
Me D-Tyr D-Trp Asn-
Ac D-Tyr D-Trp Gln-
Ac D-Tyr D-Trp Ser-
Ac D-Tyr D-Trp Thr-
Ac D-Tyr D-Trp Alb-
Ac D-Tyr D-Trp Dap(Ac)-
Ac D-Tyr D-Trp Dap(For)-
Ac D-Tyr Trp Asn-
Ac D-NMeTyr D-Trp Asn-
For D-Tyr D-Trp Asn-
Propionyl D-Tyr D-Trp Asn-
Amidino D-Tyr D-Trp Asn-
Ac D-Ala D-Trp Asn-
Ac D-Leu D-Trp Asn-
Ac D-Phe D-Trp Asn-
Ac D-Nal(1) D-Trp Asn-
Ac D-Nal(2) D-Trp Asn-
Ac D-Lys D-Trp Asn-
Ac D-Glu D-Trp Asn-
Ac D-Tyr D-Ala Asn-
Ac D-Tyr D-Leu Asn-
Ac D-Tyr D-Phe Asn-
Ac D-Tyr D-Thr Asn-
Ac D-Tyr D-Lys Asn-
Ac D-Tyr D-Glu Asn-
Ac D-Tyr D-Trp Asp-
Ac D-Tyr D-Trp D-Asn-
Ac D-Tyr D-Trp NMeAsn-
Ac D-Tyr Pro Asn-
Ac D-Tyr D-Pya(2) Asn-
Ac D-Tyr D-Pya(3) Asn-
Ac D-Tyr D-Pro Asn-
Ac D-Tyr Tic Asn-
Ac Tyr Trp Asn-
Ac D-Tyr NMeTrp Asn-
Glycoloyl D-Tyr D-Trp Asn-
Ac D-Tyr D-Trp Gly-
Ac D-Tyr D-Trp Dap-
Ac D-Tyr D-Trp Asp(NHMe)-
Ac D-Tyr D-Trp Asp(NMe2)-, and the like.

Preferred examples of the group represented by formula: $J^1$-$J^2$-C($J^{10}$)($Q^{10}$)$Y^3$C($J^{11}$)($Q^{11}$)C(=$Z^{10}$)— include:
Fmoc Trp Asn-,
Boc Tyr Asn-,
Tyr Asn-,
D-Trp Asn-,
Ac Trp Asn-,
Amidino Trp Asn-,
Ac Ala Asn-,
Ac Arg Asn-,
Ac Thr Asn-
D-Tyr D-Pya(4)-
3-(4-Hydroxyphenyl)propionyl D-Trp Asn-
D-Trp Asn-
Ac D-Trp Asn-
Hexanoyl D-Trp Asn-
Cyclohexanecarbonyl D-Trp Asn-
Benzoyl D-Trp Asn-
3-Pyridinepropionyl D-Trp Asn-
Adipoyl D-Trp Asn-
6-Aminocaproyl D-Trp Asn-
Amidino D-Trp Asn-
Glycoloyl D-Trp Asn-, and the like.

Preferred examples of the group represented by formula: $J^1$-$J^2$-C($J^{12}$)($Q^{12}$)C(=$Z^{10}$)— include:
Fmoc Asn-,
3-(Indol-3-yl)propionyl Asn-,
3-Indolecarbonyl Asn-,
3-Indoleacetyl Asn-,
4-(Indol-3-yl)butyryl Asn-,
Diphenylacetyl Asn-,
Hexanoyl Asn-,
Cyclohexanecabonyl Asn-,
2-(Indol-3-yl)ethylcabamoyl Asn-,
3-(3-Pyridyl)propionyl Asn-,
4-Imidzoleacetyl Asn-,
Piperidinecarbonyl Asn-,
1-Piperidineacetyl Asn-,
1-Methyl-1-piperidinioacetyl Asn-,
1-Pyridinioacetyl Asn-,
D-Glucuronyl Asn-,
3-Phenylpropionyl Asn-,
3-Phenylpropionyl Ala-,
Benzoyl Asn-,
Ac Asn-,
Cyclopropanecarbonyl Asn-,
2-Naphthoyl Asn-, and the like.

Preferred examples of the group represented by formula: $J^1$- include:
hydrogen atom,
GuAmb-,
3-(3-Indolyl)propionyl-,
3-(3-Pyridyl)propionyl-,
Benzoyl-,
Indole-3-carbonyl-,
Indole-3-acetyl-,
Ac-,
Hexanoyl-,
Tos-,
3-Phenylpropionyl-,
2-(Indol-3-yl)ethylcarbamoyl-,
Benzyl-,
Phenethyl-,
2-Pyridinecarbonyl-,
4-Pyridinecarbonyl-,
Propionyl-,
Isobutyryl-,
Cyclohexanecarbonyl-,
Phenylacetyl-,
2-Methylnicotinoyl-,
5-Methylnicotinoyl-,
6-Methylnicotinoyl-,
Pyrazinecarbonyl-,
Cyclopropanecarbonyl-,
Trifluoroacetyl-,
(R)-3-hydroxy-2-methylpropionyl-,
2-Hydroxyisobutyryl-,
3-Furancarbonyl-,
Pyrrole-2-carbonyl-,
4-Imidazolecarbonyl-,
6-Hydroxynicotinoyl-,
6-Chloronicotinoyl-,
6-(Trifluoromethyl)nicotinoyl-,
Dimethylcarbamoyl-, 1-Azetidinecarbonyl-,
2-Azetidinecarbonyl-,
4-Aminobenzoyl-,
4-Aminomethylbenzoyl-,
Pyrrole-3-carbonyl-,
Pyrimidine-4-carbonyl-,
Pyrimidine-2-carbonyl-,
Pyridazine-4-carbonyl-, and the like.

The metastin derivatives (I) in the metastin derivatives (III) of the present invention, wherein V' represents the group represented by formula:

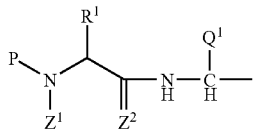

(wherein each symbol has the same significance as defined above) are a class of compound disclosed in the specification filed as PCT/JP03/16978, whereas the metastin derivatives (II), wherein V' represents the group represented by formula:

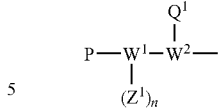

(wherein each symbol has the same significance as defined above), or the group represented by formula:

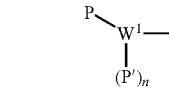

(wherein each symbol has the same significance as defined above) are novel compounds.

In the metastin derivatives (III), all compounds that the groups shown by the respective symbols are optionally combined are preferably used. Among them, the compounds shown by Compound Numbers below (TABLES 1 through 11) are preferred.

```
MS10:   Tyr-Asn-Trp-Asn-Ser-Phe-Gly-Leu-Arg-Phe-NH2
         1   2   3   4   5   6   7   8   9   10
Compound No. 17: [Pya(4)10]MS10
Tyr-Asn-Trp-Asn-Ser-Phe-Gly-Leu-Arg-Pya(4)-NH2

Compound No. 18: [Tyr(Me)10]MS10
Tyr-Asn-Trp-Asn-Ser-Phe-Gly-Leu-Arg-Tyr(Me)-NH2

Compound No. 19: [Phe(2F)10]MS10
Tyr-Asn-Trp-Asn-Ser-Phe-Gly-Leu-Arg-Phe(2F)-NH2

Compound No. 23: [Tyr5]MS10
Tyr-Asn-Trp-Asn-Tyr-Phe-Gly-Leu-Arg-Phe-NH2

Compound No. 24: [Leu5]MS10
Tyr-Asn-Trp-Asn-Leu-Phe-Gly-Leu-Arg-Phe-NH2

Compound No. 30: Acetyl-MS10
Acetyl-Tyr-Asn-Trp-Asn-Ser-Phe-Gly-Leu-Arg-Phe-NH2

Compound No. 31: Fmoc-MS10
Fmoc-Tyr-Asn-Trp-Asn-Ser-Phe-Gly-Leu-Arg-Phe-NH2

Compound No. 38: [D-Ser5]MS10
Tyr-Asn-Trp-Asn-D-Ser-Phe-Gly-Leu-Arg-Phe-NH2

Compound No. 39: [D-Asn4]MS10
Tyr-Asn-Trp-D-Asn-Ser-Phe-Gly-Leu-Arg-Phe-NH2

Compound No. 40: [D-Trp3]MS10
Tyr-Asn-D-Trp-Asn-Ser-Phe-Gly-Leu-Arg-Phe-NH2

Compound No. 41: [D-Asn2]MS10
Tyr-D-Asn-Trp-Asn-Ser-Phe-Gly-Leu-Arg-Phe-NH2

Compound No. 42: [D-Tyr1]MS10
D-Tyr-Asn-Trp-Asn-Ser-Phe-Gly-Leu-Arg-Phe-NH2

Compound No. 44: [Lys9]MS10
Tyr-Asn-Trp-Asn-Ser-Phe-Gly-Leu-Lys-Phe-NH2

Compound No. 45: [Ala8]MS10
Tyr-Asn-Trp-Asn-Ser-Phe-Gly-Ala-Arg-Phe-NH2

Compound No. 50: [Ala7]MS10
Tyr-Asn-Trp-Asn-Ser-Phe-Ala-Leu-Arg-Phe-NH2

Compound No. 51: [NMePhe10]MS10
Tyr-Asn-Trp-Asn-Ser-Phe-Gly-Leu-Arg-NMePhe-NH2

Compound No. 53: des(1-3)-Fmoc-MS10
```

-continued

Fmoc-Asn-Ser-Phe-Gly-Leu-Arg-Phe-NH$_2$

Compound No. 54: des(1-2)-Fmoc-MS10
Fmoc-Trp-Asn-Ser-Phe-Gly-Leu-Arg-Phe-NH$_2$

Compound No. 55: des(1)-Fmoc-MS10
Fmoc-Asn-Trp-Asn-Ser-Phe-Gly-Leu-Arg-Phe-NH$_2$ Compound No. 56: [Lys2]MS10
Tyr-Lys-Trp-Asn-Ser-Phe-Gly-Leu-Arg-Phe-NH$_2$ Compound No. 57: [Asp2]MS10
Tyr-Asp-Trp-Asn-Ser-Phe-Gly-Leu-Arg-Phe-NH$_2$ Compound No. 58: [Tyr2]MS10
Tyr-Tyr-Trp-Asn-Ser-Phe-Gly-Leu-Arg-Phe-NH$_2$ Compound No. 59: [Leu2]MS10
Tyr-Leu-Trp-Asn-Ser-Phe-Gly-Leu-Arg-Phe-NH$_2$ Compound No. 60: [Pya(3)10]MS10
Tyr-Asn-Trp-Asn-Ser-Phe-Gly-Leu-Arg-Pya(3)-NH$_2$ Compound No. 61: [Phe(4F)10]MS10
Tyr-Asn-Trp-Asn-Ser-Phe-Gly-Leu-Arg-Phe(4F)-NH$_2$ Compound No. 67: [Ala3]MS10
Tyr-Asn-Ala-Asn-Ser-Phe-Gly-Leu-Arg-Phe-NH$_2$ Compound No. 68: [Leu3]MS10
Tyr-Asn-Leu-Asn-Ser-Phe-Gly-Leu-Arg-Phe-NH$_2$ Compound No. 69: [Ser3]MS10
Tyr-Asn-Ser-Asn-Ser-Phe-Gly-Leu-Arg-Phe-NH$_2$ Compound No. 70: [Asp3]MS10
Tyr-Asn-Asp-Asn-Ser-Phe-Gly-Leu-Arg-Phe-NH$_2$ Compound No. 71: [Lys3]MS10
Tyr-Asn-Lys-Asn-Ser-Phe-Gly-Leu-Arg-Phe-NH$_2$ Compound No. 72: [Ala1]MS10
Ala-Asn-Trp-Asn-Ser-Phe-Gly-Leu-Arg-Phe-NH$_2$ Compound No. 73: [Leu1]MS10
Leu-Asn-Trp-Asn-Ser-Phe-Gly-Leu-Arg-Phe-NH$_2$ Compound No. 74: [Ser1]MS10
Ser-Asn-Trp-Asn-Ser-Phe-Gly-Leu-Arg-Phe-NH$_2$ Compound No. 75: [Asp1]MS10
Asp-Asn-Trp-Asn-Ser-Phe-Gly-Leu-Arg-Phe-NH$_2$ Compound No. 76: [Lys1]MS10
Lys-Asn-Trp-Asn-Ser-Phe-Gly-Leu-Arg-Phe-NH$_2$ Compound No. 77: [Phe(4CN)10]MS10
Tyr-Asn-Trp-Asn-Ser-Phe-Gly-Leu-Arg-Phe(4CN)-NH$_2$ Compound No. 78: [Trp(For)3, Phe(4CN)10]MS10
Tyr-Asn-Trp(For)-Asn-Ser-Phe-Gly-Leu-Arg-Phe(4CN)-NH$_2$ Compound No. 79: [Hph10]MS10
Tyr-Asn-Trp-Asn-Ser-Phe-Gly-Leu-Arg-Hph-NH$_2$ Compound No. 81: [NMeArg9]MS10
Tyr-Asn-Trp-Asn-Ser-Phe-Gly-Leu-NMeArg-Phe-NH$_2$ Compound No. 82: [Arg(Me)9]MS10
Tyr-Asn-Trp-Asn-Ser-Phe-Gly-Leu-Arg(Me)-Phe-NH$_2$ Compound No. 83: [Arg(asy Me$_2$)9]MS10
Tyr-Asn-Trp-Asn-Ser-Phe-Gly-Leu-Arg(asyMe$_2$)-Phe-NH$_2$ Compound No. 87: des(4-5)-Boc-MS10
Boc-Tyr-Asn-Trp-Phe-Gly-Leu-Arg-Phe-NH$_2$ Compound No. 88: des(4-5)-MS10
Tyr-Asn-Trp-Phe-Gly-Leu-Arg-Phe-NH$_2$ Compound No. 90: [Lys9,9Ψ10,CH$_2$NH]MS10

-continued
```
Tyr-Asn-Trp-Asn-Ser-Phe-Gly-Leu-LysΨ(CH₂NH)Phe-NH₂

Compound No. 91: [8ΨP9,CH₂NH]MS10
Tyr-Asn-Trp-Asn-Ser-Phe-Gly-LeuΨ(CH₂NH)Arg-Phe-NH₂

Compound No. 97: [Har9]MS10
Tyr-Asn-Trp-Asn-Ser-Phe-Gly-Leu-Har-Phe-NH₂

Compound No. 98: [Lys(Me₂)9]MS10
Tyr-Asn-Trp-Asn-Ser-Phe-Gly-Leu-Lys(Me₂)-Phe-NH₂

Compound No. 101: [Ser7]MS10
Tyr-Asn-Trp-Asn-Ser-Phe-Ser-Leu-Arg-Phe-NH₂

Compound No. 105: [Nle8]MS10
Tyr-Asn-Trp-Asn-Ser-Phe-Gly-Nle-Arg-Phe-NH₂

Compound No. 107: [Val8]MS10
Tyr-Asn-Trp-Asn-Ser-Phe-Gly-Val-Arg-Phe-NH₂

Compound No. 109: [Tyr10]MS10
Tyr-Asn-Trp-Asn-Ser-Phe-Gly-Leu-Arg-Tyr-NH₂

Compound No. 110: [Nal(2)10]MS10
Tyr-Asn-Trp-Asn-Ser-Phe-Gly-Leu-Arg-Nal(2)-NH₂

Compound No. 111: [Phe(F5)10]MS10
Tyr-Asn-Trp-Asn-Ser-Phe-Gly-Leu-Arg-Phe(F5)-NH₂

Compound No. 112: [Cha10]MS10
Tyr-Asn-Trp-Asn-Ser-Phe-Gly-Leu-Arg-Cha-NH₂

Compound No. 114: des(1-3)-3-(3-Indolyl)propionyl-MS10
3-(3-Indolyl)propionyl-Asn-Ser-Phe-Gly-Leu-Arg-Phe-NH₂

Compound No. 121: des(1-4)-[Trp5]MS10
Trp-Phe-Gly-Leu-Arg-Phe-NH₂

Compound No. 123: [NMeLeu8]MS10
Tyr-Asn-Trp-Asn-Ser-Phe-Gly-NMeLeu-Arg-Phe-NH₂

Compound No. 126: [NMeSer5]MS10
Tyr-Asn-Trp-Asn-NMeSer-Phe-Gly-Leu-Arg-Phe-NH₂

Compound No. 127: [D-Asn4,NMePhe6]MS10
Tyr-Asn-Trp-D-Asn-Ser-NMePhe-Gly-Leu-Arg-Phe-NH₂

Compound No. 128: [10Ψ,CSNH]MS10
Tyr-Asn-Trp-Asn-Ser-Phe-Gly-Leu-Arg-PheΨ(CSNH)NH₂

Compound No. 129: [Arg(symMe₂)9]MS10
Tyr-Asn-Trp-Asn-Ser-Phe-Gly-Leu-Arg(symMe₂)-Phe-NH₂

Compound No. 130: [Phe(4Cl)10]MS10
Tyr-Asn-Trp-Asn-Ser-Phe-Gly-Leu-Arg-Phe(4Cl)-NH₂

Compound No. 131: [Phe(4NH₂)10]MS10
Tyr-Asn-Trp-Asn-Ser-Phe-Gly-Leu-Arg-Phe(4NH₂)-NH₂

Compound No. 132: [Phe(4NO₂)10]MS10
Tyr-Asn-Trp-Asn-Ser-Phe-Gly-Leu-Arg-Phe(4NO₂)-NH₂

Compound No. 133: [Nal(1)10]MS10
Tyr-Asn-Trp-Asn-Ser-Phe-Gly-Leu-Arg-Nal(1)-NH₂

Compound No. 134: [Trp10]MS10
Tyr-Asn-Trp-Asn-Ser-Phe-Gly-Leu-Arg-Trp-NH₂

Compound No. 137: [Nle9]MS10
Tyr-Asn-Trp-Asn-Ser-Phe-Gly-Leu-Nle-Phe-NH₂

Compound No. 138: [Cit9]MS10
Tyr-Asn-Trp-Asn-Ser-Phe-Gly-Leu-Cit-Phe-NH₂

Compound No. 140: [Arg(Me)9,NMePhe10]MS10
Tyr-Asn-Trp-Asn-Ser-Phe-Gly-Leu-Arg(Me)-NMePhe-NH₂

Compound No. 141: [D-Tyr1,Arg(Me)9]MS10
D-Tyr-Asn-Trp-Asn-Ser-Phe-Gly-Leu-Arg(Me)-Phe-NH₂

Compound No. 142: [D-Tyr1,D-Trp3,Arg(Me)9]MS10
```

-continued

D-Tyr-Asn-D-Trp-Asn-Ser-Phe-Gly-Leu-Arg(Me)-Phe-NH$_2$

Compound No. 143: [D-Trp3,Arg(Me)9]MS10
Tyr-Asn-D-Trp-Asn-Ser-Phe-Gly-Leu-Arg(Me)-Phe-NH$_2$ Compound No. 144: des(1-3)-Fmoc-[Arg(Me)9]MS10
Fmoc-Asn-Ser-Phe-Gly-Leu-Arg(Me)-Phe-NH$_2$ Compound No. 145: des(1-2)-Fmoc-[Arg(Me)9]MS10
Fmoc-Trp-Asn-Ser-Phe-Gly-Leu-Arg(Me)-Phe-NH$_2$ Compound No. 146: [10Ψ,CSNH,D-Tyr1]MS10
D-Tyr-Asn-Trp-Asn-Ser-Phe-Gly-Leu-Arg-PheΨ(CSNH)NH$_2$ Compound No. 150: [Tyr6]MS10
Tyr-Asn-Trp-Asn-Ser-Tyr-Gly-Leu-Arg-Phe-NH$_2$ Compound No. 151: [Nal(1)6]MS10
Tyr-Asn-Trp-Asn-Ser-Nal(1)-Gly-Leu-Arg-Phe-NH$_2$ Compound No. 152: [Nal(2)6]MS10
Tyr-Asn-Trp-Asn-Ser-Nal(2)-Gly-Leu-Arg-Phe-NH$_2$ Compound No. 153: [Phe(F5)6]MS10
Tyr-Asn-Trp-Asn-Ser-Phe(F$_5$)-Gly-Leu-Arg-Phe-NH$_2$ Compound No. 154: [Phe(4F)6]MS10
Tyr-Asn-Trp-Asn-Ser-Phe(4F)-Gly-Leu-Arg-Phe-NH$_2$ Compound No. 156: [Cha6]MS10
Tyr-Asn-Trp-Asn-Ser-Cha-Gly-Leu-Arg-Phe-NH$_2$ Compound No. 163: [6Ψ7,CH$_2$NH]MS10
Tyr-Asn-Trp-Asn-Ser-PheΨ(CH$_2$NH)Gly-Leu-Arg-Phe-NH$_2$ Compound No. 165: [Dap(Gly)9]-MS10
Tyr-Asn-Trp-Asn-Ser-Phe-Gly-Leu-Dap(Gly)-Phe-NH$_2$ Compound No. 166: [6Ψ7,CSNH]MS10
Tyr-Asn-Trp-Asn-Ser-PheΨ(CSNH)Gly-Leu-Arg-Phe-NH$_2$ Compound No. 169: [D-Tyr1,Ala3,Arg(Me)9]MS10
D-Tyr-Asn-Ala-Asn-Ser-Phe-Gly-Leu-Arg(Me)-Phe-NH$_2$ Compound No. 170: [D-Tyr1,Ser3,Arg(Me)9]MS10
D-Tyr-Asn-Ser-Asn-Ser-Phe-Gly-Leu-Arg(Me)-Phe-NH$_2$ Compound No. 171: [D-Tyr1,Cha3,Arg(Me)9]MS10
D-Tyr-Asn-Cha-Asn-Ser-Phe-Gly-Leu-Arg(Me)-Phe-NH$_2$ Compound No. 172: [D-Tyr1,Cha6,Arg(Me)9]MS10
D-Tyr-Asn-Trp-Asn-Ser-Cha-Gly-Leu-Arg(Me)-Phe-NH$_2$ Compound No. 173: [D-Tyr1,Ala7,Arg(Me)9]MS10
D-Tyr-Asn-Trp-Asn-Ser-Phe-Ala-Leu-Arg(Me)-Phe-NH$_2$ Compound No. 174: [D-Tyr1,Arg(Me)9,Trp10]MS10
D-Tyr-Asn-Trp-Asn-Ser-Phe-Gly-Leu-Arg(Me)-Trp-NH$_2$ Compound No. 176: [AzaGly7]MS10
Tyr-Asn-Trp-Asn-Ser-Phe-AzaGly-Leu-Arg-Phe-NH$_2$ Compound No. 181: [D-Tyr1,Cha3,6,Arg(Me)9]MS10
D-Tyr-Asn-Cha-Asn-Ser-Cha-Gly-Leu-Arg(Me)-Phe-NH$_2$ Compound No. 182: [D-Tyr1,Cha3,6,Arg(Me)9,Trp10]MS10
D-Tyr-Asn-Cha-Asn-Ser-Cha-Gly-Leu-Arg(Me)-Trp-NH$_2$ Compound No. 183: [Phe(4NH$_2$)9]MS10
Tyr-Asn-Trp-Asn-Ser-Phe-Gly-Leu-Phe(4NH$_2$)-Phe-NH$_2$ Compound No. 184: [Phe(4-Guanidino)9]MS10
Tyr-Asn-Trp-Asn-Ser-Phe-Gly-Leu-Phe(4-Guanidino)-Phe-NH$_2$ Compound No. 185: [Dap(GnGly)9]MS10
Tyr-Asn-Trp-Asn-Ser-Phe-Gly-Leu-Dap(GnGly)-Phe-NH$_2$ Compound No. 186: [Trp(For)10]MS10
Tyr-Asn-Trp-Asn-Ser-Phe-Gly-Leu-Arg-Trp(For)-NH$_2$ Compound No. 187: [Abu8]MS10

-continued

Tyr-Asn-Trp-Asn-Ser-Phe-Gly-Abu-Arg-Phe-NH$_2$

Compound No. 189: [Ala(3-Bzt)10]MS10
Tyr-Asn-Trp-Asn-Ser-Phe-Gly-Leu-Arg-Ala(3-Bzt)-NH$_2$ Compound No. 190: [D-Tyr1,Cha3,AzaGly7,Arg(Me)9]MS10
D-Tyr-Asn-Cha-Asn-Ser-Phe-AzaGly-Leu-Arg(Me)-Phe-NH$_2$ Compound No. 191: [D-Tyr1,Ser3,AzaGly7,Arg(Me)9]MS10
D-Tyr-Asn-Ser-Asn-Ser-Phe-AzaGly-Leu-Arg(Me)-Phe-NH$_2$ Compound No. 192: [D-Tyr1,Arg(Et)9]MS10
D-Tyr-Asn-Trp-Asn-Ser-Phe-Gly-Leu-Arg(Et)-Phe-NH$_2$ Compound No. 193: [D-Tyr1,Arg(n-Pr)9]MS10
D-Tyr-Asn-Trp-Asn-Ser-Phe-Gly-Leu-Arg(n-Pr)-Phe-NH$_2$ Compound No. 194: [D-Tyr1,Arg(Ac)9]MS10
D-Tyr-Asn-Trp-Asn-Ser-Phe-Gly-Leu-Arg(Ac)-Phe-NH$_2$ Compound No. 197: [Phe(3F)10]MS10
Tyr-Asn-Trp-Asn-Ser-Phe-Gly-Leu-Arg-Phe(3F)-NH$_2$ Compound No. 198: [Phe(3,4F$_2$)10]MS10
Tyr-Asn-Trp-Asn-Ser-Phe-Gly-Leu-Arg-Phe(3,4F$_2$)-NH$_2$ Compound No. 199: [Phe(3,4Cl$_2$)10]MS10
Tyr-Asn-Trp-Asn-Ser-Phe-Gly-Leu-Arg-Phe(3,4Cl$_2$)-NH$_2$ Compound No. 200: [Phe(3CF$_3$)10]MS10
Tyr-Asn-Trp-Asn-Ser-Phe-Gly-Leu-Arg-Phe(3CF$_3$)-NH$_2$ Compound No. 201: [Ala(2-Qui)10]MS10
Tyr-Asn-Trp-Asn-Ser-Phe-Gly-Leu-Arg-Ala(2-Qui)-NH$_2$ Compound No. 203: [D-Tyr1,Cha6,Arg(Me)9]MS10
D-Tyr-Asn-Trp-Asn-Ser-Cha-Gly-Leu-Arg(Me)-Phe-NH$_2$ Compound No. 204: [D-Tyr1, Ala7, Arg(Me)9]MS10
D-Tyr-Asn-Trp-Asn-Ser-Phe-Ala-Leu-Arg(Me)-Phe-NH$_2$ Compound No. 205: [D-Tyr1,Thr3,Arg(Me)9]MS10
D-Tyr-Asn-Thr-Asn-Ser-Phe-Gly-Leu-Arg(Me)-Phe-NH$_2$ Compound No. 206: [D-Tyr1,Ile3,Arg(Me)9]MS10
D-Tyr-Asn-Ile-Asn-Ser-Phe-Gly-Leu-Arg(Me)-Phe-NH$_2$ Compound No. 207: [D-Tyr1,Ser4,Arg(Me)9]MS10
D-Tyr-Asn-Trp-Ser-Ser-Phe-Gly-Leu-Arg(Me)-Phe-NH$_2$ Compound No. 208: [D-Tyr1,Thr4,Arg(Me)9]MS10
D-Tyr-Asn-Trp-Thr-Ser-Phe-Gly-Leu-Arg(Me)-Phe-NH$_2$ Compound No. 209: [D-Tyr1,Gln4,Arg(Me)9]MS10
D-Tyr-Asn-Trp-Gln-Ser-Phe-Gly-Leu-Arg(Me)-Phe-NH$_2$ Compound No. 210: [D-Tyr1,Ala4,Arg(Me)9]MS10
D-Tyr-Asn-Trp-Ala-Ser-Phe-Gly-Leu-Arg(Me)-Phe-NH$_2$ Compound No. 211: [D-Tyr1,Thr5,Arg(Me)9]MS10
D-Tyr-Asn-Trp-Asn-Thr-Phe-Gly-Leu-Arg(Me)-Phe-NH$_2$ Compound No. 212: [D-Tyr1,Ala5,Arg(Me)9]MS10
D-Tyr-Asn-Trp-Asn-Ala-Phe-Gly-Leu-Arg(Me)-Phe-NH$_2$ Compound No. 213: [D-Tyr1,Val8,Arg(Me)9]MS10
D-Tyr-Asn-Trp-Asn-Ser-Phe-Gly-Val-Arg(Me)-Phe-NH$_2$ Compound No. 214: [D-Tyr1,Gln2,Arg(Me)9]MS10
D-Tyr-Gln-Trp-Asn-Ser-Phe-Gly-Leu-Arg(Me)-Phe-NH$_2$ Compound No. 215: [D-Tyr1,Thr2,Arg(Me)9]MS10
D-Tyr-Thr-Trp-Asn-Ser-Phe-Gly-Leu-Arg(Me)-Phe-NH$_2$ Compound No. 216: des(1)-[D-Asn2,Arg(Me)9]MS10
D-Asn-Trp-Asn-Ser-Phe-Gly-Leu-Arg(Me)-Phe-NH$_2$ Compound No. 217: des(1)-[D-Tyr2,Arg(Me)9]MS10
D-Tyr-Trp-Asn-Ser-Phe-Gly-Leu-Arg(Me)-Phe-NH$_2$ Compound No. 218: [N((CH$_2$)$_3$Gn)]Gly9]MS10

-continued

Tyr-Asn-Trp-Asn-Ser-Phe-Gly-Leu-N((CH₂)₃Gn)Gly-Phe-NH₂

Compound No. 220: [Arg(Et)9]MS10
Tyr-Asn-Trp-Asn-Ser-Phe-Gly-Leu-Arg(Et)-Phe-NH₂

Compound No. 221: [D-Tyr1,Thr3,AzaGly7,Arg(Me)9]MS10
D-Tyr-Asn-Thr-Asn-Ser-Phe-AzaGly-Leu-Arg(Me)-Phe-NH₂

Compound No. 222: des(1)-[D-Tyr2,AzaGly7,Arg(Me)9]MS10
D-Tyr-Trp-Asn-Ser-Phe-AzaGly-Leu-Arg(Me)-Phe-NH₂

Compound No. 223: des(1-2)-[D-Trp3,Arg(Me)9]MS10
D-Trp-Asn-Ser-Phe-Gly-Leu-Arg(Me)-Phe-NH₂

Compound No. 224: des(1)-[D-Tyr2,D-Trp3,Arg(Me)9]MS10
D-Tyr-D-Trp-Asn-Ser-Phe-Gly-Leu-Arg(Me)-Phe-NH₂

Compound No. 225: des(1)-[D-Asn2,D-Trp3,Arg(Me)9]MS10
D-Asn-D-Trp-Asn-Ser-Phe-Gly-Leu-Arg(Me)-Phe-NH₂

Compound No. 226: des(1)-[D-Tyr2,Ser3,Arg(Me)9]MS10
D-Tyr-Ser-Asn-Ser-Phe-Gly-Leu-Arg(Me)-Phe-NH₂

Compound No. 227: des(1)-[D-Tyr2,Thr3,Arg(Me)9]MS10
D-Tyr-Thr-Asn-Ser-Phe-Gly-Leu-Arg(Me)-Phe-NH₂

Compound No. 228: des(1)-[D-Tyr2,Ile3,Arg(Me)9]MS10
D-Tyr-Ile-Asn-Ser-Phe-Gly-Leu-Arg(Me)-Phe-NH₂

Compound No. 229: [D-Tyr1,Val3,Arg(Me)9]MS10
D-Tyr-Asn-Val-Asn-Ser-Phe-Gly-Leu-Arg(Me)-Phe-NH₂

Compound No. 230: [D-Tyr1,D-Asn2,Arg(Me)9]MS10
D-Tyr-D-Asn-Trp-Asn-Ser-Phe-Gly-Leu-Arg(Me)-Phe-NH₂

Compound No. 231: [D-Tyr1,D-Asn2,D-Trp3,Arg(Me)9]MS10
D-Tyr-D-Asn-D-Trp-Asn-Ser-Phe-Gly-Leu-Arg(Me)-Phe-NH₂

Compound No. 232: [D-Tyr1,AzaGly7,Arg(Me)9]MS10
D-Tyr-Asn-Trp-Asn-Ser-Phe-AzaGly-Leu-Arg(Me)-Phe-NH₂

Compound No. 233: [D-Tyr1,Ile3,AzaGly7,Arg(Me)9]MS10
D-Tyr-Asn-Ile-Asn-Ser-Phe-AzaGly-Leu-Arg(Me)-Phe-NH₂

Compound No. 234: [D-Tyr1,Val3,AzaGly7,Arg(Me)9]MS10
D-Tyr-Asn-Val-Asn-Ser-Phe-AzaGly-Leu-Arg(Me)-Phe-NH₂

Compound No. 235: [D-Tyr1,Ala3,AzaGly7,Arg(Me)9]MS10
D-Tyr-Asn-Ala-Asn-Ser-Phe-AzaGly-Leu-Arg(Me)-Phe-NH₂

Compound No. 236: [D-Tyr1,D-Trp3,AzaGly7,Arg(Me)9]MS10
D-Tyr-Asn-D-Trp-Asn-Ser-Phe-AzaGly-Leu-Arg(Me)-Phe-NH₂

Compound No. 237: [D-Tyr1,D-Asn2,AzaGly7,Arg(Me)9]MS10
D-Tyr-D-Asn-Trp-Asn-Ser-Phe-AzaGly-Leu-Arg(Me)-Phe-NH₂

Compound No. 238: [D-Tyr1,D-Asn2,D-Trp3,AzaGly7,Arg(Me)9]MS10
D-Tyr-D-Asn-D-Trp-Asn-Ser-Phe-AzaGly-Leu-Arg(Me)-Phe-NH₂

Compound No. 239: des(1)-[D-Tyr2,Ser3,AzaGly7,Arg(Me)9]MS10
D-Tyr-Ser-Asn-Ser-Phe-AzaGly-Leu-Arg(Me)-Phe-NH₂

Compound No. 240: des(1)-[D-Tyr2,Ile3,AzaGly7,Arg(Me)9]MS10
D-Tyr-Ile-Asn-Ser-Phe-AzaGly-Leu-Arg(Me)-Phe-NH₂

Compound No. 241: des(1)-[D-Tyr2,Thr3,AzaGly7,Arg(Me)9]MS10
D-Tyr-Thr-Asn-Ser-Phe-AzaGly-Leu-Arg(Me)-Phe-NH₂

Compound No. 242: des(1)-[D-Tyr2,D-Trp3,AzaGly7,Arg(Me)9]MS10
D-Tyr-D-Trp-Asn-Ser-Phe-AzaGly-Leu-Arg(Me)-Phe-NH₂

Compound No. 244: [D-Tyr1,Phe3,AzaGly7,Arg(Me)9]MS10
D-Tyr-Asn-Phe-Asn-Ser-Phe-AzaGly-Leu-Arg(Me)-Phe-NH₂

Compound No. 245: [D-Tyr1,Nal(1)3,AzaGly7,Arg(Me)9]MS10
D-Tyr-Asn-Nal(1)-Asn-Ser-Phe-AzaGly-Leu-Arg(Me)-Phe-NH₂

Compound No. 246: [D-Tyr1,Nal(2)3,AzaGly7,Arg(Me)9]MS10
D-Tyr-Asn-Nal(2)-Asn-Ser-Phe-AzaGly-Leu-Arg(Me)-Phe-NH₂

Compound No. 247: [D-Tyr1,Phe(2Cl)3,AzaGly7,Arg(Me)9]MS10

-continued

D-Tyr-Asn-Phe(2Cl)-Asn-Ser-Phe-AzaGly-Leu-Arg(Me)-Phe-NH₂

Compound No. 248: [D-Tyr1,Phe(3Cl)3,AzaGly7,Arg(Me)9]MS10
D-Tyr-Asn-Phe(3Cl)-Asn-Ser-Phe-AzaGly-Leu-Arg(Me)-Phe-NH₂

Compound No. 249: [D-Tyr1,Phe(4Cl)3,AzaGly7,Arg(Me)9]MS10
D-Tyr-Asn-Phe(4Cl)-Asn-Ser-Phe-AzaGly-Leu-Arg(Me)-Phe-NH₂

Compound No. 250: [D-Tyr1,Phe(4NH2)3,AzaGly7,Arg(Me)9]MS10
D-Tyr-Asn-Phe(4NH₂)-Asn-Ser-Phe-AzaGly-Leu-Arg(Me)-Phe-NH₂

Compound No. 251: [D-Tyr1,Pya(3)3,AzaGly7,Arg(Me)9]MS10
D-Tyr-Asn-Pya(3)-Asn-Ser-Phe-AzaGly-Leu-Arg(Me)-Phe-NH₂

Compound No. 252: [D-Tyr1,D-Ala3,AzaGly7,Arg(Me)9]MS10
D-Tyr-Asn-D-Ala-Asn-Ser-Phe-AzaGly-Leu-Arg(Me)-Phe-NH₂

Compound No. 253: [D-Tyr1,Pro3,AzaGly7,Arg(Me)9]MS10
D-Tyr-Asn-Pro-Asn-Ser-Phe-AzaGly-Leu-Arg(Me)-Phe-NH₂

Compound No. 254: des(1)-[D-Tyr2,Phe3,AzaGly7,Arg(Me)9]MS10
D-Tyr-Phe-Asn-Ser-Phe-AzaGly-Leu-Arg(Me)-Phe-NH₂

Compound No. 255: des(1)-[D-Tyr2,Nal(2)3,AzaGly7,Arg(Me)9]MS10
D-Tyr-Nal(2)-Asn-Ser-Phe-AzaGly-Leu-Arg(Me)-Phe-NH₂

Compound No. 256: des(1)-[D-Pya(3)2,Phe3,AzaGly7,Arg(Me)9]MS10
D-Pya(3)-Phe-Asn-Ser-Phe-AzaGly-Leu-Arg(Me)-Phe-NH₂

Compound No. 257: [D-Tyr1,D-Asn2,Phe3,AzaGly7,Arg(Me)9]MS10
D-Tyr-D-Asn-Phe-Asn-Ser-Phe-AzaGly-Leu-Arg(Me)-Phe-NH₂

Compound No. 258: [D-Pya(3)1,AzaGly7,Arg(Me)9]MS10
D-Pya(3)-Asn-Trp-Asn-Ser-Phe-AzaGly-Leu-Arg(Me)-Phe-NH₂

Compound No. 259: [D-Ala1,AzaGly7,Arg(Me)9]MS10
D-Ala-Asn-Trp-Asn-Ser-Phe-AzaGly-Leu-Arg(Me)-Phe-NH₂

Compound No. 260: des(1-3)-3-(3-Indolyl)propionyl-[AzaGly7,Arg(Me)9]MS10
3-(3-Indolyl)propionyl-Asn-Ser-Phe-AzaGly-Leu-Arg(Me)-Phe-NH₂

Compound No. 261: [7Ψ8,CH₂NH]MS10
Tyr-Asn-Trp-Asn-Ser-Phe-GlyΨ(CH₂NH)Leu-Arg-Phe-NH₂

Compound No. 265: des(1-3)-Indole-3-carbonyl-[AzaGly7,Arg(Me)9]MS10
Indole-3-carbonyl-Asn-Ser-Phe-AzaGly-Leu-Arg(Me)-Phe-NH₂

Compound No. 266: des(1-3)-Indole-3-acetyl-[AzaGly7,Arg(Me)9]MS10
Indol-3-acetyl-Asn-Ser-Phe-AzaGly-Leu-Arg(Me)-Phe-NH₂

Compound No. 267: des(1-3)-4-(3-Indolyl)butyryl-[AzaGly7,Arg(Me)9]MS10
4-(3-Indolyl)butyryl-Asn-Ser-Phe-AzaGly-Leu-Arg(Me)-Phe-NH₂

Compound No. 268: des(1-3)-Diphenylacetyl-[AzaGly7,Arg(Me)9]MS10
Diphenylacetyl-Asn-Ser-Phe-AzaGly-Leu-Arg(Me)-Phe-NH₂

Compound No. 269: des(1-3)-3-Phenylpropionyl-[AzaGly7,Arg(Me)9]MS10
3-Phenylpropionyl-Asn-Ser-Phe-AzaGly-Leu-Arg(Me)-Phe-NH₂

Compound No. 270: [D-Tyr1,Phe3,Ser-Phe5,AzaGly7,Arg(Me)9]MS10
D-Tyr-Asn-Phe-Asn-Ser-Phe-Phe-AzaGly-Leu-Arg(Me)-Phe-NH₂

Compound No. 271: des(1-2)-[AzaGly7,Arg(Me)9]MS10
Trp-Asn-Ser-Phe-AzaGly-Leu-Arg(Me)-Phe-NH₂

Compound No. 272: des(1-2)-Acetyl-[AzaGly7,Arg(Me)9]MS10
Acetyl-Trp-Asn-Ser-Phe-AzaGly-Leu-Arg(Me)-Phe-NH₂

Compound No. 273: des(1-2)-Amidino-[AzaGly7,Arg(Me)9]MS10
Amidino-Trp-Asn-Ser-Phe-AzaGly-Leu-Arg(Me)-Phe-NH₂

Compound No. 274: des(1-2)-Acetyl-[Ala3,AzaGly7,Arg(Me)9]MS10
Acetyl-Ala-Asn-Ser-Phe-AzaGly-Leu-Arg(Me)-Phe-NH₂

Compound No. 275: des(1-2)-Acetyl-[Arg3,AzaGly7,Arg(Me)9]MS10
Acetyl-Arg-Asn-Ser-Phe-AzaGly-Leu-Arg(Me)-Phe-NH₂

Compound No. 276: des(1-2)-Acetyl-[Thr3,AzaGly7,Arg(Me)9]MS10
Acetyl-Thr-Asn-Ser-Phe-AzaGly-Leu-Arg(Me)-Phe-NH₂

Compound No. 277: des(1-3)-n-Hexanoyl-[AzaGly7,Arg(Me)9]MS10

-continued n-Hexanoyl-Asn-Ser-Phe-AzaGly-Leu-Arg(Me)-Phe-NH$_2$

Compound No. 278: des(1-3)-Cyclohexanecarbonyl-[AzaGly7, Arg(Me)9]MS10
Cyclohexanecarbonyl-Asn-Ser-Phe-AzaGly-Leu-Arg(Me)-Phe-NH$_2$ Compound No. 279: des(1-3)-2-(Indol-3-yl)ethylcarbamoyl-[AzaGly7,Arg(Me)9]MS10
2-(indol-3-yl)ethylcarbamoyl-Asn-Ser-Phe-AzaGly-Leu-Arg(Me)-Phe-NH$_2$ Compound No. 281: [D-Tyr1,Pya(2)6,Arg(Me)9]MS10
D-Tyr-Asn-Trp-Asn-Ser-Pya(2)-Gly-Leu-Arg(Me)-Phe-NH$_2$ Compound No. 282: [D-Tyr1,Pya(4)6,Arg(Me)9]MS10
D-Tyr-Asn-Trp-Asn-Ser-Pya(4)-Gly-Leu-Arg(Me)-Phe-NH$_2$ Compound No. 283: [D-Tyr1,D-Asn2,Cha3,AzaGly7,Arg(Me)9]MS10
D-Tyr-D-Asn-Cha-Asn-Ser-Phe-AzaGly-Leu-Arg(Me)-Phe-NH$_2$ Compound No. 284: [D-Tyr1,D-Asn2,Thr3,AzaGly7,Arg(Me)9]MS10
D-Tyr-D-Asn-Thr-Asn-Ser-Phe-AzaGly-Leu-Arg(Me)-Phe-NH$_2$ Compound No. 285: [D-Tyr1,Pya(2)3,AzaGly7,Arg(Me)9]MS10
D-Tyr-Asn-Pya(2)-Asn-Ser-Phe-AzaGly-Leu-Arg(Me)-Phe-NH$_2$ Compound No. 286: [D-Tyr1,Pya(4)3,AzaGly7,Arg(Me)9]MS10
D-Tyr-Asn-Pya(4)-Asn-Ser-Phe-AzaGly-Leu-Arg(Me)-Phe-NH$_2$ Compound No. 287: [D-Tyr1,D-Ser2,AzaGly7,Arg(Me)9]MS10
D-Tyr-D-Ser-Trp-Asn-Ser-Phe-AzaGly-Leu-Arg(Me)-Phe-NH$_2$ Compound No. 288: [D-Tyr1,D-His2,AzaGly7,Arg(Me)9]MS10
D-Tyr-D-His-Trp-Asn-Ser-Phe-AzaGly-Leu-Arg(Me)-Phe-NH$_2$ Compound No. 289: des(1)-[D-Pya(3)2,AzaGly7,Arg(Me)9]MS10
D-Pya(3)-Trp-Asn-Ser-Phe-AzaGly-Leu-Arg(Me)-Phe-NH$_2$ Compound No. 290: [D-Pya(3)1,D-Asn2,Cha3,AzaGly7,Arg(Me)9]MS10
D-Pya(3)-D-Asn-Cha-Asn-Ser-Phe-AzaGly-Leu-Arg(Me)-Phe-NH$_2$ Compound No. 291: [D-Pya(3)1,D-Tyr2,Cha3,AzaGly7,Arg(Me)9]MS10
D-Pya(3)-D-Tyr-Cha-Asn-Ser-Phe-AzaGly-Leu-Arg(Me)-Phe-NH$_2$ Compound No. 293: [4Ψ5,CH$_2$NH]MS10
Tyr-Asn-Trp-AsnΨ(CH$_2$NH)Ser-Phe-Gly-Leu-Arg-Phe-NH$_2$ Compound No. 294: [1Ψ2,CH$_2$NH]MS10
TyrΨ(CH$_2$NH)Asn-Trp-Asn-Ser-Phe-Gly-Leu-Arg-Phe-NH$_2$ Compound No. 295: [2Ψ3,CH$_2$NH]MS10
Tyr-AsnΨ(CH$_2$NH)Trp-Asn-Ser-Phe-Gly-Leu-Arg-Phe-NH$_2$ Compound No. 296: [6Ψ7,CSNH,D-Tyr1,Arg(Me)9]MS10
D-Tyr-Asn-Trp-Asn-Ser-PheΨ(CSNH)Gly-Leu-Arg(Me)-Phe-NH$_2$ Compound No. 297: [D-Tyr1,Thr5,AzaGly7,Arg(Me)9]MS10
D-Tyr-Asn-Trp-Asn-Thr-Phe-AzaGly-Leu-Arg(Me)-Phe-NH$_2$ Compound No. 298: [D-Tyr1,D-Asn2,Thr5,AzaGly7,Arg(Me)9]MS10
D-Tyr-D-Asn-Trp-Asn-Thr-Phe-AzaGly-Leu-Arg(Me)-Phe-NH$_2$ Compound No. 299: [1Ψ2,CH$_2$NH,AzaGly7,Arg(Me)9]-MS10
TyrΨ(CH$_2$NH)Asn-Trp-Asn-Ser-Phe-AzaGly-Leu-Arg(Me)-Phe-NH$_2$ Compound No. 300: [1Ψ2,CH$_2$NH,D-Trp3,AzaGly7,Arg(Me)9]-MS10
TyrΨ(CH$_2$NH)Asn-D-Trp-Asn-Ser-Phe-AzaGly-Leu-Arg(Me)-Phe-NH$_2$ Compound No. 301: [D-Tyr1,Ala(2-Qui)3,AzaGly7,Arg(Me)9]MS10
D-Tyr-Asn-Ala(2-Qui)-Asn-Ser-Phe-AzaGly-Leu-Arg(Me)-Phe-NH$_2$ Compound No. 302: [D-Tyr1,D-Pya(4)3,AzaGly7,Arg(Me)9]MS10
D-Tyr-Asn-D-Pya(4)-Asn-Ser-Phe-AzaGly-Leu-Arg(Me)-Phe-NH$_2$ Compound No. 303: [D-Tyr1,D-Asn2,Pya(4)3,AzaGly7,Arg(Me)9]MS10
D-Tyr-D-Asn-Pya(4)-Asn-Ser-Phe-AzaGly-Leu-Arg(Me)-Phe-NH$_2$ Compound No. 304: [D-Asn2,Pya(4)3,AzaGly7,Arg(Me)9]MS10
Tyr-D-Asn-Pya(4)-Asn-Ser-Phe-AzaGly-Leu-Arg(Me)-Phe-NH$_2$ Compound No. 305: des(1)-[D-Tyr2,D-Pya(4)3,AzaGly7,Arg(Me)9]MS10
D-Tyr-D-Pya(4)-Asn-Ser-Phe-AzaGly-Leu-Arg(Me)-Phe-NH$_2$ Compound No. 306: [D-Pya(4)1,D-Asn2,Cha3,AzaGly7,Arg(Me)9]MS10

-continued

D-Pya(4)-D-Asn-Cha-Asn-Ser-Phe-AzaGly-Leu-Arg(Me)-Phe-NH$_2$

Compound No. 307: [7Ψ8,CH$_2$NH,D-Tyr1,Arg(Me)9]MS10
D-Tyr-Asn-Trp-Asn-Ser-Phe-GlyΨ(CH$_2$NH)Leu-Arg(Me)-Phe-NH$_2$ Compound No. 308: [6Ψ7,CH$_2$NH,D-Tyr1,Arg(Me)9]MS10
D-Tyr-Asn-Trp-Asn-Ser-PheΨ(CH$_2$NH)Gly-Leu-Arg(Me)-Phe-NH$_2$ Compound No. 310: [Nar9]MS10
Tyr-Asn-Trp-Asn-Ser-Phe-Gly-Leu-Nar-Phe-NH$_2$ Compound No. 311: [Nar(Me)9]MS10
Tyr-Asn-Trp-Asn-Ser-Phe-Gly-Leu-Nar(Me)-Phe-NH$_2$ Compound No. 312: [Har(Me)9]MS10
Tyr-Asn-Trp-Asn-Ser-Phe-Gly-Leu-Har(Me)-Phe-NH$_2$ Compound No. 313: [Dab9]MS10
Tyr-Asn-Trp-Asn-Ser-Phe-Gly-Leu-Dab-Phe-NH$_2$ Compound No. 314: [Orn9]MS10
Tyr-Asn-Trp-Asn-Ser-Phe-Gly-Leu-Orn-Phe-NH$_2$ Compound No. 315: des(1)-[D-Asn2,Cha3,AzaGly7,Arg(Me)9]MS10
D-Asn-Cha-Asn-Ser-Phe-AzaGly-Leu-Arg(Me)-Phe-NH$_2$ Compound No. 316: [D-Tyr1,D-Asn2,Thr3,AzaGly7,Arg(Me)9,Phe(4F)10]MS10
D-Tyr-D-Asn-Thr-Asn-Ser-Phe-AzaGly-Leu-Arg(Me)-Phe(4F)-NH$_2$ Compound No. 317: [D-Tyr1,D-Asn2,Pya(4)3,AzaGly7,Arg(Me)9,Phe(4F)10]MS10
D-Tyr-D-Asn-Pya(4)-Asn-Ser-Phe-AzaGly-Leu-Arg(Me)-Phe(4F)-NH$_2$ Compound No. 318: [D-Tyr1,AzaGly7,Arg(Me)9,Phe(4F)10]MS10
D-Tyr-Asn-Trp-Asn-Ser-Phe-AzaGly-Leu-Arg(Me)-Phe(4F)-NH$_2$ Compound No. 319: [6Ψ7,NHCO,D-Tyr1,Arg(Me)9]MS10
D-Tyr-Asn-Trp-Asn-Ser-PheΨ(NHCO)Gly-Leu-Arg(Me)-Phe-NH$_2$ Compound No. 322: des(1-3)-3-(3-Pyridyl)propionyl-[AzaGly7,Arg(Me)9]MS10
3-(3-Pyridyl)propionyl-Asn-Ser-Phe-AzaGly-Leu-Arg(Me)-Phe-NH$_2$ Compound No. 323: des(1-3)-4-Imidazoleacetyl-[AzaGly7,Arg(Me)9]MS10
4-Imidazoleacetyl-Asn-Ser-Phe-AzaGly-Leu-Arg(Me)-Phe-NH$_2$ Compound No. 324: des(1-3)-4-Piperidinecarbonyl-[AzaGly7,Arg(Me)9]MS10
Piperidinecarbonyl-Asn-Ser-Phe-AzaGly-Leu-Arg(Me)-Phe-NH$_2$ Compound No. 325: des(1-3)-1-Piperidineacetyl-[AzaGly7,Arg(Me)9]MS10
1-Piperidineacetyl-Asn-Ser-Phe-AzaGly-Leu-Arg(Me)-Phe-NH$_2$ Compound No. 326: des(1-3)-1-Methylpiperidinio-1-acetyl-[AzaGly7,Arg(Me)9]MS10
1-Methylpiperidinio-1-acetyl-Asn-Ser-Phe-AzaGly-Leu-Arg(Me)-Phe-NH$_2$ Compound No. 327: des(1-3)-1-Pyridinioacetyl-[AzaGly7,Arg(Me)9]MS10
1-Pyridinoacetyl-Asn-Ser-Phe-AzaGly-Leu-Arg(Me)-Phe-NH$_2$ Compound No. 328: des(1-3)-D-Glucuronyl-[AzaGly7,Arg(Me)9]MS10
D-Glucuronyl-Asn-Ser-Phe-AzaGly-Leu-Arg(Me)-Phe-NH$_2$ Compound No. 375: 2-Aminoethyl-Gly-[D-Tyr1,Arg(Me)9]MS10
2-Aminoethyl-Gly-D-Tyr-Asn-Trp-Asn-Ser-Phe-Gly-Leu-Arg(Me)-Phe-NH$_2$ Compound No. 385: des(1)-[D-Tyr2,D-Pya(4)3,AzaGly7,Arg(Me)9,Trp10]MS10
D-Tyr-D-Pya(4)-Asn-Ser-Phe-AzaGly-Leu-Arg(Me)-Trp-NH$_2$ Compound No. 386: des(1-3)-3-(3-Pyridyl)propionyl-[AzaGly7,Arg(Me)9,Trp10]MS10
3-(3-Pyridyl)propionyl-Asn-Ser-Phe-AzaGly-Leu-Arg(Me)-Trp-NH$_2$ Compound No. 387: Dap-[D-Tyr1,Arg(Me)9]MS10
Dap-D-Tyr-Asn-Trp-Asn-Ser-Phe-Gly-Leu-Arg(Me)-Phe-NH$_2$ Compound No. 397: Methylthiocarbamoyl-Sar-[D-Tyr1,Arg(Me)9]MS10
Methylthiocarbamoyl-Sar-D-Tyr-Asn-Trp-Asn-Ser-Phe-Gly-Leu-Arg(Me)-Phe-NH$_2$ Compound No. 400:
(S)-1-(Quinolin-8-yl-carbamoyl)-4-thiapentylcarbamoyl-[D-Tyr1,Arg(Me)9]MS10
(S)-1-(Quinolin-8-yl-carbamoyl)-4-thiapentylcarbamoyl-D-Tyr-Asn-Trp-Asn-Ser-Phe-Gly-Leu-Arg(Me)-Phe-NH$_2$ Compound No. 481: des(1)-[D-Tyr2,D-Pya(4)3,AzaGly7,Har9,Trp10]MS10
D-Tyr-D-Pya(4)-Asn-Ser-Phe-AzaGly-Leu-Har-Trp-NH$_2$ -continued Compound No. 486: des(1)-[D-Tyr2,D-Pya(4)3,AzaGly7,Orn9]MS10
D-Tyr-D-Pya(4)-Asn-Ser-Phe-AzaGly-Leu-Orn-Phe-NH$_2$ Compound No. 487: des(1)-[D-Tyr2,D-Pya(4)3,AzaGly7,Lys9]MS10
D-Tyr-D-Pya(4)-Asn-Ser-Phe-AzaGly-Leu-Lys-Phe-NH$_2$ Compound No. 488: des(1)-[D-Tyr2,D-Pya(4)3,AzaGly7,Har9]MS10
D-Tyr-D-Pya(4)-Asn-Ser-Phe-AzaGly-Leu-Har-Phe-NH$_2$ Compound No. 489: des(1)-[D-Tyr2,D-Pya(4)3,AzaGly7,Har(Me)9]MS10
D-Tyr-D-Pya(4)-Asn-Ser-Phe-AzaGly-Leu-Har(Me)-Phe-NH$_2$ Compound No. 490: des(1)-[D-Tyr2,Pya(4)3,AzaGly7,Arg(Me)9]MS10
D-Tyr-Pya(4)-Asn-Ser-Phe-AzaGly-Leu-Arg(Me)-Phe-NH$_2$ Compound No. 491: des(1)-[D-Tyr2,D-Pya(4)3,Trp5,AzaGly7,Arg(Me)9,Trp10]MS10
D-Tyr-D-Pya(4)-Asn-Trp-Phe-AzaGly-Leu-Arg(Me)-Trp-NH$_2$ Compound No. 492: des(1)-[D-Tyr2,D-Pya(4)3,Ala4,AzaGly7,Arg(Me)9,Trp10]MS10
D-Tyr-D-Pya(4)-Ala-Ser-Phe-AzaGly-Leu-Arg(Me)-Trp-NH$_2$ Compound No. 493: des(1)-[D-Tyr2,D-Pya(4)3,Thr4,AzaGly7,Arg(Me)9,Trp10]MS10
D-Tyr-D-Pya(4)-Thr-Ser-Phe-AzaGly-Leu-Arg(Me)-Trp-NH$_2$ Compound No. 494: des(1,4)-[D-Tyr2,D-Pya(4)3,AzaGly7,Arg(Me)9,Trp10]MS10
D-Tyr-D-Pya(4)-Ser-Phe-AzaGly-Leu-Arg(Me)-Trp-NH$_2$ Compound No. 495: des(1-3)-[D-Tyr4,Pya(4)5,AzaGly7,Arg(Me)9,Trp10]MS10
D-Tyr-Pya(4)-Phe-AzaGly-Leu-Arg(Me)-Trp-NH$_2$ Compound No. 496: des(1)-[D-Tyr2,D-Pya(4)3,Cha6,Arg(Me)9,Trp10]MS10
D-Tyr-D-Pya(4)-Asn-Ser-Cha-Gly-Leu-Arg(Me)-Trp-NH$_2$ Compound No. 497: des(1)-[D-Tyr2,D-Pya(4)3,Cha6,Ala7,Arg(Me)9,Trp10]MS10
D-Tyr-D-Pya(4)-Asn-Ser-Cha-Ala-Leu-Arg(Me)-Trp-NH$_2$ Compound No. 498: des(1)-[D-Tyr2,D-Pya(4)3,Ile5,AzaGly7,Arg(Me)9,Trp10]MS10
D-Tyr-D-Pya(4)-Asn-Ile-Phe-AzaGly-Leu-Arg(Me)-Trp-NH$_2$ Compound No. 499: des(1-3)-3-Phenylpropionyl-[AzaGly7,Arg(Me)9,Trp10]MS10
3-Phenylpropionyl-Asn-Ser-Phe-AzaGly-Leu-Arg(Me)-Trp-NH$_2$ Compound No. 500:
des(1-3)-3-Phenylpropionyl-[Ala4,AzaGly7,Arg(Me)9,Trp10]MS10
3-Phenylpropionyl-Ala-Ser-Phe-AzaGly-Leu-Arg(Me)-Trp-NH$_2$ Compound No. 501: des(1)-[D-Tyr2,D-Pya(4)3,Thr5,AzaGly7,Arg(Me)9,Trp10]MS10
D-Tyr-D-Pya(4)-Asn-Thr-Phe-AzaGly-Leu-Arg(Me)-Trp-NH$_2$ Compound No. 502: des(1)-[D-Tyr2,Pya(4)3,Ala4,AzaGly7,Arg(Me)9,Trp10]MS10
D-Tyr-Pya(4)-Ala-Ser-Phe-AzaGly-Leu-Arg(Me)-Trp-NH$_2$ Compound No. 503: des(1)-[D-Tyr2,D-Trp3,Ala4,AzaGly7,Arg(Me)9,Trp10]MS10
D-Tyr-D-Trp-Ala-Ser-Phe-AzaGly-Leu-Arg(Me)-Trp-NH$_2$ Compound No. 504: [Acp1,D-Tyr2,D-Pya(4)3,AzaGly7,Arg(Me)9]MS10
Acp-D-Tyr-D-Pya(4)-Asn-Ser-Phe-AzaGly-Leu-Arg(Me)-Phe-NH$_2$ Compound No. 505:
des(1-3)-3-Phenylpropionyl-[Thr5,AzaGly7,Arg(Me)9,Trp10]MS10
3-Phenylpropionyl-Asn-Thr-Phe-AzaGly-Leu-Arg(Me)-Trp-NH$_2$ Compound No. 506:
des(1-3)-3-Phenylpropionyl-[Ile5,AzaGly7,Arg(Me)9,Trp10]MS10
3-Phenylpropionyl-Asn-Ile-Phe-AzaGly-Leu-Arg(Me)-Trp-NH$_2$ Compound No. 507:
des(1-3)-3-Phenylpropionyl-[Trp6,AzaGly7,Arg(Me)9,Trp10]MS10
3-Phenylpropionyl-Asn-Ser-Trp-AzaGly-Leu-Arg(Me)-Trp-NH$_2$ Compound No. 508:
des(1-3)-3-Phenylpropionyl-[Phe(4F)6,AzaGly7,Arg(Me)9,Trp10]MS10
3-Phenylpropionyl-Asn-Ser-Phe(4F)-AzaGly-Leu-Arg(Me)-Trp-NH$_2$ Compound No. 509: des(1-3)-Benzoyl-[AzaGly7,Arg(Me)9,Trp10]MS10
Benzoyl-Asn-Ser-Phe-AzaGly-Leu-Arg(Me)-Trp-NH$_2$ Compound No. 510: des(1-3)-Ac-[AzaGly7,Arg(Me)9,Trp10]MS10
Ac-Asn-Ser-Phe-AzaGly-Leu-Arg(Me)-Trp-NH$_2$ -continued Compound No. 511:
des(1)-[D-Tyr2,D-Trp3,Ala4,Thr5,AzaGly7,Arg(Me)9,Trp10]MS10
D-Tyr-D-Trp-Ala-Thr-Phe-AzaGly-Leu-Arg(Me)-Trp-NH$_2$ Compound No. 512:
des(1)-[D-Tyr2,D-Trp3,Thr5,AzaGly7,Arg(Me)9,Trp10]MS10
D-Tyr-D-Trp-Asn-Thr-Phe-AzaGly-Leu-Arg(Me)-Trp-NH$_2$ Compound No. 513: des(1)-[D-Tyr2,D-Trp3,Abu4,AzaGly7,Arg(Me)9,Trp10]MS10
D-Tyr-D-Trp-Abu-Ser-Phe-AzaGly-Leu-Arg(Me)-Trp-NH$_2$ Compound No. 514: des(1)-[D-Tyr2,D-Phe3,Ala4,AzaGly7,Arg(Me)9,Trp10]MS10
D-Tyr-D-Phe-Ala-Ser-Phe-AzaGly-Leu-Arg(Me)-Trp-NH$_2$ Compound No. 515: des(1)-[D-Tyr2,D-Pya(4)3,Val5,AzaGly7,Arg(Me)9,Trp10]MS10
D-Tyr-D-Pya(4)-Asn-Val-Phe-AzaGly-Leu-Arg(Me)-Trp-NH$_2$ Compound No. 516: des(1)-Ac-[D-Tyr2,D-Pya(4)3,AzaGly7,Arg(Me)9]MS10
Ac-D-Tyr-D-Pya(4)-Asn-Ser-Phe-AzaGly-Leu-Arg(Me)-Phe-NH$_2$ Compound No. 517:
des(1-3)-3-Phenylpropionyl-[Hyp5,AzaGly7,Arg(Me)9,Trp10]MS10
3-Phenylpropionyl-Asn-Hyp-Phe-AzaGly-Leu-Arg(Me)-Trp-NH$_2$ Compound No. 518: des(1-3)-3-Phenylpropionyl-[Cha6,Arg(Me)9,Trp10]MS10
3-Phenylpropionyl-Asn-Ser-Cha-Gly-Leu-Arg(Me)-Trp-NH$_2$ Compound No. 519: des(1-3)-Phenylacetyl-[AzaGly7,Arg(Me)9,Trp10]MS10
Phenylacetyl-Asn-Ser-Phe-AzaGly-Leu-Arg(Me)-Trp-NH$_2$ Compound No. 521: des(1)-[D-Tyr2,D-Pya(4)3,AzaGly7]MS10
D-Tyr-D-Pya(4)-Asn-Ser-Phe-AzaGly-Leu-Arg-Phe-NH$_2$ Compound No. 522: des(1-3)-Benzoyl-[Thr5,AzaGly7,Arg(Me)9,Trp10]MS10
Benzoyl-Asn-Thr-Phe-AzaGly-Leu-Arg(Me)-Trp-NH$_2$ Compound No. 523:
des(1-3)-Benzoyl-[Thr5,Phe(4F)6,AzaGly7,Arg(Me)9,Trp10]MS10
Benzoyl-Asn-Thr-Phe(4F)-AzaGly-Leu-Arg(Me)-Trp-NH$_2$ Compound No. 524:
des(1-3)-3-Phenylpropionyl-[Pro5,AzaGly7,Arg(Me)9,Trp10]MS10
3-Phenylpropionyl-Asn-Pro-Phe-AzaGly-Leu-Arg(Me)-Trp-NH$_2$ Compound No. 527: des(1)-[D-Tyr2,D-Pya(4)3,Hyp5,AzaGly7,Arg(Me)9,Trp10]MS10
D-Tyr-D-Pya(4)-Asn-Hyp-Phe-AzaGly-Leu-Arg(Me)-Trp-NH$_2$ Compound No. 528: des(1)-[D-Tyr2,D-Pya(4)3,Pro5,AzaGly7,Arg(Me)9,Trp10]MS10
D-Tyr-D-Pya(4)-Asn-Pro-Phe-AzaGly-Leu-Arg(Me)-Trp-NH$_2$ Compound No. 529: des(1)-[D-Tyr2,D-Pya(4)3,Tle5,AzaGly7,Arg(Me)9,Trp10]MS10
D-Tyr-D-Pya(4)-Asn-Tle-Phe-AzaGly-Leu-Arg(Me)-Trp-NH$_2$ Compound No. 530: des(1)-[D-Tyr2,D-Pya(4)3,Phg5,AzaGly7,Arg(Me)9,Trp10]MS10
D-Tyr-D-Pya(4)-Asn-Phg-Phe-AzaGly-Leu-Arg(Me)-Trp-NH$_2$ Compound No. 531:
des(1-3)-3-Phenylpropionyl-[Pic(2)5,AzaGly7,Arg(Me)9,Trp10]MS10
3-Phenylpropionyl-Asn-Pic(2)-Phe-AzaGly-Leu-Arg(Me)-Trp-NH$_2$ Compound No. 532:
des(1-3)-3-Phenylpropionyl-[Aze(2)5,AzaGly7,Arg(Me)9,Trp10]MS10
3-Phenylpropionyl-Asn-Aze(2)-Phe-AzaGly-Leu-Arg(Me)-Trp-NH$_2$ Compound No. 533:
des(1-3)-3-Phenylpropionyl-[D-Pro5,AzaGly7,Arg(Me)9,Trp10]MS10
3-Phenylpropionyl-Asn-D-Pro-Phe-AzaGly-Leu-Arg(Me)-Trp-NH$_2$ Compound No. 534: des(1-3)-Cyclopropanecarbonyl-[AzaGly7,Arg(Me)9,Trp10]MS10
Cyclopropanecarbonyl-Asn-Ser-Phe-AzaGly-Leu-Arg(Me)-Trp-NH$_2$ Compound No. 535: des(1-3)-2-Naphthoyl-[AzaGly7,Arg(Me)9,Trp10]MS10
2-Naphthoyl-Asn-Ser-Phe-AzaGly-Leu-Arg(Me)-Trp-NH$_2$ Compound No. 536: [Arg1,D-Tyr2,D-Pya(4)3,AzaGly7,Arg(Me)9,Trp10]MS10
Arg-D-Tyr-D-Pya(4)-Asn-Ser-Phe-AzaGly-Leu-Arg(Me)-Trp-NH$_2$ Compound No. 537: Arg-[Arg1,D-Tyr2,D-Pya(4)3,AzaGly7,Arg(Me)9,Trp10]MS10
Arg-Arg-D-Tyr-D-Pya(4)-Asn-Ser-Phe-AzaGly-Leu-Arg(Me)-Trp-NH$_2$ Compound No. 538: Arg-[Acp1,D-Tyr2,D-Pya(4)3,AzaGly7,Arg(Me)9,Trp10]MS10
Arg-Acp-D-Tyr-D-Pya(4)-Asn-Ser-Phe-AzaGly-Leu-Arg(Me)-Trp-NH$_2$ -continued Compound No. 539: des(1)-[D-Tyr2,D-Trp3,Val5,AzaGly7,Arg(Me)9,Trp10]MS10
D-Tyr-D-Trp-Asn-Val-Phe-AzaGly-Leu-Arg(Me)-Trp-NH$_2$ Compound No. 540: des(1)-[D-Tyr2,D-Trp3,AzaGly7,Arg(Me)9,Trp10]MS10
D-Tyr-D-Trp-Asn-Ser-Phe-AzaGly-Leu-Arg(Me)-Trp-NH$_2$ Compound No. 541:
D-Arg-[Acp1,D-Tyr2,D-Trp3,Thr5,AzaGly7,Arg(Me)9,Trp10]MS10
D-Arg-Acp-D-Tyr-D-Trp-Asn-Thr-Phe-AzaGly-Leu-Arg(Me)-Trp-NH$_2$ Compound No. 542:
D-Arg-D-Arg-[Acp1,D-Tyr2,D-Trp3,Thr5,AzaGly7,Arg(Me)9,Trp10]MS10
D-Arg-D-Arg-Acp-D-Tyr-D-Trp-Asn-Thr-Phe-AzaGly-Leu-Arg(Me)-Trp-NH$_2$ Compound No. 545: des(1-3)-Benzoyl-[Phe(4F)6,AzaGly7,Arg(Me)9,Trp10]MS10
Benzoyl-Asn-Ser-Phe(4F)-AzaGly-Leu-Arg(Me)-Trp-NH$_2$ Compound No. 546:
des(1-3)-3-Phenylpropionyl-[Ser(Ac)5,AzaGly7,Arg(Me)9,Trp10]MS10
3-Phenylpropionyl-Asn-Ser(Ac)-Phe-AzaGly-Leu-Arg(Me)-Trp-NH$_2$ Compound No. 547:
des(1)-[D-Tyr2,D-Pya(4)3,Ser(Ac)5,AzaGly7,Arg(Me)9,Trp10]MS10
D-Tyr-D-Pya(4)-Asn-Ser(Ac)-Phe-AzaGly-Leu-Arg(Me)-Trp-NH$_2$ Compound No. 548: des(1)-[D-Tyr2,D-Pya(4)3,AzaGly7,Arg(Me)9,10Ψ,CSNH]MS10
D-Tyr-D-Pya(4)-Asn-Ser-Phe-AzaGly-Leu-Arg(Me)-PheΨ(CSNH)NH$_2$ Compound No. 550: des(1)-Ac-[D-Tyr2,D-Trp3,Thr5,AzaGly7,Arg(Me)9,Trp10]MS10
Ac-D-Tyr-D-Trp-Asn-Thr-Phe-AzaGly-Leu-Arg(Me)-Trp-NH$_2$ Compound No. 551
Ac-D-Arg-[Acp1,D-Tyr2,D-Trp3,Thr5,AzaGly7,Arg(Me)9,Trp10]MS10
Ac-D-Arg-Acp-D-Tyr-D-Trp-Asn-Thr-Phe-AzaGly-Leu-Arg(Me)-Trp-NH$_2$ Compound No. 552:
D-Dap-[Acp1,D-Tyr2,D-Trp3,Thr5,AzaGly7,Arg(Me)9,Trp10]MS10
D-Dap-Acp-D-Tyr-D-Trp-Asn-Thr-Phe-AzaGly-Leu-Arg(Me)-Trp-NH$_2$ Compound No. 553:
D-Nle-[Acp1,D-Tyr2,D-Trp3,Thr5,AzaGly7,Arg(Me)9,Trp10]MS10
D-Nle-Acp-D-Tyr-D-Trp-Asn-Thr-Phe-AzaGly-Leu-Arg(Me)-Trp-NH$_2$ Compound No. 554:
D-Arg-[β-Ala1,D-Tyr2,D-Trp3,Thr5,AzaGly7,Arg(Me)9,Trp10]MS10
D-Arg-β-Ala-D-Tyr-D-Trp-Asn-Thr-Phe-AzaGly-Leu-Arg(Me)-Trp-NH$_2$ Compound No. 555:
D-Arg-[γ-Abu1,D-Tyr2,D-Trp3,Thr5,AzaGly7,Arg(Me)9,Trp10]MS10
D-Arg-γ-Abu-D-Tyr-D-Trp-Asn-Thr-Phe-AzaGly-Leu-Arg(Me)-Trp-NH$_2$ Compound No. 556:
D-Arg-D-Arg-[γ-Abu1,D-Tyr2,D-Trp3,Thr5,AzaGly7,Arg(Me)9,Trp10]MS10
D-Arg-D-Arg-γ-Abu-D-Tyr-D-Trp-Asn-Thr-Phe-AzaGly-Leu-Arg(Me)-Trp-NH$_2$ Compound No. 557:
D-Arg-D-Arg-D-Arg-[γ-Abu1,D-Tyr2,D-Trp3,Thr5,AzaGly7,Arg(Me)9,Trp10]MS10
D-Arg-D-Arg-D-Arg-γ-Abu-D-Tyr-D-Trp-Asn-Thr-Phe-AzaGly-Leu-Arg(Me)-Trp-NH$_2$ Compound No. 558: des(1)-Ac-[D-Tyr2,D-Trp3,AzaGly7,Arg(Me)9,Trp10]MS10
D-Tyr-D-Trp-Asn-Ser-Phe-AzaGly-Leu-Arg(Me)-Trp-NH$_2$ Compound No. 559:
des(1-2)-3-(4-Hydroxyphenyl)propionyl-[D-Trp3,Thr5,AzaGly7,Arg(Me)9,Trp10]MS10
3-(4-Hydroxyphenyl)propionyl-D-Trp-Asn-Thr-Phe-AzaGly-Leu-Arg(Me)-Trp-NH$_2$ Compound No. 561:
D-Arg-[Acp1,D-Tyr2,D-Trp3,Abu4,AzaGly7,Arg(Me)9,Trp10]MS10
D-Arg-Acp-D-Tyr-D-Trp-Abu-Ser-Phe-AzaGly-Leu-Arg(Me)-Trp-NH$_2$ Compound No. 562:
des(1)-Ac-[D-Tyr2,D-Pya(4)3,Thr5,AzaGly7,Arg(Me)9,Trp10]MS10
Ac-D-Tyr-D-Pya(4)-Asn-Thr-Phe-AzaGly-Leu-Arg(Me)-Trp-NH$_2$ Compound No. 563:
des(1)-Ac-[D-Tyr2,D-Trp3,Aze(2)5,AzaGly7,Arg(Me)9,Trp10]MS10
Ac-D-Tyr-D-Trp-Asn-Aze(2)-Phe-AzaGly-Leu-Arg(Me)-Trp-NH$_2$ Compound No. 564: des(1)-Ac-[D-Tyr2,D-Trp3,Val5,AzaGly7,Arg(Me)9,Trp10]MS10

-continued

Ac-D-Tyr-D-Trp-Asn-Val-Phe-AzaGly-Leu-Arg(Me)-Trp-NH₂

Compound No. 565:
des(1)-Benzoyl-[D-Tyr2,D-Trp3,Thr5,AzaGly7,Arg(Me)9,Trp10]MS10
Benzoyl-D-Tyr-D-Trp-Asn-Thr-Phe-AzaGly-Leu-Arg(Me)-Trp-NH₂

Compound No. 566:
des(1)-Cyclopropanecarbonyl-[D-Tyr2,D-Trp3,Thr5,AzaGly7,Arg(Me)9,Trp10]MS10
Cyclopropanecarbonyl-D-Tyr-D-Trp-Asn-Thr-Phe-AzaGly-Leu-Arg(Me)-Trp-NH₂

Compound No. 567:
des(1)-Butyryl-[D-Tyr2,D-Trp3,Thr5,AzaGly7,Arg(Me)9,Trp10]MS10
Butyryl-D-Tyr-D-Trp-Asn-Thr-Phe-AzaGly-Leu-Arg(Me)-Trp-NH₂

Compound No. 568:
Ac-[D-Arg1,D-Tyr2,D-Trp3,Thr5,AzaGly7,Arg(Me)9,Trp10]MS10
Ac-D-Arg-D-Tyr-D-Trp-Asn-Thr-Phe-AzaGly-Leu-Arg(Me)-Trp-NH₂

Compound No. 569:
des(1)-Ac-[D-Tyr2,D-Trp3,Thr5,6Ψ7,CH₂NH,Arg(Me)9,Trp10]MS10
Ac-D-Tyr-D-Trp-Asn-Thr-PheΨ(CH₂NH)Gly-Leu-Arg(Me)-Trp-NH₂

Compound No. 570: des(1)-Me-[D-Tyr2,D-Trp3,Thr5,AzaGly7,Arg(Me)9,Trp10]MS10
Me-D-Tyr-D-Trp-Asn-Thr-Phe-AzaGly-Leu-Arg(Me)-Trp-NH₂

Compound No. 571: des(1)-Ac-[D-Tyr2,D-Trp3,Thr5,AzaGly7,Arg(Me)9]MS10
Ac-D-Tyr-D-Trp-Asn-Thr-Phe-AzaGly-Leu-Arg(Me)-Phe-NH₂

Compound No. 572: des(1)-[D-Trp2,D-Pya(4)3,AzaGly7,Arg(Me)9,Trp10]MS10
D-Trp-D-Pya(4)-Asn-Ser-Phe-AzaGly-Leu-Arg(Me)-Trp-NH₂

Compound No. 573:
des(1)-Ac-[D-Tyr2,D-Trp3,Abu4,AzaGly7,Arg(Me)9,Trp10]MS10
Ac-D-Tyr-D-Trp-Abu-Ser-Phe-AzaGly-Leu-Arg(Me)-Trp-NH₂

Compound No. 576: des(1)-Ac-[D-Tyr2,D-Trp3,Gln4,AzaGly7,Arg(Me)9,Trp10]MS10
Ac-D-Tyr-D-Trp-Gln-Ser-Phe-AzaGly-Leu-Arg(Me)-Trp-NH₂

Compound No. 577: des(1)-Ac-[D-Tyr2,D-Trp3,Ser4,AzaGly7,Arg(Me)9,Trp10]MS10
Ac-D-Tyr-D-Trp-Ser-Ser-Phe-AzaGly-Leu-Arg(Me)-Trp-NH₂

Compound No. 578: des(1)-Ac-[D-Tyr2,D-Trp3,Thr4,AzaGly7,Arg(Me)9,Trp10]MS10
Ac-D-Tyr-D-Trp-Thr-Ser-Phe-AzaGly-Leu-Arg(Me)-Trp-NH₂

Compound No. 579: des(1)-Ac-[D-Tyr2,D-Trp3,Aib4,AzaGly7,Arg(Me)9,Trp10]MS10
Ac-D-Tyr-D-Trp-Aib-Ser-Phe-AzaGly-Leu-Arg(Me)-Trp-NH₂

Compound No. 580:
des(1)-Ac-[D-Tyr2,D-Trp3,Ser(Me)5,AzaGly7,Arg(Me)9,Trp10]MS10
Ac-D-Tyr-D-Trp-Asn-Ser(Me)-Phe-AzaGly-Leu-Arg(Me)-Trp-NH₂

Compound No. 584:
des(1)-Ac-[D-Tyr2,D-Trp3,Dap(Ac)4,AzaGly7,Arg(Me)9,Trp10]MS10
Ac-D-Tyr-D-Trp-Dap(Ac)-Ser-Phe-AzaGly-Leu-Arg(Me)-Trp-NH₂

Compound No. 585:
des(1)-Ac-[D-Tyr2,D-Trp3,Dap(For)4,AzaGly7,Arg(Me)9,Trp10]MS10
Ac-D-Tyr-D-Trp-Dap(For)-Ser-Phe-AzaGly-Leu-Arg(Me)-Trp-NH₂

Compound No. 586: des(1)-Ac-[D-Tyr2,Thr5,D-Phe6,AzaGly7,Arg(Me)9,Trp10]MS10
Ac-D-Tyr-Trp-Asn-Thr-D-Phe-AzaGly-Leu-Arg(Me)-Trp-NH₂

Compound No. 589:
des(1)-Ac-[D-Tyr2,D-Trp3,Thr5,AzaGly7,Arg(Me)9,Nal(2)10]MS10
Ac-D-Tyr-D-Trp-Asn-Thr-Phe-AzaGly-Leu-Arg(Me)-Nal(2)-NH₂

Compound No. 590: des(1)-Ac-[D-Tyr2,D-Trp3,Thr5,AzaGly7,Arg(Me)9,Thi10]MS10
Ac-D-Tyr-D-Trp-Asn-Thr-Phe-AzaGly-Leu-Arg(Me)-Thi-NH₂

Compound No. 591: des(1)-Ac-[D-Tyr2,D-Trp3,Thr5,AzaGly7,Arg(Me)9,Tyr10]MS10
Ac-D-Tyr-D-Trp-Asn-Thr-Phe-AzaGly-Leu-Arg(Me)-Tyr-NH₂

Compound No. 592:
des(1)-Ac-[D-Tyr2,D-Trp3,Thr5,AzaGly7,Arg(Me)9,Phe(4F)10]MS10
Ac-D-Tyr-D-Trp-Asn-Thr-Phe-AzaGly-Leu-Arg(Me)-Phe(4F)-NH₂

Compound No. 594:
des(1)-Ac-[D-Tyr2,D-Trp3,Thr5,AzaGly7,Arg(Me)9,Hph10]MS10
Ac-D-Tyr-D-Trp-Asn-Thr-Phe-AzaGly-Leu-Arg(Me)-Hph-NH₂

-continued

Compound No. 595: des(1)-Ac-[D-Tyr2,D-Trp3,Thr5,AzaGly7,Arg(Me)9,Cha10]MS10
Ac-D-Tyr-D-Trp-Asn-Thr-Phe-AzaGly-Leu-Arg(Me)-Cha-NH$_2$ Compound No. 596: des(1)-Ac-[D-Tyr2,D-Trp3,Thr5,AzaGly7,Arg(Me)9,Leu10]MS10
Ac-D-Tyr-D-Trp-Asn-Thr-Phe-AzaGly-Leu-Arg(Me)-Leu-NH$_2$ Compound No. 597:
des(1)-Ac-[D-Tyr2,D-Trp3,Thr5,D-Phe6,AzaGly7,Arg(Me)9,Trp10]MS10
Ac-D-Tyr-D-Trp-Asn-Thr-D-Phe-AzaGly-Leu-Arg(Me)-Trp-NH$_2$ Compound No. 598: des(1)-Ac-[D-Tyr2,D-Trp3,Thr5,Arg(Me)9,Trp10]MS10
Ac-D-Tyr-D-Trp-Asn-Thr-Phe-Gly-Leu-Arg(Me)-Trp-NH$_2$ Compound No. 599: des(1)-Ac-[D-Tyr2,D-Trp3,Thr5,AzaGly7,Orn9,Trp10]MS10
Ac-D-Tyr-D-Trp-Asn-Thr-Phe-AzaGly-Leu-Orn-Trp-NH$_2$ Compound No. 600: des(1)-Ac-[D-Tyr2,D-Trp3,Thr5,AzaGly7,Trp10]MS10
Ac-D-Tyr-D-Trp-Asn-Thr-Phe-AzaGly-Leu-Arg-Trp-NH$_2$ Compound No. 601: des(1)-Ac-[D-Tyr2,D-Trp3,Thr5,D-Phe6,Arg(Me)9,Trp10]MS10
Ac-D-Tyr-D-Trp-Asn-Thr-D-Phe-Gly-Leu-Arg(Me)-Trp-NH$_2$ Compound No. 602:
des(1)-Ac-[D-NMeTyr2,D-Trp3,Thr5,AzaGly7,Arg(Me)9,Trp10]MS10
Ac-D-NMeTyr-D-Trp-Asn-Thr-Phe-AzaGly-Leu-Arg(Me)-Trp-NH$_2$ Compound No. 603:
des(1)-Ac-[D-Tyr2,D-Pya(4)3,Thr5,D-Phe6,AzaGly7,Arg(Me)9,Trp10]MS10
Ac-D-Tyr-D-Pya(4)-Asn-Thr-D-Phe-AzaGly-Leu-Arg(Me)-Trp-NH$_2$ Compound No. 604: des(1)-Ac-[D-Tyr2,D-Trp3,Thr5,AzaGly7,Arg(Tos)9,Trp10]MS10
Ac-D-Tyr-D-Trp-Asn-Thr-Phe-AzaGly-Leu-Arg(Tos)-Trp-NH$_2$ Compound No. 605:
des(1)-Ac-[D-Tyr2,D-Trp3,Thr5,AzaGly7,Arg(NO2)9,Trp10]MS10
Ac-D-Tyr-D-Trp-Asn-Thr-Phe-AzaGly-Leu-Arg(NO2)-Trp-NH$_2$ Compound No. 607:
des(1)-Ac-[D-Tyr2,D-Trp3,Thr5,AzaGly7,Arg(Me2)asym9,Trp10]MS10
Ac-D-Tyr-D-Trp-Asn-Thr-Phe-AzaGly-Leu-Arg(Me2)asym-Trp-NH$_2$ Compound No. 608:
des(1)-Ac-[D-Tyr2,D-Trp3,Thr5,AzaGly7,Arg(Me2)sym9,Trp10]MS10
Ac-D-Tyr-D-Trp-Asn-Thr-Phe-AzaGly-Leu-Arg(Me2)sym-Trp-NH$_2$ Compound No. 609: des(1)-Ac-[D-Tyr2,D-Trp3,Thr5,AzaGly7,Arg(Et)9,Trp10]MS10
Ac-D-Tyr-D-Trp-Asn-Thr-Phe-AzaGly-Leu-Arg(Et)-Trp-NH$_2$ Compound No. 610:
des(1)-Ac-[D-Tyr2,D-Trp3,Thr5,AzaGly7,Lys(Me2)9,Trp10]MS10
Ac-D-Tyr-D-Trp-Asn-Thr-Phe-AzaGly-Leu-Lys(Me2)-Trp-NH$_2$ Compound No. 611: des(1)-Ac-[Tyr2,D-Pya(4)3,Thr5,AzaGly7,Arg(Me)9,Trp10]MS10
Ac-Tyr-D-Pya(4)-Asn-Thr-Phe-AzaGly-Leu-Arg(Me)-Trp-NH$_2$ Compound No. 612: des(1)-For-[D-Tyr2,D-Trp3,Thr5,AzaGly7,Arg(Me)9,Trp10]MS10
For-D-Tyr-D-Trp-Asn-Thr-Phe-AzaGly-Leu-Arg(Me)-Trp-NH$_2$ Compound No. 613:
des(1)-Propionyl-[D-Tyr2,D-Trp3,Thr5,AzaGly7,Arg(Me)9,Trp10]MS10
Propionyl-D-Tyr-D-Trp-Asn-Thr-Phe-AzaGly-Leu-Arg(Me)-Trp-NH$_2$ Compound No. 614:
des(1)-Amidino-[D-Tyr2,D-Trp3,Thr5,AzaGly7,Arg(Me)9,Trp10]MS10
Amidino-D-Tyr-D-Trp-Asn-Thr-Phe-AzaGly-Leu-Arg(Me)-Trp-NH$_2$ Compound No. 615: des(1)-Ac-[Tyr2,D-Pya(4)3,Thr5,AzaGly7,Arg(Me)9,Trp10]MS10
Ac-Tyr-D-Pya(4)-Asn-Thr-Phe-AzaGly-Leu-Arg(Me)-Trp-NH$_2$ Compound No. 616: des(1)-Ac-[D-Ala2,D-Trp3,Thr5,AzaGly7,Arg(Me)9,Trp10]MS10
Ac-D-Ala-D-Trp-Asn-Thr-Phe-AzaGly-Leu-Arg(Me)-Trp-NH$_2$ Compound No. 617: des(1)-Ac-[D-Leu2,D-Trp3,Thr5,AzaGly7,Arg(Me)9,Trp10]MS10
Ac-D-Leu-D-Trp-Asn-Thr-Phe-AzaGly-Leu-Arg(Me)-Trp-NH$_2$ Compound No. 618: des(1)-Ac-[D-Phe2,D-Trp3,Thr5,AzaGly7,Arg(Me)9,Trp10]MS10
Ac-D-Phe-D-Trp-Asn-Thr-Phe-AzaGly-Leu-Arg(Me)-Trp-NH$_2$ Compound No. 619:
des(1)-Ac-[D-Nal(1)2,D-Trp3,Thr5,AzaGly7,Arg(Me)9,Trp10]MS10
Ac-D-Nal(1)-D-Trp-Asn-Thr-Phe-AzaGly-Leu-Arg(Me)-Trp-NH$_2$ -continued

```
Compound No. 620:
des(1)-Ac-[D-Nal(2)2,D-Trp3,Thr5,AzaGly7,Arg(Me)9,Trp10]MS10
Ac-D-Nal(2)-D-Trp-Asn-Thr-Phe-AzaGly-Leu-Arg(Me)-Trp-NH₂

Compound No. 621: des(1)-Ac-[D-Lys2,D-Trp3,Thr5,AzaGly7,Arg(Me)9,Trp10]MS10
Ac-D-Lys-D-Trp-Asn-Thr-Phe-AzaGly-Leu-Arg(Me)-Trp-NH₂

Compound No. 622: des(1)-Ac-[D-Glu2,D-Trp3,Thr5,AzaGly7,Arg(Me)9,Trp10]MS10
Ac-D-Glu-D-Trp-Asn-Thr-Phe-AzaGly-Leu-Arg(Me)-Trp-NH₂

Compound No. 623: des(1)-Ac-[D-Tyr2,Thr5,AzaGly7,Arg(Me)9,Trp10]MS10
Ac-D-Tyr-Trp-Asn-Thr-Phe-AzaGly-Leu-Arg(Me)-Trp-NH₂

Compound No. 624: des(1)-Ac-[D-Tyr2,Pya(4)3,Thr5,AzaGly7,Arg(Me)9,Trp10]MS10
Ac-D-Tyr-Pya(4)-Asn-Thr-Phe-AzaGly-Leu-Arg(Me)-Trp-NH₂

Compound No. 625: des(1)-Ac-[D-Tyr2,D-Ala3,Thr5,AzaGly7,Arg(Me)9,Trp10]MS10
Ac-D-Tyr-D-Ala-Asn-Thr-Phe-AzaGly-Leu-Arg(Me)-Trp-NH₂

Compound No. 626: des(1)-Ac-[D-Tyr2,D-Leu3,Thr5,AzaGly7,Arg(Me)9,Trp10]MS10
Ac-D-Tyr-D-Leu-Asn-Thr-Phe-AzaGly-Leu-Arg(Me)-Trp-NH₂

Compound No. 627: des(1)-Ac-[D-Tyr2,D-Phe3,Thr5,AzaGly7,Arg(Me)9,Trp10]MS10
Ac-D-Tyr-D-Phe-Asn-Thr-Phe-AzaGly-Leu-Arg(Me)-Trp-NH₂

Compound No. 628: des(1)-Ac-[D-Tyr2,D-Thr3,Thr5,AzaGly7,Arg(Me)9,Trp10]MS10
Ac-D-Tyr-D-Thr-Asn-Thr-Phe-AzaGly-Leu-Arg(Me)-Trp-NH₂

Compound No. 629: des(1)-Ac-[D-Tyr2,D-Lys3,Thr5,AzaGly7,Arg(Me)9,Trp10]MS10
Ac-D-Tyr-D-Lys-Asn-Thr-Phe-AzaGly-Leu-Arg(Me)-Trp-NH₂

Compound No. 630: des(1)-Ac-[D-Tyr2,D-Glu3,Thr5,AzaGly7,Arg(Me)9,Trp10]MS10
Ac-D-Tyr-D-Glu-Asn-Thr-Phe-AzaGly-Leu-Arg(Me)-Trp-NH₂

Compound No. 631:
des(1)-Ac-[D-Tyr2,D-Trp3,Thr5,Ala6,AzaGly7,Arg(Me)9,Trp10]MS10
Ac-D-Tyr-D-Trp-Asn-Thr-Ala-AzaGly-Leu-Arg(Me)-Trp-NH₂

Compound No. 632:
des(1)-Ac-[D-Tyr2,D-Trp3,Thr5,Leu6,AzaGly7,Arg(Me)9,Trp10]MS10
Ac-D-Tyr-D-Trp-Asn-Thr-Leu-AzaGly-Leu-Arg(Me)-Trp-NH₂

Compound No. 633:
des(1)-Ac-[D-Tyr2,D-Trp3,Thr5,Lys6,AzaGly7,Arg(Me)9,Trp10]MS10
Ac-D-Tyr-D-Trp-Asn-Thr-Lys-AzaGly-Leu-Arg(Me)-Trp-NH₂

Compound No. 634:
des(1)-Ac-[D-Tyr2,D-Trp3,Thr5,Glu6,AzaGly7,Arg(Me)9,Trp10]MS10
Ac-D-Tyr-D-Trp-Asn-Thr-Glu-AzaGly-Leu-Arg(Me)-Trp-NH₂

Compound No. 635:
des(1)-Ac-[D-Tyr2,D-Trp3,Thr5,Pya(4)6,AzaGly7,Arg(Me)9,Trp10]MS10
Ac-D-Tyr-D-Trp-Asn-Thr-Pya(4)-AzaGly-Leu-Arg(Me)-Trp-NH₂

Compound No. 636:
des(1)-Ac-[D-Tyr2,D-Trp3,Thr5,MePhe6,AzaGly7,Arg(Me)9,Trp10]MS10
Ac-D-Tyr-D-Trp-Asn-Thr-MePhe-AzaGly-Leu-Arg(Me)-Trp-NH₂

Compound No. 637:
des(1)-Ac-[D-Tyr2,D-Trp3,Thr5,Phe(4F)6,AzaGly7,Arg(Me)9,Trp10]MS10
Ac-D-Tyr-D-Trp-Asn-Thr-Phe(4F)-AzaGly-Leu-Arg(Me)-Trp-NH₂

Compound No. 638:
des(1)-Ac-[D-Tyr2,D-Pya(4)3,Thr5,Phe(4F)6,AzaGly7,Arg(Me)9,Trp10]MS10
Ac-D-Tyr-D-Pya(4)-Asn-Thr-Phe(4F)-AzaGly-Leu-Arg(Me)-Trp-NH₂

Compound No. 639: des(1)-Ac-[D-Tyr2,D-Trp3,Thr5,AzaGly7,Lys9,Trp10]MS10
Ac-D-Tyr-D-Trp-Asn-Thr-Phe-AzaGly-Leu-Lys-Trp-NH₂

Compound No. 641:
des(1)-Ac-[D-Tyr2,D-Trp3,Thr5,AzaGly7,Ala8,Arg(Me)9,Trp10]MS10
Ac-D-Tyr-D-Trp-Asn-Thr-Phe-AzaGly-Ala-Arg(Me)-Trp-NH₂

Compound No. 642:
des(1)-Ac-[D-Tyr2,D-Trp3,Thr5,AzaGly7,Val8,Arg(Me)9,Trp10]MS10
Ac-D-Tyr-D-Trp-Asn-Thr-Phe-AzaGly-Val-Arg(Me)-Trp-NH₂

Compound No. 643:
des(1)-Ac-[D-Tyr2,D-Trp3,Thr5,AzaGly7,Phe8,Arg(Me)9,Trp10]MS10
Ac-D-Tyr-D-Trp-Asn-Thr-Phe-AzaGly-Phe-Arg(Me)-Trp-NH₂
```

```
Compound No. 644:
des(1)-Ac-[D-Tyr2,D-Trp3,Thr5,AzaGly7,Ser8,Arg(Me)9,Trp10]MS10
Ac-D-Tyr-D-Trp-Asn-Thr-Phe-AzaGly-Ser-Arg(Me)-Trp-NH₂

Compound No. 645: des(1)-Ac-[D-Tyr2,D-Trp3,Thr5,AzaGly7,Har9,Trp10]MS10
Ac-D-Tyr-D-Trp-Asn-Thr-Phe-AzaGly-Leu-Har-Trp-NH₂

Compound No. 646: des(1)-Ac-[D-Tyr2,D-Trp3,Thr5,AzaGly7,Har(Me)9,Trp10]MS10
Ac-D-Tyr-D-Trp-Asn-Thr-Phe-AzaGly-Leu-Har(Me)-Trp-NH₂

Compound No. 647:
des(1)-Ac-[D-Tyr2,D-Trp3,Asp4,Thr5,AzaGly7,Arg(Me)9,Trp10]MS10
Ac-D-Tyr-D-Trp-Asp-Thr-Phe-AzaGly-Leu-Arg(Me)-Trp-NH₂

Compound No. 648: [Gly1,D-Tyr2,D-Trp3,Thr5,AzaGly7,Arg(Me)9,Trp10]MS10
Gly-D-Tyr-D-Trp-Asn-Thr-Phe-AzaGly-Leu-Arg(Me)-Trp-NH₂

Compound No. 649: Ac-[Gly1,D-Tyr2,D-Trp3,Thr5,AzaGly7,Arg(Me)9,Trp10]MS10
Ac-Gly-D-Tyr-D-Trp-Asn-Thr-Phe-AzaGly-Leu-Arg(Me)-Trp-NH₂

Compound No. 650: [D-Tyr1,D-Tyr2,D-Trp3,Thr5,AzaGly7,Arg(Me)9,Trp10]MS10
D-Tyr-D-Tyr-D-Trp-Asn-Thr-Phe-AzaGly-Leu-Arg(Me)-Trp-NH₂

Compound No. 651:
Ac-[D-Tyr1,D-Tyr2,D-Trp3,Thr5,AzaGly7,Arg(Me)9,Trp10]MS10
Ac-D-Tyr-D-Tyr-D-Trp-Asn-Thr-Phe-AzaGly-Leu-Arg(Me)-Trp-NH₂

Compound No. 652:
des(1)-pGlu-[D-Tyr2,D-Trp3,Thr5,AzaGly7,Arg(Me)9,Trp10]MS10
pGlu-D-Tyr-D-Trp-Asn-Thr-Phe-AzaGly-Leu-Arg(Me)-Trp-NH₂

Compound No. 653:
des(1)-Ac-[D-Tyr2,D-Trp3,D-Asn4,Thr5,AzaGly7,Arg(Me)9,Trp10]MS10
Ac-D-Tyr-D-Trp-D-Asn-Thr-Phe-AzaGly-Leu-Arg(Me)-Trp-NH₂

Compound No. 654:
des(1)-Ac-[D-Tyr2,D-Trp3,D-Thr5,AzaGly7,Arg(Me)9,Trp10]MS10
Ac-D-Tyr-D-Trp-Asn-D-Thr-Phe-AzaGly-Leu-Arg(Me)-Trp-NH₂

Compound No. 655:
des(1)-Ac-[D-Tyr2,D-Trp3,MeAsn4,Thr5,AzaGly7,Arg(Me)9,Trp10]MS10
Ac-D-Tyr-D-Trp-MeAsn-Thr-Phe-AzaGly-Leu-Arg(Me)-Trp-NH₂

Compound No. 656:
des(1)-Ac-[D-Tyr2,D-Trp3,MeSer5,AzaGly7,Arg(Me)9,Trp10]MS10
Ac-D-Tyr-D-Trp-Asn-MeSer-Phe-AzaGly-Leu-Arg(Me)-Trp-NH₂

Compound No. 657: des(1)-Ac-[D-Tyr2,Pro3,Thr5,AzaGly7,Arg(Me)9,Trp10]MS10
Ac-D-Tyr-Pro-Asn-Thr-Phe-AzaGly-Leu-Arg(Me)-Trp-NH₂

Compound No. 658:
des(1)-Ac-[D-Tyr2,D-Pya(2)3,Thr5,AzaGly7,Arg(Me)9,Trp10]MS10
Ac-D-Tyr-D-Pya(2)-Asn-Thr-Phe-AzaGly-Leu-Arg(Me)-Trp-NH₂

Compound No. 659:
des(1)-Ac-[D-Tyr2,D-Trp3,allo-Thr5,AzaGly7,Arg(Me)9,Trp10]MS10
Ac-D-Tyr-D-Trp-Asn-allo-Thr-Phe-AzaGly-Leu-Arg(Me)-Trp-NH₂

Compound No. 660:
des(1)-Ac-[D-Tyr2,D-Pya(3)3,Thr5,AzaGly7,Arg(Me)9,Trp10]MS10
Ac-D-Tyr-D-Pya(3)-Asn-Thr-Phe-AzaGly-Leu-Arg(Me)-Trp-NH₂

Compound No. 661: des(1)-Ac-[D-Tyr2,D-Pro3,Thr5,AzaGly7,Arg(Me)9,Trp10]MS10
Ac-D-Tyr-D-Pro-Asn-Thr-Phe-AzaGly-Leu-Arg(Me)-Trp-NH₂

Compound No. 662: des(1)-Ac-[D-Tyr2,Tic3,Thr5,AzaGly7,Arg(Me)9,Trp10]MS10
Ac-D-Tyr-Tic-Asn-Thr-Phe-AzaGly-Leu-Arg(Me)-Trp-NH₂

Compound No. 663: des(1)-Ac-[D-Trp2,D-Trp3,Thr5,AzaGly7,Arg(Me)9,Trp10]MS10
Ac-D-Trp-D-Trp-Asn-Thr-Phe-AzaGly-Leu-Arg(Me)-Trp-NH₂

Compound No. 664: des(1)-Ac-[Tyr2,Thr5,AzaGly7,Arg(Me)9,Trp10]MS10
Ac-Tyr-Trp-Asn-Thr-Phe-AzaGly-Leu-Arg(Me)-Trp-NH₂

Compound No. 665: des(1-2)-[D-Trp3,Thr5,AzaGly7,Arg(Me)9,Trp10]MS10
D-Trp-Asn-Thr-Phe-AzaGly-Leu-Arg(Me)-Trp-NH₂

Compound No. 666: des(1-2)-Ac-[D-Trp3,Thr5,AzaGly7,Arg(Me)9,Trp10]MS10
Ac-D-Trp-Asn-Thr-Phe-AzaGly-Leu-Arg(Me)-Trp-NH₂
```

-continued

Compound No. 667:
des(1-2)-Hexanoyl-[D-Trp3,Thr5,AzaGly7,Arg(Me)9,Trp10]MS10
Hexanoyl-D-Trp-Asn-Thr-Phe-AzaGly-Leu-Arg(Me)-Trp-NH2

Compound No. 668:
des(1-2)-Cyclohexanecarbonyl-[D-Trp3,Thr5,AzaGly7,Arg(Me)9,Trp10]MS10
Cyclohexanecarbonyl-D-Trp-Asn-Thr-Phe-AzaGly-Leu-Arg(Me)-Trp-NH2

Compound No. 669: des(1-2)-Benzoyl-[D-Trp3,Thr5,AzaGly7,Arg(Me)9,Trp10]MS10
Benzoyl-D-Trp-Asn-Thr-Phe-AzaGly-Leu-Arg(Me)-Trp-NH2

Compound No. 670:
des(1-2)-3-Pyridinepropionyl-[D-Trp3,Thr5,AzaGly7,Arg(Me)9,Trp10]MS10
3-Pyridinepropionyl-D-Trp-Asn-Thr-Phe-AzaGly-Leu-Arg(Me)-Trp-NH2

Compound No. 671: des(1-2)-Adipoyl-[D-Trp3,Thr5,AzaGly7,Arg(Me)9,Trp10]MS10
Adipionyl-D-Trp-Asn-Thr-Phe-AzaGly-Leu-Arg(Me)-Trp-NH2

Compound No. 672:
des(1)-Ac-[D-Tyr2,NMeTrp3,Thr5,AzaGly7,Arg(Me)9,Trp10]MS10
Ac-D-Tyr-NMeTrp-Asn-Thr-Phe-AzaGly-Leu-Arg(Me)-Trp-NH2

Compound No. 674:
des(1-2)-6-Aminocaproyl-[D-Trp3,Thr5,AzaGly7,Arg(Me)9,Trp10]MS10
6-Aminocaproyl-D-Trp-Asn-Thr-Phe-AzaGly-Leu-Arg(Me)-Trp-NH2

Compound No. 675: [D-Tyr2,D-Trp3,Thr5,AzaGly7,Arg(Me)9,Trp10]MS10
Tyr-D-Tyr-D-Trp-Asn-Thr-Phe-AzaGly-Leu-Arg(Me)-Trp-NH2

Compound No. 676: Ac-[D-Tyr2,D-Trp3,Thr5,AzaGly7,Arg(Me)9,Trp10]MS10
Ac-Tyr-D-Tyr-D-Trp-Asn-Thr-Phe-AzaGly-Leu-Arg(Me)-Trp-NH2

Compound No. 677:
Ac-des(1)-[D-Tyr2,D-Trp3,Thr5,AzaGly7,Nva8,Arg(Me)9,Trp10]MS10
Ac-D-Tyr-D-Trp-Asn-Thr-Phe-AzaGly-Nva-Arg(Me)-Trp-NH2

Compound No. 678:
Ac-des(1)-[D-Tyr2,D-Trp3,Thr5,AzaGly7,Ile8,Arg(Me)9,Trp10]MS10
Ac-D-Tyr-D-Trp-Asn-Thr-Phe-AzaGly-Ile-Arg(Me)-Trp-NH2

Compound No. 679: des(1-2)-Amidino-[D-Trp3,Thr5,AzaGly7,Arg(Me)9,Trp10]MS10
Amidino-D-Trp-Asn-Thr-Phe-AzaGly-Leu-Arg(Me)-Trp-NH2

Compound No. 680:
des(1-2)-Glycoloyl-[D-Trp3,Thr5,AzaGly7,Arg(Me)9,Trp10]MS10
Glycoloyl-D-Trp-Asn-Thr-Phe-AzaGly-Leu-Arg(Me)-Trp-NH2

Compound No. 681:
des(1)-Glycoloyl-[D-Tyr2,D-Trp3,Thr5,AzaGly7,Arg(Me)9,Trp10]MS10
Glycoloyl-D-Tyr-D-Trp-Asn-Thr-Phe-AzaGly-Leu-Arg(Me)-Trp-NH2

Compound No. 682:
des(1)-Ac-[D-Tyr2,D-Trp3,Thr5,AzaGly7,Gln8,Arg(Me)9,Trp10]MS10
Ac-D-Tyr-D-Trp-Asn-Thr-Phe-AzaGly-Gln-Arg(Me)-Trp-NH2

Compound No. 685: des(1)-Ac-[D-Tyr2,D-Pya(4)3,Thr5,AzaGly7,Arg(Me)9]MS10
Ac-D-Tyr-D-Pya(4)-Asn-Thr-Phe-AzaGly-Leu-Arg(Me)-Phe-NH2

Compound No. 686: des(1)-Ac-[D-Tyr2,D-Trp3,Gly4,AzaGly7,Arg(Me)9,Trp10]MS10
Ac-D-Tyr-D-Trp-Gly-Ser-Phe-AzaGly-Leu-Arg(Me)-Trp-NH2

Compound No. 688: des(1)-Ac-[D-Tyr2,D-Trp3,Thr5,AzaGly7,Pya(4)9,Trp10]MS10
Ac-D-Tyr-D-Trp-Asn-Thr-Phe-AzaGly-Leu-Pya(4)-Trp-NH2

Compound No. 689:
des(1)-Ac-[D-Tyr2,D-Trp3,Thr5,AzaGly7,Arg(Me)9,D-Trp10]MS10
Ac-D-Tyr-D-Trp-Asn-Thr-Phe-AzaGly-Leu-Arg(Me)-D-Trp-NH2

Compound No. 691:
des(1)-Ac-[D-Tyr2,D-Trp3,Thr5,Tyr6,AzaGly7,Arg(Me)9,Trp10]MS10
Ac-D-Tyr-D-Trp-Asn-Thr-Tyr-AzaGly-Leu-Arg(Me)-Trp-NH2

Compound No. 692:
des(1)-Ac-[D-Tyr2,D-Trp3,Thr5,Trp6,AzaGly7,Arg(Me)9,Trp10]MS10
Ac-D-Tyr-D-Trp-Asn-Thr-Trp-AzaGly-Leu-Arg(Me)-Trp-NH2

Compound No. 693:
des(1)-Ac-[D-Tyr2,D-Trp3,Thr5,Tyr(Me)6,AzaGly7,Arg(Me)9,Trp10]MS10
Ac-D-Tyr-D-Trp-Asn-Thr-Tyr(Me)-AzaGly-Leu-Arg(Me)-Trp-NH2

Compound No. 694:

```
des(1)-Ac-[D-Tyr2,D-Trp3,Thr5,Nal(2)6,AzaGly7,Arg(Me)9,Trp10]MS10
Ac-D-Tyr-D-Trp-Asn-Thr-Nal(2)-AzaGly-Leu-Arg(Me)-Trp-NH2

Compound No. 695:
des(1)-Ac-[D-Tyr2,D-Trp3,Thr5,Thi6,AzaGly7,Arg(Me)9,Trp10]MS10
Ac-D-Tyr-D-Trp-Asn-Thr-Thi-AzaGly-Leu-Arg(Me)-Trp-NH2

Compound No. 696:
des(1)-Ac-[D-Tyr2,D-Trp3,Thr5,Cha6,AzaGly7,Arg(Me)9,Trp10]MS10
Ac-D-Tyr-D-Trp-Asn-Thr-Cha-AzaGly-Leu-Arg(Me)-Trp-NH2

Compound No. 698:
des(1)-Ac-[D-Tyr2,D-Trp3,Thr5,AzaGly7,Abu8,Arg(Me)9,Trp10]MS10
Ac-D-Tyr-D-Trp-Asn-Thr-Phe-AzaGly-Abu-Arg(Me)-Trp-NH2

Compound No. 699:
des(1)-Ac-[D-Tyr2,D-Trp3,Thr5,AzaGly7,γMeLeu8,Arg(Me)9,Trp10]MS10
Ac-D-Tyr-D-Trp-Asn-Thr-Phe-AzaGly-γMeLeu-Arg(Me)-Trp-NH2

Compound No. 700: des(1)-Ac-[D-Tyr2,D-Trp3,Thr5,Aib8,,Arg(Me)9,Trp10]MS10
Ac-D-Tyr-D-Trp-Asn-Thr-Phe-Gly-Aib-Arg(Me)-Trp-NH2

Compound No. 701: des(1)-Ac-[D-Tyr2,D-Trp3,Dap4,AzaGly7,Arg(Me)9,Trp10]MS10
Ac-D-Tyr-D-Trp-Dap-Ser-Phe-AzaGly-Leu-Arg(Me)-Trp-NH2

Compound No. 702:
des(1)-Ac-[D-Tyr2,D-Trp3,Asp(NHMe)4,Thr5,AzaGly7,Arg(Me)9,Trp10]MS10
Ac-D-Tyr-D-Trp-Asp(NHMe)-Thr-Phe-AzaGly-Leu-Arg(Me)-Trp-NH2

Compound No. 703:
des(1)-Ac-[D-Tyr2,D-Trp3,Asp(NMe2)4,Thr5,AzaGly7,Arg(Me)9,Trp10]MS10
Ac-D-Tyr-D-Trp-Asp(NMe2)-Thr-Phe-AzaGly-Leu-Arg(Me)-Trp-NH2
```

However, the metastin derivatives (III) of the present invention do not include a peptide (native human metastin or its partial peptides) consisting of the following amino acid sequence in the amino acid sequence represented by SEQ ID NO: 1, i.e., the amino acid sequence of 1-54 (Compound No. 1), 2-54, 3-54, 4-54, 5-54, 6-54, 7-54, 8-54, 9-54, 10-54, 11-54, 12-54, 13-54, 14-54, 15-54, 16-54, 17-54, 18-54, 19-54, 20-54, 21-54, 22-54, 23-54, 24-54, 25-54, 26-54, 27-54, 28-54, 29-54, 30-54, 31-54, 32-54, 33-54, 34-54, 35-54, 36-54, 37-54, 38-54, 39-54, 40-54 (Compound No. 2), 41-54, 42-54 (Compound No. 32), 43-54, 44-54, 45-54 (Compound No. 3), 46-54 (Compound No. 4), 47-54, 48-54 or 49-54.

In the metastin derivatives (II), all compounds that the groups shown by the respective symbols are optionally combined are preferably used. Among them, the compounds shown by Compound Numbers below are preferred.

```
Compound No. 332: des(1-5)-GuAmb-[AzaGly7,Arg(Me)9]MS10
GuAmb-Phe-AzaGly-Leu-Arg(Me)-Phe-NH2

Compound No. 333: des(1-5)-GuAmb-[Arg(Me)9]MS10
GuAmb-Phe-Gly-Leu-Arg(Me)-Phe-NH2

Compound No. 334: des(1-5)-GuAmb-[AzaGly7,Arg(Me)9,Trp10]MS10
GuAmb-Phe-AzaGly-Leu-Arg(Me)-Trp-NH2

Compound No. 339: des(1-5)-3-(3-Indolyl)propionyl-[AzaGly7,Arg(Me)9]MS10
3-(3-Indolyl)propionyl-Phe-AzaGly-Leu-Arg(Me)-Phe-NH2

Compound No. 340: des(1-5)-3-(3-Pyridyl)propionyl-[AzaGly7,Arg(Me)9]MS10
3-(3-Pyridyl)propionyl-Phe-AzaGly-Leu-Arg(Me)-Phe-NH2

Compound No. 341: des(1-5)-Benzoyl-[AzaGly7,Arg(Me)9]MS10
Benzoyl-Phe-AzaGly-Leu-Arg(Me)-Phe-NH2

Compound No. 344: des(1-5)-Indole-3-carbonyl-[AzaGly7,Arg(Me)9]MS10
Indole-3-carbonyl-Phe-AzaGly-Leu-Arg(Me)-Phe-NH2

Compound No. 345: des(1-5)-Indole-3-acetyl-[AzaGly7,Arg(Me)9]MS10
Indole-3-acetyl-Phe-AzaGly-Leu-Arg(Me)-Phe-NH2

Compound No. 346: des(1-5)-Ac-[AzaGly7,Arg(Me)9]MS10
Ac-Phe-AzaGly-Leu-Arg(Me)-Phe-NH2

Compound No. 347: des(1-5)-n-Hexanoyl-[AzaGly7,Arg(Me)9]MS10
n-Hexanoyl-Phe-AzaGly-Leu-Arg(Me)-Phe-NH2

Compound No. 348: des(1-5)-Z-[AzaGly7,Arg(Me)9]MS10
Z-Phe-AzaGly-Leu-Arg(Me)-Phe-NH2

Compound No. 349: des(1-5)-Tos-[AzaGly7,Arg(Me)9]MS10
```

-continued

Tos-Phe-AzaGly-Leu-Arg(Me)-Phe-NH$_2$

Compound No. 351: des(1-5)-Benzoyl-MS10
Benzoyl-Phe-Gly-Leu-Arg-Phe-NH$_2$

Compound No. 352: des(1-5)-3-(3-Indolyl)propionyl-MS10
3-(3-Indolyl)propionyl-Phe-Gly-Leu-Arg-Phe-NH$_2$ Compound No. 353: des(1-5)-Benzoyl-[AzaGly7,Arg(Me)9,Trp10]MS10
Benzoyl-Phe-AzaGly-Leu-Arg(Me)-Trp-NH$_2$ Compound No. 354: des(1-5)-3-(3-Indolyl)propionyl-[AzaGly7,Arg(Me)9,Trp10]MS10
3-(3-Indolyl)propionyl-Phe-AzaGly-Leu-Arg(Me)-Trp-NH$_2$ Compound No. 358: des(1-5)-Ac-[AzaGly7,Arg(Me)9,Trp10]MS10
Ac-Phe-AzaGly-Leu-Arg(Me)-Trp-NH$_2$ Compound No. 362: des(1-6)-3-Phenylpropionyl-[AzaGly7,Arg(Me)9]MS10
3-Phenylpropionyl-AzaGly-Leu-Arg(Me)-Phe-NH$_2$ Compound No. 364: des(1-5)-2-(Indol-3-yl)ethylcarbamoyl-[AzaGly7,Arg(Me)9]MS10
2-(Indol-3-yl)ethylcarbamoyl-Phe-AzaGly-Leu-Arg(Me)-Phe-NH$_2$ Compound No. 366: des(1-5)-n-Hexanoyl-[AzaGly7,Arg(Me)9,Trp10]MS10
n-Hexanoyl-Phe-AzaGly-Leu-Arg(Me)-Trp-NH$_2$ Compound No. 367: des(1-5)-Z-[AzaGly7,Arg(Me)9,Trp10]MS10
Z-Phe-AzaGly-Leu-Arg(Me)-Trp-NH$_2$ Compound No. 368: des(1-5)-Tos-[AzaGly7,Arg(Me)9,Trp10]MS10
Tos-Phe-AzaGly-Leu-Arg(Me)-Trp-NH$_2$ Compound No. 369:
des(1-5)-2-(Indol-3-yl)ethylcarbamoyl-[AzaGly7,Arg(Me)9,Trp10]MS10
2-(Indol-3-yl)ethylcarbamoyl-Phe-AzaGly-Leu-Arg(Me)-Trp-NH$_2$ Compound No. 373:
des(1-6)-(2S)-2-acetoxy-3-phenylpropionyl-[AzaGly7,Arg(Me)9,Trp10]MS10
(2S)-2-acetoxy-3-phenylpropionyl-AzaGly-Leu-Arg(Me)-Trp-NH$_2$ Compound No. 374: des(1-6)-Z-[AzaGly7,Arg(Me)9,Trp10]MS10
Z-AzaGly-Leu-Arg(Me)-Trp-NH$_2$ Compound No. 378: des(1-6)-Diphenylacetyl-[AzaGly7,Arg(Me)9,Trp10]MS10
Diphenylacetyl-AzaGly-Leu-Arg(Me)-Trp-NH$_2$ Compound No. 379:
des(1-6)-(2S)-2-(3-Indolylprpionyloxy)-3-phenylpropionyl-[AzaGly7,Arg(Me)9,Trp10]MS10
(2S)-2-(3-Indolylprpionyloxy)-3-phenylpropionyl-AzaGly-Leu-Arg(Me)-Trp-NH$_2$ Compound No. 380:
des(1-6)-(2S)-2-Benzoyloxy-3-phenylpropionyl-[AzaGly7,Arg(Me)9,Trp10]MS10
(2S)-2-Benzoyloxy-3-phenylpropionyl-AzaGly-Leu-Arg(Me)-Trp-NH$_2$ Compound No. 392: des(1-5)-Benzoyl-[Ala6,AzaGly7,Arg(Me)9,Trp10]MS10
Benzoyl-Ala-AzaGly-Leu-Arg(Me)-Trp-NH$_2$ Compound No. 393: des(1-6)-Dibenzylcarbamoyl-[AzaGly7,Arg(Me)9,Trp10]MS10
Dibenzylcarbamoyl-AzaGly-Leu-Arg(Me)-Trp-NH$_2$ Compound No. 408:
des(1-6)-1-Oxo-isochroman-3-carbonyl-[AzaGly7,Arg(Me)9,Trp10]MS10
1-Oxo-isochroman-3-carbonyl-AzaGly-Leu-Arg(Me)-Trp-NH$_2$ Compound No. 412:
des(1-6)-(2R)-2-Benzoyloxy-3-phenylpropionyl-[AzaGly7,Arg(Me)9,Trp10]MS10
(2R)-2-Benzoyloxy-3-phenylpropionyl-AzaGly-Leu-Arg(Me)-Trp-NH$_2$ Compound No. 417:
des(1-6)-Benzylphenethylcarbamoyl-[AzaGly7,Arg(Me)9,Trp10]MS10
Benzylphenethylcarbamoyl-AzaGly-Leu-Arg(Me)-Trp-NH$_2$ Compound No. 421: des(1-5)-Benzoyl-[6Ψ7,CH2O,Arg(Me)9,Trp10]MS10
Benzoyl-PheΨ(CH2O)Gly-Leu-Arg(Me)-Trp-NH$_2$ Compound No. 423: des(1-5)-Benzoyl-[6Ψ7,NHCO,Arg(Me)9,Trp10]MS10
Benzoyl-PheΨ(NHCO)Gly-Leu-Arg(Me)-Trp-NH$_2$ Compound No. 428:
des(1-6)-Dibenzylaminocarbamoyl-[AzaGly7,Arg(Me)9,Trp10]MS10
Dibenzylaminocarbamoyl-AzaGly-Leu-Arg(Me)-Trp-NH$_2$ -continued Compound No. 431: des(1-5)-Benzoyl-[AzaPhe6,AzaGly7,Arg(Me)9,Trp10]MS10
Benzoyl-AzaPhe-AzaGly-Leu-Arg(Me)-Trp-NH$_2$ Compound No. 432: des(1-5)-3-Pyridinecarbonyl-[AzaGly7,Arg(Me)9,Trp10]MS10
3-Pyridinecarbonyl-Phe-AzaGly-Leu-Arg(Me)-Trp-NH$_2$ Compound No. 434: des(1-7)-Dibenzylaminocarbamoylacetyl-[Arg(Me)9,Trp10]MS10
Dibenzylaminocarbamoylacetyl-Leu-Arg(Me)-Trp-NH$_2$ Compound No. 435: des(1-5)-2-Pyridinecarbonyl-[AzaGly7,Arg(Me)9,Trp10]MS10
2-Pyridinecarbonyl-Phe-AzaGly-Leu-Arg(Me)-Trp-NH$_2$ Compound No. 436: des(1-5)-4-Pyridinecarbonyl-[AzaGly7,Arg(Me)9,Trp10]MS10
4-Pyridinecarbonyl-Phe-AzaGly-Leu-Arg(Me)-Trp-NH$_2$ Compound No. 437: des(1-5)-Propionyl-[AzaGly7,Arg(Me)9,Trp10]MS10
Propionyl-Phe-AzaGly-Leu-Arg(Me)-Trp-NH$_2$ Compound No. 438: des(1-5)-Isobutyryl-[AzaGly7,Arg(Me)9,Trp10]MS10
Isobutyryl-Phe-AzaGly-Leu-Arg(Me)-Trp-NH$_2$ Compound No. 439: des(1-5)-Cyclohexanecarbonyl-[AzaGly7,Arg(Me)9,Trp10]MS10
Cyclohexanecarbonyl-Phe-AzaGly-Leu-Arg(Me)-Trp-NH$_2$ Compound No. 440: des(1-5)-Phenylacetyl-[AzaGly7,Arg(Me)9,Trp10]MS10
Phenylacetyl-Phe-AzaGly-Leu-Arg(Me)-Trp-NH$_2$ Compound No. 441: des(1-5)-Benzoyl-[Pya(2)6,AzaGly7,Arg(Me)9,Trp10]MS10
Benzoyl-Pya(2)-AzaGly-Leu-Arg(Me)-Trp-NH$_2$ Compound No. 442: des(1-5)-Benzoyl-[Pya(4)6,AzaGly7,Arg(Me)9,Trp10]MS10
Benzoyl-Pya(4)-AzaGly-Leu-Arg(Me)-Trp-NH$_2$ Compound No. 443: des(1-5)-2-Methylnicotinoyl-[AzaGly7,Arg(Me)9,Trp10]MS10
2-Methylnicotinoyl-Phe-AzaGly-Leu-Arg(Me)-Trp-NH$_2$ Compound No. 444: des(1-5)-5-Methylnicotinoyl-[AzaGly7,Arg(Me)9,Trp10]MS10
5-Methylnicotinoyl-Phe-AzaGly-Leu-Arg(Me)-Trp-NH$_2$ Compound No. 445: des(1-5)-6-Methylnicotinoyl-[AzaGly7,Arg(Me)9,Trp10]MS10
6-Methylnicotinoyl-Phe-AzaGly-Leu-Arg(Me)-Trp-NH$_2$ Compound No. 446: des(1-5)-Pyrazinecarbonyl-[AzaGly7,Arg(Me)9,Trp10]MS10
Pyrazinecarbonyl-Phe-AzaGly-Leu-Arg(Me)-Trp-NH$_2$ Compound No. 447: des(1-5)-Cyclopropanecarbonyl-[AzaGly7,Arg(Me)9,Trp10]MS10
Cyclopropanecarbonyl-Phe-AzaGly-Leu-Arg(Me)-Trp-NH$_2$ Compound No. 448: des(1-5)-Trifluoroacetyl-[AzaGly7,Arg(Me)9,Trp10]MS10
Trifluoroacetyl-Phe-AzaGly-Leu-Arg(Me)-Trp-NH$_2$ Compound No. 449: des(1-5)-Benzoyl-[Cha6,AzaGly7,Arg(Me)9,Trp10]MS10
Benzoyl-Cha-AzaGly-Leu-Arg(Me)-Trp-NH$_2$ Compound No. 450: des(1-5)-Benzyl-[AzaGly7,Arg(Me)9,Trp10]MS10
Benzyl-Phe-AzaGly-Leu-Arg(Me)-Trp-NH$_2$ Compound No. 451:
des(1-5)-Cyclopropanecarbonyl-[Cha6,AzaGly7,Arg(Me)9,Trp10]MS10
Cyclopropanecarbonyl-Cha-AzaGly-Leu-Arg(Me)-Trp-NH$_2$ Compound No. 452:
des(1-5)-(R)-3-hydroxy-2-methylpropionyl-[AzaGly7,Arg(Me)9,Trp10]MS10
(R)-3-hydroxy-2-methylpropionyl-Phe-AzaGly-Leu-Arg(Me)-Trp-NH$_2$ Compound No. 453: des(1-5)-2-Hydroxyisobutyryl-[AzaGly7,Arg(Me)9,Trp10]MS10
2-Hydroxyisobutyryl-Phe-AzaGly-Leu-Arg(Me)-Trp-NH$_2$ Compound No. 454: des(1-5)-3-Furancarbonyl-[AzaGly7,Arg(Me)9,Trp10]MS10
3-Furancarbonyl-Phe-AzaGly-Leu-Arg(Me)-Trp-NH$_2$ Compound No. 455: des(1-5)-Pyrrole-2-carbonyl-[AzaGly7,Arg(Me)9,Trp10]MS10
Pyrrole-2-carbonyl-Phe-AzaGly-Leu-Arg(Me)-Trp-NH$_2$ Compound No. 459: des(1-5)-4-Imidazolecarbonyl-[AzaGly7,Arg(Me)9,Trp10]MS10
4-Imidazolecarbonyl-Phe-AzaGly-Leu-Arg(Me)-Trp-NH$_2$ Compound No. 460:
des(1-5)-4-Pyridinecarbonyl-[AzaGly7,Val8,Arg(Me)9,Trp10]MS10
4-Pyridinecarbonyl-Phe-AzaGly-Val-Arg(Me)-Trp-NH$_2$ -continued Compound No. 461: des(1-5)-4-Pyridinecarbonyl-[AzaGly7,Arg(Me)9,Nal(2)10]MS10
4-Pyridinecarbonyl-Phe-AzaGly-Leu-Arg(Me)-Nal(2)-NH$_2$ Compound No. 462: des(1-5)-6-Hydroxynicotinoyl-[AzaGly7,Arg(Me)9,Trp10]MS10
6-Hydroxynicotinoyl-Phe-AzaGly-Leu-Arg(Me)-Trp-NH$_2$ Compound No. 463: des(1-5)-6-Chloronicotinoyl-[AzaGly7,Arg(Me)9,Trp10]MS10
6-Chloronicotinoyl-Phe-AzaGly-Leu-Arg(Me)-Trp-NH$_2$ Compound No. 464:
des(1-5)-6-(Trifluoromethyl)nicotinoyl-[AzaGly7,Arg(Me)9,Trp10]MS10
6-(Trifluoromethyl)nicotinoyl-Phe-AzaGly-Leu-Arg(Me)-Trp-NH$_2$ Compound No. 466: des(1-5)-2-Azetidinecarbonyl-[AzaGly7,Arg(Me)9,Trp10]MS10
2-Azetidinecarbonyl-Phe-AzaGly-Leu-Arg(Me)-Trp-NH$_2$ Compound No. 467: des(1-5)-Dimethylcarbamoyl-[AzaGly7,Arg(Me)9,Trp10]MS10
Dimethylcarbamoyl-Phe-AzaGly-Leu-Arg(Me)-Trp-NH$_2$ Compound No. 468: des(1-5)-1-Azetidinecarbonyl-[AzaGly7,Arg(Me)9,Trp10]MS10
1-Azetidinecarbonyl-Phe-AzaGly-Leu-Arg(Me)-Trp-NH$_2$ Compound No. 471: des(1-5)-4-Pyridinecarbonyl-[AzaGly7,Arg(Me)9]MS10
4-Pyridinecarbonyl-Phe-AzaGly-Leu-Arg(Me)-Phe-NH$_2$ Compound No. 472: des(1-5)-4-Aminobenzoyl-[AzaGly7,Arg(Me)9,Trp10]MS10
4-Aminobenzoyl-Phe-AzaGly-Leu-Arg(Me)-Trp-NH$_2$ Compound No. 473:
des(1-5)-4-Aminomethylbenzoyl-[AzaGly7,Arg(Me)9,Trp10]MS10
4-Aminomethylbenzoyl-Phe-AzaGly-Leu-Arg(Me)-Trp-NH$_2$ Compound No. 474: des(1-5)-Pyrrole-3-carbonyl-[AzaGly7,Arg(Me)9,Trp10]MS10
Pyrrole-3-carbonyl-Phe-AzaGly-Leu-Arg(Me)-Trp-NH$_2$ Compound No. 475: des(1-5)-Pyrimidine-4-carbonyl-[AzaGly7,Arg(Me)9,Trp10]MS10
Pyrimidine-4-carbonyl-Phe-AzaGly-Leu-Arg(Me)-Trp-NH$_2$ Compound No. 477: des(1-5)-4-Pyridinecarbonyl-[AzaGly7,Orn9,Trp10]MS10
4-Pyridinecarbonyl-Phe-AzaGly-Leu-Orn-Trp-NH$_2$ Compound No. 478: des(1-5)-4-Pyridinecarbonyl-[AzaGly7,Har9,Trp10]MS10
4-Pyridinecarbonyl-Phe-AzaGly-Leu-Har-Trp-NH$_2$ Compound No. 479: des(1-5)-Pyrimidine-2-carbonyl-[AzaGly7,Arg(Me)9,Trp10]MS10
Pyrimidine-2-carbonyl-Phe-AzaGly-Leu-Arg(Me)-Trp-NH$_2$ Compound No. 480: des(1-5)-Pyridazine-4-carbonyl-[AzaGly7,Arg(Me)9,Trp10]MS10
Pyridazine-4-carbonyl-Phe-AzaGly-Leu-Arg(Me)-Trp-NH$_2$ Compound No. 481: des(1)-[D-Tyr2,D-Pya(4)3,AzaGly7,Har9,Trp10]MS10
D-Tyr-D-Pya(4)-Asn-Ser-Phe-AzaGly-Leu-Har-Trp-NH$_2$ Compound No. 486: des(1)-[D-Tyr2,D-Pya(4)3,AzaGly7,Orn9]MS10
D-Tyr-D-Pya(4)-Asn-Ser-Phe-AzaGly-Leu-Orn-Phe-NH$_2$ Compound No. 487: des(1)-[D-Tyr2,D-Pya(4)3,AzaGly7,Lys9]MS10
D-Tyr-D-Pya(4)-Asn-Ser-Phe-AzaGly-Leu-Lys-Phe-NH$_2$ Compound No. 488: des(1)-[D-Tyr2,D-Pya(4)3,AzaGly7,Har9]MS10
D-Tyr-D-Pya(4)-Asn-Ser-Phe-AzaGly-Leu-Har-Phe-NH$_2$ Compound No. 489: des(1)-[D-Tyr2,D-Pya(4)3,AzaGly7,Har(Me)9]MS10
D-Tyr-D-Pya(4)-Asn-Ser-Phe-AzaGly-Leu-Har(Me)-Phe-NH$_2$ Compound No. 490: des(1)-[D-Tyr2,Pya(4)3,AzaGly7,Arg(Me)9]MS10
D-Tyr-Pya(4)-Asn-Ser-Phe-AzaGly-Leu-Arg(Me)-Phe-NH$_2$ Compound No. 491: des(1)-[D-Tyr2,D-Pya(4)3,Trp5,AzaGly7,Arg(Me)9,Trp10]MS10
D-Tyr-D-Pya(4)-Asn-Trp-Phe-AzaGly-Leu-Arg(Me)-Trp-NH$_2$ Compound No. 492: des(1)-[D-Tyr2,D-Pya(4)3,Ala4,AzaGly7,Arg(Me)9,Trp10]MS10
D-Tyr-D-Pya(4)-Ala-Ser-Phe-AzaGly-Leu-Arg(Me)-Trp-NH$_2$ Compound No. 493: des(1)-[D-Tyr2,D-Pya(4)3,Thr4,AzaGly7,Arg(Me)9,Trp10]MS10
D-Tyr-D-Pya(4)-Thr-Ser-Phe-AzaGly-Leu-Arg(Me)-Trp-NH$_2$ Compound No. 494: des(1,4)-[D-Tyr2,D-Pya(4)3,AzaGly7,Arg(Me)9,Trp10]MS10
D-Tyr-D-Pya(4)-Ser-Phe-AzaGly-Leu-Arg(Me)-Trp-NH$_2$ -continued Compound No. 495: des(1-3)-[D-Tyr4,Pya(4)5,AzaGly7,Arg(Me)9,Trp10]MS10
D-Tyr-Pya(4)-Phe-AzaGly-Leu-Arg(Me)-Trp-NH$_2$ Compound No. 496: des(1)-[D-Tyr2,D-Pya(4)3,Cha6,Arg(Me)9,Trp10]MS10
D-Tyr-D-Pya(4)-Asn-Ser-Cha-Gly-Leu-Arg(Me)-Trp-NH$_2$ Compound No. 497: des(1)-[D-Tyr2,D-Pya(4)3,Cha6,Ala7,Arg(Me)9,Trp10]MS10
D-Tyr-D-Pya(4)-Asn-Ser-Cha-Ala-Leu-Arg(Me)-Trp-NH$_2$ Compound No. 498: des(1)-[D-Tyr2,D-Pya(4)3,Ile5,AzaGly7,Arg(Me)9,Trp10]MS10
D-Tyr-D-Pya(4)-Asn-Ile-Phe-AzaGly-Leu-Arg(Me)-Trp-NH$_2$ Compound No. 499: des(1-3)-3-Phenylpropionyl-[AzaGly7,Arg(Me)9,Trp10]MS10
3-Phenylpropionyl-Asn-Ser-Phe-AzaGly-Leu-Arg(Me)-Trp-NH$_2$ Compound No. 500:
des(1-3)-3-Phenylpropionyl-[Ala4,AzaGly7,Arg(Me)9,Trp10]MS10
3-Phenylpropionyl-Ala-Ser-Phe-AzaGly-Leu-Arg(Me)-Trp-NH$_2$ Compound No. 501: des(1)-[D-Tyr2,D-Pya(4)3,Thr5,AzaGly7,Arg(Me)9,Trp10]MS10
D-Tyr-D-Pya(4)-Asn-Thr-Phe-AzaGly-Leu-Arg(Me)-Trp-NH$_2$ Compound No. 502: des(1)-[D-Tyr2,Pya(4)3,Ala4,AzaGly7,Arg(Me)9,Trp10]MS10
D-Tyr-Pya(4)-Ala-Ser-Phe-AzaGly-Leu-Arg(Me)-Trp-NH$_2$ Compound No. 503: des(1)-[D-Tyr2,D-Trp3,Ala4,AzaGly7,Arg(Me)9,Trp10]MS10
D-Tyr-D-Trp-Ala-Ser-Phe-AzaGly-Leu-Arg(Me)-Trp-NH$_2$ Compound No. 504: [Acp1,D-Tyr2,D-Pya(4)3,AzaGly7,Arg(Me)9]MS10
Acp-D-Tyr-D-Pya(4)-Asn-Ser-Phe-AzaGly-Leu-Arg(Me)-Phe-NH$_2$ Compound No. 505:
des(1-3)-3-Phenylpropionyl-[Thr5,AzaGly7,Arg(Me)9,Trp10]MS10
3-Phenylpropionyl-Asn-Thr-Phe-AzaGly-Leu-Arg(Me)-Trp-NH$_2$ Compound No. 506: des(1-3)-3-Phenylpropionyl-[AzaGly7,Arg(Me)9,Trp10]MS10
3-Phenylpropionyl-Asn-Ile-Phe-AzaGly-Leu-Arg(Me)-Trp-NH$_2$ Compound No. 507:
des(1-3)-3-Phenylpropionyl-[Trp6,AzaGly7,Arg(Me)9,Trp10]MS10
3-Phenylpropionyl-Asn-Ser-Trp-AzaGly-Leu-Arg(Me)-Trp-NH$_2$ Compound No. 508:
des(1-3)-3-Phenylpropionyl-[Phe(4F)6,AzaGly7,Arg(Me)9,Trp10]MS10
3-Phenylpropionyl-Asn-Ser-Phe(4F)-AzaGly-Leu-Arg(Me)-Trp-NH$_2$ Compound No. 509: des(1-3)-Benzoyl-[AzaGly7,Arg(Me)9,Trp10]MS10
Benzoyl-Asn-Ser-Phe-AzaGly-Leu-Arg(Me)-Trp-NH$_2$ Compound No. 510: des(1-3)-Ac-[AzaGly7,Arg(Me)9,Trp10]MS10
Ac-Asn-Ser-Phe-AzaGly-Leu-Arg(Me)-Trp-NH$_2$ Compound No. 511:
des(1)-[D-Tyr2,D-Trp3,Ala4,Thr5,AzaGly7,Arg(Me)9,Trp10]MS10
D-Tyr-D-Trp-Ala-Thr-Phe-AzaGly-Leu-Arg(Me)-Trp-NH$_2$ Compound No. 512: des(1)-[D-Tyr2,D-Trp3,Thr5,AzaGly7,Arg(Me)9,Trp10]MS10
D-Tyr-D-Trp-Asn-Thr-Phe-AzaGly-Leu-Arg(Me)-Trp-NH$_2$ Compound No. 513: des(1)-[D-Tyr2,D-Trp3,Abu4,AzaGly7,Arg(Me)9,Trp10]MS10
D-Tyr-D-Trp-Abu-Ser-Phe-AzaGly-Leu-Arg(Me)-Trp-NH$_2$ Compound No. 514: des(1)-[D-Tyr2,D-Phe3,Ala4,AzaGly7,Arg(Me)9,Trp10]MS10
D-Tyr-D-Phe-Ala-Ser-Phe-AzaGly-Leu-Arg(Me)-Trp-NH$_2$ Compound No. 515: des(1)-[D-Tyr2,D-Pya(4)3,Val5,AzaGly7,Arg(Me)9,Trp10]MS10
D-Tyr-D-Pya(4)-Asn-Val-Phe-AzaGly-Leu-Arg(Me)-Trp-NH$_2$ Compound No. 516: des(1)-Ac-[D-Tyr2,D-Pya(4)3,AzaGly7,Arg(Me)9]MS10
Ac-D-Tyr-D-Pya(4)-Asn-Ser-Phe-AzaGly-Leu-Arg(Me)-Phe-NH$_2$ Compound No. 517:
des(1-3)-3-Phenylpropionyl-[Hyp5,AzaGly7,Arg(Me)9,Trp10]MS10
3-Phenylpropionyl-Asn-Hyp-Phe-AzaGly-Leu-Arg(Me)-Trp-NH$_2$ Compound No. 518: des(1-3)-3-Phenylpropionyl-[Cha6,Arg(Me)9]MS10
3-Phenylpropionyl-Asn-Ser-Cha-Gly-Leu-Arg(Me)-Trp-NH$_2$ Compound No. 519: des(1-3)-Phenylacetyl-[AzaGly7,Arg(Me)9,Trp10]MS10
Phenylacetyl-Asn-Ser-Phe-AzaGly-Leu-Arg(Me)-Trp-NH$_2$ -continued Compound No. 521: des(1)-[D-Tyr2,D-Pya(4)3,AzaGly7]MS10
D-Tyr-D-Pya(4)-Asn-Ser-Phe-AzaGly-Leu-Arg-Phe-NH₂

Compound No. 522: des(1-3)-Benzoyl-[Thr5,AzaGly7,Arg(Me)9,Trp10]MS10
Benzoyl-Asn-Thr-Phe-AzaGly-Leu-Arg(Me)-Trp-NH₂

Compound No. 523:
des(1-3)-Benzoyl-[Thr5,Phe(4F)6,AzaGly7,Arg(Me)9,Trp10]MS10
Benzoyl-Asn-Thr-Phe(4F)-AzaGly-Leu-Arg(Me)-Trp-NH₂

Compound No. 524:
des(1-3)-3-Phenylpropionyl-[Pro5,AzaGly7,Arg(Me)9,Trp10]MS10
3-Phenylpropionyl-Asn-Pro-Phe-AzaGly-Leu-Arg(Me)-Trp-NH₂

Compound No. 527: des(1)-[D-Tyr2,D-Pya(4)3,Hyp5,AzaGly7,Arg(Me)9,Trp10]MS10
D-Tyr-D-Pya(4)-Asn-Hyp-Phe-AzaGly-Leu-Arg(Me)-Trp-NH₂

Compound No. 528: des(1)-[D-Tyr2,D-Pya(4)3,Pro5,AzaGly7,Arg(Me)9,Trp10]MS10
D-Tyr-D-Pya(4)-Asn-Pro-Phe-AzaGly-Leu-Arg(Me)-Trp-NH₂

Compound No. 529: des(1)-[D-Tyr2,D-Pya(4)3,Tle5,AzaGly7,Arg(Me)9,Trp10]MS10
D-Tyr-D-Pya(4)-Asn-Tle-Phe-AzaGly-Leu-Arg(Me)-Trp-NH₂

Compound No. 530: des(1)-[D-Tyr2,D-Pya(4)3,Phg5,AzaGly7,Arg(Me)9,Trp10]MS10
D-Tyr-D-Pya(4)-Asn-Phg-Phe-AzaGly-Leu-Arg(Me)-Trp-NH₂

Compound No. 531:
des(1-3)-3-Phenylpropionyl-[Pic(2)5,AzaGly7,Arg(Me)9,Trp10]MS10
3-Phenylpropionyl-Asn-Pic(2)-Phe-AzaGly-Leu-Arg(Me)-Trp-NH₂

Compound No. 532:
des(1-3)-3-Phenylpropionyl-[Aze(2)5,AzaGly7,Arg(Me)9,Trp10]MS10
3-Phenylpropionyl-Asn-Aze(2)-Phe-AzaGly-Leu-Arg(Me)-Trp-NH₂

Compound No. 533:
des(1-3)-3-Phenylpropionyl-[D-Pro5,AzaGly7,Arg(Me)9,Trp10]MS10
3-Phenylpropionyl-Asn-D-Pro-Phe-AzaGly-Leu-Arg(Me)-Trp-NH₂

Compound No. 534: des(1-3)-Cyclopropanecarbonyl-[AzaGly7,Arg(Me)9,Trp10]MS10
Cyclopropanecarbonyl-Asn-Ser-Phe-AzaGly-Leu-Arg(Me)-Trp-NH₂

Compound No. 535: des(1-3)-2-Naphthoyl-[AzaGly7,Arg(Me)9,Trp10]MS10
2-Naphthoyl-Asn-Ser-Phe-AzaGly-Leu-Arg(Me)-Trp-NH₂

Compound No. 536: [Arg1,D-Tyr2,D-Pya(4)3,AzaGly7,Arg(Me)9,Trp10]MS10
Arg-D-Tyr-D-Pya(4)-Asn-Ser-Phe-AzaGly-Leu-Arg(Me)-Trp-NH₂

Compound No. 537: Arg-[Arg1,D-Tyr2,D-Pya(4)3,AzaGly7,Arg(Me)9,Trp10]MS10
Arg-Arg-D-Tyr-D-Pya(4)-Asn-Ser-Phe-AzaGly-Leu-Arg(Me)-Trp-NH₂

Compound No. 538: Arg-[Acp1,D-Tyr2,D-Pya(4)3,AzaGly7,Arg(Me)9,Trp10]MS10
Arg-Acp-D-Tyr-D-Pya(4)-Asn-Ser-Phe-AzaGly-Leu-Arg(Me)-Trp-NH₂

Compound No. 539: des(1)-[D-Tyr2,D-Trp3,Val5,AzaGly7,Arg(Me)9,Trp10]MS10
D-Tyr-D-Trp-Asn-Val-Phe-AzaGly-Leu-Arg(Me)-Trp-NH₂

Compound No. 540: des(1)-[D-Tyr2,D-Trp3,AzaGly7,Arg(Me)9,Trp10]MS10
D-Tyr-D-Trp-Asn-Ser-Phe-AzaGly-Leu-Arg(Me)-Trp-NH₂

Compound No. 541:
D-Arg-[Acp1,D-Tyr2,D-Trp3,Thr5,AzaGly7,Arg(Me)9,Trp10]MS10
D-Arg-Acp-D-Tyr-D-Trp-Asn-Thr-Phe-AzaGly-Leu-Arg(Me)-Trp-NH₂

Compound No. 542:
D-Arg-D-Arg-[Acp1,D-Tyr2,D-Trp3,Thr5,AzaGly7,Arg(Me)9,Trp10]MS10
D-Arg-D-Arg-Acp-D-Tyr-D-Trp-Asn-Thr-Phe-AzaGly-Leu-Arg(Me)-Trp-NH₂

Compound No. 545: des(1-3)-Benzoyl-[Phe(4F)6,AzaGly7,Arg(Me)9,Trp10]MS10
Benzoyl-Asn-Ser-Phe(4F)-AzaGly-Leu-Arg(Me)-Trp-NH₂

Compound No. 546:
des(1-3)-3-Phenylpropionyl-[Ser(Ac)5,AzaGly7,Arg(Me)9,Trp10]MS10
3-Phenylpropionyl-Asn-Ser(Ac)-Phe-AzaGly-Leu-Arg(Me)-Trp-NH₂

Compound No. 547:
des(1)-[D-Tyr2,D-Pya(4)3,Ser(Ac)5,AzaGly7,Arg(Me)9,Trp10]MS10
D-Tyr-D-Pya(4)-Asn-Ser(Ac)-Phe-AzaGly-Leu-Arg(Me)-Trp-NH₂

Compound No. 548: des(1)-[D-Tyr2,D-Pya(4)3,AzaGly7,Arg(Me)9,10Ψ,CSNH]MS10
D-Tyr-D-Pya(4)-Asn-Ser-Phe-AzaGly-Leu-Arg(Me)-PheΨ(CSNH)NH₂

-continued

Compound No. 550: des(1)-Ac-[D-Tyr2,D-Trp3,Thr5,AzaGly7,Arg(Me)9,Trp10]MS10
Ac-D-Tyr-D-Trp-Asn-Thr-Phe-AzaGly-Leu-Arg(Me)-Trp-NH$_2$ Compound No. 551:
Ac-D-Arg-[Acp1,D-Tyr2,D-Trp3,Thr5,AzaGly7,Arg(Me)9,Trp10]MS10
Ac-D-Arg-Acp-D-Tyr-D-Trp-Asn-Thr-Phe-AzaGly-Leu-Arg(Me)-Trp-NH$_2$ Compound No. 552:
D-Dap-[Acp1,D-Tyr2,D-Trp3,Thr5,AzaGly7,Arg(Me)9,Trp10]MS10
D-Dap-Acp-D-Tyr-D-Trp-Asn-Thr-Phe-AzaGly-Leu-Arg(Me)-Trp-NH$_2$ Compound No. 553:
D-Nle-[Acp1,D-Tyr2,D-Trp3,Thr5,AzaGly7,Arg(Me)9,Trp10]MS10
D-Nle-Acp-D-Tyr-D-Trp-Asn-Thr-Phe-AzaGly-Leu-Arg(Me)-Trp-NH$_2$ Compound No. 554:
D-Arg-[β-Ala1,D-Tyr2,D-Trp3,Thr5,AzaGly7,Arg(Me)9,Trp10]MS10
D-Arg-β-Ala-D-Tyr-D-Trp-Asn-Thr-Phe-AzaGly-Leu-Arg(Me)-Trp-NH$_2$ Compound No. 555:
D-Arg-[γ-Abu1,D-Tyr2,D-Trp3,Thr5,AzaGly7,Arg(Me)9,Trp10]MS10
D-Arg-γ-Abu-D-Tyr-D-Trp-Asn-Thr-Phe-AzaGly-Leu-Arg(Me)-Trp-NH$_2$ Compound No. 556:
D-Arg-D-Arg-[γ-Abu1,D-Tyr2,D-Trp3,Thr5,AzaGly7,Arg(Me)9,Trp10]MS10
D-Arg-D-Arg-γ-Abu-D-Tyr-D-Trp-Asn-Thr-Phe-AzaGly-Leu-Arg(Me)-Trp-NH$_2$ Compound No. 557:
D-Arg-D-Arg-D-Arg-[γ-Abu1,D-Tyr2,D-Trp3,Thr5,AzaGly7,Arg(Me)9,Trp10]MS10
D-Arg-D-Arg-D-Arg-γ-Abu-D-Tyr-D-Trp-Asn-Thr-Phe-AzaGly-Leu-Arg(Me)-Trp-NH$_2$ Compound No. 558: des(1)-Ac-[D-Tyr2,D-Trp3,AzaGly7,Arg(Me)9,Trp10]MS10
D-Tyr-D-Trp-Asn-Ser-Phe-AzaGly-Leu-Arg(Me)-Trp-NH$_2$ Compound No. 559:
des(1-2)-3-(4-Hydroxyphenyl)propionyl-[D-Trp3,Thr5,AzaGly7,Arg(Me)9,Trp10]MS10
3-(4-Hydroxyphenyl)propionyl-D-Trp-Asn-Thr-Phe-AzaGly-Leu-Arg(Me)-Trp-NH$_2$ Compound No. 561:
D-Arg-[Acp1,D-Tyr2,D-Trp3,Abu4,AzaGly7,Arg(Me)9,Trp10]MS10
D-Arg-Acp-D-Tyr-D-Trp-Abu-Ser-Phe-AzaGly-Leu-Arg(Me)-Trp-NH$_2$ Compound No. 562:
des(1)-Ac-[D-Tyr2,D-Pya(4)3,Thr5,AzaGly7,Arg(Me)9,Trp10]MS10
D-Tyr-D-Pya(4)-Asn-Thr-Phe-AzaGly-Leu-Arg(Me)-Trp-NH$_2$ Compound No. 563:
des(1)-Ac-[D-Tyr2,D-Trp3,Aze(2)5,AzaGly7,Arg(Me)9,Trp10]MS10
Ac-D-Tyr-D-Trp-Asn-Aze(2)-Phe-AzaGly-Leu-Arg(Me)-Trp-NH$_2$ Compound No. 564: des(1)-Ac-[D-Tyr2,D-Trp3,Val5,AzaGly7,Arg(Me)9,Trp10]MS10
Ac-D-Tyr-D-Trp-Asn-Val-Phe-AzaGly-Leu-Arg(Me)-Trp-NH$_2$ Compound No. 565:
des(1)-Benzoyl-[D-Tyr2,D-Trp3,Thr5,AzaGly7,Arg(Me)9,Trp10]MS10
Benzoyl-D-Tyr-D-Trp-Asn-Thr-Phe-AzaGly-Leu-Arg(Me)-Trp-NH$_2$ Compound No. 566:
des(1)-Cyclopropanecarbonyl-[D-Tyr2,D-Trp3,Thr5,AzaGly7,Arg(Me)9,Trp10]MS10
Cyclopropanecarbonyl-D-Tyr-D-Trp-Asn-Thr-Phe-AzaGly-Leu-Arg(Me)-Trp-NH$_2$ Compound No. 567:
des(1)-Butyryl-[D-Tyr2,D-Trp3,Thr5,AzaGly7,Arg(Me)9,Trp10]MS10
Butyryl-D-Tyr-D-Trp-Asn-Thr-Phe-AzaGly-Leu-Arg(Me)-Trp-NH$_2$ Compound No. 568:
Ac-[D-Arg1,D-Tyr2,D-Trp3,Thr5,AzaGly7,Arg(Me)9,Trp10]MS10
Ac-D-Arg-D-Tyr-D-Trp-Asn-Thr-Phe-AzaGly-Leu-Arg(Me)-Trp-NH$_2$ Compound No. 569:
des(1)-Ac-[D-Tyr2,D-Trp3,Thr5,6Ψ7,CH$_2$NH,Arg(Me)9,Trp10]MS10
Ac-D-Tyr-D-Trp-Asn-Thr-PheΨ(CH$_2$NH)Gly-Leu-Arg(Me)-Trp-NH$_2$ Compound No. 570: des(1)-Me-[D-Tyr2,D-Trp3,Thr5,AzaGly7,Arg(Me)9,Trp10]MS10
Me-D-Tyr-D-Trp-Asn-Thr-Phe-AzaGly-Leu-Arg(Me)-Trp-NH$_2$ Compound No. 571: des(1)-Ac-[D-Tyr2,D-Trp3,Thr5,AzaGly7,Arg(Me)9]MS10
Ac-D-Tyr-D-Trp-Asn-Thr-Phe-AzaGly-Leu-Arg(Me)-Phe-NH$_2$ -continued Compound No. 572: des(1)-[D-Trp2,D-Pya(4)3,AzaGly7,Arg(Me)9,Trp10]MS10
D-Trp-D-Pya(4)-Asn-Ser-Phe-AzaGly-Leu-Arg(Me)-Trp-NH$_2$ Compound No. 573:
des(1)-Ac-[D-Tyr2,D-Trp3,Abu4,AzaGly7,Arg(Me)9,Trp10]MS10
Ac-D-Tyr-D-Trp-Abu-Ser-Phe-AzaGly-Leu-Arg(Me)-Trp-NH$_2$ Compound No. 576: des(1)-Ac-[D-Tyr2,D-Trp3,Gln4,AzaGly7,Arg(Me)9,Trp10]MS10
Ac-D-Tyr-D-Trp-Gln-Ser-Phe-AzaGly-Leu-Arg(Me)-Trp-NH$_2$ Compound No. 577: des(1)-Ac-[D-Tyr2,D-Trp3,Ser4,AzaGly7,Arg(Me)9,Trp10]MS10
Ac-D-Tyr-D-Trp-Ser-Ser-Phe-AzaGly-Leu-Arg(Me)-Trp-NH$_2$ Compound No. 578: des(1)-Ac-[D-Tyr2,D-Trp3,Thr4,AzaGly7,Arg(Me)9,Trp10]MS10
Ac-D-Tyr-D-Trp-Thr-Ser-Phe-AzaGly-Leu-Arg(Me)-Trp-NH$_2$ Compound No. 579: des(1)-Ac-[D-Tyr2,D-Trp3,Aib4,AzaGly7,Arg(Me)9,Trp10]MS10
Ac-D-Tyr-D-Trp-Aib-Ser-Phe-AzaGly-Leu-Arg(Me)-Trp-NH$_2$ Compound No. 580:
des(1)-Ac-[D-Tyr2,D-Trp3,Ser(Me)5,AzaGly7,Arg(Me)9,Trp10]MS10
Ac-D-Tyr-D-Trp-Asn-Ser(Me)-Phe-AzaGly-Leu-Arg(Me)-Trp-NH$_2$ Compound No. 584:
des(1)-Ac-[D-Tyr2,D-Trp3,Dap(Ac)4,AzaGly7,Arg(Me)9,Trp10]MS10
Ac-D-Tyr-D-Trp-Dap(Ac)-Ser-Phe-AzaGly-Leu-Arg(Me)-Trp-NH$_2$ Compound No. 585:
des(1)-Ac-[D-Tyr2,D-Trp3,Dap(For)4,AzaGly7,Arg(Me)9,Trp10]MS10
Ac-D-Tyr-D-Trp-Dap(For)-Ser-Phe-AzaGly-Leu-Arg(Me)-Trp-NH$_2$ Compound No. 586: des(1)-Ac-[D-Tyr2,Thr5,D-Phe6,AzaGly7,Arg(Me)9,Trp10]MS10
Ac-D-Tyr-Trp-Asn-Thr-D-Phe-AzaGly-Leu-Arg(Me)-Trp-NH$_2$ Compound No. 589:
des(1)-Ac-[D-Tyr2,D-Trp3,Thr5,AzaGly7,Arg(Me)9,Nal(2)10]MS10
Ac-D-Tyr-D-Trp-Asn-Thr-Phe-AzaGly-Leu-Arg(Me)-Nal(2)-NH$_2$ Compound No. 590:
des(1)-Ac-[D-Tyr2,D-Trp3,Thr5,AzaGly7,Arg(Me)9,Thi(2)10]MS10
Ac-D-Tyr-D-Trp-Asn-Thr-Phe-AzaGly-Leu-Arg(Me)-Thi-NH$_2$ Compound No. 591: des(1)-Ac-[D-Tyr2,D-Trp3,Thr5,AzaGly7,Arg(Me)9,Tyr10]MS10
Ac-D-Tyr-D-Trp-Asn-Thr-Phe-AzaGly-Leu-Arg(Me)-Tyr-NH$_2$ Compound No. 592:
des(1)-Ac-[D-Tyr2,D-Trp3,Thr5,AzaGly7,Arg(Me)9,Phe(4F)10]MS10
Ac-D-Tyr-D-Trp-Asn-Thr-Phe-AzaGly-Leu-Arg(Me)-Phe(4F)-NH$_2$ Compound No. 594:
des(1)-Ac-[D-Tyr2,D-Trp3,Thr5,AzaGly7,Arg(Me)9,Hph10]MS10
Ac-D-Tyr-D-Trp-Asn-Thr-Phe-AzaGly-Leu-Arg(Me)-Hph-NH$_2$ Compound No. 595: des(1)-Ac-[D-Tyr2,D-Trp3,Thr5,AzaGly7,Arg(Me)9,Cha10]MS10
Ac-D-Tyr-D-Trp-Asn-Thr-Phe-AzaGly-Leu-Arg(Me)-Cha-NH$_2$ Compound No. 596: des(1)-Ac-[D-Tyr2,D-Trp3,Thr5,AzaGly7,Arg(Me)9,Leu10]MS10
Ac-D-Tyr-D-Trp-Asn-Thr-Phe-AzaGly-Leu-Arg(Me)-Leu-NH$_2$ Compound No. 597:
des(1)-Ac-[D-Tyr2,D-Trp3,Thr5,D-Phe6,AzaGly7,Arg(Me)9,Trp10]MS10
Ac-D-Tyr-D-Trp-Asn-Thr-D-Phe-AzaGly-Leu-Arg(Me)-Trp-NH$_2$ Compound No. 598: des(1)-Ac-[D-Tyr2,D-Trp3,Thr5,Arg(Me)9,Trp10]MS10
Ac-D-Tyr-D-Trp-Asn-Thr-Phe-Gly-Leu-Arg(Me)-Trp-NH$_2$ Compound No. 599: des(1)-Ac-[D-Tyr2,D-Trp3,Thr5,AzaGly7,Orn9,Trp10]MS10
Ac-D-Tyr-D-Trp-Asn-Thr-Phe-AzaGly-Leu-Orn-Trp-NH$_2$ Compound No. 600: des(1)-Ac-[D-Tyr2,D-Trp3,Thr5,AzaGly7,Trp10]MS10
Ac-D-Tyr-D-Trp-Asn-Thr-Phe-AzaGly-Leu-Arg-Trp-NH$_2$ Compound No. 601: des(1)-Ac-[D-Tyr2,D-Trp3,Thr5,D-Phe6,Arg(Me)9,Trp10]MS10
Ac-D-Tyr-D-Trp-Asn-Thr-D-Phe-Gly-Leu-Arg(Me)-Trp-NH$_2$ Compound No. 602:
des(1)-Ac-[D-NMeTyr2,D-Trp3,Thr5,AzaGly7,Arg(Me)9,Trp10]MS10
Ac-D-NMeTyr-D-Trp-Asn-Thr-Phe-AzaGly-Leu-Arg(Me)-Trp-NH$_2$ Compound No. 603:
des(1)-Ac-[D-Tyr2,D-Pya(4)3,Thr5,D-Phe6,AzaGly7,Arg(Me)9,Trp10]MS10

-continued

Ac-D-Tyr-D-Pya(4)-Asn-Thr-D-Phe-AzaGly-Leu-Arg(Me)-Trp-NH$_2$

Compound No. 604: des(1)-Ac-[D-Tyr2,D-Trp3,Thr5,AzaGly7,Arg(Tos)9,Trp10]MS10
Ac-D-Tyr-D-Trp-Asn-Thr-Phe-AzaGly-Leu-Arg(Tos)-Trp-NH$_2$ Compound No. 605:
des(1)-Ac-[D-Tyr2,D-Trp3,Thr5,AzaGly7,Arg(NO2)9,Trp10]MS10
Ac-D-Tyr-D-Trp-Asn-Thr-Phe-AzaGly-Leu-Arg(NO2)-Trp-NH$_2$ Compound No. 607:
des(1)-Ac-[D-Tyr2,D-Trp3,Thr5,AzaGly7,Arg(Me2)asym9,Trp10]MS10
Ac-D-Tyr-D-Trp-Asn-Thr-Phe-AzaGly-Leu-Arg(Me2)asym-Trp-NH$_2$ Compound No. 608:
des(1)-Ac-[D-Tyr2,D-Trp3,Thr5,AzaGly7,Arg(Me2)sym9,Trp10]MS10
Ac-D-Tyr-D-Trp-Asn-Thr-Phe-AzaGly-Leu-Arg(Me2)sym-Trp-NH$_2$ Compound No. 609: des(1)-Ac-[D-Tyr2,D-Trp3,Thr5,AzaGly7,Arg(Et)9,Trp10]MS10
Ac-D-Tyr-D-Trp-Asn-Thr-Phe-AzaGly-Leu-Arg(Et)-Trp-NH$_2$ Compound No. 610:
des(1)-Ac-[D-Tyr2,D-Trp3,Thr5,AzaGly7,Lys(Me2)9,Trp10]MS10
Ac-D-Tyr-D-Trp-Asn-Thr-Phe-AzaGly-Leu-Lys(Me2)-Trp-NH$_2$ Compound No. 611: des(1)-Ac-[Tyr2,D-Pya(4)3,Thr5,AzaGly7,Arg(Me)9,Trp10]MS10
Ac-Tyr-D-Pya(4)-Asn-Thr-Phe-AzaGly-Leu-Arg(Me)-Trp-NH$_2$ Compound No. 612: des(1)-For-[D-Tyr2,D-Trp3,Thr5,AzaGly7,Arg(Me)9,Trp10]MS10
For-D-Tyr-D-Trp-Asn-Thr-Phe-AzaGly-Leu-Arg(Me)-Trp-NH$_2$ Compound No. 613:
des(1)-Propionyl-[D-Tyr2,D-Trp3,Thr5,AzaGly7,Arg(Me)9,Trp10]MS10
Propionyl-D-Tyr-D-Trp-Asn-Thr-Phe-AzaGly-Leu-Arg(Me)-Trp-NH$_2$ Compound No. 614:
des(1)-Amidino-[D-Tyr2,D-Trp3,Thr5,AzaGly7,Arg(Me)9,Trp10]MS10
Amidino-D-Tyr-D-Trp-Asn-Thr-Phe-AzaGly-Leu-Arg(Me)-Trp-NH$_2$ Compound No. 615: des(1)-Ac-[Tyr2,D-Pya(4)3,Thr5,AzaGly7,Arg(Me)9,Trp10]MS10
Ac-Tyr-D-Pya(4)-Asn-Thr-Phe-AzaGly-Leu-Arg(Me)-Trp-NH$_2$ Compound No. 616: des(1)-Ac-[D-Ala2,D-Trp3,Thr5,AzaGly7,Arg(Me)9,Trp10]MS10
Ac-D-Ala-D-Trp-Asn-Thr-Phe-AzaGly-Leu-Arg(Me)-Trp-NH$_2$ Compound No. 617: des(1)-Ac-[D-Leu2,D-Trp3,Thr5,AzaGly7,Arg(Me)9,Trp10]MS10
Ac-D-Leu-D-Trp-Asn-Thr-Phe-AzaGly-Leu-Arg(Me)-Trp-NH$_2$ Compound No. 618: des(1)-Ac-[D-Phe2,D-Trp3,Thr5,AzaGly7,Arg(Me)9,Trp10]MS10
Ac-D-Phe-D-Trp-Asn-Thr-Phe-AzaGly-Leu-Arg(Me)-Trp-NH$_2$ Compound No. 619:
des(1)-Ac-[D-Nal(1)2,D-Trp3,Thr5,AzaGly7,Arg(Me)9,Trp10]MS10
Ac-D-Nal(1)-D-Trp-Asn-Thr-Phe-AzaGly-Leu-Arg(Me)-Trp-NH$_2$ Compound No. 620:
des(1)-Ac-[D-Nal(2)2,D-Trp3,Thr5,AzaGly7,Arg(Me)9,Trp10]MS10
Ac-D-Nal(2)-D-Trp-Asn-Thr-Phe-AzaGly-Leu-Arg(Me)-Trp-NH$_2$ Compound No. 621: des(1)-Ac-[D-Lys2,D-Trp3,Thr5,AzaGly7,Arg(Me)9,Trp10]MS10
Ac-D-Lys-D-Trp-Asn-Thr-Phe-AzaGly-Leu-Arg(Me)-Trp-NH$_2$ Compound No. 622: des(1)-Ac-[D-Glu2,D-Trp3,Thr5,AzaGly7,Arg(Me)9,Trp10]MS10
Ac-D-Glu-D-Trp-Asn-Thr-Phe-AzaGly-Leu-Arg(Me)-Trp-NH$_2$ Compound No. 623: des(1)-Ac-[D-Tyr2,Thr5,AzaGly7,Arg(Me)9,Trp10]MS10
Ac-D-Tyr-Trp-Asn-Thr-Phe-AzaGly-Leu-Arg(Me)-Trp-NH$_2$ Compound No. 624: des(1)-Ac-[D-Tyr2,Pya(4)3,Thr5,AzaGly7,Arg(Me)9,Trp10]MS10
Ac-D-Tyr-Pya(4)-Asn-Thr-Phe-AzaGly-Leu-Arg(Me)-Trp-NH$_2$ Compound No. 625: des(1)-Ac-[D-Tyr2,D-Ala3,Thr5,AzaGly7,Arg(Me)9,Trp10]MS10
Ac-D-Tyr-D-Ala-Asn-Thr-Phe-AzaGly-Leu-Arg(Me)-Trp-NH$_2$ Compound No. 626: des(1)-Ac-[D-Tyr2,D-Leu3,Thr5,AzaGly7,Arg(Me)9,Trp10]MS10
Ac-D-Tyr-D-Leu-Asn-Thr-Phe-AzaGly-Leu-Arg(Me)-Trp-NH$_2$ Compound No. 627: des(1)-Ac-[D-Tyr2,D-Phe3,Thr5,AzaGly7,Arg(Me)9,Trp10]MS10
Ac-D-Tyr-D-Phe-Asn-Thr-Phe-AzaGly-Leu-Arg(Me)-Trp-NH$_2$ Compound No. 628: des(1)-Ac-[D-Tyr2,D-Thr3,Thr5,AzaGly7,Arg(Me)9,Trp10]MS10
Ac-D-Tyr-D-Thr-Asn-Thr-Phe-AzaGly-Leu-Arg(Me)-Trp-NH$_2$ -continued Compound No. 629: des(1)-Ac-[D-Tyr2,D-Lys3,Thr5,AzaGly7,Arg(Me)9,Trp10]MS10
Ac-D-Tyr-D-Lys-Asn-Thr-Phe-AzaGly-Leu-Arg(Me)-Trp-NH$_2$ Compound No. 630: des(1)-Ac-[D-Tyr2,D-Glu3,Thr5,AzaGly7,Arg(Me)9,Trp10]MS10
Ac-D-Tyr-D-Glu-Asn-Thr-Phe-AzaGly-Leu-Arg(Me)-Trp-NH$_2$ Compound No. 631:
des(1)-Ac-[D-Tyr2,D-Trp3,Thr5,Ala6,AzaGly7,Arg(Me)9,Trp10]MS10
Ac-D-Tyr-D-Trp-Asn-Thr-Ala-AzaGly-Leu-Arg(Me)-Trp-NH$_2$ Compound No. 632:
des(1)-Ac-[D-Tyr2,D-Trp3,Thr5,Leu6,AzaGly7,Arg(Me)9,Trp10]MS10
Ac-D-Tyr-D-Trp-Asn-Thr-Leu-AzaGly-Leu-Arg(Me)-Trp-NH$_2$ Compound No. 633:
des(1)-Ac-[D-Tyr2,D-Trp3,Thr5,Lys6,AzaGly7,Arg(Me)9,Trp10]MS10
Ac-D-Tyr-D-Trp-Asn-Thr-Lys-AzaGly-Leu-Arg(Me)-Trp-NH$_2$ Compound No. 634:
des(1)-Ac-[D-Tyr2,D-Trp3,Thr5,Glu6,AzaGly7,Arg(Me)9,Trp10]MS10
Ac-D-Tyr-D-Trp-Asn-Thr-Glu-AzaGly-Leu-Arg(Me)-Trp-NH$_2$ Compound No. 635:
des(1)-Ac-[D-Tyr2,D-Trp3,Thr5,Pya(4)6,AzaGly7,Arg(Me)9,Trp10]MS10
Ac-D-Tyr-D-Trp-Asn-Thr-Pya(4)-AzaGly-Leu-Arg(Me)-Trp-NH$_2$ Compound No. 636:
des(1)-Ac-[D-Tyr2,D-Trp3,Thr5,NMePhe6,AzaGly7,Arg(Me)9,Trp10]MS10
Ac-D-Tyr-D-Trp-Asn-Thr-MePhe-AzaGly-Leu-Arg(Me)-Trp-NH$_2$ Compound No. 637:
des(1)-Ac-[D-Tyr2,D-Trp3,Thr5,Phe(4F)6,AzaGly7,Arg(Me)9,Trp10]MS10
Ac-D-Tyr-D-Trp-Asn-Thr-Phe(4F)-AzaGly-Leu-Arg(Me)-Trp-NH$_2$ Compound No. 638:
des(1)-Ac-[D-Tyr2,D-Pya(4)3,Thr5,Phe(4F)6,AzaGly7,Arg(Me)9,Trp10]MS10
Ac-D-Tyr-D-Pya(4)-Asn-Thr-Phe(4F)-AzaGly-Leu-Arg(Me)-Trp-NH$_2$ Compound No. 639: des(1)-Ac-[D-Tyr2,D-Trp3,Thr5,AzaGly7,Lys9,Trp10]MS10
Ac-D-Tyr-D-Trp-Asn-Thr-Phe-AzaGly-Leu-Lys-Trp-NH$_2$ Compound No. 641:
des(1)-Ac-[D-Tyr2,D-Trp3,Thr5,AzaGly7,Ala8,Arg(Me)9,Trp10]MS10
Ac-D-Tyr-D-Trp-Asn-Thr-Phe-AzaGly-Ala-Arg(Me)-Trp-NH$_2$ Compound No. 642:
des(1)-Ac-[D-Tyr2,D-Trp3,Thr5,AzaGly7,Val8,Arg(Me)9,Trp10]MS10
Ac-D-Tyr-D-Trp-Asn-Thr-Phe-AzaGly-Val-Arg(Me)-Trp-NH$_2$ Compound No. 643:
des(1)-Ac-[D-Tyr2,D-Trp3,Thr5,AzaGly7,Phe8,Arg(Me)9,Trp10]MS10
Ac-D-Tyr-D-Trp-Asn-Thr-Phe-AzaGly-Phe-Arg(Me)-Trp-NH$_2$ Compound No. 644:
des(1)-Ac-[D-Tyr2,D-Trp3,Thr5,AzaGly7,Ser8,Arg(Me)9,Trp10]MS10
Ac-D-Tyr-D-Trp-Asn-Thr-Phe-AzaGly-Ser-Arg(Me)-Trp-NH$_2$ Compound No. 645: des(1)-Ac-[D-Tyr2,D-Trp3,Thr5,AzaGly7,Har9,Trp10]MS10
Ac-D-Tyr-D-Trp-Asn-Thr-Phe-AzaGly-Leu-Har-Trp-NH$_2$ Compound No. 646: des(1)-Ac-[D-Tyr2,D-Trp3,Thr5,AzaGly7,Har(Me)9,Trp10]MS10
Ac-D-Tyr-D-Trp-Asn-Thr-Phe-AzaGly-Leu-Har(Me)-Trp-NH$_2$ Compound No. 647:
des(1)-Ac-[D-Tyr2,D-Trp3,Asp4,Thr5,AzaGly7,Arg(Me)9,Trp10]MS10
Ac-D-Tyr-D-Trp-Asp-Thr-Phe-AzaGly-Leu-Arg(Me)-Trp-NH$_2$ Compound No. 648: [Gly1,D-Tyr2,D-Trp3,Thr5,AzaGly7,Arg(Me)9,Trp10]MS10
Gly-D-Tyr-D-Trp-Asn-Thr-Phe-AzaGly-Leu-Arg(Me)-Trp-NH$_2$ Compound No. 649: Ac-[Gly1,D-Tyr2,D-Trp3,Thr5,AzaGly7,Arg(Me)9,Trp10]MS10
Ac-Gly-D-Tyr-D-Trp-Asn-Thr-Phe-AzaGly-Leu-Arg(Me)-Trp-NH$_2$ Compound No. 650: [D-Tyr1,D-Tyr2,D-Trp3,Thr5,AzaGly7,Arg(Me)9,Trp10]MS10
D-Tyr-D-Tyr-D-Trp-Asn-Thr-Phe-AzaGly-Leu-Arg(Me)-Trp-NH$_2$ Compound No. 651:
Ac-[D-Tyr1,D-Tyr2,D-Trp3,Thr5,AzaGly7,Arg(Me)9,Trp10]MS10
Ac-D-Tyr-D-Tyr-D-Trp-Asn-Thr-Phe-AzaGly-Leu-Arg(Me)-Trp-NH$_2$ -continued Compound No. 652:
pGlu-des(1)-[D-Tyr2,D-Trp3,Thr5,AzaGly7,Arg(Me)9,Trp10]MS10
pGlu-D-Tyr-D-Trp-Asn-Thr-Phe-AzaGly-Leu-Arg(Me)-Trp-NH$_2$ Compound No. 653:
des(1)-Ac-[D-Tyr2,D-Trp3,D-Asn4,Thr5,AzaGly7,Arg(Me)9,Trp10]MS10
Ac-D-Tyr-D-Trp-D-Asn-Thr-Phe-AzaGly-Leu-Arg(Me)-Trp-NH$_2$ Compound No. 654:
des(1)-Ac-[D-Tyr2,D-Trp3,D-Thr5,AzaGly7,Arg(Me)9,Trp10]MS10
Ac-D-Tyr-D-Trp-Asn-D-Thr-Phe-AzaGly-Leu-Arg(Me)-Trp-NH$_2$ Compound No. 655:
des(1)-Ac-[D-Tyr2,D-Trp3,NMeAsn4,Thr5,AzaGly7,Arg(Me)9,Trp10]MS10
Ac-D-Tyr-D-Trp-NMeAsn-Thr-Phe-AzaGly-Leu-Arg(Me)-Trp-NH$_2$ Compound No. 656:
des(1)-Ac-[D-Tyr2,D-Trp3,NMeSer5,AzaGly7,Arg(Me)9,Trp10]MS10
Ac-D-Tyr-D-Trp-Asn-NMeSer-Phe-AzaGly-Leu-Arg(Me)-Trp-NH$_2$ Compound No. 657: des(1)-Ac-[D-Tyr2,Pro3,Thr5,AzaGly7,Arg(Me)9,Trp10]MS10
Ac-D-Tyr-Pro-Asn-Thr-Phe-AzaGly-Leu-Arg(Me)-Trp-NH$_2$ Compound No. 658:
des(1)-Ac-[D-Tyr2,D-Pya(2)3,Thr5,AzaGly7,Arg(Me)9,Trp10]MS10
Ac-D-Tyr-D-Pya(2)-Asn-Thr-Phe-AzaGly-Leu-Arg(Me)-Trp-NH$_2$ Compound No. 659:
des(1)-Ac-[D-Tyr2,D-Trp3,allo-Thr5,AzaGly7,Arg(Me)9,Trp10]MS10
Ac-D-Tyr-D-Trp-Asn-allo-Thr-Phe-AzaGly-Leu-Arg(Me)-Trp-NH$_2$ Compound No. 660:
des(1)-Ac-[D-Tyr2,D-Pya(3)3,Thr5,AzaGly7,Arg(Me)9,Trp10]MS10
Ac-D-Tyr-D-Pya(3)-Asn-Thr-Phe-AzaGly-Leu-Arg(Me)-Trp-NH$_2$ Compound No. 661: des(1)-Ac-[D-Tyr2,D-Pro3,Thr5,AzaGly7,Arg(Me)9,Trp10]MS10
Ac-D-Tyr-D-Pro-Asn-Thr-Phe-AzaGly-Leu-Arg(Me)-Trp-NH$_2$ Compound No. 662: des(1)-Ac-[D-Tyr2,Tic3,Thr5,AzaGly7,Arg(Me)9,Trp10]MS10
Ac-D-Tyr-Tic-Asn-Thr-Phe-AzaGly-Leu-Arg(Me)-Trp-NH$_2$ Compound No. 663: des(1)-Ac-[D-Trp2,D-Trp3,Thr5,AzaGly7,Arg(Me)9,Trp10]MS10
Ac-D-Trp-D-Trp-Asn-Thr-Phe-AzaGly-Leu-Arg(Me)-Trp-NH$_2$ Compound No. 664: des(1)-Ac-[Tyr2,Thr5,AzaGly7,Arg(Me)9,Trp10]MS10
Ac-Tyr-Trp-Asn-Thr-Phe-AzaGly-Leu-Arg(Me)-Trp-NH$_2$ Compound No. 665: des(1-2)-[D-Trp3,Thr5,AzaGly7,Arg(Me)9,Trp10]MS10
D-Trp-Asn-Thr-Phe-AzaGly-Leu-Arg(Me)-Trp-NH$_2$ Compound No. 666: des(1-2)-Ac-[D-Trp3,Thr5,AzaGly7,Arg(Me)9,Trp10]MS10
Ac-D-Trp-Asn-Thr-Phe-AzaGly-Leu-Arg(Me)-Trp-NH$_2$ Compound No. 667:
des(1-2)-Hexanoyl-[D-Trp3,Thr5,AzaGly7,Arg(Me)9,Trp10]MS10
Hexanoyl-D-Trp-Asn-Thr-Phe-AzaGly-Leu-Arg(Me)-Trp-NH$_2$ Compound No. 668:
des(1-2)-Cyclohexanecarbonyl-[D-Trp3,Thr5,AzaGly7,Arg(Me)9,Trp10]MS10
Cyclohexanecarbonyl-D-Trp-Asn-Thr-Phe-AzaGly-Leu-Arg(Me)-Trp-NH$_2$ Compound No. 669: des(1-2)-Benzoyl-[D-Trp3,Thr5,AzaGly7,Arg(Me)9,Trp10]MS10
Benzoyl-D-Trp-Asn-Thr-Phe-AzaGly-Leu-Arg(Me)-Trp-NH$_2$ Compound No. 670:
des(1-2)-3-Pyridinepropionyl-[D-Trp3,Thr5,AzaGly7,Arg(Me)9,Trp10]MS10
3-Pyridinepropionyl-D-Trp-Asn-Thr-Phe-AzaGly-Leu-Arg(Me)-Trp-NH$_2$ Compound No. 671: des(1-2)-Adipoyl-[D-Trp3,Thr5,AzaGly7,Arg(Me)9,Trp10]MS10
Adipoyl-D-Trp-Asn-Thr-Phe-AzaGly-Leu-Arg(Me)-Trp-NH$_2$ Compound No.: 672-Ac-[D-Tyr2,NMeTrp3,Thr5,AzaGly7,Arg(Me)9,Trp10]MS10
Ac-D-Tyr-NMeTrp-Asn-Thr-Phe-AzaGly-Leu-Arg(Me)-Trp-NH$_2$ Compound No. 674:
des(1-2)-6-Aminocaproyl-[D-Trp3,Thr5,AzaGly7,Arg(Me)9,Trp10]MS10
6-Aminocaproyl-D-Trp-Asn-Thr-Phe-AzaGly-Leu-Arg(Me)-Trp-NH$_2$ Compound No. 675: [D-Tyr2,D-Trp3,Thr5,AzaGly7,Arg(Me)9,Trp10]MS10
Tyr-D-Tyr-D-Trp-Asn-Thr-Phe-AzaGly-Leu-Arg(Me)-Trp-NH$_2$ -continued Compound No. 676: Ac-[D-Tyr2,D-Trp3,Thr5,AzaGly7,Arg(Me)9,Trp10]MS10
Ac-Tyr-D-Tyr-D-Trp-Asn-Thr-Phe-AzaGly-Leu-Arg(Me)-Trp-NH$_2$ Compound No. 677:
Ac-des(1)-[D-Tyr2,D-Trp3,Thr5,AzaGly7,Nva8,Arg(Me)9,Trp10]MS10
Ac-D-Tyr-D-Trp-Asn-Thr-Phe-AzaGly-Nva-Arg(Me)-Trp-NH$_2$ Compound No. 678:
Ac-des(1)-[D-Tyr2,D-Trp3,Thr5,AzaGly7,Ile8,Arg(Me)9,Trp10]MS10
Ac-D-Tyr-D-Trp-Asn-Thr-Phe-AzaGly-Ile-Arg(Me)-Trp-NH$_2$ Compound No. 679: des(1-2)-Amidino-[D-Trp3,Thr5,AzaGly7,Arg(Me)9,Trp10]MS10
Amidino-D-Trp-Asn-Thr-Phe-AzaGly-Leu-Arg(Me)-Trp-NH$_2$ Compound No. 680:
des(1-2)-Glycoloyl-[D-Trp3,Thr5,AzaGly7,Arg(Me)9,Trp10]MS10
Glycoloyl-D-Trp-Asn-Thr-Phe-AzaGly-Leu-Arg(Me)-Trp-NH$_2$ Compound No. 681:
des(1)-Glycoloyl-[D-Tyr2,D-Trp3,Thr5,AzaGly7,Arg(Me)9,Trp10]MS10
Glycoloyl-D-Tyr-D-Trp-Asn-Thr-Phe-AzaGly-Leu-Arg(Me)-Trp-NH$_2$ Compound No. 682:
des(1)-Ac-[D-Tyr2,D-Trp3,Thr5,AzaGly7,Gln8,Arg(Me)9,Trp10]MS10
Ac-D-Tyr-D-Trp-Asn-Thr-Phe-AzaGly-Gln-Arg(Me)-Trp-NH$_2$ Compound No. 685: des(1)-Ac-[D-Tyr2,D-Pya(4)3,Thr5,AzaGly7,Arg(Me)9]MS10
Ac-D-Tyr-D-Pya(4)-Asn-Thr-Phe-AzaGly-Leu-Arg(Me)-Phe-NH$_2$ Compound No. 686: des(1)-Ac-[D-Tyr2,D-Trp3,Gly4,AzaGly7,Arg(Me)9,Trp10]MS10
Ac-D-Tyr-D-Trp-Gly-Ser-Phe-AzaGly-Leu-Arg(Me)-Trp-NH$_2$ Compound No. 688: des(1)-Ac-[D-Tyr2,D-Trp3,Thr5,AzaGly7,Pya(4)9,Trp10]MS10
Ac-D-Tyr-D-Trp-Asn-Thr-Phe-AzaGly-Leu-Pya(4)-Trp-NH$_2$ Compound No. 689:
des(1)-Ac-[D-Tyr2,D-Trp3,Thr5,AzaGly7,Arg(Me)9,D-Trp10]MS10
Ac-D-Tyr-D-Trp-Asn-Thr-Phe-AzaGly-Leu-Arg(Me)-D-Trp-NH$_2$ Compound No. 691:
des(1)-Ac-[D-Tyr2,D-Trp3,Thr5,Tyr6,AzaGly7,Arg(Me)9,Trp10]MS10
Ac-D-Tyr-D-Trp-Asn-Thr-Tyr-AzaGly-Leu-Arg(Me)-Trp-NH$_2$ Compound No. 692:
des(1)-Ac-[D-Tyr2,D-Trp3,Thr5,Trp6,AzaGly7,Arg(Me)9,Trp10]MS10
Ac-D-Tyr-D-Trp-Asn-Thr-Trp-AzaGly-Leu-Arg(Me)-Trp-NH$_2$ Compound No. 693:
des(1)-Ac-[D-Tyr2,D-Trp3,Thr5,Tyr(Me)6,AzaGly7,Arg(Me)9,Trp10]MS10
Ac-D-Tyr-D-Trp-Asn-Thr-Tyr(Me)-AzaGly-Leu-Arg(Me)-Trp-NH$_2$ Compound No. 694:
des(1)-Ac-[D-Tyr2,D-Trp3,Thr5,Nal(2)6,AzaGly7,Arg(Me)9,Trp10]MS10
Ac-D-Tyr-D-Trp-Asn-Thr-Nal(2)-AzaGly-Leu-Arg(Me)-Trp-NH$_2$ Compound No. 695:
des(1)-Ac-[D-Tyr2,D-Trp3,Thr5,Thi6,AzaGly7,Arg(Me)9,Trp10]MS10
Ac-D-Tyr-D-Trp-Asn-Thr-Thi-AzaGly-Leu-Arg(Me)-Trp-NH$_2$ Compound No. 696:
des(1)-Ac-[D-Tyr2,D-Trp3,Thr5,Cha6,AzaGly7,Arg(Me)9,Trp10]MS10
Ac-D-Tyr-D-Trp-Asn-Thr-Cha-AzaGly-Leu-Arg(Me)-Trp-NH$_2$ Compound No. 698:
des(1)-Ac-[D-Tyr2,D-Trp3,Thr5,AzaGly7,Abu8,Arg(Me)9,Trp10]MS10
Ac-D-Tyr-D-Trp-Asn-Thr-Phe-AzaGly-Abu-Arg(Me)-Trp-NH$_2$ Compound No. 699:
des(1)-Ac-[D-Tyr2,D-Trp3,Thr5,AzaGly7,γMeLeu8,Arg(Me)9,Trp10]MS10
Ac-D-Tyr-D-Trp-Asn-Thr-Phe-AzaGly-γMeLeu-Arg(Me)-Trp-NH$_2$ Compound No. 700: des(1)-Ac-[D-Tyr2,D-Trp3,Thr5,Aib8,,Arg(Me)9,Trp10]MS10
Ac-D-Tyr-D-Trp-Asn-Thr-Phe-Gly-Aib-Arg(Me)-Trp-NH$_2$ Compound No. 701: des(1)-Ac-[D-Tyr2,D-Trp3,Dap4,AzaGly7,Arg(Me)9,Trp10]MS10
Ac-D-Tyr-D-Trp-Dap-Ser-Phe-AzaGly-Leu-Arg(Me)-Trp-NH$_2$ Compound No. 702:
des(1)-Ac-[D-Tyr2,D-Trp3,Asp(NHMe)4,Thr5,AzaGly7,Arg(Me)9,Trp10]MS10
Ac-D-Tyr-D-Trp-Asp(NHMe)-Thr-Phe-AzaGly-Leu-Arg(Me)-Trp-NH$_2$ Compound No. 703:
des(1)-Ac-[D-Tyr2,D-Trp3,Asp(NMe2)4,Thr5,AzaGly7,Arg(Me)9,Trp10]MS10
Ac-D-Tyr-D-Trp-Asp(NMe2)-Thr-Phe-AzaGly-Leu-Arg(Me)-Trp-NH$_2$ For metastin derivatives (II), preferably used are metastin derivatives represented by the formula:

XX0-XX2-XX3-XX4-XX5-XX6-AzaGly-XX8-XX9-XX10-NH$_2$ (wherein:

XX0 represents formyl, C$_{1-6}$ alkanoyl (e.g., acetyl, propionyl, butyryl, hexanoyl, and so on; preferably acetyl, propionyl, butyryl; more preferably acetyl), cyclopropanecarbonyl, 6-(acetyl-D-arginylamino)caproyl, 6-((R)-2,3-diaminopropionylamino)caproyl, 6-(D-norleucylamino)caproyl, 4-(D-arginylamino)butyryl, or 3-(4-Hydroxyphenyl)propionyl, glycyl. tyrosyl, acetylglycyl, acetyltyrosyl, D-tyrosyl, acetyl-D-tyrosyl, pyroglutamyl, 3-(pyridine-3-yl)propionyl, adipoyl or 6-aminocaproyl (preferably acetyl and the like);

XX2 represents Tyr, D-Tyr, D-Ala, D-Leu, D-Phe, D-Lys, D-Trp or bond arm (preferably D-Tyr or bond arm; more preferably D-Tyr);

XX3 represents Trp, Pro, 4-pyridylalanine, Tic, D-Trp, D-Ala, D-Leu, D-Phe, D-Lys, D-Glu, D-2-pyridylalanine, D-3-pyridylalanine or D-4-pyridylalanine (preferably D-Trp or D-4-pyridylalanine);

XX4 represents Asn, 2-amino-3-ureidopropion acid, N$^\beta$-formyldiaminopropionic acid or N$^{62}$-acetyldiaminopropionic acid (preferably Asn);

XX5 represents Ser, Thr or Val (preferably Ser or Thr);

XX6 represents Phe, Tyr, Trp, Tyr(Me), Thi, Nal(2), Cha, 4-pyridylalanine or 4-fluorophenylalanine (preferably Phe or 4-fluorophenylalanine);

AzaGly represents azaglycine;

XX8 represents Leu, Nva or Val (preferably Leu);

XX9 represents Arg, OrnArg(Me), or Arg(symMe2) (preferably Arg(Me));

XX10 represents Phe, Trp, 2-naphthylalanine, 2-thienylalanine, tyrosine or 4-fluorophenylalanine (preferably Phe or Trp)), or a salt thereof. Further, compounds represented by the following compound number are preferred:

```
Ac-D-Tyr-D-Trp-Asn-Thr-Phe-AzaGly-Leu-Arg(Me)-Trp-NH2 (Compound No. 550),

Ac-D-Arg-Acp-D-Tyr-D-Trp-Asn-Thr-Phe-AzaGly-Leu-Arg(Me)-Trp-NH2
(Compound No. 551), D-Dap-Acp-D-Tyr-D-Trp-Asn-Thr-Phe-AzaGly-Leu-Arg(Me)-Trp-NH2 (Compound
No. 552), Ac-D-Tyr-D-Trp-Asn-Ser-Phe-AzaGly-Leu-Arg(Me)-Trp-NH2 (Compound No. 558), 3-(4-Hydroxyphenyl)propionyl-D-Trp-Asn-Thr-Phe-AzaGly-Leu-Arg(Me)-Trp-NH2
(Compound No. 559), Ac-D-Tyr-D-Pya(4)-Asn-Thr-Phe-AzaGly-Leu-Arg(Me)-Trp-NH2 (Compound No.
562), Ac-D-Tyr-D-Trp-Asn-Thr-Phe-AzaGly-Leu-Arg(Me)-Phe-NH2 (Compound No. 571), Ac-D-Tyr-D-Trp-Alb-Ser-Phe-AzaGly-Leu-Arg(Me)-Trp-NH2 (Compound No. 579), Ac-D-Tyr-D-Trp-Dap(For)-Ser-Phe-AzaGly-Leu-Arg(Me)-Trp-NH2 (Compound No.
585), Ac-D-Tyr-D-Trp-Asn-Thr-Phe-AzaGly-Leu-Arg(Me)-Nal(2)-NH2 (Compound No.
589), Ac-D-Tyr-D-Trp-Asn-Thr-Phe-AzaGly-Leu-Arg(Me)-Phe(4F)-NH2 (Compound No.
592), For-D-Tyr-D-Trp-Asn-Thr-Phe-AzaGly-Leu-Arg(Me)-Trp-NH2 (Compound No. 612), Propionyl-D-Tyr-D-Trp-Asn-Thr-Phe-AzaGly-Leu-Arg(Me)-Trp-NH2 (Compound No.
613), Ac-D-Phe-D-Trp-Asn-Thr-Phe-AzaGly-Leu-Arg(Me)-Trp-NH2 (Compound No. 618), Ac-D-Tyr-D-Phe-Asn-Thr-Phe-AzaGly-Leu-Arg(Me)-Trp-NH2 (Compound No. 627), Ac-D-Tyr-D-Trp-Asn-Thr-Phe(4F)-AzaGly-Leu-Arg(Me)-Trp-NH2 (Compound No.
637), Ac-D-Tyr-D-Pya(4)-Asn-Thr-Phe(4F)-AzaGly-Leu-Arg(Me)-Trp-NH2 (Compound No.
638), Ac-D-Tyr-D-Pya(2)-Asn-Thr-Phe-AzaGly-Leu-Arg(Me)-Trp-NH2 (Compound No.
658), Ac-D-Tyr-D-Pya(3)-Asn-Thr-Phe-AzaGly-Leu-Arg(Me)-Trp-NH2 (Compound No.
660), Ac-D-Trp-D-Trp-Asn-Thr-Phe-AzaGly-Leu-Arg(Me)-Trp-NH2 (Compound No. 663),
``` or salts thereof.

The metastin derivatives (II) of the present invention or their salts or prodrugs have excellent blood stability, in addition to excellent effects of suppressing cancer metastasis and cancer growth, and are useful as agents for preventing or treating cancers (for example, lung cancer, gastric cancer, liver cancer, pancreatic cancer, colorectal cancer, rectal cancer, colonic cancer, prostate cancer, ovarian cancer, cervical cancer, breast cancer, etc.). The metastin derivatives (II) of the present invention or their salts or prodrugs have an effect of controlling pancreatic function and are useful as agents for preventing or treating pancreatic diseases (e.g., acute or chronic pancreatitis, pancreatic cancer, etc.). The metastin derivatives (II) of the present invention or their salts or prodrugs have an effect of controlling placental function and are useful as agents for preventing or treating choriocarcinoma, hydatid mole, invasive mole, miscarriage, fetal hypoplasia, abnormal glucose metabolism, abnormal lipid metabolism or induction of delivery.

Moreover, the metastin derivatives (II) of the present invention or their salts or prodrugs have effects of increasing sugar level, promoting pancreatic glucagon secretion and promoting urine formation, and are useful as agents for preventing or treating obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders or lipotoxicity.

In addition, the metastin derivatives (II) of the present invention or their salts or prodrugs have excellent activities of promoting gonadotropic hormone secretion, promoting sex hormone secretion, inducing ovulation or stimulating ovulation, and are useful as low toxic and stable agents, e.g., agents for improving gonadal function, agents for preventing or treating hormone-dependent cancer (e.g., prostate cancer, breast cancer, etc.), infertility, endometriosis, early puberty, myoma of the uterus, etc., agents for inducing or stimulating ovulation, gonadotropic hormone secretagogue agents, contraceptives, sex hormone secretagogue agents, or the like.

Furthermore, the metastin derivatives (II) of the present invention or their salts or prodrugs are useful as agents for preventing or treating Alzheimer's disease, moderate cognitive impairment, etc.

The metastin derivatives (III) [including the metastin derivatives (II) and the metastin derivatives (I)] of the present invention or their salts or prodrugs are useful as agents for suppressing gonadotropic hormone secretion or sex hormone secretion; down-regulating agents for gonadotropic hormone or sex hormone; down-regulating agents for human OT7T175 (metastin receptor) protein consisting of the amino acid sequence represented by SEQ ID NO: 9; agents for preventing or treating hormone-dependent cancers (e.g., prostate cancer, breast cancer, etc.; particularly, hormone-sensitive breast cancer, hormone-sensitive prostate cancer, etc.); agents for preventing or treating endometriosis; agents for inhibiting ovarian follicular maturation; menstrual cycle-suspending agents; agents for treating myoma of the uterus; agents for treating early puberty; contraceptives, etc.

In addition, the metastin derivatives (III) [including the metastin derivatives (II) and the metastin derivatives (I)] of the present invention or their salts or prodrugs are useful as an agent for potentiating immunity (prophylactic agent for infection after bone-marrow transplant, an agent for potentiating immunity intended for cancer); a prophylactic/therapeutic agent for bulbospinal muscular atrophy; an agent for protecting ovary; a prophylactic/therapeutic agent for benign prostate hypertrophy (BPH); a prophylactic/therapeutic agent for gender identity disorder; or an agent for in vitro fertilization (IVF). In addition, it is useful as a prophylactic/therapeutic agent for infertility, hypogonadism, oligospermia, azoospermia, aspermia, asthenospermia, or necrospermia. Further, it is useful for hormone-dependent diseases such as prostate cancer, uterine cancer, breast cancer, sex hormone dependent cancer like hypophysial tumor, prostate gland enlargement, endometriosis, uterine fibroid, early puberty, dysmenorrhea, amenorrhea, menstrual syndrome, multilocular ovary syndrome, postoperative relapse of the above-mentioned cancers, metastasis of the above-mentioned cancers, hypopituitarism, dwarfism (the case where the secretion of growth hormone was compromised associating with hyposecretion of pituitary hormone), menopausal disorder, indefinite complaint, sex hormone dependent disorders such as calcium phosphor bone metabolic disorders. It is applicable for contraception (or infertility when rebound effects after cessation of the drug are utilized).

Furthermore, metastin per se, DNA encoding metastin, etc. are also useful as agents for suppressing gonadotropic hormone secretion or sex hormone secretion; down-regulating agents for gonadotropic hormone or sex hormone; down-regulating agents for human OT7T175 (metastin receptor) protein consisting of the amino acid sequence represented by SEQ ID NO: 9; agents for preventing or treating hormone-dependent cancers (e.g., prostate cancer, breast cancer, etc.; particularly, hormone-sensitive prostate cancer, hormone-sensitive breast cancer, etc.); agents for preventing or treating endometriosis; agents for inhibiting ovarian follicular maturation; menstrual cycle-suspending agents; agents for treating myoma of the uterus; agents for treating early puberty; contraceptives, etc.

BEST MODE FOR CARRYING OUT THE INVENTION

The metastin derivatives (I) and (II) of the present invention can be prepared by publicly known methods for peptide synthesis. As the methods for peptide synthesis, for example, either solid phase synthesis or liquid phase synthesis may be used. That is, the partial peptide or amino acids that can constitute the peptide of the present invention are repeatedly condensed with the remaining part to give the product having a desired sequence. Where the product has protecting groups, these protecting groups are removed to give the desired peptide. Publicly known methods for condensation and removal of the protecting groups are described in (i) to (v) below.
(1) M. Bodanszky & M. A. Ondetti: Peptide Synthesis, Interscience Publishers, New York (1966)
(2) Schroeder & Luebke: The Peptide, Academic Press, New York (1965)
(3) Nobuo Izumiya, et al.: *Peptide Gosei-no-Kiso to Jikken* (Basics and experiments of peptide synthesis), published by Maruzen Co. (1975)
(4) Haruaki Yajima & Shunpei Sakakibara: *Seikagaku Jikken Koza* (Biochemical Experiment) 1, *Tanpakushitsu no Kagaku* (Chemistry of Proteins) IV, 205 (1977)
(5) Haruaki Yajima, ed.: *Zoku Iyakuhin no Kaihatsu* (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography and recrystallization to give the partial peptide of the present invention. When the peptide obtained by the above methods is in a free form, the peptide can be converted into an appropriate salt by a publicly known method; when the protein is obtained in a salt form, it can be converted into its free form by publicly known methods.

For condensation of the protected amino acids or peptides, a variety of activation reagents for protein synthesis may be used, but trisphosphonium salts, tetramethyluronium salts, carbodiimides, etc. are particularly preferred. Examples of trisphosphonium salts include benzotriazol-1-yloxytris(pyrrolidino)phosphonium hexafluorophosphate (PyBOP), bromotris(pyrrolidino) phosphonium hexafluorophosphate (PyBroP) and 7-azabenzotriazol-1-yloxytris(pyrrolidino) phosphonium hexafluorophosphate (PyAOP), examples of tetramethyluronium salts include 2-(1H-benzotriazol-1-yl)-1,1,3,3-hexafluorophosphate (HBTU), 2-(7-azabenzotriazol-1-yl)-1,1,3,3-hexafluorophosphate (HATU), 2-(1H-benzotriazol-1-yl)-1,1,3,3-tetramethyluronium tetrafluoroborate (TBTU), 2-(5-norbornene-2,3-dicarboxyimido)-1,1,3,3-tetramethyluronium tetrafluoroborate (TNTU) and O—(N-succimidyl)-1,1,3,3-tetramethyluronium tetrafluoroborate (TSTU); examples of carbodiimides include DCC, N,N'-diisopropylcarbodiimide (DIPCDI) and N-ethyl-N'-(3-dimethylaminopropyl) carbodiimide hydrochloride (EDCI.HCl); etc. For condensation using these reagents, the addition of racemization inhibitors (e.g., HONB, HOBt, HOAt, HOOBt, etc.) is preferred. Solvents used in condensation may be appropriately chosen from solvents that are known to be usable for condensation. For example, acid amides such as anhydrous or hydrous N,N-dimethylformamide, N,N-dimethylacetamide, N-methylpyrrolidone, etc., halogenated hydrocarbons such as methylene chloride, chloroform, etc., alcohols such as trifluoroethanol, phenol, etc., sulfoxides such as dimethyl sulfoxide, etc., tertiary amines such as pyridine, etc., ethers such as dioxane, tetrahydrofuran, etc., nitriles such as acetonitrile, propionitrile, etc., esters such as methyl acetate, ethyl acetate, etc., or suitable mixtures thereof, etc. are used. The reaction temperature is appropriately chosen from the range known to be applicable to peptide binding reactions and is normally suitably chosen from the range of about −20° C. to 50° C. The activated amino acid derivatives are used generally in 1.5 to 6 times excess. In the case of solid phase synthesis, the condensation is examined using the ninhydrin reaction; when the condensation is insufficient, the condensation can be completed by repeating the condensation reaction without removal of the protecting groups. When the condensation is yet insufficient even after repeating the reaction, the unreacted amino acids are acylated with acetic anhydride or acetylimidazole to cancel any adverse effect on the subsequent reaction.

Examples of the protecting groups used to protect amino groups in the starting amino acids include Z, Boc, tert-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, trityl, etc. Examples of protecting groups for a carboxyl group include, in addition to the $C_{1-6}$ alkyl group, $C_{3-8}$ cycloalkyl group and $C_{7-14}$ aralkyl group for R described above, allyl, 2-adamantyl, 4-nitrobenzyl, 4-methoxybenzyl, 4-chlorobenzyl, phenacyl group, benzyloxycarbonylhydrazide, tert-butoxycarbonylhydrazide, tritylhydrazide, etc.

The hydroxyl group of serine and threonine can be protected, for example, by esterification or etherification. Examples of groups suitable for this esterification include a lower ($C_{2-4}$) alkanoyl group such as acetyl group, an aroyl group such as benzoyl group, etc. and a group derived from organic acid. Examples of a group suitable for the etherification include benzyl group, tetrahydropyranyl group, tert-butyl group, trytyl group (Trt), etc.

Examples of groups for protecting the phenolic hydroxyl group of tyrosine include Bzl, $Cl_2$-Bzl, 2-nitrobenzyl, Br-Z, tert-butyl, etc.

Examples of groups used to protect the imidazole moiety of histidine include Tos, 4-methoxy-2,3,6-trimethylbenzenesulfonyl (Mtr), DNP, Bom, Bum, Boc, Trt, Fmoc, etc.

Examples of protecting groups for a guanidino group of arginine include Tos, Z, 4-methoxy-2,3,6-trimethylbenzenesulfonyl (Mtr), p-methoxybenzenesulfonyl (MBS), 2,2,5,7,8-pentamethylchroman-6-sulfonyl (Pmc), mesitylene-2-sulfonyl (Mts), 2,2,4,6,7-pentamethyldihydrobenzofuran-5-sulfonyl (Pbf), Boc, Z, $NO_2$, etc.

Examples of protecting groups for side chain amino group of lysine include Z, Cl-Z, trifluoroacetyl, Boc, Fmoc, Trt, Mtr, 4,4-dimethyl-2,6-dioxocyclohexylideneyl (Dde), etc.

Examples of protecting groups for indolyl of tryptophan include formyl (For), Z, Boc, Mts, Mtr, etc.

A protecting group for asparagine and glutamine include Trt, xanthyl (Xan), 4,4'-dimethoxybenzhydryl (Mbh), 2,4,6-trimethoxybenzyl (Tmob), etc.

Examples of the activated carboxyl groups in the starting material include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccinimide, 1-hydroxybenzotriazole (HOBt) or 1-hydroxy-7-azabenzotriazole (HOAt)], etc. As the amino acids in which the amino groups in the starting material are activated, the corresponding phosphoric amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethanesulfonic acid, trifluoroacetic acid, trimethylsilane bromide (TMSBr), trimethylsilyl trifluoromethanesulfonate, tetrafluoroboric acid, tris(trifluoro)boron, boron tribromide or a mixed solution thereof, a base treatment with diisopropylethylamine, triethylamine, piperidine, piperazine, etc., and reduction with sodium in liquid ammonia. The elimination of protecting groups by the acid treatment described above is carried out generally at a temperature of approximately −20° C. to 40° C. In the acid treatment, it is efficient to add a cation scavenger such as anisole, phenol, thioanisole, m-cresol, p-cresol, etc., dimethylsulfide, 1,4-butanedithiol, 1,2-ethanedithiol, etc. Furthermore, 2,4-dinitrophenyl group known as the protecting group for the imidazole of histidine is removed by a treatment with thiophenol. Formyl group used as the protecting group of the indole of tryptophan is removed by the aforesaid acid treatment in the presence of 1,2-ethanedithiol, 1,4-butanedithiol, etc. as well as by a treatment with an alkali such as a dilute sodium hydroxide solution, dilute ammonia, etc.

Protection of functional groups that should not be involved in the reaction of the starting materials, protecting groups, removal of the protecting groups and activation of functional groups involved in the reaction may be appropriately chosen from publicly known groups and publicly known means.

In another method for obtaining the amides of the peptide, for example, the α-carboxyl group of the carboxy terminal amino acid is first protected by amidation; the peptide chain is then extended from the amino group side to a desired length. Thereafter, a peptide in which only the protecting group of the N-terminal α-amino group in the peptide chain has been removed from the peptide and a peptide (or an amino acid) in which only the protecting group of the C-terminal carboxyl group has been eliminated are prepared. The two peptides are condensed in a mixture of the solvents described above. The details of the condensation reaction are the same as described above. After the protected peptide obtained by the condensation is purified, all the protecting groups are removed by the method described above to give the desired crude peptide. This crude peptide is purified by various known purification means. Lyophilization of the major fraction gives the amide of the desired peptide.

When the metastin derivatives (I) and (II) of the present invention are present as a configurational isomer, a diastereomer, a conformer or the like, each can be isolated by the separating and purifying means described above, if desired. In addition, when the compound of the present invention is racemic, it can be separated into an S isomer and an R isomer by the conventional optical resolving means.

When the metastin derivatives (I) and (II) of the present invention have steric isomers, the present invention includes both of these isomers alone and the isomers present as a mixture thereof.

In addition, the metastin derivatives (I) and (II) of the present invention may be hydrated or non-hydrated.

The metastin derivatives (I) and (II) of the present invention may be labeled with an isotope (e.g., $^3$H, $^{14}$C, $^{35}$S), etc.

Throughout the present specification, the peptides are represented in accordance with the conventional way of describing peptides, that is, the N-terminus (amino terminus) at the left hand and the C-terminus (carboxyl terminus) at the right hand. In the peptides, the C-terminus is usually in the form of an amide (—CONH$_2$), a carboxyl group (—COOH), a carboxylate (—COO$^-$), an alkylamide (—CONHR) or an ester (—COOR) and the amide (—CONH$_2$) is particularly preferred. Examples of the ester or alkylamide as R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl group such as a phenyl-$C_{1-2}$-alkyl group, e.g., benzyl, phenethyl, etc., or an α-naphthyl-$C_{1-2}$-alkyl group such as α-naphthylmethyl, etc.; pivaloyloxymethyl group, which are widely used as an ester for oral use, and the like.

Examples of a salt of the metastin derivative (I) of the present invention include a metal salt, a salt with ammonium, a salt with an organic base, a salt with inorganic acid, a salt with organic acid, a salt with basic or acidic amino acid, and the like. Preferred examples of the metal salt include alkali metal salts such as sodium salts, potassium salts, etc.; alkaline earth metal salts such as calcium salts, magnesium salts, barium salts, etc.; aluminum salts; and the like. Preferred examples of the salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, etc. Preferred examples of the salts with inorganic acids include salts with hydrochloric acid, hydrobromic acid, nitric acid, sulfuric acid, phosphoric acid, etc. Preferred examples of salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, etc. Preferred examples of salts with basic amino acids include salts with arginine, lysine, ornithine, etc., and preferred examples of salts with acidic amino acids include salts with aspartic, glutamic acid, etc.

Among them, pharmaceutically acceptable salts are preferable. For example, when the compound has an acidic functional group, inorganic salts such as alkali metal salts (e.g., sodium salt, potassium salt, etc.), alkaline earth metal salts (e.g., calcium salt, magnesium salt, barium salt, etc.), ammonium salts, etc. are preferable. When the compound has a basic functional group, salts with inorganic acids with hydrochloric acid, hydrobromic acid, nitric acid, sulfuric acid, phosphoric acid, etc., and salts with organic acids such as acetic acid, phthalic acid, fumaric acid, oxalic acid, tartaric acid, maleic acid, citric acid, succinic acid, methanesulfonic acid, p-toluenesulfonic acid, etc. are preferable.

A prodrug of the metastin derivative (III) or a salt thereof (hereinafter sometimes simply referred to as the metastin derivative (III) of the present invention) means a metastin derivative that is converted into the metastin derivative (III) of the present invention under physiological conditions or with a reaction due to an enzyme, a gastric acid, etc., in the living body. That is, the prodrug of the present invention is a metastin derivative that undergoes enzymatic oxidation, reduction, hydrolysis, etc. to be converted into the metastin derivative (III) of the present invention, or a metastin derivative that undergoes hydrolysis, etc. by gastric acid, etc. to be converted into the metastin derivative (III) of the present invention.

The prodrugs of the metastin derivative (I) of the present invention or salts thereof (hereinafter sometimes simply referred to as the metastin derivative (I) of the present invention) and the prodrugs of the metastin derivative (II) of the present invention or salts thereof (hereinafter sometimes simply referred to as the metastin derivative (II) of the present invention), which can be used, are the same as those described for the prodrugs of the metastin derivative (III) of the present invention.

Examples of the prodrugs of the metastin derivatives (III) of the present invention include metastin derivatives wherein an amino group of the metastin derivative (III) of the present invention is substituted with an acyl, an alkyl, phosphoric acid, etc. (e.g., metastin derivatives wherein an amino group of the metastin derivative (III) of the present invention is substituted with eicosanoyl, alanyl, pentylaminocarbonyl (5-methyl-2-oxo-1,3-dioxolen-4-yl)methoxycarbonyl, tetrahydrofuranyl, pyrrolidylmethyl, pivaloyloxymethyl, tert-butyl, etc); metastin derivatives wherein a hydroxy group of the metastin derivative (I) of the present invention is substituted with an acyl, an alkyl, phosphoric acid, boric acid, etc. (e.g., metastin derivatives wherein an hydroxy group of the metastin derivative (III) of the present invention is substituted with acetyl, palmitoyl, propanoyl, pivaloyl, succinyl, fumaryl, alanyl, dimethylaminomethylcarbonyl, etc.); and metastin derivatives wherein a carboxyl group of the metastin derivative (III) of the present invention is substituted with ester, amide, etc. (e.g., metastin derivatives wherein a carboxyl group of the metastin derivative (III) of the present invention is substituted with ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester, methylamide, etc); and the like. These metastin derivatives can be produced from the metastin derivative (I) of the present invention by per se known methods.

The prodrugs of the metastin derivative (III) of the present invention may be those that are converted into the metastin derivative (III) of the present invention under the physiological conditions as described in "Pharmaceutical Research and Development", Vol. 7 (Drug Design), pages 163-198, published 1990 by Hirokawa Publishing Co.

The metastin derivatives (I), (II) or (III) of the present invention or their salts or prodrugs (hereinafter sometimes simply referred to as the compound of the present invention)

possess a cancer metastasis suppressing activity or a cancer growth suppressing activity. Thus, the metastin derivatives are useful for pharmaceuticals such as agents for preventing or treating all cancers (e.g., lung cancer, gastric cancer, liver cancer, pancreas cancer, colorectal cancer, rectal cancer, colonic cancer, prostate cancer, ovarian cancer, cervical cancer, breast cancer, etc.).

The compounds of the present invention also possess the effect of controlling pancreatic function and are thus useful as agents for preventing or treating various pancreatic diseases (e.g., acute or chronic pancreatitis, pancreatic cancer, etc.) as agents for controlling pancreatic function.

The compounds of the present invention also possess the effect of controlling placental function and are thus useful as pharmaceuticals for preventing or treating choriocarcinoma, hydatid mole, invasive mole, miscarriage, fetal hypoplasia, abnormal glucose metabolism, abnormal lipid metabolism or induction of delivery, as agents for controlling placental function.

Furthermore, the compounds of the present invention possess the effects of increasing sugar level, promoting pancreatic glucagon secretion and promoting urine formation and are thus useful as pharmaceuticals such as hyperglycemic agents, pancreatic glucagon secretagogue agents or agents for promoting urine formation, which are useful for preventing or treating obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders or lipotoxicity.

In addition, the compounds of the present invention also possess the effects of promoting gonadotropic hormone (e.g., FSH, LH, etc.) secretion, promoting sex hormone [e.g., androgens (e.g., testosterone, androstenedione, etc.), estrogens (e.g., estradiol, estrone, etc.), progesterones, etc.] secretion, improving gonadal function and inducing or stimulating ovulation, as well as a sexual maturation effect, etc., and hence, can be used as agents for improving gonadal function, agents for inducing or stimulating ovulation, gonadotropic hormone secretagogue agents or sex hormone secretagogue agents, or agents for preventing or treating hormone-dependent cancers [e.g., prostate cancer, breast cancer, etc.], infertility [e.g., irregular menstruation, dysmenorrhea, amenorrhea, weight loss-induced amenorrhea, secondary amenorrhea, anovulation, hypoovarianism, hypogonadism, spermatogenetic failure, hypogonadism (e.g., impotence, etc.), genital atrophy, testicular atrophy, testicular function disorder, azoospermia, hypoandrogenemia, etc.], endometriosis, early puberty, myoma of the uterus, etc.

Furthermore, the prodrugs of the metastin derivative (I) or (II) of the present invention or salts thereof are useful as agents for preventing or treating Alzheimer's disease, moderate cognitive impairment, etc.

Moreover, the compounds of the present invention have excellent blood stability, as compared to native metastin such as metastin 54 (1-54) or metastin 10 (45-54).

The metastin derivatives (III) [including the metastin derivatives (II) and the metastin derivatives (I)] of the present invention or their salts or prodrugs are useful as agents for suppressing gonadotropic hormone secretion or sex hormone secretion; down-regulating agents for gonadotropic hormone (e.g., FSH, LH) or sex hormone [e.g., androgen (e.g., testosterone, androstenedione), estrogen (e.g., estradiol, estrone), progesterone]; in particular, it is useful for suppressing gonadotropic hormone secretion or sex hormone secretion via down-regulation of gonadotropic hormone or sex hormone (wherein, the down-regulation of gonadotropic hormone or sex hormone may be pulse loss of LHRH or depletion of LHRH) or down-regulation of human OT7T175 (metastin receptor) protein consisting of the amino acid sequence represented by SEQ ID NO: 9; as agents for preventing or treating hormone-dependent cancers (e.g., prostate cancer, breast cancer, etc.; particularly, hormone-sensitive prostate cancer, hormone-sensitive breast cancer, etc.); agents for preventing or treating endometriosis; agents for inhibiting ovarian follicular maturation; menstrual cycle-suspending agents; agents for treating myoma of the uterus; agents for treating early puberty; or as contraceptives, etc.

Where the metastin derivative (III) of the present invention [including the metastin derivative (II) and the metastin derivative (I)] or its salt or prodrug, metastin per se, or DNA encoding metastin, etc. have normal agonist activity, an effective dose of the metastin derivative sufficient to suppress the secretion of gonadotropic hormone or sex hormone is administered at the site or tissue where the therapeutic effects are to be exerted, so that the metastin derivative is present in a dose more than required (i.e., the metastin derivative is administered in an excess over the normal effective dose, at which the metastin derivative exerts the effects of suppressing cancer metastasis, suppressing cancer growth, etc.; or the gonadotropic hormone secretagogue agent, the effect of promoting sex hormone secretion, etc.) to exhibit the effects of suppressing gonadotropic hormone secretion or sex hormone secretion. Specific examples include sustained or continuous administration of the normal effective dose (including an administration technique to gradually release the pharmaceutical ingredients by bolus administration); and the like. Further when the metastin derivative (III) of the present invention [including the metastin derivative (II) and the metastin derivative (I)] or its salt or the prodrug thereof, etc. have a sufficient agonist activity more than required (a super-agonist activity), it becomes possible to sustain the activities more than exhibited by the necessary dose at the site or tissue where the therapeutic effect are to be exhibited. It is therefore sufficient even by normal effective dose administration to suppress the secretion of gonadotropic hormone or sex hormone, whereby the effect of suppressing gonadotropic hormone secretion or sex hormone secretion is exhibited.

That is, the metastin derivative (III) [including the metastin derivative (II) and the metastin derivative (I)] or its salt or prodrug, or metastin per se, metastin-encoding DNA, etc. are administered in an effective dose sufficient to suppress the secretion of gonadotropic hormone or sex hormone. Consequently, it becomes possible to keep the metastin derivative, etc. present in a dose more than the necessary dose or sustain the activity more than exhibited by the necessary dose, at the site or tissue where the pharmaceutical effects are to be exhibited, resulting in exerting the effect of suppressing gonadotropic hormone secretion or sex hormone secretion.

The pharmaceutical compositions comprising the compounds of the present invention are low toxic and thus can be safely administered orally or parenterally (e.g., topically, rectally, intravascularly, etc.) either directly as they are or in the form of pharmaceutical preparations such as tablets (including dragees and film-coated tablets), powdery dosage forms, granules, capsules (including soft capsules), liquid dosage forms, injections, suppositories, sustained release dosage forms, etc.

The compound of the present invention is contained in the pharmaceutical preparation of the present invention in about 0.01 to about 100 wt %, based on the total weight of the preparation.

A dose of the compound of the present invention may vary depending upon subject to be administered, target organ, conditions, route of administration, etc., and in oral administration, the compound is generally administered to the patient with cancer (as 60 kg body weight) in a daily dose of about 0.1 to about 100 mg, preferably about 1.0 to about 50 mg and more preferably about 1.0 to about 20 mg. In parenteral administration, a single dose of the compound may vary depending upon subject to be administered, target organ, conditions, route of administration, etc., and in the form of an injectable dosage form, it is advantageous to administer the compound to the patient with cancer (as 60 kg body weight) generally in a daily dose of about 0.01 to about 30 mg, preferably about 0.1 to about 20 mg, and more preferably about 0.1 to about 10 mg. For other animal species, the corresponding dose as converted per 60 kg weight can be administered.

Pharmacologically acceptable carriers, which may be used in manufacturing the pharmaceutical preparation of the present invention, include various organic or inorganic carrier substances conventionally used as materials for pharmaceutical preparations. These substances include, e.g., an excipient, a lubricant, a binder and a disintegrating agent in a solid dosage form, and a solvent, a dissolution aid, a suspending agent, an isotonizing agent, a buffer, a soothing agent, etc. in a liquid dosage form. In addition, conventional additives such as a preservative, an antioxidant, a colorant, a sweetener, an adsorbent, a wetting agent, etc. can be appropriately used in suitable amounts, if necessary.

Examples of excipients include, e.g., lactose, saccharose, D-mannitol, starch, cornstarch, crystalline cellulose, light anhydrous silicic acid, etc.

Examples of useful lubricants include, e.g., magnesium stearate, calcium stearate, talc, colloidal silica, etc.

Examples of binders include, e.g., crystalline cellulose, saccharose, D-mannitol, dextrin, hydroxypropylcellulose, hydroxypropylmethylcellulose, polyvinylpyrrolidone, starch, sucrose, gelatin, methylcellulose, sodium carboxymethylcellulose, etc.

Examples of disintegrating agents include, e.g., starch, carboxymethylcellulose, carboxymethylcellulose calcium, sodium carboxymethyl starch, L-hydroxypropylcellulose, etc.

Examples of solvents include, e.g., water for injection, alcohol, propylene glycol, Macrogol, sesame oil, corn oil, olive oil, etc.

Examples of dissolution aids include, e.g., polyethylene glycol, propylene glycol, D-mannitol, benzyl benzoate, ethanol, trisaminomethane, cholesterol, triethanolamine, sodium carbonate, sodium citrate, etc.

Examples of suspending agents include, e.g., surfactants such as stearyltriethanolamine, sodium laurylsulfate, lauryl aminopropionate, lecithin, benzalkonium chloride, benzethonium chloride, glycerine monostearate, etc.; hydrophilic polymers such as polyvinyl alcohol, polyvinyl pyrrolidone, sodium carboxymethylcellulose, methylcellulose, hydroxymethylcellulose, hydroxyethylcellulose, hydroxypropylcellulose, etc.

Examples of isotonizing agents include, e.g., glucose, D-sorbitol, sodium chloride, glycerine, D-mannitol, etc.

Examples of buffers include, e.g., buffering solutions of a phosphate, acetate, carbonate, citrate, etc.

Examples of soothing agents include, e.g., benzyl alcohol, etc.

Examples of preservatives include, e.g., p-hydroxybenzoates, chlorobutanol, benzyl alcohol, phenethyl alcohol, dehydroacetic acid, sorbic acid, etc.

Examples of antioxidants include, e.g., a sulfite, ascorbic acid, α-tocopherol, etc.

Furthermore, the compound of the present invention can be used in combination with drugs other than the compound of the present invention.

Examples of the drugs, which can be used in combination with the compound of the present invention (hereinafter referred to as a combination drug), include chemotherapeutic agents for treating cancer, hormonal therapeutic agents, immunotherapeutic agents, etc.

Examples of "chemotherapeutic agents" include, e.g., alkylating agents, antimetabolites, anticancer antibiotics, and plant-derived anticancer agents.

Examples of "alkylating agents" include, e.g., nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, estramustine sodium phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, carboquone, adozelesin, cystemustine, bizelesin, etc.

Examples of "antimetabolites" include, e.g., mercaptopurine, 6-mercaptopurine riboside, thioinosine, methotrexate, enocitabine, cytarabine, cytarabine ocfosfate, ancitabine hydrochloride, 5-FU drugs (e.g., fluorouracil, tegafur, UFT, doxifluridine, carmofur, gallocitabine, emmitefur, etc.), aminopterin, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, thiazophrine, ambamustine, etc.

Examples of "anticancer antibiotics" include, e.g., actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride, etc.

Examples of "plant-derived anticancer agents" include, e.g., etoposide, etoposide phosphate, vinblastine sulfate, vincristine sulfate, vindesine sulfate, teniposide, paclitaxel, docetaxel, vinorelbine, etc.

Examples of "hormonal therapeutic agents" include, e.g., fosfestrol, diethylstylbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogens (e.g., tamoxifen citrate, toremifene citrate, etc.), pill dosage forms, mepitiostane, testrolactone, aminoglutethimide, LH-RH agonists (e.g., goserelin acetate, buserelin, Leuprorelin, etc.), droloxifene, epitiostanol, ethinylestradiol sulfonate, aromatase inhibitors (e.g., fadrozole hydrochloride, anastrozole, retrozole, exemestane, vorozole, formestane, etc.), anti-androgens (e.g., flutamide, bicartamide, nilutamide, etc.), 5α-reductase inhibitors (e.g., finasteride, episteride, etc.), adrenocorticohormone drugs (e.g., dexamethasone, prednisolone, betamethasone, triamcinolone, etc.), androgen synthesis inhibitors (e.g., abiraterone, etc.), retinoid and drugs that retard retinoid metabolism (e.g., liarozole, etc.), and among them, LH-RH agonists (e.g., goserelin acetate, buserelin, Leuprorelin, etc.) are preferable.

Examples of "immunotherapeutic agents (BRM)" include, e.g., picibanil, krestin, sizofuran, lentinan, ubenimex, interferons, interleukins, macrophage colony-stimulating factor, granulocyte colony-stimulating factor, erythropoietin, lymphotoxin, BCG vaccine, *Corynebacterium parvum*, levamisole, polysaccharide K, procodazole, etc.

The combined use of the compound of the present invention and a combination drug results in, for example, the following excellent effects.

(1) The dose of the compound of the present invention can be reduced when compared with the dose when administered alone.

(2) A combination drug with the compound of the present invention can be chosen depending on the condition (mild, severe, etc.) of a patient.

(3) A combination drug, whose functional mechanism is different from that of the compound of the present invention, can be chosen so that a treatment period can be set longer.

(4) A combination drug, whose functional mechanism is different from that of the compound of the present invention, can be chosen so that sustained therapeutic effects can be achieved.

(5) A synergistic effect can be obtained by the combined use of the compound of the present invention and a combination drug.

In addition, the compound of the present invention can reduce values of testosterone to emasculate level immediately after medication. Thus when the combination drug such as LH-RH agonist (e.g., goserelin acetate, buserelin, Leuprorelin etc.; preferably Leuprorelin) uses in combination with the compound of the present invention, the values of testosterone can be reduced to emasculate level immediately after medication of the compound of the present invention. Further, since the combined use of the combination drug such as LH-RH agonist (e.g., goserelin acetate, buserelin, Leuprorelin etc.; preferably Leuprorelin) and the compound of the present invention results in prolonged preservation of hormone-dependent period, it can advantageously be used.

Hereinafter, the combined use of Compound (I) of the present invention and a combination drug is referred to as "the combined preparation of the present invention."

When the combined preparation of the present invention is used, a dosing period of the compound of the present invention and the combination is not restricted; the compound of the present invention or its pharmaceutical composition and a combination drug or its pharmaceutical composition may be administered to the subject to be administered either simultaneously or at certain time intervals. The dose of a combination drug may be modified according to the dose used clinically and may be appropriately chosen depending upon subject to be administered, route for administration, disease, combination, etc.

A mode for administration of the combined preparation of the present invention is not particularly limited, but it is sufficient that the compound of the present invention is used in combination with a combination drug at the time of administration. For such mode of administration, there are, for example, (1) administration of a simple dosage form obtained by mixing the compound of the present invention and a combination drug together at the same time, (2) simultaneous administration of two dosage forms prepared separately from the compound of the present invention and a combination drug through the same route for administration, (3) administration of two dosage forms prepared separately from the compound of the present invention and a combination drug at certain time intervals through the same route for administration, (4) simultaneous administration of two dosage forms prepared separately from the compound of the present invention and a combination drug through different routes for administration, (5) administration of two dosage forms prepared separately from the compound of the present invention and a combination drug at certain time intervals (e.g., administration of the compound of the present invention and a combination drug in this order, or administration in a reversed order) through different routes for administration, etc.

The combined preparation of the present invention is low toxic and thus can be safely administered orally or parenterally (e.g., topically, rectally, intravascularly, etc.) either directly as they are or in the form of pharmaceutical preparations such as tablets (including dragees and film-coated tablets), powdery dosage forms, granules, capsules (including soft capsules), liquid dosage forms, injections, suppositories, sustained release dosage forms, etc., which are obtained by mixing the compound of the present invention or (and) a combination drug described above with pharmacologically acceptable carriers. Injectable dosage forms can be administered intravenously, intramuscularly or subcutaneously, into the organ, or directly at the focus.

Pharmacologically acceptable carriers, which may be used to manufacture the combined preparation of the present invention, include various organic or inorganic carrier substances conventionally used as materials for pharmaceutical preparations. These substances include, e.g., an excipient, a lubricant, a binder and a disintegrating agent in a solid dosage form, and a solvent, a dissolution aid, a suspending agent, an isotonizing agent, a buffer, a soothing agent, etc. in a liquid dosage form. In addition, conventional additives such as a preservative, an antioxidant, a colorant, a sweetener, an adsorbent, a wetting agent, etc. can be appropriately used in suitable amounts, if necessary.

Examples of excipients include, e.g., lactose, saccharose, D-mannitol, starch, cornstarch, crystalline cellulose, light anhydrous silicic acid, etc.

Examples of useful lubricants include, e.g., magnesium stearate, calcium stearate, talc, colloidal silica, etc.

Examples of binders include, e.g., crystalline cellulose, saccharose, D-mannitol, dextrin, hydroxypropylcellulose, hydroxypropylmethylcellulose, polyvinylpyrrolidone, starch, sucrose, gelatin, methylcellulose, sodium carboxymethylcellulose, etc.

Examples of disintegrating agents include, e.g., starch, carboxymethylcellulose, carboxymethylcellulose calcium, sodium carboxymethyl starch, L-hydroxypropylcellulose, etc.

Examples of solvents include, e.g., water for injection, alcohol, propylene glycol, Macrogol, sesame oil, corn oil, olive oil, etc.

Examples of dissolution aids include, e.g., polyethylene glycol, propylene glycol, D-mannitol, benzyl benzoate, ethanol, trisaminomethane, cholesterol, triethanolamine, sodium carbonate, sodium citrate, etc.

Examples of suspending agents include, e.g., surfactants such as stearyltriethanolamine, sodium laurylsulfate, lauryl aminopropionate, lecithin, benzalkonium chloride, benzethonium chloride, glycerine monostearate, etc.; hydrophilic polymers such as polyvinyl alcohol, polyvinyl pyrrolidone, sodium carboxymethylcellulose, methylcellulose, hydroxymethylcellulose, hydroxyethylcellulose, hydroxypropylcellulose, etc.

Examples of isotonizing agents include, e.g., glucose, D-sorbitol, sodium chloride, glycerine, D-mannitol, etc.

Examples of buffers include, e.g., buffering solutions of a phosphate, acetate, carbonate, citrate, etc.

Examples of soothing agents include, e.g., benzyl alcohol, etc.

Examples of preservatives include, e.g., p-hydroxybenzoates, chlorobutanol, benzyl alcohol, phenethyl alcohol, dehydroacetic acid, sorbic acid, etc.

Examples of antioxidants include, e.g., a sulfite, ascorbic acid, α-tocopherol, etc.

In the combined preparation of the present invention, a ratio of the compound of the present invention to a combination drug may be appropriately chosen depending upon subject to be administered, route for administration, disease, combination, etc.

For example, the amount of the compound of the present invention contained in the combined preparation of the present invention varies depending on the dosage form of the preparation, but is usually about 0.01 to 100% by weight, preferably about 0.1 to 50% by weight, and more preferably about 0.5 to 20% by weight, based on the total weight of the preparation.

The amount of a combination drug contained in the combined preparation of the present invention varies depending on the dosage form of the preparation, but is usually about 0.01 to 100% by weight, preferably about 0.1 to 50% by weight, and more preferably about 0.5 to 20% by weight, based on the total weight of the preparation.

The amount of additives such as a carrier, etc. contained in the combined preparation of the present invention varies depending on the dosage form of the preparation, and is usually about 1 to 99.99% by weight, preferably about 10 to 90% by weight, based on the total weight of the preparation.

These amounts may be the same, also when the compound of the present invention and a combination drug are separately prepared, respectively.

These preparations can be manufactured by per se publicly known methods generally used conventionally.

For example, an injectable dosage form can be prepared by dissolving, suspending or emulsifying the compound of the present invention or a combination drug in a dispersing agent (e.g., Tween 80 (manufactured by Atlas Powder Company, USA), HCO 60 (manufactured by Nikko Chemicals Co., Ltd.), polyethylene glycol, carboxymethyl cellulose, sodium alginate, etc.), a stabilizer (e.g., ascorbic acid, sodium pyrosulfite), a surfactant (e.g., polysorbate 80, macrogol, etc.), a solubilizing agent (e.g., glycerin, ethanol, etc.), a buffering agent (e.g., phosphoric acid or its alkali metal salt, citric acid or its alkali metal salt, etc.), an isotonizing agent (e.g., sodium chloride, potassium chloride, mannitol, sorbitol, glucose, etc.), a pH adjusting agent (e.g., hydrochloric acid, sodium hydroxide, etc.), a preservative (e.g., ethyl p-oxybenzoate, benzoic acid, methylparabene, propylparabene, benzyl alcohol, etc.), a solubilizer (e.g., concentrated glycerin, meglumine, etc.), a dissolution aid (e.g., propylene glycol, saccharose, etc.), a soothing agent (e.g., glucose, benzyl alcohol, etc.), a vegetable oil such as olive oil, sesame oil, cottonseed oil, corn oil, etc., a dissolution aid such as propylene glycol or the like to prepare into an oily injection.

An oral dosage form can be produced in a conventional manner by adding to the compound of the present invention or a combination drug, for example, an excipient (e.g., lactose, saccharose, starch, etc.), a disintegrating agent (e.g., starch, calcium carbonate, etc.), a binder (e.g., starch, gum arabic, carboxymethyl cellulose, polyvinylpyrrolidone, hydroxypropyl cellulose, etc.), a lubricant (e.g., talc, magnesium stearate, polyethylene glycol 6000, etc.) and other additives, compressing the resulting mixture and, if necessary, coating the compressed product for the purpose of taste masking, enteric degradation or sustained release by techniques per se publicly known. Coating agents for this purpose include, for example, hydroxypropylmethyl cellulose, ethyl cellulose, hydroxymethyl cellulose, hydroxypropyl cellulose, polyoxyethylene glycol, Tween 80, Prulonic F68, cellulose acetate phthalate, hydroxypropylmethyl cellulose phthalate, hydroxymethyl cellulose acetate succinate, Eudragit (manufactured by Rohm Company, Germany, methacrylic acid/acrylic acid copolymer) and dyes (e.g., iron oxide, titanium dioxide). The oral dosage form may be either a rapid release dosage form or a sustained release dosage form.

For example, in a suppository, the compound of the present invention or a combination drug is prepared into an oily or aqueous solid, semi-solid or liquid composition by techniques per se publicly known. Oily bases used for the composition described above include glycerides of higher fatty acids [e.g., cacao butter, uitepsols (manufactured by Dynamite Nobel Company, Germany), etc.], moderate fatty acids [e.g., miglyols (manufactured by Dynamite Nobel Company, Germany), etc.], vegetable oils (e.g., sesame oil, soybean oil, cottonseed oil, etc.), and the like. Aqueous bases include, for example, polyethylene glycols and propylene glycol. Bases for aqueous gels include, for example, natural rubbers, cellulose derivatives, vinyl polymers, acrylic polymers, etc.

Examples of the sustained release dosage form above include sustained release microcapsules, and the like.

Sustained release microcapsules can be obtained by per se publicly known methods, and are preferably prepared in the form of, e.g., a sustained release dosage form by the method [2] shown below and administered.

Preferably, the compound of the present invention is prepared into a dosage form for oral administration such as a solid dosage form (e.g., powdery dosage form, granules, tablets, capsules) or into a dosage form for rectal administration such as a suppository, etc. A dosage form for oral administration is particularly preferred.

A combination drug can be prepared into the dosage form described above, depending on the kind of drug.

Hereinafter, [1] an injectable preparation of the compound of the present invention or a combination drug and its production, [2] a sustained release or immediate release preparation of the compound of the present invention or a combination drug and its production and [3] a sublingual, buccal or rapid oral disintegrating preparations of the compound of the present invention or a combination drug and its production will be specifically described.

[1] Injectable Preparation and its Production

An injectable preparation obtained by dissolving the compound of the present invention or a combination drug in water is preferred. The injectable preparation may contain a benzoate and/or a salicylate.

The injectable preparation is obtained by dissolving the compound of the present invention or a combination drug and optionally a benzoate and/or a salicylate in water.

Examples of the benzoate and/or salicylate described above include an alkali metal salt such as sodium and potassium salts, etc., an alkaline earth metal salt such as calcium and magnesium salts, etc., an ammonium salt, a meglumine salt, a salt of an organic acid such as trometamol, and the like.

The concentration of the compound of the present invention or a combination drug in the injectable preparation is about 0.5 to 50 w/v %, preferably about 3 to 20 w/v %. The concentration of the benzoate and/or salicylate is 0.5 to 50 w/v %, preferably 3 to 20 w/v %.

Furthermore, additives generally used in an injectable preparation such as a stabilizer (ascorbic acid, sodium pyrosulfite, etc.), a surfactant (polysorbate 80, macrogol, etc.), a solubilizing agent (glycerin, ethanol, etc.), a buffering agent (phosphoric acid and its alkali metal salt, citric acid and its alkali metal salt, etc.), an isotonizing agent (sodium chloride, potassium chloride, etc.), a dispersing agent (hydroxypropylmethyl cellulose, dextrin), a pH adjusting agent (hydrochloric acid, sodium hydroxide, etc.), a preservative (ethyl p-oxybenzoate, benzoic acid, etc.), a solubilizer (concentrated glycerin, meglumine, etc.), a dissolution aid (propylene glycol, saccharose, etc.), a soothing agent (glucose, benzyl alcohol, etc.) are appropriately added to the preparation. Any of these additives is added in an amount generally used in an injectable preparation.

The injectable preparation is adjusted to pH of 2 to 12, preferably 2.5 to 8.0 by adding a pH adjusting agent.

The injectable preparation is obtained by dissolving both the compound of the present invention or a combination drug and optionally a benzoate and/or salicylate, and, if necessary, the above additives in water. These components may be dissolved in any order according to the same manner as in a conventional injectable preparation.

An aqueous solution for injection is preferably warmed, and used as an injectable preparation after filtration sterilization by filtration or autoclaved as in a conventional injectable preparation to provide for an injectable preparation.

An aqueous injectable preparation is preferably autoclaved, e.g., at 100 to 121° C. for 5 to 30 minutes.

Moreover, the preparation may be in a solution form to which antibacterial activity is imparted to be usable as a multiple dosage form in divided dosing.

[2] Sustained Release or Immediate Release Preparation and its Production

A preferred sustained release preparation comprises a core comprising the compound of the present invention or a combination drug, which is optionally coated with a water-insoluble material or a swelling polymer. For example, a sustained release preparation for oral administration of a once-daily dosage form is preferred.

Examples of the water-insoluble material used for the coating agent include cellulose ethers such as ethyl cellulose, butyl cellulose, etc., cellulose esters such as cellulose acetate, cellulose propionate, etc., polyvinyl esters such as polyvinyl acetate, polyvinyl butyrate, etc., acrylic acid polymers such as an acrylic acid/methacrylic acid copolymer, a methyl methacrylate copolymer, an ethoxyethyl methacrylate/cinnamoethyl methacrylate/aminoalkyl methacrylate copolymer, a polyacrylic acid, a polymethacrylic acid, a methacrylic acid alkylamide copolymer, a poly(methyl methacrylate), a polymethacrylate, an aminoalkyl methacrylate copolymer, a poly(methacrylic anhydride), a glycidyl methacrylate copolymer, in particular, a series of Eudragits (Rohm & Pharma) such as Eudragit RS-100, RL-100, RS-30D, RL-30D, RL-PO, RS-PO (ethyl acrylate/methyl methacrylate/chlorotrimethyl methacrylate/ethyl ammonium copolymer) and Eudragit NE-30D (methyl methacrylate/ethyl acrylate copolymer), etc., hydrogenated oils such as hydrogenated castor oil (e.g., LUBRI WAX (Freund Industrial Co., Ltd.), etc.), waxes such as carnauba wax, a fatty acid glycerin ester, paraffin, etc., polyglycerin fatty acid esters, etc.

The swelling polymer is preferably a polymer having an acidic removable group and exhibiting pH-dependent swelling, and a polymer having an acidic removable group, which undergoes a less swelling at an acidic pH such as in the stomach but is swollen extensively at a neutral pH such as in the small and large intestines, is preferred.

Examples of such a polymer having an acidic removable group and exhibiting pH-dependent swelling include a crosslinked polyacrylic acid polymer such as Carbomers 934P, 940, 941, 974P, 980, 1342, etc., polycarbophil and calcium polycarbophil (all manufactured by BF Goodrich Chemicals), Hivis Wakos 103, 104, 105 and 304 (all manufactured by Wako Pure Chemical Industries, Ltd.), etc.

The coating agent used in the sustained release preparation may further contain a hydrophilic material.

Examples of the hydrophilic material include a polysaccharide which may have a sulfate group, such as pullulan, dextrin, alkali metal alginates, etc., a polysaccharide having a hydroxyalkyl group or a carboxyalkyl group such as hydroxypropyl cellulose, hydroxypropylmethyl cellulose, sodium carboxymethylcellulose, etc., methyl cellulose, polyvinyl pyrrolidone, polyvinyl alcohol, polyethylene glycol, etc.

The amount of the water-insoluble material contained in the coating agent of the sustained release preparation is about 30 to about 90% (w/w), preferably about 35 to about 80% (w/w), more preferably about 40 to about 75% (w/w), and the swelling polymer content is about 3 to about 30% (w/w), preferably about 3 to about 15% (w/w). The coating agent may further contain a hydrophilic material, and the amount of the hydrophilic material contained in the coating agent is about 50% (w/w) or less, preferably about 5 to about 40% (w/w), more preferably about 5 to about 35% (w/w). As used herein, the % (w/w) above is used to mean a % by weight based on the coating agent composition, which is the remainder of the coating agent solution after removing any solvent (e.g., water, a lower alcohol such as methanol, ethanol, etc.).

The sustained release preparation is manufactured by preparing a core containing a drug as illustrated below, followed by coating the resulting core with a coating agent solution obtained by heat-melting a water-insoluble material or a swelling polymer or by dissolving or dispersing such a material in a solvent.

I. Preparation of Drug-Containing Core

The shape of a core containing a drug to be coated with a coating agent (hereinafter sometimes simply referred to as a core) is not specifically limited but preferably prepared into a particulate shape such as granules, fine granules, or the like.

When the core is granules or fine granules, they have a mean particle size of preferably about 150 to about 2,000 µm, more preferably about 500 to about 1,400 µm.

The core can be prepared in a conventional manner. For example, a drug is mixed with a suitable excipient, binder, disintegrating agent, lubricant, stabilizer, etc., and then subjected to wet extrusion granulation, fluidized bed granulation, or the like.

The drug content in the core is about 0.5 to about 95% (w/w), preferably about 5.0 to about 80% (w/w), more preferably about 30 to about 70% (w/w).

Examples of the excipient contained in the core include a saccharide such as assaccharose, lactose, mannitol, glucose, etc., starch, crystalline cellulose, calcium phosphate, cornstarch, etc. Among them, crystalline cellulose and cornstarch are preferred.

Examples of the binder used include polyvinyl alcohol, hydroxypropyl cellulose, polyethylene glycol, polyvinyl pyrrolidone, Pluronic F68, gum arabic, gelatin, starch, etc. Examples of the disintegrating agent include calcium carboxymethyl cellulose (ECG505), sodium croscarmellose (Ac-Di-Sol), crosslinked polyvinyl pyrrolidone (crospovidone), a low substituted hydroxypropyl cellulose (L-HPC), etc. Among them, hydroxypropyl cellulose, polyvinyl pyrrolidone and a low substituted hydroxypropyl cellulose are preferred. Examples of the lubricant and the anticoagulant include talc, magnesium stearate and its inorganic salts, and examples of the lubricant include polyethylene glycol, etc. Examples of the stabilizer include an acid such as tartaric acid, citric acid, succinic acid, fumaric acid, maleic acid, etc.

In addition to the technique described above, the core can be prepared by using other techniques such as an tumbling granulation technique, a pan coating technique, a fluidized bed coating technique and a melt granulation technique, wherein a drug or a mixture of the drug with an excipient, a lubricant, etc. is portionwise added to inert carrier particles as seeds for the core with spraying a binder dissolved in a suitable solvent such as water, a lower alcohol (e.g., methanol, ethanol, etc.) or the like. Examples of the inert carrier particles include those prepared from saccharose, lactose, starch, crystalline cellulose and waxes, and, preferably, these carriers have a mean particle size of about 100 µm to about 1,500 µm.

In order to separate the drug contained in the core from a coating agent, the surface of the core may be covered with a protective material. Examples of the protective material include the hydrophilic material described above and water-insoluble material. The preferred protective material is polyethylene glycol or a polysaccharide having a hydroxyalkyl group or a carboxyalkyl group, more preferably, hydroxypropylmethyl cellulose and hydroxypropyl cellulose. The protective material may contain, as a stabilizer, an acid such as tartaric acid, citric acid, succinic acid, fumaric acid, maleic acid, etc., and a lubricant such as talc. When the protective material is used, the amount thereof to be coated is about 1 to about 15% (w/w), preferably about 1 to about 10% (w/w), more preferably about 2 to about 8% (w/w) based on the core.

The protective material can be coated by a conventional coating method and specifically, the core is spray-coated with the protective material by a fluidized bed coating technique, a pan coating technique, etc.

II. Coating of Core with Coating Agent

The core obtained in I above is coated with a coating agent solution prepared by melt-heating the water-insoluble material and pH-dependent swelling polymer described above and a hydrophilic material or by dissolving or dispersing them in a solvent to obtain a sustained release preparation.

As a coating method of the core with the coating agent solution, there are, for example, spray-coating, etc.

The composition ratio of the water-insoluble material, swelling polymer and hydrophilic material in the coating agent solution can be appropriately chosen to be within the amounts of the respective components contained in the coating.

The amount of the coating agent is about 1 to about 90% (w/w), preferably about 5 to about 50% (w/w), more preferably about 5 to about 35% (w/w) based on the core (excluding the protective material coating).

As the solvent for the coating agent solution, water and an organic solvent can be used alone or as a mixture thereof. When a mixture is used, the ratio of water and the organic solvent (water/organic solvent: a weight ratio) may vary with the range of 1 to 100%, and is preferably 1 to about 30%. The organic solvent is not particularly limited so far as it can dissolve the water-insoluble material, and examples of the solvent include a lower alcohol such as methyl alcohol, ethyl alcohol, isopropyl alcohol, n-butyl alcohol, etc., a lower alkanone such as acetone, acetonitrile, chloroform, methylene chloride, etc. Among them, a lower alcohol is preferred, with ethyl alcohol and isopropyl alcohol being more preferred. Water and a mixture of water and an organic solvent are used preferably as solvents for the coating agent solution. In this case, an acid such as tartaric acid, citric acid, succinic acid, fumaric acid, maleic acid, etc. may be added to the coating agent solution, if necessary, for the purpose of stabilizing the coating agent solution.

To carry out the coating by spray coating, the coating can be made using a conventional coating method. Specifically, the core is sprayed with a coating agent solution by a fluidized bed coating technique, a pan coating technique, or the like. At this time, a lubricant such as talc, titanium oxide, magnesium stearate, calcium stearate, light silicic anhydride, etc., and a plasticizer such as glycerin fatty ester, hardened castor oil, triethyl citrate, cetyl alcohol, stearyl alcohol, etc. may also be added.

After coating with a coating agent, an antistatic agent such as talc may also be admixed, if necessary.

The immediate release preparation may be a liquid (solution, suspension, emulsion, etc.) or a solid (particles, pills, tablets, etc.). An oral preparation and a parenteral preparation such as an injectable preparation may be used, and an oral preparation is preferred.

The immediate release preparation may usually contain a carrier, additives and an excipient (hereinafter sometimes abbreviated as excipients) which are conventionally used in the pharmaceutical field, in addition to a drug which is an active ingredient. The pharmaceutical excipients are not specifically limited so long as they are excipients conventionally used in the pharmaceutical field. Examples of the excipient for an oral solid preparation include lactose, starch, corn starch, crystalline cellulose (Avicel PH101, manufactured by Asahi Kasei Corporation, etc.), powdered sugar, granulated sugar, mannitol, light silicic anhydride, magnesium carbonate, calcium carbonate, L-cysteine, etc., with corn starch and mannitol being preferred. Any of these excipients may be employed alone or in combination with each other. The amounts of the excipients are, for example, about 4.5 to about 99.4 w/w %, preferably about 20 to about 98.5 w/w %, more preferably about 30 to about 97 w/w %, based on the total weight of the immediate release preparation.

The content of drug in the immediate release preparation may appropriately be selected from about 0.5% through about 95%, preferably about 1% through about 60% to whole amount of the immediate release preparation.

When the immediate release preparation is an oral solid preparation, the preparation contains a disintegrating agent in addition to the components described above. Examples of the disintegrating agent include calcium carboxymethylcellulose (ECG505 manufactured by GOTOKU CHEMICAL Co., Ltd.), sodium-croscarmellose (for example, Ac-Di-Sol manufactured by Asahi Kasei Corporation), crospovidone (for example, COLIDON CL manufactured by BASF), low-substituted hydroxypropyl cellulose (Shin-Etsu chemical Co., Ltd.), carboxymethyl starch (MATSUTANI CHEMICAL INDUSTRY Co., Ltd.), sodium carboxymethyl starch (EXORITAB manufactured by KIMURA SANGYO), partial α starch (PCS manufactured by Asahi Kasei Corporation), etc. For example, the disintegrating agent that disintegrates granules by water absorption or swelling upon contact with water, or forming a channel between the active component comprising the core and an excipient can be used. Any of these disintegrating agents can be used alone or in combination with each other. The amount of the disintegrating agent used may be appropriately chosen depending upon the type and the amount of the drug used or a particular preparation design for the intended release performance. For example, the amount is about 0.05 to about 30 w/w %, preferably about 0.5 to about 15 w/w % based on the total weight of the immediate release preparation.

When the immediate release preparation is an oral solid preparation, the preparation may optionally contain additives conventionally used in a solid preparation, in addition to the components described above. Examples of the additives include binders (for example, sucrose, gelatin, powdery gum arabic, methyl cellulose, hydroxypropyl cellulose, hydroxypropylmethyl cellulose, carboxymethylcellulose, polyvinyl pyrrolidone, pullran, dextrin, etc.), lubricants (polyethylene glycol, magnesium stearate, talc, light silicic anhydride (for example, aerosil (NIPPON AEROSIL)), surfactants (for example, anionic surfactants such as sodium alkylsulfate, nonionic surfactants such as polyoxyethylene fatty ester, polyoxyethylene sorbitan fatty ester, polyoxyethylene castor oil derivatives, etc.), colorants (for example, tar colorants, caramel, colcothar, titanium oxide, riboflavins), if necessary, corrigents (for example, sweeteners, flavors, etc.), adsorbents, preservatives, wetting agents, antistatic agents, etc. Furthermore, an organic acid such as tartaric acid, citric acid, succinic acid, fumaric acid or the like can also be added as a stabilizer.

As the binder above, hydroxypropyl cellulose, polyethylene glycol and polyvinyl pyrrolidone, etc. are preferably used.

The immediate release preparation can be prepared by mixing the components described above and kneading the mixture, if necessary, and then molding according to a conventional technique for making pharmaceutical preparations. The mixing above can be carried out in a conventional manner, e.g., by mixing, kneading, etc. Specifically, where the immediate release preparation is in the form of particles, the preparation can be prepared by mixing components with a vertical granulator, a multi-purpose kneader (HATA IRON WORKS CO., LTD), a fluidized bed granulator FD-5S(POW-REX CORPORATION) or the like, and then granulating the resulting by wet extrusion granulation or fluidized bed granulation by a technique similar to that for preparing the core of the sustained release preparation described above.

The immediate release preparation and the sustained release preparation thus obtained can be compounded, as they are, or, together with appropriate pharmaceutical excipients, in pharmaceutical preparations separately in a conventional manner to prepare respective preparations for administering in combination with each other simultaneously or at certain time intervals. Alternatively, both preparations may be compounded in a single dosage form for oral administration (e.g., granules, fine granules, tablets, capsules) as they are, or, together with appropriate pharmaceutical excipients. Both preparations in the form of granules or fine granules may also be filled in a single capsule for oral administration.

[3] Sublingual, Buccal or Rapid Oral Disintegrating Preparation and Its Production A sublingual, buccal or rapid oral disintegrating preparation may be in the form of a solid preparation such as a tablet, or may be in the form of an oral mucosal patch (film).

The sublingual, buccal or rapid oral disintegrating preparation is preferably a preparation containing the compound of the present invention or a combination drug and an excipient. The preparation may also contain auxiliary agents such as a lubricant, an isotonizing agent, a hydrophilic carrier, a water-dispersible polymer, a stabilizer, etc. Further for the purpose of promoting the absorption and enhancing the bioavailability, the preparation may also contain β-cyclodextrin or β-cyclodextrin derivatives (e.g., hydroxypropyl-β-cyclodextrin, etc.).

Examples of the above excipient include lactose, saccharose, D-mannitol, starch, crystalline cellulose, light silicic anhydride, etc. Examples of the lubricant include magnesium stearate, calcium stearate, talc, colloidal silica, etc., with magnesium stearate and colloidal silica being preferred. Examples of the isotonizing agent include sodium chloride, glucose, fructose, mannitol, sorbitol, lactose, saccharose, glycerin and urea, with mannitol being particularly preferred. As the hydrophilic carrier, there are, for example, a swelling hydrophilic carrier such as crystalline cellulose, ethyl cellulose, crosslinked polyvinyl pyrrolidone, light silicic anhydride, silicic acid, dicalcium phosphate, calcium carbonate, etc., with crystalline cellulose (e.g., microcrystalline cellulose, etc.) being preferred. As the water-dispersible polymer, there are, for example, a gum (e.g., tragacanth gum, acacia gum, guar gum), alginate (e.g., sodium alginate), cellulose derivatives (e.g., methyl cellulose, carboxymethylcellulose, hydroxymethyl cellulose, hydroxypropyl cellulose, hydroxypropylmethyl cellulose), gelatin, water-soluble starch, polyacrylic acid (e.g., carbomer), polymethacrylic acid, polyvinyl alcohol, polyethylene glycol, polyvinyl pyrrolidone, polycarbophil, ascorbate palmitate salt, etc., with hydroxypropylmethyl cellulose, polyacrylic acid, alginate, gelatin, carboxymethylcellulose, polyvinyl pyrrolidone and polyethylene glycol being preferred. Hydroxypropylmethyl cellulose is particularly preferred. As the stabilizer, there are, for example, cysteine, thiosorbitol, tartaric acid, citric acid, sodium carbonate, ascorbic acid, glycine, sodium sulfite, etc., with citric acid and ascorbic acid being particularly preferred.

The sublingual, buccal or rapid oral disintegrating preparation can be prepared by mixing the compound of the present invention or a combination drug and an excipient by a method per se known. Furthermore, if desired, the auxiliary agents described above, such as the lubricant, isotonizing agent, hydrophilic carrier, water-dispersible polymer, stabilizer, colorant, sweetener, preservative, etc. may also be admixed. After mixing the components described above simultaneously or at certain time intervals, the mixture is compressed into tablets to obtain the sublingual, buccal or oral quick disintegration tablet. In order to obtain a suitable hardness, a solvent such as water, an alcohol, etc. can be used to moisturize or wet the components before or after tabletting, followed by drying.

In preparing the oral mucosal patch (film), the compound of the present invention or a combination drug and the water-dispersible polymer (preferably, hydroxypropyl cellulose, hydroxypropylmethyl cellulose), excipient, etc. described above are dissolved in a solvent such as water, etc. and then the resulting solution is cast into a film. In addition, additives such as a plasticizer, a stabilizer, an antioxidant, a preservative, a colorant, a buffering agent, a sweeteners, etc. may be added to the preparation. A glycol such as polyethylene glycol, propylene glycol, etc. may be added to impart an appropriate elasticity to a film, and a bioadhesive polymer (e.g., polycarbophile, carbopol) may also be added to enhance the adhesion of the film to the oral mucosal lining. The casting can be carried out by pouring a solution onto a non-adhesive surface, spreading the solution using a coater such as a doctor blade in a uniform thickness (preferably, approximately 10 to 1000 microns), and then drying the solution to form a film. The film thus formed is dried at room temperature or while warming, and then cut into pieces each having a desired surface area.

A preferred rapid oral disintegrating preparation is, for example, a rapid diffusion preparation in a solid network form, which comprises the compound of the present invention or a combination drug and a water-soluble or water-diffusible carrier inert to the compound of the present invention or the combination drug. The network is formed by sublimating a solvent from a solid composition comprising a solution of the compound of the present invention or a combination drug in a suitable solvent.

In addition to the compound of the present invention or a combination drug, the composition of the rapid oral disintegrating preparation may preferably contain a matrix-forming agent and a secondary component.

Examples of the matrix-forming agent include gelatins, dextrins and animal or vegetable proteins from soybean, wheat, psyllium seed, etc.; gummy materials such as gum arabic, guar gum, agar, xanthane gum, etc.; polysaccharides; alginates; carboxymethylcelluloses; carrageenans; dextrans; pectins; synthetic polymers such as polyvinyl pyrrolidones; materials derived from gelatin-gum arabic complexes, etc. The matrix-forming agent further includes saccharides such as mannitol, dextrose, lactose, galactose, trehalose, etc.; cyclic saccharides such as cyclodextrins, etc.; inorganic salts such as sodium phosphate, sodium chloride, aluminum silicate, etc.; amino acids having 2 to 12 carbon atoms such as glycine, L-alanine, L-aspartic acid, L-glutamic acid, L-hydroxyproline, L-isoleucine, L-leucine, L-phenylalanine, etc.

One or more matrix-forming agents can be incorporated into a solution or suspension before solidification. The matrix-forming agents may be present in addition to a surfactant, or may be present in the absence of a surfactant. The matrix-forming agents serve not only to form a matrix itself, but also assist to maintain diffusion of the compound of the present invention or a combination drug in the solution or suspension.

The composition may contain a secondary component such as a preservative, an antioxidant, a surfactant, a thickening agent, a colorant, pH adjusting agent, a flavor, a sweetener, a taste masking agent, etc. As the suitable colorant, there are, for example, iron oxide red, black and yellow, FD & C dyes available from ERIS & EVERALD such as FD & C Blue No. 2 and FD & C Red No. 40, etc. Examples of the suitable flavor include mint, raspberry, licorice, orange, lemon, grape fruit, caramel, vanilla, cherry, grape flavor and a combination thereof. Examples of the suitable pH adjusting agent include citric acid, tartaric acid, phosphoric acid, hydrochloric acid and maleic acid. Examples of the suitable sweetener include aspartame, acesulfame K and thaumatine. Examples of the suitable taste masking agent include sodium bicarbonate, ion exchange resins, cyclodextrin inclusion compounds, adsorbents and microencapsulated apomorphine.

The preparation generally contains the compound of the present invention or a combination drug in an amount of about 0.1 to about 50% by weight, preferably about 0.1 to about 30% by weight and, preferably, the preparation (the sublingual tablet, buccal, etc. described above) allows 90% or more of the compound of the present invention or a combination drug to be dissolved (in water) within a time period of about 1 to about 60 minutes, preferably about 1 minute to about 15 minutes, more preferably about 2 minutes to about 5 minutes, or is a rapid oral disintegrating preparation which disintegrates within about 1 to about 60 seconds, preferably about 1 to about 30 seconds, more preferably about 1 to about 10 seconds, after being placed in the oral cavity.

The amount of the above excipient is about 10 to about 99% by weight, preferably about 30 to about 90% by weight based on the total weight of the preparation. The amount of β-cyclodextrin or β-cyclodextrin derivative is about 0 to about 30% by weight based on the total weight of the preparation. The amount of the lubricant is about 0.01 to about 10% by weight, preferably about 1 to about 5% by weight based on the total weight of the preparation. The amount of the isotonizing agent is about 0.1 to about 90% by weight, preferably about 10 to about 70% by weight based on the total weight of the preparation. The amount of the hydrophilic carrier is about 0.1 to about 50% by weight, preferably about 10 to about 30% by weight based on the total weight of the preparation. The amount of the water-dispersible polymer is about 0.1 to about 30% by weight, preferably about 10 to about 25% by weight based on the total weight of the preparation. The amount of the stabilizer is about 0.1 to about 10% by weight, preferably about 1 to about 5% by weight based on the total weight of the preparation. If necessary, the preparation described above may further contain additives such as a colorant, a sweetener, a preservative, etc.

A dose of the combined preparations of the present invention varies depending upon kind of the compound of the present invention, age, body weight, conditions, dosage form, route for administration, dosing period, etc.

A dose of the compound of the present invention may vary depending upon subject to be administered, target organ, conditions, route of administration, etc., and in oral administration, the compound is generally administered to the patient with cancer (as 60 kg body weight) in a daily dose of about 0.1 to about 100 mg, preferably about 1.0 to about 50 mg and more preferably about 1.0 to about 20 mg. In parenteral administration, a single dose of the compound may vary depending upon subject to be administered, target organ, conditions, route of administration, etc., and in the form of an injectable dosage form, it is advantageous to administer the compound to the patient with cancer (as 60 kg body weight) generally in a daily dose of about 0.01 to about 30 mg, preferably about 0.1 to about 20 mg, and more preferably about 0.1 to about 10 mg. For other animal species, the corresponding dose as converted per 60 kg weight can be administered. Of course, the dose may vary depending on individual conditions as described above; in such a case, a dose less than the dose given above may be sufficient, or may be higher than the range above.

It is possible to set any range of a dose for the combination drug, so long as it causes no adverse side effects. A daily dose of the combination drug may vary depending on the severity of disease, subject's age, sex, body weight and susceptibility, the dosing period and intervals, the characteristics, formulation, type and active components of the pharmaceutical preparation, etc. and is not particularly limited. For example, in oral administration, the dose is about 0.001 to 2000 mg, preferably about 0.01 to 500 mg, and more preferably about 0.1 to 100 mg in terms of a drug; usually, this dose is administered by dividing 1 to 4 times per day.

When the pharmaceutical preparations of the present invention are administered, the compound of the present invention and a combination drug may be administered at the same time. Alternatively, a combination drug is first administered and then the compound of the present invention is administered, or the compound of the present invention is first administered and then a combination drug is administered. When they are administered at certain time intervals, the intervals vary depending on the active component to be administered, dosage form and route of administration; when a combination drug is first administered, the compound of the present invention may be administered within 1 minute to 3 days, preferably 10 minutes to 1 day, more preferably 15 minutes to 1 hour after the administration of the combination drug. When the compound of the present invention is first administered, a combination drug may be administered within 1 minute to 1 day, preferably 10 minutes to 6 hours, more preferably 15 minutes to 1 hour after the administration of the compound of the present invention.

As a preferred method of administration, for example, about 0.001 to 200 mg/kg of a combination drug in the form of an oral dosage preparation is administered orally and, after about 15 minutes, about 0.005 to 0.5 mg/kg of the compound of the present invention in the form of a parenteral preparation is administered parenterally as a daily dose.

As the metastins, there are used, for example, human metastin described in WO 00/24890, mouse or rat metastin described in WO 01/75104, etc.

Specific examples of human metastin include a peptide containing the N-terminal 47-54 amino acid sequence in the amino acid sequence represented by SEQ ID NO: 1 and consisting of 8 to 54 amino acid residues, and the like.

The "peptide containing the N-terminal 47-54 amino acid sequence in the amino acid sequence represented by SEQ ID NO: 1 and consisting of 8 to 54 amino acid residues" may be any peptide, as far as it is a peptide containing the N-terminal 47-54 amino acid sequence in the amino acid sequence represented by SEQ ID NO: 1 and consisting of 8 to 54 amino acid residues, but means that these peptides have substantially the same physiological activity (e.g., a receptor binding activity, a signal transduction action, a sugar level elevating action, a pancreatic glucagon secretion promoting action, a urine formation promoting action, etc.). Specifically, there are used (i) a peptide having the amino acid sequence represented by SEQ ID NO: 1, (ii) a peptide having the N-terminal 47-54 amino acid sequence at the C terminus in the amino acid sequence represented by SEQ ID NO: 1 and consisting of 8 to 54 amino acid residues, etc.

More specifically, human metastin used includes (i) a peptide consisting of the amino acid sequence represented by SEQ ID NO: 1 (human metastin 54 (1-54)), (ii) a peptide consisting of the N-terminal 40-54 amino acid sequence in the amino acid sequence represented by SEQ ID NO: 1 (human metastin 15 (40-54); SEQ ID NO: 15), (iii) a peptide consisting of the N-terminal 45-54 amino acid sequence in the amino acid sequence represented by SEQ ID NO: 1 (human metastin 10 (45-54); SEQ ID NO: 16), (iv) a peptide consisting of the N-terminal 46-54 amino acid sequence in the amino acid sequence represented by SEQ ID NO: 1 (human metastin 9 (46-54); SEQ ID NO: 17), (v) a peptide consisting of the N-terminal 47-54 amino acid sequence in the amino acid sequence represented by (human metastin 8 (47-54); SEQ ID NO: 18), etc.

As mouse metastin (A), there are used, for example, (i) a peptide containing the N-terminal 134-141 amino acid sequence in the amino acid sequence represented by SEQ ID NO: 3 and consisting of 8 to 52 amino acid residues. Specific examples of mouse metastin (A) used include (i) a peptide consisting of the N-terminal 90-141 amino acid sequence in the amino acid sequence represented by SEQ ID NO: 3, (ii) a peptide consisting of the N-terminal 132-141 amino acid sequence in the amino acid sequence represented by SEQ ID NO: 3, (iii) a peptide consisting of the N-terminal 127-141 amino acid sequence in the amino acid sequence represented by SEQ ID NO: 3, and the like.

As mouse metastin (B), there are used, for example, (i) a peptide containing the N-terminal 138-145 amino acid sequence in the amino acid sequence represented by SEQ ID NO: 5 and consisting of 8 to 52 amino acid residues. Specific examples of mouse metastin (B) used include (i) a peptide consisting of the N-terminal 94-145 amino acid sequence in the amino acid sequence represented by SEQ ID NO: 5, and the like.

As rat metastin, there are used, for example, (i) a peptide containing the N-terminal 112-119 amino acid sequence in the amino acid sequence represented by SEQ ID NO: 7 and consisting of 8 to 52 amino acid residues. Specific examples of rat metastin used include (i) a peptide consisting of the N-terminal 68-119 amino acid sequence in the amino acid sequence represented by SEQ ID NO: 7, (ii) a peptide consisting of the N-terminal 110-119 amino acid sequence in the amino acid sequence represented by SEQ ID NO: 7, (iii) a peptide consisting of the N-terminal 105-119 amino acid sequence in the amino acid sequence represented by SEQ ID NO: 7, and the like.

Throughout the specification, the metastins are represented in accordance with the conventional way of describing peptides, that is, the N-terminus (amino terminus) at the left hand and the C-terminus (carboxyl terminus) at the right hand. In the peptide represented by SEQ ID NO: 1, the C-terminus may be in any form of a carboxyl group (—COOH), a carboxylate (—COO—), an amide (—CONH$_2$) and an ester (—COOR). Herein, examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl such as a phenyl-$C_{1-2}$ alkyl group, e.g., benzyl, phenethyl, etc.; an α-naphthyl-$C_{1-2}$ alkyl group such as α-naphthylmethyl, etc.; pivaloyloxymethyl group, which are widely used as an ester for oral use, and the like.

Furthermore, the metastins include peptides, wherein the amino group at the N-terminal methionine residue is protected with a protecting group (e.g., a $C_{1-6}$ acyl group such as a $C_{2-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{2-6}$ alkanoyl group, e.g., formyl group, acetyl group, etc.), or conjugated peptides such as glycopeptides bound to sugar chains.

For salts of the metastins of the present invention, preferred are salts with physiologically acceptable acids (e.g., inorganic acids or organic acids) or bases (e.g., alkali metal salts), etc., especially physiologically acceptable acid addition salts. Examples of such salts include salts with, for example, inorganic acids (e.g., hydrochloric acid, phosphoric acid, hydrobromic acid, sulfuric acid); salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

As the DNAs encoding metastins, there are used, for example, DNAs encoding human metastin described in WO 00/24890, DNAs encoding mouse or rat metastin described in WO 01/75104, etc.

The DNAs encoding the metastins may be any of genomic DNA, genomic DNA library, cDNA derived from the cells and tissues described above, cDNA library derived from the cells and tissues described above and synthetic DNA. The vector to be used for the library may be any of bacteriophage, plasmid, cosmid and phagemid. The DNA may also be directly amplified by reverse transcriptase polymerase chain reaction (hereinafter abbreviated as RT-PCR) using the total RNA or mRNA fraction prepared from the cells and tissues described above.

The DNA encoding human metastin, mouse metastin precursor (A), mouse metastin precursor (B) or rat metastin precursor may be any DNA, so long as each is a DNA containing a base sequence represented by SEQ ID NO: 2, SEQ ID NO: 4, SEQ ID NO: 6 or SEQ ID NO: 8, or a DNA having a base sequence hybridizable to the base sequence represented by any base sequence represented by SEQ ID NO: 2, SEQ ID NO: 4, SEQ ID NO: 6 or SEQ ID NO: 8 under highly stringent conditions and encoding the human metastin, mouse metastin (A), mouse metastin (B) or rat metastin described above.

Specific examples of the DNA hybridizable to the base sequence represented by any of SEQ ID NO: 2, SEQ ID NO: 4, SEQ ID NO: 6 or SEQ ID NO: 8 under highly stringent conditions include DNAs containing a base sequence having at least about 70% homology, preferably at least about 80% homology, more preferably at least about 90% homology and the most preferably at least about 95% homology, to the base sequence represented by any of SEQ ID NO: 2, SEQ ID NO: 4, SEQ ID NO: 6 or SEQ ID NO: 8.

Homology in the base sequence can be measured under the following conditions (an expectation value=10; gaps are allowed; filtering=ON; match score=1; mismatch score=−3) using the homology scoring algorithm NCBI BLAST (National Center for Biotechnology Information Basic Local Alignment Search Tool).

The hybridization can be carried out by per se publicly known methods or by modifications of these methods, for example, according to the method described in Molecular Cloning, 2nd (J. Sambrook et al., Cold Spring Harbor Lab. Press, 1989). A commercially available library may also be used according to the instructions of the attached manufacturer's protocol. Preferably, the hybridization can be carried out under highly stringent conditions.

The highly stringent conditions used herein are, for example, those in a sodium concentration at about 19 to 40 mM, preferably about 19 to 20 mM at a temperature of about 50 to 70° C., preferably about 60 to 65° C. In particular, hybridization conditions in a sodium concentration of about 19 mM at a temperature of about 65° C. are most preferred.

Specifically, as the DNA encoding the human metastin consisting of the amino acid sequence represented by SEQ ID NO: 1, the DNA consisting of the base sequence represented by SEQ ID NO: 2 is used. Accordingly, for the base sequence encoding the human metastin consisting of the various amino acid sequences described above, a base sequence corresponding to each of the partial amino acid sequences in the amino acid sequence represented by SEQ ID NO: 1 may be chosen from the base sequence represented by SEQ ID NO: 2.

As the DNA encoding the mouse metastin precursor (A) comprising the amino acid sequence represented by SEQ ID NO: 3, there are employed a DNA consisting of the base sequence represented by SEQ ID NO: 4, and the like. Accordingly, for the base sequence encoding the mouse metastin precursor (A) consisting of the various amino acid sequences described above, a base sequence corresponding to each of the partial amino acid sequences in the amino acid sequence represented by SEQ ID NO: 3 may be chosen from the base sequence represented by SEQ ID NO: 4.

As the DNA encoding the mouse metastin precursor (B) comprising the amino acid sequence represented by SEQ ID NO: 5, there are employed a DNA consisting of the base sequence represented by SEQ ID NO: 6, and the like. Accordingly, for the base sequence encoding the mouse metastin precursor (B) consisting of the various amino acid sequences described above, a base sequence corresponding to each of the partial amino acid sequences in the amino acid sequence represented by SEQ ID NO: 5 may be chosen from the base sequence represented by SEQ ID NO: 6.

As the DNA encoding the rat metastin comprising the amino acid sequence represented by SEQ ID NO: 7, there are employed a DNA consisting of the base sequence represented by SEQ ID NO: 8, and the like. Accordingly, for the base sequence encoding the rat metastin consisting of the various amino acid sequences described above, a base sequence corresponding to each of the partial amino acid sequences in the amino acid sequence represented by SEQ ID NO: 7 may be chosen from the base sequence represented by SEQ ID NO: 8.

More specifically, for the peptide consisting of the amino acid sequence represented by SEQ ID NO: 1 (human metastin 54 (1-54)), a DNA containing the base sequence represented by SEQ ID NO: 2, etc. is used.

For the peptide consisting of the N-terminal 40-54 amino acid sequence in the amino acid sequence represented by SEQ ID NO: 1 (human metastin 15 (40-54); SEQ ID NO: 15), a DNA containing the base sequence represented by SEQ ID NO: 19, etc. is used.

For the peptide consisting of the N-terminal 45-54 amino acid sequence in the amino acid sequence represented by SEQ ID NO: 1 (human metastin 10 (45-54); represented by SEQ ID NO: 16), a DNA containing the base sequence represented by SEQ ID NO: 20, etc. is used.

For the peptide consisting of the N-terminal 46-54 amino acid sequence in the amino acid sequence represented by SEQ ID NO: 1 (human metastin 9 (46-54); represented by SEQ ID NO: 17), a DNA containing the base sequence represented by SEQ ID NO: 21, etc. is used.

For the peptide consisting of the N-terminal 47-54 amino acid sequence in the amino acid sequence represented by SEQ ID NO: 1 (human metastin 8 (47-54); represented by SEQ ID NO: 18), a DNA containing the base sequence represented by SEQ ID NO: 22, etc. is used.

As the metastin receptor, its partial peptides or salts thereof, there are used, for example, a human metastin receptor, its partial peptides or salts thereof described in WO 00/24890, a mouse or rat human metastin receptor, its partial peptides or salts thereof described in WO 01/75104, etc.

Specifically, the metastin receptor includes a protein containing the same or substantially the same amino acid sequence as the amino acid sequence represented by SEQ ID NO: 9, SEQ ID NO: 11 or SEQ ID NO: 13, etc.

The amino acid sequence which has substantially the same amino acid sequence as the amino acid sequence represented by SEQ ID NO: 9, SEQ ID NO: 11 or SEQ ID NO: 13 includes, for example, an amino acid sequence having at least about 70% homology, preferably at least about 80% homology, more preferably at least about 90% homology, and most preferably at least about 95% homology, to the amino acid sequence represented by SEQ ID NO: 9, SEQ ID NO: 11 or SEQ ID NO: 13.

Homology of the amino acid sequences can be determined under the following conditions (an expectation value=10; gaps are allowed; matrix=BLOSUM62; filtering=OFF) using a homology scoring algorithm NCBI BLAST (National Center for Biotechnology Information Basic Local Alignment Search Tool).

As the protein having substantially the same amino acid sequence as the amino acid sequence represented by SEQ ID NO: 9, SEQ ID NO: 11 or SEQ ID NO: 13, preferred is a protein having substantially the same amino acid sequence as the amino acid sequence represented by SEQ ID NO: 9, SEQ ID NO: 11 or SEQ ID NO: 13 and having the activity of the same nature as that of a protein consisting of the amino acid sequence represented by SEQ ID NO: 9, SEQ ID NO: 11 or SEQ ID NO: 13, etc.

As the activity of substantially the same nature, there are, for example, a ligand binding activity, a signal transduction activity, and the like. The "substantially the same nature" is used to mean that the nature of these activities is equivalent in terms of quality. Thus, the activities such as a ligand binding activity, a signal transduction activity, etc. are preferably equivalent (e.g., about 0.01 to 100 times, preferably about 0.1 to 10 times, more preferably 0.5 to 2 times), but differences in degree such as a level of these activities, quantitative factors such as a molecular weight of the protein may be present and allowable.

The activities such as a ligand binding activity, a signal transduction activity, etc. can be assayed by per se publicly known method with modifications and may be determined according to methods of determining a ligand or screening methods described in, e.g., WO 00/24890 or WO 01/75104.

Examples of the metastin receptor used include proteins comprising (1) (i) the amino acid sequence represented by SEQ ID NO: 9, SEQ ID NO: 11 or SEQ ID NO: 13, of which at least 1 or 2 (preferably about 1 to about 30, more preferably about 1 to about 10 and most preferably several (1 or 2)) amino acids are deleted; (ii) the amino acid sequence represented by SEQ ID NO: 9, SEQ ID NO: 11 or SEQ ID NO: 13, to which at least 1 or 2 (preferably about 1 to about 30, more preferably about 1 to about 10 and most preferably several (1 or 2)) amino acids are added; (iii) the amino acid sequence represented by SEQ ID NO: 9, SEQ ID NO: 11 or SEQ ID NO: 13, in which at least 1 or 2 (preferably about 1 to about 30, more preferably about 1 to about 10 and most preferably several (1 or 2)) amino acids are inserted; (iv) the amino acid sequence represented by SEQ ID NO: 9, SEQ ID NO: 11 or SEQ ID NO: 13, in which at least 1 or 2 (preferably about 1 to about 30, more preferably about 1 to about 10 and most preferably several (1 or 2)) amino acids are substituted by other amino acids; or (v) a combination of these amino acid sequences; and the like.

Throughout the specification, the metastin receptors are represented in accordance with the conventional way of describing peptides, that is, the N-terminus (amino terminus) at the left hand and the C-terminus (carboxyl terminus) at the right hand. In the metastin receptors including the metastin receptor represented by SEQ ID NO: 9, SEQ ID NO: 11 or SEQ ID NO: 13, the C-terminus may be in any form of a carboxyl group (—COOH), a carboxylate (—COO—), an amide (—CONH$_2$) and an ester (—COOR). Herein, examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl such as a phenyl-$C_{1-2}$ alkyl group, e.g., benzyl, phenethyl, etc.; an α-naphthyl-$C_{1-2}$ alkyl group such as α-naphthylmethyl, etc.; and pivaloyloxymethyl group, which are widely used as an ester for oral use, and the like.

Where the metastin receptors contain a carboxyl group (or a carboxylate) at a position other than the C-terminus, the carboxyl group may be amidated or esterified and such amides or esters are also included within the receptor protein of the present invention. In this case, the ester group used may be the same group as the C-terminal esters described above.

Furthermore, the metastin receptors include those wherein the amino group at the N-terminal methionine residue is protected with a protecting group (e.g., a $C_{1-6}$ acyl group such as a $C_{2-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{2-6}$ alkanoyl group, e.g., formyl group, acetyl group, etc.), or conjugated proteins such as glycoproteins bound to sugar chains.

Specific examples of the metastin receptors include human metastin receptor consisting of the amino acid sequence represented by SEQ ID NO: 9, rat metastin receptor consisting of the amino acid sequence represented by SEQ ID NO: 11, mouse metastin receptor consisting of the amino acid sequence represented by SEQ ID NO: 13, etc.

The partial peptides of the metastin receptor (hereinafter sometimes simply referred to as the partial peptide) may be any peptide, so long as they are partial peptides of the metastin receptor described above; there are used those such as protein molecules of the metastin receptor, which are the sites exposed outside the cell membrane, and having a ligand binding activity.

Specifically, the partial peptide of the metastin receptor consisting of the amino acid sequence represented by SEQ ID NO: 9, SEQ ID NO: 11 or SEQ ID NO: 13 is a peptide containing the parts analyzed to be extracellular domains (hydrophilic domains) in the hydrophobic plotting analysis. A peptide containing a hydrophobic domain in part can be used as well. In addition, the peptide may contain each domain separately or a plurality of domains together.

In the metastin receptor, preferred partial peptides are those having the number of amino acids of at least 20, preferably at least 50, and more preferably at least 100, in the amino acid sequence described above, which constitutes the metastin receptor.

The partial peptide may be a peptide having the amino acid sequence described above, of which at least 1 or 2 (preferably about 1 to about 10 and more preferably several (1 or 2)) amino acids are deleted; to which at least 1 or 2 (preferably about 1 to about 10 and more preferably several (1 or 2)) amino acids are added; or, in which at least 1 or 2 (preferably about 1 to about 10 and more preferably several (1 or 2)) amino acids are substituted by other amino acids.

In the partial peptide, the C terminus may be any form of a carboxyl group (—COOH), a carboxylate (—COO—), an amide (—CONH$_2$) and an ester (—COOR), as in the metastin receptor described above.

Furthermore, the partial peptides include peptides, wherein the amino group at the N-terminal methionine residue is protected with a protecting group; those wherein the N-terminal region is cleaved in vivo and the glutamyl group thus formed is pyroglutaminated; those wherein a substituent on the side chain of an amino acid in the molecule is protected with a suitable protecting group, or conjugated peptides such as glycopeptides bound to sugar chains, as in the metastin receptors described above.

For salts of the metastin receptor or the partial peptide, preferred are salts with physiologically acceptable acids, especially physiologically acceptable acid addition salts. Examples of the salts include salts with, for example, inorganic acids (e.g., hydrochloric acid, phosphoric acid, hydrobromic acid, sulfuric acid); salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

As the DNA encoding the metastin receptor or its partial peptides, there are used, for example, a DNA encoding the human metastin receptor or its partial peptides described in WO 00/24890, a DNA encoding the mouse or rat human metastin receptor or its partial peptides described in WO 01/75104, etc.

The DNAs encoding the metastin receptor or its partial peptides may be any of genomic DNA, genomic DNA library, cDNA derived from the cells and tissues described above, cDNA library derived from the cells and tissues described above and synthetic DNA. The vector to be used for the library may be any of bacteriophage, plasmid, cosmid and phagemid. The DNA may also be directly amplified by reverse transcriptase polymerase chain reaction (hereinafter abbreviated as RT-PCR) using the total RNA or mRNA fraction prepared from the cells and tissues described above.

Specifically, the DNA encoding human metastin receptor, mouse metastin receptor or rat metastin receptor may be any DNA, so long as it is a DNA containing each base sequence represented by SEQ ID NO: 10, SEQ ID NO: 12 or SEQ ID NO: 14, or a DNA containing a base sequence hybridizable to the base sequence represented by SEQ ID NO: 10, SEQ ID NO: 12 or SEQ ID NO: 14 under highly stringent conditions and encoding a receptor having the activity of substantially the same nature (e.g., a ligand binding activity, a signal transduction activity, etc.) as that of the human metastin receptor, mouse metastin receptor or rat metastin receptor consisting of the amino acid sequence represented by SEQ ID NO: 10, SEQ ID NO: 12 or SEQ ID NO: 14.

Examples of the DNA hybridizable to the base sequence represented by any of SEQ ID NO: 10, SEQ ID NO: 12 or SEQ ID NO: 14 include DNAs containing a base sequence having at least about 70% homology, preferably at least about 80% homology, more preferably at least about 90% homology and the most preferably at least about 95% homology, to the base sequence represented by any of SEQ ID NO: 10, SEQ ID NO: 12 or SEQ ID NO: 14.

Homology in the base sequence can be measured under the following conditions (an expectation value=10; gaps are allowed; filtering=ON; match score=1; mismatch score=−3) using the homology scoring algorithm NCBI BLAST (National Center for Biotechnology Information Basic Local Alignment Search Tool).

The hybridization can be carried out by per se publicly known methods or by modifications of these methods, for example, according to the method described in Molecular Cloning, 2nd (J. Sambrook et al., Cold Spring Harbor Lab. Press, 1989), etc. A commercially available library may also be used according to the instructions of the attached manufacturer's protocol. Preferably, the hybridization can be carried out under highly stringent conditions.

The highly stringent conditions used herein are, for example, those in a sodium concentration at about 19 to 40 mM, preferably about 19 to 20 mM at a temperature of about 50 to 70° C., preferably about 60 to 65° C. In particular, hybridization conditions in a sodium concentration of about 19 mM at a temperature of about 65° C. are most preferred.

More specifically, as the DNA encoding the human metastin receptor consisting of the amino acid sequence represented by SEQ ID NO: 9, the DNA consisting of the base sequence represented by SEQ ID NO: 10 is used.

As the DNA encoding the rat metastin receptor consisting of the amino acid sequence represented by SEQ ID NO: 11, the DNA consisting of the base sequence represented by SEQ ID NO: 12 is used.

As the DNA encoding the mouse metastin receptor consisting of the amino acid sequence represented by SEQ ID NO: 13, the DNA consisting of the base sequence represented by SEQ ID NO: 14 is used.

The metastin receptors, their partial peptides or salts thereof and the DNAs encoding the metastin receptors or their partial peptides can be obtained or produced by the methods described in WO 00/24890 or WO 01/75104.

The present invention will be described in detail by referring to EXAMPLES, FORMULATION EXAMPLES AND TEST EXAMPLES, but is not deemed to be limited thereto, and any modification may be made without departing from the scope of the present invention.

In the following EXAMPLES, the term "room temperature" normally means a temperature of about 10° C. to 35° C. In percentages, the yield is shown by mol/mol % and the solvent used in chromatography by vol %, and the remaining by wt %. In proton NMR spectra, data on OH, NH protons, etc. that are broad and unidentified are not shown.

The other abbreviations used in the specification mean as follows.

Abbreviation Description

10Ψ,CSNH: C-terminal-$CONH_2$ at the 10-position is substituted with —$CSNH_2$.
1Ψ2,$CH_2NH$: The —CONH— bond between the 1- and 2-positions is substituted with the —$CH_2NH$— bond.
2Ψ3,$CH_2NH$: The —CONH— bond between the 2- and 3-positions is substituted with the —$CH_2NH$— bond.
3Ψ4,$CH_2NH$: The —CONH— bond between the 3- and 4-positions is substituted with the —$CH_2NH$— bond.
4Ψ5,$CH_2NH$: The —CONH— bond between the 4- and 5-positions is substituted with the —$CH_2NH$— bond.
6Ψ7,CSNH: The —CONH— bond between the 6- and 7-positions is substituted with the —CSNH— bond.
6Ψ7,NHCO: The —CONH— bond between the 6- and 7-positions is substituted with the —NHCO— bond.
6Ψ7,$CH_2NH$: The —CONH— bond between the 6- and 7-positions is substituted with the —$CH_2NH$— bond.
6Ψ7,$CH_2O$: The —CONH— bond between the 6- and 7-positions is substituted with the —$CH_2O$— bond.
7Ψ8,$CH_2NH$: The —CONH— bond between the 7- and 8-positions is substituted with the —$CH_2NH$— bond.
8Ψ9,$CH_2NH$: The —CONH— bond between the 8- and 9-positions is substituted with the —$CH_2NH$— bond.
9Ψ10,$CH_2NH$: The —CONH— bond between the 9- and 10-positions is substituted with the —$CH_2NH$— bond.
Abu: 2-aminobutanic acid
Ac: acetyl
Acp: 6-aminocaproic acid
AcOEt: ethyl acetate
AcOH: acetic acid
Aib: α-aminoisobutanoic acid
Ala(2-Qui): 2-quinolylalanine
Ala(3-Bzt): 3-benzothienylalanine
Alb: Albizziin 2-amino-3-ureidopropion acid
Arg(Ac): $N^{\omega}$-acetylarginine
Arg($Boc_2$,Me): $NO^{\omega,\omega'}$-bis-tert-butoxycarbonyl-$N^{\omega}$-methylarginine
Arg(Et): $N^{\omega}$-ethylarginine
Arg(Me): $N^{\omega}$-methylarginine
Arg($asyMe_2$) or Arg($Me_2$)asym: asymmetric-$N^{\omega,\omega'}$-dimethylarginine
Arg($symMe_2$) or Arg($Me_2$)sym: symmetric-$N^{\omega,\omega'}$-dimethylarginine
Arg($NO_2$): $N^{\omega}$-methylarginine
Arg(n-Pr): $N^{\omega}$-propylarginine
Arg(Tos): $N^{\omega}$-tosylarginine
Asp(NHMe): $N^{\omega}$-methylasparagine
Asp(Nme2): $N^{\omega}$-dimethylasparagine
AzaGly: azaglycine
AzaPhe: azaphenylalanine
Aze(2): azetidine-2-carboxylic acid
β-Ala: β-alanine
Boc: tert-butoxycarbonyl
$Boc_2O$: di-tert-butyl dicarbonate
Br-Z: 2-bromobenzyloxycarbonyl
$Bu^t$: tert-butyl
Bzl: benzyl
CDI: 1,1'-carbonyldiimidazole
Cha: cyclohexylalanine CIP: 2-chloro-1,3-dimethylimidazolium tetrafluoroborate
Cit: citrulline
Clt resin: 2-chlorotrytyl resin
Cl-Z: 2-chlorobenzyloxycarbonyl
Dab: 2,4-diaminobutanoic acid
Dap: 2,3-diaminopropionic acid
Dap(Ac): $N^\beta$-acetyldiaminopropionic acid
Dap(For): $N^\beta$-formyldiaminopropionic acid
Dap(Gly): $N^\beta$-glycyldiaminopropionic acid
Dap(GnGly): $N^\beta$-(N-guanidinoglycyl)diaminopropionic acid
DCM: dichloromethane
DEA: diethylamine
DIEA: N,N-diisopropylethylamine
DIPCDI: 1,3-diisopropylcarbodiimide
DMAP: 4-dimethylaminopyridine
DMF: N,N-dimethylformamide
EDT: 1,2-ethanedithiol
Fmoc: 9-fluorenylmethoxycarbonyl
For: formyl
γ-Abu: 4-aminobutanoic acid
γ-MeLeu: γ-methylleucine
Gn: guanidino
GuAmb: 4-guanidinomethylbenzoyl
Har: homoarginine
Har(Me): $N^\omega$-methylhomoarginine
HOAt: 1-hydroxy-7-azabenzotriazole
HOBt: 1-hydroxybenzotriazole
HONB: N-hydroxy-5-norbornene-2,3-dicarboxamide
Hph: homophenylalanine
Hyp: trans-4-hydroxyproline
IndPr: 3-(indol-3-yl)propionyl
Lys(Me$_2$): $N^{\epsilon,\epsilon}$-dimethyllysine
MBHA: p-methylbenzhydrylamine
MeOH: methanol
Mtt: 4-methyltrytyl
N((CH$_2$)$_3$Gn)Gly: N-(3-guanidinopropyl)glycine
Nal(1):1-naphthylalanine
Nal(2): 2-naphthylalanine
Nar: norarginine
Nar(Me): $N^\omega$-methylnorarginine
Nle: norleucine
NMeArg: $N^\alpha$-methylarginine
NMeAsn: $N^\alpha$-methylasparagine
NMeLeu: $N^\alpha$-methylleucine
NMePhe: $N^\alpha$-methylphenylalanine
NMeSer: $N^\alpha$-methylserine
NMeTrp: $N^\alpha$-methyltryptophan
NMeTyr: $N^\alpha$-methyltyrosine
Nva: Norvaline
Orn: ornithine
Orn(Mtt): $N^\delta$-(4-methyltrytyl)ornithine
PAL: 5-(4-(9-fluorenylmethoxycarbonyl)aminomethyl-3,5-dimethoxy-phenoxy)valeric acid
Pbf: 2,2,4,6,7-pentamethyldihydrobenzofuran-5-sulfonyl
pGlu: pyroglutamic acid
Phe(2Cl): 2-chlorophenylalanine
Phe(2F): 2-fluorophenylalanine
Phe(3,4Cl$_2$): 3,4-dichlorophenylalanine
Phe(3,4F$_2$): 3,4-difluorophenylalanine
Phe(3 CF$_3$): 3-trifluoromethylphenylalanine
Phe(3Cl): 3-chlorophenylalanine
Phe(3F): 3-fluorophenylalanine
Phe(4Cl): 4-chlorophenylalanine
Phe(4CN): 4-cyanophenylalanine
Phe(4F): 4-fluorophenylalanine
Phe(4Gn): 4-guanidinophenylalanine
Phe(4NH$_2$): 4-aminophenylalanine
Phe(4NO$_2$): 4-nitrophenylalanine
Phe(4CN): 4-cyanophenylalanine
Phe(F$_5$): pentafluorophenylalanine
PheΨ(CH$_2$O)Gly: The —CONH— bond between Phe and Gly is substituted with the —CH$_2$O— bond.
PheΨ(CSNH)—NH$_2$: The C-terminal phenylalanylamide is substituted with the phenylalanylthioamide.
Phg: phenylglycine
PhOH: phenol
PhSMe: thioanisole
Pip(2): 2-aminopipecolinic acid
Pro: proline
Pya(2): 2-pyridylalanine
Pya(3): 3-pyridylalanine
Pya(4): 4-pyridylalanine
PyAOP: (7-azabenzotriazole-1-yloxy)-tris(pyrrolidino)phosphonium hexafluorophosphate
PyBOP: (benzotriazole-1-yloxy)-tris(pyrrolidino)phosphonium hexafluorophosphate
PyBrop: bromo-tris(pyrrolidino)phosphonium hexafluorophosphate
Sar: N-methylglycine
Ser(Ac): O-acetylserine
Ser(Me): O-methylserine
Thi: 2-thienylalanine
Tic: 1,2,3,4-tetrahydroisoquinoline-2-carboxylic acid
TIS: triisopropylsilane
Tle: tert-leucine
Tos: tosyl
Trp(For): $N^{in}$-foyltryptophan
Trt: trytyl
Tyr(Me): O-methyltyrosine
TyrΨ(CH$_2$NH)Asn: The —CONH— bond between Tyr and Asn is substituted with the —CH$_2$NH— bond.
TFA: trifluoroacetic acid
TFE: trifluoroethanol
Z: benzyloxycarbonyl In the specification and drawings, the codes of bases and amino acids are denoted in accordance with the IUPAC-IUB Commission on Biochemical Nomenclature or by the common codes in the art, examples of which are shown below. For amino acids that may have the optical isomer, L form is presented unless otherwise indicated.

DNA: deoxyribonucleic acid
cDNA: complementary deoxyribonucleic acid
A: adenine
T: thymine
G: guanine
C: cytosine
Y: thymine or cytosine
N: thymine, cytosine, adenine or guanine
R: adenine or guanine
M: cytosine or adenine
W: thymine or adenine
S: cytosine or guanine
RNA: ribonucleic acid
mRNA messenger ribonucleic acid
dATP: deoxyadenosine triphosphate
dTTP: deoxythymidine triphosphate
dGTP deoxyguanosine triphosphate
dCTP: deoxycytidine triphosphate
ATP: adenosine triphosphate
EDTA: ethylenediaminetetraacetic acid
SDS: sodium dodecyl sulfate
TFA: trifluoroacetic acid
EIA: enzyme immunoassay Gly or G: glycine
Ala or A: alanine
Val or V valine
Leu or L: leucine
Ile or I: isoleucine
Ser or S: serine
Thr or T: threonine
Cys or C: cysteine
Met or M: methionine
Glu or E glutamic acid
Asp or D: aspartic acid
Lys or K: lysine
Arg or R: arginine
His or H: histidine
Phe or F: phenylalanine
Tyr or Y: tyrosine
Trp or W: tryptophan
Pro or P: proline
Asn or N: asparagine
Gln or Q: glutamine
pGlu: pyroglutamic acid The sequence identification numbers in the sequence listing of the specification indicates the following sequence, respectively.

SEQ ID NO: 1
This shows the amino acid sequence of human-derived metastin (Metastin).

SEQ ID NO: 2
This shows the base sequence of DNA encoding human metastin.

SEQ ID NO: 3
This shows the amino acid sequence of mouse metastin precursor (A).

SEQ ID NO: 4
This shows the base sequence of DNA encoding mouse metastin precursor (A), which is the base sequence contained in plasmid pCMV-mKiSS-1 harbored on transformant *Escherichia coli* DH10B/pCMV-mKiSS-1.

SEQ ID NO: 5
This shows the amino acid sequence of mouse metastin precursor (B).

SEQ ID NO: 6
This shows the base sequence of DNA encoding mouse metastin precursor (B), which is the base sequence contained in plasmid pCR2.1-mKiSS-1.4A harbored on transformant *Escherichia coli* DH5α/pCR2.1-mKiSS-1.4A.

SEQ ID NO: 7
This shows the amino acid sequence of rat-derived metastin precursor.

SEQ ID NO: 8
This shows the base sequence of DNA encoding rat metastin precursor.

SEQ ID NO: 9
This shows the amino acid sequence of human OT7T175 (metastin receptor).

SEQ ID NO: 10
This shows the base sequence of DNA encoding human OT7T175 (metastin receptor).

SEQ ID NO: 11
This shows the amino acid sequence of rat OT7T175 (metastin receptor).

SEQ ID NO: 12
This shows the base sequence of DNA encoding rat OT7T175 (metastin receptor).

SEQ ID NO: 13
This shows the amino acid sequence of mouse OT7T175 (metastin receptor).

SEQ ID NO: 14
This shows the base sequence of DNA encoding mouse OT7T175 (metastin receptor).

SEQ ID NO: 15
This shows the amino acid sequence of human metastin 15 (40-54).

SEQ ID NO: 16
This shows the amino acid sequence of human metastin 10 (45-54) (MS10).

SEQ ID NO: 17
This shows the amino acid sequence of human metastin 9 (46-54).

SEQ ID NO: 18
This shows the amino acid sequence of human metastin 8 (47-54).

SEQ ID NO: 19
This shows the base sequence of DNA encoding human metastin 15 (40-54).

SEQ ID NO: 20
This shows the base sequence of DNA encoding human metastin 10 (45-54).

SEQ ID NO: 21
This shows the base sequence of DNA encoding human metastin 9 (46-54).

SEQ ID NO: 22
This shows the base sequence of DNA encoding human metastin 8 (47-54).

The transformant *Escherichia coli* DH10B/pCMV-mKiSS-1 has been on deposit since Jan. 24, 2000 with International Patent Organisms Depository, National Institute of Advanced Industrial Science and Technology (the former Ministry of International Trade and Industry, Agency of Industrial Science and Technology, National Institute of Bioscience and Human Technology (NIBH)), located at Central 6, 1-1-1 Higashi, Tsukuba, Ibaraki (postal code 305-8566), Japan as the Accession Number FERM BP-7003 and since Dec. 16, 1999 with Institute for Fermentation (IFO), located at 2-17-85 Juso-Honmachi, Yodogawa-ku, Osaka-shi, Osaka, Japan, as the Accession Number IFO 16348.

The transformant *Escherichia coli* DH5α/pCR2.1-mKiSS-1.4A has been on deposit since Mar. 6, 2000 with International Patent Organisms Depository, National Institute of Advanced Industrial Science and Technology (the former Ministry of International Trade and Industry, Agency of Industrial Science and Technology, National Institute of Bioscience and Human Technology (NIBH)), located at Central 6, 1-1-1 Higashi, Tsukuba, Ibaraki (postal code 305-8566), Japan as the Accession Number FERM BP-7073 and since Feb. 16, 2000 with Institute for Fermentation (IFO), located at 2-17-85 Juso-Honmachi, Yodogawa-ku, Osaka-shi, Osaka, Japan, as the Accession Number IFO 16360.

In the present invention, Tyr-Asn-Trp-Asn-Ser-Phe-Gly-Leu-Arg-Phe-$NH_2$ (SEQ ID NO: 16) is referred to as metastin 10 (Metastin10), i.e., MS10.

In EXAMPLES later described, the N-terminal Tyr and the C-terminal Phe in MS10 are counted as the 1- and 10-positions, respectively.

```
Tyr-Asn-Trp-Asn-Ser-Phe-Gly-Leu-Arg-Phe-NH₂
 1   2   3   4   5   6   7   8   9   10
```

For example, [Hph10]MS10 of Compound No. 79 (EXAMPLE 1) means a peptide wherein the C-terminal Phe (10-position) of MS10 is substituted with Hph.

For example, des(1)-MS10 of Compound No. 4 means a peptide wherein the N-terminal Tyr (1-position) is deleted.

For example, des(1-3)-Fmoc-MS10 of Compound No. 53 means a peptide wherein the N-terminal Tyr-Asn-Trp (1 to 3-positions) is deleted and the amino group of Asn at the 4-position is modified and protected with Fmoc.

Example 1

Synthesis Process A

Preparation of [Hph10]MS10 (Compound No. 79)

Using 51 mg of Fmoc-Hph-PAL resin (sub. 0.39 mmol/g), which was prepared by introducing Fmoc-Hph into commercially available PAL resin, the peptide chain was extended on a multiple peptide synthesizer ACT-396 to give Tyr(Bu$^t$)Asn(Trt)Trp(Boc)Asn(Trt)Ser(Bu$^t$)PheGlyLeuArg(Pbf)Hph-PAL resin. To 18.2 mg of the resin, 200 μL of TFA/PhSMe/m-cresol/TIS/EDT (85/5/5/2.5/2.5) was added and the mixture was shaken for 2 hours. Diethyl ether was added to the reaction solution, the resulting precipitate was centrifuged and the supernatant was removed. This procedure was repeated for washing. The residue was extracted with an aqueous acetic acid solution and the extract was filtered to remove the resin. Then, linear density gradient elution was performed with eluants A/B: 73/27-63/37 using elution A: 0.1% TFA in water and eluant B: 0.1% TFA-containing acetonitrile on preparative HPLC using YMC D-ODS-5-ST S-5 120A column (20×150 mm). The fractions containing the product were collected and lyophilized to give 2.6 mg of white powders.

Mass spectrum (M+H)$^+$ 1316.5 (Calcd. 1316.7)
Elution time on HPLC: 20.6 min
Elution Conditions
Column: Wakosil-II 5C18 HG (4.6×100 mm)
Eluant: linear density gradient elution with eluants A/B=100/0-30/70, using 0.1% TFA in water as eluant A and acetonitrile containing 0.1% TFA (35 mins.)
Flow rate: 1.0 ml/min.

Example 2

Synthesis Process B

Preparation of [Trp10]MS10 (Compound No. 186)

Using 379 mg of Fmoc-Arg(Pbf)-O-Clt resin (sub. 0.33 mmol/g), which was prepared by introducing Fmoc-Arg(Pbf)-OH into commercially available 2-chlorotritylchloride resin (Clt resin, 1.33 mmol/g), the peptide chain was extended on ABI 433A to give 540 mg of Boc-Tyr(Bu$^t$)Asn(Trt)Trp(Boc)Asn(Trt)Ser(Bu$^t$)PheGlyLeuArg(Pbf)-O-Clt resin. To 270 mg of the peptide, 10 mL of AcOH/TFE/DCM (1/1/8) was added the mixture was shaken for 30 minutes. After the resin was removed by filtration, the solvent was concentrated and the residue was dissolved in AcOEt. The solution was then washed with satd. NaCl aq. solution. After drying over Na$_2$SO$_4$, the solvent was concentrated and diethyl ether-petroleum ether was added to the residue to give 68 mg of Boc-Tyr(Bu$^t$)Asn(Trt)Trp(Boc)Asn(Trt)Ser(Bu$^t$)PheGlyLeuArg(Pbf)-OH as the precipitate. To 22 mg of the peptide, 4 mg of HCl H-Trp(For)-NH$_2$ (prepared by treating Boc-Trp(For)-NH$_2$ with 9.7 N HCl/dioxane at 0° C. for 30 minutes), 10 mg of PyAOP, 5 mg of HOAt and 11 μL of DIEA were added. The mixture was stirred for 15 hours. After the solvent was concentrated, chloroform-diethyl ether was added to the residue to give Boc-Tyr(Bu$^t$)Asn(Trt)Trp(Boc)Asn(Trt)Ser(Bu$^t$)PheGlyLeuArg(Pbf)Trp(For)-NH$_2$ as the precipitate. To the peptide, 1 mL of TFA/PhSMe/m-cresol/TIS/EDT (85/5/5/2.5/2.5) was added and the mixture was stirred for 2 hours. Diethyl ether was added to the reaction solution, the resulting precipitate was centrifuged and the supernatant was removed. This procedure was repeated for washing. The residue was extracted with an aqueous acetic acid solution and the extract was filtered to remove the resin. Then, linear density gradient elution (30 minutes) was performed with eluants A/B: 73/27-63/37 using eluant A: 0.1% TFA in water and eluant B: 0.1% TFA-containing acetonitrile on preparative HPLC using YMC D-ODS-5-ST S-5 120A column (20×150 mm). The fractions containing the product were collected and lyophilized to give 2.0 mg of white powders.

Mass spectrum (M+H)$^+$ 1369.3 (Calcd. 1369.6)
Elution time on HPLC: 19.6 min
Elution Conditions
Column: Wakosil-II 5C18 HG (4.6×100 mm)
Eluant: linear density gradient elution with eluants A/B=100/0-30/70, using 0.1% TFA in water as eluant A and acetonitrile containing 0.1% TFA (35 mins.)
Flow rate: 1.0 ml/min.

Example 3

Synthesis Process C

Preparation of [10Ψ,CSNH]MS10 (Compound No. 128)

After 264 mg of Boc-Phe-NH$_2$ was dissolved in 20 mL of THF, 1.62 g of Lawesson's reagent was added to the solution, followed by stirring for 24 hours. Insoluble matters were removed by filtration, the solvent was concentrated and the concentrate was dissolved in AcOEt. The solution washed over satd. NaHCO$_3$ aq. solution and then satd. NaCl aq. solution. After drying over Na$_2$SO$_4$, the solvent was concentrated and the concentrate was purified by flush column chromatography. Diethyl ether-petroleum ether was added to give 275 mg (yield 98%) of (S)-2-tert-Butoxycarbonylamino-3-phenylpropanethioamide(Boc-PheΨ(CSNH)—NH$_2$) as the precipitate. After 42 mg of the peptide was treated at 0° C. with 9.7 N HCl to remove Boc, the removal of Fmoc with 10% DEA/DMF treatment followed by condensation by the PyBOP/HOBt method were repeated to give 66 mg of Fmoc-LeuArg(Pbf)PheΨ(CSNH)—NH$_2$ (yield 93%). To 17 mg of Boc-Tyr(Bu$^t$)Asn(Trt)Trp(Boc)Asn(Trt)Ser(Bu$^t$)PheGly-OH prepared as in EXAMPLE 2, H-LeuArg(Pbf)PheΨ(CSNH)—NH$_2$ (prepared by treating 14 mg of Fmoc-LeuArg(Pbf)PheΨ(CSNH)—NH$_2$ with 10% DEA/DMF), 9 mg of PyBrop, 3 mg of HOAt and 7 mL of DIEA were added and the mixture was stirred for 15 hours. After the solvent was concentrated, chloroform-diethyl ether was added thereto for precipitation. To 10 mg of the product, 100 μL of TFA/PhSMe/m-cresol/TIS/EDT (85/5/5/2.5/2.5) was added and the mixture was stirred for 2 hours. Diethyl ether was added to the reaction solution, the resulting precipitate was centrifuged and the supernatant was removed. This procedure was repeated for washing. The residue was extracted with an aqueous acetic acid solution and the extract was filtered to remove the resin. Then, linear density gradient elution (30 minutes) was performed with eluants A/B: 72/28-62/38 using: 0.1% TFA in water and eluant B: 0.1% TFA-containing acetonitrile on preparative HPLC using YMC D-ODS-5-ST S-5 120A column (20×150 mm). The fractions containing the product were collected and lyophilized to give 1.0 mg of white powders.

Mass spectrum (M+H)+ 1318.4 (Calcd. 1318.6)
Elution time on HPLC: 21.8 min
Elution Conditions:
Column: Wakosil-II 5C18 HG (4.6×100 mm)
Eluant: linear density gradient elution with eluants A/B=100/0-30/70, using 0.1% TFA in water as eluant A and acetonitrile containing 0.1% TFA (35 mins.)
Flow rate: 1.0 ml/min.

Example 4

Synthesis Process D

Preparation of [6Ψ7,CH$_2$NH]MS10 (Compound No. 163)

Using 321 mg of Fmoc-Phe-PAL resin, which was prepared by introducing Fmoc-Phe into commercially available PAL resin, the peptide chain was extended on ABI 433A to give Fmoc-LeuArg(Pbf)Phe-PAL resin. To a half volume of the peptide, Fmoc-Gly was condensed to give 190 mg of Fmoc-GlyLeuArg(Pbf)Phe-PAL resin. After 76 mg of the product was subjected to Fmoc deprotection, 2 mL of DMF, 50 μL of AcOH, 46 mg of Fmoc-Phe-H and 8 mg of NaBH$_3$CN were added thereto, followed by shaking an hour. After the resin washed, 2 mL of DMF, 22 μL of DIEA and 18 μL of Z—Cl were added thereto and the mixture was shaken for 3 hours. After the resin washed, the peptide chain was extended on ABI 433A to give Boc-Tyr(Bu$^r$)Asn(Trt)Trp(Boc)Asn(Trt)Ser(But)PheΨ(CH$_2$NZ)GlyLeuArg(Pbf)Phe-PAL resin. Under ice cooling, 46 μL of TMS-Br, 42 μL of PhSMe, 38 μL of m-cresol, 18 μL of EDT and 227 μL of TFA were added to 15 mg of the peptide an the mixture was stirred for 2 hours. After the solvent was removed by distillation, diethyl ether was added to the residue, the resulting precipitate was centrifuged and the supernatant was removed. This procedure was repeated for washing. The residue was extracted with an aqueous acetic acid solution and the extract was filtered to remove the resin. Then, linear density gradient elution (30 minutes) was performed with eluants A/B: 72/28-62/38 using: 0.1% TFA in water and eluant B: 0.1% TFA-containing acetonitrile on preparative HPLC using YMC D-ODS-5-ST S-5 120A column (20×150 mm). The fractions containing the product were collected and lyophilized to give 2.0 mg of white powders.
Mass spectrum (M+H)+ 1288.7 (Calcd. 1288.7)
Elution time on HPLC: 18.2 min
Elution Conditions:
Column: Wakosil-II 5C18 HG (4.6×100 mm)
Eluant: linear density gradient elution with eluants A/B=100/0-0/70, using 0.1% TFA in water as eluant A and acetonitrile containing 0.1% TFA (35 mins.)
Flow rate: 1.0 ml/min.

Reference Example 1

Preparation of N-methyl-N,N'-Bis-Boc-1-guanylpyrazole

Under a nitrogen flow, 720 mg of 60% NaH in oil was dissolved in 20 mL of dry DMF and 20 mL of dry DMF solution of 5.59 g of N,N'-Bis-Boc-1-guanylpyrazole commercially available was added to the solution at 0° C., followed by stirring for 10 minutes. After 1.68 mL of methyl iodide was added thereto, the mixture was stirred at room temperature for 24 hours. After the solvent was distilled off, the residue was dissolved in AcOEt and the solution washed with 1N HCl aq. solution, satd. NaHCO$_3$ aq. solution and then satd. NaCl aq. solution. After drying over Na$_2$SO$_4$, the solvent was concentrated and the concentrate was purified by flush column chromatography (ethyl acetate/n-hexane=1/4) using silica gel 60 (200 mL) to give 5.35 g (yield 91.6%) of N-methyl-N,N'-bis-Boc-1-guanylpyrazole.
$^1$H NMR (300 MHz, CDCl$_3$): δ 8.00 (br s, 1H), 7.69 (br s, 1H), 6.42 (dd, 1H, J=2.7, 1.5 Hz), 3.25 (s, 3H), 1.53 (s, 9H), 1.30 (s, 9H)
Elemental analysis as C$_{15}$H$_{24}$N$_4$O$_4$
Calcd.: C, 55.54; H, 7.46; N, 17.27.
Found: C, 55.36; H, 7.48; N, 17.06.
Rf1: 0.64, Rf2: 0.79
Developing solvent for TLC: Rf1 (ethyl acetate/n-hexane=1/2), Rf2 (methanol/chloroform=2/98)
Elution time on HPLC: 26.7 min
Elution Conditions:
Column: Wakosil-II 5C18 HG (4.6×100 mm)
Eluant: linear density gradient elution with eluants A/B=100/0-20/80, using 0.1% TFA in water as eluant A and acetonitrile containing 0.1% TFA (40 mins.)
Flow rate: 1.0 ml/min.

Reference Example 2

Preparation of N-methyl-N,N'-Bis-Z-1-guanylpyrazole

In an argon atmosphere, 40 mg of 60% NaH in oil was dissolved in 5 mL of dry DMF and 5 mL of dry DMF solution of 380 mg of N,N'-Bis-Z-1-guanylpyrazole commercially available was added to the solution at 0° C., followed by stirring for 10 minutes. After 125 μL of methyl iodide was added thereto, the mixture was stirred at room temperature for 15 hours. After the solvent was distilled off, the residue was dissolved in AcOEt and the solution washed with 1N HCl aq. solution, satd. NaHCO$_3$ aq. solution and then satd. NaCl aq. solution. After drying over Na$_2$SO$_4$, the solvent was concentrated to give 393 mg of the crude product. From the crude product 170 mg was purified by flush column chromatography (ethyl acetate/n-hexane=1/4) using silica gel 60 (75 mL) to give 152 mg (yield 89.5%) of N-methyl-N,N'-bis-Z-1-guanylpyrazole.
$^1$H NMR (300 MHz, CDCl$_3$): δ 7.97 (br s, 1H), 7.61 (d, 1H, J=1.0 Hz), 7.37-7.32 (m, 4H), 7.29-7.26 (m, 4H), 7.16-7.13 (m, 2H), 6.36 (dd, 1H, J=2.8, 1.6 Hz), 5.18 (s, 2H), 5.04 (s, 2H), 3.22 (s, 3H)
Elemental analysis as C$_{21}$H$_{20}$N$_4$O$_4$
Calcd.: C, 64.28; H, 5.14; N, 14.28.
Found: C, 64.09; H, 5.24; N, 14.43.
Rf1: 0.50, Rf2: 0.86
Developing solvent for TLC: Rf1(ethyl acetate/n-hexane=1/2), Rf2(methanol/chloroform=2/98)
Elution time on HPLC: 28.9 min
Elution Conditions:
Column: Wakosil-II 5C18 HG (4.6×100 mm)
Eluant: linear density gradient elution with eluants A/B=100/0-20/80, using 0.1% TFA in water as eluant A and acetonitrile containing 0.1% TFA (40 mins.)
Flow rate: 1.0 ml/min.

Example 5

Synthesis Process E

Preparation of [Arg(Me)9]MS10 (Compound No. 82)

Using 480 mg of Fmoc-Phe-Rink Amide MBHA resin, which was prepared by introducing Fmoc-Phe into Rink Amide MBHA resin commercially available, the peptide chain was extended on ABI 433A to give 1080 mg of Boc-Tyr(Bu$^t$)Asn(Trt)Trp(Boc)Asn(Trt)Ser(Bu$^t$)PheGlyLeuOrn(Mtt)Phe-Rink Amide MBHA resin. To 540 mg of the peptide, 10 mL of TFA/TIS/DCM (Jan. 5, 1994) was added and the mixture was shaken for 50 minutes. The resin washed and then dried. After 2 mL of DMF, 49 mg of N-methyl-N,N'-bis-Boc-1-guanylpyrazole prepared in REFERENCE EXAMPLE 1 and 87 µL of DIEA were added to 2/5 volume of the resin, the mixture was shaken for 15 hours to give 220 mg of Boc-Tyr(Bu$^t$)Asn(Trt)Trp(Boc)Asn(Trt)Ser(Bu$^t$)PheGlyLeuArg(Boc$_2$,Me)Phe-Rink Amide MBHA resin. To 50 mg of the peptide, 1 mL of TFA/PhSMe/m-cresol/TIS/EDT (85/5/5/2.5/2.5) was added and the mixture was stirred for 2 hours. Diethyl ether was added to the reaction solution, the resulting precipitate was centrifuged and the supernatant was removed. This procedure was repeated for washing. The residue was extracted with an aqueous acetic acid solution and the extract was filtered to remove the resin. Then, linear density gradient elution (30 minutes) was performed with eluants A/B: 74/26-64/36 using: 0.1% TFA in water and eluant B: 0.1% TFA-containing acetonitrile on preparative HPLC using YMC D-ODS-5-ST S-5 120A column (20×150 mm). The fractions containing the product were collected and lyophilized to give 10.5 mg of white powders.

Mass spectrum (M+H)$^+$ 1316.5 (Calcd. 1316.7)
Elution time on HPLC: 20.1 min
Elution Conditions:
Column: Wakosil-II 5C18 HG (4.6×100 mm)
Eluant: linear density gradient elution with eluants A/B=100/0-30/70, using 0.1% TFA in water as eluant A and acetonitrile containing 0.1% TFA (35 mins.)
Flow rate: 1.0 ml/min.

N-Methyl-N,N'-bis-Boc-1-guanylpyrazole used to convert the amino acid at the 9-position into N$^\omega$-methylated Arg in this EXAMPLE is a reagent useful for producing peptides containing N$^\omega$-methylated Arg, and is advantageously used also in general peptides to produce peptides containing N$^\omega$-methylated Arg characterized by reacting N-methyl-N,N'-bis-Boc-1-guanylpyrazole with Orn in peptides followed by deprotection.

Furthermore, blood stability is improved by converting Arg into N$^\omega$-methylated Arg not only in the N$^\omega$-methylated Arg-containing peptide obtained in this EXAMPLE but also in general peptides. Therefore, substituents on the side chain of N$^\omega$-methylated Arg are useful for a method of enhancing blood stability, which comprises converting Arg in a peptide into N$^\omega$-methylated Arg.

Moreover, a method of enhancing blood stability, which comprises introducing one or two (preferably one) alkyl group, preferably $C_{1-4}$ alkyl group, more preferably methyl group into the side chain of Arg in the Arg-containing peptide, may be provided. Herein, the Arg-containing peptide includes, for example, a peptide having a partial peptide characterized by the structure -Arg-XXX-, wherein XXX represents an amino acid having optionally substituted aromatic ring group into the side chain, preferably Phe, Trp, Tyr, etc.

The N$^\omega$-methylated Arg-containing peptides can also be produced using not only N-methyl-N,N'-bis-Boc-1-guanylpyrazole but N-methyl-N,N'-bis-Z-1-guanylpyrazole prepared in REFERENCE EXAMPLE 2.

Example 6

Synthesis Process F

Preparation of [6Ψ7,CSNH]MS10 (Compound No. 166)

In 10 mL of DMF, 503 mg of HCl H-Gly-OBu$^t$ was dissolved and 1162 mg of Fmoc-Phe, 608 mg of HOBt, 1874 mg of PyBOP and 784 µL of DIEA were added at 0° C., followed by stirring for 4 hours. The solvent was concentrated and the concentrate was dissolved in AcOEt. The solution was then washed with 1N HCl aq. solution, satd. NaHCO$_3$ aq. solution and then satd. NaCl aq. solution. After drying over Na$_2$SO$_4$, the solvent was concentrated and diethyl ether-petroleum ether was added to give 1.48 g (yield 99%) of Fmoc-PheGly-OBu$^t$ as the precipitate. After 250 mg of the product was dissolved in 10 mL of toluene, 404 mg of Lawesson's reagent was added to the solution, followed by stirring at 80° C. for 2 hours. The solvent was concentrated and the concentrate was dissolved in AcOEt. The solution was then washed with 1N HCl aq. solution, satd. NaHCO$_3$ aq. solution and then satd. NaCl aq. solution. After drying over Na$_2$SO$_4$, the solvent was concentrated and the concentrate was purified by flush column chromatography. Diethyl ether-petroleum ether was added to the eluate to give 207 mg (yield 80%) of Fmoc-PheΨ(CSNH)Gly-OBu$^t$ as the precipitate. To 103 mg of the product, TFA/H$_2$O (95/5) was added and the mixture was stirred for an hour. After the solvent was concentrated, diethyl ether was added to give 82.4 mg (yield 90%) of Fmoc-PheΨ(CSNH)Gly-OH as the precipitate. Using Fmoc-Phe-PAL resin, which was prepared by introducing Fmoc-Phe into commercially available PAL resin, the peptide chain was extended on ABI 433A and 80 mg of Fmoc-LeuArg(Pbf)Phe-PAL resin thus extended was subjected to Fmoc deprotection. Then 35 mg of Fmoc-PheΨ(CSNH)Gly-OH, 47 mg of PyBrop, 14 mg of HOAt and 35 µL of DIEA were added to the resin, followed by shaking for 15 hours. After the resin washed, the peptide chain was extended on ABI 433A to give Boc-Tyr(Bu$^t$)Asn(Trt)Trp(Boc)Asn(Trt)Ser(Bu$^t$)PheΨ(CSNH)GlyLeuArg(Pbf)Phe-PA L resin. To 15 mg of the product, 200 µL of TFA/PhSMe/m-cresol/TIS/EDT (85/5/5/2.5/2.5) was added, followed by stirring for 2 hours. Diethyl ether was added to the reaction solution, the resulting precipitate was centrifuged and the supernatant was removed. This procedure was repeated for washing. The residue was extracted with an aqueous acetic acid solution and the extract was filtered to remove the resin. Then, linear density gradient elution (60 minutes) was performed with eluants A/B: 77/23-57/43 using: 0.1% TFA in water and eluant B: 0.1% TFA-containing acetonitrile on preparative HPLC using YMC D-ODS-5-ST S-5 120A column (20×150 mm). The fractions containing the product were collected and lyophilized to give 1.0 mg of white powders.

Mass spectrum (M+H)$^+$ 1318.7 (Calcd. 1318.6)
Elution time on HPLC: 20.8 min
Elution Conditions:
Column: Wakosil-II 5C18 HG (4.6×100 mm)
Eluant: linear density gradient elution with eluants A/B=100/0-30/70, using 0.1% TFA in water as eluant A and acetonitrile containing 0.1% TFA (35 mins.)
Flow rate: 1.0 ml/min.

Example 7

Synthesis Process G

Preparation of [AzaGly7]MS10 (Compound No. 176)

Using 321 mg of Fmoc-Phe-PAL resin, which was prepared by introducing Fmoc-Phe into commercially available PAL resin, the peptide chain was extended on ABI 433A and 80 mg of Fmoc-LeuArg(Pbf)Phe-PAL resin thus extended was subjected to Fmoc deprotection. After 2 mL of THF and 16 mg of CDI were added, the mixture was shaken for 2 hours.

Then 6 μL of hydrazine monohydrate was added to the mixture. The mixture was shaken for an hour and the resin was then washed. After 39 mg of Fmoc-Phe, 93 mg of PyBrop, 27 mg of HOAt and 105 μL of DIEA were added to the system, followed by shaking for 2 hours. After the resin washed, the peptide chain was extended on ABI 433A to give Boc-Tyr(Bu$^t$)Asn(Trt)Trp(Boc)Asn(Trt)Ser(Bu$^t$)PheAzaGlyLeuArg(Pbf)Phe-PAL resin. To 25 mg of the product, 1 mL of TFA/PhSMe/m-cresol/TIS/EDT (85/5/5/2.5/2.5) was added, followed by shaking for 2 hours. Diethyl ether was added to the reaction solution, the resulting precipitate was centrifuged and the supernatant was removed. This procedure was repeated for washing. The residue was extracted with an aqueous acetic acid solution and the extract was filtered to remove the resin. Then, linear density gradient elution (30 minutes) was performed with eluants A/B: 74/26-64/36 using: 0.1% TFA in water and eluant B: 0.1% TFA-containing acetonitrile on preparative HPLC using YMC D-ODS-5-ST S-5 120A column (20×150 mm). The fractions containing the product were collected and lyophilized to give 5.5 mg of white powders.

Mass spectrum (M+H)$^+$ 1303.3 (Calcd. 1303.6)

Elution time on HPLC: 18.9 min

Elution Conditions:

Column: Wakosil-II 5C18 HG (4.6×100 mm)

Eluant: linear density gradient elution with eluants A/B=100/0-30/70, using 0.1% TFA in water as eluant A and acetonitrile containing 0.1% TFA (35 mins.)

Flow rate: 1.0 ml/min.

Example 8

Synthesis Process H

Preparation of [D-Tyr1,AzaGly7,Arg(Me)9]MS10 (Compound No. 232)

Fmoc-Phe,Fmoc-Orn(Mtt) was introduced into 4 g (0.55 mmol/g) of Rink Amide MBHA resin commercially available to prepare Fmoc-Orn(Mtt)-Phe-Rink Amide MBHA resin, and 50 mL of TFA/TIS/DCM (Jan. 5, 1994) was added to the resin, followed by shaking for 50 minutes. After the resin washed, 40 mL of DCM and 2.27 g of N-methyl-N,N'-bis-Boc-1-guanylpyrazole prepared in REFERENCE EXAMPLE 1 were added to the resin. DIEA was added to the mixture to adjust pH of the solution to 9. The mixture was shaken for 15 hours to give 4.74 g of Fmoc-Arg(Boc$_2$,Me)Phe-Rink Amide MBHA resin. Separately, 145 mg of Fmoc-NHNH$_2$HCl was suspended in 10 mL of THF. Under ice cooling, 89 mg of CDI and 87 mL of DIEA were added to the suspension, followed by stirring at room temperature for an hour. Under ice cooling, a solution of 224 mg of H-Leu-OBu$^t$ HCl in 5 mL of DMF 5 mL was added to the mixture. While reverting to room temperature, the mixture was stirred for 18 hours. After the solvent was distilled off, the residue was dissolved in AcOEt and the solution washed with 1N HCl aq. solution, satd. NaHCO$_3$ aq. solution and then satd. NaCl aq. solution. After drying over Na$_2$SO$_4$, the solvent was concentrated and the concentrate was purified by flush column chromatography to give 230 mg (yield 99%) of Fmoc-AzaGly-Leu-OBu$^t$. To 187 mg of the product, 10 mL of TFA/H$_2$O (9/1) was added, followed by stirring for an hour. After the solvent was distilled off, the residue was dissolved in AcOEt and the solution washed with satd. NaCl aq. solution. After drying over Na$_2$SO$_4$, the solvent was concentrated and diethyl ether was added to give 143 mg of Fmoc-AzaGly-Leu-OH as the precipitate (yield 87%). The resulting Fmoc-AzaGly-Leu-OH, Trt-Phe was introduced into Fmoc-Arg(Boc$_2$,Me)Phe-Rink Amide MBHA resin. To the thus prepared Trt-Phe-AzaGly-Leu-Arg(Boc$_2$,Me)Phe-Rink Amide MBHA resin, 50 mL of TFA/TIS/DCM (Jan. 5, 1994) was added and the mixture was shaken for 50 minutes. After the resin washed and neutralized, Fmoc-Ser(Bu$^t$) and then Fmoc-Asn(Trt) were introduced thereinto. Using 80.3 mg of the resulting Fmoc-Asn(Trt)Ser(Bu$^t$)Phe-AzaGly-LeuArg(Boc$_2$,Me)Phe-Rink Amide MBHA resin, the peptide chain was extended to give 97.2 mg of H-$_D$-Tyr(But)Asn(Trt)Trp(Boc)Asn(Trt)Ser(But)Phe-AzaGly-LeuArg(Boc$_2$,Me)Phe-Rink Amide MBHA resin.

To the resin obtained, 1 mL of TFA/PhSMe/m-cresol/H$_2$O/TIS/EDT (80/5/5/5/2.5/2.5) was added, followed by stirring for 90 minutes. Diethyl ether was added to the reaction solution, the resulting precipitate was centrifuged and the supernatant was removed. This procedure was repeated for washing. The residue was extracted with an aqueous acetic acid solution and the extract was filtered to remove the resin. Then, linear density gradient elution (60 minutes) was performed with eluants A/B: 76/24-66/34 using: 0.1% TFA in water and eluant B: 0.1% TFA-containing acetonitrile on preparative HPLC using YMC SH-343-5 S-5, 120A column (20×250 mm). The fractions containing the product were collected and lyophilized to give 11.7 mg of white powders.

Mass spectrum (M+H)$^+$ 1317.0 (Calcd. 1317.6)

Elution time on HPLC: 21.0 min

Elution Conditions:

Column: Wakosil-II 5C18 HG (4.6×100 mm)

Eluant: linear density gradient elution with eluants A/B=100/0-30/70, using 0.1% TFA in water as eluant A and acetonitrile containing 0.1% TFA (35 mins.)

Flow rate: 1.0 ml/min.

Example 9

Synthesis Process I

Preparation of des(1-3)-3-(3-pyridyl)propionyl-[AzaGly7,Arg(Me)9]MS10 (Compound No. 322)

After 48.2 mg of Fmoc-Asn(Trt)Ser(Bu$^t$)Phe-AzaGly-LeuArg(Boc$_2$,Me)Phe-Rink Amide MBHA resin prepared in EXAMPLE 8 was subjected to Fmoc deprotection, the resin was treated with 15.2 mg of 3-(3-pyridyl)propionic acid commercially available, 15.9 μL of DIPCDI and 200 μL of 0.5M HOAt/DMF at room temperature for 90 minutes. After the resin obtained washed and dried, 1 mL of TFA/PhSMe/m-cresol/H$_2$O/TIS/EDT (80/5/5/5/2.5/2.5) was added to the resin, followed by stirring for 90 minutes. Diethyl ether was added to the reaction solution, the resulting precipitate was centrifuged and the supernatant was removed. This procedure was repeated for washing. The residue was extracted with an aqueous acetic acid solution and the extract was filtered to remove the resin. Then, linear density gradient elution (60 minutes) was performed with eluants A/B: 80/20-60/40 using: 0.1% TFA in water and eluant B: 0.1% TFA-containing acetonitrile on preparative HPLC using YMC SH-343-5 S-5, 120A column (20×250 mm). The fractions containing the product were collected and lyophilized to give 6.0 mg of white powders.

Mass spectrum (M+H)$^+$ 987.4 (Calcd. 987.5)

Elution time on HPLC: 8.1 min

Elution Conditions:
Column YMC-AM301 (4.6×100 mm)
Eluant: linear density gradient elution with eluants A/B=80/20-30/70, using 0.1% TFA in water as eluant A and acetonitrile containing 0.1% TFA (25 mins.)
Flow rate: 1.0 ml/min.

Example 10

Synthesis Process J

Preparation of des(1-2)-Amidino-[AzaGly7,Arg(Me)9]MS10 (Compound No. 273)

After Fmoc-Trp(Boc) was introduced into 48.2 mg of Fmoc-Asn(Trt)Ser(Bu$^t$)Phe-AzaGly-LeuArg(Boc$_2$,Me)Phe-Rink Amide MBHA resin prepared in EXAMPLE 8, the resin was subjected to Fmoc deprotection to give H-Trp(Boc)Asn(Trt)Ser(Bu$^t$)Phe-AzaGly-LeuArg(Boc$_2$,Me)Phe-Rink Amide MBHA resin. The resin obtained was treated in DMF with 29.3 mg of N,N'-bis-Boc-1-guanylpyrazole and 34.8 µL of DIEA for 14 hours to give Amidino-Trp(Boc)Asn(Trt)Ser(Bu$^t$)Phe-AzaGly-LeuArg(Boc$_2$,Me)Phe-Rink Amide MBHA resin. After the resin obtained washed and dried, 1 mL of TFA/PhSMe/m-cresol/H$_2$O/TIS/EDT (80/5/5/5/2.5/2.5) was added, followed by stirring for 90 minutes. Diethyl ether was added to the reaction solution, the resulting precipitate was centrifuged and the supernatant was removed. This procedure was repeated for washing. The residue was extracted with an aqueous acetic acid solution and the extract was filtered to remove the resin. Then, linear density gradient elution (60 minutes) was performed with eluants A/B: 78/22-58/42 using: 0.1% TFA in water and eluant B: 0.1% TFA-containing acetonitrile on preparative HPLC using YMC SH-343-5 S-5, 120A column (20×250 mm). The fractions containing the product were collected and lyophilized to give 0.6 mg of white powders.

Mass spectrum (M+H)$^+$ 1082.3 (Calcd. 1082.6)
Elution time on HPLC: 11.4 min
Elution Conditions:
Column: YMC-AM301 (4.6×100 mm)
Eluant: linear density gradient elution with eluants A/B=80/20-30/70, using 0.1% TFA in water as eluant A and acetonitrile containing 0.1% TFA (25 mins.)
Flow rate: 1.0 ml/min.

Example 11

Synthesis Process K

Preparation of [6Ψ7,NHCO,D-Tyr1,Arg(Me)9]MS10 (Compound No. 319)

In 30 mL of MeCN, 5.99 g of Z-Phe was dissolved and 3.94 g of HONB and 4.59 g of WSCD HCl were added to the solution at 0° C., followed by stirring at room temperature for 4 hours. While keeping at 0° C., 3.4 mL of 25% NH$_3$ aq. solution and 10 mL of DMF were added to the mixture, followed by stirring for 4 hours. After the solvent was distilled off, the residue was dissolved in AcOEt and the solution washed with 1N HCl aq. solution, satd. NaHCO$_3$ aq. solution and then satd. NaCl aq. solution. After drying over Na$_2$SO$_4$, the solvent was concentrated and diethyl ether was added to give 1.48 g (yield 99%) of Z-Phe-NH$_2$ as the precipitate. After 1.94 g of [Bis(trifluoroacetoxy)iodo]benzene was dissolved in 20 mL of MeCN and 5 mL of H$_2$O, 890 mg of Z-Phe-NH$_2$ prepared above and 972 µL of pyridine were added to the precipitate at 0° C., followed by stirring at room temperature for 15 hours. After the solvent was concentrated, the concentrate was subjected to liquid-liquid separation with diethyl ether-1N HCl aq. solution and the 1N HCl aq. solution layer was concentrated and then dried. Its half volume was dissolved in 5 mL of DMF, and 486 µL of mono-tert-butyl malonate and 540 mg of HOBt were added to the solution. Then, 2.08 g of PyBOP and 1394 µL of DIEA were added at 0° C. to the mixture, followed by stirring at room temperature for 15 hours. After the solvent was distilled off, the residue was dissolved in AcOEt and the solution washed with 1N HCl aq. solution, satd. NaHCO$_3$ aq. solution and then satd. NaCl aq. solution. After drying over Na$_2$SO$_4$, the solvent was concentrated and the concentrate was purified by flush column chromatography. Diethyl ether-petroleum ether was added to give 304 mg (yield 33%) of Z-PheΨ(NHCO)Gly-OBu$^t$ as the precipitate. After 154 mg of the product was dissolved in 20 mL of MeOH, 10% Pd—C was added to the solution, followed by catalytic hydrogenation for 2 hours in a hydrogen flow. After removal of the catalyst by filtration, the solvent was concentrated and dried. The residue was dissolved in 10 mL of MeCN 10 mL and 152 mg of Fmoc-OSu and 78 µL of DIEA were added to the solution, followed by stirring for 15 hours. After the solvent was distilled off, the residue was dissolved in AcOEt and the solution washed with 1N HCl aq. solution, satd. NaHCO$_3$ aq. solution and then satd. NaCl aq. solution. After drying over Na$_2$SO$_4$, the solvent was concentrated and diethyl ether-petroleum ether was added to give 127 mg (yield 68%) of Fmoc-PheΨ(NHCO)Gly-OBu$^t$ as the precipitate. Fmoc-Leu was introduced into 63 mg of Fmoc-Arg(Boc$_2$,Me)Phe-Rink Amide MBHA resin prepared in EXAMPLE 10. After Fmoc deprotection, Fmoc-PheΨ(NHCO)Gly-OH (prepared by treating 25 mg of Fmoc-PheΨ(NHCO)Gly-OBu$^t$ with TFA for 3 minutes), 300 µL of 0.5M HOAt, 78 mg of PyAOP and 52 µL of DIEA were added to the resin, followed by shaking for 6 hours. After the resin washed, 2 mL of DMF, 9 µL of DIEA and 12 µL of Ac$_2$O were added to the resin, followed by shaking for 30 minutes. After the resin washed, the peptide chain was extended on ABI 433A to give Boc-D-Tyr(Bu$^t$)Asn(Trt)Trp(Boc)Asn(Trt)Ser(Bu$^t$)PheΨ(NHCO)GlyLeuArg(Boc$_2$,Me)Phe-Rink Amide MBHA resin. To 34 mg of the product, 200 µL of TFA/PhSMe/m-cresol/TIS/EDT (85/5/5/2.5/2.5) was added, followed by stirring for 2 hours. Ether was added to the reaction solution, the resulting precipitate was centrifuged and the supernatant was removed. This procedure was repeated for washing. The residue was extracted with an aqueous acetic acid solution and the extract was filtered to remove the resin. Then, linear density gradient elution (30 minutes) was performed with eluants A/B: 76/24-66/34 using: 0.1% TFA in water and eluant B: 0.1% TFA-containing acetonitrile on preparative HPLC using YMC D-ODS-5-ST S-5 120A column (20×150 mm). The fractions containing the product were collected and lyophilized to give 0.7 mg of white powders.

Mass spectrum (M+H)$^+$ 1316.3 (Calcd. 1316.7)
Elution time on HPLC: 18.7 min
Elution Conditions:
Column: Wakosil-II 5C18 HG (4.6×100 mm)
Eluant: linear density gradient elution with eluants A/B=100/0-0/70, using 0.1% TFA in water as eluant A and acetonitrile containing 0.1% TFA (35 mins.)
Flow rate: 1.0 ml/min.

Example 12

Synthesis Process L

Preparation of [N((CH$_2$)$_3$Gn)Gly9]-MS10 (Compound No. 218)

Using 192 mg of Fmoc-Phe-Rink Amide MBHA resin, the peptide chain was extended on ABI 433A to give Fmoc-GlyPhe-Rink Amide MBHA resin. After a 1/4 volume of the product was subjected to Fmoc deprotection, 2 mL of DMF, 50 µL of AcOH, 5 mg of Boc-β-Ala-H and 16 mg of NaBH$_3$CN were added thereto and the mixture was shaken for 30 minutes. After the resin washed, 71 mg of Fmoc-Leu, 56 mg of CIP, 27 mg of HOAt and 105 mL of DIEA were added, followed by shaking for 15 hours. After the resin washed, the peptide chain was extended on ABI 433A to give Z-Tyr(Bzl)Asn(Trt)Trp(Boc)Asn(Trt)Ser(Bu$^t$)PheGlyLeuN((CH$_2$)$_3$NHBoc)GlyPhe-Rink Amide MBHA resin. To the product, 1 mL of TFA/PhOH/H$_2$O/TIS/EDT (87.5/5/2.5/2.5/2.5) was added and the mixture was stirred for 2 hours. After the resin was removed by filtration and then concentrated, ether was added to the concentrate. A half volume of the resulting precipitate was dissolved in 500 µL of DMF, 9 mg of 1H-pyrazole-1-carboxamidine hydrochloride and 22 mL of DIEA were added to the solution, followed by stirring for 15 hours. The solvent was distilled off and ether was added to precipitate. Under ice cooling, 60 µL of PhSMe, 56 µL of m-cresol, 26 µL of EDT, 337 µL of TFA and 65 µL of TMSBr were added to the mixture, followed by stirring for 2 hours. After the solvent was distilled off, ether was added to the residue, the resulting precipitate was centrifuged and the supernatant was removed. This procedure was repeated for washing. The residue was extracted with an aqueous acetic acid solution and the extract was filtered to remove the resin. Then, linear density gradient elution (60 minutes) was performed with eluants A/B: 74/26-64/36 using: 0.1% TFA in water and eluant B: 0.1% TFA-containing acetonitrile on preparative HPLC using YMC D-ODS-5-ST S-5 120A column (20×150 mm). The fractions containing the product were collected and lyophilized to give 1.8 mg of white powders.

Mass spectrum (M+H)$^+$ 1302.5 (Calcd. 1302.7)
Elution time on HPLC: 18.6 min
Elution Conditions:
Column: Wakosil-II 5C18 HG (4.6×100 mm)
Eluant: linear density gradient elution with eluants A/B=100/0-30/70, using 0.1% TFA in water as eluant A and acetonitrile containing 0.1% TFA (35 mins.)
Flow rate: 1.0 ml/min.

Example 13

Synthesis Process M

Preparation of MS10 (Compound No. 3)

Commercially available p-methyl BHA resin (0.77 mmole/g resin) was charged in a reaction tank of peptide synthesizer ABI 430A. Thereafter, Boc-Phe.Boc-Arg(Tos), Boc-Leu.Boc-Gly, Boc-Phe.Boc-Ser(Bzl), Boc-Asn.Boc-Trp(For) and Boc-Asn.Boc-Tyr(Br-Z) were introduced into the resin in this order according to the Boc-strategy (DCC-HOBt) peptide synthesis to give the desired protected peptide resin. The resin, 0.11 g, was stirred at 0° C. for 60 minutes in 10 ml of anhydrous hydrogen fluoride containing 1 ml of p-cresol and 1.2 ml of 1,4-butanediol. Thereafter the hydrogen fluoride was distilled off in vacuum. Diethyl ether was added to the residue and the precipitate was filtrated. To the precipitate 50% acetic acid aqueous solution was added for extraction and insoluble matters were removed. After the extract was sufficiently concentrated, the concentrate was applied to Sephadex (trade name) G-25 column (2.0×80 cm) filled with 50% acetic acid aqueous solution followed by development with the same solvent. The main fractions were collected and lyophilized to give 40 mg of white powders. A half volume of the powders was applied to column chromatography (2.6×60 cm) packed with LiChroprep (trade name) RP-18 followed by washing with 200 ml of water containing 0.1% TFA. Then linear density gradient elution was performed with 300 ml of 0.1% TFA in water and 300 ml of 0.1% TFA-containing 33% acetonitrile. The main fractions were collected and lyophilized to give 2.2 mg of the desired peptide.

Mass spectrum (M+H) 1302.5 (Calcd. 1302.6)
Elution time on HPLC: 18.7 min
Elution Conditions:
Column: Wakosil-II 5C18T 4.6×100 mm
Eluant: linear density gradient elution with eluants A/B=95/5-45/55, using 0.1% TFA in water as eluant A and acetonitrile containing 0.1% TFA (25 mins.)
Flow rate: 1.0 ml/min.

Example 14

Synthesis Process N

Preparation of des(1-3)-2-(Indol-3-yl)ethylcarbamoyl-[AzaGly7,Arg(Me)9]MS10 (Compound No. 279)

Fmoc-Asn(Trt)Ser(Bu$^t$)PheAzaGlyLeuArg(Me,Boc$_2$)Phe-Rink-Amide MBHA resin prepared in EXAMPLE 8 was subjected to Fmoc deprotection. To 64 mg (20 µmol) of H-Asn(Trt)Ser(Bu$^t$)PheAzaGlyLeuArg(Me,Boc$_2$)Phe-Rink Amide MBHA resin, 1.5 mL of THF and 13 mg of CDI were added, followed by shaking for 2 hours. After 32 mg of tryptamine hydrochloride, 28 µL of DIEA and 500 µL of DMF were added to the mixture, followed by shaking for 24 hours. Thereafter the resin washed to give 2-(Indol-3-yl)ethylcarbamoyl-Asn(Trt)Ser(But)PheAzaGlyLeuArg(Me,Boc$_2$)Phe-Rink Amied MBHA resin. To 15 mg of the product, 200 µL of TFA/PhSMe/m-cresol/TIS/EDT (85/5/5/2.5/2.5) was added, followed by stirring for 2 hours. Ether was added to the reaction solution, the resulting precipitate was centrifuged and the supernatant was removed. This procedure was repeated for washing. The residue was extracted with an aqueous acetic acid solution and the extract was filtered to remove the resin. Then, linear density gradient elution (60 minutes) was performed with eluants A/B: 69/31-59/41 using: 0.1% TFA in water and eluant B: 0.1% TFA-containing acetonitrile on preparative HPLC using YMC D-ODS-5-ST S-5 120A column (20×150 mm). The fractions containing the product were collected and lyophilized to give 1.1 mg of white powders.

Mass spectrum (M+H)$^+$ 1040.2 (Calcd. 1040.5)
Elution time on HPLC: 20.1 min
Elution Conditions:
Column: Wakosil-II 5C18 HG (4.6×100 mm)
Eluant: linear density gradient elution with eluants A/B=100/0-0/50, using 0.1% TFA in water as eluant A and acetonitrile containing 0.1% TFA (25 mins.)
Flow rate: 1.0 ml/min.

Example 15

Preparation of Fmoc-AzaGly-Leu-Arg(Boc₂,Me)-Trp(Boc)-Rink Amide MBHA resin

Commercially available Rink Amide MBHA resin, 5 g (0.4 mmol/g), was swollen in DMF, and treated with 50 ml of 20% piperidine/DMF solution for 20 minutes to remove the Fmoc group. After the resin obtained washed with DMF, Trp(Boc) was introduced by treating the resin at room temperature with 4.213 g (8 mmol) of Fmoc-Trp(Boc)-OH, 1.272 mL (8 mmol) of DIPCDI and 16 mL (8 mmol) of 0.5M HOAt/DMF solution for 90 minutes to give Fmoc-Trp(Boc)-Rink Amide MBHA resin. In a similar manner, Orn(Mtt) was introduced to give 2 mmol of Fmoc-Orn(Mtt)-Trp(Boc)-Rink Amide MBHA resin. After the resin obtained washed and swollen with DCM, 50 mL of TFA/TIS/DCM (Jan. 5, 1994) was added, the mixture was shaken for 10 minutes and the solution was distilled off. This procedure was repeated until yellow coloration caused by free Mtt group in a TFA/TIS/DCM (Jan. 5, 1994) solution disappeared when the solution was added, thus the Mtt group was removed.

The resulting Fmoc-Orn-Trp(Boc)-Rink Amide MBHA resin was neutralized with 5%-DIEA/DCM solution. After washing with DCM, 25 mL of DCM-TFE (4:1) and 1.946 g (6 mmol) of N-methyl-N,N'-bis-Boc-1-guanylpyrazole obtained in REFERENCE EXAMPLE 1 were added to the resin. DIEA was added to the mixture to adjust pH of the solution to 10, and the mixture was shaken for 15 hours to give 6.195 g of Fmoc-Arg(Boc₂,Me)-Trp(Boc)-Rink Amide MBHA resin. Fmoc-Leu was introduced into the obtained resin as in the same manner described above. The resin was divided in half and the Fmoc group was removed from the thus obtained Fmoc-Leu-Arg(Boc₂,Me)-Trp(Boc)-Rink Amide MBHA resin (1 mmol) to give H-Leu-Arg(Boc₂,Me)-Trp(Boc)-Rink Amide MBHA resin (1 mmol).

Separately, 1.745 g (6 mmol) of Fmoc-NHNH₂HCl was suspended in 20 mL of DMF-THF (4:1). Under ice cooling, 973 mg (6 mmol) of CDI and 2.09 mL (12 mmol) of DIEA were added to the suspension, followed by stirring at room temperature for an hour. The resulting reaction solution was added to H-Leu-Arg(Boc₂,Me)-Trp(Boc)-Rink Amide MBHA resin described above, followed by stirring at room temperature for 15 hours. After completion of the reaction, the resin washed and dried to give 3.314 g of Fmoc-AzaGly-Leu-Arg(Boc₂,Me)-Trp(Boc)-Rink Amide MBHA resin.

Example 16

Synthesis Process O

Preparation of des(1)-[D-Tyr2,D-Pya(4)₃,AzaGly7,Arg(Me)9,Trp10]MS10 (Compound No. 385)

After 100 mg (0.03 mmol) of Fmoc-AzaGly-Leu-Arg(Boc₂,Me)-Trp(Boc)-Rink Amide MBHA resin was swollen in DMF, the resin was treated with 2 ml of 20% piperidine/DMF solution for 20 minutes to remove the Fmoc group. After the resin obtained washed with DMF, Phe was introduced by treating the resin with 77.5 g (0.2 mmol) of Fmoc-Phe-OH, 31.8 µL (0.2 mmol) of DIPCDI and 0.4 mL (0.2 mmol) of 0.5M HOAt/DMF solution at room temperature for 90 minutes. In a similar manner, Ser(ᵗBu) and Asn(Trt) were introduced to give Fmoc-Asn(Trt)-Ser(ᵗBu)-Phe-AzaGly-Leu-Arg(Boc₂,Me)-Trp(Boc)-Rink Amide MBHA resin. The obtained resin was subjected to Fmoc deprotection and treated with 77.6 mg (0.2 mmol) of Fmoc-D-Pya(4)-OH, 104.2 mg (0.2 mmol) of PyAOP, 400 µL (0.2 mmol) of 0.5M HOAt/DMF and 174.2 µL (0.2 mmol) of DIEA at room temperature for 90 minutes to introduce $_D$-Pya(4) and then D-Tyr(ᵗBu), followed by Fmoc deprotection. Thus, 135 mg of H-$_D$-Tyr(ᵗBu)-D-Pya(4)-Asn(Trt)-Ser(ᵗBu)-Phe-AzaGly-Leu-Arg(Boc₂,Me)-Trp(Boc)-Rink Amide MBHA resin was obtained.

To the resin obtained, 1 mL of TFA/PhSMe/m-cresol/H₂O/TIS/EDT (80/5/5/5/2.5/2.5) was added, followed by stirring for 90 minutes. Diethyl ether was added to the reaction solution, the resulting precipitate was centrifuged and the supernatant was removed. This procedure was repeated twice for washing. The residue was extracted with an aqueous acetic acid solution and the extract was filtered to remove the resin. Then, linear density gradient elution (60 minutes) was performed at a flow rate of 15 ml/min with eluants A/B: 79/21-69/31 using: 0.1% TFA in water and eluant B: 0.1% TFA-containing acetonitrile on preparative HPLC using YMC Pack R&D-ODS-5-B S-5, 120A column (30×250 mm). The fractions containing the product were collected and lyophilized. The white powders obtained were dissolved in 10 mL of water and 100 µL of ion exchange resin BioRAD AG1×8 AcO⁻ form was added to the solution. While manually stirring the solution sometimes, the reaction solution was settled for an hour. The solution was filtered through a membrane filter to remove the resin and give 6.6 mg of white powders as the acetate.

Mass spectrum (M+H)⁺ 1204.5 (Calcd. 1204.6)
Elution time on HPLC: 8.2 min
Elution Conditions:
Column YMC-AM301 (4.6×100 mm)
Eluant: linear density gradient elution with eluants A/B=80/20-30/70, using 0.1% TFA in water as eluant A and acetonitrile containing 0.1% TFA (25 mins.)
Flow rate: 1.0 ml/min.

Example 17

Synthesis Process P

Preparation of des(1-6)-Dibenzylcarbamoyl-[AzaGly7,Arg(Me)9,Trp10]MS10 (Compound No. 393)

After 35.2 mg (0.015 mmol) of Fmoc-AzaGly-Leu-Arg(Boc₂,Me)-Trp(Boc)-Rink Amide MBHA resin was swollen in DMF, the resin was treated with 2 ml of 20% piperidine/DMF solution for 20 minutes to remove the Fmoc group. Separately, 19.2 µL (0.1 mmol) of dibenzylamine was dissolved in THF. Under ice cooling, 16.2 mg (0.1 mmol) of CDI and 2.6 µL (0.015 mmol) of DIEA were added to the solution, followed by stirring at room temperature for an hour. After Fmoc deprotection, the resulting solution was added to H-AzaGly-Leu-Arg(Boc₂,Me)-Trp(Boc)-Rink Amide MBHA resin, followed by stirring at room temperature for 15 hours.

To Bzl₂NCO-AzaGly-Leu-Arg(Boc₂,Me)-Trp(Boc)-Rink Amide MBHA resin obtained, 1 mL of TFA/PhSMe/m-cresol/H₂O/TIS/EDT (80/5/5/5/2.5/2.5) was added, and the mixture was stirred for 90 minutes. Diethyl ether was added to the reaction solution, the resulting precipitate was centrifuged and the supernatant was removed. This procedure was repeated twice for washing. The residue was extracted with an aqueous acetic acid solution and the extract was filtered to remove the resin. Then, linear density gradient elution (60 minutes) was performed at a flow rate of 8 ml/min. with eluants A/B: 63/37-53/47 using: 0.1% TFA in water and eluant B: 0.1% TFA-containing acetonitrile on preparative HPLC using YMC SH-343-5 S-5, 120A column (20×250 mm). The fractions containing the product were collected and lyophilized. The white powders obtained were dissolved in 10 mL of water and 100 µL of ion exchange resin BioRAD AG1×8 AcO⁻ form was added to the solution. While manually stirring the solution sometimes, the reaction solution was settled for an hour. The solution was filtered through a membrane filter to remove the resin and give 2.2 mg of white powders as the acetate.

Mass spectrum $(M+H)^+$ 768.7 (Calcd. 768.4)

Elution time on HPLC: 16.9 min

Elution Conditions:

Column YMC-AM301 (4.6×100 mm)

Eluant: linear density gradient elution with eluants A/B=80/20-30/70, using 0.1% TFA in water as eluant A and acetonitrile containing 0.1% TFA (25 mins.)

Flow rate: 1.0 ml/min.

Example 18

Synthesis Process Q

Preparation of des(1-5)-Benzoyl-[6Ψ7,CH₂O,Arg(Me)9,Trp10]MS10 (Compound No. 421)

After 1.80 g of Z-Phe was dissolved in 20 mL of MeOH, 下 73 mg of DMAP and 1.38 g of WSCD HCl were added to the solution at 0° C., followed by stirring at 4° C. for 12 hours. The solvent was concentrated and the concentrate was dissolved in AcOEt. The solution was then washed with 1N HCl aq. solution, satd. NaHCO₃ aq. solution and then satd. NaCl aq. solution. After drying over Na₂SO₄, the solvent was concentrated to give Z-Phe-OMe as oil. After dissolving in 20 mL of dry THF, 196 mg of LiBH₄ was added to the solution, followed by stirring at room temperature for 15 hours. The solvent was concentrated and the residue was dissolved in AcOEt and the solution washed with 1N HCl aq. solution, satd. NaHCO₃ aq. solution and then satd. NaCl aq. solution. After drying over Na₂SO₄, the solvent was concentrated and ether-petroleum ether was added to the concentrate to give 1.45 g (yield 85%) of Z-Phe-ol as the precipitate. After 60 mg of 60% NaH was suspended in 10 mL of dry THF, 285 mg of Z-Phe-ol, 264 mg of 18-crown-6 and 1.48 mL of tert-butyl bromoacetate were added to the solution at 0° C. While reverting to room temperature, the mixture was stirred for 15 hours. After the solvent was distilled off in vacuum, the residue was dissolved in AcOEt and the solution washed with 1N HCl aq. solution, satd. NaHCO₃ aq. solution and satd. NaCl aq. solution. After drying over Na₂SO₄, the solvent was concentrated and the concentrate was purified by flush column chromatography to give 217 mg (yield 54%) of Z-PheΨ(CH₂O)Gly-OBuᵗ as oil. After 160 mg of Z-PheΨ(CH₂O)Gly-OBuᵗ was dissolved in 20 mL of MeOH, 10% Pd—C was added to the solution, followed by catalytic hydrogenation for 3 hours in a nitrogen flow. The catalyst was removed by filtration and the solvent was concentrated followed by drying. The concentrate was dissolved in 15 mL of DCM, and 114 mg of Fmoc-Cl and 139 µL of DIEA were added to the solution, followed by stirring for 12 hours. After the solvent was distilled off, the residue was dissolved in AcOEt and the solution washed with 1N HCl aq. solution, satd. NaHCO₃ aq. solution and then satd. NaCl aq. solution. After drying over Na₂SO₄, the solvent was concentrated and the concentrate was purified by flush column chromatography. Diethyl ether-petroleum ether was added to give 150 mg (yield 77%) of Fmoc-PheΨ(CH₂O)Gly-OBuᵗ as the precipitate. To the precipitate, were added 31 mg (15 µmol) of H-LeuArg(Me,Boc₂)Trp(Boc)-Rink amide MBHA resin obtained in a manner similar to the process of EXAMPLE 15, 19 mg of Fmoc-PheΨ(CH₂O)Gly-OH (prepared by treating Fmoc-PheΨ(CH₂O)Gly-OBuᵗ with 50% TFA/DCM for an hour), 180 µL of 0.5M HOAt, 42 mg of PyBrop and 47 µL of DIEA. The mixture was shaken for 18 hours. After the resin washed, 5 mL of 20% piperidine/DMF was added to the resin, followed by stirring at room temperature for 30 minutes. After the resin washed, 9 µL of benzoyl chloride, 13 µL of DIEA and 1 mL of DMF 1 were added to the resin, followed by stirring at room temperature for 2 hours. After the resin washed and dried, 200 µL of TFA/PhSMe/m-cresol/TIS/EDT (85/5/5/2.5/2.5) was added to the resin, followed by stirring for 2 hours. Ether was added to the reaction solution, the resulting precipitate was centrifuged and the supernatant was removed. This procedure was repeated for washing. The residue was extracted with an aqueous acetic acid solution and the extract was filtered to remove the resin. Then, linear density gradient elution (60 minutes) was performed with eluants A/B: 75/25-65/35 using: 0.1% TFA in water and eluant B: 0.1% TFA-containing acetonitrile on preparative HPLC using YMC D-ODS-5-ST S-5 120A column (20×150 mm). The fractions containing the product were collected and lyophilized to give 2.5 mg of white powders. Mass spectrum $(M+H)^+$ 782.2 (Calcd. 782.4)

Elution time on HPLC: 22.1 min

Elution Conditions:

Column: Wakosil-II 5C18 HG (4.6×100 mm)

Eluant: linear density gradient elution with eluants A/B=100/0-0/50, using 0.1% TFA in water as eluant A and acetonitrile containing 0.1% TFA (25 mins.)

Flow rate: 1.0 ml/min.

Example 19

Synthesis Process R

Preparation of des(1-7)-Dibenzylaminocarbamoylacetyl-[Arg(Me)9,Trp10]MS10 (Compound No. 434)

After 1.54 mL of mono-tert-butyl malonate, 1.08 g of fluorenylmethanol and 61 mg of DMAP were dissolved in 20 mL of DCM 20, 1.15 g of WSCD HCl was added to the solution, followed by stirring at room temperature for 24 hours. The solvent was distilled off in vacuum, the residue was dissolved in AcOEt. The solution was then washed with 1N HCl aq. solution, satd. NaHCO₃ aq. solution and then satd. NaCl aq. solution. After drying over Na₂SO₄, the solvent was concentrated and the concentrate was purified by flush column chromatography to give 1.62 g (yield 96%) of tert-butyl fluorenylmethyl malonate. In 20 mL of TFA, 61 mg of tert-butyl fluorenylmethyl malonate was dissolved and the solution was stirred at room temperature for 2 hours. After the solvent was distilled off in vacuum, the residue was dissolved in AcOEt, followed by washing with satd. NaCl aq. solution. After drying over Na₂SO₄, the solvent was concentrated and purified by flush column chromatography to give 850 mg (yield 67%) of mono-fluorenylmethyl malonate. After 5 mL of 20% piperidine/DMF was added to 46 mg (15 µmol) of Fmoc-LeuArg(Me,Boc₂)Trp(Boc)-Rink amide MBHA resin prepared in a manner similar to EXAMPLE 15, the solution was shaken at room temperature for 30 minutes. After the resin washed, 42 mg of mono-fluorenylmethyl malonate, 70 mg of PyBrop, 300 µL of 0.5M HOAt/DMF, 52 µL of DIEA and 1 mL of DMF were added to the resin, and the mixture was shaken for 15 hours. After this procedure was repeated twice, 8 µL of Ac$_2$O, 5 µL of DIEA and 2 mL of DCM were added, followed by stirring at room temperature for 30 minutes. After the resin washed and then dried, 5 mL of 20% piperidine/DMF was added to a half of the resin, followed by stirring at room temperature for 30 minutes. After the resin washed, 13 mg of dibenzylhydrazine, 28 mg of PyBrop, 120 µL of 0.5M HOAt/DMF, 21 µL of DIEA and 1 mL of DMF were added to the resin, followed by shaking for 15 hours. After the resin washed and then dried, 200 µL of TFA/PhSMe/m-cresol/TIS/EDT (85/5/5/2.5/2.5) was added to the resin, followed by stirring for 2 hours. Ether was added to the reaction solution, the resulting precipitate was centrifuged and the supernatant was removed. This procedure was repeated for washing. The residue was extracted with an aqueous acetic acid solution and the extract was filtered to remove the resin. Then, linear density gradient elution (120 minutes) was performed with eluants A/B: 83/17-63/37 using: 0.1% TFA in water and eluant B: 0.1% TFA-containing acetonitrile on preparative HPLC using YMC D-ODS-5-ST S-5 120A column (20×150 mm). The fractions containing the product were collected and lyophilized to give 21.6 mg of white powders.

Mass spectrum (M+H)$^+$ 767.6 (Calcd. 767.4)
Elution time on HPLC: 14.5 min
Elution Conditions:
Column: Wakosil-II 5C18 HG (4.6×100 mm)
Eluant: linear density gradient elution with eluants A/B=100/0-30/70, using 0.1% TFA in water as eluant A and acetonitrile containing 0.1% TFA (25 mins.)
Flow rate: 1.0 ml/min.

Example 20

Synthesis Process S

Preparation of des(1-5)-4-Pyridinecarbonyl-[Aza-Gly7,Arg(Me)9,Trp10]MS10 (Compound No. 436)

After 340.1 mg (0.1 mmol) of Fmoc-AzaGly-Leu-Arg(Boc$_2$,Me)-Trp(Boc)-Rink Amide MBHA resin was swollen in DMF, the resin was treated in 20 ml of 20% piperidine/DMF solution for 20 minutes to remove the Fmoc group. The resin obtained washed with DMF and treated with 155.0 mg (0.4 mmol) of Fmoc-Phe-OH, 63.6 µL (0.4 mmol) of DIPCDI and 0.8 mL (0.4 mmol) of 0.5M HOAt/DMF solution at room temperature for 90 minutes to introduce Phe. After Fmoc-Phe-AzaGly-Leu-Arg(Boc$_2$,Me)-Trp(Boc)-Rink Amide MBHA resin obtained was subjected to Fmoc deprotection and then treated with 49.2 mg (0.4 mmol) of 4-Pyridinecarboxylic acid, 63.6 µL (0.4 mmol) of DIPCDI and 0.8 mL (0.4 mmol) of 0.5M HOAt/DMF solution at room temperature for 90 minutes. Then, the resin washed and dried to give 353.5 mg of 4-Pyridinecarbonyl-Phe-AzaGly-Leu-Arg(Boc$_2$,Me)-Trp(Boc)-Rink Amide MBHA resin. To the resulting resin, 3.5 mL of TFA/PhSMe/m-cresol/H$_2$O/TIS/EDT (80/5/5/5/2.5/2.5) was added and the mixture was stirred for 90 minutes. Diethyl ether was added to the reaction solution, the resulting precipitate was centrifuged and the supernatant was removed. This procedure was repeated twice for washing. The residue was extracted with an aqueous acetic acid solution and the extract was filtered to remove the resin. Then, linear density gradient elution (60 minutes) was performed at a flow rate of 15 ml/min with eluants A/B: 79/21-69/31 using: 0.1% TFA in water and eluant B: 0.1% TFA-containing acetonitrile on preparative HPLC using YMC Pack R&D-ODS-5-B S-5, 120A column (30×250 mm). The fractions containing the product were collected and lyophilized. The white powders obtained were dissolved in 6 mL of water and 200 µL of ion exchange resin BioRAD AG1×8 AcO$^-$ form was added to the solution. While manually stirring the solution sometimes, the reaction solution was settled for an hour. The solution was filtered through a membrane filter to remove the resin and give 21.6 mg of white powders as the acetate.

Mass spectrum (M+H)$^+$ 797.8 (Calcd. 797.4)
Elution time on HPLC: 8.8 min
Elution Conditions:
Column YMC-AM301 (4.6×100 mm)
Eluant: linear density gradient elution with eluants A/B=80/20-30/70, using 0.1% TFA in water as eluant A and acetonitrile containing 0.1% TFA (25 mins.)
Flow rate: 1.0 ml/min.

Example 21

Synthesis Process T

Preparation of des(1-3)-3-Phenylpropionyl-[Aza-Gly7,Arg(Me)9,Trp10]MS10 (Compound No. 499)

After 170.1 mg (0.05 mmol) of Fmoc-AzaGly-Leu-Arg(Boc$_2$,Me)-Trp(Boc)-Rink Amide MBHA resin was swollen in DMF, the resin was treated with 5 ml of 20% piperidine/DMF solution for 20 minutes to remove the Fmoc group. The resin obtained washed with DMF and treated with 77.5 mg (0.2 mmol) of Fmoc-Phe-OH, 31.8 µL (0.2 mmol) of DIPCDI, and 0.4 mL (0.2 mmol) of 0.5M HOAt/DMF solution at room temperature for 90 minutes to introduce Phe. In a similar manner, Ser($^t$Bu) and Asn(Trt) were introduced to give Fmoc-Asn(Trt)-Ser($^t$Bu)-Phe-AzaGly-Leu-Arg(Boc$_2$,Me)-Trp(Boc)-Rink Amide MBHA resin. The resin obtained was subjected to Fmoc deprotection and then treated with 30.0 mg (0.2 mmol) of phenylpropionic acid, 31.8 µL (0.2 mmol) of DIPCDI and 0.4 mL (0.2 mmol) of 0.5M HOAt/DMF solution at room temperature for 90 minutes. Then, the resin washed and dried to give 209.6 mg of 3-Phenylpropionyl-Phe-AzaGly-Leu-Arg(Boc$_2$,Me)-Trp(Boc)-Rink Amide MBHA resin. To the resin obtained, 1.5 mL of TFA/PhSMe/m-cresol/H$_2$O/TIS/EDT (80/5/5/5/2.5/2.5) was added and the mixture was stirred for 90 minutes. Diethyl ether was added to the reaction solution, the resulting precipitate was centrifuged and the supernatant was removed. This procedure was repeated twice for washing. The residue was extracted with an aqueous acetic acid solution and the extract was filtered to remove the resin. Then, linear density gradient elution (60 minutes) was performed at a flow rate of 8 ml/min with eluants A/B: 71/29-61/39 using: 0.1% TFA in water and eluant B: 0.1% TFA-containing acetonitrile on preparative HPLC using YMC SH-343-5 S-5, 120A column (20×250 mm). The fractions containing the product were collected and lyophilized. The white powders obtained were dissolved in 10 mL of water and 125 µL of ion exchange resin BioRAD AG1×8 AcO$^-$ form was added to the solution. While manually stirring the solution sometimes, the reaction solution was settled for an hour. The solution was filtered through a membrane filter to remove the resin and give 5.2 mg of white powders as the acetate.

Mass spectrum (M+H)$^+$ 1025.3 (Calcd. 1025.5)
Elution time on HPLC: 13.6 min
Elution Conditions:
Column YMC-AM301 (4.6×100 mm)
Eluant: linear density gradient elution with eluants A/B=80/20-30/70, using 0.1% TFA in water as eluant A and acetonitrile containing 0.1% TFA (25 mins.)
Flow rate: 1.0 ml/min.

Example 22

Synthesis Process U

Preparation of des(1-5)-Benzoyl-[AzaPhe6,AzaGly7, Arg(Me)9,Trp10]MS10 (Compound No. 431)

After 500 mg (2.56 mmol) of benzylhidrazine.2HCl was dissolved in DCM, the solution was cooled to −78° C. on dry ice. Then, 727.1 mg (3.33 mmol) of Boc$_2$O and 0.982 ml (5.64 mmol) of DIEA were added to the solution. Dry ice was removed and the mixture was stirred for 30 minutes. After confirming by TLC that the reaction proceeded, 327 µl (2.82 mmol) of benzoyl chloride and 580.4 µl (3.33 mmol) of DIEA were added to the mixture, followed by stirring at room temperature overnight. Citric acid crystals were added to the reaction solution and the mixture was concentrated. A 10% citric acid aqueous solution was added to the mixture. The precipitated residue was extracted with AcOEt and the extract washed with 10% citric acid aqueous solution, 5% NaHCO$_3$ aq. solution and then satd. NaCl aq. solution, followed by drying over anhydrous Na$_2$SO$_4$. The residue obtained was crystallized from ether-hexane (1:1) to give 435.5 mg of white crystals.

After 46.3 mg (0.015 mmol) of Fmoc-AzaGly-Leu-Arg(Boc$_2$,Me)-Trp(Boc)-NH-Rink Amide MBHA resin was swollen in DMF, the resin was treated with 5 ml of 20% piperidine/DMF solution for 20 minutes to remove the Fmoc group. The resin obtained washed with DMF and treated in THF with 3.65 mg (0.023 mmol) of CDI at room temperature for an hour. Separately, 32.6 mg (0.1 mmol) of the white powders above were treated with 0.3 ml of 4N HCl/dioxane for an hour. The solvent was then distilled off and the residue washed with ether. The residue obtained was dissolved in THF, and 17.4 µl (0.1 mmol) of DIEA was added to the solution. The resulting solution was added to the resin, followed by stirring overnight. The resin washed and dried to give 29.5 mg of Benzoyl-AzaPhe-AzaGly-Leu-Arg(Boc$_2$, Me)-Trp(Boc)-NH-Rink Amide MBHA resin. To the resin obtained, 0.5 mL of TFA/PhSMe/m-cresol/H$_2$O/TIS/EDT (80/5/5/2.5/2.5) was added and the mixture was stirred for 90 minutes. Diethyl ether was added to the reaction solution, the resulting precipitate was centrifuged and the supernatant was removed. This procedure was repeated twice for washing. The residue was extracted with an aqueous acetic acid solution and the extract was filtered to remove the resin. Then, linear density gradient elution (60 minutes) was performed at a flow rate of 8 ml/min with eluants A/B: 66/34-56/44 using: 0.1% TFA in water and eluant B: 0.1% TFA-containing acetonitrile on preparative HPLC using YMC SH-343-5 S-5, 120A column (20×250 mm). The fractions containing the product were collected and lyophilized to give 3.2 mg of white powders.

Mass spectrum (M+H)$^+$ 797.7 (Calcd. 797.4)

Elution time on HPLC: 15.3 min

Elution Conditions:

Column YMC-AM301 (4.6×100 mm)

Eluant: linear density gradient elution with eluants A/B=80/20-30/70, using 0.1% TFA in water as eluant A and acetonitrile containing 0.1% TFA (25 mins.)

Flow rate: 1.0 ml/min.

Example 23

Synthesis Process V

Preparation of des(1)-[D-Tyr2,D-Pya(4)$_3$,AzaGly7, Arg(Me)9,10Ψ,CSNH]MS10 (Compound No. 548)

Fmoc-Leu-OH was introduced into commercially available 2-chlorotritylchloride resin. After Fmoc deprotection, 5 mL of THF and 162 mg of CDI were added to 403 mg of Fmoc-Leu-O-Clt resin (sub. 0.62 mmol/g) obtained. The mixture was shaken for an hour. After 97 µL of hydrazine monohydrate was added to the system, the mixture was shaken for 2 hours and the resin was then washed. To the resin, 581 mg of Fmoc-Phe, 699 mg of PyBrop, 3 mL of 0.5M HOAt/DMF solution and 784 µL of DIEA were added, followed by shaking for 12 hours. After the resin washed, the peptide chain was extended on ABI 433A to give 0.47 g of Boc-D-Tyr(Bu$^r$)D-Pya(4)Asn(Trt)Ser(Bu$^r$)PheAzaGlyLeu-O-Clt resin. To the resin, 10 mL of AcOH/TFE/DCM (1/1/8) was added, followed by shaking for 30 minutes. The resin was removed by filtration and the solvent was concentrated. The residue was dissolved in chloroform and the resulting solution washed with satd. NaCl aq. solution. After drying over Na$_2$SO$_4$, the solvent was concentrated and AcOEt-diethyl ether was added to the concentrate to give 320 mg (yield 98%) of Boc-D-Tyr(Bu$^r$)D-Pya(4)Asn(Trt)Ser(Bu$^r$)PheAzaGlyLeu-OH as the precipitate. On the other hand, 5 mL of 4N HCl/AcOEt was added to 264 mg (1 mmol) of Boc-Phe-NH$_2$ under ice cooling, followed by stirring for 30 minutes. The solvent was distilled off and ether was then added for precipitation. The precipitate was dissolved in 20 mL of DMF, and 455 mg of Fmoc-Orn(Boc), 540 mg of HOBt, 382 mg of WSCD.HCl and 348 µL of DIEA were added to the solution, followed by stirring for 6 hours. After the solvent was distilled off in vacuum, the residue was dissolved in ethyl acetate and the solution washed with 1N HCl aq. solution, satd. NaHCO$_3$ aq. solution and then satd. NaCl aq. solution. After drying over Na$_2$SO$_4$, the solvent was concentrated. Ether-petroleum ether was added to the concentrate to give 594.4 mg (yield 99%) of Fmoc-Orn(Boc)-Phe-NH$_2$ as the precipitate. Under ice cooling, 5 mL of 4N HCl/AcOEt was added to 132 mg of the product, followed by stirring for 30 minutes. After the solvent was distilled off, ether was added to give 111.1 mg (yield 94%) of Fmoc-Orn-Phe-NH$_2$.HCl as the precipitate. The precipitate was dissolved in 3 mL of chloroform/TFE (3/1), and 194 mg of N-methyl-N,N'-Bis-Boc-1-guanylpyrazole obtained in REFERENCE EXAMPLE 1 and 105 µL of DIEA were added to the solution, followed by stirring for 24 hours. After the solvent was distilled off, ether-petroleum ether was added to give 108.5 mg (yield 72%) of Fmoc-Arg(Boc$_2$,Me)-Phe-NH$_2$ as the precipitate. In 5 mL of THF, 38 mg of the product was dissolved and 142 mg of Lawesson's Reagent was added to the solution, followed by stirring for 15 hours. After the solvent was distilled off in vacuum, the residue was dissolved in ethyl acetate and the solution washed with NaHCO$_3$ aq. solution and then satd. NaCl aq. solution. After drying over Na$_2$SO$_4$, the solvent was concentrated. After purification by flush column chromatography, ether-petroleum ether was added to give 18.7 mg (yield 48%) of Fmoc-Arg(Me,Boc$_2$)-PheΨ(CSNH)—NH$_2$ as the precipitate. To 11 mg of the product, 1 mL of 10% DEA/DMF was added and the mixture was stirred for 2 hours. After the solvent was distilled off, the residue was dissolved in 1 mL of DMF, and 18 mg of Boc-D-Tyr(Bu$^r$)-D-Pya(4)-Asn(Trt)-Ser(Bu$^r$)-Phe-AzaGly-Leu-OH previously obtained, 7.6 mg of HOBt, 5.4 mg of WSCD.HCl and 4.9 µL of DIEA were added to the solution, followed by stirring for 15 hours. The solvent was distilled off and ether was added to the residue for precipitation. To the precipitate, 1 mL of TFA/PhSMe/m-cresol/TIS/EDT (85/5/5/2.5/2.5) was added, and the mixture was stirred for 2 hours. Ether was added to the reaction solution, the resulting precipitate was centrifuged and the supernatant was removed. This procedure was repeated for washing. The residue was extracted with an aqueous acetic acid solution and the extract was filtered to remove the resin. Then, linear density gradient elution (60 minutes) was performed with eluants A/B: 82/18-72/28 using: 0.1% TFA in water and eluant B: 0.1% TFA-containing acetonitrile on preparative HPLC using YMC D-ODS-5-ST S-5 120A column (20×150 mm). The fractions containing the product were collected and lyophilized to give 0.9 mg of white powders.

Mass spectrum (M+H)$^+$ 1181.5 (Calcd. 1181.6)

Elution time on HPLC: 14.9 min

Elution Conditions:

Column: Wakosil-II 5C18 HG (4.6×100 mm)

Eluant: linear density gradient elution with eluants A/B=100/0-0150, using 0.1% TFA in water as eluant A and acetonitrile containing 0.1% TFA (25 mins.)

Flow rate: 1.0 ml/min.

Example 24

Synthesis Process W

Preparation of Ac-des(1)-[D-Tyr2,D-Trp3,Thr5,Aza-Gly7,Arg(Me)9,Trp10]MS10 (Compound No. 550)

After 5 g (0.4 mmol/g) of commercially available Rink Amide MBHA resin was swollen in DMF, the resin was treated with 50 ml of 20% piperidine/DMF solution for 20 minutes to remove the Fmoc group. After the resin obtained washed with DMF, Trp(Boc) was introduced by treating the resin with 4.213 g (8 mmol) of Fmoc-Trp(Boc)-OH, 1.272 mL (8 mmol) of DIPCDI and 16 mL (8 mmol) of 0.5M HOAt/DMF solution at room temperature for 90 minutes. In a similar manner, Orn(Mtt) was introduced to give 2 mmol of Fmoc-Orn(Mtt)-Trp(Boc)-Rink Amide MBHA resin. The resin obtained washed with DCM, after swelling, 50 mL of TFA/TIS/TFE/DCM (1/5/19/75) was added, the mixture was shaken for 10 minutes and the solution was distilled off. This procedure was repeated until yellow coloration caused by free Mtt group in a TFA/TIS/TFE/DCM (1/5/19/75) solution disappeared when the solution was added, thus the Mtt group was removed.

The resulting Fmoc-Orn-Trp(Boc)-Rink Amide MBHA resin was neutralized with 5%-DIEA/DCM solution. After washing with DCM, 25 mL of DCM-TFE (4:1) and 1.946 g (6 mmol) of N-methyl-N,N'-bis-Boc-1-guanylpyrazole obtained in REFERENCE EXAMPLE 1 were added to the resin. DIEA was added to the mixture to adjust pH of the solution to 10, and the mixture was shaken for 15 hours to give Fmoc-Arg(Boc$_2$,Me)-Trp(Boc)-Rink Amide MBHA resin. Fmoc-Leu was introduced into the obtained resin as in the same manner described above. The Fmoc group was removed from the thus obtained Fmoc-Leu-Arg(Boc$_2$,Me)-Trp(Boc)-Rink Amide MBHA resin (2 mmol) to give H-Leu-Arg(Boc$_2$, Me)-Trp(Boc)-Rink Amide MBHA resin (2 mmol).

Separately, 2.326 g (8 mmol) of Fmoc-NHNH$_2$.HCl was suspended in 20 mL of DMF. Under ice cooling, a suspension of 297 mg (8 mmol) of CDI in 20 mL of THF and then 2.787 mL (16 mmol) of DIEA was added to the suspension, followed by stirring at room temperature for an hour. The resulting reaction solution was added to H-Leu-Arg(Boc$_2$,Me)-Trp (Boc)-Rink Amide MBHA resin described above, followed by stirring at room temperature for 15 hours. After completion of the reaction, the resin washed and dried to give 6.394 g of Fmoc-AzaGly-Leu-Arg(Boc$_2$,Me)-Trp(Boc)-Rink Amide MBHA resin.

After 3.197 g (1 mmol) of the resin obtained was swollen in DMF, the resin was treated with 30 ml of 20% piperidine/DMF solution for 20 minutes to remove the Fmoc group. After the resin obtained washed with DMF, the resin was treated with 1.806 g (4 mmol) of Trt-Phe-OH.0.5AcOEt, 2.086 g (4 mmol) of PyAOP, 8 mL (4 mmol) of 0.5M HOAt/DMF and 2.787 mL (16 mmol) of DIEA at room temperature for 90 minutes to give Trt-Phe-AzaGly-Leu-Arg(Boc$_2$,Me)-Trp(Boc)-Rink Amide MBHA resin Phe. The resin obtained washed with DCM, after swelling, 30 mL of TFA/TIS/TFE/DCM (1/5/19/75) was added, the mixture was shaken for 10 minutes and the solution was distilled off. This procedure was repeated until yellow coloration caused by free Trt group in a TFA/TIS/TFE/DCM (1/5/19/75) solution disappeared when the solution was added, thus the Trt group was removed. The H-Phe-AzaGly-Leu-Arg(Boc$_2$,Me)-Trp(Boc)-Rink Amide MBHA resin obtained was neutralized with 5%-DIEA/DMF solution and washed with DMF. Thereafter, the resin was treated with 1.590 g (4 mmol) of Fmoc-Thr($^t$Bu)-OH, 0.636 mL (4 mmol) of DIPCDI and 8 mL (4 mmol) of 0.5M HOAt/DMF at room temperature for 90 minutes to introduce Thr ($^t$Bu). Subsequently, the Fmoc deprotection by treatment with 30 ml of 20% piperidine/DMF solution for 20 minutes and condensation by the DIPCDI/HOAt method similar to introduction of Thr($^t$Bu) were repeated so that Asn(Trt), $_D$-Trp (Boc), and $_D$-Tyr($^t$Bu) were introduced to give Fmoc-$_D$-Tyr (BU)-D-Trp(Boc)-Asn(Trt)-Thr($^t$Bu)-Phe-AzaGly-Leu-Arg (Boc$_2$,Me)-Trp(Boc)-Rink Amide MBHA resin. The resin obtained was treated with 30 ml of 20% piperidine/DMF solution for 20 minutes to remove the Fmoc group. The resin obtained washed to give H-$_D$-Tyr($^t$Bu)-D-Trp(Boc)-Asn (Trt)-Thr($^t$Bu)-Phe-AzaGly-Leu-Arg(Boc$_2$,Me)-Trp(Boc)-Rink Amide MBHA resin. The resin obtained was treated with 188.7 μL (2 mmol) of Ac$_2$O and 348.4 μL (2 mmol) of DIEA in 20 mL of DMF at room temperature for 30 minutes to acetylate the N terminus. The resin was then washed and dried to give 4.168 g of Ac-$_D$-Tyr($^t$Bu)-D-Trp(Boc)-Asn(Trt)-Thr ($^t$Bu)-Phe-AzaGly-Leu-Arg(Boc$_2$,Me)-Trp(Boc)-Rink Amide MBHA resin.

To a half of the resin obtained, i.e., 2.111 g, 15 mL of TFA/PhSMe/m-cresol/H$_2$O/TIS/EDT (80/5/5/5/2.5/2.5) was added and the mixture was stirred for 90 minutes. Diethyl ether was added to the reaction solution, the resulting precipitate was centrifuged and the supernatant was removed. This procedure was repeated twice for washing. After the residue was extracted with an aqueous acetic acid solution, the extract was filtered to remove the resin and lyophilized to give crude peptide powders. With respect to the remaining half of the resin, deprotection was performed under the same conditions to give about 650 mg of crude peptide powders in total. About 50 mg each of the crude peptide obtained was purified by applying sequentially to linear density gradient elution (60 minutes) at a flow rate of 15 ml/min with eluants A/B: 71/29-61/39 using: 0.1% TFA in water and eluant B: 0.1% TFA-containing acetonitrile on preparative HPLC using YMC Pack R&D-ODS-5-B S-5, 120A column (30×250 mm). The fractions containing the product were collected and lyophilized to give 255.5 mg of white powders as the purified sample.

All of the white powders were dissolved in 200 mL of aqueous acetonitrile solution and 492 μL of ion exchange resin AG1×8 AcO$^-$ form, which was obtained by converting commercially available BioRAD AG1×8 Cl$^-$ form into the acetate type in a conventional manner, was added to the solution. While manually stirring the reaction solution sometimes, the reaction solution was settled for an hour. The solution was concentrated to remove acetonitrile as much as possible. The concentrate was then filtered through a membrane filter and lyophilized to give 225.3 mg of white powders as the acetate.

Mass spectrum (M+H)$^+$ 1298.7 (Calcd. 1298.6)
Elution time on HPLC: 15.6 min
Elution Conditions:
  Column YMC-AM301 (4.6×100 mm)
  Eluant: linear density gradient elution with eluants A/B=80/20-30/70, using 0.1% TFA in water as eluant A and acetonitrile containing 0.1% TFA (25 mins.)
  Flow rate: 1.0 ml/min.

Example 25

Preparation of Ac-des(1)-[D-Tyr2,D-Pya(4)$_3$,Thr5, AzaGly7,Arg(Me)9,Trp10]MS10 (Compound No. 562)

After 5.455 g (0.455 mmol/g) of commercially available Rink Amide MBHA resin was swollen in DMF, the resin was treated with 50 ml of 20% piperidine/DMF solution for 20 minutes to remove the Fmoc group. After the resin obtained was washed with DMF, Trp(Boc) was introduced by treating the resin with 6.319 g (12 mmol) of Fmoc-Trp(Boc)-OH, 1.908 mL (12 mmol) of DIPCDI and 24 mL (12 mmol) of 0.5M HOAt/DMF solution at room temperature for 90 minutes to give Fmoc-Trp(Boc)-Rink Amide MBHA resin. In a similar manner, Orn(Mtt) was introduced to give 3 mmol of Fmoc-Orn(Mtt)-Trp(Boc)-Rink Amide MBHA resin. The resin obtained was washed with DCM, after swelling, 75 mL of TFA/TIS/TFE/DCM (1/5/19/75) was added, the mixture was shaken for 10 minutes and the solution was distilled off. This procedure was repeated until yellow coloration caused by free Mtt group in a TFA/TIS/TFE/DCM (1/5/19/75) solution disappeared when the solution was added, thus the Mtt group was removed.

The resulting Fmoc-Orn-Trp(Boc)-Rink Amide MBHA resin was neutralized with 5%-DIEA/DCM solution. After washing with DCM, 40 mL of DCM-TFE (4:1) and 2.919 g (9 mmol) of N-methyl-N,N'-bis-Boc-1-guanylpyrazole obtained in REFERENCE EXAMPLE 1 were added to the resin. DIEA was added to the mixture to adjust pH of the solution to 10, and the mixture was shaken for 15 hours to give Fmoc-Arg(Boc$_2$,Me)-Trp(Boc)-Rink Amide MBHA resin. Fmoc-Leu was introduced into the obtained resin as in the same manner described above. The Fmoc group was removed from the thus obtained Fmoc-Leu-Arg(Boc$_2$,Me)-Trp(Boc)-Rink Amide MBHA resin (2 mmol) to give H-Leu-Arg(Boc$_2$, Me)-Trp(Boc)-Rink Amide MBHA resin (2 mmol).

Separately, 3.489 g (12 mmol) of Fmoc-NHNH$_2$.HCl was suspended in 30 mL of DMF. Under ice cooling, a suspension of 1.849 mg (11.4 mmol) of CDI in 20 mL of THF and then 4.181 mL (24 mmol) of DIEA was added to the suspension, followed by stirring at room temperature for an hour. The resulting reaction solution was added to H-Leu-Arg(Boc$_2$, Me)-Trp(Boc)-Rink Amide MBHA resin described above, followed by stirring at room temperature for 15 hours. After completion of the reaction, the resin washed and dried to give 8.2496 g of Fmoc-AzaGly-Leu-Arg(Boc$_2$,Me)-Trp(Boc)-Rink Amide MBHA resin.

After 2.646 g (1 mmol) of the resin obtained was swollen in DMF, the resin was treated with 30 ml of 20% piperidine/DMF solution for 20 minutes to remove the Fmoc group. After the resin obtained was washed with DMF, the resin was treated with 1.630 g (4 mmol) of Trt-Phe-OH, 2.086 g (4 mmol) of PyAOP, 8 mL (4 mmol) of 0.5M HOAt/DMF and 2.787 mL (16 mmol) of DIEA at room temperature for 90 minutes to give Trt-Phe-AzaGly-Leu-Arg(Boc$_2$,Me)-Trp (Boc)-Rink Amide MBHA resin Phe. The resin obtained was washed with DCM, after swelling, 30 mL of TFA/TIS/TFE/DCM (1/5/19/75) was added, the mixture was shaken for 10 minutes and the solution was distilled off. This procedure was repeated until yellow coloration caused by free Trt group in a TFA/TIS/TFE/DCM (1/5/19/75) solution disappeared when the solution was added, thus the Trt group was removed. The H-Phe-AzaGly-Leu-Arg(Boc$_2$,Me)-Trp(Boc)-Rink Amide MBHA resin obtained was neutralized with 5%-DIEA/DMF solution and washed with DMF. Thereafter, the resin was treated with 1.590 g (4 mmol) of Fmoc-Thr($^t$Bu)-OH, 0.636 mL (4 mmol) of DIPCDI and 8 mL (4 mmol) of 0.5M HOAt/DMF at room temperature for 90 minutes to introduce Thr ($^t$Bu). Subsequently, the Fmoc deprotection by treatment with 30 ml of 20% piperidine/DMF solution for 20 minutes and condensation by the DIPCDI/HOAt method similar to introduction of Thr($^t$Bu) were performed to give Fmoc-Asn(Trt)-Ser($^t$Bu)-Phe-AzaGly-Leu-Arg(Boc$_2$,Me)-Trp(Boc)-Rink Amide MBHA resin. The resin obtained was Fmoc-deprotected. Then the resin was treated with 1.476 g (3.8 mmol) of Fmoc-$_D$-Pya(4)-OH, 2.086 mg (4 mmol) of PyAOP, 8 mL of 0.5 M HOAt/DMF (4 mmol) and 2.439 mL of DIEA (14 mmol) at room temperature for 90 minutes to introduce $_D$-Pya (4). Subsequently, by the DIPCDI/HOAt method similar to introduction of Thr($^t$Bu), $_D$-Tyr($^t$Bu) was introduced to the resin to give Fmoc-$_D$-Tyr($^t$Bu)-$_D$-Pya(4)-Asn(Trt)-Thr($^t$Bu)-Phe-AzaGly-Leu-Arg(Boc$_2$,Me)-Trp(Boc)-Rink Amide MBHA resin. The resin obtained was treated with 30 ml of 20% piperidine/DMF solution for 20 minutes to remove the Fmoc group. The resin obtained was washed to give H-$_D$-Tyr ($^t$Bu)-$_D$-Pya(4)-Asn(Trt)-Thr($^t$Bu)-Phe-AzaGly-Leu-Arg (Boc$_2$,Me)-Trp(Boc)-Rink Amide MBHA resin. The resin obtained was treated with 188.7 μL (2 mmol) of Ac$_2$O and 348.4 μL (2 mmol) of DIEA in 20 mL of DMF at room temperature for 30 minutes to acetylate the N terminus. The resin was then washed and dried to give 1 mmol of Ac-$_D$-Tyr (BU)-$_D$-Pya(4)-Asn(Trt)-Thr($^t$Bu)-Phe-AzaGly-Leu-Arg (Boc$_2$,Me)-Trp(Boc)-Rink Amide MBHA resin.

To the resin obtained, 30 mL of TFA/PhSMe/m-cresol/H$_2$O/TIS/EDT (80/5/5/5/2.5/2.5) was added and the mixture was stirred for 90 minutes. Diethyl ether was added to the reaction solution, the resulting precipitate was centrifuged and the supernatant was removed. This procedure was repeated twice for washing. After the residue was extracted with an aqueous acetic acid solution, the extract was filtered to remove the resin and lyophilized to give 949.0 mg of crude peptide powders. About 50 mg each of the crude peptide obtained was purified by applying to preparative HPLC using YMC Pack R&D-ODS-5-B S-5, 120A column (30×250 mm) at a flow rate of 15 ml/min sequentially with initial eluants A/B: 90/10 for 8 minutes, A/B: 75/25, wherein it took 7 minutes to increase the concentration, and linear density gradient elution (60 minutes) with eluants A/B: 75/25-65/35 using eluant A: 0.05% TFA in water and eluant B: 0.05% TFA-containing acetonitrile. The fractions containing the product were collected and lyophilized to give 361.1 mg of white powders as the purified sample.

All of the white powders obtained were dissolved in 200 mL of aqueous acetonitrile solution and 1.434 mL of ion exchange resin AG1×8 AcO$^-$ form, which was obtained by converting commercially available BioRAD AG1×8 Cl$^-$ form into the acetate type in a conventional manner, was added to the solution. While manually stirring the reaction solution sometimes, the reaction solution was settled for an hour. The solution was concentrated to remove acetonitrile as much as possible. The concentrate was then filtered through a membrane filter and lyophilized to give 309.3 mg of white powders as the acetate.

Mass spectrum (M+H)+ 1260.4 (Calcd. 1260.4)
Elution time on HPLC: 15.5 min
Elution Conditions:
Column Wakosil-II 5C18 HG (4.6×100 mm)
Eluant: linear density gradient elution with eluants A/B=100/0-50/50, using 0.1% TFA in water as eluant A and acetonitrile containing 0.1% TFA as eluant B (25 mins.)
Flow rate: 1.0 ml/min.

Example 26

Preparation of Ac-des(1)-[D-Tyr2,D-Trp3,Thr5,Aza-Gly7,Arg(Me)9]MS10 (Compound No. 571)

After 2.5 g (0.4 mmol/g) of commercially available Rink Amide MBHA resin was swollen in DMF, the resin was treated with 50 ml of 20% piperidine/DMF solution for 20 minutes to remove the Fmoc group. After the resin obtained was washed with DMF, Phe was introduced by treating the resin with 1.550 g (4 mmol) of Fmoc-Phe-OH, 0.636 mL (4 mmol) of DIPCDI and 8 mL (4 mmol) of 0.5M HOAt/DMF solution at room temperature for 90 minutes to give Fmoc-Phe-Rink Amide MBHA resin. In a similar manner, Orn(Mtt) was introduced to give 1 mmol of Fmoc-Orn(Mtt)-Trp(Boc)-Rink Amide MBHA resin. The resin obtained was washed with DCM, after swelling, 25 mL of TFA/TIS/TFE/DCM (1/5/19/75) was added, the mixture was shaken for 10 minutes and the solution was distilled off. This procedure was repeated until yellow coloration caused by free Mtt group in a TFA/TIS/TFE/DCM (1/5/19/75) solution disappeared when the solution was added, thus the Mtt group was removed.

The resulting Fmoc-Orn-Phe-Rink Amide MBHA resin was neutralized with 5%-DIEA/DCM solution. After washing with DCM, 25 mL of DCM-TFE (4:1) and 0.973 g (3 mmol) of N-methyl-N,N'-bis-Boc-1-guanylpyrazole obtained in REFERENCE EXAMPLE 1 were added to the resin. DIEA was added to the mixture to adjust pH of the solution to 10, and the mixture was shaken for 15 hours to give Fmoc-Arg(Boc$_2$,Me)-Phe-Rink Amide MBHA resin. Fmoc-Leu was introduced into the obtained resin as in the same manner described above. The Fmoc group was removed from the thus obtained Fmoc-Leu-Arg(Boc$_2$,Me)-Phe-Rink Amide MBHA resin (1 mmol) to give H-Leu-Arg(Boc$_2$,Me)-Phe-Rink Amide MBHA resin (1 mmol).

Separately, 1.163 g (4 mmol) of Fmoc-NHNH$_2$·HCl was suspended in 10 mL of DMF. Under ice cooling, a suspension of 0.568 mg (3.5 mmol) of CDI in 10 mL of THF and then 1.307 mL (7.5 mmol) of DIEA was added to the suspension, followed by stirring at room temperature for an hour. The resulting reaction solution was added to H-Leu-Arg(Boc$_2$, Me)-Phe-Rink Amide MBHA resin described above, followed by stirring at room temperature for 15 hours. After completion of the reaction, the resin washed and dried to give 3.134 g of Fmoc-AzaGly-Leu-Arg(Boc$_2$,Me)-Phe-Rink Amide MBHA resin.

Using this resin, 1.94 g of Trt-Phe-AzaGly-Leu-Arg(Boc$_2$, Me)-Trp(Boc)-Rink Amide MBHA resin obtained by the condensation of Trt-Phe-OH 0.5AcOEt in similar to EXAMPLE 24, was washed with DCM. After swelling, 12 mL of TFA/TIS/TFE/DCM (1/5/19/75) was added, the mixture was shaken for 10 minutes and the solution was distilled off. This procedure was repeated until brownish yellow coloration caused by free Trt group in a TFA/TIS/TFE/DCM (1/5/19/75) solution disappeared when the solution was added, thus the Trt group was removed. By washing the resin, 1.66 g of H-Phe-AzaGly-Leu-Arg(Boc$_2$,Me)-Phe-Rink Amide MBHA resin were obtained. Using 553 mg of the resin obtained, peptide chain was extended with the peptide synthesizer ABI-433A (Fmoc/DCC/HOBt) to give H-D-Tyr (But)-D-Trp(Boc)-Asn(Trt)-Thr(But)-Phe-AzaGly-Leu-Arg (Boc$_2$,Me)-Phe-Rink amide MBHA resin. To this product, 5 mL of DMF, 111 mg of AcONB and 44 ml of DIEA was added and the resin was shaken for two hours. The resin was dried after washing to give 0.78 g of Ac-D-Tyr(But)-D-Trp(Boc)-Asn(Trt)-Thr(But)-Phe-AzaGly-Leu-Arg(Boc$_2$,Me)-Phe-R ink amide MBHA resin. To the resin, 6 mL of TFA/thioanisole/m-cresol/H$_2$O/TIS/EDT (80/5/5/5/2.5/2.5) was added and the resin was shaken for two hours. After removal of the resin by filtration, solvent was distilled off. By adding diethylether, precipitation was obtained. After centrifugation, washing by removal of the supernatant was repeated twice, and the residues were extracted with acetate solution. After the resin was removed by filtration, the fraction was purified by applying to preparative HPLC using YMC Pack R&D-ODS-5-B S-5, 120A column (30×250 mm) at a flow rate of 15 ml/min sequentially with linear density gradient elution (60 minutes) with eluants A/B: 71/29-61/39 using eluant A: 0.1% TFA in water and eluant B: 0.1% TFA-containing acetonitrile. The fractions containing the product were collected and lyophilized to give white powders as the purified sample. The purified sample was lyophilized. The crude peptide obtained in the similar manner using 553 mg of H-Phe-AzaGly-Leu-Arg(Boc$_2$,Me)-Phe-Rink amide MBHA resin was purified on preparative HPLC to give total 237.6 mg of purified sample as white powders.

The white powders obtained, 236.1 mg were dissolved in 200 mL of aqueous acetonitrile solution and 935 μL of ion exchange resin AG1×8 AcO⁻ form, which was obtained by converting commercially available BioRAD AG1×8 Cl⁻ form into the acetate type in a conventional manner, was added to the solution. While manually stirring the reaction solution sometimes, the reaction solution was settled for an hour. The solution was concentrated to remove acetonitrile as much as possible. The concentrate was then filtered through a membrane filter and lyophilized to give 204.6 mg of white powders as the acetate.

Mass spectrum (M+H)+ 1259.5 (Calcd. 1259.6)
Elution time on HPLC: 13.2 min
Elution Conditions:
Column YMC-AM301 (4.6×100 mm)
Eluant: linear density gradient elution with eluants A/B=80/20-30/70, using 0.1% TFA in water as eluant A and acetonitrile containing 0.1% TFA as eluant B (25 mins.)
Flow rate: 1.0 ml/min.

Example 27

Preparation of Ac-des(1)-[D-Tyr2,D-Trp3,Alb4,Aza-Gly7,Arg(Me)9,Trp10]MS10 (Compound No. 579)

After 5 g (0.4 mmol/g) of commercially available Rink Amide MBHA resin was swollen in DMF, the resin was treated with 50 ml of 20% piperidine/DMF solution for 20 minutes to remove the Fmoc group. After the resin obtained was washed with DMF, Trp(Boc) was introduced by treating the resin with 4.213 g (8 mmol) of Fmoc-Trp(Boc)-OH, 1.272 mL (8 mmol) of DIPCDI and 16 mL (8 mmol) of 0.5M HOAt/DMF solution at room temperature for 90 minutes to give Fmoc-Trp(Boc)-Rink Amide MBHA resin. In a similar manner, Orn(Mtt) was introduced to give 2 mmol of Fmoc-Orn(Mtt)-Trp(Boc)-Rink Amide MBHA resin. The resin obtained was washed with DCM, after swelling, 50 mL of TFA/TIS/TFE/DCM (1/5/19/75) was added, the mixture was shaken for 10 minutes and the solution was distilled off. This procedure was repeated until yellow coloration caused by free Mtt group in a TFA/TIS/TFE/DCM (1/5/19/75) solution disappeared when the solution was added, thus the Mtt group was removed.

The resulting Fmoc-Orn-Trp(Boc)-Rink Amide MBHA resin was neutralized with 5%-DIEA/DCM solution. After washing with DCM, 25 mL of DCM-TFE (4:1) and 1.946 g (6 mmol) of N-methyl-N,N'-bis-Boc-1-guanylpyrazole obtained in REFERENCE EXAMPLE 1 were added to the resin. DIEA was added to the mixture to adjust pH of the solution to 10, and the mixture was shaken for 15 hours to give Fmoc-Arg(Boc$_2$,Me)-Trp(Boc)-Rink Amide MBHA resin. Fmoc-Leu was introduced into the obtained resin as in the same manner described above. The Fmoc group was removed from the thus obtained Fmoc-Leu-Arg(Boc$_2$,Me)-Trp(Boc)-Rink Amide MBHA resin (2 mmol) to give H-Leu-Arg(Boc$_2$, Me)-Trp(Boc)-Rink Amide MBHA resin (2 mmol).

Separately, 2.326 g (8 mmol) of Fmoc-NHNH$_2$.HCl was suspended in 20 mL of DMF. Under ice cooling, a suspension of 1.297 mg (8 mmol) of CDI in 20 mL of THF and then 2.787 mL (16 mmol) of DIEA was added to the suspension, followed by stirring at room temperature for an hour. The resulting reaction solution was added to H-Leu-Arg(Boc$_2$,Me)-Trp(Boc)-Rink Amide MBHA resin described above, followed by stirring at room temperature for 15 hours. After completion of the reaction, the resin washed and dried to give 2 mmol of Fmoc-AzaGly-Leu-Arg(Boc$_2$,Me)-Trp(Boc)-Rink Amide MBHA resin.

Using 868 mg (0.257 mmol) of Fmoc-AzaGly-Leu-Arg (Boc$_2$,Me)-Trp(Boc)-Rink Amide MBHA resin, Thr($^t$Bu), Alb, $_D$-Trp(Boc), and $_D$-Tyr($^t$Bu) were introduced by repeating condensation using DCC/HOBt method with ABI 433A to give a H-$_D$-Tyr(BU)-$_D$-Trp(Boc)-Alb-Ser($^t$Bu)-Phe-Aza-Gly-Leu-Arg(Boc$_2$,Me)-Trp(Boc)-Rink Amide MBHA resin. N-terminus od the obtained resin was acetylated by treating with 111 mg (0.5 mmol) of AcONB and 87 µL (0.5 mmol) of DIEA in 5 mL of DMF at room temperature for 10 hours. Subsequently, the resin was washed and dried to give a Ac-$_D$-Tyr($^t$Bu)-$_D$-Trp(Boc)-Alb-Ser($^t$Bu)-Phe-AzaGly-Leu-Arg(Boc$_2$,Me)-Trp(Boc)-Rink Amide MBHA resin.

To the resin obtained, 6 mL of TFA/PhSMe/m-cresol/H$_2$O/TIS/EDT(80/5/5/5/2.5/2.5) was added, and the suspension was shaken for two hours. After removal of the resin by filtration, solvent was distilled off. By adding diethylether, precipitation was obtained. After centrifugation, washing by removal of the supernatant was repeated twice, and the residues were extracted with acetate solution. After the resin was removed by filtration, the fraction was purified by applying to preparative HPLC using YMC Pack R&D-ODS-5-B S-5, 120A column (30×250 mm) at a flow rate of 15 ml/min sequentially with linear density gradient elution (60 minutes) with eluants A/B: 69/31-59/41 using eluant A: 0.1% TFA in water and eluant B: 0.1% TFA-containing acetonitrile. The fractions containing the product were collected and lyophilized to give 106.5 mg of white powders as the purified sample.

All the white powders obtained were dissolved in 100 mL of aqueous acetonitrile solution and 400 µL of ion exchange resin AG1×8 AcO$^-$ form, which was obtained by converting commercially available BioRAD AG1×8 Cl$^-$ form into the acetate type in a conventional manner, was added to the solution. While manually stirring the reaction solution sometimes, the reaction solution was settled for an hour. The solution was concentrated to remove acetonitrile as much as possible. The concentrate was then filtered through a membrane filter and lyophilized to give 97.5 mg of white powders as the acetate.

Mass spectrum (M+H)$^+$ 1299.5 (Calcd. 1299.6)
Elution time on HPLC: 19.0 min
Elution Conditions:
 Column Wakosil-II (4.6×100 mm)
 Eluant: linear density gradient elution with eluants A/B=100/0-50/50, using 0.1% TFA in water as eluant A and acetonitrile containing 0.1% TFA as eluant B (25 mins.)
 Flow rate: 1.0 ml/min.

Example 28

Synthesis Process X

Preparation of Ac-des(1)-[D-Tyr2,D-Trp3,Dap(For)$_4$, AzaGly7,Arg(Me)9,Trp10]MS10 (Compound No. 585)

After 5 g (0.4 mmol/g) of commercially available Rink Amide MBHA resin was swollen in DMF, the resin was treated with 50 ml of 20% piperidine/DMF solution for 20 minutes to remove the Fmoc group. After the resin obtained was washed with DMF, Trp(Boc) was introduced by treating the resin with 4.213 g (8 mmol) of Fmoc-Trp(Boc)-OH, 1.272 mL (8 mmol) of DIPCDI and 16 mL (8 mmol) of 0.5M HOAt/DMF solution at room temperature for 90 minutes to give Fmoc-Trp(Boc)-Rink Amide MBHA resin. In a similar manner, Orn(Mtt) was introduced to give 2 mmol of Fmoc-Orn(Mtt)-Trp(Boc)-Rink Amide MBHA resin. The resin obtained was washed with DCM, after swelling, 50 mL of TFA/TIS/TFE/DCM (1/5119/75) was added, the mixture was shaken for 10 minutes and the solution was distilled off. This procedure was repeated until yellow coloration caused by free Mtt group in a TFA/TIS/TFE/DCM (1/5/19/75) solution disappeared when the solution was added, thus the Mtt group was removed.

The resulting Fmoc-Orn-Trp(Boc)-Rink Amide MBHA resin was neutralized with 5%-DIEA/DCM solution. After washing with DCM, 25 mL of DCM-TFE (4:1) and 1.946 g (6 mmol) of N-methyl-N,N'-bis-Boc-1-guanylpyrazole obtained in REFERENCE EXAMPLE 1 were added to the resin. DIEA was added to the mixture to adjust pH of the solution to 10, and the mixture was shaken for 15 hours to give Fmoc-Arg(Boc$_2$,Me)-Trp(Boc)-Rink Amide MBHA resin. Fmoc-Leu was introduced into the obtained resin as in the same manner described above. The Fmoc group was removed from the thus obtained Fmoc-Leu-Arg(Boc$_2$,Me)-Trp(Boc)-Rink Amide MBHA resin (2 mmol) to give H-Leu-Arg(Boc$_2$, Me)-Trp(Boc)-Rink Amide MBHA resin (2 mmol).

Separately, 2.326 g (8 mmol) of Fmoc-NHNH$_2$.HCl was suspended in 20 mL of DMF. Under ice cooling, a suspension of 1.297 mg (8 mmol) of CDI in 20 mL of THF and then 2.787 mL (16 mmol) of DIEA was added to the suspension, followed by stirring at room temperature for an hour. The resulting reaction solution was added to H-Leu-Arg(Boc$_2$,Me)-Trp(Boc)-Rink Amide MBHA resin described above, followed by stirring at room temperature for 15 hours. After completion of the reaction, the resin washed and dried to give 2 mmol of Fmoc-AzaGly-Leu-Arg(Boc$_2$,Me)-Trp(Boc)-Rink Amide MBHA resin.

Using 868 mg (0.257 mmol) of Fmoc-AzaGly-Leu-Arg (Boc$_2$,Me)-Trp(Boc)-Rink Amide MBHA resin, Thr($^t$Bu), Dap(Mtt), $_D$-Trp(Boc) and $_D$-Tyr($^t$Bu) were introduced by repeating condensation using DCC/HOBt method with ABI 433A to give a H-$_D$-Tyr(BU)-$_D$-Trp(Boc)-Dap(Mtt)-Ser (tBu)-Phe-AzaGly-Leu-Arg(Boc2,Me)-Trp(Boc)-Rink Amide MBHA resin. N-terminus od the obtained resin was acetylated by treating with 111 mg (0.5 mmol) of AcONB and 87 µL (0.5 mmol) of DIEA in 5 mL of DMF at room temperature for 4 hours. Subsequently, the resin was washed and dried to give a Ac-D-Tyr(tBu)-D-Trp(Boc)-Dap(Mtt)-Ser(tBu)-Phe-AzaGly-Leu-Arg(Boc2,Me)-Trp(Boc)-Rink Amide MBHA resin.

To the resin obtained, 6 mL of TFA/PhSMe/m-cresol/H2O/TIS/EDT(80/5/5/5/2.5/2.5) was added, and the suspension was shaken for two hours. After removal of the resin by filtration, solvent was distilled off. By adding diethylether, precipitation was obtained. After centrifugation, washing by removal of the supernatant was repeated twice, and the residues were extracted with acetate solution. After the resin was removed by filtration, the fraction was purified by applying to preparative HPLC using YMC Pack R&D-ODS-5-B S-5, 120A column (30×250 mm) at a flow rate of 15 ml/min sequentially with linear density gradient elution (60 minutes) with eluants A/B: 71/29-61/39 using eluant A: 0.1% TFA in water and eluant B: 0.1% TFA-containing acetonitrile. The fractions containing the product were collected and lyophilized to give 106.5 mg of white powders as the purified sample.

All the white powders obtained were dissolved in 100 mL of aqueous acetonitrile solution and 400 µL of ion exchange resin AG1×8 AcO$^-$ form, which was obtained by converting commercially available BioRAD AG1×8 Cl$^-$ form into the acetate type in a conventional manner, was added to the solution. While manually stirring the reaction solution sometimes, the reaction solution was settled for an hour. The solution was concentrated to remove acetonitrile as much as possible. The concentrate was then filtered through a membrane filter and lyophilized to give 58.3 mg of white powders as the acetate.

Mass spectrum (M+H)$^+$ 1284.7 (Calcd. 1284.6)

Elution time on HPLC: 17.9 min

Elution Conditions:

Column Wakosil-II (4.6×100 mm)

Eluant: linear density gradient elution with eluants A/B=100/0-50/50, using 0.1% TFA in water as eluant A and acetonitrile containing 0.1% TFA as eluant B (25 mins.)

Flow rate: 1.0 ml/min.

The structures of compounds synthesized as in EXAMPLES 1 to 24 and physicochemical properties of these compounds are shown in TABLES 1 to 11, below.

TABLE 1

| Comp. No. | | M + H+ (obs.) | M + H+ (cal.) | HPLC (min.) | HPLC mode | Synth Proc |
|---|---|---|---|---|---|---|
| 1 | Metastin | 5858.4 | 5858.5 | 18.1 | d | M |
| 2 | Lys-Asp-Leu-Pro-Asn-MS10 | 1869.6 | 1869.9 | 18.6 | d | M |
| 3 | MS10 | 1302.5 | 1302.6 | 18.7 | d | M |
| 4 | des(1)-MS10 | 1139.6 | 1139.6 | 18.1 | d | M |
| 17 | [Pya(4)10]MS10 | 1303.6 | 1303.6 | 14.7 | d | M |
| 18 | [Tyr(Me)10]MS10 | 1332.7 | 1332.7 | 17.7 | d | M |
| 19 | [Phe(2F)10]MS10 | 1320.5 | 1320.6 | 17.8 | d | M |
| 23 | [Tyr5]MS10 | 1378.6 | 1378.8 | 18.6 | d | M |
| 24 | [Leu5]MS10 | 1328.7 | 1328.7 | 19.8 | d | M |
| 30 | Acetyl-MS10 | 1344.5 | 1344.6 | 29.2 | b | A |
| 31 | Fmoc-MS10 | 1524.6 | 1524.7 | 23.1 | b | A |
| 38 | [D-Ser5]MS10 | 1302.5 | 1302.6 | 11.8 | c | A |
| 39 | [D-Asn4]MS10 | 1302.5 | 1302.6 | 11.6 | c | A |
| 40 | [D-Trp3]MS10 | 1302.5 | 1302.6 | 11.5 | c | A |
| 41 | [D-Asn2]MS10 | 1302.5 | 1302.6 | 11.7 | c | A |
| 42 | [D-Tyr1]MS10 | 1302.5 | 1302.6 | 11.4 | c | A |
| 44 | [Lys9]MS10 | 1274.6 | 1274.6 | 11.7 | c | A |
| 45 | [Ala8]MS10 | 1260.5 | 1260.6 | 10.0 | c | A |
| 50 | [Ala7]MS10 | 1316.3 | 1316.7 | 12.2 | c | A |
| 51 | [NMePhe10]MS10 | 1316.3 | 1316.7 | 22.7 | a | A |
| 53 | des(1-3)-Fmoc-MS10 | 1061.2 | 1061.5 | 27.3 | a | A |
| 54 | des(1-2)-Fmoc-MS10 | 1247.4 | 1247.6 | 29.6 | a | A |
| 55 | des(1)-Fmoc-MS10 | 1361.6 | 1361.6 | 28.2 | a | A |
| 56 | [Lys2]MS10 | 1316.6 | 1316.7 | 16.8 | d | M |
| 57 | [Asp2]MS10 | 1303.7 | 1303.6 | 17.7 | d | M |
| 58 | [Tyr2]MS10 | 1351.7 | 1351.7 | 18.2 | d | M |
| 59 | [Leu2]MS10 | 1301.6 | 1301.7 | 19.2 | d | M |
| 60 | [Pya(3)10]MS10 | 1303.6 | 1303.6 | 14.7 | d | M |
| 61 | [Phe(4F)10]MS10 | 1320.6 | 1320.6 | 18.0 | d | M |
| 67 | [Ala3]MS10 | 1187.4 | 1187.6 | 9.3 | c | A |
| 68 | [Leu3]MS10 | 1229.6 | 1229.6 | 11.1 | c | A |
| 69 | [Ser3]MS10 | 1203.5 | 1203.6 | 8.9 | c | A |
| 70 | [Asp3]MS10 | 1231.6 | 1231.6 | 9.0 | c | A |
| 71 | [Lys3]MS10 | 1244.6 | 1244.7 | 8.1 | c | A |
| 72 | [Ala1]MS10 | 1210.5 | 1210.6 | 11.1 | c | A |
| 73 | [Leu1]MS10 | 1252.6 | 1252.7 | 12.5 | c | A |
| 74 | [Ser1]MS10 | 1226.6 | 1226.6 | 10.9 | c | A |
| 75 | [Asp1]MS10 | 1254.4 | 1254.6 | 11.0 | c | A |

TABLE 2

| | | | | | | |
|---|---|---|---|---|---|---|
| 76 | [Lys1]MS10 | 1267.6 | 1267.7 | 10 | c | A |
| 77 | [Phe(4CN)10]MS10 | 1327.5 | 1327.6 | 17.2 | d | M |

TABLE 2-continued

| | | | | | | | |
|---|---|---|---|---|---|---|---|
| 78 | [Trp(For)3, Phe(4CN)10]MS10 | 1355.6 | 1355.6 | 17.4 | d | M | |
| 79 | [Hph10]MS10 | 1316.5 | 1316.7 | 20.6 | a | A | |
| 81 | [NMeArg9]MS10 | 1316.3 | 1316.7 | 23.3 | a | A | |
| 82 | [Arg(Me)9]MS10 | 1316.5 | 1316.7 | 20.1 | a | E | |
| 83 | [Arg(Me2)asy9]MS10 | 1330.4 | 1330.7 | 21.3 | a | A | |
| 87 | des(4-5)-Boc-MS10 | 1201.6 | 1201.6 | 22.5 | d | M | |
| 88 | des(4-5)-MS10 | 1101.5 | 1101.5 | 18.6 | d | M | |
| 90 | [Lys9,9Ψ10,CH2NH]MS10 | 1260.6 | 1260.7 | 19.8 | a | D | |
| 91 | [8Ψ9,CH2NH]MS10 | 1288.7 | 1288.7 | 20.5 | a | D | |
| 97 | [Har9]MS10 | 1316.3 | 1316.7 | 11.9 | c | A | |
| 98 | [Lys(Me2)9]MS10 | 1302.6 | 1302.7 | 11.8 | c | A | |
| 101 | [Ser7]MS10 | 1332.6 | 1332.6 | 11.6 | c | A | |
| 105 | [Nle8]MS10 | 1302.3 | 1302.6 | 11.9 | c | A | |
| 107 | [Val8]MS10 | 1288.5 | 1288.6 | 11 | c | A | |
| 109 | [Tyr10]MS10 | 1408.4 | 1408.7 | 10.2 | c | A | |
| 110 | [Nal(2)10]MS10 | 1332.4 | 1332.6 | 13.5 | c | A | |
| 111 | [Phe(F5)10]MS10 | 1392.2 | 1392.6 | 13.5 | c | A | |
| 112 | [Cha10]MS10 | 1308.4 | 1308.7 | 13.4 | c | A | |
| 114 | des(1-3)-3-(3-Indolyl)propionyl-MS10 | 1010.5 | 1010.5 | 13.8 | c | A + I | |
| 121 | des(1-4)-[Trp5]MS10 | 824.3 | 824.5 | 22.5 | d | M | |
| 123 | [NMeLeu8]MS10 | 1316.7 | 1316.7 | 12.7 | c | A | |
| 126 | [NMeSer5]MS10 | 1317 | 1316.7 | 11.8 | c | A | |
| 127 | [D-Asn4,NMePhe6]MS10 | 1316.7 | 1316.7 | 11.8 | c | A | |
| 128 | [10Ψ,CSNH]MS10 | 1318.4 | 1318.6 | 21.8 | a | C | |
| 129 | [Arg(Me2)sy9]MS10 | 1331.2 | 1330.7 | 20.9 | a | A | |
| 130 | [Phe(4Cl)10]MS10 | 1336.4 | 1336.6 | 13.1 | c | A | |
| 131 | [Phe(4NH2)10]MS10 | 1317.4 | 1317.6 | 8.3 | c | A | |
| 132 | [Phe(4NO2)10]MS10 | 1347.4 | 1347.6 | 12.2 | c | A | |
| 133 | [Nal(1)10]MS10 | 1352.6 | 1352.7 | 13.5 | c | A | |
| 134 | [Trp10]MS10 | 1341.5 | 1341.6 | 12 | c | A | |
| 137 | [Nle9]MS10 | 1259.4 | 1259.6 | 15.3 | c | A | |
| 138 | [Cit9]MS10 | 1303.4 | 1303.6 | 12.2 | c | A | |
| 140 | [Arg(Me)9,NMePhe10]MS10 | 1330.4 | 1330.7 | 21 | a | E | |
| 141 | [D-Tyr1,Arg(Me)9]MS10 | 1316.9 | 1316.7 | 20.2 | a | E | |
| 142 | [D-Tyr1,D-Trp3,Arg(Me)9]MS10 | 1316.7 | 1316.7 | 20.1 | a | E | |
| 143 | [D-Trp3,Arg(Me)9]MS10 | 1316.7 | 1316.7 | 20.3 | a | E | |
| 144 | des(1-3)-Fmoc-[Arg(Me)9]MS10 | 1075.2 | 1075.5 | 26 | a | E | |
| 145 | des(1-2)-Fmoc-[Arg(Me)9]MS10 | 1261.2 | 1261.6 | 28.6 | a | E | |

TABLE 3

| | | | | | | | |
|---|---|---|---|---|---|---|---|
| 146 | [10Ψ,CSNH,D-Tyr1]MS10 | 1318.4 | 1318.6 | 21.4 | a | C | |
| 150 | [Tyr6]MS10 | 1318.4 | 1318.6 | 10.2 | c | A | |
| 151 | [Nal(1)6]MS10 | 1352.6 | 1352.7 | 13.5 | c | A | |
| 152 | [Nal(2)6]MS10 | 1352.6 | 1352.7 | 13.6 | c | A | |
| 153 | [Phe(F5)6]MS10 | 1392.6 | 1392.6 | 13.7 | c | A | |
| 154 | [Phe(4F)6]MS10 | 1320.8 | 1320.6 | 12.3 | c | A | |
| 156 | [Cha6]MS10 | 1308.2 | 1308.5 | 13.2 | c | A | |
| 163 | [6Ψ7,CH2NH]MS10 | 1288.7 | 1288.7 | 18.2 | a | D | |
| 165 | [Dap(Gly)9] MS10 | 1289.8 | 1289.6 | 19.2 | a | E | |
| 166 | [6Ψ7,CSNH]MS10 | 1318.7 | 1318.6 | 20.8 | a | F | |
| 169 | [D-Tyr1,Ala3,Arg(Me)9]MS10 | 1202.1 | 1201.6 | 9.0 | c | E | |
| 170 | [D-Tyr1,Ser3,Arg(Me)9]MS10 | 1218.2 | 1217.6 | 8.8 | c | E | |
| 171 | [D-Tyr1,Cha3,Arg(Me)9]MS10 | 1284.2 | 1283.7 | 12.1 | c | E | |
| 172 | [D-Tyr1,Cha6,Arg(Me)9]MS10 | 1402.9 | 1322.7 | 13.1 | c | E | |
| 173 | [D-Tyr1,Ala7,Arg(Me)9]MS10 | 1410.9 | 1330.7 | 12.2 | c | E | |
| 174 | [D-Tyr1,Arg(Me)9,Trp10]MS10 | 1335.3 | 1335.7 | 11.7 | c | E | |
| 176 | [AzaGly7]MS10 | 1303.3 | 1303.6 | 18.9 | a | G | |
| 181 | [D-Tyr1,Cha3,6,Arg(Me)9]MS10 | 1370.6 | 1370.6 | 13.9 | c | E | |
| 182 | [D-Tyr1,Cha3,6,Arg(Me)9,Trp10] MS10 | 1328.2 | 1328.7 | 21.3 | a | E | |
| 183 | [Phe(4NH2)9]MS10 | 1328.2 | 1308.6 | 19.4 | a | A | |
| 184 | [Phe(4-Guanidino)9]MS10 | 1350.4 | 1350.6 | 19.7 | a | E | |
| 185 | [Dap(GnGly)9]MS10 | 1331.2 | 1331.6 | 19.1 | a | E | |
| 186 | [Trp(For)10]MS10 | 1369.3 | 1369.6 | 19.6 | a | B | |
| 187 | [Abu8]MS10 | 1274.4 | 1274.6 | 10.4 | c | A | |
| 189 | [Ala(3-Bzt)10]MS10 | 1358.4 | 1358.6 | 13.4 | c | A | |
| 190 | [D-Tyr1,Cha3,AzaGly7,Arg(Me)9] MS10 | 1284.5 | 1284.7 | 19.3 | a | H | |
| 191 | [D-Tyr1,Ser3,AzaGly7,Arg(Me)9] MS10 | 1218.4 | 1218.6 | 15.9 | a | H | |
| 192 | [D-Tyr1,Arg(Et)9]MS10 | 1330.5 | 1330.7 | 18.9 | a | E | |
| 193 | [D-Tyr1,Arg(n-Pr)9]MS10 | 1344.8 | 1344.7 | 19.4 | a | E | |
| 194 | [D-Tyr1,Arg(Ac)9]MS10 | 1345.1 | 1344.6 | 18.8 | a | E | |
| 197 | [Phe(3F)10]MS10 | 1320.6 | 1320.6 | 12.2 | c | A | |
| 198 | [Phe(3,4F2)10]MS10 | 1338.7 | 1338.6 | 12.7 | c | A | |
| 199 | [Phe(3,4Cl2)10]MS10 | 1370.6 | 1370.6 | 13.1 | c | A | |
| 200 | [Phe(3CF3)10]MS10 | 1370.6 | 1370.6 | 13.1 | c | A | |
| 201 | [Ala(2-Qui)10]MS10 | 1353.4 | 1353.6 | 9.8 | c | A | |

TABLE 3-continued

| | | | | | | |
|---|---|---|---|---|---|---|
| 203 | [D-Tyr1,Cha6,Arg(Me)9]MS10 | 1322.4 | 1322.7 | 12.9 | c | E |
| 204 | [D-Tyr1,Ala7,Arg(Me)9]MS10 | 1330.4 | 1330.7 | 11.7 | c | E |
| 205 | [D-Tyr1,Thr3,Arg(Me)9]MS10 | 1231.4 | 1231.6 | 9.0 | c | E |
| 206 | [D-Tyr1,Ile3,Arg(Me)9]MS10 | 1243.6 | 1243.7 | 10.1 | c | E |
| 207 | [D-Tyr1,Ser4,Arg(Me)9]MS10 | 1289.5 | 1289.6 | 11.7 | c | E |

TABLE 4

| | | | | | | |
|---|---|---|---|---|---|---|
| 208 | [D-Tyr1,Thr4,Arg(Me)9]MS10 | 1303.4 | 1303.7 | 12.0 | c | E |
| 209 | [D-Tyr1,Gln4,Arg(Me)9]MS10 | 1330.8 | 1330.7 | 11.6 | c | E |
| 210 | [D-Tyr1,Ala4,Arg(Me)9]MS10 | 1273.7 | 1273.6 | 12.3 | c | E |
| 211 | [D-Tyr1,Thr5,Arg(Me)9]MS10 | 1330.7 | 1330.7 | 11.7 | c | E |
| 212 | [D-Tyr1,Ala5,Arg(Me)9]MS10 | 1300.5 | 1300.7 | 12.1 | c | E |
| 213 | [D-Tyr1,Val8,Arg(Me)9]MS10 | 1302.5 | 1302.6 | 10.4 | c | E |
| 214 | [D-Tyr1,Gln2,Arg(Me)9]MS10 | 1330.5 | 1330.7 | 11.4 | c | E |
| 215 | [D-Tyr1,Thr2,Arg(Me)9]MS10 | 1303.4 | 1303.7 | 11.9 | c | E |
| 216 | des(1)-[D-Asn2,Arg(Me)9]MS10 | 1153.3 | 1153.6 | 11.1 | c | E |
| 217 | des(1)-[D-Tyr2,Arg(Me)9]MS10 | 1202.4 | 1202.6 | 12.3 | c | E |
| 218 | [N((CH2)3Gn))Gly9]MS10 | 1302.5 | 1302.7 | 18.6 | a | L |
| 220 | [Arg(Et)9]MS10 | 1330.7 | 1330.7 | 19.5 | a | E |
| 221 | [D-Tyr1,Thr3,AzaGly7,Arg(Me)9] MS10 | 1232.5 | 1232.6 | 16.1 | a | H |
| 222 | des(1)-[D-Tyr2,AzaGly7,Arg(Me)9]MS10 | 1203.5 | 1203.6 | 19.3 | a | H |
| 223 | des(1-2)-[D-Trp3,Arg(Me)9]MS10 | 1039.5 | 1039.5 | 11.0 | c | E |
| 224 | des(1)-[D-Tyr2,D-Trp3,Arg(Me)9]MS10 | 1202.4 | 1202.6 | 12.2 | c | E |
| 225 | des(1)-[D-Asn2,D-Trp3,Arg(Me)9]MS10 | 1153.6 | 1153.6 | 11.1 | c | E |
| 226 | des(1)-[D-Tyr2,Ser3,Arg(Me)9] MS10 | 1103.5 | 1103.6 | 9.5 | c | E |
| 227 | des(1)-[D-Tyr2,Thr3,Arg(Me)9] MS10 | 1117.3 | 1117.6 | 9.8 | c | E |
| 228 | des(1)-[D-Tyr2,Ile3,Arg(Me)9]MS10 | 1129.6 | 1129.6 | 11.5 | c | E |
| 229 | [D-Tyr1,Val3,Arg(Me)9]MS10 | 1229.5 | 1229.6 | 9.7 | c | E |
| 230 | [D-Tyr1,D-Asn2,Arg(Me)9]MS10 | 1316.5 | 1316.7 | 11.8 | c | E |
| 231 | [D-Tyr1,D-Asn2,D-Trp3,Arg(Me)9]MS10 | 1316.3 | 1316.7 | 11.7 | c | E |
| 232 | [D-Tyr1,AzaGly7,Arg(Me)9]MS10 | 1317.0 | 1317.6 | 21.0 | a | H |
| 233 | [D-Tyr1,Ile3,AzaGly7,Arg(Me)9] MS10 | 1244.1 | 1244.7 | 20.9 | a | H |
| 234 | [D-Tyr1,Val3,AzaGly7,Arg(Me)9] MS10 | 1230.5 | 1230.6 | 20.6 | a | H |
| 235 | [D-Tyr1,Ala3,AzaGly7,Arg(Me)9] MS10 | 1202.5 | 1202.6 | 20.5 | a | H |
| 236 | [D-Tyr1,D-Trp3,AzaGly7,Arg(Me)9] MS10 | 1317.6 | 1317.6 | 20.9 | a | H |
| 237 | [D-Tyr1,D-Asn2,AzaGly7,Arg(Me)9] MS10 | 1317.6 | 1317.6 | 20.9 | a | H |
| 238 | [D-Tyr1,D-Asn2,D-Trp3,AzaGly7,Arg(Me)9]MS10 | 1317.6 | 1317.6 | 20.6 | a | H |
| 239 | des(1)-[D-Tyr2,Ser3,AzaGly7,Arg(Me)9]MS10 | 1104.1 | 1104.6 | 19.0 | a | H |
| 240 | des(1)-[D-Tyr2,Ile3,AzaGly7,Arg(Me)9]MS10 | 1130.1 | 1130.6 | 20.3 | a | H |
| 241 | des(1)-[D-Tyr2,Thr3,AzaGly7,Arg(Me)9]MS10 | 1188.0 | 1118.6 | 20.3 | a | H |
| 242 | des(1)-[D-Tyr2,D-Trp3,AzaGly7,Arg(Me)9]MS10 | 1202.9 | 1203.6 | 21.2 | a | H |
| 244 | [D-Tyr1,Phe3,AzaGly7,Arg(Me)9] MS10 | 1278.6 | 1278.6 | 10.5 | c | H |
| 245 | [D-Tyr1,Nal(1)3,AzaGly7,Arg(Me)9]MS10 | 1328.5 | 1328.7 | 12.3 | c | H |
| 246 | [D-Tyr1,Nal(2)3,AzaGly7,Arg(Me)9]MS10 | 1328.7 | 1328.7 | 12.3 | c | H |
| 247 | [D-Tyr1,Phe(2Cl)3,AzaGly7,Arg(Me)9]MS10 | 1315.6 | 1312.6 | 11.3 | c | H |

TABLE 5

| | | | | | | |
|---|---|---|---|---|---|---|
| 248 | [D-Tyr1,Phe(3Cl)3,AzaGly7,Arg(Me)9]MS10 | 1312.5 | 1312.6 | 11.6 | c | H |
| 249 | [D-Tyr1,Phe(4Cl)3,AzaGly7,Arg(Me)9]MS10 | 1312.5 | 1312.6 | 11.7 | c | H |
| 250 | [D-Tyr1,Phe(4NH2)3,AzaGly7,Arg(Me)9]MS10 | 1293.4 | 1293.6 | 7.8 | c | H |
| 251 | [D-Tyr1,Pya(3)3,AzaGly7,Arg(Me)9]MS10 | 1279.4 | 1279.6 | 7.8 | c | H |
| 252 | [D-Tyr1,D-Ala3,AzaGly7,Arg(Me)9]MS10 | 1202.4 | 1202.6 | 8.5 | c | H |
| 253 | [D-Tyr1,Pro3,AzaGly7,Arg(Me)9] MS10 | 1228.4 | 1228.6 | 8.6 | c | H |
| 254 | des(1)-[D-Tyr2,Phe3,AzaGly7,Arg(Me)9]MS10 | 1164.4 | 1164.6 | 11.8 | c | H |
| 255 | des(1)-[D-Tyr2,Nal(2)3,AzaGly7,Arg(Me)9]MS10 | 1214.5 | 1214.6 | 13.7 | c | H |
| 256 | des(1)-[D-Pya(3)2,Phe3,AzaGly7,Arg(Me)9]MS10 | 1149.3 | 1149.6 | 9.5 | c | H |
| 257 | [D-Tyr1,D-Asn2,Phe3,AzaGly7,Arg(Me)9]MS10 | 1278.5 | 1278.6 | 10.9 | c | H |
| 258 | [D-Pya(3)1,AzaGly7,Arg(Me)9] MS10 | 1302.3 | 1302.6 | 10.1 | c | H |
| 259 | [D-Ala1,AzaGly7,Arg(Me)9]MS10 | 1225.5 | 1225.6 | 10.7 | c | H |
| 260 | des(1-3)-3-(3-Indolyl)propionyl-[AzaGly7,Arg(Me)9]MS10 | 1025.2 | 1025.5 | 13.7 | c | I |
| 261 | [7Ψ8,CH2NH]MS10 | 1288.1 | 1288.7 | 17.2 | a | D |
| 265 | des(1-3)-Indole-3-carbonyl-[AzaGly7,Arg(Me)9]MS10 | 997.3 | 997.5 | 12.6 | c | I |
| 266 | des(1-3)-Indole-3-acetyl-[AzaGly7,Arg(Me)9]MS10 | 1011.3 | 1011.5 | 12.7 | c | I |
| 267 | des(1-3)-4-(3-Indolyl)butyryl-[AzaGly7,Arg(Me)9]MS10 | 1039.3 | 1039.5 | 14.4 | c | I |

TABLE 5-continued

| | | | | | | |
|---|---|---|---|---|---|---|
| 268 | des(1-3)-Diphenylacetyl-[AzaGly7,Arg(Me)9]MS10 | 1048.5 | 1048.5 | 15.7 | c | I |
| 269 | des(1-3)-3-Phenylpropionyl-[AzaGly7,Arg(Me)9]MS10 | 986.7 | 986.5 | 13.5 | c | I |
| 270 | Endo-Phe5a-[D-Tyr1,Phe3,AzaGly7,Arg(Me)9]MS10 | 1425.5 | 1425.7 | 13.4 | c | H |
| 271 | des(1-2)-[AzaGly7,Arg(Me)9]MS10 | 1040.2 | 1040.5 | 10.4 | c | H |
| 272 | des(1-2)-Acetyl-[AzaGly7,Arg(Me)9]MS10 | 1082.3 | 1082.6 | 12.8 | c | H |
| 273 | des(1-2)-Amidino-[AzaGly7,Arg(Me)9]MS10 | 1082.3 | 1082.6 | 11.4 | c | J |
| 274 | des(1-2)-Acetyl-[Ala3,AzaGly7,Arg(Me)9]MS10 | 967.3 | 967.5 | 9.6 | c | H |
| 275 | des(1-2)-Acetyl-[Arg3,AzaGly7,Arg(Me)9]MS10 | 1052.2 | 1052.6 | 8.5 | c | H |
| 276 | des(1-2)-Acetyl-[Thr3,AzaGly7,Arg(Me)9]MS10 | 997.2 | 997.5 | 9.4 | c | H |
| 277 | des(1-3)-n-Hexanoyl-[AzaGly7,Arg(Me)9]MS10 | 952.2 | 952.5 | 13.4 | c | I |
| 278 | des(1-3)-Cyclohexanecarbonyl-[AzaGly7,Arg(Me)9]MS10 | 964.3 | 964.5 | 13.2 | c | I |
| 279 | des(1-3)-2-(Indol-3-yl)ethylcarbamoyl-[AzaGly7,Arg(Me)9]MS10 | 1040.2 | 1040.5 | 20.1 | a | N |
| 281 | [D-Tyr1,Pya(2)6,Arg(Me)9]MS10 | 1317.3 | 1317.6 | 7.8 | c | E |
| 282 | [D-Tyr1,Pya(4)6,Arg(Me)9]MS10 | 1317.2 | 1317.6 | 8.0 | c | E |

TABLE 6

| | | | | | | |
|---|---|---|---|---|---|---|
| 283 | [D-Tyr1,D-Asn2,Cha3,AzaGly7,Arg(Me)9]MS10 | 1284.3 | 1284.7 | 12.3 | c | H |
| 284 | [D-Tyr1,D-Asn2,Thr3,AzaGly7,Arg(Me)9]MS10 | 1232.2 | 1232.6 | 8.6 | c | H |
| 285 | [D-Tyr1,Pya(2)3,AzaGly7,Arg(Me)9]MS10 | 1279.2 | 1279.6 | 7.9 | c | H |
| 286 | [D-Tyr1,Pya(4)3,AzaGly7,Arg(Me)9]MS10 | 1279.2 | 1279.6 | 7.7 | c | H |
| 287 | [D-Tyr1,D-Ser2,AzaGly7,Arg(Me)9]MS10 | 1290.1 | 1290.6 | 11.4 | c | H |
| 288 | [D-Tyr1,D-His2,AzaGly7,Arg(Me)9]MS10 | 1340.2 | 1340.7 | 10.3 | c | H |
| 289 | des(1)-[D-Pya(3)2,AzaGly7,Arg(Me)9]MS10 | 1188.2 | 1188.6 | 10.0 | c | H |
| 290 | [D-Pya(3)1,D-Asn2,Cha3,AzaGly7,Arg(Me)9]MS10 | 1269.5 | 1269.7 | 10.9 | c | H |
| 291 | [D-Pya(3)1,D-Tyr2,Cha3,AzaGly7,Arg(Me)9]MS10 | 1317.4 | 1318.7 | 12.0 | c | H |
| 293 | [4Ψ5,CH2NH]MS10 | 1288.1 | 1288.7 | 18.4 | a | D |
| 294 | [1Ψ2,CH2NH]MS10 | 1288.4 | 1288.7 | 19.2 | a | D |
| 295 | [2Ψ3,CH2NH]MS10 | 1288.1 | 1288.7 | 18.2 | a | D |
| 296 | [6Ψ7,CSNH,D-Tyr1,Arg(Me)9]MS10 | 1332.1 | 1332.6 | 20.5 | a | F |
| 297 | [D-Tyr1,Thr5,AzaGly7,Arg(Me)9] MS10 | 1331.2 | 1330.7 | 11.3 | c | H |
| 298 | [D-Tyr1,D-Asn2,Thr5,AzaGly7,Arg(Me)9]MS10 | 1331.1 | 1330.7 | 11.6 | c | H |
| 299 | [1Ψ2,CH2NH,AzaGly7,Arg(Me)9]MS10 | 1303.4 | 1330.7 | 11.3 | c | D + H |
| 300 | [1Ψ2,CH2NH,D-Trp3,AzaGly7,Arg(Me)9]MS10 | 1303.4 | 1303.7 | 10.8 | c | D + H |
| 301 | [D-Tyr1,Ala(2-Qui)3,AzaGly7,Arg(Me)9]MS10 | 1329.4 | 1329.6 | 9.0 | c | H |
| 302 | [D-Tyr1,D-Pya(4)3,AzaGly7,Arg(Me)9]MS10 | 1279.4 | 1279.6 | 7.6 | c | H |
| 303 | [D-Tyr1,D-Asn2,Pya(4)3,AzaGly7,Arg(Me)9]MS10 | 1279.4 | 1279.6 | 7.6 | c | H |
| 304 | [D-Asn2,Pya(4)3,AzaGly7,Arg(Me)9]MS10 | 1279.4 | 1279.6 | 7.7 | c | H |
| 305 | des(1)-[D-Tyr2,D-Pya(4)3,AzaGly7,Arg(Me)9]MS10 | 1165.4 | 1165.6 | 8.0 | c | H |
| 306 | [D-Pya(4)1,D-Asn2,Cha3,AzaGly7,Arg(Me)9]MS10 | 1269.5 | 1269.5 | 10.8 | c | H |
| 307 | [7Ψ8,CH2NH,D-Tyr1,Arg(Me)9] MS10 | 1302.2 | 1302.7 | 17.9 | a | D + E |
| 308 | [6Ψ7,CH2NH,D-Tyr1,Arg(Me)9] MS10 | 1302.3 | 1302.7 | 18.1 | a | D + E |
| 310 | [Nar9]MS10 | 1288.8 | 1288.6 | 19.4 | a | E |
| 311 | [Nar(Me)9]MS10 | 1302.3 | 1302.6 | 19.5 | a | E |
| 312 | [Har(Me)9]MS10 | 1330.2 | 1330.7 | 19.5 | a | E |
| 313 | [Dab9]MS10 | 1246.1 | 1246.6 | 19.3 | a | A |
| 314 | [Orn9]MS10 | 1260.2 | 1260.6 | 19.3 | a | A |
| 315 | des(1)-[D-Asn2,Cha3,AzaGly7,Arg(Me)9]MS10 | 1121.3 | 1121.6 | 11.4 | c | H |
| 316 | [D-Tyr1,D-Asn2,Thr3,AzaGly7,Arg(Me)9,Phe(4F)10]MS10 | 1250.5 | 1250.6 | 17.0 | a | H |
| 317 | [D-Tyr1,D-Asn2,Pya(4)3,AzaGly7,Arg(Me)9,Phe(4F)10]MS10 | 1297.4 | 1297.6 | 16.4 | a | H |
| 318 | [D-Tyr1,AzaGly7,Arg(Me)9,Phe(4F)10]MS10 | 1335.4 | 1335.6 | 19.0 | a | H |

TABLE 7

| | | | | | | |
|---|---|---|---|---|---|---|
| 319 | [6Ψ7,NHCO,D-Tyr1,Arg(Me)9] MS10 | 1316.3 | 1316.7 | 18.7 | a | K |
| 322 | des(1-3)-3-(3-Pyridyl)propionyl-[AzaGly7,Arg(Me)9]MS10 | 987.4 | 987.5 | 8.1 | c | I |

TABLE 7-continued

| | | | | | | |
|---|---|---|---|---|---|---|
| 323 | des(1-3)-4-Imidazoleacetyl-[AzaGly7,Arg(Me)9]MS10 | 962.5 | 962.5 | 7.9 | c | I |
| 324 | des(1-3)-4-Piperidinecarbonyl-[AzaGly7,Arg(Me)9]MS10 | 965.5 | 965.5 | 7.7 | c | I |
| 325 | des(1-3)-1-Piperidineacetyl-[AzaGly7,Arg(Me)9]MS10 | 979.5 | 979.5 | 8.5 | c | I |
| 326 | des(1-3)-1-Methylpiperidinio-1-acetyl-[AzaGly7,Arg(Me)9]MS10 | 993.4 | 993.6 | 8.7 | c | I |
| 327 | des(1-3)-1-Pyridinioacetyl-[AzaGly7,Arg(Me)9]MS10 | 973.4 | 973.5 | 8.1 | c | I |
| 328 | des(1-3)-D-Glucronyl-[AzaGly7,Arg(Me)9]MS10 | 1030.2 | 1030.5 | 7.5 | c | I |
| 332 | des(1-5)-GuAmb-[AzaGly7,Arg(Me)9]MS10 | 828.6 | 828.5 | 9.9 | c | H + J |
| 333 | des(1-5)-GuAmb-[Arg(Me)9]MS10 | 827.6 | 827.5 | 10.6 | c | E + J |
| 334 | des(1-5)-GuAmb-[AzaGly7,Arg(Me)9,Trp10]MS10 | 867.6 | 867.5 | 10.3 | c | H + J |
| 339 | des(1-5)-3-(3-Indoly)propionyl-[AzaGly7,Arg(Me)9]MS10 | 824.6 | 824.5 | 16.0 | c | S |
| 340 | des(1-5)-3-(3-Pyridyl)propionyl-[AzaGly7,Arg(Me)9]MS10 | 786.4 | 786.4 | 8.5 | c | S |
| 341 | des(1-5)-Benzoyl-[AzaGly7,Arg(Me)9]MS10 | 757.2 | 757.4 | 14.8 | c | S |
| 344 | des(1-5)-Indole-3-carbonyl-[AzaGly7,Arg(Me)9]MS10 | 796.8 | 796.4 | 14.5 | c | S |
| 345 | des(1-5)-Indole-3-acetyl-[AzaGly7,Arg(Me)9]MS10 | 810.5 | 810.4 | 15.2 | c | S |
| 346 | des(1-5)-Ac-[AzaGly7,Arg(Me)9]MS10 | 695.5 | 695.4 | 10.7 | c | S |
| 347 | des(1-5)-n-Hexanoyl-[AzaGly7,Arg(Me)9]MS10 | 751.7 | 751.5 | 16.2 | c | S |
| 348 | des(1-5)-Z-[AzaGly7,Arg(Me)9]MS10 | 787.5 | 787.4 | 16.7 | c | S |
| 349 | des(1-5)-Tos-[AzaGly7,Arg(Me)9]MS10 | 807.5 | 807.4 | 15.9 | c | S |
| 351 | des(1-5)-Benzoyl-MS10 | 742.4 | 742.4 | 15.1 | c | A + I |
| 352 | des(1-5)-3-(3-Indolyl)propionyl-MS10 | 809.6 | 809.4 | 16.2 | c | A + I |
| 353 | des(1-5)-Benzoyl-[AzaGly7,Arg(Me)9,Trp10]MS10 | 796.4 | 796.4 | 15.0 | c | S |
| 354 | des(1-5)-3-(3-Indolyl)propionyl-[AzaGly7,Arg(Me)9,Trp10]MS10 | 863.4 | 863.5 | 16.2 | c | S |
| 358 | des(1-5)-Ac [AzaGly7,Arg(Me)9,Trp10]MS10 | 734.4 | 734.4 | 11.2 | c | S |
| 362 | des(1-6)-3-Phenylpropionyl-[AzaGly7,Arg(Me)9]MS10 | 638.4 | 638.4 | 12.5 | c | S |
| 364 | des(1-5)-2-(Indol-3-yl)ethylcarbamoyl-[AzaGly7,Arg(Me)9]MS10 | 839.6 | 839.5 | 15.8 | c | N |
| 366 | des(1-5)-n-Hexanoyl-[AzaGly7,Arg(Me)9,Trp10]MS10 | 790.5 | 790.5 | 16.5 | c | S |
| 367 | des(1-5)-Z-[AzaGly7,Arg(Me)9,Trp10]MS10 | 826.5 | 826.4 | 16.8 | c | S |
| 368 | des(1-5)-Tos-[AzaGly7,Arg(Me)9,Trp10]MS10 | 846.6 | 846.4 | 16.0 | c | S |
| 369 | des(1-5)-2-(Indol-3-yl)ethylcarbamoyl-[AzaGly7,Arg(Me)9,Trp10]MS10 | 878.9 | 878.5 | 16.1 | c | N |

TABLE 8

| | | | | | | |
|---|---|---|---|---|---|---|
| 373 | des(1-6)-(2S)-2-acethoxy-3-phenylpropionyl-[AzaGly7,Arg(Me)9,Trp10]MS10 | 735.5 | 735.4 | 13.6 | c | S |
| 374 | des(1-6)-Z-[AzaGly7,Arg(Me)9,Trp10]MS10 | 679.5 | 679.4 | 31.2 | c | S |
| 375 | 2-Aminoethyl-Gly-[D-Tyr1,Arg(Me)9]MS10 | 1416.4 | 1416.7 | 17.3 | e | E |
| 378 | des(1-6)-Diphenylacetyl-[AzaGly7,Arg(Me)9,Trp10]MS10 | 739.4 | 739.4 | 15.9 | c | S |
| 379 | des(1-6)-(2S)-2-(3-Indolylprpionyloxy)-3-phenylpropionyl-[AzaGly7,Arg(Me)9,Trp10]MS10 | 864.7 | 864.5 | 18.2 | c | S |
| 380 | des(1-6)-(2S)-2-Benzoyloxy-3-phenylpropionyl-[AzaGly7,Arg(Me)9,Trp10]MS10 | 797.6 | 797.4 | 17.2 | c | S |
| 385 | des(1)-[D-Tyr2,D-Pya(4)3,AzaGly7,Arg(Me)9,Trp10]MS10 | 1204.4 | 1204.6 | 8.3 | c | O |
| 386 | des(1-3)-3-(3-Pyridyl)propionyl-[AzaGly7,Arg(Me)9,Trp10]MS10 | 1026.4 | 1026.2 | 8.5 | c | I |
| 387 | Dap-[D-Tyr1,Arg(Me)9]MS10 | 1402.7 | 1402.7 | 17.0 | e | E |
| 392 | des(1-5)-Benzoyl-[Ala6,Arg(Me)9,Trp10]MS10 | 720.5 | 720.4 | 11.4 | c | S |
| 393 | des(1-6)-Dibenzylcarbamoyl-[AzaGly7,Arg(Me)9,Trp10]MS10 | 768.7 | 768.4 | 16.9 | c | P |
| 397 | Methylthiocarbamoyl-Sar-[D-Tyr1,Arg(Me)9]MS10 | 1461.2 | 1460.7 | 20.0 | e | E |
| 400 | (S)-1-(Quinolin-8-yl-carbamoyl)-4-thiapentylcarbamoyl-[D-Tyr1,Arg(Me)9]MS10 | 1617.9 | 1617.7 | 21.7 | e | E |
| 408 | des(1-6)-1-Oxo-isochroman-3-carbonyl-[AzaGly7,Arg(Me)9,Trp10]MS10 | 719.1 | 719.4 | 11.3 | c | S |
| 412 | des(1-6)-(2R)-2-Benzoyloxy-3-phenylpropionyl-[AzaGly7,Arg(Me)9,Trp10]MS10 | 796.8 | 797.4 | 17.1 | c | S |
| 417 | des(1-6)-Benzylphenethylcarbamoyl-[AzaGly7,Arg(Me)9,Trp10]MS10 | 782.9 | 782.4 | 17.8 | c | P |
| 421 | des(1-5)-Benzoyl-[6Ψ7,CH2O,Arg(Me)9,Trp10]MS10 | 782.2 | 782.4 | 22.1 | e | Q |
| 423 | des(1-5)-Benzoyl-[6Ψ7,NHCO,Arg(Me)9,Trp10]MS10 | 795.4 | 795.4 | 19.8 | e | I + K |
| 428 | des(1-6)-Dibenzylaminocarbamoyl-[AzaGly7,Arg(Me)9,Trp10]MS10 | 783.8 | 783.4 | 17.0 | c | P |
| 431 | des(1-5)-Benzoyl-[AzaPhe6,AzaGly7,Arg(Me)9,Trp10]MS10 | 797.7 | 797.4 | 15.3 | c | U |
| 432 | des(1-5)-3-(3-Pyridyl)propionyl-[AzaGly7,Arg(Me)9,Trp10]MS10 | 797.8 | 797.4 | 9.2 | c | S |
| 434 | des(1-7)-Dibenzylaminocarbamoylacetyl-[Arg(Me)9,Trp10]MS10 | 767.6 | 767.4 | 14.5 | e | R |
| 435 | des(1-5)-2-Pyridinecarbonyl-[AzaGly7,Arg(Me)9,Trp10]MS10 | 797.7 | 797.4 | 14.1 | c | S |
| 436 | des(1-5)-4-Pyridinecarbonyl-[AzaGly7,Arg(Me)9,Trp10]MS10 | 797.8 | 797.4 | 8.8 | c | S |
| 437 | des(1-5)-Propionyl-[AzaGly7,Arg(Me)9,Trp10]MS10 | 748.7 | 748.4 | 14.4 | c | S |
| 438 | des(1-5)-Isobutyryl-[AzaGly7,Arg(Me)9,Trp10]MS10 | 762.4 | 762.4 | 13.7 | c | S |
| 439 | des(1-5)-Cyclohexanecarbonyl-[AzaGly7,Arg(Me)9,Trp10]MS10 | 802.6 | 802.5 | 16.3 | c | S |

TABLE 9

| | | | | | | |
|---|---|---|---|---|---|---|
| 440 | des(1-5)-Phenylacetyl-[AzaGly7,Arg(Me)9,Trp10]MS10 | 810.1 | 810.4 | 15.6 | c | S |
| 441 | des(1-5)-Benzoyl-[Pya(2)6,AzaGly7,Arg(Me)9,Trp10]MS10 | 797.6 | 797.4 | 9.5 | c | S |
| 442 | des(1-5)-Benzoyl-[Pya(4)6,AzaGly7,Arg(Me)9,Trp10]MS10 | 797.6 | 797.4 | 9.1 | c | S |

TABLE 9-continued

| | | | | | | |
|---|---|---|---|---|---|---|
| 443 | des(1-5)-2-Methylnicotinoyl-[AzaGly7,Arg(Me)9,Trp10]MS10 | 811.6 | 811.4 | 9.0 | c | S |
| 444 | des(1-5)-5-Methylnicotinoyl-[AzaGly7,Arg(Me)9,Trp10]MS10 | 811.5 | 811.4 | 9.2 | c | S |
| 445 | des(1-5)-6-Methylnicotinoyl-[AzaGly7,Arg(Me)9,Trp10]MS10 | 811.4 | 811.4 | 8.6 | c | S |
| 446 | des(1-5)-Pyrazinecarbonyl-[AzaGly7,Arg(Me)9,Trp10]MS10 | 798.4 | 798.4 | 12.4 | c | S |
| 447 | des(1-5)-Cyclopropanecarbonyl-[AzaGly7,Arg(Me)9,Trp10]MS10 | 765.9 | 766.5 | 13.0 | c | S |
| 448 | des(1-5)-Trifluoroacetyl-[AzaGly7,Arg(Me)9,Trp10]MS10 | 788.6 | 788.4 | 14.6 | c | S |
| 449 | des(1-5)-Benzoyl-[Cha6,AzaGly7,Arg(Me)9,Trp10]MS10 | 802.6 | 802.5 | 17.2 | c | S |
| 450 | des(1-5)-Benzyl-[AzaGly7,Arg(Me)9,Trp10]MS10 | 782.7 | 782.4 | 11.2 | c | H + D |
| 451 | des(1-5)-Cyclopropanecarbonyl-[Cha6,AzaGly7,Arg(Me)9,Trp10]MS10 | 765.9 | 766.5 | 15.1 | c | S |
| 452 | des(1-5)-(R)-3-hydroxy-2-methylpropionyl-[AzaGly7,Arg(Me)9,Trp10]MS10 | 777.8 | 778.4 | 11.4 | c | S |
| 453 | des(1-5)-2-Hydroxyisobutyryl-[AzaGly7,Arg(Me)9,Trp10]MS10 | 777.9 | 778.4 | 11.9 | c | S |
| 454 | des(1-5)-3-Furancarbonyl-[AzaGly7,Arg(Me)9,Trp10]MS10 | 786.8 | 786.4 | 13.7 | c | S |
| 455 | des(1-5)-Pyrrole-2-carbonyl-[AzaGly7,Arg(Me)9,Trp10]MS10 | 785.7 | 785.4 | 13.9 | c | S |
| 459 | des(1-5)-4-Imidazolecarbonyl-[AzaGly7,Arg(Me)9,Trp10]MS10 | 786.6 | 786.4 | 8.5 | c | S |
| 460 | des(1-5)-4-Pyridinecarbonyl-[AzaGly7,Val8,Arg(Me)9,Trp10]MS10 | 783.5 | 783.4 | 6.7 | c | S |
| 461 | des(1-5)-4-Pyridinecarbonyl-[AzaGly7,Arg(Me)9,Nal(2)10]MS10 | 808.5 | 808.4 | 11.1 | c | S |
| 462 | des(1-5)-6-Hydroxynicotinoyl-[AzaGly7,Arg(Me)9,Trp10]MS10 | 813.8 | 813.4 | 10.2 | c | S |
| 463 | des(1-5)-6-Chloronicotinoyl-[AzaGly7,Arg(Me)9,Trp10]MS10 | 831.8 | 831.4 | 14.3 | c | S |
| 464 | des(1-5)-6-(Trifluoromethyl)nicotinoyl-[AzaGly7,Arg(Me)9,Trp10]MS10 | 865.7 | 865.4 | 15.8 | c | S |
| 466 | des(1-5)-2-Azetidinecarbonyl-[AzaGly7,Arg(Me)9,Trp10]MS10 | 775.8 | 775.4 | 8.9 | c | H |
| 467 | des(1-5)-Dimethylcarbamoyl-[AzaGly7,Arg(Me)9,Trp10]MS10 | 763.7 | 763.4 | 12.5 | c | H + N |
| 468 | des(1-5)-1-Azetidinecarbonyl-[AzaGly7,Arg(Me)9,Trp10]MS10 | 775.4 | 775.4 | 12.5 | e | H + N |
| 471 | des(1-5)-4-Pyridinecarbonyl-[AzaGly7,Arg(Me)9]MS10 | 758.8 | 758.5 | 9.1 | c | S |
| 472 | des(1-5)-4-Aminobenzoyl-[AzaGly7,Arg(Me)9,Trp10]MS10 | 811.8 | 811.4 | 11.2 | c | H |
| 473 | des(1-5)-4-Aminomethylbenzoyl-[AzaGly7,Arg(Me)9,Trp10]MS10 | 825.8 | 825.5 | 9.5 | c | H |

TABLE 10

| | | | | | | |
|---|---|---|---|---|---|---|
| 474 | des(1-5)-Pyrrole-3-carbonyl-[AzaGly7,Arg(Me)9,Trp10]MS10 | 785.8 | 785.4 | 12.2 | c | S |
| 475 | des(1-5)-Pyrimidine-4-carbonyl-[AzaGly7,Arg(Me)9,Trp10]MS10 | 798.8 | 798.4 | 12.2 | c | S |
| 477 | des(1-5)-4-Pyridinecarbonyl-[AzaGly7,Orn9,Trp10]MS10 | 741.6 | 741.3 | 8.6 | c | G + I |
| 478 | des(1-5)-4-Pyridinecarbonyl-[AzaGly7,Har9,Trp10]MS10 | 797.9 | 797.4 | 8.6 | c | G + I |
| 479 | des(1-5)-Pyrimidine-2-carbonyl-[AzaGly7,Arg(Me)9,Trp10]MS10 | 798.8 | 798.4 | 11.8 | c | S |
| 480 | des(1-5)-Pyridazine-4-carbonyl-[AzaGly7,Arg(Me)9,Trp10]MS10 | 798.8 | 798.4 | 10.7 | c | S |
| 481 | des(1)-[D-Tyr2,D-Pya(4)3,AzaGly7,Har9,Trp10]MS10 | 1204.8 | 1204.6 | 8.2 | c | G |
| 486 | des(1)-[D-Tyr2,D-Pya(4)3,AzaGly7,Orn9]MS10 | 1109.6 | 1109.6 | 13.6 | e | G |
| 487 | des(1)-[D-Tyr2,D-Pya(4)3,AzaGly7,Lys9]MS10 | 1123.5 | 1123.6 | 13.5 | e | G |
| 488 | des(1)-[D-Tyr2,D-Pya(4)3,AzaGly7,Har9]MS10 | 1165.6 | 1165.6 | 14.1 | e | G |
| 489 | des(1)-[D-Tyr2,D-Pya(4)3,AzaGly7,Har(Me)9]MS10 | 1179.6 | 1179.6 | 13.9 | e | O |
| 490 | des(1)-[D-Tyr2,Pya(4)3,AzaGly7,Arg(Me)9]MS10 | 1165.6 | 1165.6 | 7.6 | c | H |
| 491 | des(1)-[D-Tyr2,D-Pya(4)3,Trp5,AzaGly7,Arg(Me)9]MS10 | 1303.8 | 1303.6 | 17.2 | c | O |
| 492 | des(1)-[D-Tyr2,D-Pya(4)3,Ala4,AzaGly7,Arg(Me)9]MS10 | 1161.9 | 1161.6 | 14.3 | e | O |
| 493 | des(1)-[D-Tyr2,D-Pya(4)3,Thr4,AzaGly7,Arg(Me)9]MS10 | 1191.9 | 1191.6 | 14.2 | e | O |
| 494 | des(1,4)-[D-Tyr2,D-Pya(4)3,AzaGly7,Arg(Me)9]MS10 | 1090.9 | 1090.6 | 8.4 | c | O |
| 495 | des(1-3)-[D-Tyr4,Pya(4)5,AzaGly7,Arg(Me)9,Trp10]MS10 | 1003.9 | 1003.5 | 7.6 | c | O |
| 496 | des(1)-[D-Tyr2,D-Pya(4)3,Cha6,Arg(Me)9,Trp10]MS10 | 1209.8 | 1209.7 | 10.4 | c | E |
| 497 | des(1)-[D-Tyr2,D-Pya(4)3,Cha6,Ala7,Arg(Me)9,Trp10]MS10 | 1223.7 | 1223.7 | 10.5 | c | E |
| 498 | des(1)-[D-Tyr2,D-Pya(4)3,Ile5,AzaGly7,Arg(Me)9,Trp10]MS10 | 1230.7 | 1230.7 | 16.8 | c | O |
| 499 | des(1-3)-3-Phenylpropionyl-[AzaGly7,Arg(Me)9,Trp10]MS10 | 1025.3 | 1025.5 | 13.6 | c | T |
| 500 | des(1-3)-3-Phenylpropionyl-[Ala4,AzaGly7,Arg(Me)9,Trp10]MS10 | 982.5 | 982.5 | 15.1 | c | T |

TABLE 10-continued

| | | | | | | |
|---|---|---|---|---|---|---|
| 501 | des(1)-[D-Tyr2,D-Pya(4)3,Thr5,AzaGly7,Arg(Me)9,Trp10]MS10 | 1218.7 | 1218.6 | 14.2 | e | O |
| 502 | des(1)-[D-Tyr2,Pya(4)3,Ala4,AzaGly7,Arg(Me)9,Trp10]MS10 | 1161.4 | 1161.6 | 14.0 | e | O |
| 503 | des(1)-[D-Tyr2,D-Trp3,Ala4,AzaGly7,Arg(Me)9,Trp10]MS10 | 1199.3 | 1199.6 | 17.8 | e | O |
| 504 | [Acp1,D-Tyr2,D-Pya(4)3,AzaGly7,Arg(Me)9]MS10 | 1278.6 | 1278.5 | 8.1 | c | H |
| 505 | des(1-3)-3-Phenylpropionyl-[Thr5,AzaGly7,Arg(Me)9,Trp10]MS10 | 1040.0 | 1039.6 | 13.9 | c | T |
| 506 | des(1-3)-3-Phenylpropionyl-[Ile5,AzaGly7,Arg(Me)9,Trp10]MS10 | 1052.0 | 1051.6 | 17.6 | c | T |
| 507 | des(1-3)-3-Phenylpropionyl-[Trp6,AzaGly7,Arg(Me)9,Trp10]MS10 | 1064.2 | 1064.5 | 13.7 | c | T |

TABLE 11

| | | | | | | |
|---|---|---|---|---|---|---|
| 508 | des(1-3)-3-Phenylpropionyl-[Phe(4F)6,AzaGly7,Arg(Me)9,Trp10]MS10 | 1043.2 | 1043.5 | 14.1 | c | T |
| 509 | des(1-3)-Benzoyl-[AzaGly7,Arg(Me)9,Trp10]MS10 | 997.8 | 997.5 | 12.4 | c | T |
| 510 | des(1-3)-Ac-[AzaGly7,Arg(Me)9,Trp10]MS10 | 935.9 | 935.5 | 9.5 | c | T |
| 511 | des(1)-[D-Tyr2,D-Trp3,Ala4,Thr5,AzaGly7,Arg(Me)9,Trp10]MS10 | 1213.6 | 1213.6 | 17.9 | e | O |
| 512 | des(1)-[D-Tyr2,D-Trp3,Thr5,AzaGly7,Arg(Me)9,Trp10]MS10 | 1256.7 | 1256.6 | 17.0 | e | O |
| 513 | des(1)-[D-Tyr2,D-Trp3,Abu4,AzaGly7,Arg(Me)9,Trp10]MS10 | 1213.8 | 1213.6 | 18.5 | e | O |
| 514 | des(1)-[D-Tyr2,D-Phe3,Ala4,AzaGly7,Arg(Me)9,Trp10]MS10 | 1160.8 | 1160.6 | 17.9 | e | O |
| 515 | des(1)-[D-Tyr2,D-Pya(4)3,Val5,AzaGly7,Arg(Me)9,Trp10]MS10 | 1216.8 | 1216.6 | 15.7 | e | O | a: 0-70% AcCN/35 min, flow 1 ml/min, Wakosil-II 5C18 HG (4.6 × 100 mm)
b: 0-70% AcCN/35 min, flow 1 ml/min, YMC ODS AM-301 (4.6 × 100 mm)
c: 20-70% AcCN/25 min, flow 1 ml/min, YMC ODS AM-301 (4.6 × 100 mm)
d: 5-75% AcCN/35 min, flow 1 ml/min, Wakosil-II 5C18 HG (4.6 × 100 mm)
e: 0-50% AcCN/25 min, flow 1 ml/min, Wakosil-II 5C18 HG (4.6 × 100 mm)
Only compound no. 1 represents M+ value.

The structures of compounds synthesized as in EXAMPLES 1 to 24 and physicochemical properties of these compounds are shown in TABLE 12 below.

TABLE 12

| Comp. No. | | M + H+ (obs.) | M + H+ (cal.) | HPLC (min.) | HPLC mode |
|---|---|---|---|---|---|
| 516 | Ac-des(1)-[D-Tyr2,D-Pya(4)3,AzaGly7,Arg(Me)9]MS10 | 1207.8 | 1207.6 | 9.2 | c |
| 517 | des(1-3)-3-Phenylpropionyl-[Hyp5,AzaGly7,Arg(Me)9,Trp10]MS10 | 1051.6 | 1051.5 | 13.7 | c |
| 518 | des(1-3)-3-Phenylpropionyl-[Cha6,Arg(Me)9,Trp10]MS10 | 1030.5 | 1030.6 | 15.8 | c |
| 519 | des(1-3)-Phenylacetyl-[AzaGly7,Arg(Me)9,Trp10]MS10 | 1011.5 | 1011.5 | 12.7 | c |
| 521 | des(1)-[D-Tyr2,D-Pya(4)3,AzaGly7]MS10 | 1151.5 | 1151.6 | 13.4 | e |
| 522 | des(1-3)-Benzoyl-[Thr5,AzaGly7,Arg(Me)9,Trp10]MS10 | 1011.9 | 1011.5 | 12.7 | c |
| 523 | des(1-3)-Benzoyl-[Thr5,Phe(4F)6,AzaGly7,Arg(Me)9,Trp10]MS10 | 1029.9 | 1029.5 | 13.3 | c |
| 524 | des(1-3)-3-Phenylpropionyl-[Pro5,AzaGly7,Arg(Me)9,Trp10]MS10 | 1036 | 1035.6 | 15.8 | c |
| 527 | des(1)-[D-Tyr2,D-Pya(4)3,Hyp5,AzaGly7,Arg(Me)9,Trp10]MS10 | 1230.5 | 1230.6 | 14.3 | c |
| 528 | des(1)-[D-Tyr2,D-Pya(4)3,Pro5,AzaGly7,Arg(Me)9,Trp10]MS10 | 1214.7 | 1214.6 | 15.7 | e |
| 529 | des(1)-[D-Tyr2,D-Pya(4)3,Tle5,AzaGly7,Arg(Me)9,Trp10]MS10 | 1230.7 | 1230.7 | 16.5 | e |
| 530 | des(1)-[D-Tyr2,D-Pya(4)3,Phg5,AzaGly7,Arg(Me)9,Trp10]MS10 | 1250.6 | 1250.6 | 16.8 | c |
| 531 | des(1-3)-3-Phenylpropionyl-[Pic(2)5,AzaGly7,Arg(Me)9,Trp10]MS10 | 1049.6 | 1049.6 | 16.4 | c |
| 532 | des(1-3)-3-Phenylpropionyl-[Aze(2)5,AzaGly7,Arg(Me)9,Trp10]MS10 | 1021.8 | 1021.5 | 14.4 | c |
| 533 | des(1-3)-3-Phenylpropionyl-[D-Pro5,AzaGly7,Arg(Me)9,Trp10]MS10 | 1035.7 | 1035.6 | 15.2 | c |
| 534 | des(1-3)-Cyclopropanecarbonyl-[AzaGly7,Arg(Me)9,Trp10]MS10 | 961.6 | 961.5 | 10.7 | c |
| 535 | des(1-3)-2-Naphthoyl-[AzaGly7,Arg(Me)9,Trp10]MS10 | 1047.6 | 1047.5 | 14.7 | c |
| 536 | [Arg1,D-Tyr2,D-Pya(4)3,AzaGly7,Arg(Me)9,Trp10]MS10 | 1360.3 | 1360.7 | 14 | e |
| 537 | Arg-[Arg1,D-Tyr2,D-Pya(4)3,AzaGly7,Arg(Me)9,Trp10]MS10 | 1516.5 | 1516.8 | 13.4 | e |
| 538 | Arg-[Acp1,D-Tyr2,D-Pya(4)3,AzaGly7,Arg(Me)9,Trp10]MS10 | 1473.8 | 1473.8 | 13.9 | e |
| 539 | des(1)-[D-Tyr2,D-Trp3,Val5,AzaGly7,Arg(Me)9,Trp10]MS10 | 1254.7 | 1254.7 | 18.7 | e |
| 540 | des(1)-[D-Tyr2,D-Trp3,AzaGly7,Arg(Me)9,Trp10]MS10 | 1242.4 | 1242.6 | 11.8 | e |
| 541 | D-Arg-[Acp1,D-Tyr2,D-Trp3,Thr5,AzaGly7,Arg(Me)9,Trp10]MS10 | 1525.8 | 1525.8 | 16.7 | e |
| 542 | D-Arg-D-Arg-[Acp1,D-Tyr2,D-Trp3,Thr5,AzaGly7,Arg(Me)9,Trp10]MS10 | 1681.9 | 1681.9 | 16.3 | e |
| 545 | des(1-3)-Benzoyl-[Phe(4F)6,AzaGly7,Arg(Me)9,Trp10]MS10 | 1015.7 | 1015.5 | 13 | c |
| 546 | des(1-3)-3-Phenylpropionyl-[Ser(Ac)5,AzaGly7,Arg(Me)9,Trp10]MS10 | 1067.6 | 1067.5 | 15.2 | c |
| 547 | des(1)-[D-Tyr2,D-Pya(4)3,Ser(Ac)5,AzaGly7,Arg(Me)9,Trp10]MS10 | 1246.6 | 1246.7 | 9.4 | c |
| 548 | des(1)-[D-Tyr2,D-Pya(4)3,AzaGly7,Arg(Me)9,10Ψ,CSNH]MS10 | 1181.5 | 1181.6 | 14.9 | e |
| 550 | Ac-des(1)-[D-Tyr2,D-Trp3,Thr5,AzaGly7,Arg(Me)9,Trp10]MS10 | 1298.7 | 1298.6 | 13.6 | c |
| 551 | Ac-D-Arg-[Acp1,D-Tyr2,D-Trp3,Thr5,AzaGly7,Arg(Me)9,Trp10]MS10 | 1567.8 | 1567.8 | 12.4 | c |
| 552 | D-Dap-[Acp1,D-Tyr2,D-Trp3,Thr5,AzaGly7,Arg(Me)9,Trp10]MS10 | 1455.8 | 1455.8 | 11.5 | c |

TABLE 12-continued

| | | | | | |
|---|---|---|---|---|---|
| 553 | D-Nle-[Acp1,D-Tyr2,D-Trp3,Thr5,AzaGly7,Arg(Me)9,Trp10]MS10 | 1482.5 | 1482.8 | 13.3 | c |
| 554 | D-Arg-[b-Ala1,D-Tyr2,D-Trp3,Thr5,AzaGly7,Arg(Me)9,Trp10]MS10 | 1483.7 | 1483.8 | 16.5 | e |
| 555 | D-Arg-[g-Abu1,D-Tyr2,D-Trp3,Thr5,AzaGly7,Arg(Me)9,Trp10]MS10 | 1497.7 | 1497.8 | 16.6 | e |
| 556 | D-Arg-D-Arg-[g-Abu1,D-Tyr2,D-Trp3,Thr5,AzaGly7,Arg(Me)9,Trp10]MS10 | 1654 | 1653.9 | 15.7 | e |
| 557 | D-Arg-D-Arg-[g-Abu1,D-Tyr2,D-Trp3,Thr5,AzaGly7,Arg(Me)9,Trp10]MS10 | 1809.8 | 1810 | 15.6 | e |
| 558 | Ac-des(1)-[D-Tyr2,D-Trp3,AzaGly7,Arg(Me)9,Trp10]MS10 | 1284.6 | 1284.6 | 13.3 | c |
| 559 | 3-(4-Hydroxyphenyl)propionyl-des(1-2)-[D-Trp3,Thr5,AzaGly7,Arg(Me)9,Trp10]MS10 | 1241.3 | 1241.6 | 14.4 | c |
| 561 | D-Arg-[Acp1,D-Tyr2,D-Trp3,Abu4,AzaGly7,Arg(Me)9,Trp10]MS10 | 1482.8 | 1482.8 | 17.5 | e |
| 562 | Ac-des(1)-[D-Tyr2,D-Pya(4)3,Thr5,AzaGly7,Arg(Me)9,Trp10]MS10 | 1260.4 | 1260.4 | 15.5 | e |
| 563 | Ac-des(1)-[D-Tyr2,D-Trp3,Aze(2)5,AzaGly7,Arg(Me)9,Trp10]MS10 | 1280.6 | 1280.6 | 19.1 | e |
| 564 | Ac-des(1)-[D-Tyr2,D-Trp3,Val5,AzaGly7,Arg(Me)9,Trp10]MS10 | 1296.5 | 1296.7 | 19.9 | e |
| 565 | Benzoyl-des(1)-[D-Tyr2,D-Trp3,Thr5,AzaGly7,Arg(Me)9,Trp10]MS10 | 1360.8 | 1360.7 | 15.7 | c |
| 566 | Cyclopropanecarbonyl-des(1)-[D-Tyr2,D-Trp3,Thr5,AzaGly7,Arg(Me)9,Trp10]MS10 | 1324.8 | 1324.7 | 14.5 | c |
| 567 | Butyryl-des(1)-[D-Tyr2,D-Trp3,Thr5,AzaGly7,Arg(Me)9,Trp10]MS10 | 1326.8 | 1326.7 | 14.8 | c |
| 568 | Ac-[D-Arg1,D-Tyr2,D-Trp3,Thr5,AzaGly7,Arg(Me)9,Trp10]MS10 | 1454.7 | 1454.7 | 17.2 | e |
| 569 | Ac-des(1)-[D-Tyr2,D-Trp3,Thr5,6Ψ7,CH2NH,Arg(Me)9,Trp10]MS10 | 1283.7 | 1283.7 | 17.7 | e |
| 570 | Me-des(1)-[D-Tyr2,D-Trp3,Thr5,AzaGly7,Arg(Me)9,Trp10]MS10 | 1270.6 | 1270.6 | 16.5 | c |
| 571 | Ac-des(1)-[D-Tyr2,D-Trp3,Thr5,AzaGly7,Arg(Me)9,]MS10 | 1259.5 | 1259.6 | 13.2 | c |
| 572 | des(1)-[D-Trp2,D-Pya(4)3,AzaGly7,Arg(Me)9,Trp10]MS10 | 1227.6 | 1227.6 | 10.1 | c |
| 573 | Ac-des(1)-[D-Tyr2,D-Trp3,Abu4,AzaGly7,Arg(Me)9,Trp10]MS10 | 1255.6 | 1255.6 | 19.4 | e |
| 576 | Ac-des(1)-[D-Tyr2,D-Trp3,Gln4,AzaGly7,Arg(Me)9,Trp10]MS10 | 1298.8 | 1298.6 | 18.2 | e |
| 577 | Ac-des(1)-[D-Tyr2,D-Trp3,Sor4,AzaGly7,Arg(Me)9,Trp10]MS10 | 1257.7 | 1257.6 | 18.8 | c |
| 578 | Ac-des(1)-[D-Tyr2,D-Trp3,Thr4,AzaGly7,Arg(Me)9,Trp10]MS10 | 1271.6 | 1271.6 | 18.8 | e |
| 579 | Ac-des(1)-[D-Tyr2,D-Trp3,Alb4,AzaGly7,Arg(Me)9,Trp10]MS10 | 1299.5 | 1299.6 | 19 | e |
| 580 | Ac-des(1)-[D-Tyr2,D-Trp3,Ser(Me)5,AzaGly7,Arg(Me)9,Trp10]MS10 | 1298.4 | 1298.6 | 19.3 | e |

| Comp. No. | Structure | M + H+ (obs.) | M + H+ (cal.) | HPLC (min.) | HPLC mode | Syn. Proc. |
|---|---|---|---|---|---|---|
| 584 | des(1)-Ac-[D-Tyr2,D-Trp3,Dap(Ac)4,AzaGly7,Arg(Me)9,Trp10]MS10 | 1298.7 | 1298.6 | 18.7 | e | X |
| 585 | des(1)-Ac-[D-Tyr2,D-Trp3,Dap(For)4,AzaGly7,Arg(Me)9,Trp10]MS10 | 1284.7 | 1284.6 | 17.9 | c | X |
| 586 | des(1)-Ac-[D-Tyr2,Thr5,D-Phe5,AzaGly7,Arg(Me)9,Trp10]MS10 | | | | | W |
| 589 | des(1)-Ac-[D-Tyr2,D-Trp3,Thr5,AzaGly7,Arg(Me)9,Nal(2)10]MS10 | 1309.6 | 1309.6 | 15.2 | c | W |
| 590 | des(1)-Ac-[D-Tyr2,D-Trp3,Thr5,AzaGly7,Arg(Me)9,Thi10]MS10 | 1265.5 | 1265.6 | 13.4 | c | W |
| 591 | des(1)-Ac-[D-Tyr2,D-Trp3,Thr5,AzaGly7,Arg(Me)9,Tyr10]MS10 | 1275.5 | 1275.6 | 12.2 | c | W |
| 592 | des(1)-Ac-[D-Tyr2,D-Trp3,Thr5,AzaGly7,Arg(Me)9,Phe(4F)10]MS10 | 1277.5 | 1277.6 | 14 | c | W |
| 594 | des(1)-Ac-[D-Tyr2,D-Trp3,Thr5,AzaGly7,Arg(Me)9,Hph10]MS10 | 1273.8 | 1273.6 | 14.6 | c | W |
| 597 | des(1)-Ac-[D-Tyr2,D-Trp3,Thr5,D-Phe6,AzaGly7,Arg(Me)9,Trp10]MS10 | 1298.8 | 1298.7 | 14.1 | c | W |
| 598 | des(1)-Ac-[D-Tyr2,D-Trp3,Thr5,Arg(Me)9,Trp10]MS10 | 1297.5 | 1297.6 | 18.5 | e | H + W |
| 599 | des(1)-Ac-[D-Tyr2,D-Trp3,Thr5,AzaGly7,Orn9,Trp10]MS10 | 1242.4 | 1242.6 | 17.8 | c | G + W |
| 600 | des(1)-Ac-[D-Tyr2,D-Trp3,Thr5,AzaGly7,Trp10]MS10 | 1284.7 | 1284.6 | 17.9 | c | G + W |
| 601 | des(1)-Ac-[D-Tyr2,D-Trp3,Thr5,D-Phe6,Arg(Me)9,Trp10]MS10 | 1297.6 | 1297.6 | 18.2 | c | H + W |
| 602 | des(1)-Ac-[D-NMeTyr2,D-Trp3,Thr5,AzaGly7,Arg(Me)9,Trp10]MS10 | 1312.7 | 1312.7 | 19 | c | W |
| 603 | des(1)-Ac-[D-Tyr2,D-Pya(4)3,Thr5,D-Phe6,AzaGly7,Arg(Me)9,Trp10]MS1 | 1260.6 | 1260.6 | 15.3 | e | W |
| 604 | des(1)-Ac-[D-Tyr2,D-Trp3,Thr5,AzaGly7,Arg(Tos)9,Trp10]MS10 | 1438.6 | 1438.6 | 20.5 | e | G + W |
| 605 | des(1)-Ac-[D-Tyr2,D-Trp3,Thr5,AzaGly7,Arg(NO2)9,Trp10]MS10 | 1329.4 | 1329.6 | 18.7 | e | G + W |
| 607 | des(1)-Ac-[D-Tyr2,D-Trp3,Thr5,AzaGly7,Arg(Me2)asym9,Trp10]MS10 | 1312.9 | 1312.7 | 18.1 | c | W |
| 608 | des(1)-Ac-[D-Tyr2,D-Trp3,Thr5,AzaGly7,Arg(Me2)sym9,Trp10]MS10 | 1312.3 | 1312.7 | 18.1 | c | W |
| 609 | des(1)-Ac-[D-Tyr2,D-Trp3,Thr5,AzaGly7,Arg(Et)9,Trp10]MS10 | 1312.8 | 1312.7 | 17.7 | c | W |
| 610 | des(1)-Ac-[D-Tyr2,D-Trp3,Thr5,AzaGly7,Lys(Me2)9,Trp10]MS10 | 1284.9 | 1284.7 | 17.7 | e | G + W |
| 611 | des(1)-Ac-[Tyr2,D-Pya(4)3,Thr5,AzaGly7,Arg(Me)9,Trp10]MS10 | 1260.9 | 1260.6 | 14.4 | e | W |
| 612 | des(1)-For-[D-Tyr2,D-Trp3,Thr5,AzaGly7,Arg(Me)9,Trp10]MS10 | 1284.7 | 1284.6 | 17.8 | c | T + W |
| 613 | des(1)-Propionyl-[D-Tyr2,D-Trp3,Thr5,AzaGly7,Arg(Me)9,Trp10]MS10 | 1312.6 | 1312.7 | 18.3 | c | T + W |
| 614 | des(1)-Amidino-[D-Tyr2,D-Trp3,Thr5,AzaGly7,Arg(Me)9,Trp10]MS10 | 1298.4 | 1298.7 | 16.9 | e | J + W |
| 615 | des(1)-Ac-[D-Tyr2,D-Pya(4)3,Thr5,AzaGly7,Arg(Me)9,Trp10]MS10 | 1299 | 1298.6 | 13.9 | c | W |
| 616 | des(1)-Ac-[D-Ala2,D-Trp3,Thr5,AzaGly7,Arg(Me)9,Trp10]MS10 | 1206.8 | 1206.4 | 13.1 | c | W |
| 617 | des(1)-Ac-[D-Leu2,D-Trp3,Thr5,AzaGly7,Arg(Me)9,Trp10]MS10 | 1248.9 | 1248.7 | 15.5 | c | W |
| 618 | des(1)-Ac-[D-Phe2,D-Trp3,Thr5,AzaGly7,Arg(Me)9,Trp10]MS10 | 1282.7 | 1282.6 | 15.8 | c | W |
| 619 | des(1)-Ac-[D-Nal(1)2,D-Trp3,Thr5,AzaGly7,Arg(Me)9,Trp10]MS10 | 1332.6 | 1332.7 | 17.6 | c | W |
| 620 | des(1)-Ac-[D-Nal(2)2,D-Trp3,Thr5,AzaGly7,Arg(Me)9,Trp10]MS10 | 1332.4 | 1332.7 | 17.7 | c | W |
| 621 | des(1)-Ac-[D-Lys2,D-Trp3,Thr5,AzaGly7,Arg(Me)9,Trp10]MS10 | 1263.5 | 1263.7 | 11.3 | c | W |
| 622 | des(1)-Ac-[D-Glu2,D-Trp3,Thr5,AzaGly7,Arg(Me)9,Trp10]MS10 | 1264.6 | 1264.4 | 12.7 | c | W |
| 623 | des(1)-Ac-[D-Tyr2,Trp3,Thr5,AzaGly7,Arg(Me)9,Trp10]MS10 | 1298.9 | 1298.6 | 14.2 | c | W |
| 624 | des(1)-Ac-[D-Tyr2,Pya(4)3,Thr5,AzaGly7,Arg(Me)9,Trp10]MS10 | 1260.8 | 1260.6 | 10.2 | c | W |
| 625 | des(1)-Ac-[D-Tyr2,D-Ala3,Thr5,AzaGly7,Arg(Me)9,Trp10]MS10 | 1183.8 | 1183.6 | 11.4 | c | W |
| 626 | des(1)-Ac-[D-Tyr2,D-Leu3,Thr5,AzaGly7,Arg(Me)9,Trp10]MS10 | 1226 | 1225.6 | 13.3 | c | W |
| 627 | des(1)-Ac-[D-Tyr2,D-Phe3,Thr5,AzaGly7,Arg(Me)9,Trp10]MS10 | 1259.9 | 1259.6 | 13.8 | c | W |
| 628 | des(1)-Ac-[D-Tyr2,D-Thr3,Thr5,AzaGly7,Arg(Me)9,Trp10]MS10 | 1213.9 | 1213.6 | 11.1 | c | W |
| 629 | des(1)-Ac-[D-Tyr2,D-Lys3,Thr5,AzaGly7,Arg(Me)9,Trp10]MS10 | 1240.9 | 1240.7 | 10.1 | c | W |
| 630 | des(1)-Ac-[D-Tyr2,D-Glu3,Thr5,AzaGly7,Arg(Me)9,Trp10]MS10 | 1241.9 | 1241.6 | 11.2 | c | W |
| 631 | des(1)-Ac-[D-Tyr2,D-Trp3,Thr5,Ala6,AzaGly7,Arg(Me)9,Trp10]MS10 | 1222.9 | 1222.6 | 11.6 | c | W |
| 632 | des(1)-Ac-[D-Tyr2,D-Trp3,Thr5,Leu6,AzaGly7,Arg(Me)9,Trp10]MS10 | 1265 | 1264.7 | 13.5 | c | W |
| 633 | des(1)-Ac-[D-Tyr2,D-Trp3,Thr5,Lys6,AzaGly7,Arg(Me)9,Trp10]MS10 | 1279.8 | 1279.7 | 10.4 | c | W |
| 634 | des(1)-Ac-[D-Tyr2,D-Trp3,Thr5,Glu6,AzaGly7,Arg(Me)9,Trp10]MS10 | 1280.8 | 1280.6 | 11.5 | c | W |
| 635 | des(1)-Ac-[D-Tyr2,D-Trp3,Thr5,Pya(4)3,AzaGly7,Arg(Me)9,Trp10]MS10 | 1299.9 | 1299.6 | 10.5 | c | W |
| 636 | des(1)-Ac-[D-Tyr2,D-Trp3,Thr5,McPhe6,AzaGly7,Arg(Me)9,Trp10]MS10 | 1312.4 | 1312.7 | 15.4 | c | W |
| 637 | des(1)-Ac-[D-Tyr2,D-Trp3,Thr5,Phe(4F)6,AzaGly7,Arg(Me)9,Trp10]MS10 | 1316.5 | 1316.6 | 14.4 | c | W |
| 638 | des(1)-Ac-[D-Tyr2,D-Trp3,Thr5,Phe(4F)6,AzaGly7,Arg(Me)9,Trp10]MS10 | 1278.6 | 1278.6 | 10.7 | c | W |

TABLE 12-continued

| | | | | | | |
|---|---|---|---|---|---|---|
| 639 | des(1)-Ac-[D-Tyr2,D-Trp3,Thr5,AzaGly7,Lys9,Trp10]MS10 | 1256.9 | 1256.6 | 17.5 | c | G + W |
| 640 | des(1)-Ac-[D-Tyr2,D-Trp3,Thr5,AzaGly7,D-Leu8,Arg(Me)9,Trp10]MS10 | 1298.7 | 1298.6 | 17.6 | e | W |
| 641 | des(1)-Ac-[D-Tyr2,D-Trp3,Thr5,AzaGly7,Ala8,Arg(Me)9,Trp10]MS10 | 1256.9 | 1256.6 | 16.5 | e | W |
| 642 | des(1)-Ac-[D-Tyr2,D-Trp3,Thr5,AzaGly7,Val8,Arg(Me)9,Trp10]MS10 | 1284.5 | 1284.6 | 17.4 | c | W |
| 643 | des(1)-Ac-[D-Tyr2,D-Trp3,Thr5,AzaGly7,Phe8,Arg(Me)9,Trp10]MS10 | 1332.4 | 1332.6 | 18.3 | c | W |
| 644 | des(1)-Ac-[D-Tyr2,D-Trp3,Thr5,AzaGly7,Ser8,Arg(Me)9,Trp10]MS10 | 1272.9 | 1272.6 | 15.5 | e | W |
| 645 | des(1)-Ac-[D-Tyr2,D-Trp3,Thr5,AzaGly7,Har9,Trp10]MS10 | 1299.1 | 1298.6 | 17.7 | e | G + W |
| 646 | des(1)-Ac-[D-Tyr2,D-Trp3,Thr5,AzaGly7,Har(Me)9,Trp10]MS10 | 1313.1 | 1312.7 | 17.9 | e | W |
| 647 | des(1)-Ac-[D-Tyr2,D-Trp3,Asp4,Thr5,AzaGly7,Arg(Me)9,Trp10]MS10 | 1299.9 | 1299.6 | 18.2 | e | W |
| 648 | [Gly1,D-Tyr2,D-Trp3,Thr5,AzaGly7,Arg(Me)9,Trp10]MS10 | 1313.6 | 1313.7 | 16 | c | W |
| 649 | Ac-[Gly1,D-Tyr2,D-Trp3,Thr5,AzaGly7,Arg(Me)9,Trp10]MS10 | 1355.9 | 1355.7 | 17.4 | c | W |
| 650 | [D-Tyr1,D-Tyr2,D-Trp3,Thr5,AzaGly7,Arg(Me)9,Trp10]MS10 | 1419.8 | 1419.7 | 16.6 | c | W |
| 651 | Ac-[D-Tyr1,D-Tyr2,D-Trp3,Thr5,AzaGly7,Arg(Me)9,Trp10]MS10 | 1461.4 | 1461.7 | 18 | e | W |
| 652 | pGlu-des(1)-[D-Tyr2,D-Trp3,Thr5,AzaGly7,Arg(Me)9,Trp10]MS10 | 1367.4 | 1367.7 | 17.6 | c | W |
| 653 | des(1)-Ac-[D-Tyr2,D-Trp3,D-Asn4,Thr5,AzaGly7,Arg(Me)9,Trp10]MS10 | 1298.8 | 1298.6 | 18.2 | c | W |
| 654 | des(1)-Ac-[D-Tyr2,D-Trp3,D-Thr5,AzaGly7,Arg(Me)9,Trp10]MS10 | 1298.8 | 1298.6 | 17.6 | e | W |
| 655 | des(1)-Ac-[D-Tyr2,D-Trp3,MeAsn4,Thr5,AzaGly7,Arg(Me)9,Trp10]MS10 | 1312.8 | 1312.7 | 18.3 | e | W |
| 656 | des(1)-Ac-[D-Tyr2,D-Trp3,MeSer5,AzaGly7,Arg(Me)9,Trp10]MS10 | 1298.8 | 1298.6 | 17.8 | e | W |
| 657 | des(1)-Ac-[D-Tyr2,D-Pro3,Thr5,AzaGly7,Arg(Me)9,Trp10]MS10 | 1209.2 | 1209.6 | 12.4 | c | W |
| 658 | des(1)-Ac-[D-Tyr2,D-Pya(2)3,Thr5,AzaGly7,Arg(Me)9,Trp10]MS10 | 1260.3 | 1260.6 | 10.4 | c | W |
| 659 | des(1)-Ac-[D-Tyr2,D-Trp3,allo-Thr5,AzaGly7,Arg(Me)9,Trp10]MS10 | 1298.8 | 1298.6 | 17.9 | c | W |
| 660 | des(1)-Ac-[D-Tyr2,D-Pya(3)3,Thr5,AzaGly7,Arg(Me)9,Trp10]MS10 | 1260.8 | 1260.6 | 10.3 | c | W |
| 661 | des(1)-Ac-[D-Tyr2,D-Pro3,Thr5,AzaGly7,Arg(Me)9,Trp10]MS10 | 1209.8 | 1209.6 | 11.5 | c | W |
| 662 | des(1)-Ac-[D-Tyr2,Tic3,Thr5,AzaGly7,Arg(Me)9,Trp10]MS10 | 1271.4 | 1271.4 | 13.9 | c | W |
| 663 | des(1)-Ac-[D-Trp2,D-Trp3,Thr5,AzaGly7,Arg(Me)9,Trp10]MS10 | 1321.7 | 1321.7 | 15.9 | c | W |
| 664 | des(1)-Ac-[Tyr2,Thr5,AzaGly7,Arg(Me)9,Trp10]MS10 | 1298.7 | 1298.6 | 14.1 | c | W |
| 665 | des(1-2)-[D-Trp3,Thr5,AzaGly7,Arg(Me)9,Trp10]MS10 | 1093.7 | 1093.6 | 11.1 | c | O |
| 666 | des(1-2)-Ac-[D-Trp3,Thr5,AzaGly7,Arg(Me)9,Trp10]MS10 | 1135.7 | 1135.6 | 13.4 | c | T + W |
| 667 | des(1-2)-Hexanoyl-[D-Trp3,Thr5,AzaGly7,Arg(Me)9,Trp10]MS10 | 1191.4 | 1191.6 | 17.2 | c | T + W |
| 668 | des(1-2)-Cyclohexanecarbonyl-[D-Trp3,Thr5,AzaGly7,Arg(Me)9,Trp10]MS | 1203.3 | 1203.6 | 17.1 | c | T + W |
| 669 | des(1-2)-Benzoyl-[D-Trp3,Thr5,AzaGly7,Arg(Me)9,Trp10]MS10 | 1197.8 | 1197.6 | 16 | c | T + W |
| 670 | des(1-2)-3-Pyridinepropionyl-[D-Trp3,Thr5,AzaGly7,Arg(Me)9,Trp10]MS1 | 1226.7 | 1226.6 | 11.5 | c | T + W |
| 671 | des(1-2)-Adipionyl-[D-Trp3,Thr5,AzaGly7,Arg(Me)9,Trp10]MS10 | 1221.6 | 1221.6 | 13.5 | c | T + W |
| 672 | des(1)-Ac-[D-Tyr2,MeTrp3,Thr5,AzaGly7,Arg(Me)9,Trp10]MS10 | 1312.9 | 1312.7 | 14.5 | c | W |
| 674 | des(1)-Ac-[Acp2,D-Trp3,Thr5,AzaGly7,Arg(Me)9,Trp10]MS10 | 1206.7 | 1206.7 | 11.5 | c | T + W |
| 675 | [D-Tyr2,D-Trp3,Thr5,AzaGly7,Arg(Me)9,Trp10]MS10 | 1419.6 | 1419.7 | 16.8 | e | W |
| 676 | Ac-[D-Tyr2,D-Trp3,Thr5,AzaGly7,Arg(Me)9,Trp10]MS10 | 1461.4 | 1461.7 | 18 | e | W |
| 677 | Ac-des(1)-[D-Tyr2,D-Trp3,Thr5,AzaGly7,Nva8,Arg(Me)9,Trp10]MS10 | 1284.9 | 1284.6 | 17.1 | e | W |
| 678 | Ac-des(1)-[D-Tyr2,D-Trp3,Thr5,AzaGly7,Ile8,Arg(Me)9,Trp10]MS10 | 1298.9 | 1298.6 | 17.8 | e | W |
| 679 | des(1-2)-Amidino-[D-Trp3,Thr5,AzaGly7,Arg(Me)9,Trp10]MS10 | 1135.7 | 1135.5 | 11.7 | c | J + W |
| 680 | des(1-2)-Glycoloyl-[D-Trp3,Thr5,AzaGly7,Arg(Me)9,Trp10]MS10 | 1151.9 | 1151.6 | 12.9 | c | W |
| 681 | des(1)-Glycoloyl-[D-Tyr2,D-Trp3,Thr5,AzaGly7,Arg(Me)9,Trp10]MS10 | 1314.8 | 1314.6 | 13.5 | c | W |
| 682 | des(1)-Ac-[D-Tyr2,D-,Trp3,Thr5AzaGly7,Gln8,Arg(Me)9,Trp10]MS10 | 1313.9 | 1313.6 | 15.7 | e | W |
| 685 | des(1)-Ac-[D-Tyr2,D-Pya(4)3,Thr5,AzaGly7,Arg(Me)9]MS10 | 1221.8 | 1221.6 | 9.9 | c | W |
| 686 | des(1)-Ac-[D-Tyr2,D-Trp3,Gly4,AzaGly7,Arg(Me)9,Trp10]MS10 | 1227.8 | 1227.6 | 14.2 | c | W |
| 688 | des(1)-Ac-[D-Tyr2,D-Trp3,Thr5,AzaGly7,Pya(4)9,Trp10]MS10 | 1276.8 | 1276.6 | 13.9 | c | W |
| 689 | des(1)-Ac-[D-Tyr2,D-Trp3,Thr5,AzaGly7,Arg(Me)9,D-Trp10]MS10 | 1298.8 | 1298.6 | 13.6 | c | W |
| 691 | des(1)-Ac-[D-Tyr2,D-Trp3,Thr5,Tyr6,AzaGly7,Arg(Me)9,Trp10]MS10 | 1314.4 | 1314.6 | 12.3 | c | W |
| 692 | des(1)-Ac-[D-Tyr2,D-Trp3,Thr5,Trp6,AzaGly7,Arg(Me)9,Trp10]MS10 | 1337.5 | 1337.7 | 14 | c | W |
| 693 | des(1)-Ac-[D-Tyr2,D-Trp3,Thr5,Tyr(Me)6,AzaGly7,Arg(Me)9,Trp10]MS10 | 1328.9 | 1328.7 | 13.9 | c | W |
| 694 | des(1)-Ac-[D-Tyr2,D-Trp3,Thr5,Nal(2)6,AzaGly7,Arg(Me)9,Trp10]MS10 | 1348.9 | 1348.7 | 15.7 | c | W |
| 695 | des(1)-Ac-[D-Tyr2,D-Trp3,Thr5,Thi6,AzaGly7,Arg(Me)9,Trp10]MS10 | 1304.7 | 1304.6 | 13.6 | c | W |
| 696 | des(1)-Ac-[D-Tyr2,D-Trp3,Thr5,Cha6,AzaGly7,Arg(Me)9,Trp10]MS10 | 1304.9 | 1304.7 | 15.3 | c | W |
| 698 | des(1)-Ac-[D-Tyr2,D-Trp3,Thr5,AzaGly7,Abu8,Arg(Me)9,Trp10]MS10 | 1270.7 | 1270.6 | 16.7 | c | W |
| 699 | des(1)-Ac-[D-Tyr2,D-Trp3,Thr5,AzaGly7,γMeLeu8,Arg(Me)9,Trp10]MS10 | 1312.6 | 1312.7 | 18.4 | e | W |
| 700 | des(1)-Ac-[D-Tyr2,D-Trp3,Thr5,Aib8..Arg(Me)9,Trp10]MS10 | 1269.9 | 1269.6 | 16.8 | e | E |
| 701 | des(1)-Ac-[D-Tyr2,D-Trp3,Dap4,AzaGly7,Arg(Me)9,Trp10]MS10 | 1257 | 1256.6 | 16.7 | e | W |
| 702 | des(1)-Ac-[D-Tyr2,D-Trp3,Asp(NHMe)4,Thr5,AzaGly7,Arg(Me)9,Trp10]MS | 1312.8 | 1312.7 | 17.9 | e | W |

Formulation Example 1

| | |
|---|---|
| (1) Compound No. 305 | 10.0 mg |
| (2) Lactose | 60.0 mg |
| (3) Cornstarch | 35.0 mg |
| (4) Gelatin | 3.0 mg |
| (5) Magnesium stearate | 2.0 mg |

A mixture of 10.0 mg of Compound No. 305, 60.0 mg of lactose and 35.0 mg of cornstarch is granulated with 0.03 ml of 10% aqueous gelatin solution (3.0 mg as gelatin) through a sieve of 1 mm mesh, dried at 40° C. and sieved again. The granules thus obtained are mixed with 2.0 mg of magnesium stearate and compressed. The resulting core tablets are coated with sugar-coating of an aqueous suspension of sucrose, titanium dioxide, talc and gum arabic. The coated tablets are polished with yellow beeswax to obtain coated tablets.

Formulation Example 2

| | |
|---|---|
| (1) Compound No. 305 | 10.0 mg |
| (2) Lactose | 70.0 mg |
| (3) Cornstarch | 50.0 mg |
| (4) Soluble starch | 7.0 mg |
| (5) Magnesium stearate | 3.0 mg |

A mixture of 10 mg of Compound 305 and 3.0 mg of magnesium stearate is granulated with 0.07 ml of an aqueous solution of a soluble starch (7.0 mg as soluble starch), dried, and mixed with 70.0 mg of lactose and 50.0 mg of cornstarch. The mixture is compressed to obtain tablets.

Formulation Example 3

| | |
|---|---|
| (1) Compound No. 305 | 5.0 mg |
| (2) Salt | 20.0 mg |
| (3) Distilled water to make the whole volume | 2 ml |

After 5.0 mg of Compound No. 305 and 20.0 mg of salt are dissolved in distilled water, water is added to the solution to make the whole volume 2.0 ml. The solution is filtered and filled in a 2 ml ampoule under aseptic conditions. The ampoule is sterilized and sealed to obtain a solution for injection.

Formulation Example 4

| | |
|---|---|
| (1) Compound No. 550 | 10.0 mg |
| (2) Lactose | 60.0 mg |
| (3) Cornstarch | 35.0 mg |
| (4) Gelatin | 3.0 mg |
| (5) Magnesium stearate | 2.0 mg |

A mixture of 10.0 mg of Compound No. 550, 60.0 mg of lactose and 35.0 mg of cornstarch is granulated with 0.03 ml of 10% aqueous gelatin solution (3.0 mg as gelatin) through a sieve of 1 mm mesh, dried at 40° C. and sieved again. The granules thus obtained are mixed with 2.0 mg of magnesium stearate and compressed. The resulting core tablets are coated with sugar-coating of an aqueous suspension of sucrose, titanium dioxide, talc and gum arabic. The coated tablets are polished with yellow beeswax to obtain coated tablets.

Formulation Example 5

| | |
|---|---|
| (1) Compound No. 550 | 10.0 mg |
| (2) Lactose | 70.0 mg |
| (3) Cornstarch | 50.0 mg |
| (4) Soluble starch | 7.0 mg |
| (5) Magnesium stearate | 3.0 mg |

A mixture of 10 mg of Compound 550 and 3.0 mg of magnesium stearate is granulated with 0.07 ml of an aqueous solution of a soluble starch (7.0 mg as soluble starch), dried, and mixed with 70.0 mg of lactose and 50.0 mg of cornstarch. The mixture is compressed to obtain tablets.

Formulation Example 6

| | |
|---|---|
| (1) Compound No. 550 | 5.0 mg |
| (2) Salt | 20.0 mg |
| (3) Distilled water to make the whole volume | 2 ml |

After 5.0 mg of Compound No. 550 and 20.0 mg of salt are dissolved in distilled water, water is added to the solution to make the whole volume 2.0 ml. The solution is filtered and filled in a 2 ml ampoule under aseptic conditions. The ampoule is sterilized and sealed to obtain a solution for injection.

Formulation Example 7

| | |
|---|---|
| (1) Compound No. 562 | 10.0 mg |
| (2) Lactose | 60.0 mg |
| (3) Cornstarch | 35.0 mg |
| (4) Gelatin | 3.0 mg |
| (5) Magnesium stearate | 2.0 mg |

A mixture of 10.0 mg of Compound No. 562, 60.0 mg of lactose and 35.0 mg of cornstarch is granulated with 0.03 ml of 10% aqueous gelatin solution (3.0 mg as gelatin) through a sieve of 1 mm mesh, dried at 40° C. and sieved again. The granules thus obtained are mixed with 2.0 mg of magnesium stearate and compressed. The resulting core tablets are coated with sugar-coating of an aqueous suspension of sucrose, titanium dioxide, talc and gum arabic. The coated tablets are polished with yellow beeswax to obtain coated tablets.

Formulation Example 8

| | |
|---|---|
| (1) Compound No. 562 | 10.0 mg |
| (2) Lactose | 70.0 mg |
| (3) Cornstarch | 50.0 mg |
| (4) Soluble starch | 7.0 mg |
| (5) Magnesium stearate | 3.0 mg |

A mixture of 10 mg of Compound 562 and 3.0 mg of magnesium stearate is granulated with 0.07 ml of an aqueous solution of a soluble starch (7.0 mg as soluble starch), dried, and mixed with 70.0 mg of lactose and 50.0 mg of cornstarch. The mixture is compressed to obtain tablets.

Formulation Example 9

| | |
|---|---|
| (1) Compound No. 562 | 5.0 mg |
| (2) Salt | 20.0 mg |
| (3) Distilled water to make the whole volume | 2 ml |

After 5.0 mg of Compound No. 562 and 20.0 mg of salt are dissolved in distilled water, water is added to the solution to make the whole volume 2.0 ml. The solution is filtered and filled in a 2 ml ampoule under aseptic conditions. The ampoule is sterilized and sealed to obtain a solution for injection.

Formulation Example 10

| | |
|---|---|
| (1) Compound No. 571 | 10.0 mg |
| (2) Lactose | 60.0 mg |
| (3) Cornstarch | 35.0 mg |
| (4) Gelatin | 3.0 mg |
| (5) Magnesium stearate | 2.0 mg |

A mixture of 10.0 mg of Compound No. 571, 60.0 mg of lactose and 35.0 mg of cornstarch is granulated with 0.03 ml of 10% aqueous gelatin solution (3.0 mg as gelatin) through a sieve of 1 mm mesh, dried at 40° C. and sieved again. The granules thus obtained are mixed with 2.0 mg of magnesium stearate and compressed. The resulting core tablets are coated with sugar-coating of an aqueous suspension of sucrose, titanium dioxide, talc and gum arabic. The coated tablets are polished with yellow beeswax to obtain coated tablets.

Formulation Example 11

| (1) Compound No. 571 | 10.0 mg |
|---|---|
| (2) Lactose | 70.0 mg |
| (3) Cornstarch | 50.0 mg |
| (4) Soluble starch | 7.0 mg |
| (5) Magnesium stearate | 3.0 mg |

A mixture of 10 mg of Compound 571 and 3.0 mg of magnesium stearate is granulated with 0.07 ml of an aqueous solution of a soluble starch (7.0 mg as soluble starch), dried, and mixed with 70.0 mg of lactose and 50.0 mg of cornstarch. The mixture is compressed to obtain tablets.

Formulation Example 12

| (1) Compound No. 571 | 5.0 mg |
|---|---|
| (2) Salt | 20.0 mg |
| (3) Distilled water to make the whole volume | 2 ml |

After 5.0 mg of Compound No. 571 and 20.0 mg of salt are dissolved in distilled water, water is added to the solution to make the whole volume 2.0 ml. The solution is filtered and filled in a 2 ml ampoule under aseptic conditions. The ampoule is sterilized and sealed to obtain a solution for injection.

Formulation Example 13

| (1) Compound No. 579 | 10.0 mg |
|---|---|
| (2) Lactose | 60.0 mg |
| (3) Cornstarch | 35.0 mg |
| (4) Gelatin | 3.0 mg |
| (5) Magnesium stearate | 2.0 mg |

A mixture of 10.0 mg of Compound No. 579, 60.0 mg of lactose and 35.0 mg of cornstarch is granulated with 0.03 ml of 10% aqueous gelatin solution (3.0 mg as gelatin) through a sieve of 1 mm mesh, dried at 40° C. and sieved again. The granules thus obtained are mixed with 2.0 mg of magnesium stearate and compressed. The resulting core tablets are coated with sugar-coating of an aqueous suspension of sucrose, titanium dioxide, talc and gum arabic. The coated tablets are polished with yellow beeswax to obtain coated tablets.

Formulation Example 14

| (1) Compound No. 579 | 10.0 mg |
|---|---|
| (2) Lactose | 70.0 mg |
| (3) Cornstarch | 50.0 mg |
| (4) Soluble starch | 7.0 mg |
| (5) Magnesium stearate | 3.0 mg |

A mixture of 10 mg of Compound 579 and 3.0 mg of magnesium stearate is granulated with 0.07 ml of an aqueous solution of a soluble starch (7.0 mg as soluble starch), dried, and mixed with 70.0 mg of lactose and 50.0 mg of cornstarch. The mixture is compressed to obtain tablets.

Formulation Example 15

| (1) Compound No. 579 | 5.0 mg |
|---|---|
| (2) Salt | 20.0 mg |
| (3) Distilled water to make the whole volume | 2 ml |

After 5.0 mg of Compound No. 579 and 20.0 mg of salt are dissolved in distilled water, water is added to the solution to make the whole volume 2.0 ml. The solution is filtered and filled in a 2 ml ampoule under aseptic conditions. The ampoule is sterilized and sealed to obtain a solution for injection.

Formulation Example 16

| (1) Compound No. 585 | 10.0 mg |
|---|---|
| (2) Lactose | 60.0 mg |
| (3) Cornstarch | 35.0 mg |
| (4) Gelatin | 3.0 mg |
| (5) Magnesium stearate | 2.0 mg |

A mixture of 10.0 mg of Compound No. 585, 60.0 mg of lactose and 35.0 mg of cornstarch is granulated with 0.03 ml of 10% aqueous gelatin solution (3.0 mg as gelatin) through a sieve of 1 mm mesh, dried at 40° C. and sieved again. The granules thus obtained are mixed with 2.0 mg of magnesium stearate and compressed. The resulting core tablets are coated with sugar-coating of an aqueous suspension of sucrose, titanium dioxide, talc and gum arabic. The coated tablets are polished with yellow beeswax to obtain coated tablets.

Formulation Example 17

| (1) Compound No. 585 | 10.0 mg |
|---|---|
| (2) Lactose | 70.0 mg |
| (3) Cornstarch | 50.0 mg |
| (4) Soluble starch | 7.0 mg |
| (5) Magnesium stearate | 3.0 mg |

A mixture of 10 mg of Compound 585 and 3.0 mg of magnesium stearate is granulated with 0.07 ml of an aqueous solution of a soluble starch (7.0 mg as soluble starch), dried, and mixed with 70.0 mg of lactose and 50.0 mg of cornstarch. The mixture is compressed to obtain tablets.

Formulation Example 18

| (1) Compound No. 585 | 5.0 mg |
|---|---|
| (2) Salt | 20.0 mg |
| (3) Distilled water to make the whole volume | 2 ml |

After 5.0 mg of Compound No. 585 and 20.0 mg of salt are dissolved in distilled water, water is added to the solution to make the whole volume 2.0 ml. The solution is filtered and filled in a 2 ml ampoule under aseptic conditions. The ampoule is sterilized and sealed to obtain a solution for injection.

Test Example 1

Assay for hOT7T175 Receptor Binding Activity (1) Preparation of Cy-5-Labeled Metastin (40-54)
A synthetic peptide having 40-54 amino acid sequence in the amino acid sequence of metastin, into which Cy-5 was introduced via the 1-amino group of lysine located at the amino terminus and the carboxyl terminus was amidated, was prepared in accordance with the synthesis technique Amersham Bioscience, Inc. Using this synthetic peptide, a test for binding inhibition was carried out.
Sequence: (Cy-5)-KDLPNYNWNSFGLRF-NH$_2$
(2) Test for Binding Inhibition Using a Test Compound, Cy-5-Labeled Metastin (40-54) and hOT7T175-Expressed Cho Cell
hOT7T175-Expressed CHO cells were cultured in MEM-α medium (nucleic acid-free) containing 10% dialyzed serum. The medium was removed and the adhered cells were washed with PBS. Then, PBS containing 5 mM EDTA was added and the cells were scraped from a flask with a cell scraper.
After centrifugation, the cells were suspended at $1.11 \times 10^5$ cells/ml in assay buffer (10 mM HEPES pH 7.4, 140 mM NaCl, 2.5 mM CaCl$_2$, 3 mM MgCl$_2$, 0.5% BSA, 0.01% NaN$_3$) and Cy-5-labeled metastin (40-54) was added to the suspension in a final concentration of 1 nM. To each well of a 96-Well Black Clear Bottom Microplate (Applied Biosystems, Inc.), 10 μL of assay buffer containing 1% dimethylsulfoxide was added to examine total binding, 10 μL of 10 μM non-labeled peptide (having the same amino acid sequence as that of labeled one) solution diluted with assay buffer to examine non-specific binding, and 10 μL of a test compound diluted with assay buffer to examine a binding inhibition activity of the test compound, and furthermore, 90 μL each of the cell suspension was dispensed to each well. After an hour, the level of Cy-5-labeled metastin (40-54) bound to the cells was determined by the FMAT 8100 HTS system (Applied Biosystems, Inc.). Specific binding is calculated as non-specific binding subtracted from total binding. The binding inhibition activity of a test compound is shown by a ratio of the value obtained by subtracting a measured value in presence of a test compound from the total binding to the specific binding. The receptor binding activity of test compound is shown in TABLES 13 through 18.

TABLE 13

| Compound Number | | IC50(M) |
|---|---|---|
| 1 | Metastin | 1.7E−07 |
| 3 | MS10 | 6.5E−09 |
| 4 | des(1)-MS10 | 2.6E−07 |
| 17 | [Pya(4)10]MS10 | 6.6E−12 |
| 18 | [Tyr(Me)10]MS10 | 7.7E−09 |
| 19 | [Phe(2F)10]MS10 | 8.6E−09 |
| 23 | [Tyr5]MS10 | 4.0E−07 |
| 24 | [Leu5]MS10 | 8.3E−10 |
| 30 | Acetyl-MS10 | 3.1E−08 |
| 31 | Fmoc-MS10 | 9.3E−07 |
| 32 | Leu-Pro-Asn-MS10 | 2.5E−08 |
| 39 | [D-Asn4]MS10 | 8.3E−07 |
| 40 | [D-Trp3]MS10 | 1.9E−08 |
| 41 | [D-Asn2]MS10 | 2.1E−07 |
| 42 | [D-Tyr1]MS10 | 5.7E−08 |
| 44 | [Lys9]MS10 | 1.9E−07 |
| 50 | [Ala7]MS10 | 1.9E−07 |
| 54 | des(1-2)-Fmoc-MS10 | 4.5E−07 |
| 57 | [Asp2]MS10 | 1.0E−07 |
| 58 | [Tyr2]MS10 | 1.6E−08 |
| 59 | [Leu2]MS10 | 3.4E−07 |
| 60 | [Pya(3)10]MS10 | 1.7E−07 |
| 61 | [Phe(4F)10]MS10 | 1.3E−08 |
| 67 | [Ala3]MS10 | 2.7E−08 |
| 68 | [Leu3]MS10 | 7.7E−09 |
| 69 | [Ser3]MS10 | 8.3E−08 |
| 70 | [Asp3]MS10 | 2.0E−07 |
| 71 | [Lys3]MS10 | 6.6E−08 |
| 72 | [Ala1]MS10 | 5.4E−07 |
| 73 | [Leu1]MS10 | 2.2E−07 |
| 75 | [Asp1]MS10 | 8.8E−07 |

TABLE 14

| Compound Number | | IC50(M) |
|---|---|---|
| 77 | [Phe(4CN)10]MS10 | 7.4E−09 |
| 78 | [Trp(CHO)3, Phe(4CN)10]MS10 | 2.5E−08 |
| 82 | [Arg(Me)9]MS10 | 4.1E−09 |
| 83 | [Arg(Me2)asy9]MS10 | 2.5E−08 |
| 97 | [Har9]MS10 | 3.7E−07 |
| 101 | [Ser7]MS10 | 1.0E−07 |
| 105 | [Nle8]MS10 | 8.8E−07 |
| 107 | [Val8]MS10 | 1.2E−07 |
| 109 | [Tyr10]MS10 | 2.3E−08 |
| 110 | [Nal(2)10]MS10 | 2.4E−08 |
| 111 | [Phe(F5)10]MS10 | 1.4E−07 |
| 112 | [Cha10]MS10 | 3.7E−07 |
| 114 | des(1-3)-3-(3-Indolyl)propionyl-MS10 | 5.5E−07 |
| 128 | [10Ψ,CSNH]MS10 | 5.5E−08 |
| 129 | [Arg(Me2)sy9]MS10 | 8.3E−08 |
| 130 | [Phe(4Cl)10]MS10 | 4.2E−08 |
| 131 | [Phe(4NH2)10]MS10 | 1.2E−07 |
| 132 | [Phe(4NO2)10]MS10 | 9.3E−08 |
| 133 | [Nal(1)10]MS10 | 3.3E−07 |
| 134 | [Trp10]MS10 | 1.1E−07 |
| 141 | [D-Tyr1,Arg(Me)9]MS10 | 5.1E−08 |
| 142 | [D-Tyr1,D-Trp3,Arg(Me)9]MS10 | 2.6E−08 |
| 143 | [D-Trp3,Arg(Me)9]MS10 | 7.7E−09 |
| 145 | des(1-2)-Fmoc-[Arg(Me)9]MS10 | 1.2E−07 |
| 146 | [10Ψ,CSNH,D-Tyr1]MS10 | 3.7E−07 |
| 150 | [Tyr6]MS10 | 3.2E−07 |
| 151 | [Nal(1)6]MS10 | 3.0E−07 |
| 152 | [Nal(2)6]MS10 | 1.8E−07 |
| 153 | [Phe(F5)6]MS10 | 3.9E−07 |
| 154 | [Phe(4F)6]MS10 | 6.0E−08 |
| 156 | [Cha6]MS10 | 4.9E−08 |
| 163 | [6Ψ7,CH2NH]MS10 | 2.5E−07 |
| 166 | [6Ψ7,CSNH]MS10 | 9.4E−09 |
| 169 | [D-Tyr1,Ala3,Arg(Me)9]MS10 | 1.6E−07 |
| 170 | [D-Tyr1,Ser3,Arg(Me)9]MS10 | 2.6E−07 |

TABLE 15

| Compound Number | | IC50(M) |
|---|---|---|
| 171 | [D-Tyr1,Cha3,Arg(Me)9]MS10 | 1.1E−07 |
| 174 | [D-Tyr1,Arg(Me)9,Trp10]MS10 | 4.2E−07 |
| 176 | [AzaGly7]MS10 | 5.2E−08 |
| 181 | [D-Tyr1,Cha3,6,Arg(Me)9]MS10 | 1.9E−08 |
| 182 | [D-Tyr1,Cha3,6,Arg(Me)9,Trp10]MS10 | 9.8E−08 |
| 186 | [Trp(CHO)10]MS10 | 4.6E−07 |
| 187 | [Abu8]MS10 | 7.2E−07 |
| 189 | [Ala(3-Bzt)10]MS10 | 2.3E−07 |
| 190 | [D-Tyr1,Cha3,AzaGly7,Arg(Me)9]MS10 | 1.2E−08 |
| 191 | [D-Tyr1,Ser3,AzaGly7,Arg(Me)9]MS10 | 3.0E−07 |
| 192 | [D-Tyr1,Arg(Et)9]MS10 | 5.3E−07 |
| 193 | [D-Tyr1,Arg(n-Pr)9]MS10 | 9.2E−07 |
| 194 | [D-Tyr1,Arg(Ac)9]MS10 | 2.1E−07 |
| 197 | [Phe(3F)10]MS10 | 1.7E−07 |
| 198 | [Phe(3,4F2)10]MS10 | 1.7E−07 |
| 199 | [Phe(3,4Cl2)10]MS10 | 4.7E−07 |
| 200 | [Phe(3CF3)10]MS10 | 3.4E−07 |
| 201 | [Ala(2-Qui)10]MS10 | 8.2E−07 |
| 203 | [D-Tyr1,Cha6,Arg(Me)9]MS10 | 3.7E−08 |
| 204 | [D-Tyr1,Ala7,Arg(Me)9]MS10 | 6.8E−07 |
| 205 | [D-Tyr1,Thr3,Arg(Me)9]MS10 | 2.6E−07 |
| 206 | [D-Tyr1,Ile3,Arg(Me)9]MS10 | 8.5E−08 |
| 208 | [D-Tyr1,Thr4,Arg(Me)9]MS10 | 8.3E−07 |

TABLE 15-continued

| | | |
|---|---|---|
| 210 | [D-Tyr1,Ala4,Arg(Me)9]MS10 | 7.3E−07 |
| 211 | [D-Tyr1,Thr5,Arg(Me)9]MS10 | 4.4E−08 |
| 212 | [D-Tyr1,Ala5,Arg(Me)9]MS10 | 3.6E−08 |
| 213 | [D-Tyr1,Val8,Arg(Me)9]MS10 | 1.9E−07 |
| 214 | [D-Tyr1,Gln2,Arg(Me)9]MS10 | 3.9E−07 |
| 215 | [D-Tyr1,Thr2,Arg(Me)9]MS10 | 2.5E−07 |
| 216 | des(1)-[D-Asn2,Arg(Me)9]MS10 | 7.0E−07 |
| 217 | des(1)-[D-Tyr2,Arg(Me)9]MS10 | 2.5E−07 |
| 220 | [Arg(Et)9]MS10 | 3.3E−07 |
| 221 | [D-Tyr1,Thr3,AzaGly7,Arg(Me)9]MS10 | 9.5E−08 |
| 222 | des(1)-[D-Tyr2,AzaGly7,Arg(Me)9]MS10 | 3.3E−08 |
| 223 | des(1-2)-[D-Trp3,Arg(Me)9]MS10 | 7.6E−07 |

TABLE 16

| | | |
|---|---|---|
| 224 | des(1)-[D-Tyr2,D-Trp3,Arg(Me)9]MS10 | 1.4E−07 |
| 225 | des(1)-[D-Asn2,D-Trp3,Arg(Me)9]MS10 | 4.1E−07 |
| 226 | des(1)-[D-Tyr2,Ser3,Arg(Me)9]MS10 | 1.0E−07 |
| 227 | des(1)-[D-Tyr2,Thr3,Arg(Me)9]MS10 | 4.8E−08 |
| 228 | des(1)-[D-Tyr2,Ile3,Arg(Me)9]MS10 | 4.0E−08 |
| 229 | [D-Tyr1,Val3,Arg(Me)9]MS10 | 1.3E−07 |
| 230 | [D-Tyr1,D-Asn2,Arg(Me)9]MS10 | 2.5E−07 |
| 231 | [D-Tyr1,D-Asn2,D-Trp3,Arg(Me)9]MS10 | 5.5E−08 |
| 232 | [D-Tyr1,AzaGly7,Arg(Me)9]MS10 | 4.9E−08 |
| 233 | [D-Tyr1,Ile3,AzaGly7,Arg(Me)9]MS10 | 2.3E−08 |
| 234 | [D-Tyr1,Val3,AzaGly7,Arg(Me)9]MS10 | 4.7E−08 |
| 235 | [D-Tyr1,Ala3,AzaGly7,Arg(Me)9]MS10 | 1.0E−07 |
| 236 | [D-Tyr1,D-Trp3,AzaGly7,Arg(Me)9]MS10 | 4.2E−08 |
| 237 | [D-Tyr1,D-Asn2,AzaGly7,Arg(Me)9]MS10 | 2.7E−08 |
| 238 | [D-Tyr1,D-Asn2,D-Trp3,AzaGly7,Arg(Me)9]MS10 | 4.9E−08 |
| 239 | des(1)-[D-Tyr2,Ser3,AzaGly7,Arg(Me)9]MS10 | 1.2E−07 |
| 240 | des(1)-[D-Tyr2,Ile3,AzaGly7,Arg(Me)9]MS10 | 1.7E−08 |
| 241 | des(1)-[D-Tyr2,Thr3,AzaGly7,Arg(Me)9]MS10 | 5.6E−08 |
| 242 | des(1)-[D-Tyr2,D-Trp3,AzaGly7,Arg(Me)9]MS10 | 7.0E−08 |
| 244 | [D-Tyr1,Phe3,AzaGly7,Arg(Me)9]MS10 | 7.7E−08 |
| 245 | [D-Tyr1,Nal(1)3,AzaGly7,Arg(Me)9]MS10 | 9.8E−08 |
| 246 | [D-Tyr1,Nal(2)3,AzaGly7,Arg(Me)9]MS10 | 7.1E−09 |
| 247 | [D-Tyr1,Phe(2Cl)3,AzaGly7,Arg(Me)9]MS10 | 4.5E−08 |
| 248 | [D-Tyr1,Phe(3Cl)3,AzaGly7,Arg(Me)9]MS10 | 5.8E−08 |
| 249 | [D-Tyr1,Phe(4Cl)3,AzaGly7,Arg(Me)9]MS10 | 1.5E−07 |
| 250 | [D-Tyr1,Phe(4NH2)3,AzaGly7,Arg(Me)9]MS10 | 3.7E−09 |
| 251 | [D-Tyr1,Pya(3)3,AzaGly7,Arg(Me)9]MS10 | 8.7E−08 |
| 252 | [D-Tyr1,D-Ala3,AzaGly7,Arg(Me)9]MS10 | 5.8E−07 |
| 253 | [D-Tyr1,Pro3,AzaGly7,Arg(Me)9]MS10 | 2.7E−08 |
| 254 | des(1)-[D-Tyr2,Phe3,AzaGly7,Arg(Me)9]MS10 | 1.1E−08 |
| 255 | des(1)-[D-Tyr2,Nal(2)3,AzaGly7,Arg(Me)9]MS10 | 3.3E−08 |
| 256 | des(1)-[D-Pya(3)2,Phe3,AzaGly7,Arg(Me)9]MS10 | 2.2E−08 |
| 257 | [D-Tyr1,D-Asn2,Phe3,AzaGly7,Arg(Me)9]MS10 | 4.0E−08 |
| 258 | [D-Pya(3)1,AzaGly7,Arg(Me)9]MS10 | 9.0E−08 |
| 259 | [D-Ala1,AzaGly7,Arg(Me)9]MS10 | 2.5E−07 |

TABLE 17

| | | |
|---|---|---|
| 260 | des(1-3)-1-(3-Indolyl)propionyl-[AzaGly7,Arg(Me)9]MS10 | 3.2E−07 |
| 261 | [7Ψ8,CH2NH]MS10 | 3.9E−07 |
| 265 | des(1-3)-Indole-3-carboxyl-[AzaGly7,Arg(Me)9]MS10 | 9.5E−08 |
| 266 | des(1-3)-Indole-3-acetyl-[AzaGly7,Arg(Me)9]MS10 | 2.3E−07 |
| 267 | des(1-3)-4-(34-Indolyl)butyryl-[AzaGly7,Arg(Me)9]MS10 | 3.6E−07 |
| 268 | des(1-3)-Diphenylacetyl-[AzaGly7,Arg(Me)9]MS10 | 5.5E−07 |
| 269 | des(1-3)-3-Phenylpropionyl-[AzaGly7,Arg(Me)9]MS10 | 4.7E−07 |
| 270 | Endo-Phe5a-[D-Tyr1,Phe3,AzaGly7,Arg(Me)9]MS10 | 1.5E−08 |
| 271 | des(1-2)-[AzaGly7,Arg(Me)9]MS10 | 1.2E−07 |
| 272 | des(1-2)-Acetyl-[AzaGly7,Arg(Me)9]MS10 | 5.4E−07 |
| 273 | des(1-2)-Amidino-[AzaGly7,Arg(Me)9]MS10 | 3.0E−07 |
| 275 | des(1-2)-Acetyl-[Arg3,AzaGly7,Arg(Me)9]MS10 | 4.1E−07 |
| 276 | des(1-2)-Acetyl-[Thr3,AzaGly7,Arg(Me)9]MS10 | 4.8E−07 |
| 277 | des(1-3)-n-Hexanoyl-[AzaGly7,Arg(Me)9]MS10 | 5.4E−08 |
| 278 | des(1-3)-Cyclohexanecarbonyl-[AzaGly7,Arg(Me)9]MS10 | 1.1E−07 |
| 279 | des(1-3)-2-(Indol-3-yl)ethylcarbamoyl-[AzaGly7,Arg(Me)9]MS10 | 2.9E−08 |

TABLE 17-continued

| | | |
|---|---|---|
| 281 | [D-Tyr1,Pya(2)6,Arg(Me)9]MS10 | 2.3E−07 |
| 283 | [D-Tyr1,D-Asn2,Cha3,AzaGly7,Arg(Me)9]MS10 | 6.9E−10 |
| 284 | [D-Tyr1,D-Asn2,Thr3,AzaGly7,Arg(Me)9]MS10 | 3.4E−08 |
| 285 | [D-Tyr1,Pya(2)3,AzaGly7,Arg(Me)9]MS10 | 4.0E−08 |
| 286 | [D-Tyr1,Pya(4)3,AzaGly7,Arg(Me)9]MS10 | 1.7E−08 |
| 287 | [D-Tyr1,D-Ser2,AzaGly7,Arg(Me)9]MS10 | 2.3E−09 |
| 288 | [D-Tyr1,D-His2,AzaGly7,Arg(Me)9]MS10 | 7.2E−11 |
| 289 | [D-Pya(3)2,AzaGly7,Arg(Me)9]MS10-(2-10) | 8.4E−09 |
| 290 | [D-Pya(3)1,D-Asn2,Cha3,AzaGly7,Arg(Me)9]MS10 | 1.4E−09 |
| 291 | [D-Pya(3)1,D-Tyr2,Cha3,AzaGly7,Arg(Me)9]MS10 | 4.1E−10 |
| 294 | [1Ψ2,CH2NH]MS10 | 3.0E−08 |
| 295 | [2Ψ3,CH2NH]MS10 | 6.8E−07 |
| 296 | [6Ψ7,CSNH,D-Tyr1,Arg(Me)9]MS10 | 1.4E−08 |
| 297 | [D-Tyr1,Thr5,AzaGly7,Arg(Me)9]MS10 | 9.3E−10 |
| 298 | [D-Tyr1,D-Asn2,Thr5,AzaGly7,Arg(Me)9]MS10 | 2.5E−10 |
| 299 | [1Ψ2,CH2NH,AzaGly7,Arg(Me)9]-MS10 | 1.2E−09 |
| 300 | [1Ψ2,CH2NH,D-Trp3,AzaGly7,Arg(Me)9]-MS10 | 3.8E−09 |
| 301 | [D-Tyr1,Ala(2-Qui)3,AzaGly7,Arg(Me)9]MS10 | 1.5E−08 |

TABLE 18

| | | |
|---|---|---|
| 302 | [D-Tyr1,D-Pya(4)3,AzaGly7,Arg(Me)9]MS10 | 7.7E−09 |
| 303 | [D-Tyr1,D-Asn2,Pya(4)3,AzaGly7,Arg(Me)9]MS10 | 5.0E−10 |
| 304 | [D-Asn2,Pya(4)3,AzaGly7,Arg(Me)9]MS10 | 5.0E−09 |
| 305 | des(1)-[D-Tyr2,D-Pya(4)3,AzaGly7,Arg(Me)9]MS10 | 1.3E−09 |
| 306 | [D-Pya(4)1,D-Asn2,Cha3,AzaGly7,Arg(Me)9]MS10 | 4.4E−09 |
| 307 | [7Ψ8,CH2NH,D-Tyr1,Arg(Me)9]MS10 | 6.4E−08 |
| 308 | [6Ψ7,CH2NH,D-Tyr1,Arg(Me)9]MS10 | 3.5E−07 |
| 310 | [Nar9]MS10 | 3.1E−07 |
| 311 | [Nar(Me)9]MS10 | 4.7E−07 |
| 312 | [Har(Me)9]MS10 | 1.0E−07 |
| 313 | [Dab9]MS10 | 6.9E−07 |
| 314 | [Orn9]MS10 | 4.7E−07 |
| 316 | [D-Tyr1,D-Asn2,Thr3,AzaGly7,Arg(Me)9,Phe(4F)10]MS10 | 2.6E−08 |
| 317 | [D-Tyr1,D-Asn2,Pya(4)3,AzaGly7,Arg(Me)9,Phe(4F)10]MS10 | 2.1E−09 |
| 318 | [D-Tyr1,AzaGly7,Arg(Me)9,Phe(4F)10]MS10 | 9.9E−10 |
| 319 | [6Ψ7,NHCO,D-Tyr1,Arg(Me)9]MS10 | 9.7E−09 |
| 322 | des(1-3)-3-Pyridylpropionyl-[AzaGly7,Arg(Me)9]MS10 | 5.4E−08 |
| 323 | des(1-3)-4-Imidazoleacetyl-[AzaGly7,Arg(Me)9]MS10 | 2.8E−07 |
| 328 | des(1-3)-D-Glucronyl-[AzaGly7,Arg(Me)9]MS10 | 4.7E−07 |

Test Example 2

Assay for Intracellular Ca Ion Level-Increasing Activity Using FLIPR

In accordance with the method described in JPA 2000-312590, the intracellular Ca ion level-increasing activity was measured using FLIPR.

The stable expression cell line rOT7T175 was obtained by transduction of expression plasmid pAK-rOT175 for animal cell into CHO/dhfr cells, using CellPhect Transfection Kit (Amersham Pharmacia Biotech, Inc.). First, 240 μL of Buffer A (attached to CellPhect Transfection Kit) was added to 9.6 μg of plasmid DNA dissolved in 240 μL of distilled water followed by stirring. After the mixture was settled for 10 minutes, 480 μL of Buffer B (attached to CellPhect Transfection Kit) was added to the mixture, which was vigorously stirred to form liposomes containing the DNA. Then, 4×10⁵ CHO/dhfr⁻ cells (obtained from ATCC) were inoculated on a 60 mm Petri dish. After culturing the cells in Ham's F-12 medium (Nissui Seiyaku Co., Ltd.) supplemented with 10% fetal bovine serum (BIO WHITTAKER, Inc.) at 37° C. for 2 days in 5% carbon dioxide gas, 480 μL of the liposomes were dropwise added to the cells in the Petri dish. After culturing the cells at 37° C. for 6 hours in 5% carbon dioxide gas, the cells were washed twice with serum-free Ham's F-12 medium and 3 µL of 15% glycerol was added to the cells in the Petri dish followed by treatment for 2 minutes. The cells were again washed twice with serum-free Ham's F-12 medium followed by incubation in Ham's F-12 medium supplemented with 10% fetal bovine serum at 37° C. for 15 hours in 5% carbon dioxide gas. The cells were dispersed by trypsin treatment to recover from the Petri dish. The recovered cells were inoculated on a 6-well plate in $1.25 \times 10^4$ cells/well and began to incubate at 37° C. in Dulbecco's modified Eagle medium (DMEM) medium (Nissui Seiyaku Co., Ltd.) containing 10% dialyzed fetal bovine serum (JRH BIOSCIENCES, Inc.) in 5% carbon dioxide gas. The plasmid-transfected transformed CHO cells grew in the medium but the non-transfected cells gradually died. The medium was exchanged on Days 1 and 2 to remove the cells died. Approximately 20 colonies of the transformed CHO cells that kept growing on Days 8 to 10 after the incubation were isolated. From the cells in these colonies, cells showing high reactivity with the ligand peptide metastin (hereinafter merely referred to as hOT7T175/CHO) were selected to provide for the following experiment.

The intracellular Ca ion level-increasing activity of the synthetic peptide in hOT7T175/CHO was determined using FLIPR (Molecular Devices, Inc.).

hOT7T175/CHO was subcultured in DMEM supplemented with 10% dialyzed fetal bovine serum (hereinafter abbreviated as dFBS) and provided for the experiment (hereinafter abbreviated as 10% dFBS/DMEM). The hOT7T175/CHO was suspended in 10% dFBS-DMEM in $15 \times 10^4$ cells/ml. The suspension was inoculated on a 96-well plate for FLIPR (Black Plate Clear Bottom, Coster, Inc.) at 200 µl each ($3.0 \times 10^4$ cells/200 µl), followed by incubation at 37° C. overnight in a 5% $CO_2$ incubator. The cells thus incubated were used (hereinafter simply referred to as the cell plate). Then, 21 ml of HANKS/HBSS (9.8 g of HANKS', 0.35 g of sodium hydrogencarbonate, 20 ml of 1M HEPES; after adjusting the pH to 7.4 with 1N sodium hydroxide, the mixture was subjected to sterilization through a filter), 210 µl of 250 µmM Probenecid and 210 µl of fetal bovine serum (FBS) were mixed (HANKS/HBSS-Probenecid-FBS).

Furthermore, 2 vials of Fluo3-AM (50 µg/vial) were dissolved in 21 µL of dimethylsulfoxide and 21 µL of 20% Pluronic acid. The resulting solution was added to and mixed with 10 ml of HANKS/HBSS-Probenecid-FBS described above. After the culture medium was removed, the mixture was dispensed onto the cell plate in 100 µl each/well, followed by incubation at 37° C. for an hour in a 5% $CO_2$ incubator (pigment loading). The peptide was dissolved in dimethylsulfoxide in $1 \times 10^{-3}$ M. The peptide solution was diluted with HANKS'/HBSS containing 2.5 mM Probenecid and 0.2% BSA. The dilution was transferred to a 96-well plate for FLIPR (V-Bottom plate, Coster, Inc.) (hereinafter referred to as a sample plate). After completion of the pigment loading onto the cell plate, the cell plate washed 4 times with wash buffer, which was obtained by adding 2.5 mM Probenecid to HANKS'/HBSS, using a plate washer to leave 100 µL of wash buffer after the washing. The cell plate and the sample plate were set in FLIPR and 0.05 ml of a sample from the sample plate was automatically transferred to the cell plate with the FLIPR device to promote the cell response. A change in intracellular calcium ion level for 180 seconds was measured with passage of time.

The intracellular Ca ion level-increasing activity [specific activity to Metastin (1-54)] is shown in TABLES 19 to 23.

TABLE 19

| Comp. No. | Specific Act. |
|---|---|
| Metastin (1-54) | 1 |
| Metastin (45-54) | 10 |
| 17 | 5 |
| 18 | 1 |
| 19 | 2 |
| 24 | 1 |
| 30 | 10 |
| 31 | 2 |
| 32 | 10 |
| 40 | 30 |
| 41 | 10 |
| 42 | 30 |
| 45 | 1 |
| 50 | 30 |
| 53 | 1 |
| 54 | 5 |
| 55 | 5 |
| 56 | 1 |
| 74 | 1 |
| 75 | 1 |
| 76 | 1 |
| 78 | 10 |
| 79 | 1 |
| 87 | 1 |
| 88 | 1 |
| 97 | 10 |
| 98 | ½ |
| 101 | 10 |
| 105 | 1 |
| 109 | 20 |
| 110 | 20 |
| 111 | 3 |
| 112 | 2 |
| 114 | 3 |
| 128 | 10 |
| 130 | 10 |
| 131 | 3 |
| 132 | 10 |
| 133 | 3 |
| 134 | 30 |
| 141 | 10 |
| 142 | 2 |
| 143 | 3 |
| 144 | 1 |
| 146 | 10 |
| 151 | 1 |
| 152 | 5 |
| 154 | 5 |
| 156 | 2 |
| 163 | 1 |
| 166 | 5 |
| 169 | 2 |
| 170 | 1 |
| 171 | 10 |
| 172 | 1 |
| 173 | 1 |

TABLE 20

| | |
|---|---|
| 174 | 10 |
| 176 | 5 |
| 182 | 5 |
| 187 | 1 |
| 189 | 10 |
| 190 | 10 |
| 192 | 1 |
| 193 | ½ |
| 194 | 1 |
| 197 | 10 |
| 198 | 10 |
| 199 | 3 |
| 200 | 10 |
| 201 | 1 |
| 203 | 10 |
| 204 | 5 |

TABLE 20-continued

| | |
|---|---|
| 205 | 10 |
| 206 | 10 |
| 207 | 1/2 |
| 208 | 1 |
| 209 | 1/2 |
| 210 | 1 |
| 211 | 10 |
| 212 | 10 |
| 213 | 2 |
| 214 | 10 |
| 215 | 10 |
| 216 | 1 |
| 217 | 20 |
| 220 | 5 |
| 222 | 10 |
| 224 | 2 |
| 225 | 1 |
| 226 | 1 |
| 227 | 1 |
| 228 | 5 |
| 229 | 1 |
| 230 | 10 |
| 231 | 1 |
| 232 | 3 |
| 233 | 1 |
| 234 | 1 |
| 235 | 1 |
| 236 | 2 |
| 237 | 3 |
| 238 | 1 |
| 241 | 1 |
| 242 | 2 |
| 244 | 1 |
| 245 | 1 |
| 246 | 2 |
| 247 | 1 |
| 248 | 2 |
| 249 | 1 |
| 250 | 1 |
| 254 | 1 |
| 255 | 1 |

TABLE 21

| | |
|---|---|
| 256 | 1 |
| 257 | 3 |
| 258 | 2 |
| 259 | 1 |
| 260 | 5 |
| 261 | 1 |
| 265 | 3 |
| 266 | 2 |
| 267 | 2 |
| 268 | 1 |
| 269 | 3 |
| 270 | 1 |
| 271 | 1 |
| 272 | 2 |
| 273 | 5 |
| 274 | 1 |
| 277 | 2 |
| 278 | 2 |
| 279 | 5 |
| 281 | 1/2 |
| 284 | 1 |
| 286 | 2 |
| 287 | 2 |
| 288 | 1 |
| 289 | 1 |
| 290 | 1 |
| 291 | 2 |
| 294 | 10 |
| 295 | 1 |
| 296 | 3 |
| 297 | 1 |
| 298 | 5 |
| 299 | 5 |

TABLE 21-continued

| | |
|---|---|
| 300 | 5 |
| 301 | 1 |
| 302 | 2 |
| 303 | 5 |
| 304 | 3 |
| 305 | 5 |
| 306 | 2 |
| 307 | 1 |
| 308 | 2 |
| 310 | 3 |
| 311 | 1 |
| 312 | 3 |
| 314 | 1 |
| 315 | 1 |
| 316 | 1 |
| 317 | 1 |
| 318 | 5 |
| 319 | 3 |
| 322 | 1 |
| 323 | 1 |
| 332 | 2 |
| 333 | 1 |
| 334 | 5 |
| 339 | 2 |

TABLE 22

| | |
|---|---|
| 340 | 1/3 |
| 341 | 2 |
| 344 | 1/2 |
| 345 | 2 |
| 346 | 2 |
| 347 | 1/2 |
| 348 | 1/3 |
| 349 | 1/3 |
| 351 | 1/2 |
| 352 | 1/3 |
| 353 | 10 |
| 354 | 10 |
| 358 | 2 |
| 362 | 1/10 |
| 364 | 1 |
| 366 | 1/3 |
| 367 | 1/3 |
| 368 | 1/2 |
| 369 | 2 |
| 373 | 2 |
| 374 | 1/3 |
| 375 | 2 |
| 378 | 1/2 |
| 379 | 2 |
| 380 | 5 |
| 385 | 10 |
| 386 | 7 |
| 387 | 1 |
| 392 | 1/3 |
| 393 | 1 |
| 397 | 5 |
| 400 | 1 |
| 408 | 1/3 |
| 412 | 1/3 |
| 417 | 1 |
| 421 | 1/3 |
| 423 | 5 |
| 428 | 1/10 |
| 431 | 1 |
| 432 | 2 |
| 434 | 1/10 |
| 435 | 10 |
| 436 | 5 |
| 437 | 2 |
| 438 | 3 |
| 439 | 2 |
| 440 | 1 |
| 441 | 1 |
| 442 | 1/2 |
| 443 | 1/2 |

TABLE 22-continued

| | |
|---|---|
| 444 | 1/3 |
| 445 | 5 |
| 446 | 1 |
| 447 | 5 |
| 448 | 3 |
| 449 | 5 |
| 450 | 1/3 |

TABLE 23

| | |
|---|---|
| 451 | 5 |
| 452 | 1 |
| 453 | 1 |
| 454 | 6 |
| 455 | 5 |
| 459 | 2 |
| 460 | 1/3 |
| 461 | 1/3 |
| 462 | 1 |
| 463 | 2 |
| 464 | 1 |
| 466 | 1/3 |
| 467 | 1 |
| 468 | 1 |
| 471 | 1 |
| 472 | 3 |
| 473 | 3 |
| 474 | 5 |
| 475 | 3 |
| 477 | 1/5 |
| 478 | 1/3 |
| 479 | 5 |
| 480 | 1 |
| 481 | 5 |
| 486 | 1/2 |
| 487 | 1 |
| 488 | 1 |
| 489 | 1/2 |
| 490 | 3 |
| 491 | 7 |
| 492 | 5 |
| 493 | 2 |
| 494 | 1/3 |
| 495 | 1/6 |
| 496 | 5 |
| 497 | 2 |
| 498 | 7 |
| 499 | 10 |
| 500 | 1 |
| 501 | 10 |
| 502 | 10 |
| 503 | 10 |
| 504 | 2 |
| 505 | 20 |
| 506 | 1 |
| 507 | 5 |
| 508 | 10 |
| 509 | 20 |
| 510 | 3 |
| 511 | 10 |
| 512 | 30 |
| 513 | 20 |
| 514 | 10 |
| 515 | 10 |

Test Example 3

Assay for Intracellular Ca Ion Level-Increasing Activity Using FLIPR

The intracellular Ca ion level-increasing activity was measured using FLIPR as in TEST EXAMPLE 2. However, (1) the evaluation in TEST EXAMPLE 2 for measuring a change in intracellular Ca ion level for 180 seconds with passage of time was changed to the evaluation for 40 seconds after initiation of the reaction. Also, (2) indication of the activity is changed to $EC_{50}$/MS10 $EC_{50}$ from the specific activity to Metastin (1-54).

A part of the evaluation results are shown in TABLE 24.

TABLE 24

| Comp. No. | Specific Act. |
|---|---|
| 40 | 1.6 |
| 41 | 2.7 |
| 42 | 1.6 |
| 82 | 1.0 |
| 97 | 2.9 |
| 109 | 2.6 |
| 114 | 4.1 |
| 128 | 0.5 |
| 134 | 0.5 |
| 141 | 1.6 |
| 146 | 1.5 |
| 152 | 1.4 |
| 156 | 0.9 |
| 174 | 2.3 |
| 176 | 1.3 |
| 187 | 1.9 |
| 206 | 4.8 |
| 208 | 7.3 |
| 210 | 9.3 |
| 211 | 1.3 |
| 212 | 1.1 |
| 217 | 3.1 |
| 222 | 2.7 |
| 232 | 3.9 |
| 239 | 6.7 |
| 240 | 4.9 |
| 241 | 5.3 |
| 242 | 1.4 |
| 260 | 4.3 |
| 265 | 4.4 |
| 266 | 5.4 |
| 268 | 4.5 |
| 269 | 3.4 |
| 279 | 6.4 |
| 294 | 0.7 |
| 296 | 5.2 |
| 297 | 5.5 |
| 298 | 1.8 |
| 303 | 6.9 |
| 305 | 2.0 |
| 308 | 2.6 |
| 310 | 2.0 |
| 311 | 6.2 |
| 312 | 4.0 |
| 314 | 4.4 |
| 318 | 2.9 |
| 319 | 3.1 |
| 322 | 5.4 |
| 332 | 4.9 |
| 333 | 5.0 |
| 334 | 1.4 |
| 339 | 5.9 |
| 341 | 2.8 |
| 353 | 0.8 |
| 354 | 0.8 |
| 358 | 5.6 |
| 369 | 4.8 |
| 375 | 5.2 |
| 378 | 10.4 |
| 379 | 3.0 |
| 385 | 0.7 |
| 386 | 2.9 |
| 387 | 5.0 |
| 393 | 5.9 |
| 423 | 5.6 |
| 436 | 1.4 |
| 438 | 3.0 |
| 445 | 4.2 |
| 447 | 1.4 |
| 449 | 4.2 |
| 451 | 2.6 |
| 454 | 2.5 |

TABLE 24-continued

| Comp. No. | Specific Act. |
|---|---|
| 455 | 4.1 |
| 459 | 7.3 |
| 463 | 4.6 |
| 464 | 10.5 |
| 467 | 4.0 |
| 468 | 5.2 |
| 472 | 3.4 |
| 473 | 4.2 |
| 474 | 3.2 |
| 475 | 4.2 |
| 479 | 2.6 |
| 480 | 8.3 |
| 481 | 2.4 |
| 488 | 5.5 |
| 490 | 6.2 |
| 491 | 1.0 |
| 492 | 1.1 |
| 493 | 2.2 |
| 494 | 8.6 |
| 496 | 0.7 |
| 497 | 1.4 |
| 498 | 1.5 |
| 499 | 1.4 |
| 500 | 3.2 |
| 501 | 1.1 |
| 502 | 1.4 |
| 503 | 0.4 |
| 504 | 6.9 |
| 505 | 0.7 |
| 506 | 1.3 |
| 507 | 1.7 |
| 508 | 1.0 |
| 509 | 2.0 |
| 510 | 3.5 |
| 511 | 0.5 |
| 512 | 0.8 |
| 513 | 0.4 |
| 514 | 0.7 |
| 515 | 1.0 |
| 516 | 3.7 |
| 517 | 1.0 |
| 518 | 10.5 |
| 519 | 2.4 |
| 521 | 2.4 |
| 522 | 1.9 |
| 523 | 1.1 |
| 524 | 1.1 |
| 527 | 3.3 |
| 528 | 1.4 |
| 529 | 1.8 |
| 530 | 3.4 |
| 531 | 1.8 |
| 532 | 1.0 |
| 533 | 9.7 |
| 534 | 5.6 |
| 535 | 0.8 |
| 536 | 1.8 |
| 537 | 4.7 |
| 538 | 3.3 |
| 539 | 1.2 |
| 540 | 0.7 |
| 541 | 2.0 |
| 542 | 1.4 |
| 545 | 1.1 |
| 546 | 1.9 |
| 547 | 2.5 |
| 548 | 1.7 |
| 550 | 0.7 |
| 551 | 1.2 |
| 552 | 2.3 |
| 553 | 1.9 |
| 554 | 1.3 |
| 555 | 1.5 |
| 556 | 2.8 |
| 557 | 3.2 |
| 558 | 0.4 |
| 559 | 0.3 |
| 561 | 1.6 |

TABLE 24-continued

| Comp. No. | Specific Act. |
|---|---|
| 562 | 1.0 |
| 563 | 0.7 |
| 564 | 0.5 |
| 565 | 0.6 |
| 566 | 0.8 |
| 567 | 0.8 |
| 568 | 0.6 |
| 569 | 0.5 |
| 570 | 0.5 |
| 571 | 1.2 |
| 572 | 0.7 |
| 573 | 0.7 |
| 576 | 0.8 |
| 577 | 0.7 |
| 578 | 0.8 |
| 579 | 0.6 |
| 580 | 0.6 |
| 584 | 0.4 |
| 585 | 0.4 |
| 586 | 0.3 |
| 589 | 2.3 |
| 590 | 1.4 |
| 591 | 1.2 |
| 592 | 1.1 |
| 594 | 2.1 |
| 595 | 11.4 |
| 597 | 0.6 |
| 598 | 0.3 |
| 599 | 0.5 |
| 600 | 0.3 |
| 601 | 3.1 |
| 602 | 2.4 |
| 603 | 1.7 |
| 604 | 6.3 |
| 605 | 3.9 |
| 607 | 2.2 |
| 608 | 2.2 |
| 609 | 0.9 |
| 610 | 1.9 |
| 611 | 1.7 |
| 612 | 0.8 |
| 613 | 0.4 |
| 614 | 0.8 |
| 615 | 0.7 |
| 616 | 1.1 |
| 617 | 2.4 |
| 618 | 1.6 |
| 619 | 1.5 |
| 620 | 1.7 |
| 621 | 1.9 |
| 622 | 2.8 |
| 623 | 0.6 |
| 624 | 1.2 |
| 625 | 2.8 |
| 626 | 2.1 |
| 627 | 1.6 |
| 628 | 4.4 |
| 629 | 3.4 |
| 630 | 4.2 |
| 631 | 2 |
| 632 | 1.1 |
| 633 | 3.4 |
| 634 | 10.5 |
| 635 | 1.4 |
| 637 | 0.8 |
| 638 | 1.7 |
| 639 | 2 |
| 641 | 3.5 |
| 642 | 3.7 |
| 643 | 2.5 |
| 644 | 2.5 |
| 645 | 1.1 |
| 646 | 1.8 |
| 647 | 10.6 |
| 648 | 1.6 |
| 649 | 1 |
| 650 | 0.6 |
| 651 | 0.7 |

TABLE 24-continued

| Comp. No. | Specific Act. |
|---|---|
| 652 | 0.9 |
| 653 | 1.3 |
| 654 | 2.9 |
| 655 | 4.7 |
| 656 | 2.9 |
| 657 | 1.1 |
| 658 | 0.4 |
| 659 | 0.6 |
| 660 | 1.1 |
| 661 | 8.5 |
| 662 | 0.7 |
| 663 | 0.8 |
| 664 | 0.6 |
| 665 | 1.1 |
| 666 | 1.1 |
| 667 | 1.4 |
| 668 | 1.2 |
| 669 | 0.5 |
| 670 | 0.9 |
| 671 | 3.6 |
| 672 | 2.1 |
| 674 | 2 |
| 675 | 0.8 |
| 676 | 1.4 |
| 677 | 0.3 |
| 678 | 1.1 |
| 679 | 1.8 |
| 680 | 2.5 |
| 681 | 1.2 |
| 682 | 7.3 |
| 685 | 4.8 |
| 686 | 0.6 |
| 688 | 9.7 |
| 689 | 2.3 |
| 691 | 1.1 |
| 692 | 0.7 |
| 693 | 1.5 |
| 694 | 1.7 |
| 695 | 0.7 |
| 696 | 0.5 |
| 698 | 2.2 |
| 699 | 1.3 |
| 700 | 0.8 |
| 701 | 1.4 |
| 702 | 0.6 |
| 703 | 3.7 |

Test Example 4

Assay for Cell Growth Inhibition Activity in hOT7T175-Expressed CHO Cells hOT7T175-Expressed CHO cells (hereinafter hOT7T175) was cultured in DMEM supplemented with 10% dialyzed FBS (hereinafter 10% dFBS/DMEM), which was used for the following assay. hOT7T175 was suspended in 10% dFBS/DMEM at 10,000 cells/ml. The cells were plated on a 96 well plate at 100 µL each/well (1,000 cells/well), followed by culturing at 37° C. –5% $CO_2$ incubator overnight. On the following day, the medium was removed and 90 µL of 10% dFBS/DMEM supplemented with 0.5% BSA (hereinafter, 0.5% BSA/10% dFBS/DMEM) was added. Subsequently, 10 µL of a solution of metastin or metastin derivative in 0.5% BSA/10% dFBS/DMEM was added to each well, followed by culturing at 37° C. –5% $CO_2$ incubator for 3 days. After 10 µL of Cell Counting Kit-8 solution (Dojin Chemical Laboratory) was added to each well, incubation was performed at 37° C. –5% $CO_2$ incubator for 4 hours, absorbance was measured at 450 nm.

The cell inhibition activities of Metastin (1-54), Metastin (45-54) and synthetic compound are shown in TABLE 25.

TABLE 25

| Compound Number | IC50 (M) |
|---|---|
| 305 | 8.94E−09 |
| 232 | 9.67E−09 |
| 286 | 1.83E−08 |
| 303 | 4.12E−08 |
| 322 | 7.19E−08 |
| 141 | 8.70E−08 |
| 1-54 | 2.12E−07 |
| 45-54 | 8.51E−06 |

*"1-54" and "45-54" represent Metastin (1-54) and Metastin (45-54), respectively.

Test Example 5

Assay for Chemotaxis Inhibition Activity in hOT7T175-Expressed CHO Cells hOT7T175-Expressed CHO cells (hereinafter hOT7T175) was cultured in DMEM supplemented with 10% dialyzed FBS (hereinafter 10% dFBS/DMEM), which was provided for assay. Also a 24-well 6.5 mm Transwell (pore size 8.0 µm) (COSTAR) was treated with fibronectin by the following method. Specifically, 0.5 ml of 1 µg/ml bovine fibronectin (Yagai Co., Ltd.) was added to the upper and lower chambers of Transwell. After the mixture was settled at room temperature for 10 minutes, the fibronectin solution was removed and further air-dried. After hOT7T175 washed with DMEM 3 times, the cells were suspended in DMEM containing 0.5% BSA (hereinafter 0.5% BSA/DMEM) at a density of $2.5 \times 10^6$ cells/ml. Metastin or a metastin derivative was diluted with 0.5% BSA/DMEM. After 600 µL of 0.5% BSA/DMEM supplemented with 20% FBS (or 0.5% BSA/DMEM for negative control) was added to the lower chamber of Transwell, and 50 µL of the cell suspension and 50 µL of the metastin or a metastin derivative dilution (or 0.5% BSA/DMEM for positive control) were added to the upper chamber. After incubation at 37° C. in a 5% $CO_2$ incubator for 7 hours, the culture medium was removed and the upper side of the filter was wiped with a cotton swab wetted with phosphate-buffered saline to remove all cells on the upper side of the filter. The filter was fixed and stained with DifQuick (International Reagents Corporation) and the cells migrated toward the lower side of the filter were counted. The chemotaxis inhibition activity is shown in FIG. 1.

Test Example 6

Evaluation of Tumor Growth Inhibition Activity

The tumor growth inhibition effect of Metastin (1-54) (hereinafter referred to as Metastin) and Compounds (Compound Nos. 305 and 322) in vivo using tumor-bearing mice with human colonic carcinoma-derived cell line SW620.

Figure 2:
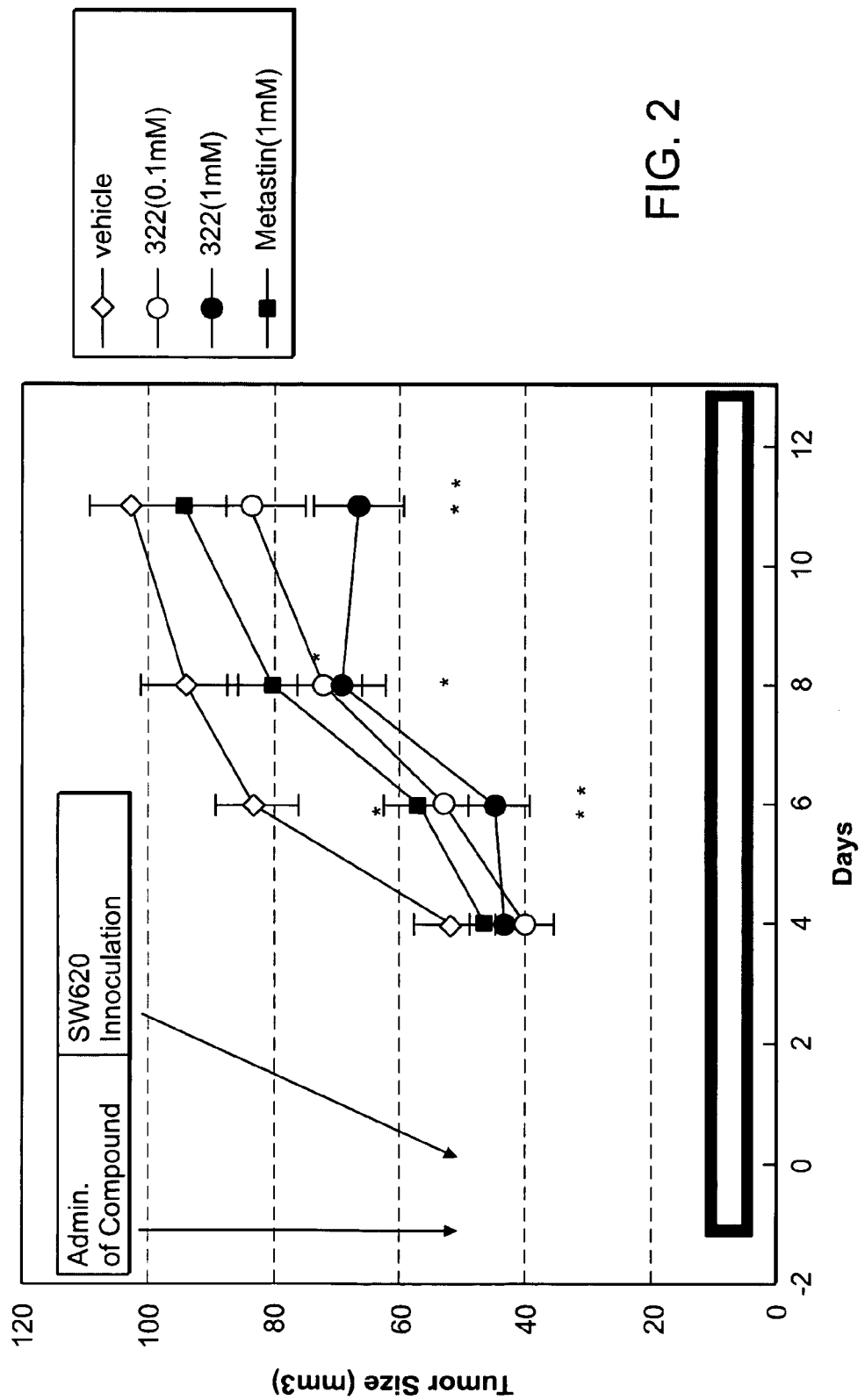
FIG. 2 shows evaluation of the tumor growth inhibition activity of Compound No. 322 and Metastin (1-54) using tumor-bearing mice with human colonic carcinoma-derived cell line SW620, wherein the value indicates (mean value)± (standard error). Symbols open diamond, open circle, closed circle and closed square designate the results obtained when Vehicle (distilled water), Compound No. 322 (0.1 mM), Compound No. 322 (1 mM), and Metastin (Metastin 1-54) were added, respectively. The abscissa denotes the number of days after injection. The bar on the abscissa designates a dosing period. The ordinate denotes a tumor size (mm$^3$).

Alza osmotic pump (0.25 µL/hour, 14 days release, Model 1002) filled with 100 µL each of 1 mM Metastin, 0.1 mM and 1 mM Compounds dissolved in distilled water (Otsuka Joryusui K.K.) and distilled water as a vehicle was subcutaneously embedded into the back of BALB/cAnN-nu mice (6 weeks old, female, Charles River Japan, Inc.) under ether anesthesia to initiate intermittent administration for 14 days. The number of experiments was n=10 in the Metastin group and the vehicle group and n=11 in the both Compound groups. On the following day, human colonic carcinoma-derived cell line SW620 (ATCC) was dissolved in 20 mM phosphate buffered saline (pH 7.2)(PBS) containing 200 µL of 0.15M NaCl at a density of 2×10⁶ cells. The resulting solution was subcutaneously injected into the left flank of the mice above. The day when the cells were injected was made Day 0. Tumor was measured with an electronic caliper every other or 2 other days during Days 4 to 13 from the cell administration, and tumor size was calculated by the equation: (shorter diameter)$^2$×longer diameter/2. As shown in FIG. 2, the Metastin group (24 mol/day/mouse×14 days) showed a significant effect of tumor growth inhibition on Day 6, when compared to the vehicle group. On the other hand, the Compound No. 322 group showed a significant tumor growth inhibition activity in a 1/10 dose (2.4 mol/day/mouse×14 days) of Metastin from Days 6 to 8. Also, the Compound No. 322 group (24 mol/day/mouse×14 days) receiving the same dose as that of Metastin showed a significant tumor growth inhibition activity from Days 6 to 11, when compared to the vehicle group and on Day 11, showed a significant tumor growth inhibition activity even when compared with the Metastin group. The foregoing results reveal that Metastin shows the effect of tumor growth inhibition in vivo as well and Compound No. 322 has the effect of tumor growth inhibition of 10 times higher than with Metastin.

Figure 3:
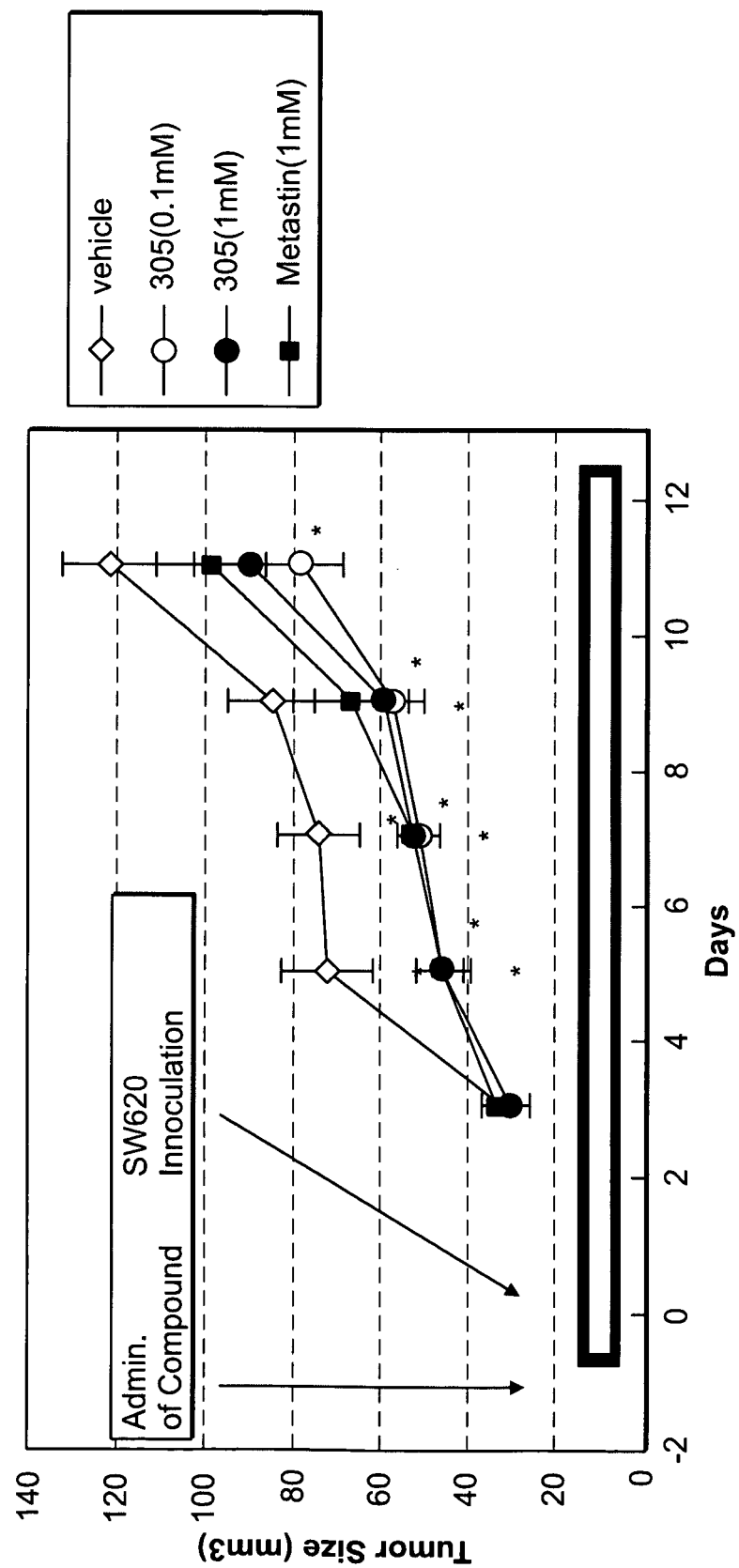
FIG. 3 shows evaluation of the tumor growth inhibition activity of Compound No. 305 and Metastin (1-54) using tumor-bearing mice with human colonic carcinoma-derived cell line SW620, wherein the value indicates (mean value)± (standard error). Symbols open diamond, open circle, closed circle and closed square designate the results obtained when Vehicle (distilled water), Compound No. 305 (0.1 mM), Compound No. 305 (1 mM), and Metastin (Metastin 1-54) were added, respectively. The abscissa denotes the number of days after injection. The bar on the abscissa designates a dosing period. The ordinate denotes a tumor size (mm$^3$).

The results of Compound No. 305 are also shown in FIG. 3. The Metastin group (24 mol/day/mouse×14 days) showed a significant effect of tumor growth inhibition from Days 5 to 7, when compared to the vehicle group. On the other hand, the Compound No. 305 group (2.4 nmol/day/mouse×14 days) receiving a 1/10 dose as that of Metastin showed a significant tumor growth inhibition activity from Days 5 to 11, when compared to the vehicle group. Furthermore, the Compound No. 305 group (24 nmol/day/mouse×14 days) receiving the same dose as that of Metastin showed a significant effect of tumor growth inhibition from Days 5 to 9 and on Day 11, when compared to the vehicle group, revealing that Compound No. 305 also shows the in vivo effect of tumor growth inhibition of 10 times higher than with Metastin.

Test Example 7

Effect of Elevating Sugar Level by Metastin

In order to study the effect of metastin on sugar level by peripheral administration, an operation was performed in free moving animal to collect blood. Mature Wistar male rats (weighing 210-230 g at the time of operation) were anesthetized by intraperitoneal injection of 50 mg/kg pentobarbital. The animal was taped dorsally to the dissection pad and the left jugular vein was exposed. A polyethylene tube SP35 (inner diameter of 0.5 mm, outer diameter of 0.9 mm, Natsume Seisakusho Co., Ltd.) was cut into a length of about 30 cm and filled up with 200 units/ml of heparinated saline. Thereafter, the tube was inserted into the jugular vein to a depth of about 4.5 cm and fixed. The other end of the tube was subcutaneously inserted into the back to expose at the jugular (back).

Figure 4:
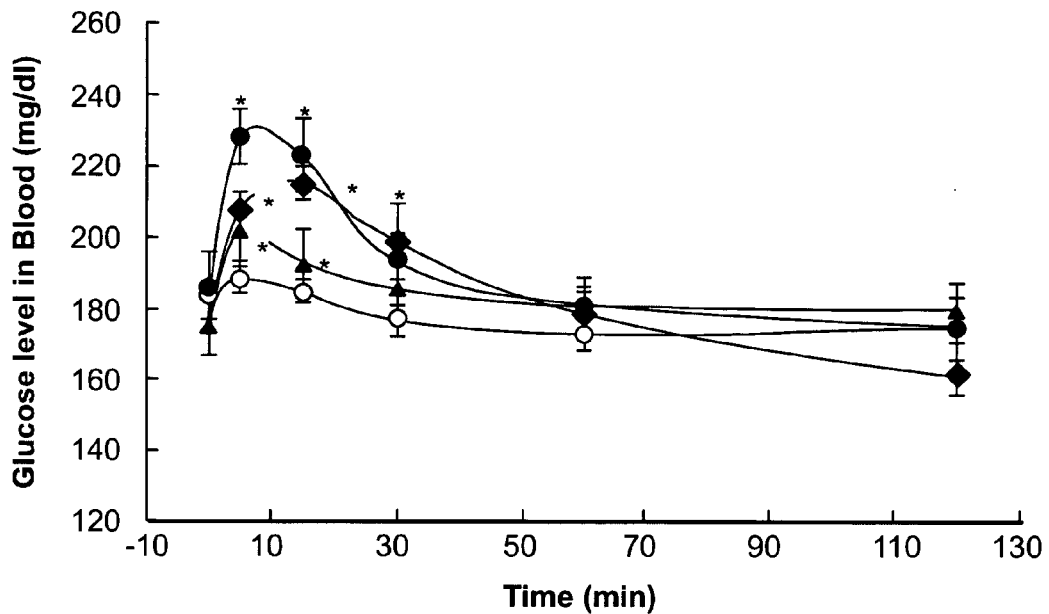
FIG. 4 shows the results obtained by monitoring changes in blood glucose level when metastin was intravenously injected into rats under no anesthesia. In the figure, symbols open circle, closed triangle, closed circle and closed diamond designate blood glucose level in the saline group, the 17 nmol/kg metastin group, the 80 nmol/kg metastin group and the 170 nmol/kg metastin group, respectively. The value indicates (mean±SE) (n=5). Symbol * designates that the P-value is 0.05 or less, when compared to the saline group and symbol ** designates that the P-value is 0.01 or less, when compared to the saline group.

After the operation, the animal was maintained overnight. Prior to administration of metastin, 300 µl of blood was drawn through a 1 ml tuberculin syringe and a 25-gauge needle (both by Terumo Co., Ltd.). To prevent blood clotting, 3 µl of 300 KIU/ml aprotinin solution containing 3 mg/ml EDTA had previously been filled in the syringe. Otsuka saline or 1 mL saline solution of metastin (17, 80 or 170 nmol) was intravenously injected in a dose of 1 mL/kg through the tube. Blood was collected from the jugular vein by 3001 each 0, 5, 15, 30 and 60 minutes starting from the intravenous injection. The collected blood was centrifuged (13,000 rpm, 5 minutes) with a high speed refrigerated centrifuge (MR-150, Tomy Seiko Co., Ltd.) to recover the supernatant (plasma). Glucose level in blood was measured using Fuji Drychem 3500 (FUJI FILM). As shown in FIG. 4, the Metastin group showed a significant effect (p<0.005, n=5) of enhancing glucose level in blood dose-dependently (17-170 nmol/kg) from 5 minutes after the intravenous injection, when compared to the control group. In the blood glucose level, a prolonged period of time (30 minutes at maximum) for enhancing the sugar level accompanied by an increase of the maximum level was noted metastin, as the dose increased.

Test Example 8

Effect of Promoting Pancreatic Glucagon Secretion by Metastin

Figure 5:
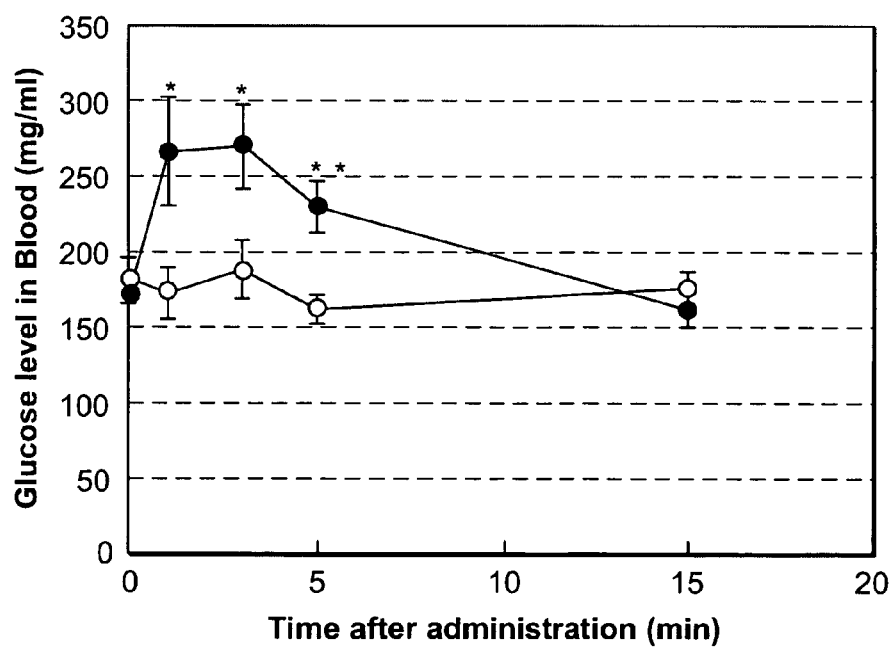
FIG. 5 shows the results obtained by monitoring changes in blood glucagon level when metastin was intravenously injected into rats under no anesthesia. In the figure, symbols open circle and closed circle designate blood glucagon level in the saline group and the 80 nmol/kg metastin group, respectively. The value indicates (mean±SE) (n=6-9). Symbol * designates that the P-value is 0.05 or less, when compared to the saline group and symbol ** designates that the P-value is 0.01 or less, when compared to the saline group.
Figure 6:
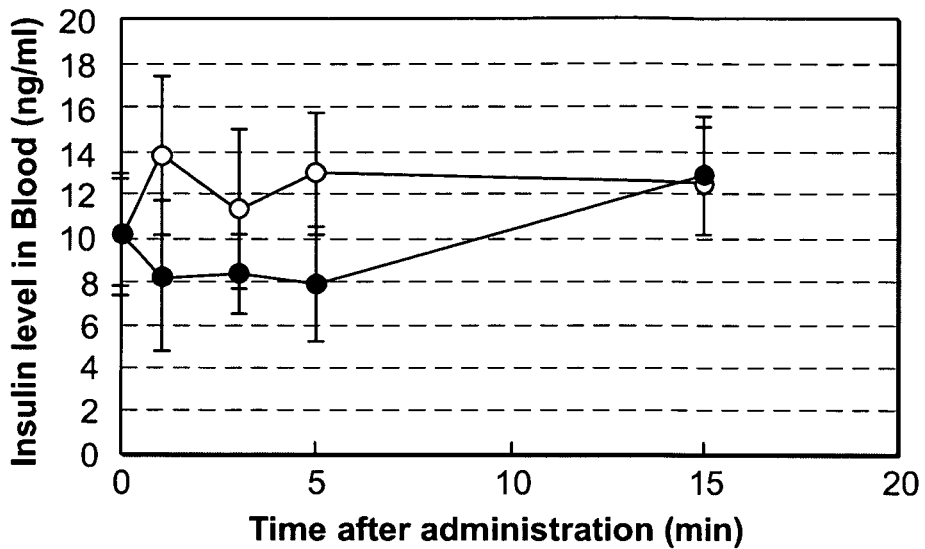
FIG. 6 shows the results obtained by monitoring changes in blood insulin level when metastin was intravenously injected into rats under no anesthesia. In the figure, symbols open circle and closed circle designate blood insulin level in the saline group and the 80 nmol/kg metastin group, respectively. The value indicates (mean±SE) (n=6-9).
Figure 7:
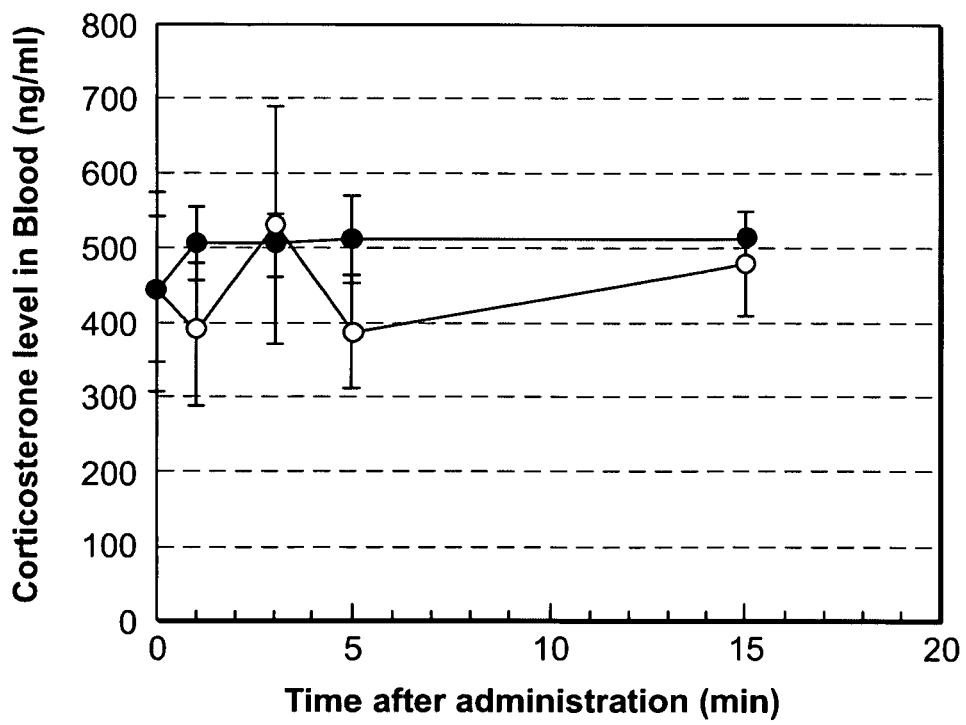
FIG. 7 shows the results obtained by monitoring changes in blood corticosterone level when metastin was intravenously injected into rats under no anesthesia. In the figure, symbols open circle and closed circle designate blood corticosterone level in the saline group and the 80 nmol/kg metastin group, respectively. The value indicates (mean±SE) (n=4-5).
Figure 8:
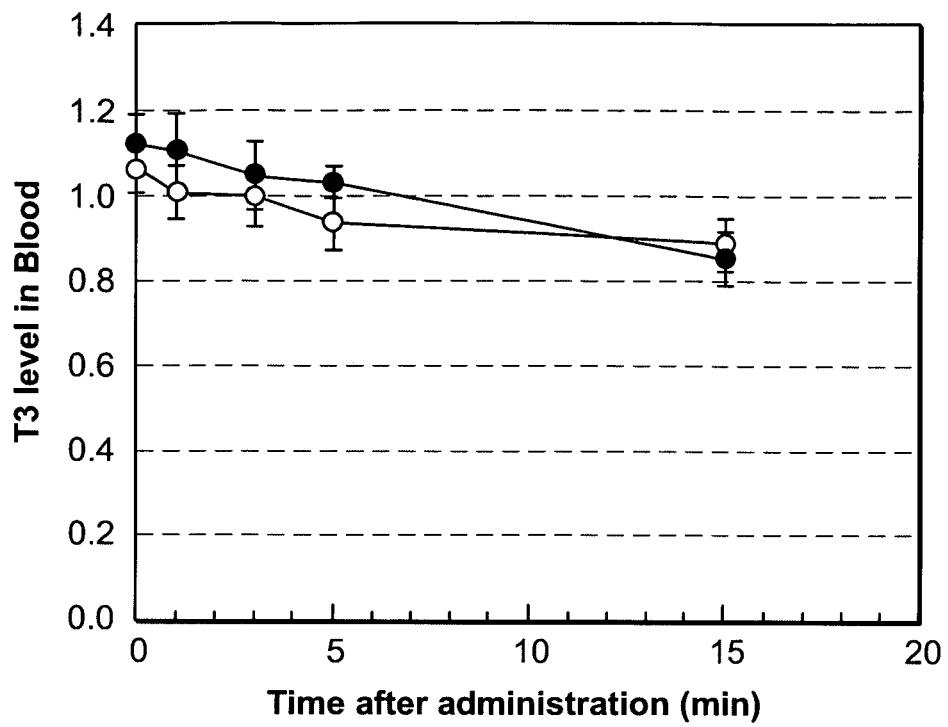
FIG. 8 shows the results obtained by monitoring changes in thyroid hormone (T3) level in blood when metastin was intravenously injected into rats under no anesthesia. In the figure, symbols open circle and closed circle designate thyroid hormone (T3) level in blood in the saline group and the 80 nmol/kg metastin group, respectively. The value indicates (mean±SE) (n=4-5).
Figure 9:
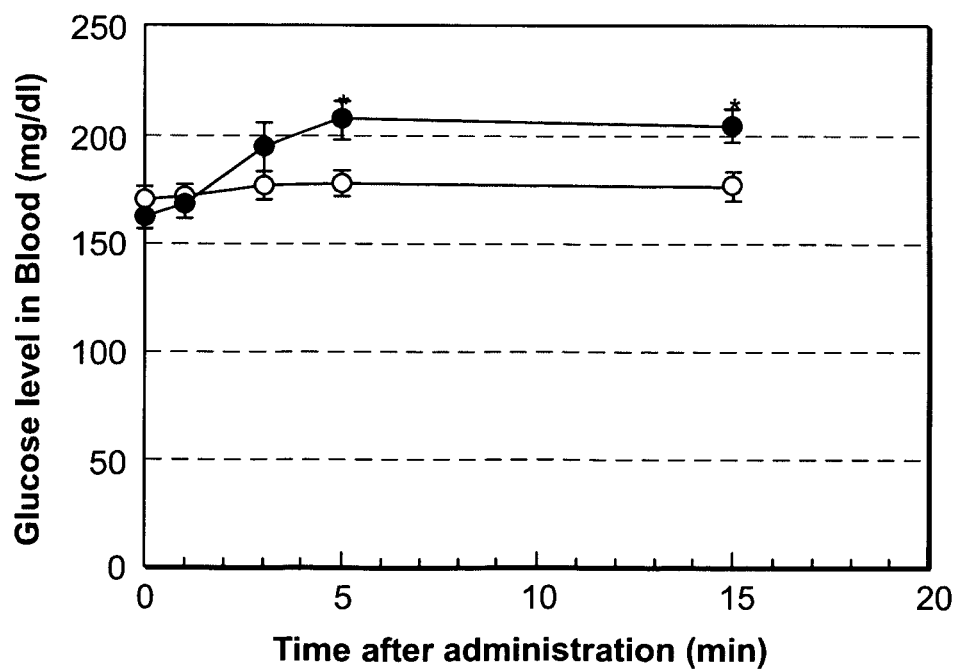
FIG. 9 shows the results obtained by monitoring changes in blood glucose level when metastin was intravenously injected into rats under no anesthesia. In the figure, symbols open circle and closed circle designate blood glucose level in the saline group and the 80 nmol/kg metastin group, respectively. The value indicates (mean±SE) (n 6-9). Symbol * designates that the P-value is 0.05 or less, when compared to the saline group

In order to study the mechanism of metastin for the effect of enhancing glucose level in blood, effects of metastin on the level of blood glucagon, insulin, corticosterone and thyroid hormone (T3) known to be hormones affecting glucose level in blood were examined. An operation was performed in free moving mature Wistar male rats (weighing 260-300 g at the time of operation) to collect blood. After the operation, the animal was maintained overnight. Prior to administration of metastin, 300 µl of blood was drawn through a 1 ml tuberculin syringe and a 25-gauge needle (both by Terumo Co., Ltd.). To prevent blood clotting, 3 µl of 300 KIU/ml aprotinin solution containing 3 mg/ml EDTA had previously been filled in the syringe. Otsuka saline or a saline solution of metastin (80 nmol/mL) was intravenously injected in a dose of 1 mL/kg through the tube. Blood was collected from the jugular vein by 300 µl each 1, 3, 5 and 15 minutes starting from the intravenous injection. The collected blood was centrifuged (13,000 rpm, 5 minutes) with a high speed refrigerated centrifuge (MR-150, Tomy Seiko Co., Ltd.) to recover the supernatant (plasma). Glucagon level in blood was measured using a glucagon kit "Daiichi" (Daiichi Radioisotope Laboratories Ltd.), insulin level in blood using rat insulin [$^{125}$I] assay system (Amersham Biosciences), corticosterone level in blood using rat corticosterone [$^{125}$I] assay system (Amersham Biosciences), thyroid hormone (T3) in blood using T-3.RIA beads (Dinabott Co. Ltd.), and glucose level in blood using Fuji Drychem 3500 (FUJI FILM). As shown in FIG. 5, the Metastin group showed a significant effect of enhancing glucagon level in blood 1 minute after the injection, when compared to the control group. The significant effect of enhancing glucagon level continued until 5 minutes after the injection. On the other hand, in the insulin level in blood (FIG. 6), corticosterone level in blood (FIG. 7) and thyroid hormone (T3) level in blood (FIG. 8), no change was noted by the injection of metastin. Based on these results and the observed increase in blood glucagon level followed by blood glucose level (FIG. 9), it was considered that the effect of blood glucose level by intravenous injection of metastin would be induced due to stimulation of glucagon secretion by metastin.

Test Example 9

Effect of Elevating Sugar Level by Metastin Derivatives

Figure 10:
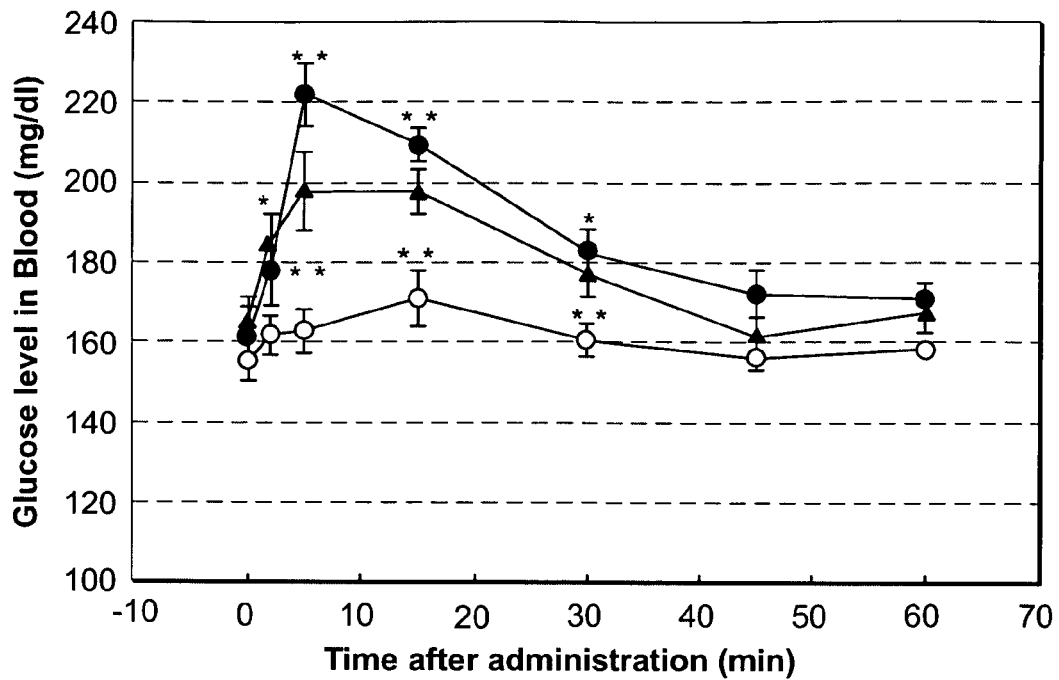
FIG. 10 shows the results obtained by monitoring changes in blood glucose level when a metastin derivative was intravenously injected into rats under no anesthesia. In the figure, symbols open circle, closed circle and closed triangle designate blood glucose level in the saline group, the 80 nmol/kg KiSS1-305 group and the 80 mmol/kg metastin group, respectively. The value indicates (mean±SE) (n=5). Symbol * designates that the P-value is 0.05 or less, when compared to the saline group and symbol ** designates that the P-value is 0.01 or less, when compared to the saline group.
Figure 11:
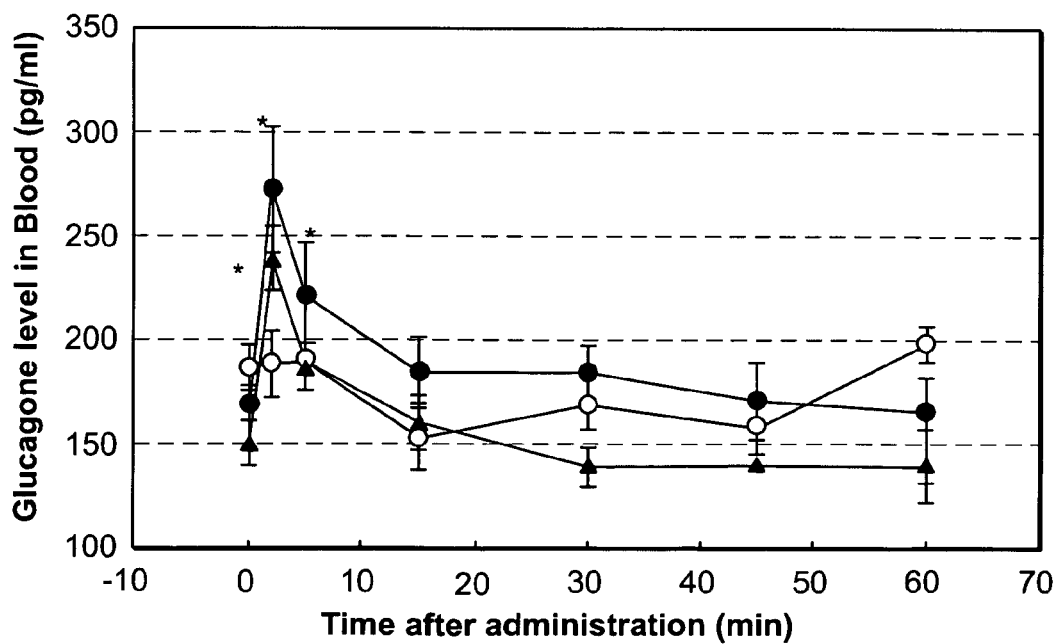
FIG. 11 shows the results obtained by monitoring changes in blood glucagon level when metastin was intravenously injected into rats under no anesthesia. In the figure, symbols open circle, closed circle and closed triangle designate blood glucagon level in the saline group and the 80 nmol/kg KiSS1-305 (Compound No. 305) group, the 80 nmol/kg KiSS1-322 (Compound No. 322) group, respectively. The value indicates (mean±SE) (n=5). Symbol * designates that the P-value is 0.05 or less, when compared to the saline group.

The effect of metastin derivatives KiSS305 (Compound No. 305) and KiSS322 (Compound No. 322) on blood glucose level and blood glucagon level was examined. An operation was performed in free moving mature Wistar male rats (weighing 260-3000 g at the time of operation) in a manner similar to TEST EXAMPLE 1 to collect blood. After the operation, the animal was maintained overnight. Prior to administration of metastin, 300 μl of blood was drawn through a 1 ml tuberculin syringe and a 25-gauge needle (both by Terumo Co., Ltd.). To prevent blood clotting, 3 μl of 300 KIU/ml aprotinin solution containing 3 mg/ml EDTA had previously been filled in the syringe. Otsuka saline or a saline solution of metastin (80 nmol/mL) was intravenously injected in a dose of 1 mL/kg through the tube. Blood was collected from the jugular vein by 300 μl each 2, 5, 15, 30, 45 and 60 minutes starting from the intravenous injection. The collected blood was centrifuged (13,000 rpm, 5 minutes) with a high speed refrigerated centrifuge (MR-150, Tomy Seiko Co, Ltd.) to recover the supernatant (plasma). Glucose level in blood was measured using Fuji Drychem 3500 (FUJI FILM) and glucagon level in blood was measured using a glucagon kit "Daiichi" (Daiichi Radioisotope Laboratories Ltd.), as in TEST EXAMPLE 1 or 2. As shown in FIG. 10, both compounds showed an increase in the blood glucose level. Also, both compounds showed an increase in the blood glucagon level, as shown in FIG. 11.

Test Example 10

Induction of Ovulation by Human Metastin in Immature Rat

Equine chorionic gonadotropin (eCG, serotropin, Dainippon Pharmaceutical Co., Ltd.) was dissolved in saline (Otsuka Pharmaceutical Co., Ltd.) in a concentration of 100 IU/mL. Using a 1 ml tuberculin syringe and a 26-gauge needle (both by Terumo Co., Ltd.), eCG was subcutaneously injected into the dorsal area of female Wistar rats of 23 days old after birth (Charles River Japan, Inc.) in a dose of 10 IU/animal, during 9:30 to 10:00 AM. Following the eCG injection, the animal was grouped after 47 to 48 hours as shown below, to which groups, each drug was injected.

Group A (5 rats): Human chorionic gonadotropin (hCG, gonadotropin, Dainippon Pharmaceutical Co., Ltd.) was dissolved in saline at 100 IU/mL and the solution was subcutaneously injected into the back in a dose of 20 IU/animal.

Group B (5 rats): Human metastin was dissolved in saline at 100 nmol/mL and the solution was subcutaneously injected into the back in a dose of 20 nmol/animal.

Group C (5 rats): Human metastin was dissolved in saline at 33.3 nmol/mL and the solution was subcutaneously injected into the back in a dose of 6.67 mmol/animal.

Group D (6 rats): Saline was subcutaneously injected into the back in a dose of 200 μL/animal.

After administration of the drugs described above, the animal was sacrificed by decapitation after 24 to 25 hours to recover blood, bilateral oviducts and uterus. In collecting blood, 90 μl of 10 KIU/ml aprotinin solution (Trasylol, Bayer) containing 3 mg/ml EDTA had been previously filled in a tube for recovery to prevent blood clotting. After blood recovery, the blood was thoroughly blended and the mixture was centrifuged at 2,000 G for 25 minutes. After the supernatant was recovered, the product was used as a plasma sample.

The number of oocytes was counted as follows.

Where retention of oocytes in the oviducal ampulla was confirmed by stereomicroscopic observation of the oviduct, the ampulla was punctured with a syringe with 27-gauge needle for syringe (Terumo) to retrieve the oocytes. After granulosa cells surrounding the oocytes were removed by trypsin treatment, the number of oocytes was counted. Where retention of oocytes in the oviducal ampulla was not confirmed by stereomicroscopic observation of the oviduct, a 27-gauge needle with the polished tip for syringe was inserted into the tubal ostium and more than 400 μL of saline was flushed into the oviduct and uterine for rinsing. Then, the presence or absence of oocytes in the effluent was observed.

The number of oocytes obtained is shown in TABLE 26.

TABLE 26

|   | Group A | Group B | Group C | Group D |
|---|---------|---------|---------|---------|
| 1 | 36 | 29 | 29 | 0 |
| 2 | 35 | 56 | 39 | 0 |
| 3 | 40 | 17 | 32 | 0 |
| 4 | 42 | 25 | 22 | 0 |
| 5 | 35 | 32 | 16 | 0 |
| Average of Ovulation | 37.6 | 31.8 | 27.6 | 0.00 |
| Standard Deviation | 3.21 | 14.65 | 8.91 | 0.00 |

In the table, the numbers "1" through "5" represent a number for individual rat.

In Group A, which is a multipurpose superovulation treatment group, ovulation of 37.6 oocytes in average per rat was confirmed. In Groups B and C receiving metastin, ovulation of 31.8 and 27.6 oocytes in average, respectively, were confirmed. Turning to Group D receiving saline, the number of oocytes was 0.6 in average, indicating that voluntary ovulation was little observed in the absence of ovulation stimulation.

Figure 12:
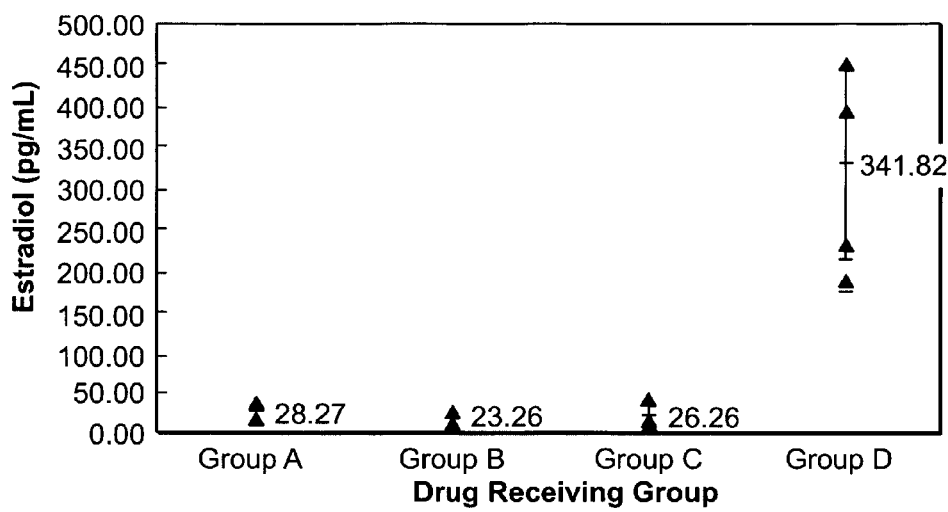
FIG. 12 shows the level of estradiol contained in the rat plasma. In the figure, the ordinate and the abscissa denote the estradiol level and the drug receiving groups, respectively.

The level of estradiol contained in the plasma collected from the rats shown in TABLE 22 was determined by radioimmunoassay (DPC-Estradiol Kit; Diagnostic Products Corporation). The results are shown in FIG. 12.

The results reveal that among Groups A, B and C, there is no difference in the level of estradiol contained in plasma, showing that the level of estradiol was extremely high only in Group D receiving saline.

Figure 13:
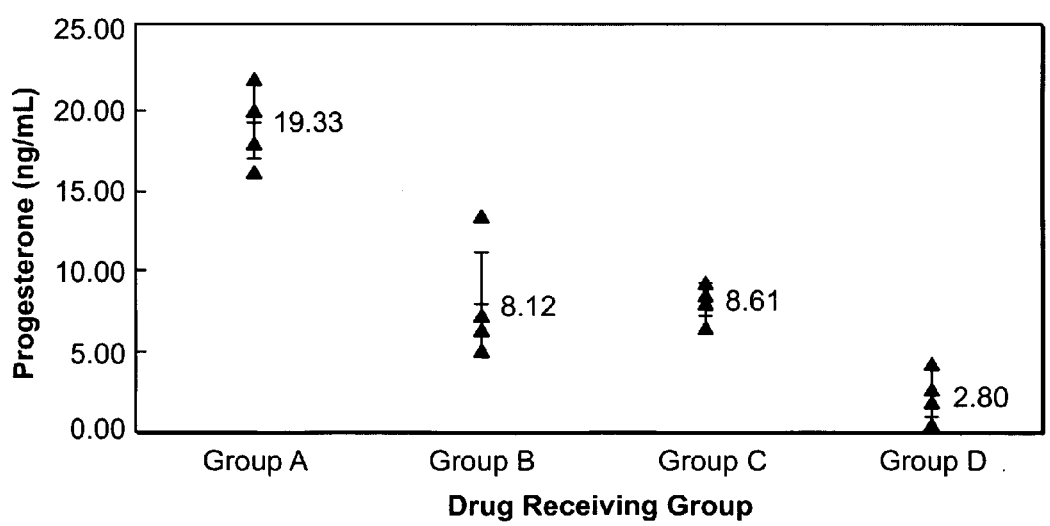
FIG. 13 shows the level of progesterone contained in the rat plasma. In the figure, the ordinate and the abscissa denote the estradiol level and the drug receiving groups, respectively.

The level of progesterone contained in plasma was determined by radioimmunoassay (DPC.Progesterone; Diagnostic Products Corporation). The results are shown in FIG. 13.

The results reveal that the level of progesterone was highest in Group A and in Groups B and C, the blood level was approximately half that of Group A and that the progesterone level was extremely low in Group D.

In general, the major steroid hormone produced in rat mouse and human ovaries is estrogen in the mature phase of ovarian follicle, whereas it is progesterone after ovulation was induced. It is understood actually from the results in FIG. 12 and FIG. 13 that Group D receiving saline maintained the state where estrogen was highly produced, because of no induction of ovulation; whereas in Group A receiving hCG, production of estrogen increased. In Groups B and C, which are groups receiving Metastin, the plasma estrogen level was very low but the level of progesterone increased, indicating that metastin induced ovulation in the rat ovary via its normal ovulatory process. It is also considered that since the progesterone level in Groups B and C was lower than in Group A, metastin would have a milder ovarian stimulation.

Test Example 11

Gonadotropin-Releasing Effect of Human Metastin in Immature Rat

Human metastin dissolved in saline in a concentration of 33.3 nmol/mL was subcutaneously injected into the dorsal area of female Wistar rats of 25 days old after birth (Charles River Japan, Inc.) in a dose of 200 μL/animal, i.e., 6.67 mmol as human metastin, during 9:00 to 10:00 AM. Prior to the metastin injection and 1, 2 and 4 hours after the injection, the animal was decapitated to recover blood. In recovery of blood, 90 µl of 10 KIU/ml aprotinin solution (Trasylol, Bayer) containing 3 mg/ml EDTA had been previously filled in a centrifuging tube for recovery to prevent blood clotting. After blood recovery, the blood was thoroughly blended and the mixture was centrifuged at 2,000 G for 25 minutes. After the supernatant was recovered, the product was used as a plasma sample. The levels of FSH (follicle-stimulating hormone), LH (luteinizing hormone) and progesterone contained in the plasma were determined by radioimmunoassay (Rat Follicle Stimulating Hormone (rFSH) [$^{125}$I] Biotrack Assay System with Magnetic Separation, Rat Luteinizing Hormone (rLH) [$^{125}$I] Biotrack Assay System with Magnetic Separation, both by Amersham Bioscience, and DPC.Progesterone by Diagnostic Products Corporation).

Figure 14:
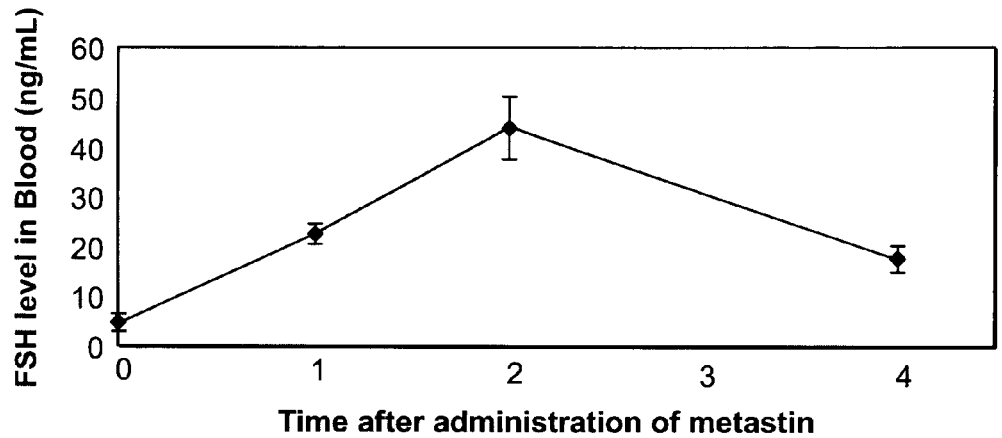
FIG. 14 shows changes in the blood FSH level in immature rat by metastin injection.

The results obtained by monitoring changes in the FSH level in blood from the immature rat by the metastin injection are shown in FIG. 14. One hour after the metastin injection, the blood FSH level began to significantly increase and reached the maximum after 2 hours. While a decrease in the blood FSH level was noted after 4 hours, the FSH level was still maintained higher than the level prior to the injection.

Figure 15:
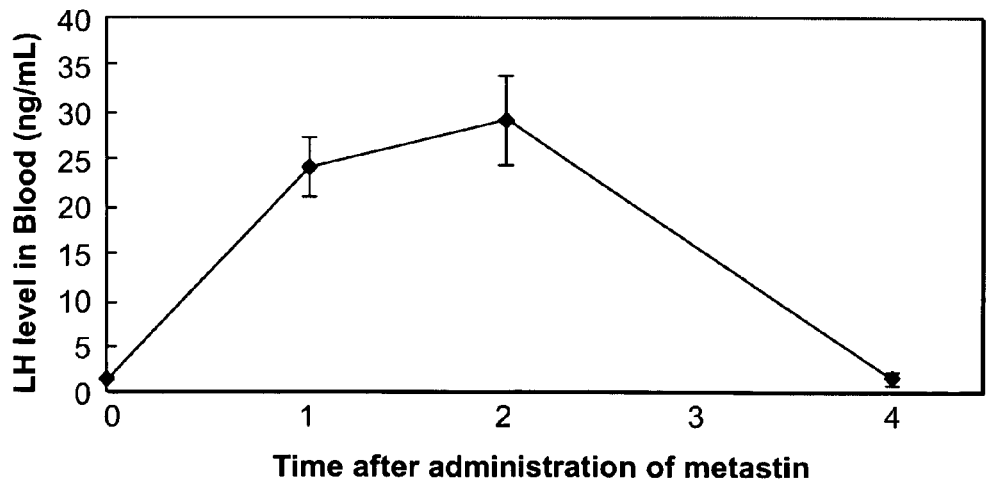
FIG. 15 shows changes in the blood LH level in immature rat by metastin injection.

The results obtained by monitoring changes in the LH level in blood from the immature rat by the metastin injection are shown in FIG. 15. Similarly to the case of FSH, the blood LH level began to significantly increase 1 hour after and reached the maximum after 2 hours. While a decrease in the blood LH level was noted after 4 hours, the LH level was still maintained higher than the level prior to the injection.

Figure 16:
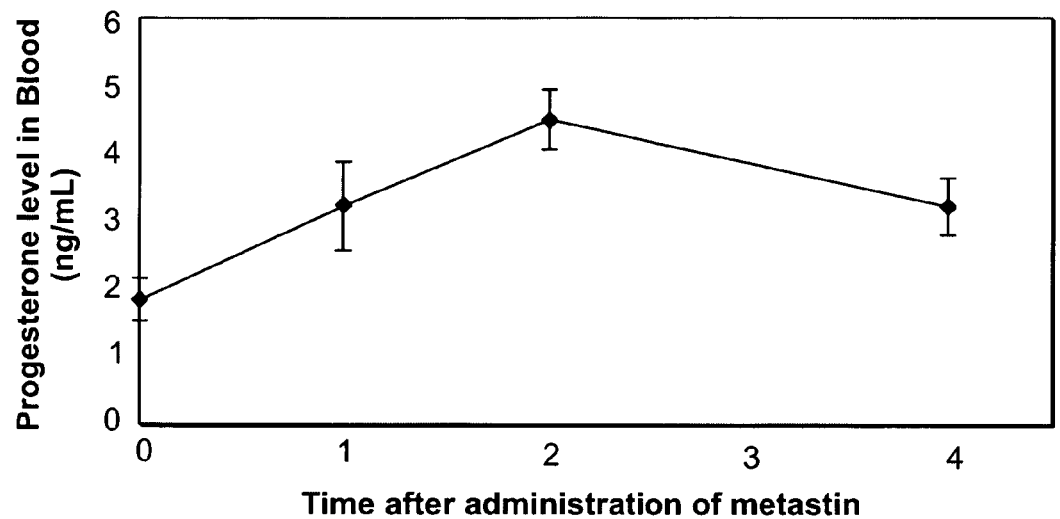
FIG. 16 shows changes in the blood progesterone level in immature rat by metastin injection.

The results obtained by monitoring changes in the progesterone level in blood from the immature rat by the metastin injection are shown in FIG. 16. Reflecting the increase of blood LH level, the progesterone level began to increase slowly 1 hour after the metastin injection and showed a significantly higher level than the level prior to the injection.

The results of FIG. 14 and FIG. 15 reveal that peripheral administration of metastin induces release of gonadotropin such as FSH, LH, etc. The induction of ovulation by metastin demonstrated in TEST EXAMPLE 9 is considered to be mediated by this gonadotropin release, particularly LH release.

The effect of inducing ovulation demonstrated in TEST EXAMPLE 9 is an action in rats receiving eCG but the effect in this TEST EXAMPLE shows the results obtained using nude rats. No eCG pretreatment is required for the effect of releasing gonadotropin by metastin.

The results shown in FIG. 16 mean that the release of gonadotropin by the metastin injection imparts physiological stimulation also to the ovary, resulting in increasing the production of progesterone.

Test Example 12

Gonadotropin-Releasing Effect of Human Metastin in Mature Male Rat

Human metastin dissolved in saline in a concentration of 175 nmol/mL was subcutaneously injected into the dorsal area of male Wistar rats of 11 weeks old after birth (Charles River Japan, Inc.) in a dose of 200 µL/animal, i.e., 35 mmol as human metastin, during 10:30 to 11:30 AM. Prior to the metastin injection and 1, 2 and 4 hours after the injection, the animal was decapitated to recover blood. In recovery of blood, 300 µl of 10 KIU/ml aprotinin solution (Trasylol, Bayer) containing 3 mg/ml EDTA had been previously filled in a centrifuging tube for recovery to prevent blood clotting. After blood recovery, the blood was thoroughly blended and the mixture was centrifuged at 2,000 G for 25 minutes. After the supernatant was recovered, the product was used as a plasma sample. The levels of FSH (follicle-stimulating hormone), LH (luteinizing hormone) and testosterone contained in the plasma were determined by radioimmunoassay (Rat Follicle Stimulating Hormone (rFSH) [$^{125}$I] Biotrack Assay System with Magnetic Separation, Rat Luteinizing Hormone (rLH) [$^{125}$I] Biotrack Assay System with Magnetic Separation, both by Amersham Bioscience, and DPC.Total Testosterone by Diagnostic Products Corporation).

Figure 17:
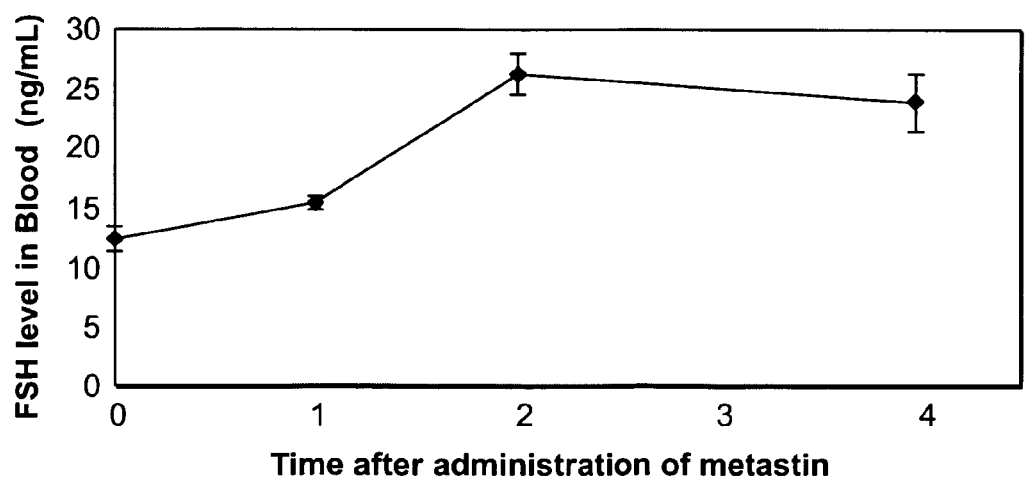
FIG. 17 shows changes in the blood FSH level in rat by metastin injection.

The results obtained by monitoring changes in the blood FSH level in rat by the metastin injection are shown in FIG. 17. One hour after the metastin injection, the blood FSH level began to significantly increase and reached the maximum after 2 hours, and even after 4 hours, still maintained a higher state.

Figure 18:
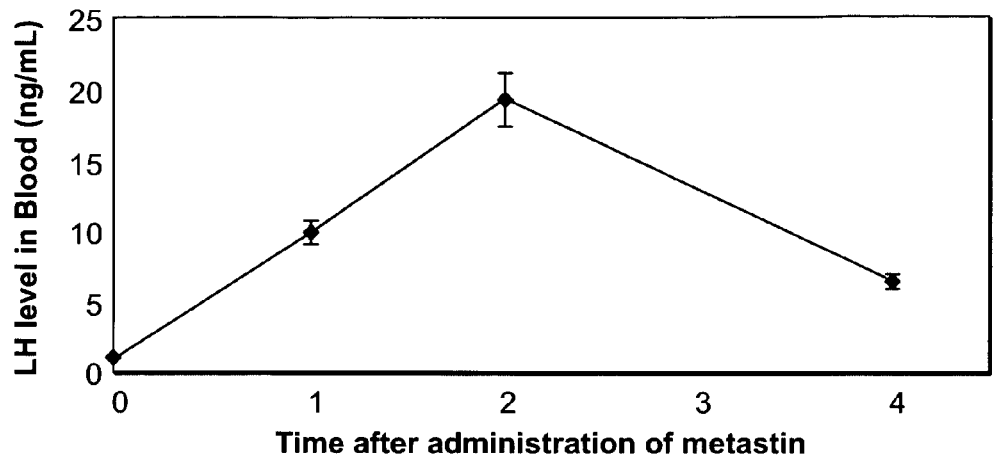
FIG. 18 shows changes in the blood LH level in rat by metastin injection.

The results obtained by monitoring changes in the blood LH level in rat by the metastin injection are shown in FIG. 18. Similarly to the case of FSH, the blood LH level began to significantly increase 1 hour after and reached the maximum after 2 hours. While a decrease in the blood LH level was noted after 4 hours, the LH level was still maintained higher than the level prior to the injection.

Figure 19:
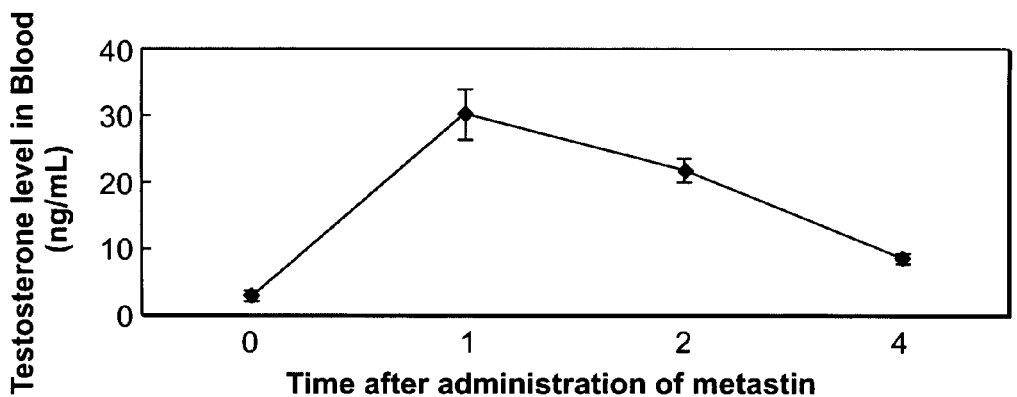
FIG. 19 shows changes in the blood testosterone level in rat by metastin injection.

The results obtained by monitoring changes in the blood testosterone level in rat by the metastin injection are shown in FIG. 19. The testosterone level showed a rapid increase in 1 hour after the metastin injection. While a decrease in the blood testosterone level was noted after 2 and 4 hours, the testosterone level was still maintained at both points of time higher than the level prior to the injection.

The results of FIG. 17 and FIG. 18 reveal that peripheral administration of metastin induces release of gonadotropin such as FSH, LH, etc. in male rat. In view of the results of TEST EXAMPLE 10, metastin is considered to be an extremely important factor in both female and male rats, in stimulating the release of gonadotropin.

The results shown in FIG. 19 mean that the release of gonadotropin by the metastin injection imparts physiological stimulation also to the testis, resulting in increasing the production of testosterone.

From these results it is considered that administration of metastin would stimulate the testis mediated by release of gonadotropin. This suggests that metastin possibly affects the male reproductive function including seminal maturation, hormone secretion, etc.

Test Example 13

Test on Stability of Compound in Blood

Blood was drawn from Balb/c mouse of 8 weeks old (female), settled at 37° C. for 30 minutes and centrifuged at 13000 rpm for 10 minutes to give mouse serum. The serum thus obtained was frozen-stored at −80° C.

The stability test was performed by addition of 5 nmol of Compound (5 µL of aqueous solution) to 45 µL of serum and then settlement of the mixture at 37° C. The settlement was made at 3 points of time, including 2, 10 and 30 minutes. The sample after the settlement was boiled for 3 minutes and cooled on an ice bath. After 200 µL of acetonitrile/water (3/1) was added to the sample, the mixture was ultrasonicated for 5 minutes and then centrifuged at 5000 rpm for 1 minute. After 150 µL of the supernatant was diluted with 250 µL of distilled water, insoluble matters were removed by filtration through a filter having a pore size of 0.45 g/m and 200 µL of the filtrate was applied on HPLC (220 nm) to determine the peak area of Compound. A ratio of the peak area to the area when Compound was treated for 0 minute under the same conditions was calculated as a mean value in 4 respective runs to determine the residual ratio. Next, by taking the calculated residual ratio on the ordinate and time on the abscissa, a graph was prepared and approximated by an exponential function. Thus, the time when the residual ratio reached 50% was calculated as a half life.

The LC-VP series manufactured by Shimadzu Corporation was used as preparative HPLC and Wakosil-II 5C18 HG (4.6 mm×100 mm) manufactured by Wako Pure Chemical Industries, Ltd. was used as a column. Eluant A (0.1% TFA-containing water) and eluant B (0.1% TFA-containing acetonitrile) were used as eluants. Linear density gradient elution was performed at a flow rate of 1.0 ml/min. using eluants A/B: 100/0-0/50 (25 minutes).

Compounds tested and the $t_{1/2}$ (min) values are shown in TABLE 27.

TABLE 27

| Compound Number | $t_{1/2}$ (min) |
|---|---|
| 1 | 22.5 |
| 3 | 0.6 |
| 42 | 0.7 |
| 82 | 1.8 |
| 134 | 2.4 |
| 141 | 8.7 |
| 232 | 28.2 |
| 286 | 57.5 |
| 296 | 47.2 |
| 305 | 66.6 |
| 308 | 13.2 |
| 319 | 33.0 |
| 322 | 94.2 |

Test Example 14

Induction of Ovulation in Immature Rat Using Metastin Derivatives

Equine chorionic gonadotropin (eCG, serotropin, Dainippon Pharmaceutical Co., Ltd.) was dissolved in saline (Otsuka Pharmaceutical Co., Ltd.) in a concentration of 100 IU/mL. Using a 1 ml tuberculin syringe and a 26-gauge needle (both by Terumo Co., Ltd.), eCG was subcutaneously injected into the dorsal area of female Wistar rats of 23 days old after birth (Charles River Japan, Inc.) in a dose of 10 IU/animal, during 9:00 to 10:00 AM. Following the eCG injection, the animal was grouped after 47 to 48 hours as shown below, to which groups, each drug was injected.

Group A (5 rats): Human chorionic gonadotropin (hCG, gonadotropin, Dainippon Pharmaceutical Co., Ltd.) was dissolved in saline at 100 IU/mL and the solution was subcutaneously injected into the back in a dose of 20 IU/animal.

Group B (5 rats): Compound No. 305 was dissolved in saline at 33.3 nmol/mL and the solution was subcutaneously injected into the back in a dose of 6.7 nmol/animal.

Group C (5 rats): Compound No. 305 was dissolved in saline at 10.0 mmol/mL and the solution was subcutaneously injected into the back in a dose of 2.0 nmol/animal.

Group D (5 rats): Compound No. 322 was dissolved in saline at 33.3 nmol/mL and the solution was subcutaneously injected into the back in a dose of 6.7 nmol/animal.

Group E (5 rats): Compound No. 322 was dissolved in saline at 10.0 nmol/mL and the solution was subcutaneously injected into the back in a dose of 2.0 nmol/animal.

Group F (6 rats): Saline was subcutaneously injected into the back in a dose of 200 µL/animal.

After administration of these drugs, the animal was sacrificed by decapitation after 24 to 25 hours to recover blood, bilateral oviducts and uterus. In collecting blood, 90 µl of 10 KIU/mL aprotinin solution (Trasylol, Bayer) containing 3 mg/ml EDTA had been previously filled in a tube for recovery to prevent blood clotting. After blood recovery, the blood was thoroughly blended and the mixture was centrifuged at 2,000 G for 25 minutes. After the supernatant was recovered, the product was used as a plasma sample.

The number of oocytes was counted by referring to the method described in Eur. J. Endocrinol., 138, 594-600 (1998).

Where retention of oocytes in the oviducal ampulla was confirmed by stereomicroscopic observation of the oviduct, the ampulla was punctured with a 27-gauge needle for syringe (Terumo) to retrieve the oocytes. After granulosa cells surrounding the oocytes were removed by trypsin treatment, the number of oocytes was counted. Where retention of oocytes in the oviducal ampulla was not confirmed by stereomicroscopic observation of the oviduct, a with 27-gauge needle with the polished tip for syringe was inserted into the tubal ostium and more than 400 µL of saline was flushed into the oviduct and uterine for rinsing. Then, the presence or absence of oocytes in the effluent was observed.

Figure 20:
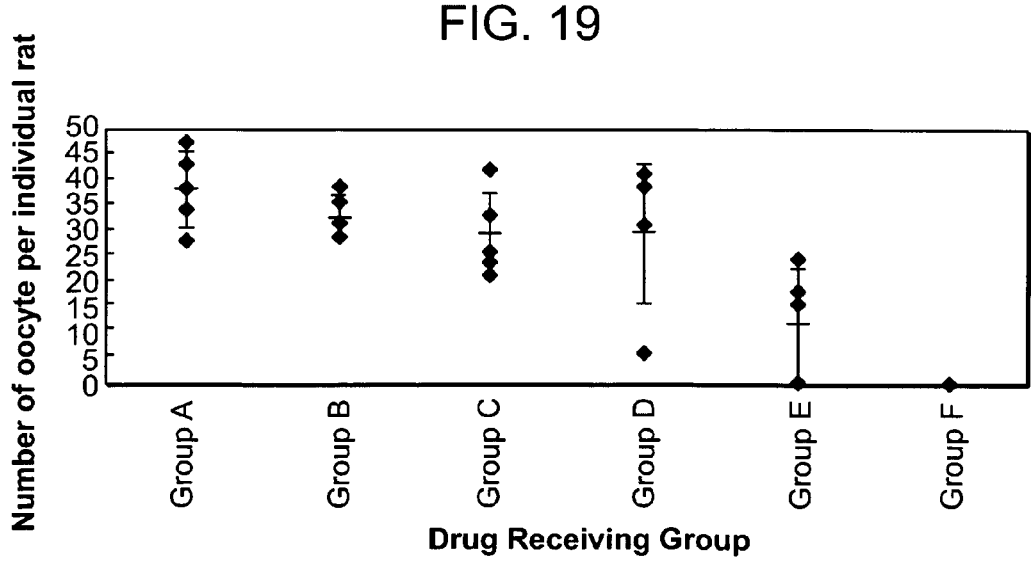
FIG. 20 shows the number of oocytes per individual rat in each group measured in TEST EXAMPLE 13. In the figure, symbol closed diamond designates data for per individual rat and symbol closed square designates a mean value in each group.

The number of oocytes thus obtained is shown in FIG. 20. In Group A, which is a multipurpose superovulation treatment group, the number of oocytes was 38.0 oocytes in average per rat. In Groups B, C and D, the number of oocytes was 32.6, 29.4 and 29.6 oocytes in average, respectively, indicating that ovulation was substantially equivalent to Group A. Turning to Group E receiving 2.0 mmol of Compound No. 322, 3 out of 5 rats were ovulated and the number of oocytes was 11.6 in average, which was less than Group A. Further in Group A for negative control, no ovulation was observed.

The results of FIG. 20 reveal that for induction of ovulation equivalent to hCG, at least 2.0 mmol/animal of Compound No. 305 and at least 6.7 mmol/animal of Compound No. 322 should be administered.

Figure 21:
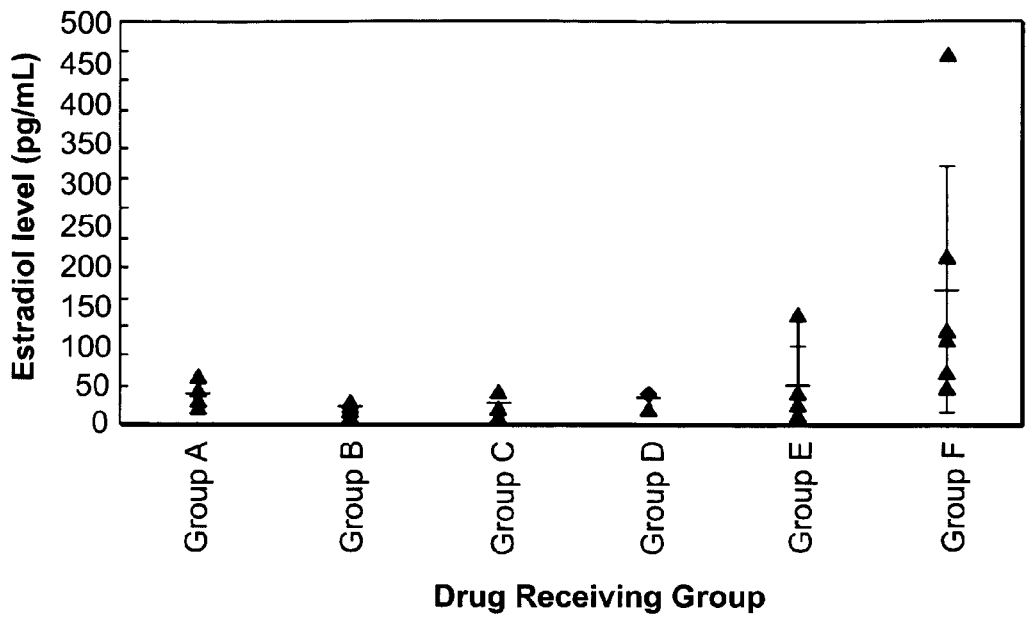
FIG. 21 shows the blood estradiol level in each dosing group measured in TEST EXAMPLE 13. In the figure, symbol closed triangle designates data for per individual rat and symbol closed square designates a mean value in each group.

The results obtained by measuring the level of estradiol contained in plasma are shown in FIG. 21. The blood estradiol level was measured by radioimmunoassay (DPC.Estradiol Kit, Iatron, Inc.). As shown in FIG. 21, no difference was found among Groups A, B, C and D in terms of estradiol and only Group F showed a high level. Group E had a tendency to show a higher level in rats with no ovulation induction.

Figure 22:
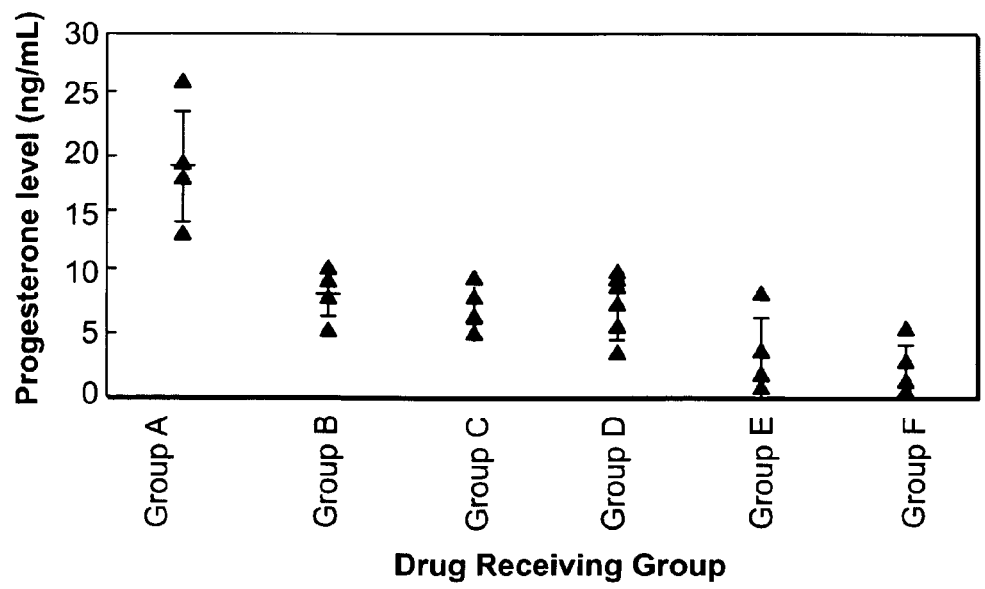
FIG. 22 shows the blood progesterone level in each group measured in TEST EXAMPLE 13. In the figure, symbol closed triangle designates data for per individual rat and symbol closed square designates a mean value in each group.

The results obtained by measuring the level of progesterone contained in plasma are shown in FIG. 22. The blood progesterone level was measured by radioimmunoassay (DPC.Progesterone, Iatron, Inc.). As shown in FIG. 22, the blood progesterone level was highest in Group A and in Groups B, C and D, the progesterone level shows less than a half of the level in Group A. Groups E and F shows a very low level.

The results of FIG. 21 and FIG. 22 reveal that more than 2.0 nmol/animal of Compound No. 305 and more than 6.7 mmol/animal of Compound No. 322 were administered to induce normal differentiation from estrogen-producing granulosa cells to progesterone-producing luteal cells. Furthermore, when Compound No. 305 or KiSS-322 was administered, the progesterone level was lower than in the hCG administration, suggesting that the stimulating effect of these derivatives on ovary would be milder than that of hCG.

Test Example 15

Evaluation of Blood Testosterone Level Decreasing Effect of Metastin Peptide Derivatives Using Mature Male Rat A metastin peptide derivative (hereinafter peptide) was dissolved in distilled water (Otsuka Joryusui K.K.) to prepare 2 mM peptide solution. This peptide solution was filled in 5 ALZET osmotic pumps (Model 2001, 0.2 ml in volume, release rate: 0.001 ml/hr, DURECT Corporation). The ALZET pumps filled with the peptide solution were implanted subcutaneously in 5 CD(SD)IGS male rats of 9 weeks old after birth (Charles River Japan, Inc.) on the back under ether anesthesia by one pump for one animal. For negative control, distilled water (Otsuka Pharmaceutical Co., Ltd.) was filled in 5 ALZET osmotic pumps, which were similarly implanted in 5 male CD(SD)IGS rats (Charles River Japan, Inc.), respectively. These pump-implanted rats were fed for 6 days under normal feeding conditions. After weighing, the animal was decapitated to collect blood. After 0.03 ml/ml blood of aprotinin solution (Trasylol, Bayer) containing 0.1 mg/ml EDTA.2Na was added to blood, the mixture was centrifuged at 1,800 G for 25 minutes to isolate/recover plasma. From the plasma obtained, 0.05 ml was applied to radioimmunoassay (DPC.Total Testosterone Kit, Diagnostic Products Corporation) to measure the plasma testosterone level of each rat. The value below the limit of measurement (0.04 ng/ml of plasma level) in radioimmunoassay was treated as 0. A mean value of the testosterone levels from 5 rats receiving the peptide was calculated and a relative value (percent) of the mean value to a mean value from 5 rats receiving distilled water.

Using this evaluation method, various peptides were evaluated and a part of the results are shown in TABLES 28 and 29.

TABLE 28

| Comp. No. | Teststerone level in Blood |
|---|---|
| 334 | 40% |
| 354 | 43% |
| 436 | 35% |
| 269 | 7% |
| 386 | 23% |
| 499 | 2% |
| 305 | 2% |
| 385 | 2% |
| 492 | 65% |
| 496 | 3% |
| 134 | 50% |
| 141 | 31% |
| 176 | 12% |

TABLE 29

| Comp. No. | Teststerone level in Blood |
|---|---|
| 505 | 40% |
| 508 | 9% |
| 509 | 2% |
| 512 | 2% |
| 515 | 2% |
| 517 | 79% |

Test Example 16

In a manner similar to TEST EXAMPLE 14, evaluation was made using 0.1 mM peptide solution and a part of the results obtained are shown in TABLE 30.

TABLE 30

| Compond Number | Teststerone level in Blood |
|---|---|
| 305 | 48% |
| 385 | 33% |
| 499 | 32% |
| 512 | 38% |
| 516 | 3% |
| 523 | 72% |
| 538 | 45% |
| 540 | 55% |
| 545 | 37% |
| 547 | 65% |
| 550 | 2% |
| 551 | 8% |
| 552 | 21% |
| 553 | 39% |
| 554 | 52% |
| 555 | 73% |
| 558 | 2% |
| 559 | 17% |
| 562 | 11% |
| 564 | 66% |
| 565 | 80% |
| 566 | 89% |
| 567 | 86% |
| 571 | 17% |

Test Example 17

Evaluation of Metastin Peptide Derivatives for Action of Reducing Testosterone Level in Blood Using Mature Male Rat Peptide solutions at the concentration of 1 mM was prepared by dissolving the metastin peptide derivatives (hereinafter referred to as peptide) in 50% DMSO aqueous solution. The peptide was encapsulated in five ALZET osmotic pump (Model 2001, 0.2 ml of volume, releasing rate 0.001 ml/hr, DURECT Corporation). The ALZET pumps encapsulated with the peptide solution were implanted to dorsal subcutaneous of five male CD (SD) IGS rat at nine weeks age (Charles River Japan, Inc.) anesthesized with ether for one pump to one rat. Separately, for negative controls, the ALZET osmotic pumps encapsulated with distilled water were implanted to five male CD (SD) IGS rat (Charles River Japan, Inc.) The rats were bred for six days under the normal conditions. After weighing, blood was collected by decapitation. To 1 ml of blood, 0.03 ml of aprotinin (Trasylol, Byer) solution containing 0.1 g/ml EDTA 2Na was added. The plasma was isolated by centrifugation at 1,800×g for 25 minutes and collected. The thus obtained plasma, 0.05 ml was effected by radioimmunoassay. (DPC Total Testosterone Kit, Diagnostic Products Corporation) to measure testosterone level in blood of each rat. The value beneath measuring limit of radioimmunoassay (0.04 ng/ml as concentration of plasma) was treated as zero. The mean values for testosterone level of five rats, to which the peptide was given, was calculated and the relative value (percentage) for the mean values of testosterone level of five rats, to which distilled watrer was given, was estimated. One example of the results evaluated for various peptides using this evaluation method was shown in TABLE 31.

TABLE 31

| Comp. No. | Testosterone level in Blood |
|---|---|
| 305 | 2% |
| 501 | 2% |

TABLE 31-continued

| Comp. No. | Testosterone level in Blood |
|---|---|
| 545 | 2% |
| 548 | 18% |
| 555 | 2% |
| 564 | 2% |
| 589 | 2% |
| 590 | 2% |
| 591 | 2% |
| 592 | 2% |
| 595 | 3% |
| 598 | 2% |
| 599 | 2% |
| 600 | 2% |
| 602 | 2% |
| 608 | 2% |
| 612 | 2% |
| 613 | 2% |
| 615 | 2% |
| 616 | 2% |
| 617 | 2% |
| 618 | 2% |
| 621 | 2% |
| 623 | 2% |
| 625 | 2% |
| 626 | 2% |
| 627 | 2% |
| 629 | 2% |
| 630 | 2% |
| 635 | 2% |
| 637 | 2% |
| 638 | 2% |
| 642 | 2% |
| 648 | 2% |
| 649 | 2% |
| 650 | 2% |
| 651 | 2% |
| 652 | 2% |
| 657 | 2% |
| 658 | 2% |
| 660 | 2% |
| 662 | 2% |
| 663 | 2% |
| 664 | 6% |
| 666 | 2% |
| 667 | 2% |
| 670 | 2% |
| 671 | 2% |
| 672 | 2% |
| 674 | 2% |
| 675 | 2% |
| 676 | 2% |
| 677 | 2% |

[Sequence Listing Free Text]
SEQ ID NO: 15 The C terminus is amidated.
SEQ ID NO: 16 The C terminus is amidated.
SEQ ID NO: 17 The C terminus is amidated.
SEQ ID NO: 18 The C terminus is amidated.

The invention claimed is:

1. A metastin derivative represented by formula:

Ac-D-Tyr-XX3-Asn-XX5-Phe-AzaGly-Leu-Arg(Me)-XX10-NH$_2$

XX3 represents D-Trp or D-4-pyridylalanine;
XX5 represents Ser, or Thr;
AzaGly represents azaglycine;
XX10 represents Phe, or Trp, or a salt thereof.

2. A pharmaceutical composition comprising the metastin derivative of claim 1 or a salt thereof and a pharmaceutically acceptable carrier.

3. A metastin derivative selected from the group consisting of

AC-D-Tyr-D-Pya(4)-Asn-Ser-Phe-AzaGly-Leu-Arg(Me)-Phe-NH$_2$ (Compound No. 516),
Ac-D-Tyr-D-Trp-Asn-Ser-Phe-AzaGly-Leu-Arg(Me)-Trp-NH$_2$ (Compound No. 558),
Ac-D-Tyr-D-Pya(4)-Asn-Thr-Phe-AzaGly-Leu-Arg(Me)-Trp-NH$_2$ (Compound No. 562),
Ac-D-Tyr-D-Trp-Asn-Thr-Phe-AzaGly-Leu-Arg(Me)-Phe-NH$_2$ (Compound No. 571),
and salts thereof.

4. A metastin derivative which is Ac-D-Tyr-D-Pya(4)-Asn-Thr-Phe-AzaGly-Leu-Arg(Me)-Trp-NH$_2$ (Compound No. 562) or salts thereof.

* * * * *

SEQUENCE LISTING

```
<160> NUMBER OF SEQ ID NOS: 22

<210> SEQ ID NO 1
<211> LENGTH: 54
<212> TYPE: PRT
<213> ORGANISM: Homo sapiens

<400> SEQUENCE: 1

Gly Thr Ser Leu Ser Pro Pro Glu Ser Ser Gly Ser Arg Gln Gln
 1               5                  10                  15

Pro Gly Leu Ser Ala Pro His Ser Arg Gln Ile Pro Ala Pro Gln Gly
                20                  25                  30

Ala Val Leu Val Gln Arg Glu Lys Asp Leu Pro Asn Tyr Asn Trp Asn
        35                  40                  45

Ser Phe Gly Leu Arg Phe
    50

<210> SEQ ID NO 2
<211> LENGTH: 162
<212> TYPE: DNA
<213> ORGANISM: Homo sapiens

<400> SEQUENCE: 2
ggtacttctc tgtctccgcc gccggaatct tctggttctc gtcagcagcc gggtctgtct      60
gctccgcact ctcgtcagat cccggctccg cagggtgctg ttctggttca gcgtgaaaaa     120
gacctgccga actacaactg gaactctttc ggtctgcgtt tc                        162

<210> SEQ ID NO 3
<211> LENGTH: 152
<212> TYPE: PRT
<213> ORGANISM: Mus musculus

<400> SEQUENCE: 3
```

Met Tyr Leu Arg Phe Gly Val Asp Val Cys Ser Leu Ser Pro Trp Lys
1               5                  10                 15

Glu Thr Val Asp Leu Pro Leu Pro Pro Arg Met Ile Ser Met Ala Ser
            20                 25                 30

Trp Gln Leu Leu Leu Leu Leu Cys Val Ala Thr Tyr Gly Glu Pro Leu
        35                 40                 45

Ala Lys Val Ala Pro Gly Ser Thr Gly Gln Gln Ser Gly Pro Gln Glu
    50                 55                 60

Leu Val Asn Ala Trp Glu Lys Glu Ser Arg Tyr Ala Glu Ser Lys Pro
65              70                 75                  80

Gly Ser Ala Gly Leu Arg Ala Arg Arg Ser Ser Pro Cys Pro Pro Val
                85                 90                 95

Glu Gly Pro Ala Gly Arg Gln Arg Pro Leu Cys Ala Ser Arg Ser Arg
            100                105                110

Leu Ile Pro Ala Pro Arg Gly Ala Val Leu Val Gln Arg Glu Lys Asp
        115                120                125

Leu Ser Thr Tyr Asn Trp Asn Ser Phe Gly Leu Arg Tyr Gly Arg Arg
    130                135                140

Gln Ala Ala Arg Ala Ala Arg Gly
145                 150

<210> SEQ ID NO 4
<211> LENGTH: 456
<212> TYPE: DNA
<213> ORGANISM: Mus musculus

<400> SEQUENCE: 4
atgtatctga gatttggcgt tgatgtctgc agcctgagtc cctggaagga gactgtagac    60
ctgccccttc ctcccagaat gatctcaatg gcttcttggc agctgctgct tctcctctgt   120
gtcgccacct atggggagcc gctggcaaaa gtgaagcctg gatccacagg ccagcagtcc   180
ggaccccagg aactcgttaa tgcctgggaa aaggaatcgc ggtatgcaga gagcaagcct   240
gggtctgcag gctgcgcgc tcgtaggtcg tcgccatgcc cgccggttga gggccccgcg   300
gggcgccagc ggcccctgtg tgcctcccgc agtcgcctga tccctgcgcc ccgcggagcg   360
gtgctggtgc agcgggagaa ggacctgtcc acctacaact ggaactcctt cggcctgcgc   420
tacggcagga ggcaggcggc gcgggcagca cggggc                             456

<210> SEQ ID NO 5
<211> LENGTH: 156
<212> TYPE: PRT
<213> ORGANISM: Mus musculus

<400> SEQUENCE: 5

Met Tyr Leu Arg Phe Gly Val Asp Val Cys Ser Leu Ser Pro Trp Lys
1               5                  10                 15

Glu Thr Val Asp Leu Pro Leu Pro Pro Arg Met Ile Ser Met Ala Ser
            20                 25                 30

Trp Gln Leu Leu Leu Leu Leu Cys Val Ala Thr Tyr Gly Glu Pro Leu
        35                 40                 45

Ala Lys Val Ala Pro Leu Val Lys Pro Gly Ser Thr Gly Gln Gln Ser
    50                 55                 60

Gly Pro Gln Glu Leu Val Asn Ala Trp Glu Lys Glu Ser Arg Tyr Ala
65              70                 75                  80

Glu Ser Lys Pro Gly Ser Ala Gly Leu Arg Ala Arg Arg Ser Ser Pro

```
                85                  90                  95
Cys Pro Pro Val Glu Pro Ala Gly Arg Gln Arg Pro Leu Cys Ala
            100                 105                 110

Ser Arg Ser Arg Leu Ile Pro Ala Pro Arg Gly Ala Val Leu Val Gln
            115                 120                 125

Arg Glu Lys Asp Leu Ser Thr Tyr Asn Trp Asn Ser Phe Gly Leu Arg
130                 135                 140

Tyr Gly Arg Arg Gln Ala Ala Arg Ala Ala Arg Gly
145                 150                 155

<210> SEQ ID NO 6
<211> LENGTH: 468
<212> TYPE: DNA
<213> ORGANISM: Mus musculus

<400> SEQUENCE: 6
atgtatctga gatttggcgt tgatgtctgc agcctgagtc cctggaagga gactgtagac      60
ctgccccttc ctcccagaat gatctcaatg gcttcttggc agctgctgct tctcctctgt     120
gtcgccacct atggggagcc gctggcaaaa gtggcacctt tggtgaagcc tggatccaca     180
ggccagcagt ccggacccca ggaactcgtt aatgcctggg aaaaggaatc gcggtatgca     240
gagagcaagc ctgggtctgc agggctgcgc gctcgtaggt cgtcgccatg cccgccggtt     300
gagggccccg cggggcgcca gcggcccctg tgtgcctccc gcagtcgcct gatccctgcg     360
ccccgcggag cggtgctggt gcagcgggag aaggacctgt ccacctacaa ctggaactcc     420
ttcggcctgc gctacggcag gaggcaggcg gcgcgggcag cacgggc                   468

<210> SEQ ID NO 7
<211> LENGTH: 130
<212> TYPE: PRT
<213> ORGANISM: Rattus sp.

<400> SEQUENCE: 7

Met Thr Ser Leu Ala Ser Trp Gln Leu Leu Leu Leu Leu Cys Val Ala
                5                   10                  15

Ser Phe Gly Glu Pro Leu Ala Lys Met Ala Pro Val Val Asn Pro Glu
            20                  25                  30

Pro Thr Gly Gln Gln Ser Gly Pro Gln Glu Leu Val Asn Ala Trp Gln
        35                  40                  45

Lys Gly Pro Arg Tyr Ala Glu Ser Lys Pro Gly Ala Ala Gly Leu Arg
    50                  55                  60

Ala Arg Arg Thr Ser Pro Cys Pro Pro Val Glu Asn Pro Thr Gly His
65                  70                  75                  80

Gln Arg Pro Pro Cys Ala Thr Arg Ser Arg Leu Ile Pro Ala Pro Arg
                85                  90                  95

Gly Ser Val Leu Val Gln Arg Glu Lys Asp Met Ser Ala Tyr Asn Trp
            100                 105                 110

Asn Ser Phe Gly Leu Arg Tyr Gly Arg Arg Gln Val Ala Arg Ala Ala
        115                 120                 125

Arg Gly
    130

<210> SEQ ID NO 8
<211> LENGTH: 390
<212> TYPE: DNA
<213> ORGANISM: Rattus sp.
```

<400> SEQUENCE: 8

```
atgacctcgc tggcttcttg gcagctgctg cttctcctct gtgtggcctc ttttggggag      60
ccactggcaa aaatggcacc tgtggtgaac cctgaaccca caggccaaca gtccggaccc     120
caggaactcg ttaatgcctg gcaaaagggc ccgcggtatg cagagagcaa gcctggggct     180
gcaggactgc gcgctcgccg aacatcgcca tgcccgccgg tggagaaccc cacggggcac     240
cagcggcccc cgtgtgccac ccgcagtcgc ctgatccctg cgccccgcgg atcggtgctg     300
gtgcagcgcg agaaggacat gtcagcctac aactggaact cctttggcct cgctacggc     360
aggaggcagg tggcgcgggc ggcacggggc                                       390
```

<210> SEQ ID NO 9
<211> LENGTH: 398
<212> TYPE: PRT
<213> ORGANISM: Homo sapiens

<400> SEQUENCE: 9

```
Met His Thr Val Ala Thr Ser Gly Pro Asn Ala Ser Trp Gly Ala Pro
                 5                  10                  15
Ala Asn Ala Ser Gly Cys Pro Gly Cys Gly Ala Asn Ala Ser Asp Gly
             20                  25                  30
Pro Val Pro Ser Pro Arg Ala Val Asp Ala Trp Leu Val Pro Leu Phe
         35                  40                  45
Phe Ala Ala Leu Met Leu Leu Gly Leu Val Gly Asn Ser Leu Val Ile
     50                  55                  60
Tyr Val Ile Cys Arg His Lys Pro Met Arg Thr Val Thr Asn Phe Tyr
 65                  70                  75                  80
Ile Ala Asn Leu Ala Ala Thr Asp Val Thr Phe Leu Leu Cys Cys Val
                 85                  90                  95
Pro Phe Thr Ala Leu Leu Tyr Pro Leu Pro Gly Trp Val Leu Gly Asp
            100                 105                 110
Phe Met Cys Lys Phe Val Asn Tyr Ile Gln Gln Val Ser Val Gln Ala
        115                 120                 125
Thr Cys Ala Thr Leu Thr Ala Met Ser Val Asp Arg Trp Tyr Val Thr
    130                 135                 140
Val Phe Pro Leu Arg Ala Leu His Arg Arg Thr Pro Arg Leu Ala Leu
145                 150                 155                 160
Ala Val Ser Leu Ser Ile Trp Val Gly Ser Ala Val Ser Ala Pro
                165                 170                 175
Val Leu Ala Leu His Arg Leu Ser Pro Gly Pro Arg Ala Tyr Cys Ser
            180                 185                 190
Glu Ala Phe Pro Ser Arg Ala Leu Glu Arg Ala Phe Ala Leu Tyr Asn
        195                 200                 205
Leu Leu Ala Leu Tyr Leu Leu Pro Leu Leu Ala Thr Cys Ala Cys Tyr
    210                 215                 220
Ala Ala Met Leu Arg His Leu Gly Arg Val Ala Val Arg Pro Ala Pro
225                 230                 235                 240
Ala Asp Ser Ala Leu Gln Gly Gln Val Leu Ala Glu Arg Ala Gly Ala
                245                 250                 255
Val Arg Ala Lys Val Ser Arg Leu Val Ala Ala Val Val Leu Leu Phe
            260                 265                 270
Ala Ala Cys Trp Gly Pro Ile Gln Leu Phe Leu Val Leu Gln Ala Leu
        275                 280                 285
Gly Pro Ala Gly Ser Trp His Pro Arg Ser Tyr Ala Ala Tyr Ala Leu
```

```
                290                 295                 300
Lys Thr Trp Ala His Cys Met Ser Tyr Ser Asn Ser Ala Leu Asn Pro
305                 310                 315                 320

Leu Leu Tyr Ala Phe Leu Gly Ser His Phe Arg Gln Ala Phe Arg Arg
                325                 330                 335

Val Cys Pro Cys Ala Pro Arg Arg Pro Arg Arg Pro Arg Arg Pro Gly
                340                 345                 350

Pro Ser Asp Pro Ala Ala Pro His Ala Glu Leu His Arg Leu Gly Ser
                355                 360                 365

His Pro Ala Pro Ala Arg Ala Gln Lys Pro Gly Ser Ser Gly Leu Ala
                370                 375                 380

Ala Arg Gly Leu Cys Val Leu Gly Glu Asp Asn Ala Pro Leu
385                 390                 395
```

<210> SEQ ID NO 10
<211> LENGTH: 1194
<212> TYPE: DNA
<213> ORGANISM: Homo sapiens

<400> SEQUENCE: 10

```
atgcacaccg tggctacgtc cggacccaac gcgtcctggg gggcaccggc caacgcctcc      60
ggctgcccgg gctgtggcgc caacgcctcg gacggcccag tcccttcgcc gcgggccgtg     120
gacgcctggc tcgtgccgct cttcttcgcg gcgctgatgc tgctgggcct ggtggggaac     180
tcgctggtca tctacgtcat ctgccgccac aagccgatgc ggaccgtgac caacttctac     240
atcgccaacc tggcggccac ggacgtgacc ttcctcctgt gctgcgtccc cttcacggcc     300
ctgctgtacc cgctgcccgg ctgggtgctg gcgacttca tgtgcaagtt cgtcaactac     360
atccagcagg tctcggtgca ggccacgtgt gccactctga ccgccatgag cgtggaccgc     420
tggtacgtga cggtgttccc gttgcgcgcc ctgaccgcc gcacgccccg cctggcgctg     480
gctgtcagcc tcagcatctg ggtaggctct cggcggtgt ctgcgccggt gctcgccctg     540
caccgcctgt caccgggcc gcgcgcctac tgcagtgagg ccttccccag ccgcgccctg     600
gagcgcgcct tcgcactgta caacctgctg gcgctgtacc tgctgccgct gctcgccacc     660
tgcgcctgct atgcggccat gctgcgccac ctgggccggg tcgccgtgcg ccccgcgccc     720
gccgatagcg ccctgcaggg gcaggtgctg gcagagcgcg caggcgccgt gcgggccaag     780
gtctcgcggc tggtggcggc cgtggtcctg ctcttcgccg cctgctgggg ccccatccag     840
ctgttcctgg tgctgcaggc gctgggcccc gcgggctcct ggcacccacg cagctacgcc     900
gcctacgcgc ttaagacctg gctcactgc atgtcctaca gcaactccgc gctgaacccg     960
ctgctctacg ccttcctggg ctcgcacttc cgacaggcct tccgccgcgt ctgcccctgc    1020
gcgccgcgcc gccccgccg cccggccgg cccggaccct cggacccgc agccccacac    1080
gcggagctgc accgcctggg gtcccacccg gcccccgcca gggcgcagaa gccagggagc    1140
agtgggctgg ccgcgcgcgg gctgtgcgtc ctggggagg acaacgcccc tctc          1194
```

<210> SEQ ID NO 11
<211> LENGTH: 396
<212> TYPE: PRT
<213> ORGANISM: Rattus sp.

<400> SEQUENCE: 11

```
Met Ala Ala Glu Ala Thr Leu Gly Pro Asn Val Ser Trp Trp Ala Pro
                5                  10                  15
```

Ser Asn Ala Ser Gly Cys Pro Gly Cys Gly Val Asn Ala Ser Asp Gly
            20                  25                  30

Pro Gly Ser Ala Pro Arg Pro Leu Asp Ala Trp Leu Val Pro Leu Phe
        35                  40                  45

Phe Ala Ala Leu Met Leu Leu Gly Leu Val Gly Asn Ser Leu Val Ile
    50                  55                  60

Phe Val Ile Cys Arg His Lys His Met Gln Thr Val Thr Asn Phe Tyr
65                  70                  75                  80

Ile Ala Asn Leu Ala Ala Thr Asp Val Thr Phe Leu Leu Cys Cys Val
                85                  90                  95

Pro Phe Thr Ala Leu Leu Tyr Pro Leu Pro Thr Trp Val Leu Gly Asp
            100                 105                 110

Phe Met Cys Lys Phe Val Asn Tyr Ile Gln Gln Val Ser Val Gln Ala
        115                 120                 125

Thr Cys Ala Thr Leu Thr Ala Met Ser Val Asp Arg Trp Tyr Val Thr
    130                 135                 140

Val Phe Pro Leu Arg Ala Leu His Arg Arg Thr Pro Arg Leu Ala Leu
145                 150                 155                 160

Thr Val Ser Leu Ser Ile Trp Val Gly Ser Ala Val Ser Ala Pro
                165                 170                 175

Val Leu Ala Leu His Arg Leu Ser Pro Gly Pro His Thr Tyr Cys Ser
            180                 185                 190

Glu Ala Phe Pro Ser Arg Ala Leu Glu Arg Ala Phe Ala Leu Tyr Asn
        195                 200                 205

Leu Leu Ala Leu Tyr Leu Leu Pro Leu Ala Thr Cys Ala Cys Tyr
    210                 215                 220

Gly Ala Met Leu Arg His Leu Gly Arg Ala Ala Val Arg Pro Ala Pro
225                 230                 235                 240

Thr Asp Gly Ala Leu Gln Gly Gln Leu Leu Ala Gln Arg Ala Gly Ala
                245                 250                 255

Val Arg Thr Lys Val Ser Arg Leu Val Ala Ala Val Leu Leu Phe
            260                 265                 270

Ala Ala Cys Trp Gly Pro Ile Gln Leu Phe Leu Val Leu Gln Ala Leu
        275                 280                 285

Gly Pro Ser Gly Ala Trp His Pro Arg Ser Tyr Ala Ala Tyr Ala Leu
    290                 295                 300

Lys Ile Trp Ala His Cys Met Ser Tyr Ser Asn Ser Ala Leu Asn Pro
305                 310                 315                 320

Leu Leu Tyr Ala Phe Leu Gly Ser His Phe Arg Gln Ala Phe Cys Arg
                325                 330                 335

Val Cys Pro Cys Gly Pro Gln Arg Gln Arg Arg Pro His Ala Ser Ala
            340                 345                 350

His Ser Asp Arg Ala Ala Pro His Ser Val Pro His Ser Arg Ala Ala
        355                 360                 365

His Pro Val Arg Val Arg Thr Pro Glu Pro Gly Asn Pro Val Val Arg
    370                 375                 380

Ser Pro Ser Val Gln Asp Glu His Thr Ala Pro Leu
385                 390                 395

<210> SEQ ID NO 12
<211> LENGTH: 1188
<212> TYPE: DNA
<213> ORGANISM: Rattus sp.

<400> SEQUENCE: 12

```
atggccgcag aggcgacgtt gggtccgaac gtgagctggt gggctccgtc aacgcttcg      60
ggatgcccgg gctgcggtgt caatgcctcg gatgcccag gctccgcgcc aaggcccctg     120
gatgcctggc tggtgcccct gttttcgct gccctaatgt tgctggggct agtcgggaac     180
tcactggtca tcttcgttat ctgccgccac aagcacatgc agaccgtcac caatttctac    240
atcgctaacc tggcggccac agatgtcact ttccttctgt gctgcgtacc cttcaccgcg    300
ctcctctatc cgctgcccac ctgggtgctg gagacttca tgtgcaaatt cgtcaactac     360
atccagcagg tctcggtgca agccacatgt gccactttga cagccatgag tgtggaccgc    420
tggtacgtga ctgtgttccc gctgcgtgca cttcaccgcc gcactccgcg cctggccctg    480
actgtcagcc ttagcatctg ggtgggttcc gcagctgttt ccgccccggt gctggctctg    540
caccgcctgt cgcccgggcc tcacacctac tgcagtgagg cgtttcccag ccgtgccctg    600
gagcgcgctt tcgcgctcta caacctgctg gccctatacc tgctgccgct gctcgccacc    660
tgcgcctgct acggtgccat gctgcgccac ctgggccgcg ccgctgtacg ccccgcaccc    720
actgatggcg ccctgcaggg gcagctgcta gcacagcgcg ctggagcagt gcgcaccaag    780
gtctcccggc tggtggccgc tgtcgtcctg ctcttcgccg cctgctgggg cccgatccag    840
ctgttcctgg tgcttcaagc cctgggcccc tcgggggcct ggcaccctcg aagctatgcc    900
gcctacgcgc tcaagatctg ggctcactgc atgtcctaca gcaattctgc gctcaacccg    960
ctgctctatg ccttcctggg ttcccacttc agacaggcct tctgccgcgt gtgcccctgc   1020
ggcccgcaac gccagcgtcg gccccacgcg tcagcgcact cggaccgagc cgcaccccat   1080
agtgtgccgc acagccgggc tgcgcaccct gtccgggtca ggaccccga gcctgggaac    1140
cctgtggtgc gctcgccctc tgttcaggat gaacacactg ccccactc                1188
```

<210> SEQ ID NO 13
<211> LENGTH: 396
<212> TYPE: PRT
<213> ORGANISM: Mus musculus

<400> SEQUENCE: 13

```
Met Ala Thr Glu Ala Thr Leu Ala Pro Asn Val Thr Trp Trp Ala Pro
1               5                   10                  15

Ser Asn Ala Ser Gly Cys Pro Gly Cys Gly Val Asn Ala Ser Asp Asp
            20                  25                  30

Pro Gly Ser Ala Pro Arg Pro Leu Asp Ala Trp Leu Val Pro Leu Phe
        35                  40                  45

Phe Ala Thr Leu Met Leu Leu Gly Leu Val Gly Asn Ser Leu Val Ile
    50                  55                  60

Tyr Val Ile Cys Arg His Lys His Met Gln Thr Val Thr Asn Phe Tyr
65                  70                  75                  80

Ile Ala Asn Leu Ala Ala Thr Asp Val Thr Phe Leu Leu Cys Cys Val
                85                  90                  95

Pro Phe Thr Ala Leu Leu Tyr Pro Leu Pro Ala Trp Val Leu Gly Asp
            100                 105                 110

Phe Met Cys Lys Phe Val Asn Tyr Ile Gln Gln Val Ser Val Gln Ala
        115                 120                 125

Thr Cys Ala Thr Leu Thr Ala Met Ser Val Asp Arg Trp Tyr Val Thr
    130                 135                 140

Val Phe Pro Leu Arg Ala Leu His Arg Arg Thr Pro Arg Leu Ala Leu
145                 150                 155                 160
```

```
Ala Val Ser Leu Ser Ile Trp Val Gly Ser Ala Val Ser Ala Pro
            165                 170                 175

Val Leu Ala Leu His Arg Leu Ser Pro Gly Pro Arg Thr Tyr Cys Ser
            180                 185                 190

Glu Ala Phe Pro Ser Arg Ala Leu Glu Arg Ala Phe Ala Leu Tyr Asn
            195                 200                 205

Leu Leu Ala Leu Tyr Leu Leu Pro Leu Leu Ala Thr Cys Ala Cys Tyr
            210                 215                 220

Gly Ala Met Leu Arg His Leu Gly Arg Ala Ala Val Arg Pro Ala Pro
225                 230                 235                 240

Thr Asp Gly Ala Leu Gln Gly Gln Leu Ala Gln Arg Ala Gly Ala
            245                 250                 255

Val Arg Thr Lys Val Ser Arg Leu Val Ala Ala Val Leu Leu Phe
            260                 265                 270

Ala Ala Cys Trp Gly Pro Ile Gln Leu Phe Leu Val Leu Gln Ala Leu
            275                 280                 285

Gly Pro Ser Gly Ala Trp His Pro Arg Ser Tyr Ala Ala Tyr Ala Val
            290                 295                 300

Lys Ile Trp Ala His Cys Met Ser Tyr Ser Asn Ser Ala Leu Asn Pro
305                 310                 315                 320

Leu Leu Tyr Ala Phe Leu Gly Ser His Phe Arg Gln Ala Phe Cys Arg
            325                 330                 335

Val Cys Pro Cys Cys Arg Gln Arg Gln Arg Arg Pro His Thr Ser Ala
            340                 345                 350

His Ser Asp Arg Ala Ala Thr His Thr Val Pro His Ser Arg Ala Ala
            355                 360                 365

His Pro Val Arg Ile Arg Ser Pro Glu Pro Gly Asn Pro Val Val Arg
            370                 375                 380

Ser Pro Cys Ala Gln Ser Glu Arg Thr Ala Ser Leu
385                 390                 395

<210> SEQ ID NO 14
<211> LENGTH: 1188
<212> TYPE: DNA
<213> ORGANISM: Mus musculus

<400> SEQUENCE: 14
atggccaccg aggcgacatt ggctcccaat gtgacctggt gggctccgtc caacgcttca      60
ggatgcccag gctgcggtgt caacgcctcg gatgacccag gctctgcgcc aaggcccctg     120
gatgcctggc tggttcccct gttttttcgct acactcatgt tgcttgggct ggtcggaaac     180
tcattggtca tctacgttat ctgccgccac aagcacatgc agacagttac caacttctac     240
atcgctaacc tggctgccac agacgtcact ttcctactgt gctgcgtgcc cttcaccgca     300
ctcctctacc cgctgcccgc ctgggtgctg ggagacttca tgtgcaaatt cgtcaactac     360
atccagcagg tctcggtgca agccacatgt gccactctga cggccatgag gtggaccgc     420 tggtatgtga ctgtgttccc gctgcgtgca cttcaccgcc gcactccgcg cctggccctg     480
gctgtcagcc tcagcatctg ggtggggtca gcagctgtgt ccgccccggt gctggccctg     540
caccgcctgt cgccagggcc tcgcacctac tgcagcgagg cgtttcccag ccgcgccctg     600
gagcgcgcct tcgcgctcta caacctgctg gctctatatc tgctgccgct gctcgccacc     660
tgcgcctgct acggcgccat gctgcgccac ctgggccgtg cggctgtacg ccccgcaccc     720
actgacggcg ccctgcaggg acagctgcta gcacagcgcg ccggagcagt gcgcaccaag     780
```

```
gtctcccggc tggtggccgc tgtcgtcctg ctcttcgccg cctgctgggg cccgatccag    840
ctgttcctgg tgcttcaagc cctgggcccc tcggggggcct ggcaccctcg aagctatgcc    900
gcctacgcgg tcaagatctg ggctcactgc atgtcctaca gcaactcggc gctcaatccg    960
ctgctctatg ccttcctggg ttcacacttc agacaggcct tctgccgcgt gtgccctgc    1020 tgccggcaac gccagcgccg gccccacacg tcagcgcact cggaccgagc tgcaactcac    1080
actgtgccgc acagccgtgc tgcgcaccct gtgcggatca ggagcccgga gcctgggaac    1140
cctgtggtgc gctcgccctg cgctcagagt gaacgcactg cctcactc                1188
```

<210> SEQ ID NO 15
<211> LENGTH: 15
<212> TYPE: PRT
<213> ORGANISM: Artificial
<220> FEATURE:
<223> OTHER INFORMATION: the C-terminus of the polypeptide is amide
      (-CONH2) form

<400> SEQUENCE: 15

```
Lys Asp Leu Pro Asn Tyr Asn Trp Asn Ser Phe Gly Leu Arg Phe
1               5                   10                  15
```

<210> SEQ ID NO 16
<211> LENGTH: 10
<212> TYPE: PRT
<213> ORGANISM: Artificial
<220> FEATURE:
<223> OTHER INFORMATION: the C-terminus of the polypeptide is amide
      (-CONH2) form

<400> SEQUENCE: 16

```
Tyr Asn Trp Asn Ser Phe Gly Leu Arg Phe
1               5                   10
```

<210> SEQ ID NO 17
<211> LENGTH: 9
<212> TYPE: PRT
<213> ORGANISM: Artificial
<220> FEATURE:
<223> OTHER INFORMATION: the C-terminus of the polypeptide is amide
      (-CONH2) form

<400> SEQUENCE: 17

```
Asn Trp Asn Ser Phe Gly Leu Arg Phe
1               5                 9
```

<210> SEQ ID NO 18
<211> LENGTH: 8
<212> TYPE: PRT
<213> ORGANISM: Artificial
<220> FEATURE:
<223> OTHER INFORMATION: the C-terminus of the polypeptide is amide
      (-CONH2) form

<400> SEQUENCE: 18

```
Trp Asn Ser Phe Gly Leu Arg Phe
1               5             8
```

<210> SEQ ID NO 19
<211> LENGTH: 45
<212> TYPE: DNA
<213> ORGANISM: Homo sapiens

<400> SEQUENCE: 19

```
aaggacctgc cgaactacaa ctggaactcc ttcggcctgc gcttc              45
```

```
<210> SEQ ID NO 20
<211> LENGTH: 30
<212> TYPE: DNA
<213> ORGANISM: Homo sapiens

<400> SEQUENCE: 20
tacaactgga actccttcgg cctgcgcttc                                      30

<210> SEQ ID NO 21
<211> LENGTH: 27
<212> TYPE: DNA
<213> ORGANISM: Homo sapiens

<400> SEQUENCE: 21
aactggaact ccttcggcct gcgcttc                                         27

<210> SEQ ID NO 22
<211> LENGTH: 24
<212> TYPE: DNA
<213> ORGANISM: Homo sapiens

<400> SEQUENCE: 22
tggaactcct tcggcctgcg cttc                                            24
```